United States Patent
Woolford et al.

(10) Patent No.: US 9,676,768 B2
(45) Date of Patent: *Jun. 13, 2017

(54) BICYCLIC HETEROCYCLE COMPOUNDS AND THEIR USES IN THERAPY

(71) Applicant: ASTEX THERAPEUTICS LIMITED, Cambridge (GB)

(72) Inventors: Alison Jo-Anne Woolford, Cambridge (GB); Steven Howard, Cambridge (GB); Ildiko Maria Buck, London (GB); Gianni Chessari, Cambridge (GB); Christopher Norbert Johnson, Saffron Walden (GB); Emiliano Tamanini, Cambridge (GB); James Edward Harvey Day, Cambridge (GB); Elisabetta Chiarparin, Cambridge (GB); Thomas Daniel Heightman, Harpenden (GB); Martyn Frederickson, Cambridge (GB); Charlotte Mary Griffiths-Jones, Cambridge (GB)

(73) Assignee: ASTEX THERAPEUTICS LIMITED, Cambridge (GB)

(*) Notice: Subject to any disclaimer, the term of this patent is extended or adjusted under 35 U.S.C. 154(b) by 0 days.

This patent is subject to a terminal disclaimer.

(21) Appl. No.: 14/663,534

(22) Filed: Mar. 20, 2015

(65) Prior Publication Data

US 2015/0291586 A1 Oct. 15, 2015

Related U.S. Application Data

(63) Continuation of application No. 14/112,597, filed as application No. PCT/GB2012/050867 on Apr. 20, 2012, now Pat. No. 9,018,214.

(30) Foreign Application Priority Data

Apr. 21, 2011 (GB) .................................. 1106817.8

(51) Int. Cl.
*A61K 31/497* (2006.01)
*A61K 31/501* (2006.01)
(Continued)

(52) U.S. Cl.
CPC .......... *C07D 471/04* (2013.01); *A61K 31/496* (2013.01); *A61K 31/497* (2013.01); *A61K 31/501* (2013.01); *A61K 31/506* (2013.01); *A61K 31/5025* (2013.01); *A61K 31/5377* (2013.01); *C07D 401/06* (2013.01); *C07D 403/06* (2013.01); *C07D 403/14* (2013.01); *C07D 413/14* (2013.01);
(Continued)

(58) Field of Classification Search
CPC .. A61K 31/496; A61K 31/497; A61K 31/501; A61K 31/5025; A61K 31/506; A61K 31/5377; C07D 401/06; C07D 403/06; C07D 403/14; C07D 413/14; C07D 471/04; C07D 471/10; C07D 487/04; C07D 487/10; C07D 519/00
USPC .............. 514/234.5, 253.04, 253.09, 254.09, 514/210.18, 252.02, 252.11, 235.2, 248, 514/252.18, 254.03, 254.04, 254.05
See application file for complete search history.

(56) References Cited

U.S. PATENT DOCUMENTS

| | | |
|---|---|---|
| 4,080,330 A | 3/1978 | Kubela et al. |
| 4,138,494 A | 2/1979 | Kubela et al. |

(Continued)

FOREIGN PATENT DOCUMENTS

| | | |
|---|---|---|
| CA | 2433090 A1 | 7/2002 |
| EP | 302008 A2 | 2/1989 |

(Continued)

OTHER PUBLICATIONS

Flygare, J., et al., "Small-molecule pan-IAP antagonists: a patent review", Expert Opinion on Therapeutic Patents, Informa Healthcare, GB, vol. 20 (2), pp. 251-267 (2010).

(Continued)

*Primary Examiner* — My-Chau T Tran
(74) *Attorney, Agent, or Firm* — Heslin Rothenberg Farley & Mesiti P.C.

(57) ABSTRACT

The invention relates to bicyclic heterocycle compounds of formula (I):

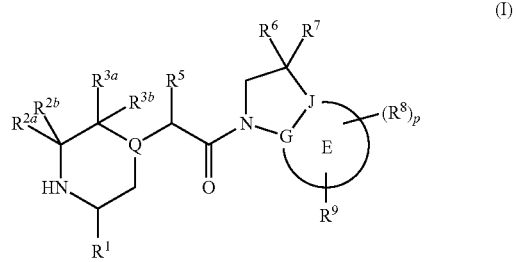

or tautomeric or stereochemically isomeric forms, N-oxides, pharmaceutically acceptable salts or the solvates thereof; wherein $R^1$, $R^{2a}$, $R^{2b}$, $R^{3a}$, $R^{3b}$, $R^5$, $R^6$, $R^7$, $R^8$, $R^9$, p and E are as defined herein; to pharmaceutical compositions comprising said compounds and to the use of said compounds in the treatment of diseases, e.g. cancer.

16 Claims, No Drawings

Related U.S. Application Data

(60) Provisional application No. 61/477,726, filed on Apr. 21, 2011.

(51) Int. Cl.

| | | |
|---|---|---|
| *C07D 403/04* | (2006.01) | |
| *C07D 419/00* | (2006.01) | |
| *C07D 471/04* | (2006.01) | |
| *C07D 401/06* | (2006.01) | |
| *C07D 471/10* | (2006.01) | |
| *C07D 403/06* | (2006.01) | |
| *C07D 487/10* | (2006.01) | |
| *C07D 403/14* | (2006.01) | |
| *A61K 31/496* | (2006.01) | |
| *A61K 31/5025* | (2006.01) | |
| *A61K 31/506* | (2006.01) | |
| *A61K 31/5377* | (2006.01) | |
| *C07D 413/14* | (2006.01) | |
| *C07D 487/04* | (2006.01) | |
| *C07D 519/00* | (2006.01) | |

(52) U.S. Cl.
CPC ......... *C07D 471/10* (2013.01); *C07D 487/04* (2013.01); *C07D 487/10* (2013.01); *C07D 519/00* (2013.01)

(56) References Cited

U.S. PATENT DOCUMENTS

| | | | |
|---|---|---|---|
| 4,153,789 A | 5/1979 | Kubela et al. | |
| 6,084,098 A | 7/2000 | Kover et al. | |
| 7,935,819 B2 | 5/2011 | Halley et al. | |
| 7,977,477 B2 | 7/2011 | Berdini et al. | |
| 8,044,206 B2 | 10/2011 | Kikuchi et al. | |
| 8,415,486 B2 | 4/2013 | Condon et al. | |
| 9,018,214 B2 | 4/2015 | Woolford et al. | |
| 9,155,743 B2 | 10/2015 | Buck et al. | |
| 9,458,158 B2 | 10/2016 | Buck et al. | |
| 9,617,248 B2 | 4/2017 | Chessari et al. | |
| 9,617,283 B2 | 4/2017 | Chessari et al. | |
| 2005/0245537 A1 | 11/2005 | Tsuchimori et al. | |
| 2014/0045831 A1 | 2/2014 | Buck et al. | |
| 2014/0179666 A1 | 6/2014 | Woolford et al. | |
| 2015/0259359 A1 | 9/2015 | Chessari et al. | |
| 2015/0266873 A1 | 9/2015 | Chessari et al. | |
| 2015/0291586 A1 | 10/2015 | Woolford et al. | |
| 2015/0353537 A1 | 12/2015 | Chessari et al. | |
| 2016/0083377 A1 | 3/2016 | Buck et al. | |
| 2017/0029419 A1 | 2/2017 | Chessari et al. | |

FOREIGN PATENT DOCUMENTS

| | | |
|---|---|---|
| EP | 560235 A1 | 9/1993 |
| EP | 778277 A1 | 6/1997 |
| GB | 1550230 | 8/1979 |
| JP | S52-012162 A | 1/1977 |
| WO | 97/16440 A1 | 5/1997 |
| WO | 97/30971 A1 | 8/1997 |
| WO | 97/38665 A2 | 10/1997 |
| WO | 98/00401 A1 | 1/1998 |
| WO | 98/50346 A1 | 11/1998 |
| WO | 98/50358 A1 | 11/1998 |
| WO | 99/28313 A1 | 6/1999 |
| WO | 99/50247 A1 | 10/1999 |
| WO | 00/15612 A1 | 3/2000 |
| WO | 00/51984 A1 | 9/2000 |
| WO | 00/55143 A1 | 9/2000 |
| WO | 01/05763 A2 | 1/2001 |
| WO | 01/12600 A1 | 2/2001 |
| WO | 01/17942 A1 | 3/2001 |
| WO | 01/44226 A1 | 6/2001 |
| WO | 02/50061 A1 | 6/2002 |
| WO | 02/080853 A2 | 10/2002 |
| WO | 02/088101 A2 | 11/2002 |
| WO | 2005/019167 A2 | 3/2005 |
| WO | 2005/039572 A1 | 5/2005 |
| WO | 2006/010118 A2 | 1/2006 |
| WO | 2006/032987 A1 | 3/2006 |
| WO | 2006/069063 A1 | 6/2006 |
| WO | 2007/054453 A1 | 5/2007 |
| WO | 2007/073405 A1 | 6/2007 |
| WO | 2007/090617 A2 | 8/2007 |
| WO | 2008/045905 A1 | 4/2008 |
| WO | 2008/109181 A2 | 9/2008 |
| WO | 2008/116107 A2 | 9/2008 |
| WO | 2009/094287 A1 | 7/2009 |
| WO | 2009/147476 A1 | 12/2009 |
| WO | 2010/011666 A2 | 1/2010 |
| WO | 2010/048149 A2 | 4/2010 |
| WO | 2010/121212 A2 | 10/2010 |
| WO | 2010/129467 A1 | 11/2010 |
| WO | 2012/143725 A1 | 10/2012 |
| WO | 2012/143726 A1 | 10/2012 |
| WO | 2013/052110 A1 | 4/2013 |
| WO | 2013/102242 A1 | 7/2013 |
| WO | 2014/060767 A1 | 4/2014 |
| WO | 2014/060768 A1 | 4/2014 |
| WO | 2014/060770 A1 | 4/2014 |
| WO | 2015/092420 A1 | 6/2015 |
| WO | 2015/106025 A1 | 7/2015 |

OTHER PUBLICATIONS

Eckelman, B.P., et al "The mechanism of peptide-binding specificity of IAP-BIR domains", Cell Death and Differentiation, Nature Publishing Group, GB, vol. 15(5), pp. 920-928 (2008).

Ashton, K., et al., "Small Molecule Disruptors of the Glucokinase-Glucokinase Regulatory Protein Interaction: 1. Discovery of a Novel Tool Compound for in Vivo Proof-of-Concept", Journal of Medicinal Chemistry, vol. 57(2), pp. 309-324 (2014).

Moore, C., et al., "Structural and Biophysical Characterization of XIAP BIR3 G306E Mutant: Insights in Protein Dynamics and Application for Fragment-Based Drug Design", Chem. Biol. Drug Design, vol. 74(3), pp. 212-223 (2009).

Zhao, H., et al., "Indoline and Piperazine Containing Derivatives as a Novel Class of Mixed D2/D4 Receptor Antagonists. Part 1: Identification and Structure-Activity Relationships" Bioorganic & Medicinal Chemistry Letters, vol. 12, pp. 3105-3109 (2002).

International Search Report for PCT/GB2012/050867 dated Sep. 10, 2012.

GB Search Report for GB1106817.8 dated Aug. 9, 2011.

Vippagunta, S R et al., Crystalline Solids, *Advanced Drug Delivery Reviews*, vol. 48, pp. 3-26 (2001).

BICYCLIC HETEROCYCLE COMPOUNDS AND THEIR USES IN THERAPY

CROSS REFERENCE TO RELATED APPLICATIONS

This application is a continuation of U.S. application Ser. No. 14/112,597, filed on Oct. 18, 2013, which is a national stage filing under section 371 of International Application No. PCT/GB2012/050867, filed on Apr. 20, 2012, and published in English on Oct. 26, 2012 as WO/2012/143726, and claims priority to British Application No. 1106817.8 filed on Apr. 21, 2011, and to U.S. Provisional Application No. 61/477,726, filed on Apr. 21, 2011. The entire disclosures of each of the prior applications are hereby incorporated herein by reference.

FIELD OF THE INVENTION

The invention relates to new bicyclic heterocycle compounds, to pharmaceutical compositions comprising said compounds and to the use of said compounds in the treatment of diseases, e.g. cancer.

RELATED APPLICATIONS

This application is related to: U.S. provisional patent application No. 61/477,726 filed 21 Apr. 2011 and United Kingdom patent application number 1106817.8 filed 21 Apr. 2011, the contents of both of which are incorporated herein by reference in their entirety.

BACKGROUND OF THE INVENTION

IAP Family

The family of inhibitor of apoptosis (IAP) proteins comprises 8 members, XIAP, cIAP1, cIAP2, NAIP, ILP2, ML-IAP, survivin and BRUCE (also known as apollon). Members of the IAP family have been shown to inhibit programmed cell death through their ability to directly inhibit members of the caspase family of apoptotic enzymes, although the precise role of all 8 members is yet to be fully defined. The common structural feature of all IAP family members is a ~70 amino acid zinc-binding fold termed the baculovirus IAP repeat (BIR) domain, which is present in one to three copies.

Many interactions between IAPs and other proteins are mediated via a surface groove on the BIR domain. BIR domains may be classified by their peptide-binding specificity. There are three types of BIR domains; type III domains (capable of binding caspase (and caspase-like) peptides with a specificity for proline in the third (P3) position (e.g. XIAP. BIR3), type II domains (like type III domains but lacking the proline requirement e.g. XIAP BIR2) and type I domains (which do not bind caspases or similar peptides, e.g. XIAP BIR1) (Eckelman et al. Cell Death and Differentiation 2008; 15: 920-928). BIRs are small (~70 amino acids) Zn-coordinated domains and a variety of proteins use their N-terminal to interact with the BIR domains grooves. BIR antagonists prevent caspases binding to BIRs and hence result in increased caspase activity thereby inducing auto-ubiquitination and proteasomal degradation of IAPs.

IAPs are overexpressed in many cancers including renal, melanoma, colon, lung, breast, ovarian and prostate cancers (Tamm et al., Clin. Cancer Research 2000; 6(5): 1796-803), and have been implicated in tumour growth, pathogenesis and resistance to chemo- and radio-therapy (Tamm 2000).

XIAP

XIAP is a 57 kDa protein with three BIR domains, the second and third of which bind caspases and a RING-type zinc finger (E3 ligase). XIAP binds several proteins in addition to caspases, including ligation substrates such as TAK1 and cofactor TAB1, MURR1 involved in copper homeostasis (Burstein et al., EMBO 2004; 23: 244-254), endogenous inhibitors such as second mitochondria-derived activator of caspases (SMAC), and those of less clear function such as MAGE-D1, NRAGE (Jordan et al., J. Biol. Chem. 2001; 276: 39985-39989).

The BIR3 domain binds and inhibits caspase-9, an apical caspase in the mitochondrial pathway of caspase activation. A groove on the surface of the BIR3 domain interacts with the N-terminus of the small subunit of caspase-9, locking capsase-9 in its inactive monomeric form with an incompetent catalytic site (Shiozaki et al., Mol. Cell 2003; 11: 519-527).

In addition to caspase-binding, XIAP also inhibits apoptosis through other mechanisms. XIAP forms a complex with TAK1 kinase and its cofactor TAB1 that leads to activation of JNK and MAPK signal transduction pathways, in turn leading to activation of NFκB (Sanna et al., Mol Cell Biol 2002; 22: 1754-1766). XIAP also activates NFκB by promoting NFκB translocation to the nucleus and degradation of IκB (Hofer-Warbinek et al., J. Biol. Chem. 2000; 275: 22064-22068, Levkau et al., Circ. Res. 2001; 88: 282-290).

Cells transfected with XIAP are able to block programmed cell death in response to a variety of apoptotic stimuli (Duckett et al., EMBO 1996; 15: 2685-2694, Duckett et al., MCB 1998; 18: 608-615, Bratton, Lewis, Butterworth, Duckett and Cohen, Cell Death and Differentiation 2002; 9: 881-892).

XIAP is ubiquitously expressed in all normal tissues, but it is pathologically elevated in many acute and chronic leukaemias, prostate, lung, renal, and other types of tumours (Byrd et al., 2002; Ferreira et al., 2001; Hofmann et al., 2002; Krajewska et al., 2003; Schimmer et al., 2003; Tamm et al., 2000). In de novo acute myeloid leukaemia (AML), XIAP expression correlates with myelomonocytic French-American-British (FAB) subtypes M4/M5 (P<0.05) and expression of monocytic markers in AML blasts. In addition, XIAP was found to be overexpressed in normal monocytes but undetectable in granulocytes. In AML, XIAP expression was significantly lower in patients with favourable rather than intermediate or poor cytogenetics (n=74; P<0.05) (Tamm et al., Hematol. J. 2004; 5(6): 489-95).

Overexpression renders cells resistant to multi-agent therapy and is associated with poor clinical outcome in disease including AML, renal cancer, melanoma (Tamm et al., Clin. Cancer Research 2000; 6: 1796-1803) and lung cancer (Hofmann et al., J. Cancer Res. Clin. Oncology 2002; 128(10): 554-60).

XIAP is translated by a cap-independent mechanism of translation initiation that is mediated by a unique internal ribosome entry site (IRES) sequence element located in its 5' untranslated region. This allows XIAP mRNA to be actively translated during conditions of cellular stress when the majority of cellular protein synthesis is inhibited. Translational upregulation of XIAP in response to stress increases resistance to radiation induced cell death (Holcik et al., Oncogene 2000; 19: 4174-4177).

XIAP inhibition has been investigated in vitro via several techniques including RNA silencing, gene knockout, peptidic ligand mimetics and small molecule antagonists, and has been shown to promote apoptosis as a monotherapy and to sensitise many tumour types to chemotherapy, including bladder (Kunze et al., 2008; 28(4B): 2259-63). XIAP knockout mice are born at the expected Mendelian frequency, with no obvious physical or histological defects, and normal life spans (Harlin et al., Mol. Cell Biol. 2001; 21(10): 3604-3608). This indicates that lacking XIAP activity is not toxic in normal tissues and suggests a therapeutic window over tumour cells. It was noted that the cIAP1 and cIAP2 levels are upregulated in the XIAP knockout mouse and may protect from pathology via a compensatory mechanism, suggesting pan-inhibition may be required for functional knockout. Similarly, cIAP1 and cIAP2 knockout mice are also asympotomatic (Conze et al., Mol. Biol. Cell 2005; 25(8): 3348-56). While lack of any one of the IAPs produced no overt phenotype in mice, deletion of cIAP1 with cIAP2 or XIAP resulted in mid embryonic lethality (Moulin, EMBO J., 2012).

Endogenous IAP antagonists such as SMAC have been used to validate members of this family as targets for therapeutic agents. SMAC peptides chemosensitise tumour cells, and in combination with platins and Tumour Necrosis Factor α-related apoptosis inducing ligand (TRAIL) in xenografts, results in tumour growth delay (Fulda et al., Nat. Med. 2002; 808-815; Yang et al., Cancer Res. 2003; 63: 831-837).

A natural product, embellin, was identified as binding at the surface groove of the BIR3 domain of XIAP with similar affinity to the natural SMAC peptide. Embellin induces apoptosis in cell lines in vitro and results in tumour growth delay in xenografts (Nikolovska-Coleska et al., J. Med. Chem. 2004; 47(10): 2430-2440; Chitra et al., Chemotherapy 1994; 40: 109-113).

XIAP antisense oligonucleotides have been developed as therapeutic agents for solid tumour and haematological malignancies. In vitro these antisense oligonucleotides have been shown to knockdown protein expression levels by ~70%, induce apoptosis and sensitise cells to chemotherapy and delay tumour growth in vivo. One of these agents, AEG351156, has been studied in clinical trials (Hu et al., Clin. Cancer Res. 2003; 9: 2826-2836; Cummings et al., Br. J. Cancer 2005; 92: 532-538).

Small molecule antagonists of XIAP developed include peptidomimetics as well as synthetic agents. The peptidomimetics target the BIR3 domain, mimicking SMAC disruption of caspase-9 binding to XIAP, have shown induction of apoptosis in a variety of tumour cell lines as a single agent, as well as chemosensitisers and are being further investigated clinically (Oost et al., J. Med. Chem. 2004; 47: 4417-4426; Sun et al., Bioorg. Med. Chem. Lett. 2005; 15: 793-797).

Synthetic small molecule antagonists of BIR3 and BIR2 domains also demonstrate anti-tumour activity in several different models, including induction of apoptosis by annexin-V staining and IC50s of <10 µM against over one-third of the NCl60 cell line panel. XIAP antagonists also induced dose-dependent cell death of primary-cultured leukaemia cells in 5 out of 5 chronic lymphocytic leukaemia cell lines and 4 out of 5 acute myeloid leukaemia cell lines (Schimmer et al., Cancer Cell 2004; 5: 25-35; Berezovskaya et al., Cancer Res. 2005; 65(6): 2378-86).

High levels of XIAP protein in tumour cell lines were inversely correlated with sensitivity to some anti-cancer drugs, particularly cytarabine and other nucleosides (Tamm et al., Clin. Cancer Research 2000; 6: 1796-1803). XIAP inhibition potentiates TRAIL-induced antitumor activity in two preclinical models of pancreatic cancer in vivo (Vogler 2008). Gene expression and transfection studies suggest that the increased expression of apoptosis suppressor XIAP plays an important role in anoikis resistance and in the survival of circulating human prostate carcinoma cells, thereby promoting metastasis. Small molecule antagonists were found to be anti-metastatic in these models (Berezovskaya et al., Cancer Res. 2005; 65(6): 2378-86).

XIAP has also been found to be involved in other pathways associated with cancer and other diseases and these may also benefit from XIAP targeted agents. The E3 ligase activity of the RING finger domain of XIAP is able to bind both to TAB1 and to an upstream BMP receptor (type 1), suggesting that XIAP may signal in a TGF-β-mediated pathway (Yamaguchi et al., EMBO 1999; 179-187). Focal adhesion kinase (FAK) overexpression has been shown to result in upregulated XIAP expression (Sonoda et al., J. Biol. Chem. 2000; 275: 16309-16315). E3 ligases are attractive therapeutic targets and molecules which target this activity in other proteins such as MDM2 are being developed (Vassilev et al., Science 2004; 303: 844-848). Direct or indirect inhibition of the XIAP ligase activity may also be useful in the treatment of cancer and other diseases. Dysregulated apoptotic signalling, which would result from inhibition of IAP function in controlling programmed cell death, has also been implicated in many diseases, including disorders associated with cell accumulation (e.g. cancer, autoimmunity, inflammation and restenosis) or disorders where excessive apoptosis results in cell loss (e.g. stroke, heart failure, neurodegeneration such as Alzheimer's disease, Parkinson's disease, Huntington's disease, amyotrophic lateral sclerosis, AIDS, ischaemia (stroke, myocardial infarction) and osteoporosis).

XIAP is an important apoptotic regulator in experimental autoimmune encephalomyelitis and a potential pharmacological target for treating autoimmune diseases such as multiple sclerosis (MS) (Moore et al., 2004; 203(1): 79-93). Antisense-mediated knockdown of XIAP reverses paralysis in an animal model of MS suggesting that treatments targeting XIAP, and perhaps other IAPs, may have utility in the treatment of MS (Hebb et al., Curr. Drug Disc. Tech. 2008; 5(1): 75-7).

cIAP1, cIAP-2, XIAP and survivin are overexpressed in malignant pleural mesothelioma and are responsible for a large degree of the resistance of cultured mesothelioma cells to cisplatin. Levels of circulating TNF-α are significantly higher in mesothelioma patients prior to surgical tumor debulking compared with those after surgery. TNF-α increases mRNA and protein levels of IAP-1, IAP-2 and XIAP (Gordon et al., 2007). NF-Kb upregulation plays an important survival role in mesotheliomas in response to the inflammatory effects of exposure to asbestos fibres (Sartore-Bianchi et al., 2007). IAP antagonists have the potential to reverse the pro-survival effect of TNF-α.

The ability of cell lines to upregulate TNF-alpha expression sufficiently to act in an autocrine fashion and kill the cells, once cIAP1 & 2 are depleted, is believed to be important for IAP activity (Nature Reviews Cancer (2010), 10(8), 561-74, Gryd-Hansen, M). In vivo, however, certain tumour types are surrounded by a pro-inflammatory cytokine network and hence the tumour cells which, on depletion of cIAP1/2 are switched towards cell killing by apoptosis, may be triggered to apoptose by TNF-alpha (or other Death Receptor cytokine agonists) already being produced by surrounding cells in the tumour microenvironment, such as tumour-associated macrophages, or indeed by the tumour cells themselves. Certain tumour types such as breast, ovarian and melanoma display this "inflammatory phenotype" which could potentially be targeted by IAP antagonists.

cIAP1 and cIAP2

Cellular IAP (cIAP) 1 and 2 are closely related members of the IAP family with three BIR domains, a RING domain and a caspase-recruitment (CARD) domain. A functional nuclear export signal exists within the CARD domain of cIAP1 which appears to be important for cell differentiation (Plenchette et al., Blood 2004; 104: 2035-2043). The presence of this CARD domain is unique to cIAP1 and cIAP2 within the IAP family of proteins. These two genes reside in tandem on chromosome 11q22 and given their high degree of similarity are thought to have arisen via gene duplication.

cIAP1, like XIAP and survivin, is widely expressed in tumour cell lines, and has been found to be expressed at high levels in colorectal cancers in particular, as well as lung, ovarian, renal, CNS and breast cancers (Tamm et al., Clin. Cancer Res. 2000; 6: 1796-1803). cIAP2 expression is generally more restricted and is thought to be regulated though constitutive ubiquitination and degradation by cIAP1 (Conze et al., Mol. Biol. Cell 2005; 25(8): 3348-56; Mahoney et al., PNAS 2008; 105: 11778-11783). Immunohistochemistry and western blot analysis identified cIAP1 and cIAP2 as potential oncogenes as both are overexpressed in multiple lung cancers with or without higher copy numbers (Dia et al., Human Mol. Genetics 2003; 12(7): 791-801). cIAP1 expression level preferentially seems to play an important role in low-stage adenocarcinoma (Hofmann et al., J. Cancer Res. Clin. Oncology 2002; 128(10): 554-60).

Increased levels of cIAP1 and cIAP2 and reduced levels of endogenous inhibitors are associated with chemoresistance as has been seen for XIAP. cIAP overexpression has been found to correlate in vitro to resistance to DNA alkylating agents such as carboplatin, cisplatin and topoisomerase inhibitor VP-16 (Tamm et al., Clin. Cancer Res. 2000; 6: 1796-1803). Levels of cIAP1 and survivin were found to be high in thyroid cancer cells after cisplatin and doxorubicin treatment. Cells resistant to chemotherapy such as taxol showed reduced expression of SMAC and released minimal amounts of this protein from the mitochondria. Down-regulation of cIAP1 and survivin has been found to increase the cytotoxicity of cisplatin and doxorubicin, whereas overexpression of SMAC improved the efficacy of taxol. However, silencing of cIAP1 and survivin by RNA interference restored sensitivity to doxorubicin and cisplatin (TirrO et al.; Cancer Res. 2006; 66(8): 4263-72).

SMAC mimetics such as LBW242 were originally thought to primarily target XIAP. However studies have shown that cIAP1 was targeted for degradation by autoubiquitination in cells (Yang et al., J. Biol. Chem. 2004; 279(17): 16963-16970) and may have contributed to the apoptotic effects that resulted. SiRNA of cIAP1 and Tumour Necrosis Factor (TNF)-alpha induction (or stimulation) were found to combine synergistically and render cell lines more sensitive (Gaither et al. Cancer Res. 2007; 67 (24): 11493-11498).

cIAP1 and cIAP2 have been demonstrated to be critical regulators of the NFκB signalling pathway which is involved in a diverse range of biological processes, particularly in innate and adaptive immunity as well as in proliferation and survival. NFκB pathway deregulation is associated with inflammation and cancers including hepatitis and ulcerative colitis, gastritis, hepatocellular carcinoma colorectal cancer and gastric cancers, as well as angiogenesis and metastasis (Shen et al., Apoptosis 2009; 14: 348-363).

On ligand binding, the TNF Receptor (TNFR) recruits TNFR-associated Death Domain (TRADD) and receptor-interacting protein (RIP) 1. TRAF2 and cIAP1/cIAP2 are then recruited to form a large membrane complex. RIP1 is ubiquitinated and these polyubiquitin chains serve as a docking site for downstream kinases, resulting in NFκB pathway signalling effects (Ea et al., Mol. Cell 2006; 22: 245-257; Wu et al., Nat. Cell Biol. 2006; 8: 398-406). The extended roles are complex and yet to be fully defined but cIAP1 and cIAP2 are identified as key components of TNF-alpha mediated NFκB signalling regulation as well as constitutive (ligand-independent/classical) NFκB signalling (Varfolomeev et al., Cell 2007; 131(4): 669-81). cIAP1 and cIAP2 have been shown to bind TRAF2, an adapter protein that functions in both the classical and alternative NFκB pathways as well as MAPK pathway signalling pathway (Rothe et al., Cell 2005; 83: 1243-1252). cIAP1 and cIAP2 directly target RIP1 for ubiquitination in vitro (Betrand et al., Mol. Cell 2008; 30: 689-700).

TNF-alpha regulates many cellular functions, including apoptosis, inflammation, immune response, and cell growth and differentiation (Trace et al., Annu. Rev. Med. 1994; 45: 491-503) and therapeutic IAP antagonists may be of benefit in conditions where these functions are affected.

Production of TNF-alpha is seen in many malignant tumours, and is one of the key drivers of cancer-related inflammation that drives tumour development and/or progression. cIAPs protect cancer cells from the lethal effects of TNF-alpha.

NAIP

NAIP was the first IAP to be discovered (Roy et al., Cell 1995; 80: 167-178). NAIP is unique among the IAPs in that it possesses a nucleotide-binding and oligomerisation domain, as well as leucine rich repeats which are similar to those contained in proteins normally involved in innate immunity. There are indications that NAIP may also be over expressed in some cancers including breast and oesophageal cancer (Nemoto et al., Exp. Mol. Pathol. 2004; 76(3): 253-9) as well as MS (Choi et al., J. Korean Med. 2007; 22 Suppl: S17-23; Hebb et al., Mult. Sclerosis 2008; 14(5): 577-94).

ML-IAP

Melanoma inhibitor of apoptosis protein (ML-IAP) contains a single BIR and RING finger motif. ML-IAP is a powerful inhibitor of apoptosis induced by death receptors and chemotherapeutic agents, probably functioning as a direct inhibitor of downstream effector caspases (Vucic et al., Curr. Biol. 2000; 10(21): 1359-66). ML-IAP is also known as Baculoviral IAP repeat-containing protein 7 (BIRC7), Kidney inhibitor of apoptosis protein (KIAP), RING finger protein 50 (RNF50) and Livin. The BIR domain of ML-IAP possesses an evolutionarily conserved fold that is necessary for anti-apoptotic activity. It has been found that the majority of melanoma cell lines express high levels of ML-IAP in contrast to primary melanocytes, which expressed undetectable levels. These melanoma cells were significantly more resistant to drug-induced apoptosis. Elevated expression of ML-IAP renders melanoma cells resistant to apoptotic stimuli and thereby potentially contributes to the pathogenesis of this malignancy.

ILP-2

ILP-2, also known as BIRC8, has a single BIR domain and a RING domain. ILP-2 is expressed only in testis in normal cells, and binds to caspase 9 (Richter et al, Mol. Cell. Biol. 2001; 21: 4292-301).

Survivin

Survivin, also known as BIRC5, inhibits both caspase 3 and caspase 7, but its primary function is mitotic progression regulation, rather than the regulation of apoptosis. Survivin promotes formation of microtubules in the mitotic spindle, counteracting apoptosis during cell cycle. Apoptosis inhibition by survivin is predictive of poor outcome in colorectal cancer (Kawasaki et al., Cancer Res. 1998; 58(22): 5071-5074) and stage III gastric cancer (Song et al., Japanese J. Clin. Oncol. 2009; 39(5): 290-296).

BRUCE

BRUCE (BIR repeat-containing ubiquitin-conjugating enzyme) is a peripheral membrane protein in the trans-Golgi network with a single BIR domain, most similar to that of survivin. BRUCE is inhibited via three mechanisms: (i) SMAC binding, (ii) HtrA2 protease and (iii) caspase-mediated cleavage. In addition, BRUCE acts as a E2/E3 ubiquitin ligase via ubiquitin-conjugating (UBC) domain.

SUMMARY OF THE INVENTION

The present invention provides compounds of formula (I). The present invention provides compounds which are useful in therapy, in particular in the treatment of cancer. The compounds of formula (I) may be antagonists of the IAP family of proteins (IAP), and especially XIAP, and/or cIAP (such as cIAP1 and/or cIAP2) and may be useful in the treatment of IAP-mediated conditions.

According to a first aspect of the invention, there is provided a compound of formula (I):

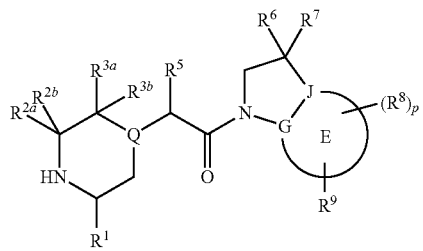

(I)

or tautomeric or stereochemically isomeric forms, N-oxides, pharmaceutically acceptable salts or the solvates thereof; wherein Ring E represents a 6 membered aromatic carbocyclic or heterocyclic group;
G and J are independently selected from C or N;
Q is $CR^4$ or N;
$R^1$ is selected from $C_{1-4}$ alkyl, $C_{2-4}$ alkenyl and $-(CH_2)_s-C_{3-8}$ cycloalkyl, wherein said $C_{1-4}$ alkyl, $C_{2-4}$ alkenyl, and $C_{3-8}$ cycloalkyl may be optionally substituted by one or more $R^a$ groups;
$R^a$ is selected from halogen, $-OH$ and $-O-C_{1-6}$alkyl;
$R^{2a}$ and $R^{2b}$ are independently selected from hydrogen, $C_{1-6}$ alkyl, $C_{2-6}$ alkenyl, $C_{2-6}$ alkynyl, $-C(=O)NH_{(2-q)}(C_{1-6}$ alkyl$)_q$, $-(CH_2)_s-(3-12$ membered heterocyclyl), and $-(CH_2)_s-C_{3-12}$ carbocyclyl, or $R^{2a}$ and $R^{2b}$ groups, together with the carbon atom to which they are attached, can join to form a 3-10 membered saturated carbocyclyl or heterocyclyl group, wherein said $C_{1-6}$ alkyl, $C_{2-6}$ alkenyl, $C_{2-6}$ alkynyl, heterocyclyl and carbocyclyl groups may be optionally substituted by one or more $R^b$ groups;
$R^{3a}$ and $R^{3b}$ are independently selected from hydrogen, $C_{1-6}$ alkyl, $C_{2-6}$ alkenyl, $C_{2-6}$ alkynyl, $-C(=O)NH_{(2-q)}(C_{1-6}$ alkyl$)_q$, $-(CH_2)_s-(3-12$ membered heterocyclyl), $-(CH_2)_s-C_{3-12}$ carbocyclyl, $-C(=O)-(3-12$ membered heterocyclyl), and $-C(=O)-C_{3-12}$ carbocyclyl,
or $R^{3a}$ and $R^{3b}$ groups, together with the carbon atom to which they are attached, can join to form a 3-10 membered saturated carbocyclyl or heterocyclyl group, wherein said $C_{1-6}$ alkyl, $C_{2-6}$ alkenyl, $C_{2-6}$ alkynyl, heterocyclyl and carbocyclyl groups may be optionally substituted by one or more $R^b$ groups;
$R^4$ is selected from hydrogen, $C_{1-6}$ alkyl, $C_{2-6}$ alkenyl, $C_{2-6}$ alkynyl, $-C(=O)NH_{(2-q)}(C_{1-6}$ alkyl$)_q$, $-(CH_2)_s-(3-12$ membered heterocyclyl), $-(CH_2)_s-C_{3-12}$ carbocyclyl, $-C(=O)-(3-12$ membered heterocyclyl), and $-C(=O)-C_{3-12}$ carbocyclyl, wherein said $C_{1-6}$ alkyl, $C_{2-6}$ alkenyl, $C_{2-6}$ alkynyl, heterocyclyl and carbocyclyl groups may be optionally substituted by one or more $R^b$ groups;
$R^5$ is selected from hydrogen, $C_{1-6}$ alkyl, $C_{2-6}$ alkenyl, $C_{2-6}$ alkynyl, $-(CH_2)_s-C_{3-8}$ cycloalkyl and $-(CH_2)_s-C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups;
$R^6$ and $R^7$ are independently selected from hydrogen, $C_{1-8}$ alkyl, $C_{2-8}$ alkenyl, $C_{2-8}$ alkynyl, $-Y-C_{3-12}$ carbocyclyl, $-Z-(3-12$ membered heterocyclyl), $-(CR^xR^y)_s-O-R^z$, $-O-(CR^xR^y)_n-OR^z$, $-(CH_2)_s-CN$, $-S(O)_q-R^x$, $-C(=O)R^x$, $-C(=S)R^x$, $-C(=N)R^x$, $-(CR^xR^y)_s-C(=O)OR^z$, $-(CR^xR^y)_s-O-C(=O)-R^z$, $-(CR^xR^y)_s-C(=O)NR^xR^y$, $-(CH_2)_s-NR^xC(=O)R^y$, $-(CH_2)_s-OC(=O)NR^xR^y$, $-(CH_2)_s-NR^xC(=O)OR^y$, $-(CH_2)_s-NR^xR^y$, $-NR^x-(CH_2)_s-R^z$, $-(CR^xR^y)_s-C(=S)NR^z$, $-(CR^xR^y)_s-C(=N)NR^z$, $-(CH_2)_s-O-C(=O)-C_{1-4}$alkyl-$NR^xR^y$, $-(CH_2)_s-NR^x-(CH_2)_n-O-C(=O)-R^z$, $-(CH_2)_s-NR^x-(CH_2)_s-SO_2-R^y$, $-(CH_2)_s-NH-SO_2-NR^xR^y$ and $-(CH_2)_s-SO_2NR^xR^y$ groups,
or $R^6$ and $R^7$ groups, together with the carbon atom to which they are attached, can join to form a 3-10 membered partially or fully saturated carbocyclyl or heterocyclyl group, and which may be optionally fused to a 5-6 membered aromatic carbocyclyl or heterocyclyl ring, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^b$ groups;
$R^8$ and $R^9$ are independently selected from hydrogen, halogen, $C_{1-8}$ alkyl, $C_{2-8}$ alkenyl, $C_{2-8}$ alkynyl, $-Y-C_{3-12}$ carbocyclyl, $-Z-(3-12$ membered heterocyclyl), $-(CR^xR^y)_s-O-R^z$, $-O-(CR^xR^y)_n-OR^z$, $=O$, $=S$, nitro, $Si(R^x)_4$, $-(CH_2)_s-CN$, $-S(O)_q-(CR^xR^y)_s-R^z$, $-C(=O)R^x$, $-C(=S)R^x$, $-C(=N)R^x$, $-(CR^xR^y)_s-C(=O)OR^z$, $-(CR^xR^y)_s-O-C(=O)-R^z$, $-(CR^xR^y)_s-C(=O)NR^xR^y$, $-(CH_2)_s-NR^xC(=O)R^y$, $-(CH_2)_s-OC(=O)NR^xR^y$, $-(CH_2)_s-NR^xC(=O)OR^y$, $-(CH_2)_s-NR^xR^y$, $-NR^x-(CH_2)_s-R^z$, $-(CR^xR^y)_s-C(=S)NR^z$, $-(CR^xR^y)_s-C(=N)NR^x$, $-S(O)(=NR^x)R^y$, $-(CH_2)_s-O-C(=O)-C_{1-4}$alkyl-$NR^xR^y$, $-(CH_2)_s-NR^x-(CH_2)_n-O-C(=O)-R^z$, $-(CH_2)_s-NR^x-(CH_2)_s-SO_2-R^y$, $-(CH_2)_s-NH-SO_2-NR^xR^y$, $-(CH_2)_s-SO_2NR^xR^y$ groups and $-P(=O)(R^x)_2$, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^b$ groups;
$R^b$ is independently selected from halogen, $C_{1-6}$ alkyl, $C_{2-6}$ alkenyl, $C_{2-6}$ alkynyl, $-(CH_2)_s-C_{3-8}$ cycloalkyl, $-(CH_2)_s-C_{3-8}$ cycloalkenyl, $-(CH_2)_s$-phenyl, $-(CH_2)_s$-(4-7 membered saturated heterocyclyl), $-(CR^xR^y)_s-O-R^z$, $-O-(CR^xR^y)_n-OR^z$, halo$C_{1-6}$ alkyl, halo$C_{1-6}$ alkoxy, $C_{1-6}$ alkanol, $=O$, $=S$, nitro, $Si(R^x)_4$, $-(CH_2)_s-CN$, $-S(O)_q-R^x$, $-C(=O)R^x$, $-(CR^xR^y)_s-C(=O)OR^z$, —$(CR^xR^y)_s$—O—C(=O)—$R^z$, —$(CR^xR^y)_s$—C(=O)NR$^x$R$^y$, —$(CH_2)_s$—NR$^x$C(=O)R$^y$, —$(CH_2)_s$—OC(=O)NR$^x$R$^y$, —$(CH_2)_s$—NR$^x$C(=O)OR$^y$—$(CH_2)_s$—NR$^x$R$^y$, —NR$^x$—$(CH_2)_s$—R$^z$, —$(CH_2)_s$—O—C(=O)—$C_{1-4}$alkyl-NR$^x$R$^y$, —$(CH_2)_s$—NR$^x$—$(CH_2)_n$—O—C(=O)—R$^z$, —$(CH_2)_s$—NR$^x$—$(CH_2)_s$—SO$_2$—R$^y$, —$(CH_2)_s$—NH—SO$_2$—NR$^x$R$^y$, —$(CH_2)_s$—SO$_2$NR$^x$R$^y$ groups and —P(=O)(R$^x$)$_2$, wherein said $C_{1-6}$ alkyl, $C_{2-6}$ alkenyl, $C_{2-6}$ alkynyl, $C_{3-8}$ cycloalkyl, $C_{3-8}$ cycloalkenyl and heterocyclyl groups may be optionally substituted by one or more R$^x$ groups; R$^x$, R$^y$ and R$^z$ independently represent halogen, hydrogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), $C_{1-6}$ alkanol optionally substituted with one or more halo, —C(=O)OC$_{1-6}$ alkyl, hydroxy, $C_{1-6}$ alkoxy, haloC$_{1-6}$ alkyl, —$(CH_2)_n$—O—$C_{1-6}$alkyl, —C(=O)—$(CH_2)_n$—$C_{1-6}$ alkoxy, —$(CH_2)_s$—CN, $C_{1-6}$ alkyl-N(H)$_{2-q}$(C$_{1-6}$alkyl)$_q$, —N(H)$_{2-q}$(C$_{1-6}$alkyl)$_q$, —C(=O)—N(H)$_{2-q}$(C$_{1-6}$alkyl)$_q$, —$(CH_2)_s$—NH—SO$_2$—N(H)$_{2-q}$(C$_{1-6}$alkyl)$_q$, —$(CH_2)_s$—N(C$_{1-4}$alkyl)-SO$_2$—N(H)$_{2-q}$(C$_{1-6}$alkyl)$_q$ and —$(CH_2)_s$—O—C(=O)—C$_{1-4}$alkyl-N(H)$_{2-q}$(C$_{1-6}$alkyl)$_q$, and when attached to nitrogen, carbon, silicon or phosphorus atom R$^x$ and R$^y$ may join to form a 3-7 membered ring optionally containing one or two additional heteroatoms selected from O, N, S and oxidised forms of N or S;

Y and Z are independently selected from a bond, —$(CR^xR^y)_m$—, —C(=CR$^x$)—, —O(=O)—, —NR$^x$, —C(=O)NR$^x$—, —NR$^x$C(=O)—, —$(CR^xR^y)_q$—O—, —O—$(CR^xR^y)_q$—, —S(O)$_2$—NH, NH—S(O)$_2$— and —S(O)$_q$—; s independently represents an integer from 0-4; n independently represents an integer from 1-4;
p independently represents an integer from 0-4;
q represents an integer from 0-2; and
m represents an integer from 1-2.

In a further aspect of the invention there is provided a compound of formula (I) for use in the prophylaxis or treatment of a disease or condition as described herein, pharmaceutical compositions comprising a compound of formula (I) and processes for the synthesis of compound of formula (I).

DEFINITIONS

Unless the context indicates otherwise, references to formula (I) in all sections of this document (including the uses, methods and other aspects of the invention) include references to all other sub-formula, sub-groups, preferences, embodiments and examples as defined herein.

By "IAP" we mean any of the IAP family members XIAP, cIAP (cIAP1 and/or cIAP2), NAIP, ILP2, ML-IAP, survivin and/or BRUCE, in particular XIAP, cIAP1, cIAP2, ML-IAP, more particularly XIAP, cIAP1 and/or cIAP2, most particularly XIAP and/or cIAP1. In particular we mean the BIR domains of IAP, in particular the BIR domains of XIAP, cIAP1, or cIAP2.

By "one or more IAP family members" we mean any of the IAP family members in particular XIAP, cIAP1 and/or cIAP2, more particularly XIAP and/or cIAP1.

"Potency" is a measure of drug activity expressed in terms of the amount required to produce an effect of given intensity. A highly potent drug evokes a larger response at low concentrations. Potency is proportional to affinity and efficacy. Affinity is the ability of the drug to bind to a receptor. Efficacy is the relationship between receptor occupancy and the ability to initiate a response at the molecular, cellular, tissue or system level.

The term "antagonist" refers to a type of receptor ligand or drug that blocks or dampens agonist-mediated biological responses. Antagonists have affinity but no agonistic efficacy for their cognate receptors, and binding will disrupt the interaction and inhibit the function of any ligand (e.g. endogenous ligands or substrates, an agonist or inverse agonist) at receptors. The antagonism may arise directly or indirectly, and may be mediated by any mechanism and at any physiological level. An example of indirect antagonism, would be the indirect antagonism of cIAP as a consequence of ubiquination of cIAP resulting in its degradation. As a result, antagonism of ligands may under different circumstances manifest itself in functionally different ways. Antagonists mediate their effects by binding to the active site or to allosteric sites on receptors, or they may interact at unique binding sites not normally involved in the biological regulation of the receptor's activity. Antagonist activity may be reversible or irreversible depending on the longevity of the antagonistreceptor complex, which, in turn, depends on the nature of antagonist receptor binding.

The term "treatment" as used herein in the context of treating a condition i.e. state, disorder or disease, pertains generally to treatment and therapy, whether for a human or an animal (e.g. in veterinary applications), in which some desired therapeutic effect is achieved, for example, the inhibition of the progress of the condition, and includes a reduction in the rate of progress, a halt in the rate of progress, amelioration of the condition, diminishment or alleviation of at least one symptom associated or caused by the condition being treated and cure of the condition. For example, treatment can be diminishment of one or several symptoms of a disorder or complete eradication of a disorder.

The term "prophylaxis" (i.e. use of a compound as prophylactic measure) as used herein in the context of treating a condition i.e. state, disorder or disease, pertains generally to the prophylaxis or prevention, whether for a human or an animal (e.g. in veterinary applications), in which some desired preventative effect is achieved, for example, in preventing occurance of a disease or guarding from a disease. Prophylaxis includes complete and total blocking of all symptoms of a disorder for an indefinite period of time, the mere slowing of the onset of one or several symptoms of the disease, or making the disease less likely to occur.

References to the prophylaxis or treatment of a disease state or condition such as cancer include within their scope alleviating or reducing the incidence of cancer.

As used herein, the term "mediated", as used e.g. in conjunction with IAP as described herein (and applied for example to various physiological processes, diseases, states, conditions, therapies, treatments or interventions) is intended to operate limitatively so that the various processes, diseases, states, conditions, treatments and interventions to which the term is applied are those in which the protein plays a biological role. In cases where the term is applied to a disease, state or condition, the biological role played by the protein may be direct or indirect and may be necessary and/or sufficient for the manifestation of the symptoms of the disease, state or condition (or its aetiology or progression). Thus, the protein function (and in particular aberrant levels of function, e.g. over- or under-expression) need not necessarily be the proximal cause of the disease, state or condition: rather, it is contemplated that the mediated diseases, states or conditions include those having multifactorial aetiologies and complex progressions in which the protein in question is only partially involved. In cases where the term is applied to treatment, prophylaxis or intervention, the role played by the protein may be direct or indirect and may be necessary and/or sufficient for the operation of the treatment, prophylaxis or outcome of the intervention. Thus, a disease state or condition mediated by a protein includes the development of resistance to any particular cancer drug or treatment.

The term 'optionally substituted' as used herein refers to a group which may be substituted or unsubstituted by a substituent as herein defined.

The prefix "$C_{x-y}$" (where x and y are integers) as used herein refers to the number of carbon atoms in a given group. Thus, a $C_{1-6}$ alkyl group contains from 1 to 6 carbon atoms, a $C_{3-6}$ cycloalkyl group contains from 3 to 6 carbon atoms, a $C_{1-4}$ alkoxy group contains from 1 to 4 carbon atoms, and so on.

The term 'halo' or 'halogen' as used herein refers to fluorine, chlorine, bromine or iodine.

The term 'nitro' as used herein refers to an $NO_2$ group.

The term '$C_{1-4}$alkyl', '$C_{1-6}$alkyl' or '$C_{1-8}$alkyl' as used herein as a group or part of a group refers to a linear or branched saturated hydrocarbon group containing from 1 to 4, 1 to 6 or 1 to 8 carbon atoms, respectively. Examples of such groups include methyl, ethyl, n-propyl, isopropyl, n-butyl, isobutyl, sec-butyl, tert butyl, n-pentyl, isopentyl, neopentyl or hexyl and the like.

The term '$C_{2-4}$alkenyl', '$C_{2-6}$alkenyl' or '$C_{2-8}$alkenyl' as used herein as a group or part of a group refers to a linear or branched hydrocarbon group containing from 2 to 4, 2 to 6 or 2 to 8 carbon atoms, respectively, and containing a carbon carbon double bond. Examples of such groups include $C_{3-4}$alkenyl or $C_{3-6}$alkenyl groups, such as ethenyl (vinyl), 1-propenyl, 2-propenyl (allyl), isopropenyl, butenyl, buta-1,4-dienyl, pentenyl, and hexenyl.

The term '$C_{2-6}$alkynyl' or '$C_{2-8}$alkynyl' as used herein as a group or part of a group refers to a linear or branched hydrocarbon group having from 2 to 6 or 2 to 8 carbon atoms, respectively, and containing a carbon carbon triple bond. Examples of such groups include $C_{3-4}$alkynyl or $C_{3-6}$alkynyl groups such as ethynyl and 2 propynyl (propargyl) groups.

The term '$C_{1-4}$alkoxy' or '$C_{1-6}$alkoxy' as used herein as a group or part of a group refers to an O—$C_{1-4}$alkyl or O—$C_{1-6}$alkyl group wherein $C_{1-4}$alkyl and $C_{1-6}$alkyl are as defined herein. Examples of such groups include methoxy, ethoxy, propoxy, butoxy, and the like.

The term '$C_{1-6}$alkanol' as used herein as a group or part of a group refers to a $C_{1-6}$ alkyl group as defined herein wherein one or more than one hydrogen atom is replaced with a hydroxyl group.

The term '$C_{3-8}$cycloalkyl' as used herein refers to a saturated monocyclic hydrocarbon ring of 3 to 8 carbon atoms. Examples of such groups include cyclopropyl, cyclobutyl, cyclopentyl, cyclohexyl, cycloheptyl or cyclooctyl and the like.

The term '$C_{3-8}$cycloalkenyl' as used herein refers to a monocyclic hydrocarbon ring of 3 to 8 carbon atoms having a carbon carbon double bond.

The term 'halo$C_{1-4}$alkyl' or 'halo$C_{1-6}$alkyl' as used herein as a group or part of a group refers to a $C_{1-4}$alkyl or $C_{1-6}$alkyl group as defined herein wherein one or more than one hydrogen atom is replaced with a halogen. The terms 'halo$C_{1-4}$alkyl' or 'halo$C_{1-6}$alkyl' therefore include monohalo$C_{1-4}$alkyl and also polyhalo$C_{1-6}$alkyl. There may be one, two, three or more hydrogen atoms replaced with a halogen, so the halo$C_{1-4}$alkyl or halo$C_{1-6}$alkyl may have one, two, three or more halogens. Examples of such groups include fluoroethyl, fluoromethyl, trifluoromethyl or trifluoroethyl and the like.

The term 'halo$C_{1-6}$alkoxy' as used herein as a group or part of a group refers to a —O—$C_{1-6}$ alkyl group as defined herein wherein one or more than one hydrogen atom is replaced with a halogen. The term 'halo$C_{1-6}$alkoxy' therefore includes monohalo$C_{1-6}$alkoxy and also polyhalo$C_{1-6}$alkoxy. There may be one, two, three or more hydrogen atoms replaced with a halogen, so the halo$C_{1-6}$alkoxy may have one, two, three or more halogens. Examples of such groups include fluoroethyloxy, difluoromethoxy or trifluoromethoxy and the like.

The term "heterocyclyl" and "carbocyclyl" as used herein shall, unless the context indicates otherwise, include both aromatic and non-aromatic ring systems. Thus, for example, the term "heterocyclyl group" and "carbocyclyl group" include within their scope aromatic, non-aromatic, unsaturated, partially saturated and fully saturated carbocyclyl or heterocyclyl ring systems. In general, unless the context indicates otherwise, such groups may be monocyclic or bicyclic (including fused and bridged bicyclic groups) and may contain, for example, 3 to 12 ring members, more usually 5 to 10 ring members. Reference to 4 to 7 ring members include 4, 5, 6 or 7 atoms in the ring and reference to 4 to 6 ring members include 4, 5, or 6 atoms in the ring. Examples of monocyclic groups are groups containing 3, 4, 5, 6, 7 and 8 ring members, more usually 3 to 7, or 4 to 7 and preferably 5, 6 or 7 ring members, more preferably 5 or 6 ring members. Examples of bicyclic groups are those containing 8, 9, 10, 11 and 12 ring members, and more usually 9 or 10 ring members. The heterocyclyl groups can be heteroaryl groups having from 5 to 12 ring members, more usually from 5 to 10 ring members. Where reference is made herein to heterocyclyl or carbocyclyl groups, the heterocyclyl or carbocyclyl ring can, unless the context indicates otherwise, be optionally substituted i.e. unsubstituted or substituted by one or more (e.g. 1, 2, 3, or 4 in particular one or two) substituents as defined herein.

The heterocyclyl group can be, for example, a five membered or six membered monocyclic ring or a bicyclic structure formed from fused five and six membered rings or two fused six membered rings, or two fused five membered rings. Each ring may contain up to five heteroatoms typically selected from nitrogen, sulfur and oxygen. Typically the heterocyclyl ring will contain up to 4 heteroatoms, more typically up to 3 heteroatoms, more usually up to 2, for example a single heteroatom. In one embodiment, the heterocyclyl ring will contain one or two heteroatoms selected from N, O, S and oxidised forms of N or S. In one embodiment, the heterocyclyl ring contains at least one ring nitrogen atom. The nitrogen atoms in the heterocyclyl rings can be basic, as in the case of an imidazole or pyridine, or essentially non-basic as in the case of an indole or pyrrole nitrogen. In general the number of basic nitrogen atoms present in the heterocyclyl group, including any amino group substituents of the ring, will be less than five.

The heterocyclyl groups can be attached via a carbon atom or a heteroatom (e.g. nitrogen). Equally the heterocyclyl groups can be substituted on a carbon atom or on a heteroatom (e.g. nitrogen).

The term "heteroaryl" is used herein to denote a heterocyclyl group having aromatic character. The term "heteroaryl" embraces polycyclic (e.g. bicyclic) ring systems wherein one or more rings are non-aromatic, provided that at least one ring is aromatic. In such polycyclic systems, the group may be attached by the aromatic ring, or by a non-aromatic ring.

Examples of heteroaryl groups are monocyclic and bicyclic groups containing from five to twelve ring members, and more usually from five to ten ring members.

Examples of five membered heteroaryl groups include but are not limited to pyrrole, furan, thiophene, imidazole, furazan, oxazole, oxadiazole, oxatriazole, isoxazole, thiazole, thiadiazole, isothiazole, pyrazole, triazole and tetrazole groups.

Examples of six membered heteroaryl groups include but are not limited to pyridine, pyrazine, pyridazine, pyrimidine and triazine.

A bicyclic heteroaryl group may be, for example, a group selected from:
  a) a benzene ring fused to a 5- or 6-membered ring containing 1, 2 or 3 ring heteroatoms;
  b) a pyridine ring fused to a 5- or 6-membered ring containing 0, 1, 2 or 3 ring heteroatoms;
  c) a pyrimidine ring fused to a 5- or 6-membered ring containing 0, 1 or 2 ring heteroatoms;
  d) a pyrrole ring fused to a 5- or 6-membered ring containing 0, 1, 2 or 3 ring heteroatoms;
  e) a pyrazole ring fused to a 5- or 6-membered ring containing 0, 1 or 2 ring heteroatoms;
  f) an imidazole ring fused to a 5- or 6-membered ring containing 0, 1 or 2 ring heteroatoms;
  g) an oxazole ring fused to a 5- or 6-membered ring containing 0, 1 or 2 ring heteroatoms;
  h) an isoxazole ring fused to a 5- or 6-membered ring containing 0, 1 or 2 ring heteroatoms;
  i) a thiazole ring fused to a 5- or 6-membered ring containing 0, 1 or 2 ring heteroatoms;
  j) an isothiazole ring fused to a 5- or 6-membered ring containing 0, 1 or 2 ring heteroatoms;
  k) a thiophene ring fused to a 5- or 6-membered ring containing 0, 1, 2 or 3 ring heteroatoms;
  l) a furan ring fused to a 5- or 6-membered ring containing 0, 1, 2 or 3 ring heteroatoms;
  m) a cyclohexyl ring fused to a 5- or 6-membered ring containing 1, 2 or 3 ring heteroatoms; and
  n) a cyclopentyl ring fused to a 5- or 6-membered ring containing 1, 2 or 3 ring heteroatoms.

Particular examples of bicyclic heteroaryl groups containing a five membered ring fused to another five membered ring include but are not limited to imidazothiazole (e.g. imidazo[2,1-b]thiazole) and imidazoimidazole (e.g. imidazo[1,2-a]imidazole).

Particular examples of bicyclic heteroaryl groups containing a six membered ring fused to a five membered ring include but are not limited to benzofuran, benzothiophene, benzimidazole, benzoxazole, isobenzoxazole, benzisoxazole, benzothiazole, benzisothiazole, isobenzofuran, indole, isoindole, indolizine, indoline, isoindoline, purine (e.g., adenine, guanine), indazole, pyrazolopyrimidine (e.g. pyrazolo[1,5-a]pyrimidine), triazolopyrimidine (e.g. [1,2,4]triazolo[1,5-a]pyrimidine), benzodioxole, imidazopyridine and pyrazolopyridine (e.g. pyrazolo[1,5-a]pyridine) groups.

Particular examples of bicyclic heteroaryl groups containing two fused six membered rings include but are not limited to quinoline, isoquinoline, chroman, thiochroman, isochroman, chromene, isochromene, benzodioxan, quinolizine, benzoxazine, pyridopyridine, quinoxaline, quinazoline, cinnoline, phthalazine, naphthyridine and pteridine groups.

Examples of polycyclic heteroaryl groups containing an aromatic ring and a non-aromatic ring include, tetrahydroisoquinoline, tetrahydroquinoline, dihydrobenzthiophene, dihydrobenzofuran, 2,3-dihydro-benzo[1,4]dioxine, benzo[1,3]dioxole, 4,5,6,7-tetrahydrobenzofuran, tetrahydrotriazolopyrazine (e.g. 5,6,7,8-tetrahydro-[1,2,4]triazolo[4,3-a]pyrazine), chroman, thiochroman, isochroman, chromene, isochromene, benzodioxan, benzoxazine, benzodiazepine, and indoline groups.

A nitrogen-containing heteroaryl ring must contain at least one ring nitrogen atom. The nitrogen-containing heteroaryl ring can be N-linked or C-linked. Each ring may, in addition, contain up to about four other heteroatoms typically selected from nitrogen, sulfur and oxygen. Typically the heteroaryl ring will contain up to 3 heteroatoms, for example 1, 2 or 3, more usually up to 2 nitrogens, for example a single nitrogen. The nitrogen atoms in the heteroaryl rings can be basic, as in the case of an imidazole or pyridine, or essentially non-basic as in the case of an indole or pyrrole nitrogen. In general the number of basic nitrogen atoms present in the heteroaryl group, including any amino group substituents of the ring, will be less than five.

Examples of nitrogen-containing heteroaryl groups include, but are not limited to, pyridyl, pyrrolyl, imidazolyl, oxazolyl, oxadiazolyl, thiadiazolyl, oxatriazolyl, isoxazolyl, thiazolyl, isothiazolyl, furazanyl, pyrazolyl, pyrazinyl, pyrimidinyl, pyridazinyl, triazinyl, triazolyl (e.g., 1,2,3-triazolyl, 1,2,4-triazolyl), tetrazolyl, quinolinyl, isoquinolinyl, benzimidazolyl, benzoxazolyl, benzisoxazole, benzothiazolyl and benzisothiazole, indolyl, 3H-indolyl, isoindolyl, indolizinyl, isoindolinyl, purinyl (e.g., adenine [6-aminopurine], guanine[2-amino-6-hydroxypurine]), indazolyl, quinolizinyl, benzoxazinyl, benzodiazepinyl, pyridopyridinyl, quinoxalinyl, quinazolinyl, cinnolinyl, phthalazinyl, naphthyridinyl and pteridinyl.

Examples of nitrogen-containing polycyclic heteroaryl groups containing an aromatic ring and a non-aromatic ring include tetrahydroisoquinolinyl, tetrahydroquinolinyl, and indolinyl.

The term "non-aromatic group" embraces, unless the context indicates otherwise, unsaturated ring systems without aromatic character, partially saturated and fully saturated heterocyclyl ring systems. The terms "unsaturated" and "partially saturated" refer to rings wherein the ring structure(s) contains atoms sharing more than one valence bond i.e. the ring contains at least one multiple bond e.g. a C=C, C≡C or N=C bond. The term "fully saturated" refers to rings where there are no multiple bonds between ring atoms. Saturated heterocyclyl groups include piperidine, morpholine, thiomorpholine. Partially saturated heterocyclyl groups include pyrazolines, for example pyrazolin-2-yl and pyrazolin-3-yl.

Examples of non-aromatic heterocyclyl groups are groups having from 3 to 12 ring members, more usually 5 to 10 ring members. Such groups can be monocyclic or bicyclic, for example, and typically have from 1 to 5 heteroatom ring members (more usually 1, 2, 3 or 4 heteroatom ring members), usually selected from nitrogen, oxygen and sulfur. The heterocyclyl groups can contain, for example, cyclic ether moieties (e.g. as in tetrahydrofuran and dioxane), cyclic thioether moieties (e.g. as in tetrahydrothiophene and dithiane), cyclic amine moieties (e.g. as in pyrrolidine), cyclic amide moieties (e.g. as in pyrrolidone), cyclic thioamides, cyclic thioesters, cyclic ureas (e.g. as in imidazolidin-2-one) cyclic ester moieties (e.g. as in butyrolactone), cyclic sulfones (e.g. as in sulfolane and sulfolene), cyclic sulfoxides, cyclic sulfonamides and combinations thereof (e.g. thiomorpholine).

Particular examples include morpholine, piperidine (e.g. piperidin-1-yl, piperidin-2-yl, piperidin-3-yl and piperidin-4-yl), piperidinone, pyrrolidine (e.g. pyrrolidin-1-yl, pyrrolidin-2-yl and pyrrolidin-3-yl), pyrrolidone, azetidine, pyran (2H-pyran or 4H-pyran), dihydrothiophene, dihydropyran, dihydrofuran, dihydrothiazole, tetrahydrofuran, tetrahydrothiophene, dioxane, tetrahydropyran (e.g. tetrahydropyran-4-yl), imidazoline, imidazolidinone, oxazoline, thiazoline, pyrazolin-2-yl, pyrazolidine, piperazinone, piperazine, and N-alkyl piperazines such as N-methyl piperazine. In general, preferred non-aromatic heterocyclyl groups include saturated groups such as piperidine, pyrrolidine, azetidine, morpholine, piperazine and N-alkyl piperazines.

In a nitrogen-containing non-aromatic heterocyclyl ring the ring must contain at least one ring nitrogen atom. The nitrogen-containing heterocyclyl ring can be N-linked or C-linked. The heterocylic groups can contain, for example cyclic amine moieties (e.g. as in pyrrolidine), cyclic amides (such as a pyrrolidinone, piperidinone or caprolactam), cyclic sulfonamides (such as an isothiazolidine 1,1-dioxide, [1,2]thiazinane 1,1-dioxide or [1,2]thiazepane 1,1-dioxide) and combinations thereof.

Particular examples of nitrogen-containing non-aromatic heterocyclyl groups include aziridine, morpholine, thiomorpholine, piperidine (e.g. piperidin-1-yl, piperidin-2-yl, piperidin-3-yl and piperidin-4-yl), pyrrolidine (e.g. pyrrolidin-1-yl, pyrrolidin-2-yl and pyrrolidin-3-yl), pyrrolidone, dihydrothiazole, imidazoline, imidazolidinone, oxazoline, thiazoline, 6H-1,2,5-thiadiazine, pyrazolin-2-yl, pyrazolin-3-yl, pyrazolidine, piperazine, and N-alkyl piperazines such as N-methyl piperazine.

The heterocyclyl groups can be polycyclic fused ring systems or bridged ring systems such as the oxa- and aza analogues of bicycloalkanes, tricycloalkanes (e.g. adamantane and oxa-adamantane). For an explanation of the distinction between fused and bridged ring systems, see *Advanced Organic Chemistry*, by Jerry March, 4$^{th}$ Edition, Wiley Interscience, pages 131-133, 1992.

The carbocyclyl groups can be aryl groups having from 5 to 12 ring members, more usually from 5 to 10 ring members. The term 'aryl' as used herein refers to carbocyclyl aromatic groups including phenyl, naphthyl, indanyl, indenyl, and tetrahydronaphthyl groups. The term "aryl" embraces polycyclic (e.g. bicyclic) ring systems wherein one or more rings are non-aromatic, provided that at least one ring is aromatic. Examples of polycyclic (e.g. bicyclic) aryl groups containing an aromatic ring and a non-aromatic ring include indanyl groups. In such polycyclic systems, the group may be attached by the aromatic ring, or by a non-aromatic ring. Non-aromatic carbocyclic groups include cycloalkyl and cycloalkenyl groups as defined herein.

The heterocyclyl or carbocyclyl groups can each be unsubstituted or substituted by one or more substituent groups. For example, heterocyclyl or carbocyclyl groups can be unsubstituted or substituted by 1, 2, 3 or 4 substituents. Where the heterocyclyl or carbocyclyl group is monocyclic or bicyclic, typically it is unsubstituted or has 1, 2 or 3 substituents as defined herein.

A combination of substituents is permissible only if such as combination results in a stable or chemically feasible compound (i.e. one that is not substantially altered when kept at 40° C. or less for at least a week).

The various functional groups and substituents making up the compounds of the invention are typically chosen such that the molecular weight of the compound of the invention does not exceed 1000. More usually, the molecular weight of the compound will be less than 750, for example less than 700, or less than 650, or less than 600, or less than 550. More preferably, the molecular weight is less than 525 and, for example, is 510, 500 or less.

DETAILED DESCRIPTION OF THE INVENTION

In one embodiment, G and J are both carbon, or one is carbon and the other is nitrogen. In a further embodiment, G and J are both carbon. In one embodiment, G⋯-J is C⋯C, C⋯N or N⋯C. In a further embodiment, G⋯J is C⋯C, where ⋯ indicates an aromatic or single bond as required by formula I.

In one embodiment, ring E represents a 6 membered aromatic heterocyclic ring system. In one embodiment, ring E represents a 6 membered aromatic carbocyclyl ring system. In one embodiment, ring E represents a pyrimidinyl, pyridazinyl, phenyl or pyridyl ring. In a further embodiment, ring E represents a phenyl, pyridyl or pyridazinyl ring. In a further embodiment, ring E represents a phenyl or pyridyl ring. In a yet further embodiment, ring E represents a pyridyl ring. In a yet further embodiment, ring E represents a phenyl ring.

In one embodiment, ring E represents one of the following rings E1-E6:

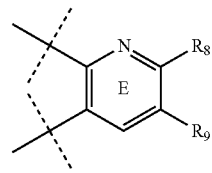

E1

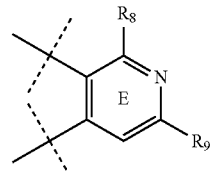

E2

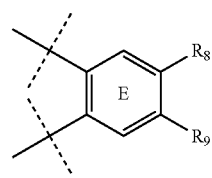

E3

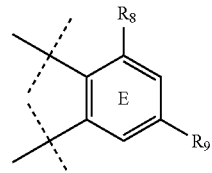

E4

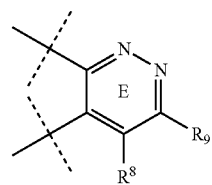

E5

-continued

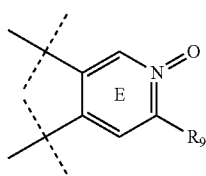
E6

In a further embodiment, ring E represents one of the following rings E1-E4.

In a yet further embodiment, ring E represents rings E1 or E1A.

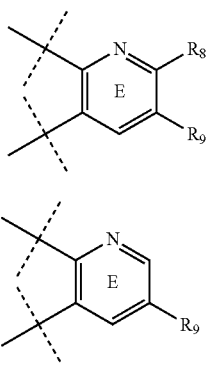
E1

E1A

In a yet further embodiment, ring E represents ring E1A.

In one embodiment, $R^1$ is optionally substituted by one or two $R^a$ groups. In one embodiment, $R^1$ represents $C_{1-4}$ alkyl optionally substituted by one or more $R^a$ groups. In a further embodiment, $R^1$ represents methyl optionally substituted by one or more $R^a$ groups. In one embodiment $R^a$ is halogen. In another embodiment $R^a$ is fluorine, for example $R^1$ represents —$CF_3$ or —$CH_2F$.

In one embodiment, $R^1$ represents $C_{1-4}$ alkyl (e.g. methyl) optionally substituted by one, two or three halo groups. In one embodiment $R^1$ represents —$CH_3$, —$CF_3$ or —$CH_2F$. In a yet further embodiment, $R^1$ represents unsubstituted $C_{1-4}$ alkyl (e.g. methyl). In one embodiment, $R^1$ is selected from unsubstituted methyl (e.g. —$CH_3$ or —$CD_3$), monohalomethyl or trihalomethyl. In one embodiment, $R^1$ is unsubstituted methyl (e.g. —$CH_3$ or —$CD_3$). In a further embodiment, $R^1$ is —$CH_3$.

In one embodiment, $R^1$ is attached to the piperazine ring having (2R) stereochemistry.

In one embodiment $R^{2a}$ and $R^{2b}$ groups, together with the carbon atom to which they are attached, join to form a 3-10 membered saturated carbocyclyl group or heterocyclyl group containing one or two heteroatoms selected from N, O, S and oxidised forms of N or S, wherein said heterocyclyl and carbocyclyl groups may be optionally substituted by one or more $R^b$ groups.

In one embodiment $R^{2a}$ and $R^{2b}$ are independently selected from hydrogen, $C_{1-6}$ alkyl, —C(═O)NH$_{(2-q)}$($C_{1-6}$ alkyl)$_q$, —(CH$_2$)$_s$-(3-12 membered heterocyclyl) and —(CH$_2$)$_s$—C$_{3-12}$ carbocyclyl, wherein said $C_{1-6}$ alkyl, heterocyclyl and carbocyclyl groups may be optionally substituted by one or more $R^b$ groups.

In one embodiment $R^{2a}$ and $R^{2b}$ are independently selected from hydrogen and $C_{1-4}$ alkyl. In a further embodiment, $R^{2a}$ and $R^{2b}$ both represent hydrogen.

In one embodiment, $R^{3a}$ and $R^{3b}$ groups, together with the carbon atom to which they are attached, join to form a 3-10 membered saturated carbocyclyl group or heterocyclyl group containing one or two heteroatoms selected from N, O, S and oxidised forms of N or S, wherein said heterocyclyl and carbocyclyl groups may be optionally substituted by one or more $R^b$ groups.

In one embodiment $R^{3a}$ and $R^{3b}$ are independently selected from hydrogen, $C_{1-6}$ alkyl, —C(═O)NH$_{(2-q)}$($C_{1-6}$ alkyl)$_q$, —(CH$_2$)$_s$-(3-12 membered heterocyclyl), —(CH$_2$)$_s$—C$_{3-12}$ carbocyclyl, —C(═O)-(3-12 membered heterocyclyl), and —C(═O)—C$_{3-12}$ carbocyclyl, wherein said $C_{1-6}$ alkyl, heterocyclyl and carbocyclyl groups may be optionally substituted by one or more $R^b$ groups.

In an alternative embodiment $R^{3a}$ and $R^{3b}$ are independently selected from hydrogen, $C_{1-6}$ alkyl, —C(═O)NH$_{(2-q)}$($C_{1-6}$ alkyl)$_q$, —(CH$_2$)$_s$-(3-12 membered heterocyclyl), —(CH$_2$)$_s$—C$_{3-12}$ carbocyclyl, —C(═O)-(3-12 membered heterocyclyl), and —C(═O)—C$_{3-12}$ carbocyclyl, wherein said $C_{1-6}$ alkyl, heterocyclyl and carbocyclyl groups may be optionally substituted by one or more $R^b$ groups.

In one embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(3-12 membered heterocyclyl), —CH$_2$-(3-12 membered heterocyclyl), and —C(═O)-(3-12 membered heterocyclyl), wherein said $C_{1-6}$ alkyl, heterocyclyl and carbocyclyl groups may be optionally substituted by one or more $R^b$ groups.

In an alternative embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(3-12 membered heterocyclyl), —CH$_2$-(3-12 membered heterocyclyl), and —C(═O)-(3-12 membered heterocyclyl), wherein said $C_{1-6}$ alkyl, heterocyclyl and carbocyclyl groups may be optionally substituted by one or more $R^b$ groups.

In an alternative embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(4-7 membered heterocyclyl), —CH$_2$-(4-7 membered heterocyclyl), and —C(═O)-(4-7 membered heterocyclyl), wherein said $C_{1-6}$ alkyl, heterocyclyl and carbocyclyl groups may be optionally substituted by one or more $R^b$ groups.

In one embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(4-6 membered heterocyclyl), —CH$_2$-(4-6 membered heterocyclyl), and —C(═O)-(4-6 membered heterocyclyl), wherein said $C_{1-6}$ alkyl, heterocyclyl and carbocyclyl groups may be optionally substituted by one or more $R^b$ groups.

In an alternative embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(4-6 membered heterocyclyl), —CH$_2$-(4-6 membered heterocyclyl), and —C(═O)-(4-6 membered heterocyclyl), wherein said $C_{1-6}$ alkyl, heterocyclyl and carbocyclyl groups may be optionally substituted by one or more $R^b$ groups.

In one embodiment $R^{3a}$ and $R^{3b}$ are independently selected from hydrogen, $C_{1-6}$ alkyl, —C(═O)NH$_{(2-q)}$($C_{1-6}$ alkyl)$_q$, -(4-6 membered aromatic heterocyclyl), —CH$_2$-(4-6 membered aromatic heterocyclyl), —CH$_2$-(4-6 membered saturated heterocyclyl), —CH$_2$-(9-10 membered bicyclic heterocyclyl), and —C(═O)-(4-6 membered saturated heterocyclyl), wherein said $C_{1-6}$ alkyl, heterocyclyl and carbocyclyl groups may be optionally substituted by one or more $R^b$ groups.

In an alternative embodiment $R^{3a}$ and $R^{3b}$ are independently selected from hydrogen, $C_{1-6}$ alkyl, —C(=O)NH$_{(2-q)}$($C_{1-6}$ alkyl)$_q$, -(4-6 membered aromatic heterocyclyl), —CH$_2$-(4-6 membered aromatic heterocyclyl), and —C(=O)-(4-6 membered saturated heterocyclyl), wherein said $C_{1-6}$ alkyl, heterocyclyl and carbocyclyl groups may be optionally substituted by one or more $R^b$ groups.

In one embodiment one of $R^{3a}$ and $R^{3b}$ represents hydrogen and the other represents: $C_{1-6}$ alkyl, optionally substituted by —(CR$^x$R$^y$)$_s$—O—R$^z$ or one or more halogen atoms; —(CH$_2$)$_s$—NR$^x$C(=O)R$^y$); —C(=O)NH$_{(2-q)}$($C_{1-6}$ alkyl)$_q$; —(CH$_2$)$_s$-(3-6 membered heterocyclyl); —CH$_2$-(9-10 membered bicyclic heterocyclyl); or —C(=O)-(3-6 membered heterocyclyl), wherein said $C_{1-6}$ alkyl, heterocyclyl and carbocyclyl groups may be optionally substituted by one or more $R^b$ groups.

In an alternative embodiment one of $R^{3a}$ and $R^{3b}$ represents hydrogen and the other represents: $C_{1-6}$ alkyl, optionally substituted by —(CR$^x$R$^y$)$_s$—O—R$^z$; —(CH$_2$)$_s$—NR$^x$C(=O)R$^y$); —C(=O)NH$_{(2-q)}$($C_{1-6}$ alkyl)$_q$; —(CH$_2$)$_s$-(3-6 membered heterocyclyl); or —C(=O)-(3-6 membered heterocyclyl).

In one embodiment, one of $R^{3a}$ and $R^{3b}$ represents hydrogen and the other represents: $C_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH), —(CH$_2$)$_s$—NR$^x$C(=O)R$^y$) (e.g. —CH$_2$—NHC(=O)CH$_3$), or one or more halogen atoms (e.g. —CH$_2$F or —CHF$_2$), —C(=O)NH$_{(2-q)}$($C_{1-6}$ alkyl)$_q$ (e.g. —C(=O)NHCH$_3$ or —C(=O)N(CH$_3$)$_2$), —(CH$_2$)$_s$-(3-12 membered heterocyclyl) (e.g. —CH$_2$-pyrazolyl, —CH$_2$-thiazolyl, —CH$_2$-triazolyl, —CH$_2$-pyrazinyl, —CH$_2$-pyridazinyl, —CH$_2$-oxazolidinyl, —CH$_2$-imidazolidinyl, —CH$_2$-pyrimidinyl, —CH$_2$-pyridinyl, —CH$_2$-pyrrolidinyl, —CH$_2$-piperazinyl, —CH$_2$-morpholinyl or —CH$_2$-pyrrolopyridinyl) or —C(=O)-(3-12 membered heterocyclyl) (e.g. —C(=O)-azetidinyl, —C(=O)-pyrrolidinyl, —C(=O)-piperidinyl or —C(=O)-morpholinyl), wherein said $C_{1-6}$ alkyl, heterocyclyl and carbocyclyl groups may be optionally substituted by one or more $R^b$ groups.

In an alternative embodiment, one of $R^{3a}$ and $R^{3b}$ represents hydrogen and the other represents: $C_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH), —(CH$_2$)$_s$—NR$^x$C(=O)R$^y$) (e.g. —CH$_2$—NHC(=O)CH$_3$), —C(=O)NH$_{(2-6)}$($C_{1-6}$ alkyl)$_q$ (e.g. —C(=O)NHCH$_3$ or —C(=O)N(CH$_3$)$_2$), —(CH$_2$)$_s$-(3-12 membered heterocyclyl) (e.g. —CH$_2$-pyrazolyl) or —C(=O)-(3-12 membered heterocyclyl) (e.g. —C(=O)-azetidinyl or —C(=O)-morpholinyl).

In one embodiment, $R^{3b}$ is hydrogen.

In one embodiment, $R^{3a}$ represents hydrogen, $C_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH), —(CH$_2$)$_s$—NR$^x$C(=O)R$^y$) (e.g. —CH$_2$—NHC(=O)CH$_3$), or one or more halogen atoms (e.g. —CH$_2$F or —CHF$_2$), —C(=O)NH$_{(2-q)}$($C_{1-6}$ alkyl)$_q$, —(CH$_2$)$_s$-(3-12 membered heterocyclyl) (e.g. —(CH$_2$)$_s$-5-6 membered heteroaryl, —(CH$_2$)$_s$-5-6 membered saturated heterocyclyl or —(CH$_2$)$_s$-9-10 membered bicyclic heterocyclyl) or —C(=O)-(4-6 membered saturated heterocyclyl).

In an alternative embodiment, $R^{3a}$ represents hydrogen, $C_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH), —(CH$_2$)$_s$—NR$^x$C(=O)R$^y$) (e.g. —CH$_2$—NHC(=O)CH$_3$), —C(=O)NH$_{(2-q)}$($C_{1-6}$ alkyl)$_q$, —(CH$_2$)$_s$-(3-12 membered heterocyclyl) (e.g. —(CH$_2$)$_s$-5-6 membered heteroaryl) or —C(=O)-(4-6 membered saturated heterocyclyl).

In another embodiment, $R^{3a}$ represents hydrogen, methyl, ethyl, CH(CH$_3$)$_2$, —CH$_2$OCH$_3$, —CH$_2$OH, —CH$_2$—NHC(=O)CH$_3$, —CH$_2$F, CHF$_2$, —C(=O)NHCH$_3$, —C(=O)N(CH$_3$)$_2$, —CH$_2$-(pyrazolyl), —CH$_2$-thiazolyl, —CH$_2$-triazolyl, —CH$_2$-pyrazinyl, —CH$_2$-pyridazinyl, —CH$_2$-oxazolidinyl, —CH$_2$-imidazolidinyl, —CH$_2$—Pyrimidinyl, —CH$_2$-pyridinyl, —CH$_2$—Pyrrolidinyl, —CH$_2$-piperidinyl, —CH$_2$-piperazinyl, —CH$_2$-morpholinyl, —CH$_2$-pyrrolopyridinyl, —C(=O)-azetidinyl, —C(=O)-pyrrolidinyl, —C(=O)-piperidinyl or —C(=O)-morpholinyl.

In an alternative embodiment, $R^{3a}$ represents hydrogen, methyl, ethyl, CH(CH$_3$)$_2$, —CH$_2$OCH$_3$, —CH$_2$OH, —CH$_2$—NHC(=O)CH$_3$, —C(=O)NHCH$_3$, —C(=O)N(CH$_3$)$_2$, —CH$_2$-(pyrazolyl), —C(=O)-azetidinyl or —C(=O)-morpholinyl.

In another embodiment, $R^{3a}$ represents hydrogen, methyl, ethyl, CH(CH$_3$)$_2$, —CH$_2$OCH$_3$, —CH$_2$OH, —CH$_2$—NHC(=O)CH$_3$, —CH$_2$F, CHF$_2$, —C(=O)NHCH$_3$, —C(=O)N(CH$_3$)$_2$, —CH$_2$-(pyrazol-1-yl), —CH$_2$-(thiazol-2-yl), —CH$_2$-(1,2,4-triazol-1-yl), —CH$_2$-(pyrazin-1-yl), —CH$_2$-(pyridazin-2-yl), —CH$_2$-(oxazolidin-3-yl), —CH$_2$-(imidazolidin-1-yl), —CH$_2$-(Pyrimidin-1-yl), —CH$_2$-(pyridine-1-yl), —CH$_2$-(pyrrolidin-1-yl), —CH$_2$-(piperidin-1-yl), —CH$_2$-(piperazin-4-yl), —CH$_2$-(morpholin-4-yl), —CH$_2$-(pyrrolopyridin-1-yl), —C(=O)-(azetidin-1-yl) or —C(=O)-(morpholin-4-yl).

In an alternative embodiment, $R^{3a}$ represents hydrogen, methyl, ethyl, CH(CH$_3$)$_2$, —CH$_2$OCH$_3$, —CH$_2$OH, —CH$_2$—NHC(=O)CH$_3$, —C(=O)NHCH$_3$, —C(=O)N(CH$_3$)$_2$, —CH$_2$-(pyrazol-1-yl), C(=O)-(azetidin-1-yl) or —C(=O)-(morpholin-4-yl).

In one embodiment $R^{3b}$ is hydrogen, and $R^{3a}$ is selected from -(5-6 membered heteroaryl), —CH$_2$-(5-6 membered heteroaryl), —CH$_2$-(4-6 saturated membered heterocyclyl) and —C(=O)-(4-6 saturated membered heterocyclyl).

In an alternative embodiment $R^{3b}$ is hydrogen, and $R^{3a}$ is selected from -(5-6 membered heteroaryl), —CH$_2$-(5-6 membered heteroaryl), —CH$_2$-(3-12 membered heterocyclyl) and —C(=O)-(4-6 saturated membered heterocyclyl).

In one embodiment $R^{3b}$ is hydrogen, and $R^{3a}$ is —C(=O)-(4-6 saturated membered heterocyclyl) e.g. —C(=O)-morpholinyl, —C(=O)-pyrrolidinyl, —C(=O)-piperidinyl, or —C(=O)-azetidinyl, wherein said heterocyclyl group may be optionally substituted by one or more $R^b$ groups. In an alternative embodiment $R^{3b}$ is hydrogen, and $R^{3a}$ is —C(=O)-(4-6 saturated membered heterocyclyl) e.g. —C(=O)-morpholinyl or —C(=O)-azetidinyl, wherein said heterocyclyl group may be optionally substituted by one or more $R^b$ groups. In one embodiment $R^{3b}$ is hydrogen, and $R^{3a}$ is —C(=O)-(unsubstituted 4-6 saturated membered heterocyclyl) e.g. —C(=O)-morpholinyl, —C(=O)-pyrrolidinyl, —C(=O)-piperidinyl or —C(=O)-azetidinyl. In an alternative embodiment $R^{3b}$ is hydrogen, and $R^{3a}$ is —C(=O)-(unsubstituted 4-6 saturated membered heterocyclyl) e.g. —C(=O)-morpholinyl or —C(=O)-azetidinyl. In one embodiment $R^{3b}$ is hydrogen, and $R^{3a}$ is —C(=O)-(morpholin-4-yl), —C(=O)-(pyrrolidin-1-yl), —C(=O)-(piperidin-1-yl) or —C(=O)-(azetidin-1-yl). In an alternative embodiment $R^{3b}$ is hydrogen, and $R^{3a}$ is —C(=O)-(morpholin-4-yl) or —C(=O)-(azetidin-1-yl). In a further embodiment $R^{3b}$ is hydrogen, and $R^{3a}$ is —C(=O)-morpholinyl e.g. —C(=O)-(morpholin-4-yl).

In one embodiment $R^{3b}$ is hydrogen, and $R^{3a}$ is —CH$_2$-(4-6 membered aromatic heterocyclyl) e.g. CH$_2$-pyrazolyl, —CH$_2$-thiazolyl, —CH$_2$-triazolyl, —CH$_2$-pyrazinyl, —CH$_2$-pyridazinyl, —CH$_2$-pyrimidinyl or —CH$_2$-pyridinyl, wherein said heterocyclyl group may be optionally substituted by one or more $R^b$ groups (e.g. =O or $C_{1-6}$ alkyl, such as methyl).

In an alternative embodiment $R^{3b}$ is hydrogen, and $R^{3a}$ is —CH$_2$-(4-6 membered aromatic heterocyclyl) e.g. —CH$_2$-pyrazolyl, wherein said heterocyclyl group may be optionally substituted by one or more $R^b$ groups.

In one embodiment $R^{3b}$ is hydrogen, and $R^{3a}$ is —CH$_2$-(unsubstituted 4-6 membered aromatic heterocyclyl) e.g. —CH$_2$-pyrazolyl or —CH$_2$-thiazolyl. In an alternative embodiment $R^{3b}$ is hydrogen, and $R^{3a}$ is —CH$_2$-(unsubstituted 4-6 membered aromatic heterocyclyl) e.g. —CH$_2$-pyrazolyl. In one embodiment $R^{3b}$ is hydrogen, and $R^{3a}$ is CH$_2$-(pyrazol-1-yl).

In one embodiment $R^{3b}$ is hydrogen, and $R^{3a}$ is —CH$_2$-(3-12 membered heterocyclyl) e.g. pyrrolopyridinyl, wherein said heterocyclyl group may be optionally substituted by one or more $R^b$ groups. In a further embodiment $R^{3b}$ is hydrogen, and $R^{3a}$ is —CH$_2$-(unsubstituted 3-12 membered heterocyclyl) e.g. pyrrolopyridinyl (such as pyrrolopyridin-1-yl).

In one embodiment $R^{3b}$ is hydrogen, and $R^{3a}$ is —CH$_2$-(4-6 membered saturated heterocyclyl) e.g. —CH$_2$-oxazolidinyl, —CH$_2$-imidazolidinyl, —CH$_2$-pyrrolidinyl, —CH$_2$-piperidinyl, —CH$_2$-piperazinyl or —CH$_2$-morpholinyl, wherein said heterocyclyl group may be optionally substituted by one or more $R^b$ groups (e.g. =O, halogen (such as fluorine), $C_{1-6}$ alkyl (such as methyl or ethyl) or —(CR$^x$R$^y$)$_s$—O—R$^z$ (e.g. —CH$_2$OCH$_3$). In a further embodiment $R^{3b}$ is hydrogen, and $R^{3a}$ is —CH$_2$-(4-6 membered saturated heterocyclyl) e.g. —CH$_2$-(oxazolidin-3-yl), —CH$_2$-(imidazolidin-1-yl), —CH$_2$-(pyrrolidin-1-yl), —CH$_2$-(piperidin-1-yl), —CH$_2$-(piperazin-4-yl) or —CH$_2$-(morpholin-4-yl), wherein said heterocyclyl group may be optionally substituted by one or more $R^b$ groups (e.g. =O, halogen (such as fluorine), $C_{1-6}$ alkyl (such as methyl or ethyl) or —(CR$^x$R$^y$)$_s$—O—R$^z$ (e.g. —CH$_2$OCH$_3$).

In one embodiment $R^{3b}$ is hydrogen, and $R^{3a}$ is —(CH$_2$)$_s$-(3-12 membered heterocyclyl), such as —CH$_2$-(3-12 membered heterocyclyl). In a further embodiment $R^{3a}$ is —(CH$_2$)$_s$-(3-7 membered heterocyclyl), such as —CH$_2$-(3-7 membered non-aromatic heterocyclyl).

In one further embodiment $R^{3b}$ is hydrogen, and $R^{3a}$ is —CH$_2$-(3-7 membered saturated heterocyclyl) e.g. —CH$_2$-pyrrolidinyl, —CH$_2$-piperidinyl, —CH$_2$-piperazinyl or —CH$_2$-morpholinyl, wherein said heterocyclyl group may be optionally substituted by one or more $R^b$ groups (e.g. =O, halogen (such as fluorine), $C_{1-6}$ alkyl (such as methyl or ethyl) or —(CR$^x$R$^y$)$_s$—O—R$^z$ (e.g. —CH$_2$OCH$_3$).

In one yet further embodiment $R^{3b}$ is hydrogen, and $R^{3a}$ is —CH$_2$-(6 membered saturated heterocyclyl) e.g. —CH$_2$-piperidinyl, —CH$_2$-piperazinyl or —CH$_2$-morpholinyl, wherein said heterocyclyl group may be optionally substituted by one or more $R^b$ groups (e.g. =O, $C_{1-6}$ alkyl (such as methyl or ethyl) or —(CR$^x$R$^y$)$_s$—O—R$^z$ (e.g. —CH$_2$OCH$_3$).

In a further embodiment $R^{3b}$ is hydrogen, and $R^{3a}$ is —CH$_2$-(morpholin-4-yl) optionally substituted by one or more $R^b$ groups as defined herein.

In a further embodiment $R^{3b}$ is hydrogen, and $R^{3a}$ is —CH$_2$-(morpholin-4-yl) optionally substituted by one or more $R^b$ groups such as halogen, $C_{1-6}$ alkyl, $C_{2-6}$ alkynyl, $C_{2-6}$ alkynyl, —(CH$_2$)$_s$—C$_{3-8}$ cycloalkyl, —(CH$_2$)$_s$—C$_{3-8}$ cycloalkenyl, —(CR$^x$R$^y$)$_s$—O—R$^z$, —O—(CR$^x$R$^y$)$_n$—OR$^z$ or haloC$_{1-6}$ alkyl.

In a further embodiment $R^{3b}$ is hydrogen, and $R^{3a}$ is —CH$_2$-(morpholin-4-yl) optionally substituted by from 0 to 2 $R^b$ groups such as halogen, $C_{1-6}$ alkyl, $C_{2-6}$ alkenyl, $C_{2-6}$ alkynyl, —(CH$_2$)$_s$—C$_{3-8}$ cycloalkyl, —(CH$_2$)$_s$—C$_{3-8}$ cycloalkenyl, —(CR$^x$R$^y$)$_s$—O—R$^z$, —O—(CR$^x$R$^y$)$_n$—OR$^z$ or haloC$_{1-6}$ alkyl.

In a further embodiment $R^{3b}$ is hydrogen, and $R^{3a}$ is —CH$_2$-(morpholin-4-yl) optionally substituted by one or zero $R^b$ groups such as halogen, $C_{1-6}$ alkyl, $C_{2-6}$ alkenyl, $C_{2-6}$ alkynyl, —(CH$_2$)$_s$—C$_{3-8}$ cycloalkyl, —(CH$_2$)$_s$—C$_{3-8}$ cycloalkenyl, —(CR$^x$R$^y$)$_s$—O—R$^z$, —O—(CR$^x$R$^y$)$_n$—OR$^z$ or haloC$_{1-6}$ alkyl.

In a further embodiment $R^{3b}$ is hydrogen, and $R^{3a}$ is —CH$_2$-(morpholin-4-yl) optionally substituted by one $R^b$ group such as halogen, $C_{1-6}$ alkyl, $C_{2-6}$ alkenyl, $C_{2-6}$ alkynyl, —(CH$_2$)$_s$—C$_{3-8}$ cycloalkyl, —(CH$_2$)$_s$—C$_{3-8}$ cycloalkenyl, —(CR$^x$R$^y$)$_n$—O—R$^z$, —O—(CR$^x$R$^y$)$_n$—OR$^z$ or haloC$_{1-6}$ alkyl.

In a further embodiment $R^{3b}$ is hydrogen, and $R^{3a}$ is —CH$_2$-(morpholin-4-yl) optionally substituted by 0, 1 or 2 $R^b$ groups (e.g. =O, $C_{1-6}$ alkyl (such as methyl or ethyl) or —(CR$^x$R$^y$)$_s$—O—R$^z$ (e.g. —CH$_2$OCH$_3$).

In one embodiment $R^{3b}$ is hydrogen, and $R^{3a}$ is —CH$_2$-(morpholin-4-yl) substituted by one or more $R^b$ groups (e.g. $C_{1-6}$ alkyl (such as methyl).

In another embodiment $R^{3b}$ is hydrogen, and $R^{3a}$ is —CH$_2$-(morpholin-4-yl) substituted by one or more $R^b$ groups such as methyl.

In another embodiment $R^{3b}$ is hydrogen, and $R^{3a}$ is —CH$_2$-(morpholin-4-yl) substituted by one or two $R^b$ groups such as methyl.

In another embodiment $R^{3b}$ is hydrogen, and $R^{3a}$ is —CH$_2$-(morpholin-4-yl) substituted by a single $R^b$ group such as methyl (e.g. 3-methyl).

In one embodiment $R^{3b}$ is hydrogen, and $R^{3a}$ is morpholinomethyl (e.g. 3-methyl-morpholin-4-yl, such as (R)-3-methyl-morpholin-4-yl).

In one embodiment $R^{3a}$ and $R^{3b}$ are independently selected from hydrogen and $C_{1-6}$ alkyl, wherein said $C_{1-6}$ alkyl may be optionally substituted by one or more halo groups.

In one embodiment $R^{3b}$ is hydrogen and $R^{3a}$ is $C_{1-6}$ alkyl optionally substituted by one or more halo groups. In one embodiment $R^{3b}$ is hydrogen and $R^{3a}$ is $C_{1-6}$ alkyl (e.g. methyl) optionally substituted by one or two halo (e.g. fluoro) groups. In a further embodiment $R^{3b}$ is hydrogen and $R^{3a}$ is $C_{1-6}$ alkyl (e.g. methyl) substituted by one or two halo (e.g. fluoro) groups (e.g. —CH$_2$F or CHF$_2$).

In one embodiment, $R^{3a}$ and $R^{3b}$ both represent hydrogen.

In an alternative embodiment, one of $R^{3a}$ and $R^{3b}$ represents hydrogen and the other represents $C_{1-6}$ alkyl (e.g. methyl, ethyl or CH(CH$_3$)$_2$) optionally substituted by one or more $R^b$ groups.

In a further embodiment, one of $R^{3a}$ and $R^{3b}$ represents hydrogen and the other represents ethyl, CH(CH$_3$)$_2$, —CH$_2$OH, CH$_2$OCH$_3$, —CH$_2$NHC(=O)CH$_3$, —C(=O)NHCH$_3$ or —C(=O)N(CH$_3$)$_2$. In a yet further embodiment, one of $R^{3a}$ and $R^{3b}$ represents hydrogen and the other represents CH$_2$OCH$_3$.

In one embodiment, $R^{3a}$ is attached to the piperazine ring having (5R) stereochemistry.

In one embodiment, Q represents N.

When Q represents CR$^4$, in one embodiment R$^4$ is selected from hydrogen and $C_{1-4}$ alkyl.

In one embodiment, R$^5$ represents hydrogen or $C_{1-6}$ alkyl. In a further embodiment, R$^5$ represents hydrogen, methyl or ethyl. In a yet further embodiment, R$^5$ represents hydrogen or methyl. In a yet further embodiment, R$^5$ represents hydrogen.

In one embodiment $R^6$ and $R^7$ are independently selected from hydrogen and $C_{1-8}$ alkyl. In a further embodiment $R^6$ and $R^7$ are independently selected from hydrogen and $C_{1-4}$ alkyl. In a yet further embodiment $R^6$ and $R^7$ are independently selected from hydrogen and unsubstituted methyl (e.g. —CH$_3$ or —CD$_3$).

In one embodiment, $R^6$ and $R^7$ both represent hydrogen. In a further embodiment, $R^6$ and $R^7$ both represent $C_{1-6}$ alkyl (e.g. methyl or ethyl). In an alternative embodiment, $R^6$ and $R^7$ both represent $C_{1-6}$ alkyl (e.g. methyl). In one embodiment, one of $R^6$ and $R^7$ represents methyl and the other represents ethyl. In one embodiment, $R^6$ and $R^7$ both represent ethyl. In one embodiment, $R^6$ and $R^7$ both represent methyl.

In one embodiment, one of $R^6$ and $R^7$ represents $C_{1-6}$ alkyl (e.g. methyl) and the other represents —Y—$C_{3-12}$ carbocyclyl (e.g. -phenyl or —CH$_2$-phenyl), —Z-(3-12 membered heterocyclyl) (e.g. -pyridyl or -oxazolyl), —(CR$^x$R$^y$)$_s$—C(=O)OR$^z$ (e.g. —COOCH$_3$) or —(CR$^x$R$^y$)$_s$—O—R$^z$ (e.g. —CH$_2$—O—CH$_2$-phenyl or —CH$_2$OCH$_3$), wherein said heterocyclyl group may be optionally substituted by one or more $R^b$ groups (e.g. $C_{1-6}$ alkyl, such as methyl). In an alternative embodiment, one of $R^6$ and $R^7$ represents $C_{1-6}$ alkyl (e.g. methyl) and the other represents —Y—$C_{3-12}$ carbocyclyl (e.g. —CH$_2$-phenyl) or —(CR$^x$R$^y$)$_s$—O—R$^z$ (e.g. —CH$_2$—O—CH$_2$-phenyl). In a further embodiment, one of $R^6$ and $R^7$ represents $C_{1-6}$ alkyl (e.g. methyl) and the other represents —(CR$^x$R$^y$)$_s$—O—R$^z$ (e.g. —CH$_2$—O—CH$_2$-phenyl).

In one embodiment $R^6$ and $R^7$ are independently selected from hydrogen, $C_{1-6}$ alkyl, (e.g. unsubstituted methyl or ethyl), —Y—$C_{3-12}$ carbocyclyl (e.g. —Y-phenyl) —Z-(3-12 membered heterocyclyl) (e.g. —Z-pyridyl or —Z-oxazolyl), —(CR$^x$R$^y$)$_s$—C(=O)OR$^z$ (e.g. —COOCH$_3$) or —(CR$^x$R$^y$)$_s$—O—R$^z$ such as —CH$_2$OCH$_3$ or —CH$_2$—O—CH$_2$-phenyl. In an alternative embodiment $R^6$ and $R^7$ are independently selected from hydrogen, $C_{1-6}$ alkyl, (e.g. unsubstituted methyl), —Y—$C_{3-12}$ carbocyclyl (e.g. —Y-phenyl); or —(CR$^x$R$^y$)$_s$—O—R$^z$ such as —CH$_2$—O—CH$_2$-phenyl. In another embodiment $R^6$ and $R^7$ are independently selected from hydrogen, $C_{1-6}$ alkyl, —Y—$C_{3-6}$ carbocyclyl; or —(CR$^x$R$^y$)$_s$—O—R$^z$.

In an alternative embodiment, $R^6$ and $R^7$ are independently selected from hydrogen, $C_{1-6}$ alkyl, such as unsubstituted methyl or ethyl, —Y—$C_{3-12}$ carbocyclyl such as -phenyl or —CH$_2$-phenyl; —Z-(3-12 membered heterocyclyl) such as -pyridyl or -oxazolyl; —(CR$^x$R$^y$)$_s$—C(=O)OR such as —COOCH$_3$ or —(CR$^x$R$^y$)$_s$—O—R$^z$ such as —CH$_2$OCH$_3$ or —CH$_2$—O—CH$_2$-phenyl. In an alternative embodiment, $R^6$ and $R^7$ are independently selected from hydrogen, $C_{1-6}$ alkyl, such as unsubstituted methyl, —Y—$C_{3-12}$ carbocyclyl such as —CH$_2$-phenyl; or —(CR$^x$R$^y$)$_s$—O—R$^z$ such as —CH$_2$—O—CH$_2$-phenyl. In an alternative embodiment, $R^6$ and $R^7$ are independently selected from hydrogen, $C_{1-6}$ alkyl, such as unsubstituted methyl, —Y—$C_{3-12}$ carbocyclyl such as phenyl, —CH$_2$-phenyl; or —(CR$^x$R$^y$)$_s$—O—R$^z$ such as —CH$_2$—O—CH$_2$-phenyl. In an alternative embodiment, $R^6$ and $R^7$ are independently selected from unsubstituted methyl and —Y—$C_{3-12}$ carbocyclyl such as phenyl or —CH$_2$-phenyl. In an alternative embodiment, $R^6$ and $R^7$ are independently selected from unsubstituted methyl and phenyl, in particular one of $R^6$ or $R^7$ is unsubstituted methyl and the other is phenyl or —CH$_2$-phenyl, e.g. phenyl.

In one embodiment $R^6$ and $R^7$ groups, together with the carbon atom to which they are attached, join to form a 3-10 membered partially or fully (e.g. fully) saturated carbocyclyl group or heterocyclyl group containing one or two heteroatoms selected from N, O, S and oxidised forms of N or S, and which may be optionally fused to a 5-6 membered aromatic carbocyclyl or heterocyclyl ring, wherein said carbocyclyl and heterocyclyl groups may be optionally substituted by one or more (e.g. 1, 2 or 3) $R^b$ groups.

In one embodiment $R^6$ and $R^7$ groups, together with the carbon atom to which they are attached, join to form a 3-10 membered partially or fully (e.g. fully) saturated carbocyclyl group which may be optionally fused to a 5-6 membered aromatic carbocyclyl or heterocyclyl ring, optionally substituted by one or more (e.g. 1, 2 or 3) $R^b$ groups.

In one embodiment $R^6$ and $R^7$ groups, together with the carbon atom to which they are attached, join to form a 3-10 membered partially or fully (e.g. fully) saturated carbocyclyl group selected from cyclopropyl, cyclobutyl, and cyclopentyl, which may be optionally fused to a 5-6 membered aromatic carbocyclyl or heterocyclyl ring, optionally substituted by one or more (e.g. 1, 2 or 3) $R^b$ groups.

In one embodiment $R^6$ and $R^7$ groups, together with the carbon atom to which they are attached, join to form a 3-10 membered partially or fully (e.g. fully) saturated carbocyclyl group selected from cyclopropyl, cyclobutyl, and cyclopentyl which may be optionally fused to a 5-6 membered aromatic carbocyclyl or heterocyclyl ring.

In one embodiment $R^6$ and $R^7$ groups, together with the carbon atom to which they are attached, join to form a 3-6 membered partially or fully (e.g. fully) saturated carbocyclyl group or heterocyclyl group containing one or two heteroatoms selected from N, O, S and oxidised forms of N or S, wherein said carbocyclyl and heterocyclyl groups may be optionally substituted by one or more (e.g. 1, 2 or 3) $R^b$ groups.

In one embodiment $R^6$ and $R^7$ groups, together with the carbon atom to which they are attached, join to form a 3-6 membered fully saturated carbocyclyl or heterocyclyl group containing one or two heteroatoms selected from N, O, S and oxidised forms of N or S, and which may be optionally fused to a 5-6 membered aromatic carbocyclyl or heterocyclyl ring, wherein said carbocyclyl and heterocyclyl groups may be optionally substituted by 1, 2 or 3 $R^b$ groups.

In one embodiment $R^6$ and $R^7$ groups, together with the carbon atom to which they are attached, join to form a 3-6 membered partially or fully (e.g. fully) saturated carbocyclyl or heterocyclyl group containing one or two nitrogen heteroatoms, wherein said carbocyclyl and heterocyclyl groups may be optionally substituted by one or more (e.g. 1, 2 or 3) $R^b$ groups.

In one embodiment $R^6$ and $R^7$ groups, together with the carbon atom to which they are attached, join to form a 3-10 membered fully saturated carbocyclyl group or heterocyclyl group containing one or two heteroatoms selected from N, O, S and oxidised forms of N or S, and which may be optionally fused to a 5-6 membered aromatic carbocyclyl or heterocyclyl ring.

In one embodiment $R^6$ and $R^7$ groups, together with the carbon atom to which they are attached, join to form a 3-6 membered fully saturated carbocyclyl or heterocyclyl group selected from cyclopropyl, cyclobutyl, cyclopentyl, azetidine, piperidine, wherein said heterocyclyl groups may be optionally substituted by one $R^b$ group.

In one embodiment $R^6$ and $R^7$ groups, together with the carbon atom to which they are attached, join to form a 3-6 membered fully saturated carbocyclyl or heterocyclyl group selected from cyclopropyl, cyclobutyl, cyclopentyl, azetidine, piperidine, wherein said heterocyclyl groups may be optionally substituted by one C(=O)R$^x$ group. In a further embodiment $R^6$ and $R^7$ groups, together with the carbon atom to which they are attached, join to form an azetidine group optionally substituted by one C(=O)$R^x$ group (e.g. —C(=O)CH$_3$).

In a further embodiment $R^6$ and $R^7$ groups, together with the carbon atom to which they are attached, join to form an azetidinyl or piperidinyl group substituted by —C(=O) CH$_3$, or said piperidinyl group is substituted —C(=O)O—CH$_2$-phenyl.

In one embodiment $R^6$ and $R^7$ groups, together with the carbon atom to which they are attached, join to form a 3-10 membered partially or fully (e.g. fully) saturated carbocyclyl group or heterocyclyl group containing one or two heteroatoms selected from N, O, S and oxidised forms of N or S, which is fused to a 5-6 membered aromatic carbocyclyl or heterocyclyl ring, wherein said carbocyclyl and heterocyclyl groups may be optionally substituted by one or more (e.g. 1, 2 or 3) $R^b$ groups.

In one embodiment $R^6$ and $R^7$ groups, together with the carbon atom to which they are attached, join to form a 3-6 (e.g. 4-5) membered partially or fully (e.g. fully) saturated carbocyclyl group or heterocyclyl group containing one or two heteroatoms selected from N, O, S and oxidised forms of N or S, which is fused to a 5-6 membered aromatic carbocyclyl or heterocyclyl ring, wherein said carbocyclyl and heterocyclyl groups may be optionally substituted by one or more (e.g. 1, 2 or 3) $R^b$ groups.

In one embodiment $R^6$ and $R^7$ groups, together with the carbon atom to which they are attached, join to form a 5 membered partially or fully (e.g. fully) saturated carbocyclyl group, which is fused to a 6 membered aromatic carbocyclyl or heterocyclyl ring, wherein said carbocyclyl and heterocyclyl groups may be optionally substituted by one or more (e.g. 1, 2 or 3) $R^b$ groups. In one embodiment $R^6$ and $R^7$ groups, together with the carbon atom to which they are attached, join to form a cyclopentyl, which is fused to a phenyl, pyrazinyl or pyridazinyl ring, wherein said carbocyclyl or heterocyclyl groups may be optionally substituted by one or more (e.g. 1, 2 or 3) $R^b$ groups. In one embodiment $R^6$ and $R^7$ groups, together with the carbon atom to which they are attached, join to form a cyclopentyl, which is fused to a phenyl ring, wherein said carbocyclyl groups may be optionally substituted by one or more (e.g. 1, 2 or 3) $R^b$ groups. In one embodiment $R^6$ and $R^7$ groups, together with the carbon atom to which they are attached, join to optionally substituted (e.g. unsubstituted) indanyl.

In one embodiment $R^6$ and $R^7$ independently represent hydrogen, $C_{1-6}$ alkyl (e.g. methyl), —Y—$C_{3-12}$ carbocyclyl (e.g. —CH$_2$-phenyl), —(CR$^x$R$^y$)$_s$—O—R$^x$ (e.g. —CH$_2$—O—CH$_2$-phenyl), or $R^6$ and $R^7$ groups, together with the carbon atom to which they are attached, join to form a 3-6 membered fully saturated carbocyclyl and heterocyclyl group selected from cyclopropyl, cyclobutyl, cyclopentyl, azetidine, piperidine, which is optionally fused to a phenyl ring, wherein said heterocyclyl groups may be optionally substituted by one —C(=O)$R^x$ group (e.g. —C(=O)CH$_3$) or —C(=O)O$R^z$ (—C(=O)O—CH$_2$-phenyl). In one embodiment, $R^6$ and $R^7$ independently represent hydrogen, methyl, CH$_2$-phenyl, —CH$_2$—O—CH$_2$-phenyl, or $R^6$ and $R^7$ groups, together with the carbon atom to which they are attached, join to form cyclopropyl, cyclobutyl, cyclopentyl, azetidine, piperidine, or indanyl, wherein said azetidinyl and piperidinyl groups are substituted by —C(=O)CH$_3$, or said piperidinyl group is substituted —C(=O)O—CH$_2$-phenyl.

In one embodiment p is 0. In one embodiment p is 1. In one embodiment p is 2. In one embodiment p is 0.

In one embodiment $R^8$ is independently selected from hydrogen, $C_{1-6}$ alkyl, halogen, =O and —(CR$^x$R$^y$)$_s$—O—R$^z$. In an alternative embodiment $R^8$ is independently selected from hydrogen, halogen, =O and —(CR$^x$R$^y$)$_s$—O—R$^z$.

In one embodiment $R^8$ is independently selected from hydrogen, $C_{1-6}$ alkyl, halogen and —(CR$^x$R$^y$)$_s$—O—R$^z$. In an alternative embodiment $R^8$ is independently selected from hydrogen, halogen and —(CR$^x$R$^y$)$_s$—O—R$^z$.

In one embodiment $R^8$ is independently selected from hydrogen, $C_{1-6}$ alkyl, halogen and —O—R$^x$. In an alternative embodiment $R^8$ is independently selected from hydrogen, halogen and —O—R$^x$.

In one embodiment $R^8$ is independently selected from hydrogen, halogen (e.g. chlorine, fluorine or bromine), $C_{1-6}$ alkyl (e.g. methyl) and —O—$C_{1-6}$alkyl (e.g. —O—CH$_3$). In an alternative embodiment $R^8$ is independently selected from hydrogen, halogen (e.g. chlorine, fluorine or bromine) and —O—$C_{1-6}$alkyl (e.g. —O—CH$_3$). In one embodiment $R^8$ is independently selected from hydrogen, halogen (e.g. fluorine or bromine) and —O—$C_{1-6}$alkyl (e.g. —O—CH$_3$).

In one embodiment p is 1 and $R^8$ is selected from halogen, =O and —(CR$^x$R$^y$)$_s$—O—R$^z$.

In one embodiment p is 1 and $R^8$ is =O.

In one embodiment p is 1 and $R^8$ is $C_{1-6}$ alkyl (e.g. methyl).

In one embodiment p is 1 and $R^8$ is halogen (e.g. chlorine, fluorine or bromine).

In one embodiment p is 2 and $R^8$ is independently selected from halogen, =O and —(CR$^x$R$^y$)$_s$—O—R$^z$. In one embodiment p is 2 and one $R^8$ is =O.

In one embodiment p is 2 and $R^8$ is independently selected from halogen (e.g. chlorine), =O and —(CR$^x$R$^y$)$_s$—O—R$^z$.

In one embodiment $R^9$ is selected from hydrogen, halogen, $C_{1-8}$ alkyl, —Y—$C_{3-12}$ carbocyclyl, —Z-(3-12 membered heterocyclyl), —(CR$^x$R$^y$)$_s$—O—R$^z$, —(CH$_2$)$_s$—CN, —S(O)$_q$—(CR$^x$R$^y$)$_s$—R$^z$, —C(=O)R$^x$, —(CR$^x$R$^y$)$_s$—C(=O)OR$^z$, —(CR$^x$R$^y$)$_s$—C(=O)NR$^x$R$^y$, —(CH$_2$)$_s$—NR$^x$R$^y$, —(CH$_2$)$_s$—NR$^x$—(CH$_2$)$_s$—SO$_2$—R$^y$, — and —(CH$_2$)$_s$—SO$_2$NR$^x$R$^y$ groups, wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^b$ groups.

In one embodiment $R^9$ is selected from halogen, $C_{1-8}$ alkyl, —Y—$C_{3-12}$ carbocyclyl, —Z-(3-12 membered heterocyclyl), —(CR$^x$R$^y$)$_s$—O—R$^z$, —(CH$_2$)$_s$—CN, —S(O)$_q$—(CR$^x$R$^y$)$_s$—R$^z$, —(CR$^x$R$^y$)$_s$—C(=O)OR$^z$, —(CR$^x$R$^y$)$_s$—C(=O)NR$^x$R$^y$, —(CH$_2$)$_s$—NR$^x$R$^y$, —NR$^x$—(CH$_2$)$_s$—R$^z$, and —(CH$_2$)$_s$—SO$_2$NR$^x$R$^y$ groups, wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^b$ groups.

In one embodiment $R^9$ is selected from hydrogen, halogen, $C_{1-8}$ alkyl, —Y—$C_{3-12}$ carbocyclyl, —Z-(3-12 membered heterocyclyl), —(CR$^x$R$^y$)$_s$—O—R$^z$, —(CH$_2$)$_s$—CN, —S(O)$_q$—(CR$^x$R$^y$)$_s$—R$^z$, —(CR$^x$R$^y$)$_s$—C(=O)OR$^z$, —(CR$^x$R$^y$)$_s$—C(=O)NR$^x$R$^y$, —(CH$_2$)$_s$—NR$^x$R$^y$, and —(CH$_2$)$_s$—SO$_2$NR$^x$R$^y$ groups, wherein said $C_{1-8}$ alkyl groups may be optionally substituted by one or more $R^b$ groups and wherein said carbocyclyl and heterocyclyl groups may be optionally substituted by one or more (e.g. 1, 2 or 3) $R^b$ groups.

In one embodiment $R^9$ is selected from hydrogen, halogen (e.g. bromine, chlorine, or fluorine), $C_{1-8}$ alkyl (e.g. methyl, ethyl, propyl, butyl, or pentyl), —Y—$C_{3-12}$ carbocyclyl (e.g.

—Y-cyclopropyl, —Y-phenyl, —Y-cyclobutyl, —Y-cyclopentyl, —Y-cyclopentenyl, —Y-cyclohexyl, —Y-cyclohexenyl), —Z-(3-12 membered heterocyclyl) (e.g. —Z-furanyl, —Z-pyrazolyl, —Z-pyrrolidinyl, —Z-thienyl, —Z— oxadiazolyl, —Z-tetrazolyl or —Z-benzofuranyl), —O—$R^x$, —$(CH_2)_s$—CN, —$S(O)_q$—$(CR^xR^y)_s$—$R^z$, —$(CR^xR^y)_s$—C(=O)$OR^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-8}$ alkyl groups may be optionally substituted by one or more $R^a$ groups, wherein said carbocyclyl and heterocyclyl groups may be optionally substituted by one or more (e.g. 1, 2 or 3) $R^b$ groups and wherein $R^x$, $R^y$ and $R^z$ independently represent hydrogen, $C_{1-6}$ alkyl (e.g. methyl, ethyl, propyl, butyl), —$(CH_2)_s$—$C_{3-8}$ cycloalkyl, —$(CH_2)_s$-phenyl, and —$(CH_2)_s$-(4-7 membered saturated heterocyclyl).

In an alternative embodiment $R^9$ is selected from hydrogen, halogen (e.g. bromine, chlorine, or fluorine), $C_{1-8}$ alkyl (e.g. methyl, propyl butyl, or pentyl), —Y—$C_{3-12}$ carbocyclyl (e.g. —Y— cyclopropyl, —Y-phenyl, —Y-cyclopentyl, —Y-cyclopentenyl, —Y-cyclohexyl, —Y-cyclohexenyl), —Z-(3-12 membered heterocyclyl), —O—$R^x$, —$(CH_2)_s$—CN, —$S(O)_q$—$(CR^xR^y)_s$—$R^z$, —$(CR^xR^y)_s$—C(=O)$OR^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-8}$ alkyl groups may be optionally substituted by one or more $R^a$ groups, wherein said carbocyclyl and heterocyclyl groups may be optionally substituted by one or more (e.g. 1, 2 or 3) $R^b$ groups and wherein $R^x$, $R^y$ and $R^z$ independently represent hydrogen, $C_{1-6}$ alkyl (e.g. methyl, ethyl, propyl, butyl), —$(CH_2)_s$—$C_{3-8}$ cycloalkyl, —$(CH_2)_s$-phenyl, and —$(CH_2)_s$-(4-7 membered saturated heterocyclyl).

In one embodiment $R^9$ is selected from hydrogen, halogen (e.g. bromine, chlorine, or fluorine), $C_{1-6}$ alkyl (e.g. methyl, ethyl, propyl, isopropyl, isobutyl, butyl or isopentyl), —Y—$C_{3-6}$ carbocyclyl (e.g. —Y-cyclopropyl, —Y-phenyl, —Y-cyclobutyl, —Y-cyclopentyl, —Y-cyclopentenyl, —Y-cyclohexyl, —Y-cyclohexenyl), —Z-(4-6 membered heterocyclyl) (e.g. —Z-furanyl, —Z-pyrazolyl, —Z-pyrrolidinyl, —Z-thienyl, —Z-oxadiazolyl, —Z-tetrazolyl or —Z-benzofuranyl), —O—$R^x$, —$(CH_2)_s$—CN, —$S(O)_q$—$(CR^xR^y)_s$—$R^z$, —$(CR^xR^y)_s$—C(=O)$OR^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-6}$ alkyl groups may be optionally substituted by one or more $R^a$ groups, wherein said carbocyclyl and heterocyclyl groups may be optionally substituted by one or more (e.g. 1, 2 or 3) $R^b$ groups and wherein $R^x$, $R^y$ and $R^z$ independently represent hydrogen, $C_{1-6}$ alkyl (e.g. methyl, ethyl, propyl, butyl), —$(CH_2)_s$—$C_{3-6}$ cycloalkyl, —$(CH_2)_s$-phenyl, and —$(CH_2)_s$-(4-7 membered saturated heterocyclyl e.g. pyrrolidinyl).

In an alternative embodiment $R^9$ is selected from hydrogen, halogen (e.g. bromine, chlorine, or fluorine), $C_{1-6}$ alkyl (e.g. methyl, isopropyl, isobutyl, or isopentyl), —Y—$C_{3-6}$ carbocyclyl (e.g. —Y— cyclopropyl, —Y-phenyl, —Y-cyclopentyl, —Y-cyclopentenyl, —Y-cyclohexyl, —Y-cyclohexenyl), —Z-(4-6 membered heterocyclyl), —O—$R^x$, —$(CH_2)_s$—CN, —$S(O)_q$—$(CR^xR^y)_s$—$R^z$, —$(CR^xR^y)_s$—C(=O)$OR^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-6}$ alkyl groups may be optionally substituted by one or more $R^a$ groups, wherein said carbocyclyl and heterocyclyl groups may be optionally substituted by one or more (e.g. 1, 2 or 3) $R^b$ groups and wherein $R^x$, $R^y$ and $R^z$ independently represent hydrogen, $C_{1-6}$ alkyl (e.g. methyl, ethyl, propyl, butyl), —$(CH_2)_s$—$C_{3-6}$ cycloalkyl, —$(CH_2)_s$-phenyl, and —$(CH_2)_s$-(4-7 membered saturated heterocyclyl e.g. pyrrolidinyl).

In one embodiment $R^9$ is selected from hydrogen, halogen, $C_{1-6}$ alkyl, —Y—$C_{3-12}$ carbocyclyl, —Z-(3-12 membered heterocyclyl), —$(CR^xR^y)_s$—O—$R^z$, —$(CH_2)_s$—CN, —$S(O)_q$—$(CR^xR^y)_s$—$R^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-6}$ alkyl groups may be optionally substituted by one or more $R^b$ groups and wherein said carbocyclyl and heterocyclyl groups may be optionally substituted by one or more (e.g. 1, 2 or 3) $R^b$ groups.

In one embodiment $R^9$ is selected from halogen, $C_{1-6}$ alkyl, —Y—$C_{3-12}$ carbocyclyl, —Z-(3-12 membered heterocyclyl), —$(CR^xR^y)_s$—O—$R^z$, —$(CH_2)_s$—CN, —$S(O)_q$—$(CR^xR^y)_s$—$R^z$, —$(CR^xR^y)_s$—C(=O)$NR^xR^y$, —$(CH_2)_s$—$NR^xR^y$, and —$(CH_2)_s$—$SO_2NR^xR^y$ groups, wherein said $C_{1-6}$ alkyl groups may be optionally substituted by one or more $R^b$ groups and wherein said carbocyclyl and heterocyclyl groups may be optionally substituted by one or more (e.g. 1, 2 or 3) $R^b$ groups.

In one embodiment $R^9$ is selected from halogen; $C_{1-6}$ alkyl; —Y-cyclopropyl; —Y-phenyl; —Y— cyclobutyl; —Y-cyclopentyl; —Y-cyclopentenyl; —Y-cyclohexyl; —Y-cyclohexenyl; —Z-pyrrolidinyl; —Z— pyrazolyl; —Z-furanyl; —Z-thienyl; —Z-oxadiazolyl; —Z-tetrazolyl; —Z-benzofuranyl; —O—$R^x$; —$(CH_2)_s$—CN; —$S(O)_q$—$(CR^xR^y)_s$—$R^z$; —$(CR^xR^y)_s$—C(=O)$OR^z$; —$(CR^xR^y)_s$—C(=O)$NR^xR^y$; —$(CH_2)_s$—$NR^xR^y$; and —$(CH_2)_s$—$SO_2NR^xR^y$ groups, wherein said $C_{1-6}$ alkyl groups may be optionally substituted by one or more $R^a$ groups, wherein said carbocyclyl and heterocyclyl groups may be optionally substituted by 1, 2 or 3 $R^b$ groups and wherein $R^x$, $R^y$ and $R^z$ independently represent hydrogen, $C_{1-6}$ alkyl, —$(CH_2)_s$—$C_{3-8}$ cycloalkyl, —$(CH_2)_s$-phenyl, and —$(CH_2)_s$-(4-7 membered saturated heterocyclyl).

In an alternative embodiment $R^9$ is selected from halogen; $C_{1-6}$ alkyl; —Y-cyclopropyl; —Y-phenyl; —Y-cyclopentyl; —Y-cyclopentenyl; —Y-cyclohexyl; —Y-cyclohexenyl; —Z-pyrrolidinyl; —Z-pyrazolyl; —O—$R^x$; —$(CH_2)_s$—CN; —$S(O)_q$—$(CR^xR^y)_s$—$R^z$; —$(CR^xR^y)_s$—C(=O)$OR^z$; —$(CR^xR^y)_s$—C(=O)$NR^xR^y$; —$(CH_2)_s$—$NR^xR^y$; and —$(CH_2)_s$—$SO_2NR^xR^y$ groups, wherein said $C_{1-6}$ alkyl groups may be optionally substituted by one or more $R^a$ groups, wherein said carbocyclyl and heterocyclyl groups may be optionally substituted by 1, 2 or 3 $R^b$ groups and wherein $R^x$, $R^y$ and $R^z$ independently represent hydrogen, $C_{1-6}$ alkyl, —$(CH_2)_s$—$C_{3-8}$ cycloalkyl, —$(CH_2)_s$-phenyl, and —$(CH_2)_s$-(4-7 membered saturated heterocyclyl).

In one embodiment $R^9$ is selected from —$S(O)_q$—$(CR^xR^y)_s$—$R^z$ and —Y—$C_{3-12}$ carbocyclyl optionally substituted by one or more (e.g. 1, 2 or 3) $R^b$ groups wherein Y is selected from a bond, —$(CR^xR^y)_m$—, —C(=O)—, —$NR^x$, —O—, and —$S(O)_q$—. In one embodiment $R^9$ is selected from —$S(O)_2$—$CH_2$-phenyl and —Y-phenyl wherein said phenyl group is optionally substituted by one or more (e.g. 1, 2 or 3) $R^b$ groups and wherein Y is selected from a bond, —$CH_2$—, —$CH(CH_3)$—, —C(=O)—, —NH, —$NCH_3$—, —O— and —$S(O)_2$—.

In one embodiment $R^9$ is —Y—$C_{3-12}$ carbocyclyl optionally substituted by one or more (e.g. 1, 2 or 3) $R^b$ groups and Y is selected from a bond, —$(CR^xR^y)_m$—, —C(=O)—, —$NR^x$, —O—, and —$S(O)_q$—. In one embodiment $R^9$ is —Y—$C_{3-12}$ carbocyclyl optionally substituted by one or more (e.g. 1, 2 or 3) $R^b$ groups and Y is selected from a bond, —$CR^xR^y$, —$(CR^xR^y)$—$(CR^xR^y)$—, —C(=O)—, —$NR^x$, —O—, and —$S(O)_2$—. In an alternative embodiment $R^9$ is —Y—$C_{3-12}$ carbocyclyl optionally substituted by one or more (e.g. 1, 2 or 3) $R^b$ groups and Y is selected from a bond, —$CR^xR^y$, —C(=O)—, —$NR^x$, —O—, and —$S(O)_2$—. In one embodiment $R^9$ is —Y—$C_{3-6}$ carbocyclyl optionally substituted by one or more (e.g. 1, 2 or 3) $R^b$ groups and Y is selected from a bond, —$CR^xR^y$—, —($CR^xR^y$)—($CR^xR^y$)—, —C(=O)—, —$NR^x$, —O—, and —$S(O)_2$—. In an alternative embodiment $R^9$ is —Y—$C_{3-6}$ carbocyclyl optionally substituted by one or more (e.g. 1, 2 or 3) $R^b$ groups and Y is selected from a bond, —$CR^xR^y$—, —C(=O)—, —$NR^x$, —O—, and —$S(O)_2$—. In one embodiment the $C_{3-6}$ carbocyclyl group is selected from —Y-cyclopropyl, —Y-phenyl, —Y-cyclobutyl, —Y-cyclopentyl, —Y-cyclopentenyl, —Y-cyclohexyl, and —Y-cyclohexenyl. In an alternative embodiment the $C_{3-6}$ carbocyclyl group is selected from —Y-cyclopropyl, —Y— phenyl, —Y-cyclopentyl, —Y-cyclopentenyl, —Y-cyclohexyl, and —Y-cyclohexenyl. In one embodiment $R^9$ is —Y-phenyl wherein said phenyl group is optionally substituted by one or more (e.g. 1, 2 or 3) $R^b$ groups and wherein Y is selected from a bond, —$CH_2$—, —$CF_2$—, —$CF_2$—$CH_2$—, —$CH(CH_3)$—, —$CH(OCH_3)$—, —C(=O)—, —NH, —$NCH_3$—, —O— and —$S(O)_2$—. In an alternative embodiment $R^9$ is —Y-phenyl wherein said phenyl group is optionally substituted by one or more (e.g. 1, 2 or 3) $R^b$ groups and wherein Y is selected from a bond, —$CH_2$—, —$CH(CH_3)$—, —C(=O)—, —NH, —$NCH_3$—, —O— and —$S(O)_2$—. In one embodiment $R^9$ is —Y-phenyl optionally substituted by one or more (e.g. 1, 2 or 3) groups selected from halogen (e.g. chlorine or fluorine), $C_{1-4}$ alkyl, (e.g. methyl), $C_{1-4}$ alkoxyl (e.g. $OCH_3$) and —CN, and Y is selected from a bond, —$CR^xR^y$—, —C(=O)—, —$NR^x$, —O—, and —$S(O)_2$—.

In one embodiment $R^9$ is —Y—$C_{3-12}$ carbocyclyl (e.g —Y-phenyl or Y-cyclopropyl) optionally substituted by one or more (e.g. 1, 2 or 3) $R^b$ groups selected from halogen (e.g. chlorine or fluorine), $C_{1-4}$ alkyl, (e.g. methyl), $C_{1-4}$ alkoxyl (e.g. $OCH_3$) and —CN, Y is selected from —$CR^xR^y$— and $R^x$ and $R^y$ are independently selected from hydrogen, halogen (e.g. fluorine), $C_{1-4}$alkoxyl (e.g. methoxy). In an alternative embodiment $R^9$ is —Y—$C_{3-12}$ carbocyclyl (e.g —Y-phenyl) optionally substituted by one or more (e.g. 1, 2 or 3) $R^b$ groups selected from halogen (e.g. chlorine or fluorine), $C_{1-4}$ alkyl, (e.g. methyl), $C_{1-4}$ alkoxyl (e.g. $OCH_3$) and —CN, Y is selected from —$CR^xR^y$—, —C(=O)— or —O—, and $R^x$ and $R^y$ are independently selected from hydrogen, halogen (e.g. fluorine), $C_{1-4}$alkoxyl (e.g. methoxy). In one embodiment Y is —$CR^xR^y$— which is independently selected from —$CH(OCH_3)$—, —$CH(CH_3)$—, —$CH_2CH_2$—, —$CF_2$— and —$CH_2$—. In an alternative embodiment Y is —$CR^xR^y$— which is independently selected from —$CH(OCH_3)$—, —$CH(CH_3)$—, —$CH_2CH_2$—, —$CF_2CH_2$—, —$CF_2$— and —$CH_2$—.

In one embodiment $R^9$ is —Z-(3-12 membered heterocyclyl) e.g. —Z-pyrazolyl, —Z-furanyl, —Z— thienyl, —Z-oxadiazolyl, —Z-tetrazolyl, —Z-benzofuranyl or —Z-pyrrolidinyl wherein said heretocyclyl group is optionally substituted by one or more (e.g. 1, 2 or 3) $R^b$ groups. In an alternative embodiment $R^9$ is —Z-(3-12 membered heterocyclyl) wherein said heretocyclyl group is optionally substituted by one or more (e.g. 1, 2 or 3) $R^b$ groups. In one embodiment $R^9$ is —Z-(3-6 membered heterocyclyl) e.g. —Z-pyrazolyl, —Z-furanyl, —Z-thienyl, —Z-oxadiazolyl, —Z-tetrazolyl, or —Z-pyrrolidinyl which is optionally substituted by one or more (e.g. 1, 2 or 3) $R^b$ groups. In an alternative embodiment $R^9$ is —Z-(3-6 membered heterocyclyl) e.g. —Z-pyrazolyl or —Z— pyrrolidinyl is optionally substituted by one or more (e.g. 1, 2 or 3) $R^b$ groups. In one embodiment $R^9$ is —Z-(4-6 membered saturated heterocyclyl) e.g. —Z-pyrrolidinyl optionally substituted by =O. In an alternative embodiment $R^9$ is —Z-(4-6 membered saturated heterocyclyl) e.g. —$CH_2$-pyrrolidinyl optionally substituted by =O. In one embodiment $R^9$ is —Z-(5 membered heteroaryl) e.g. —Z-pyrazolyl, —Z-furanyl, —Z-thienyl, —Z-oxadiazolyl or —Z-tetrazolyl. In a further embodiment $R^9$ is —Z-(5 membered heteroaryl) e.g. -pyrazolyl, -furanyl, -thienyl, -oxadiazolyl or -tetrazolyl. In an alternative embodiment $R^9$ is —Z-(5 membered heteroaryl) e.g. —Z-pyrazolyl. In one embodiment $R^9$ is 5 membered heteroaryl. In one embodiment $R^9$ is —$CH_2$-pyrazolyl.

In one embodiment $R^9$ is independently selected from halogen (e.g. chlorine), $C_{1-8}$ alkyl (e.g. methyl), halo$C_{1-8}$alkyl (e.g. $CF_3$), and —$(CH_2)_s$—CN (e.g. —CN).

In one embodiment $R^9$ is independently selected from chlorine and —CN.

In one embodiment $R^9$ is —CN.

In one embodiment $R^9$ is selected from hydrogen, halogen (e.g. bromine, chlorine, or fluorine), $C_{1-6}$ alkyl (e.g. methyl, ethyl, propyl, butyl, or pentyl), $C_{1-6}$ alkyl substituted with halogen (e.g. —$CF_3$, —$CF_2$—$CH_3$, —$CF_2$—$CH_2$—$CH_3$, —$CF_2$—$CH(CH_3)_2$, —$CF_2$—$CH_2$—$CH_2$—$CH_3$, —$CF_2$—$CH_2$—$CH(CH_3)_2$), —Y— carbocyclyl (e.g. -phenyl, —$CH_2$-phenyl, —$CF_2$-phenyl, —$CH(CH_3)$-phenyl, —CH($OCH_3$)-phenyl, —C(=$CH_2$)-phenyl, —NH-phenyl, —N($CH_3$)-phenyl, —O-phenyl, —$SO_2$-phenyl, —C(=O)-phenyl, —$CH_2$-cyclohexyl, —$CF_2$-cyclopropyl, —$CF_2$—$CH_2$-cyclopropyl, —$CF_2$-cyclobutyl, cyclopentenyl, cyclopentyl, cyclohexyl, cyclohexenyl, —$SO_2$-cyclopropyl), —Z-(4-6 membered heterocyclyl) (e.g. —$SO_2$-pyrrolidinyl, —C(=O)-pyrrolidininyl, pyrrolidinyl, —$CH_2$-pyrazolyl, -pyrazolyl, -furanyl, -thienyl, -oxadiazolyl, -pyrrolidinyl or -tetrazolyl), —O—$R^x$ (e.g. —$OCH_3$ or —$OCF_3$), —$(CH_2)_s$—CN (e.g. —CN), —$S(O)_q$—$(CR^xR^y)_s$—$R^z$ (e.g. —$SO_2CH_3$, —$SO_2CH_2CH_3$, —$SO_2$—$CH_2CH(CH_3)_2$), —$(CR^xR^y)_s$—C(=O)$OR^z$ (e.g. —C(=O)$OCH_3$), —$(CR^xR^y)_s$—C(=O)$NR^xR^y$ (e.g. —C(=O)$NHCH_3$, —C(=O)N($CH_3$)$_2$)—$(CH_2)_s$—$NR^xR^y$ (e.g. —$NH_2$), and —$(CH_2)_s$—$SO_2NR^xR^y$ (e.g. —$SO_2$—$CH_2$-phenyl, —$SO_2NHCH_3$, —$SO_2N(CH_3)_2$, —$SO_2NHCH(CH_3)_2$) groups, wherein said carbocyclyl or heterocycyl groups can be optionally substituted by one or more (e.g. 1, 2 or 3) groups selected from halogen (e.g. chlorine or fluorine), =O, $C_{1-4}$ alkyl, (e.g. methyl), $C_{1-4}$ alkoxyl (e.g. —$OCH_3$) and —CN; wherein Y and Z are independently selected from a bond, —$CR^xR^y$—, —C(=O)—, —$NR^x$, —O—, and —$S(O)_2$— (e.g. a bond, —$CH_2$—, —$CH(CH_3)$—, —C(=O)—, —NH, —$NCH_3$—, —O— and —$S(O)_2$—); and wherein $R^x$, $R^y$ and $R^z$ independently represent hydrogen, $C_{1-4}$ alkyl (e.g. methyl, ethyl, isopropyl), halo$C_{1-4}$ alkyl (e.g. trifluoromethyl) and —$(CH_2)_s$-phenyl (e.g. —$CH_2$-phenyl).

In an alternative embodiment $R^9$ is selected from hydrogen, halogen (e.g. bromine, chlorine, or fluorine), $C_{1-6}$ alkyl (e.g. methyl, propyl, butyl, or pentyl), $C_{1-4}$ alkyl substituted with halogen (e.g. —$CF_3$), —Y-carbocyclyl (e.g. -phenyl, —$CH_2$-phenyl, —$CH(CH_3)$-phenyl, —C(=$CH_2$)-phenyl, —NH— phenyl, —N($CH_3$)-phenyl, O-phenyl, —$SO_2$-phenyl, —C(=O)-phenyl, —$CH_2$-cyclohexyl, cyclopentenyl, cyclopentyl, cyclohexenyl, —$SO_2$-cyclopropyl), —Z-(4-6 membered heterocyclyl) (e.g. —$SO_2$-pyrrolidinyl, —C(=O)-pyrrolidininyl, pyrrolidinyl, —$CH_2$-pyrazolyl), —O—$R^x$ (e.g. —$OCH_3$ or —$OCF_3$), —$(CH_2)_s$—CN (e.g. —CN), —$S(O)_q$—$(CR^xR^y)_s$—$R^z$ (e.g. —$SO_2CH_3$, —$SO_2CH_2CH_3$, —$SO_2$—$CH_2CH(CH_3)_2$), —$(CR^xR^y)_s$—C(=O)$OR^z$ (e.g. —C(=O)$OCH_3$), —$(CR^xR^y)_s$—C(=O)$NR^xR^y$ (e.g. —C(=O)$NHCH_3$, —C(=O)N($CH_3$)$_2$)—$(CH_2)_s$—$NR^xR^y$ (e.g. —$NH_2$), and —$(CH_2)_s$—

SO$_2$NR$^x$R$^y$ (e.g. —SO$_2$—CH$_2$-phenyl, —SO$_2$NHCH$_3$, —SO$_2$N(CH$_3$)$_2$, —SO$_2$NHCH(CH$_3$)$_2$) groups, wherein said carbocyclyl or heterocycyl groups can be optionally substituted by one or more (e.g. 1, 2 or 3) groups selected from halogen (e.g. chlorine or fluorine), =O, C$_{1-4}$ alkyl, (e.g. methyl), C$_{1-4}$ alkoxyl (e.g. —OCH$_3$) and —CN; wherein Y and Z are independently selected from a bond, —CR$^x$R$^y$, —C(=O)—, —NR$^x$, —O—, and —S(O)$_2$— (e.g. a bond, —CH$_2$—, —CH(CH$_3$)—, —C(=O)—, —NH, —NCH$_3$—, —O— and —S(O)$_2$—); and wherein R$^x$, R$^y$ and R$^z$ independently represent hydrogen, C$_{1-4}$ alkyl (e.g. methyl, ethyl, isopropyl), haloC$_{1-4}$ alkyl (e.g. trifluoromethyl) and —(CH$_2$)$_s$-phenyl (e.g. —CH$_2$-phenyl).

In one embodiment, R$^9$ is selected from hydrogen, halogen (e.g. bromine, chlorine, or fluorine), C$_{1-6}$ alkyl (e.g. methyl, ethyl, propyl, isopropyl, isobutyl, butyl or isopentyl), —Y-cyclopropyl, —Y— phenyl, —Y-cyclobutyl, —Y-cyclopentyl, —Y-cyclopentenyl, —Y-cyclohexyl, —Y-cyclohexenyl, —Z-(4-6 membered heterocyclyl) (e.g. —Z-pyrazolyl, —Z-furanyl, —Z-thienyl, —Z-oxadiazolyl, —Z-tetrazolyl, or —Z-pyrrolidinyl), —O—R$^x$, —(CH$_2$)$_s$—CN, —S(O)$_q$—(CR$^x$R$^y$)$_s$—R$^z$, —C(=O)R$^x$, —(CR$^x$R$^y$)$_s$—C(=O)OR$^z$, —(CR$^x$R$^y$)$_s$—C(=O)NR$^x$R$^y$, —(CH$_2$)$_s$—NR$^x$R$^y$, —(CH$_2$)$_s$—NR$^x$—SO$_2$—R$^y$— and —(CH$_2$)$_s$—SO$_2$NR$^x$R$^y$ groups, wherein Y and Z are independently selected from a bond, —CR$^x$R$^y$, —(CR$^x$R$^y$)—(CR$^x$R$^y$)—, —C(=O)—, —NR$^x$, —O—, and —S(O)$_2$— and wherein R$^x$, R$^y$ and R$^z$ independently represent hydrogen, C$_{1-6}$ alkyl (e.g. methyl, ethyl, propyl, butyl), —(CH$_2$)$_s$—C$_{3-6}$ cycloalkyl, —(CH$_2$)$_s$-phenyl, and —(CH$_2$)$_s$-(4-7 membered saturated heterocyclyl e.g. pyrrolidinyl).

In an alternative embodiment, R$^9$ is selected from hydrogen, halogen (e.g. bromine, chlorine, or fluorine), C$_{1-6}$ alkyl (e.g. methyl, isopropyl, isobutyl, or isopentyl), —Y-cyclopropyl, —Y-phenyl, —Y— cyclopentyl, —Y-cyclopentenyl, —Y-cyclohexyl, —Y-cyclohexenyl, —Z-(4-6 membered heterocyclyl), —O—R$^x$, —(CH$_2$)$_s$—CN, —S(O)$_q$—(CR$^x$R$^y$)$_s$—R$^z$, —C(=O)R$^x$, —(CR$^x$R$^y$)$_s$—C(=O)OR$^z$, —(CR$^x$R$^y$)$_s$—C(=O)NR$^x$R$^y$, —(CH$_2$)$_s$—NR$^x$R$^y$, —(CH$_2$)$_s$—NR$^x$—SO$_2$—R$^y$— and —(CH$_2$)$_s$—SO$_2$NR$^x$R$^y$ groups, wherein Y and Z are independently selected from a bond, —CR$^x$R$^y$—, —C(=O)—, —NR$^x$, —O—, and —S(O)$_2$— and wherein R$^x$, R$^y$ and R$^z$ independently represent hydrogen, C$_{1-6}$ alkyl (e.g. methyl, ethyl, propyl, butyl), —(CH$_2$)$_s$—C$_{3-6}$ cycloalkyl, —(CH$_2$)$_s$-phenyl, and —(CH$_2$)$_s$-(4-7 membered saturated heterocyclyl e.g. pyrrolidinyl).

In one embodiment R$^9$ is independently selected from halogen (e.g. chlorine, fluorine or bromine), —(CH$_2$)$_s$—CN (e.g. —CN), C$_{1-8}$ alkyl (e.g. ethyl, propyl, isobutyl, butyl or —(CH$_2$)$_2$—CH(CH$_3$)$_2$), —Y—C$_{3-12}$ carbocyclyl (e.g. —CH$_2$-phenyl, —CF$_2$-phenyl, —CH(CH$_3$)-phenyl, —CH(OCH$_3$)-phenyl, —C(=CH$_2$)-phenyl, —O-phenyl, —SO$_2$-phenyl, —C(=O)-phenyl, —CF$_2$-cyclopropyl, —CF$_2$-cyclobutyl, —CF$_2$—CH$_2$-cyclobutyl, -cyclopentyl, -cyclopentenyl, —CH$_2$-cyclohexyl, cyclohexyl or cyclohexenyl), —Z-(3-12 membered heterocyclyl) (e.g. -pyrazolyl, -furanyl, -thienyl, -oxadiazolyl, -tetrazolyl, -benzofuranyl or —CH$_2$-pyrrolidinyl), —S(O)$_q$—(CR$^x$R$^y$)$_s$—R$^z$ (e.g. —SO$_2$CH$_3$, —SO$_2$—CH$_2$CH(CH$_3$)$_2$ or —SO$_2$—CH$_2$-phenyl) or —(CH$_2$)$_s$—SO$_2$NR$^x$R$^y$ (e.g. —SO$_2$N(CH$_3$)$_2$), wherein said carbocyclyl groups (e.g. phenyl) or heterocyclyl groups (e.g. pyrazolyl, furanyl, thienyl, oxadiazolyl, tetrazolyl, benzofuranyl or pyrrolidinyl) may be optionally substituted by one or more R$^b$ groups such as =O, halogen (e.g. fluorine or chlorine), C$_{1-6}$ alkyl (e.g. methyl), —(CH$_2$)$_s$—CN (e.g. —CN), —(CR$^x$R$^y$)$_s$—O—R$^z$ (e.g. methoxy).

In an alternative embodiment R$^9$ is independently selected from halogen (e.g. chlorine), —(CH$_2$)$_s$—CN (e.g. —CN), C$_{1-8}$ alkyl (e.g. —(CH$_2$)$_2$—CH(CH$_3$)$_2$), —Y—C$_{3-12}$ carbocyclyl (e.g. —CH$_2$-phenyl, —CH(CH$_3$)-phenyl, —C(=CH$_2$)-phenyl, —O-phenyl, —SO$_2$-phenyl, —C(=O)-phenyl, -cyclopentyl, -cyclopentenyl, —CH$_2$-cyclohexyl or cyclohexenyl), —S(O)$_q$—(CR$^x$R$^y$)$_s$—R$^z$ (e.g. —SO$_2$CH$_3$, —SO$_2$—CH$_2$CH(CH$_3$)$_2$ or —SO$_2$—CH$_2$-phenyl) or —(CH$_2$)$_s$—SO$_2$NR$^x$R$^y$ (e.g. —SO$_2$N(CH$_3$)$_2$), wherein said carbocyclyl groups (e.g. phenyl) may be optionally substituted by one or more R$^b$ groups such as halogen (e.g. fluorine or chlorine), C$_{1-6}$ alkyl (e.g. methyl), —(CH$_2$)$_s$—CN (e.g. —CN), —(CR$^x$R$^y$)$_s$—O—R$^z$ (e.g. methoxy).

In one embodiment, R$^9$ is independently selected from —Y—C$_{3-12}$ carbocyclyl (e.g. —CH$_2$-phenyl) and C$_{1-8}$ alkyl (e.g. ethyl, propyl, or butyl) wherein said alkyl group is optionally substituted by one or more halogen atoms (e.g. fluorine) and said carbocyclyl group is optionally substituted by one or more halogen atoms (e.g. fluorine).

In a further embodiment, R$^9$ is independently selected from —(CR$^x$R$^y$)$_{1-2}$-cyclopropyl, —(CR$^x$R$^y$)-cyclobutyl, —(CR$^x$R$^y$)-phenyl, ethyl, propyl or butyl each of which may be optionally substituted by one or more halogen atoms (e.g. fluorine) and wherein R$^x$ and R$^y$ are independently selected from hydrogen and fluorine.

In a further embodiment, R$^9$ is independently selected from —(CR$^x$R$^y$)-phenyl, ethyl, propyl or butyl each of which may be optionally substituted by one or more halogen atoms (e.g. fluorine) and wherein R$^x$ and R$^y$ are independently selected from hydrogen and fluorine.

In a further embodiment, R$^9$ is independently selected from —CF$_2$-(phenyl), —CH$_2$-(phenyl), —CH$_2$-(2-fluorophenyl), —CH$_2$-(4-fluorophenyl), —CH$_2$-(2,4-difluorophenyl), —CF$_2$-cyclopropyl, —CF$_2$-cyclobutyl, —CF$_2$—CH$_2$-cyclobutyl, —CF$_2$—CH$_3$, —CF$_2$—CH$_2$—CH$_3$, —CF$_2$—CH(CH$_3$)$_2$, —CF$_2$—CH$_2$—CH(CH$_3$)$_2$ or —CF$_2$—CH$_2$—CH$_2$—CH$_3$.

In a further embodiment, R$^9$ is independently selected from —CH$_2$-phenyl, ethyl, propyl or butyl each of which may be optionally substituted by one or more halogen atoms (e.g. fluorine).

In a further embodiment, R$^9$ is independently selected from —CH$_2$-(phenyl), —CH$_2$-(2-fluorophenyl), —CH$_2$-(4-fluorophenyl), —CH$_2$-(2,4-difluorophenyl), —CF$_2$—CH$_3$, —CF$_2$—CH$_2$—CH$_3$, —CF$_2$—CH(CH$_3$)$_2$, —CF$_2$—CH$_2$—CH(CH$_3$)$_2$ or —CF$_2$—CH$_2$—CH$_2$—CH$_3$. In a further embodiment, R$^9$ is independently selected from —CH$_2$-(2-fluorophenyl), —CH$_2$-(4-fluorophenyl), —CH$_2$-(2,4-difluorophenyl), —CF$_2$—CH$_3$, —CF$_2$—CH$_2$—CH$_3$, —CF$_2$—CH(CH$_3$)$_2$, —CF$_2$—CH$_2$—CH(CH$_3$)$_2$ or —CF$_2$—CH$_2$—CH$_2$—CH$_3$ In one embodiment R$^9$ is —Y-phenyl optionally substituted by one or more (e.g. 1, 2 or 3) R$^b$ groups selected from halogen (e.g. chlorine or fluorine), C$_{1-4}$ alkyl, (e.g. methyl), C$_{1-4}$ alkoxyl (e.g. OCH$_3$) and —CN, Y is selected from —CR$^x$R$^y$— and R$^x$ and R$^y$ are independently selected from hydrogen, halogen (e.g. fluorine), C$_{1-4}$alkoxyl (e.g. methoxy).

In a further embodiment R$^9$ is —CH$_2$-phenyl optionally substituted by one or more (e.g. 1, 2 or 3) R$^b$ groups selected from halogen (e.g. chlorine or fluorine), C$_{1-4}$ alkyl, (e.g. methyl), C$_{1-4}$ alkoxyl (e.g. OCH$_3$) and —CN.

In one embodiment R$^9$ is —CH$_2$-phenyl substituted by one or more (e.g. 1, 2 or 3) R$^b$ groups selected from halogen (e.g. chlorine or fluorine).

In one embodiment $R^9$ is —$CH_2$-phenyl optionally substituted (in particular substituted) by a single $R^b$ group, such as a halogen (e.g. chlorine or fluorine).

In one embodiment $R^9$ is —$CH_2$-phenyl optionally substituted (in particular substituted) by a single fluorine atom.

In one embodiment $R^9$ is —$CH_2$-(4-fluorophenyl).

In one embodiment one of $R^8$ and $R^9$ must be other than hydrogen. In one embodiment $R^8$ is other than hydrogen. In one embodiment $R^9$ is other than hydrogen.

In one embodiment Y and Z are independently selected from a bond, —$(CR^xR^y)_m$—, —$C(=R^x)$—, —$C(=O)$—, —$NR^x$, —O—, and —$S(O)_q$—.

In one embodiment Y and Z are independently selected from a bond, —$(CR^xR^y)_m$—, —$C(=R^x)$—, —$NR^x$, —O—, and —$S(O)_q$—.

In one embodiment Y and Z are independently selected from a bond, —$C(=CR^x)$— (e.g. —$C(=CH_2)$—) and —$(CR^xR^y)_m$—. In one embodiment Y or Z is —$CR^xR^y$— which is independently selected from —$CH(OCH_3)$—, —$CH(CH_3)$—, —$CH_2CH_2$—, —$CF_2CH_2$—, —$CF_2$— and —$CH_2$—. In an alternative embodiment Y or Z is —$CR^xR^y$— which is independently selected from —$CH(OCH_3)$—, —$CH(CH_3)$—, —$CH_2CH_2$—, —$CF_2$— and —$CH_2$—.

In one embodiment m is 1. In another embodiment Y and Z are independently selected from a bond, —$CH(CH_3)$—, —$CH_2CH_2$—, —$CF_2$— and —$CH_2$—.

In another embodiment Y and Z are independently selected from a bond, —$CH(CH_3)$, —$CH_2CH_2$ and —$CH_2$—. In another embodiment Y and Z are independently selected from a bond and —$CH_2$—. In a further embodiment, Y represents —$CH_2$—.

In one embodiment, when ring E represents a phenyl ring and $R^9$ represents a —$SO_2$— heterocyclyl ring, said heterocyclyl ring is substituted by an $R^b$ group other than —$C_{3-8}$ cycloalkyl, phenyl or 4-7 membered saturated heterocyclyl.

In one embodiment, $R^6$ and $R^7$ represent a group other than —Y—$C_{3-12}$ carbocyclyl or —Z-(3-12 membered heterocyclyl).

In one embodiment, $R^{2a}$, $R^{2b}$, $R^{3a}$ and $R^{3b}$ each represent a group other than —$(CH_2)_s$-(3-12 membered heterocyclyl) or —$(CH_2)_s$—$C_{3-12}$ carbocyclyl.

In one embodiment, $R^6$, $R^7$, $R^8$ and $R^9$ are optionally substituted by $R^b$ or $R^c$ which are independently selected from halogen, $C_{1-6}$ alkyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, —$(CH_2)_s$—CN, —$S(O)_q$—$R^x$, —$C(=O)R^x$, —$(CR^xR^y)_s$—$C(=O)OR^z$, —$(CR^xR^y)_s$—O—$C(=O)$—$R^z$, —$(CR^xR^y)_s$—$C(=O)NR^xR^y$, —$(CH_2)$—$NR^xC(=O)R^y$, —$(CH_2)_s$—$OC(=O)NR^xR^y$, —$(CH_2)_s$—$NR^xC(=O)OR^y$, —$(CH_2)_s$—$NR^xR^y$, —$(CH_2)_s$—NH—$SO_2$—$NR^xR^y$, —$(CH_2)_s$—$SO_2NR^xR^y$ groups, wherein said $C_{1-6}$ alkyl, $C_{3-8}$ cycloalkyl, $C_{3-8}$ cycloalkenyl and heterocyclyl groups may be optionally substituted by one or more $R^x$ groups.

In one embodiment, $R^6$, $R^7$, $R^8$ and $R^9$ are optionally substituted by $R^b$ or $R^c$ which are independently selected from halogen, $C_{1-6}$ alkyl, —$(CR^xR^y)_s$—O—$R^z$, —$(CH_2)_s$—CN, $C_{1-6}$ alkyl-$N(H)_{2-q}(C_{1-6}$alkyl$)_q$, —$N(H)_{2-q}(C_{1-6}$-alkyl$)_q$, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$S(O)_q$—$R^x$, —$C(=O)R^x$, —$(CR^xR^y)_s$—$C(=O)OR^z$, —$(CR^xR^y)_s$—O—$C(=O)$—$R^z$, —$(CR^xR^y)_s$—$C(=O)NR^xR^y$, —$(CH_2)_s$—$NR^xC(=O)R^y$, —$(CH_2)_s$—$OC(=O)NR^xR^y$, —$(CH_2)_s$—$NR^xC(=O)OR^y$, —$(CH_2)_s$—$NR^xR^y$; wherein said $C_{1-6}$ alkyl, $C_{3-8}$ cycloalkyl, $C_{3-8}$ cycloalkenyl, phenyl and heterocyclyl groups may be optionally substituted by one or more $R^x$ groups; $R^x$, $R^y$ and $R^z$ independently represent hydrogen, $C_{1-6}$ alkyl, —$(CH_2)_s$—$C_{3-8}$ cycloalkyl, —$(CH_2)_s$—$C_{3-8}$ cycloalkenyl, —$(CH_2)_s$-(4-7 membered saturated heterocyclyl), $C_{1-6}$ alkanol, —$C(=O)OC_{1-6}$ alkyl, hydroxy, $C_{1-6}$ alkoxy, halo$C_{1-6}$ alkyl, —$(CH_2)_n$—O—$C_{1-6}$alkyl, —$C(=O)$—$C_{1-6}$alkyl, —$(CH_2)_s$—CN, $C_{1-6}$ alkyl-$N(H)_{2-q}(C_{1-6}$-alkyl$)_q$, —$N(H)_{2-q}$ $(C_{1-6}$-alkyl$)_q$, —$C(=O)$—$N(H)_{2-q}(C_{1-6}$-alkyl$)_q$, and when attached to nitrogen or carbon or atom $R^x$ and $R^y$ may join to form a 3-7 membered ring optionally containing one or two additional heteroatoms selected from O, N, S and oxidised forms of N or S.

In one embodiment, $R^6$, $R^7$, $R^8$ and $R^9$ are optionally substituted by $R^b$ or $R^c$ which are independently selected from halogen, $C_{1-6}$ alkyl, —$(CR^xR^y)_s$—O—$R^z$, —$(CH_2)_s$—CN, $C_{1-6}$ alkyl-$N(H)_{2-q}(C_{1-6}$alkyl$)_q$, —$N(H)_{2-q}(C_{1-6}$-alkyl$)_q$, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$S(O)_q$—$R^x$, —$C(=O)R^x$, —$(CR^xR^y)_s$—$C(=O)OR^z$, —$(CR^xR^y)_s$—O—$C(=O)$—$R^z$, —$(CR^xR^y)_s$—$C(=O)NR^xR^y$, —$(CH_2)_s$—$NR^xC(=O)R^y$, —$(CH_2)_s$—$OC(=O)NR^xR^y$, —$(CH_2)_s$—$NR^xC(=O)OR^y$, —$(CH_2)_s$—$NR^xR^y$; wherein said $C_{1-6}$ alkyl, $C_{3-8}$ cycloalkyl, $C_{3-8}$ cycloalkenyl, phenyl and heterocyclyl groups may be optionally substituted by one or more $R^x$ groups;

$R^x$, $R^y$ and $R^z$ independently represent hydrogen, $C_{1-6}$ alkyl, $C_{1-6}$ alkanol, —$C(=O)OC_{1-6}$ alkyl, hydroxy, $C_{1-6}$ alkoxy, halo$C_{1-6}$ alkyl, —$(CH_2)_n$—O—$C_{1-6}$alkyl, —$C(=O)$—$C_{1-6}$alkyl, —$(CH_2)_s$—CN, $C_{1-6}$ alkyl-$N(H)_{2-q}(C_{1-6}$alkyl$)_q$, —$N(H)_{2-q}(C_{1-6}$alkyl$)_q$, —$C(=O)$—$N(H)_{2-q}(C_{1-6}$alkyl$)_q$, and when attached to nitrogen or carbon or atom $R^x$ and $R^y$ may join to form a 3-7 membered ring optionally containing one or two additional heteroatoms selected from O, N, S and oxidised forms of N or S.

In one embodiment, $R^6$, $R^7$, $R^8$ and $R^9$ are optionally substituted by $R^b$ or $R^c$ which are independently selected from halogen, $C_{1-6}$ alkyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, —$(CH_2)_s$—CN, $C_{1-6}$ alkyl-$N(H)_{2-q}(R^x)_q$, —$N(H)_{2-q}(R^x)_q$, —$S(O)_q$—$R^x$, —$C(=O)R^x$, and —$(CH_2)_s$—$N(H)_{2-q}(R^x)_q$, wherein said $C_{1-6}$ alkyl, $C_{3-8}$ cycloalkyl, $C_{3-8}$ cycloalkenyl, phenyl and heterocyclyl groups may be optionally substituted by one or more $R^x$ groups and wherein $R^x$ is independently selected from hydrogen, halogen, $C_{1-6}$ alkyl, $C_{1-6}$ alkanol, hydroxy, $C_{1-6}$ alkoxy, and halo$C_{1-6}$ alkyl.

In one embodiment, $R^6$, $R^7$, $R^8$ and $R^9$ are optionally substituted by $R^b$ or $R^c$ which are independently selected from halogen, $C_{1-6}$ alkyl, —$(CH_2)_s$—O—$R^x$, —$(CH_2)_s$—CN, $C_{1-6}$ alkyl-$N(H)_{2-q}(R^x)_q$, —$N(H)_{2-q}(R^x)_q$, —$S(O)_q$—$R^x$, —$C(=O)R^x$, —$(CH_2)_s$—$N(H)_{2-q}(R^x)_q$ where $R^x$ is independently selected from hydrogen, $C_{1-6}$ alkyl, $C_{1-6}$ alkanol, hydroxy, $C_{1-6}$ alkoxy, and halo$C_{1-6}$ alkyl.

In one embodiment, $R^6$, $R^7$, $R^8$ and $R^9$ are optionally substituted by $R^b$ or $R^c$ which are independently selected from halogen, $C_{1-6}$ alkyl, $C_{1-6}$alkoxy, —$(CH_2)_s$—CN, $C_{1-6}$ alkyl-$N(H)_{2-q}(C_{1-6}$alkyl$)_q$, —$N(H)_{2-q}(C_{1-6}$alkyl$)_q$, —$S(O)_q$—$C_{1-6}$alkyl, —$C(=O)C_{1-6}$alkyl, —$(CH_2)_s$—$N(H)_{2-q}(C_{1-6}$alkyl$)_q$.

In one embodiment, $R^6$, $R^7$, $R^8$ and $R^9$ are optionally substituted by $R^b$ or $R^c$ which are independently selected from halogen, $C_{1-6}$ alkyl, halo$C_{1-6}$ alkyl, halo$C_{1-6}$ alkoxy, $C_{1-6}$ alkanol, $-(CH_2)_s-O-C_{1-6}$ alkyl, $-C(=O)$ $C_{1-6}$alkyl, $-(CH_2)_s-C_{3-8}$ cycloalkyl, $-(CH_2)_s-C_{3-8}$ cycloalkenyl, and $-(CH_2)_s$-(4-7 membered saturated heterocyclyl).

In one embodiment, $R^6$, $R^7$, $R^8$ and $R^9$ are optionally substituted by $R^b$ or $R^c$ which are independently selected from fluorine, chlorine, methoxy, ethoxy, difluoromethoxy, methyl, ethyl, isopropyl, tert-butyl, trifluoromethyl, $-C(=O)$methyl, $-N(H)_{2-q}(C_{1-6}alkyl)_q$, morpholino, trifluoromethyl, N-methylpiperazinyl, piperazinyl, piperidinyl, pyrrolidinyl, pyrrolidinylmethyl, and morpholinomethyl.

In one embodiment, $R^6$, $R^7$, $R^8$ and $R^9$ are optionally substituted by $R^b$ or $R^c$ which are independently selected from fluorine, chlorine, methyl, methoxy and $-CN$.

The groups $R^6$, $R^7$, $R^8$ and $R^9$ may be substituted by more than one substituent. Thus, for example, there may be 1 or 2 or 3 or 4 substituents, more typically 1, 2 or 3 substituents. In one embodiment, where $R^6$, $R^7$, $R^8$ or $R^9$ contains a six membered ring (such as a phenyl ring), there may be a single substituent which may be located at any one of the 2-, 3- and 4-positions on the ring. In another embodiment, there may be two or three substituents and these may be located at the 2-, 3-, 4- or 6-positions around the ring. By way of example, a $R^6$, $R^7$, $R^8$ or $R^9$ phenyl ring may be 2,6-disubstituted, 2,3-disubstituted, 2,4-disubstituted 2,5-disubstituted, 2,3,6-trisubstituted or 2,4,6-trisubstituted.

In one embodiment, where $R^8$ and $R^9$ are a phenyl or benzyl ring it may be mono substituted at the 2-, 3- or 4-position or disubstituted at positions 2- and 6- with substituents independently selected from fluorine and chlorine.

In one embodiment $R^x$, $R^y$ and $R^z$ independently represent hydrogen, $C_{1-6}$ alkyl, $C_{2-6}$ alkenyl, $C_{2-6}$ alkynyl, $-(CH_2)_s-C_{3-8}$ cycloalkyl, $-(CH_2)_s-C_{3-8}$ cycloalkenyl, $-(CH_2)_s$-phenyl, $-(CH_2)_s$-(4-7 membered saturated heterocyclyl), $C_{1-6}$ alkanol optionally substituted with one or more halo, $-C(=O)OC_{1-6}$ alkyl, hydroxy, $C_{1-6}$ alkoxy, halo$C_{1-6}$ alkyl, $-(CH_2)_n-O-C_{1-6}$alkyl, $-C(=O)-(CH_2)_n-C_{1-6}$ alkoxy, $-C(=O)-C_{1-6}$alkyl, $-(CH_2)_s-CN$, $C_{1-6}$ alkyl-$N(H)_{2-q}(C_{1-6}alkyl)_q$, $-N(H)_{2-q}(C_{1-6}alkyl)_q$, $-C(=O)-N(H)_{2-q}(C_{1-6}alkyl)_q$, $-(CH_2)_s-NH-SO_2-N(H)_{2-q}(C_{1-6}alkyl)_q$, $-(CH_2)_s-N(C_{1-4}alkyl)-SO_2-N(H)_{2-q}(C_{1-6}alkyl)_q$ and $-(CH_2)_s-O-C(=O)-C_{1-4}alkyl-N(H)_{2-q}(C_{1-6}$-alkyl$)_q$, and when attached to nitrogen, carbon, silicon or phosphorus atom $R^x$ and $R^y$ may join to form a 3-7 membered ring optionally containing a one or two heteroatoms selected from O, N, S and oxidised forms of N or S.

In one embodiment $R^x$, $R^y$ and $R^z$ independently represent hydrogen, $C_{1-6}$ alkyl (e.g. methyl, ethyl, propyl, butyl), $-(CH_2)_s-C_{3-8}$ cycloalkyl, $-(CH_2)_s$-phenyl, and $-(CH_2)_s$-(4-7 membered saturated heterocyclyl) [e.g. pyrrolidinyl].

In one embodiment, $R^x$, $R^y$ and $R^z$ independently represent hydrogen or $C_{1-6}$ alkyl. In one embodiment, $R^x$, $R^y$ and $R^z$ independently represent hydrogen or methyl. In one embodiment, $R^x$ and $R^y$ represent hydrogen.

Sub-Formulae

In one embodiment, the compound of formula (I) is a compound of formula (Ia):

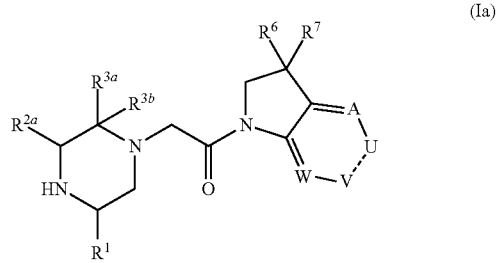

(Ia)

or tautomeric or stereochemically isomeric forms, N-oxides, pharmaceutically acceptable salts or the solvates thereof;
wherein ---- represents a single or double bond,
and when ---- represents a double bond then
A is selected from $CR^8$ and N,
W is selected from CH and N,
U is selected from $CR^8$ and N, and
V is selected from $CR^9$ and N,
or when ---- represents a single bond then
A is selected from $CR^8$ and N,
W is selected from CH and N, and
U is C(=O) and V is $NR^9$, or V is C(=O) and U is $NR^9$,
provided that no more than two of A, U, V and W are nitrogen;
wherein $R^1$, $R^{2a}$, $R^{3a}$, $R^{3b}$, $R^6$, $R^7$, $R^8$ and $R^9$ are as herein defined or in any of the embodiments.

In one embodiment ---- represents a double bond, A is $CR^8$ (e.g. CH), W is CH, U is $CR^8$, and V is N.

In one embodiment ---- represents a double bond, A is $CR^8$ (e.g. CH), W is CH, U is N, and V is $CR^9$.

In one embodiment ---- represents a double bond, A is $CR^8$ (e.g. CH), W is N, U is $CR^8$ (e.g. CH), and V is $CR^9$.

In one embodiment ---- represents a double bond, A is $CR^8$ (e.g. CH), W is CH, U is $CR^8$ (e.g. CH), and V is $CR^9$.

In one embodiment ---- represents a single bond, A is selected from $CR^8$ (e.g. CH) and N (e.g. A is CH), W is selected from CH and N (e.g. CH), and U is C(=O) and V is $NR^9$.

In one embodiment $R^9$ is independently selected from hydrogen, halogen, $C_{1-8}$ alkyl, $C_{2-8}$ alkenyl, $C_{2-8}$ alkynyl, $-Y-C_{3-12}$ carbocyclyl, $-Z$-(3-12 membered heterocyclyl), $-(CH_2)_s-CN$, $-(CR^xR^y)_s-O-R^z$, $-S(O)_q-R^x$, $-C(=O)R^x$, $-C(=S)R^x$, $-C(=N)R^x$, $-(CR^xR^y)_s-C(=O)OR^z$, $-(CR^xR^y)_s-C(=O)NR^xR^y$, $-(CH_2)_s-NR^xR^y$, $-(CR^xR^y)_s-C(=S)NR^z$, $-(CR^xR^y)_s-C(=N)NR^z$, $-(CH_2)_s-NR^x-(CH_2)_s-SO_2-R^y$, and $-(CH_2)_s-SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups. In an alternative embodiment $R^9$ is independently selected from hydrogen, $C_{1-8}$ alkyl, $C_{2-8}$ alkenyl, $C_{2-8}$ alkynyl, $-Y-C_{3-12}$ carbocyclyl, $-Z$-(3-12 membered heterocyclyl), $-(CH_2)_s-CN$, $-S(O)_q-R^x$, $-C(=O)R^x$, $-C(=S)R^x$, $-C(=N)R^x$, $-(CR^xR^y)_s-C(=O)OR^z$, $-(CR^xR^y)_s-C(=O)NR^xR^y$, $-(CR^xR^y)_s-C(=S)NR^z$, $-(CR^xR^y)_s-C(=N)NR^z$, and $-(CH_2)_s-SO_2NR^xR^y$ groups, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more (e.g. 1, 2 or 3) $R^c$ groups.

When .... represents a single bond, in one embodiment, A is selected from $CR^8$, such as CH.

When .... represents a single bond, in one embodiment, W is CH.

When .... represents a single bond, in one embodiment, U is C(=O) and V is $NR^9$. When V represents $NR^9$, in one embodiment, $R^9$ represents $C_{1-8}$ alkyl (e.g. methyl or —$CH_2$—$CH(CH_3)_2$) or —Y—$C_{3-12}$ carbocyclyl (e.g. —$CH_2$-phenyl). When V represents $NR^9$, in one embodiment, $R^9$ represents methyl.

In one embodiment at least one of A, U, V, W is N and one $R^8$ is =O. In one embodiment one of A, U, V, W is N and one $R^8$ is =O.

In one embodiment, the compound of formula (I) is a compound of formula (Ib):

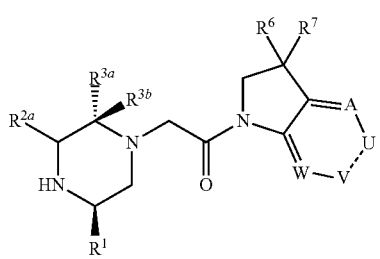

(Ib)

or tautomeric or stereochemically isomeric forms, N-oxides, pharmaceutically acceptable salts or the solvates thereof; wherein $R^1$, $R^{2a}$, $R^{3a}$, $R^{3b}$, $R^6$, $R^7$, A, U, V and W are as herein defined or in any of the embodiments.

In one embodiment W is CH, U is $CR^8$, and V is N.

In one embodiment W is CH, U is N, and V is $CR^9$.

In one embodiment W is N, U is $CR^8$ (e.g. CH), and V is $CR^9$.

In one embodiment W is CH, U is $CR^8$ (e.g. CH), and V is $CR^9$.

In one embodiment, the compound of formula (I) is a compound of formula (Ic):

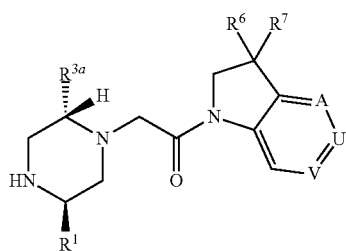

(Ic)

or tautomeric or stereochemically isomeric forms, N-oxides, pharmaceutically acceptable salts or the solvates thereof; wherein $R^1$, $R^{3a}$, $R^6$, $R^7$, A, U, and V are as herein defined or in any of the embodiments.

In one embodiment A is CH, U is $CR^8$, and V is N.

In one embodiment A is CH, U is N, and V is $CR^9$.

In one embodiment A is N, U is $CR^8$ (e.g. CH), and V is $CR^9$.

In one embodiment A is CH, U is $CR^8$ (e.g. CH), and V is $CR^9$.

In one embodiment, the compound of formula (I) is a compound of formula (Id)$^a$ or (Id)$^b$:

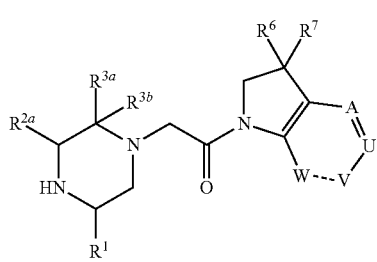

(Id)$^a$

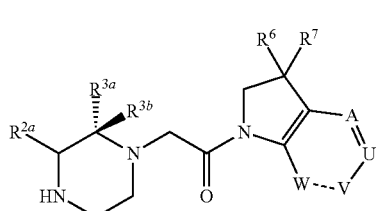

(Id)$^b$ or tautomeric or stereochemically isomeric forms, N-oxides, pharmaceutically acceptable salts or the solvates thereof; wherein .... represents a single or double bond, and when .... represents a double bond then
A is selected from $CR^8$ and N,
W is selected from CH and N,
U is selected from $CR^8$ and N, and
V is selected from $CR^9$ and N,
or when .... represents a single bond then
A is selected from $CR^8$ and N,
U is selected from CH and N, and
W is C(=O) and V is $NR^9$, or V is C(=O) and W is $NR^9$, provided that no more than two of A, W, U and W are nitrogen;
wherein $R^1$, $R^{2a}$, $R^{3a}$, $R^{3b}$, $R^6$, $R^7$, $R^8$ and $R^9$ are as herein defined or in any of the embodiments.

In one embodiment, the compound of formula (I) is a compound of formula (Ie)$^a$ or (Ie)$^b$:

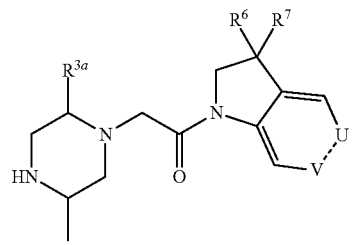

(Ie)$^a$

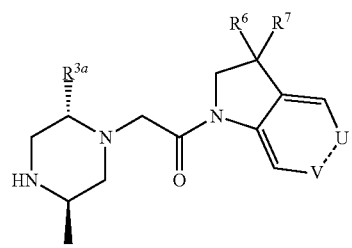

(Ie)$^b$ or tautomeric or stereochemically isomeric forms, N-oxides, pharmaceutically acceptable salts or the solvates thereof; wherein .... represents a single or double bond, and when .... represents a double bond then U is selected from $CR^8$ and N, and V is $CR^9$;

or when .... represents a single bond then

U is C(=O) and V is $NR^9$;

wherein $R^{3a}$, $R^6$, $R^7$, $R^8$ and $R^9$ are as herein defined or in any of the embodiments.

In a further embodiment of the compound of formula $(Ie)^a$ or $(Ie)^b$, $R^{3a}$ represents hydrogen, $C_{1-6}$ alkyl (e.g. methyl, ethyl or $CH(CH_3)_2$) optionally substituted by one or more $R^b$ groups wherein the $R^b$ groups are selected from halogen (e.g. fluorine), $-(CR^xR^y)_s-O-R^z$ (e.g. $-CH_2O-CH_3$), $-(CH_2)_s-NR^xC(=O)R^y)$ (e.g. $-CH_2NHC(=O)CH_3$), $-C(=O)NH_{(2-q)}(C_{1-6}$ alkyl$)_q$ (e.g. $-C(=O)NH\ CH_3$ or $-C(=O)N(CH_3)_2$), $-(CH_2)_s$-(3-12 membered heterocyclyl) (e.g. $-CH_2$-pyrazolyl, $-CH_2$-thiazolyl, $-CH_2$-piperazinyl, $-CH_2$-pyrrolopyridinyl, $-CH_2$-triazolyl, $-CH_2$-imidazolidinyl, $-CH_2$-pyrazinyl, $-CH_2$-pyridazinyl, $-CH_2$-piperidinyl, $-CH_2$-morpholinyl, $-CH_2$-oxazolidinyl, $-CH_2$-pyrimidinyl, $-CH_2$-pyrrolidinyl or $-CH_2$-pyridinyl) or $-C(=O)$-(3-12 membered heterocyclyl) (e.g. $-C(=O)$-azetidinyl, $-C(=O)$-pyrrolidinyl, $-C(=O)$-piperidinyl or $-C(=O)$-morpholinyl).

In a further alternative embodiment of the compound of formula $(Ie)^a$ or $(Ie)^b$, $R^{3a}$ represents hydrogen, $C_{1-6}$ alkyl (e.g. methyl, ethyl or $CH(CH_3)_2$) optionally substituted by one or more $R^b$ groups wherein the $R^b$ groups are selected from $-(CR^xR^y)_s-O-R^z$ (e.g. $-CH_2O-CH_3$), $-(CH_2)_s-NR^xC(=O)R^y)$ (e.g. $-CH_2NHC(=O)CH_3$), $-C(=O)NH_{(2-q)}(C_{1-6}$ alkyl$)_q$ (e.g. $-C(=O)NH\ CH_3$ or $-C(=O)N(CH_3)_2$), $-(CH_2)_s$-(3-12 membered heterocyclyl) (e.g. $-CH_2$-pyrazolyl) or $-C(=O)$-(3-12 membered heterocyclyl) (e.g. $-C(=O)$-azetidinyl or $-C(=O)$-morpholinyl).

In a further embodiment of the compound of formula $(Ie)^a$ or $(Ie)^b$:

$R^6$ and $R^7$ both represent hydrogen; or $R^6$ and $R^7$ both represent $C_{1-6}$ alkyl (e.g. methyl); or $R^6$ and $R^7$ both represent $C_{1-6}$ alkyl (e.g. ethyl); or one of $R^6$ and $R^7$ represents $C_{1-6}$ alkyl (e.g. methyl) and the other represents $C_{1-6}$ alkyl (e.g. ethyl), $-(CR^xR^y)_s-O-R^z$ (e.g. $-CH_2-O-CH_3$ or $-CH_2-O-CH_2$-phenyl), $-(CR^xR^y)_s-C(=O)OR^z$ (e.g. $-COOCH_3$), $-Z$-(3-12 membered heterocyclyl) (e.g. -pyridyl or -oxazolyl), wherein said heterocyclyl may optionally be substituted by one or more $C_{1-6}$ alkyl groups (e.g. methyl), or $-Y-C_{3-12}$ carbocyclyl, (e.g. -phenyl or $-CH_2$-phenyl); or $R^6$ and $R^7$, together with the carbon atom to which they are attached, join to form a 3-6 membered saturated carbocyclyl (e.g. cyclopropyl, cyclobutyl or cyclopentyl) or heterocyclyl group (e.g. azetidine or piperidine), optionally substituted by one C(=O)$R^x$ group (e.g. $-C(=O)CH_3$) or one $-(CR^xR^y)_s-C(=O)OR^z$ (e.g. $-COO-CH_2$-phenyl); or $R^6$ and $R^7$, together with the carbon atom to which they are attached, join to form a 5 membered saturated carbocyclyl group, which is fused to a 6 membered aromatic carbocyclyl or heterocyclyl ring, wherein said carbocyclyl and heterocyclyl groups may be optionally substituted by one or more (e.g. 1, 2 or 3) $R^b$ groups, such as optionally substituted (e.g. unsubstituted) indanyl.

In a further alternative embodiment of the compound of formula $(Ie)^a$ or $(Ie)^b$:

$R^6$ and $R^7$ both represent hydrogen; or $R^6$ and $R^7$ both represent $C_{1-6}$ alkyl (e.g. methyl); or one of $R^6$ and $R^7$ represents $C_{1-6}$ alkyl (e.g. methyl) and the other represents $-(CR^xR^y)_s-O-R^z$ (e.g. $-CH_2-O-CH_2$-phenyl) or $-Y-C_{3-12}$ carbocyclyl, (e.g. -phenyl); or $R^6$ and $R^7$, together with the carbon atom to which they are attached, join to form a 3-6 membered saturated carbocyclyl and heterocyclyl group (e.g. azetidine), optionally substituted by one C(=O)$R^x$ group (e.g. $-C(=O)CH_3$); or $R^6$ and $R^7$, together with the carbon atom to which they are attached, join to form a 5 membered saturated carbocyclyl group, which is fused to a 6 membered aromatic carbocyclyl or heterocyclyl ring, wherein said carbocyclyl and heterocyclyl groups may be optionally substituted by one or more (e.g. 1, 2 or 3) $R^b$ groups, such as optionally substituted (e.g. unsubstituted) indanyl.

In a further embodiment of the compound of formula $(Ie)^a$ or $(Ie)^b$:

$R^6$ and $R^7$ both represent hydrogen; or $R^6$ and $R^7$ both represent $C_{1-6}$ alkyl (e.g. methyl); or one of $R^6$ and $R^7$ represents $C_{1-6}$ alkyl (e.g. methyl) and the other represents $-(CR^xR^y)_s-O-R^z$ (e.g. $-CH_2-O-CH_2$-phenyl); or $R^6$ and $R^7$, together with the carbon atom to which they are attached, join to form a 3-6 membered saturated carbocyclyl and heterocyclyl group (e.g. azetidine), optionally substituted by one C(=O)$R^x$ group (e.g. $-C(=O)CH_3$); or $R^6$ and $R^7$, together with the carbon atom to which they are attached, join to form a 5 membered saturated carbocyclyl group, which is fused to a 6 membered aromatic carbocyclyl or heterocyclyl ring, wherein said carbocyclyl and heterocyclyl groups may be optionally substituted by one or more (e.g. 1, 2 or 3) $R^b$ groups, such as optionally substituted (e.g. unsubstituted) indanyl.

In a further embodiment of the compound of formula $(Ie)^a$ or $(Ie)^b$, $R^8$ is halogen (e.g. fluorine, chlorine or bromine), =O or $C_{1-6}$ alkyl (e.g. methyl). In a yet further embodiment of the compound of formula (Ie), $R^8$ is halogen (e.g. fluorine).

In a further embodiment of the compound of formula $(Ie)^a$ or $(Ie)^b$, $R^9$ is selected from halogen (e.g. chlorine, fluorine or bromine), $-(CH_2)_s-CN$ (e.g. $-CN$), $C_{1-8}$ alkyl (e.g. methyl, ethyl, propyl, isopropyl, isobutyl, butyl or $-(CH_2)_2-CH(CH_3)_2)$, $-Y-C_{3-12}$ carbocyclyl (e.g. -phenyl, $-CH_2$-phenyl, $-CF_2$-phenyl, $-CH(CH_3)$-phenyl, $-CH(OCH_3)$-phenyl, $-C(=CH_2)$-phenyl, $-N(H)$-phenyl, $-N(CH_3)$-phenyl, $-O$-phenyl, $-SO_2$-phenyl, $-C(=O)$-phenyl, $-CH_2$-cyclohexyl, $-CF_2$-cyclopropyl, $-CF_2-CH_2$-cyclopropyl, $-SO_2$-cyclopropyl, $-CF_2$-cyclobutyl, cyclopentenyl, cyclopentyl, cyclohexyl or cyclohexenyl), $-Z$-(3-12 membered heterocyclyl) (e.g. -furanyl, -pyrazolyl, $-CH_2$-pyrrolidinyl, -thienyl, -oxadiazolyl, -benzofuranyl, -tetrazolyl, $-CO$-pyrrolidinyl, $-SO_2$-pyrrolidinyl, $-CH_2$-pyrazolyl, pyrrolidinyl), $-S(O)_q-(CR^xR^y)_s-R^z$ (e.g. $-SO_2-CH_3$, $-SO_2-CH_2CH(CH_3)_2$ or $-SO_2-CH_2$-phenyl) or $-(CH_2)_s-SO_2NR^xR^y$ (e.g. $-SO_2N(CH_3)_2$), wherein said carbocyclyl groups (e.g. phenyl) or heterocyclyl groups (e.g. furanyl, pyrazolyl, pyrrolidinyl, thienyl, oxadiazolyl, benzofuranyl or tetrazolyl) may be optionally substituted by one or more $R^b$ groups such as =O, halogen (e.g. fluorine or chlorine), $C_{1-6}$ alkyl (e.g. methyl), $-(CH_2)_s-CN$ (e.g. $-CN$) or $-(CR^xR^y)_s-O-R^z$ (e.g. methoxy).

In a further alternative embodiment of the compound of formula $(Ie)^a$ or $(Ie)^b$, $R^9$ is selected from halogen (e.g. chlorine), $-(CH_2)_s-CN$ (e.g. $-CN$), $C_{1-8}$ alkyl (e.g. $-(CH_2)_2-CH(CH_3)_2)$, $-Y-C_{3-12}$ carbocyclyl (e.g. $-CH_2$-phenyl, $-CH(CH_3)$-phenyl, $-C(=CH_2)$-phenyl, —O-phenyl, —SO$_2$-phenyl, —C(=O)-phenyl, —CH$_2$-cyclohexyl, cyclopentenyl, cyclopentyl or cyclohexenyl), —S(O)$_q$—(CR$^x$R$^y$)$_s$—R$^z$ (e.g. —SO$_2$CH$_3$, —SO$_2$—CH$_2$CH(CH$_3$)$_2$ or —SO$_2$—CH$_2$-phenyl) or —(CH$_2$)$_s$—SO$_2$NR$^x$R$^y$ (e.g. —SO$_2$N(CH$_3$)$_2$), wherein said carbocyclyl groups (e.g. phenyl) may be optionally substituted by one or more R$^b$ groups such as halogen (e.g. fluorine or chlorine), C$_{1-6}$ alkyl (e.g. methyl), —(CH$_2$)$_s$—CN (e.g. —CN) or —(CR$^x$R$^y$)$_s$—O—R$^z$ (e.g. methoxy).

In one embodiment, the compound of formula (I) is a compound of formula (If)$^a$ or (If)$^b$:

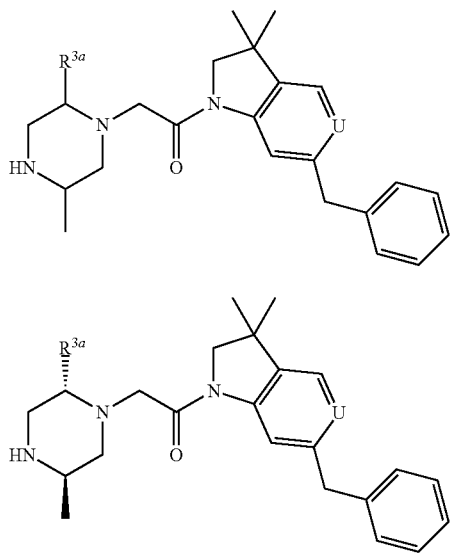

(If)$^a$ (If)$^b$ or tautomeric or stereochemically isomeric forms, N-oxides, pharmaceutically acceptable salts or the solvates thereof; wherein U is selected from CH and N;

and R$^{3a}$ is as herein defined or in any of the embodiments.

In a further embodiment of the compound of formula (If)$^a$ or (If)$^b$, R$^{3a}$ represents —(CR$^x$R$^y$)$_s$—O—R$^z$ (e.g. —CH$_2$OCH$_3$), —(CH$_2$)$_s$-(3-12 membered heterocyclyl) (e.g. —CH$_2$-pyrazolyl, —CH$_2$-thiazolyl, —CH$_2$-piperazinyl, —CH$_2$-pyrrolopyridinyl, —CH$_2$-triazolyl, —CH$_2$-imidazolidinyl, —CH$_2$-pyrazinyl, —CH$_2$-pyridazinyl, —CH$_2$-piperidinyl, —CH$_2$-morpholinyl, —CH$_2$-oxazolidinyl, —CH$_2$-pyrimidinyl, —CH$_2$-pyrrolidinyl or —CH$_2$-pyridinyl) or —C(=O)-(3-12 membered heterocyclyl) (e.g. —C(=O)-morpholinyl). In a further alternative embodiment of the compound of formula (If), R$^{3a}$ represents —(CR$^x$R$^y$)$_s$—O—R$^z$ (e.g. —CH$_2$OCH$_3$), —(CH$_2$)$_s$-(3-12 membered heterocyclyl) (e.g. —CH$_2$-pyrazolyl or —C(=O)-(3-12 membered heterocyclyl) (e.g. —C(=O)-morpholinyl). In a further embodiment of the compound of formula (If), R$^{3a}$ represents —CH$_2$OCH$_3$, —CH$_2$-pyrazolyl (e.g. —CH$_2$-(pyrazol-1-yl) or —C(=O)-morpholinyl (—C(=O)-(morpholin-4-yl)).

In one embodiment of the compound of formula (If)$^a$ or (If)$^b$, R$^{3a}$ represents —(CH$_2$)$_s$-(3-12 membered heterocyclyl) (e.g. —CH$_2$-morpholinyl) optionally substituted by one or more C$_{1-6}$ alkyl groups (e.g. methyl).

In one embodiment, the compound of formula (I) is a compound of formula (Ig)$^a$ or (Ig)$^b$:

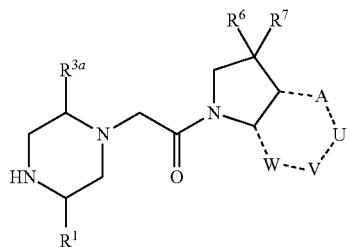

(Ig)$^a$

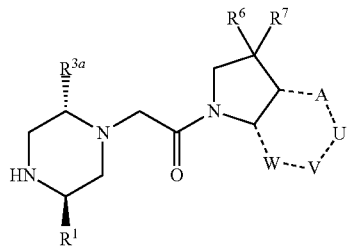

(Ig)$^b$ or tautomeric or stereochemically isomeric forms, N-oxides, pharmaceutically acceptable salts or the solvates thereof; wherein R$^1$, R$^{3a}$, R$^6$, R$^7$, A, U, V, and W are as herein defined or in any of the embodiments.

In one embodiment, the compound of formula (I) is a compound of formula (Ig)$^a$ or (Ig)$^b$:

wherein

A is selected from CH and C—Cl;

W is selected from CH and N;

U is selected from CR$^8$ and N;

V is selected from CR$^9$ and N;

R$^1$ is C$_{1-4}$ alkyl (e.g. methyl) optionally substituted by one, two or three halo groups;

R$^{3a}$ is selected from hydrogen, C$_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH) or —(CH$_2$)$_s$—NR$^x$C(=O)R$^y$) (e.g. —NHC(=O)CH$_3$), —C(=O)NH$_{(2-q)}$(C$_{1-6}$ alkyl)$_q$ (e.g. —CONHCH$_3$ or CON(CH$_3$)$_2$), —(CH$_2$)$_s$-(3-12 membered heterocyclyl) (e.g. —(CH$_2$)$_s$-5-6 membered heteroaryl) or —C(=O)-(4-6 membered saturated heterocyclyl);

R$^6$ and R$^7$ are independently selected from hydrogen, C$_{1-6}$ alkyl (e.g. methyl or ethyl), —Y—C$_{3-12}$ carbocyclyl (e.g. -phenyl or —CH$_2$-phenyl), —(CR$^x$R$^y$)$_s$—C(=O)OR$^z$ (e.g. —COOCH$_3$), —(CR$^x$R$^y$)$_s$—O—R$^x$ (e.g. —CH$_2$—O—CH$_3$ or —CH$_2$—O—CH$_2$-phenyl), —Z-(3-12 membered heterocyclyl) (e.g. -pyridyl or -oxazolyl), wherein said heterocyclyl may optionally be substituted by one or more C$_{1-6}$ alkyl groups (e.g. methyl), or R$^6$ and R$^7$ groups, together with the carbon atom to which they are attached, join to form a 3-6 membered fully saturated carbocyclyl and heterocyclyl group selected from cyclopropyl, cyclobutyl, cyclopentyl, azetidine, piperidine, which is optionally fused to a phenyl ring, wherein said heterocyclyl groups may be optionally substituted by one —C(=O)R$^x$ group (e.g. —C(=O)CH$_3$) or —C(=O)OR$^z$ (—C(=O)O—CH$_2$-phenyl);

R$^8$ is selected from hydrogen, halogen (e.g. chlorine, bromine or fluorine), =O, C$_{1-6}$ alkyl (e.g. methyl) and —O—C$_{1-6}$alkyl (e.g. —O—CH$_3$);

R$^9$ is selected from hydrogen, halogen (e.g. bromine, chlorine, or fluorine), C$_{1-6}$ alkyl (e.g. methyl, ethyl, propyl, isopropyl, butyl, isobutyl or pentyl), C$_{1-4}$ alkyl substituted with halogen (e.g. —CF$_3$, —CF$_2$—CH$_3$, —CF$_2$—CH$_2$—CH$_3$, —CF$_2$—CH(CH$_3$)$_2$, —CF$_2$—CH$_2$—CH(CH$_3$)$_2$ or —CF$_2$—CH$_2$—CH$_2$—CH$_3$), —Y-phenyl, —Y-cyclopentyl, —Y-cyclopentenyl, —Y-cyclohexyl, —Y-cyclohexenyl, —Y-cyclopropyl, Y-cyclobutyl (e.g. -phenyl, —CH$_2$-phenyl, —CF$_2$-phenyl, —CH(CH$_3$)-phenyl, —CH(OCH$_3$)-phenyl, —C(=CH$_2$)-phenyl, —NH-phenyl, —N(CH$_3$)-phenyl, —O-phenyl, —SO$_2$-phenyl, —C(=O)-phenyl, —CH$_2$-cyclohexyl, cyclopentenyl, cyclopentyl, cyclohexyl, cyclohexenyl, —CF$_2$-cyclopropyl, —CF$_2$—CH$_2$-cyclopropyl, —CF$_2$-cyclobutyl, —SO$_2$-cyclopropyl), —Z-pyrazolyl, —Z-furanyl, —Z-thienyl, —Z— oxadiazolyl, —Z-benzofuranyl, —Z-tetrazolyl or —Z-pyrrolidinyl (e.g. —SO$_2$-pyrrolidinyl, —C(=O)-pyrrolidinyl, pyrrolidinyl, —CH$_2$-pyrrolidinyl, —CH$_2$-pyrazolyl, -furanyl, -pyrazolyl, -thienyl, -oxadiazolyl, -benzofuranyl or -tetrazolyl), —O—R$^x$ (e.g. —OCH$_3$ or —OCF$_3$), —(CH$_2$)$_s$—CN (e.g. —CN), —S(O)$_q$—(CR$^x$R$^y$)$_s$—R$^z$ (e.g. —SO$_2$CH$_3$, —SO$_2$CH$_2$CH$_3$, —SO$_2$—CH$_2$CH(CH$_3$)$_2$), —(CR$^x$R$^y$)$_s$—C(=O)OR$^z$ (e.g. —C(=O)OCH$_3$), —(CR$^x$R$^y$)$_s$—C(=O)NR$^x$R$^y$ (e.g. —C(=O)NHCH$_3$, —C(=O)N(CH$_3$)$_2$)—(CH$_2$)$_s$—NR$^x$R$^y$ (e.g. —NH$_2$), —(CH$_2$)$_s$—NR$^x$—(CH$_2$)$_s$—SO$_2$—R (e.g. —NHSO$_2$CH$_3$) and —(CH$_2$)$_s$—SO$_2$NR$^x$R$^y$ (e.g. —SO$_2$—CH$_2$-phenyl, —SO$_2$NHCH$_3$, —SO$_2$N(CH$_3$)$_2$, —SO$_2$NHCH(CH$_3$)$_2$) groups, wherein said carbocyclyl or heterocycyl groups can be optionally substituted by one or more (e.g. 1, 2 or 3) groups selected from halogen (e.g. chlorine or fluorine), =O, C$_{1-4}$ alkyl, (e.g. methyl), C$_{1-4}$ alkoxyl (e.g. —OCH$_3$) and —CN; wherein Y and Z are independently selected from a bond, —CR$^x$R$^y$—, —C(=O)—, —NR$^x$, —O—, and —S(O)$_2$— (e.g. a bond, —CH$_2$—, —CH(CH$_3$)—, —C(=O)—, —NH, —NCH$_3$—, —O— and —S(O)$_2$—); and
wherein R$^x$, R$^y$ and R$^z$ independently represent hydrogen, C$_{1-4}$ alkyl (e.g. methyl, ethyl, isopropyl), haloC$_{1-4}$ alkyl (e.g. trifluoromethyl) and —(CH$_2$)$_s$-phenyl (e.g. —CH$_2$-phenyl).

In an alternative embodiment, the compound of formula (I) is a compound of formula (Ig)$^a$ or (Ig)$^b$:
wherein
A is selected from CH and C—Cl;
W is selected from CH and N;
U is selected from CR$^8$ and N;
V is selected from CR$^9$ and N;
R$^1$ is C$_{1-4}$ alkyl (e.g. methyl) optionally substituted by one, two or three halo groups;
R$^{3a}$ is selected from hydrogen, C$_{1-6}$ alkyl (e.g. methyl, ethyl or CH(CH$_3$)$_2$) optionally substituted by —(CR$^x$R$^y$)$_s$—O—R$^z$ (e.g. —OCH$_3$ or —OH) or —(CH$_2$)$_s$—NR$^x$C(=O)R$^y$) (e.g. —NHC(=O)CH$_3$), —C(=O)NH$_{(2-q)}$(C$_{1-6}$ alkyl)$_q$, —(CH$_2$)$_s$-(3-12 membered heterocyclyl) (e.g. —(CH$_2$)$_s$-5-6 membered heteroaryl) or —C(=O)-(4-6 membered saturated heterocyclyl);
R$^6$ and R$^7$ are independently selected from hydrogen, C$_{1-6}$ alkyl (e.g. methyl), —Y—C$_{3-12}$ carbocyclyl (e.g. —CH$_2$-phenyl), —(CR$^x$R$^y$)$_s$—O—R$^x$ (e.g. —CH$_2$—O—CH$_2$-phenyl), or R$^6$ and R$^7$ groups, together with the carbon atom to which they are attached, join to form a 3-6 membered fully saturated carbocyclyl and heterocyclyl group selected from cyclopropyl, cyclobutyl, cyclopentyl, azetidine, piperidine, which is optionally fused to a phenyl ring, wherein said heterocyclyl groups may be optionally substituted by one —C(=O)R$^x$ group (e.g. —C(=O)CH$_3$) or —C(=O)OR$^z$ (—C(=O)O—CH$_2$-phenyl);
R$^8$ is selected from hydrogen, halogen (e.g. bromine, fluorine), =O and —O—C$_{1-6}$alkyl (e.g. —O—CH$_3$);
R$^9$ is selected from hydrogen, halogen (e.g. bromine, chlorine, or fluorine), C$_{1-6}$ alkyl (e.g. methyl, propyl, butyl, or pentyl), C$_{1-4}$ alkyl substituted with halogen (e.g. —CF$_3$), —Y-phenyl, —Y— cyclopentyl, —Y-cyclopentenyl, —Y-cyclohexyl, —Y-cyclohexenyl, —Y-cyclopropyl (e.g. -phenyl, —CH$_2$-phenyl, —CH(CH$_3$)-phenyl, —C(=CH$_2$)-phenyl, —NH-phenyl, —N(CH$_3$)-phenyl, O-phenyl, —SO$_2$-phenyl, —C(=O)-phenyl, —CH$_2$-cyclohexyl, cyclopentenyl, cyclopentyl, cyclohexenyl, —SO$_2$-cyclopropyl), —Z-pyrazolyl or —Z-pyrrolidinyl (e.g. —SO$_2$-pyrrolidinyl, —C(=O)-pyrrolidininyl, pyrrolidinyl, —CH$_2$-pyrazolyl), —O—R$^x$ (e.g. —OCH$_3$ or —OCF$_3$), —(CH$_2$)$_s$—CN (e.g. —CN), —S(O)$_q$—(CR$^x$R$^y$)$_s$—R$^z$ (e.g. —SO$_2$CH$_3$, —SO$_2$CH$_2$CH$_3$, —SO$_2$—CH$_2$CH(CH$_3$)$_2$), —(CR$^x$R$^y$)$_s$—C(=O)OR$^z$ (e.g. —C(=O)OCH$_3$), —(CR$^x$R$^y$)$_s$—C(=O)NR$^x$R$^y$ (e.g. —C(=O)NHCH$_3$, —C(=O)N(CH$_3$)$_2$) —(CH$_2$)$_s$—NR$^x$R$^y$ (e.g. —NH$_2$), and —(CH$_2$)$_s$—SO$_2$NR$^x$R$^y$ (e.g. —SO$_2$—CH$_2$-phenyl, —SO$_2$NHCH$_3$, —SO$_2$N(CH$_3$)$_2$, —SO$_2$NHCH(CH$_3$)$_2$) groups, wherein said carbocyclyl or heterocycyl groups can be optionally substituted by one or more (e.g. 1, 2 or 3) groups selected from halogen (e.g. chlorine or fluorine), =O, C$_{1-4}$ alkyl, (e.g. methyl), C$_{1-4}$ alkoxyl (e.g. —OCH$_3$) and —CN; wherein Y and Z are independently selected from a bond, —CR$^x$R$^y$—, —C(=O)—, —NR$^x$, —O—, and —S(O)$_2$— (e.g. a bond, —CH$_2$—, —CH(CH$_3$)—, —C(=O)—, —NH, —NCH$_3$—, —O— and —S(O)$_2$—); and wherein R$^x$, R$^y$ and R$^z$ independently represent hydrogen, C$_{1-4}$ alkyl (e.g. methyl, ethyl, isopropyl), haloC$_{1-4}$ alkyl (e.g. trifluoromethyl) and —(CH$_2$)$_s$-phenyl (e.g. —CH$_2$-phenyl).

In one embodiment, the compound of formula (I) is a compound of formula (Ig)$^a$ or (Ig)$^b$:
wherein;
A is selected from CH and C—Cl;
W is selected from CH and N;
U is selected from CR$^8$ and N;
V is selected from CR$^9$ and N;
R$^1$ represents —CH$_3$, —CF$_3$ or —CH$_2$F.
R$^{3a}$ represents hydrogen, methyl, ethyl, CH(CH$_3$)$_2$, —CH$_2$O—CH$_3$, —CH$_2$OH, —CH$_2$—NHC(=O)CH$_3$, —C(=O)NHCH$_3$, —C(=O)N(CH$_3$)$_2$, —CH$_2$-(pyrazol-1-yl), —CH$_2$-(thiazol-2-yl), —CH$_2$-(piperazin-4-yl), —CH$_2$-(pyrrolopyridin-1-yl), —CH$_2$-(triazol-1-yl), —CH$_2$-(imidazolidin-1-yl), —CH$_2$-(pyrazin-1-yl), —CH$_2$-(pyridazin-2-yl), —CH$_2$-(piperidin-1-yl), —CH$_2$-(morpholin-4-yl), —CH$_2$-(oxazolidin-3-yl), —CH$_2$-(pyrimidin-1-yl), —CH$_2$-(pyrrolidin-1-yl) or —CH$_2$-(pyridin-1-yl), —C(=O)-azetidinyl, —C(=O)-pyrrolidinyl, —C(=O)-piperidinyl or —C(=O)-morpholinyl;
R$^6$ and R$^7$ independently represent hydrogen, methyl, ethyl, -phenyl, CH$_2$-phenyl, —CH$_2$—O—CH$_3$, —COOCH$_3$, —CH$_2$—O—CH$_2$-phenyl, pyridinyl, oxazolyl or R$^6$ and R$^7$ groups, together with the carbon atom to which they are attached, join to form cyclopropyl, cyclobutyl, cyclopentyl, azetidine, piperidine, or indanyl, wherein said azetidinyl and piperidinyl groups are substituted by —C(=O)CH$_3$, or said piperidinyl group is substituted —C(=O)O—CH$_2$-phenyl;
R$^8$ is selected from hydrogen, bromine, fluorine, chlorine, =O, methyl and —O—CH$_3$;
R$^9$ is independently selected from hydrogen, bromine, chlorine, fluorine, methyl, ethyl, propyl, isopropyl, butyl, isobutyl, isopentyl, —CF$_3$, —CF$_2$—CH$_3$, —CF$_2$—CH$_2$—CH$_3$, —CF$_2$—CH(CH$_3$)$_2$, —CF$_2$—CH$_2$—CH(CH$_3$)$_2$, —CF$_2$—CH$_2$—CH$_2$—CH$_3$, -phenyl, —CF$_2$-phenyl, fluorochlorophenyl (e.g. 2-fluoro-5-chlorophenyl), —CH$_2$-phenyl, —CH(OCH$_3$)-phenyl, —CH$_2$-nitrophenyl (—CH$_2$-3-nitrophenyl), —CH$_2$-fluorophenyl (e.g. —CH$_2$-2-fluorophenyl, —CH$_2$-3-fluorophenyl, —CH$_2$-4-fluorophenyl or —CH$_2$-2,4-difluorophenyl), —CH$_2$-difluorophenyl (—CH$_2$-2,4-difluorophenyl), —CH$_2$-chlorophenyl (e.g. —CH$_2$-2-chlorophenyl, —CH$_2$-3-chlorophenyl, —CH$_2$-4-chlorophenyl), —CH$_2$-methoxyphenyl (e.g. —CH$_2$-3-methoxyphenyl, —CH₂-4-methoxyphenyl), —CH(CH₃)-phenyl, —C(═CH₂)-phenyl, —NH-phenyl, —N(CH₃)-phenyl, —O-phenyl, —O-chlorophenyl (e.g. O-(2-chlorophenyl)), —O-fluorophenyl (e.g. —O-(2,6-difluorophenyl)), —O-chloromethylphenyl (e.g. —O-(2-chloro-6-methylphenyl)), —O— methylphenyl (e.g. O-(2-methylphenyl) or —O-(2,6-dimethylphenyl)), —SO₂-phenyl, —SO₂-methoxyphenyl (e.g. —SO₂-(p-methoxyphenyl), —C(═O)-phenyl, —C(═O)-pyrrolidininyl, —CH₂-cyclohexyl, cyclohexyl, cyclopentenyl, cyclopentyl, cyclohexenyl, —SO₂-cyclopropyl, —CF₂-cyclopropyl, —CF₂—CH₂-cyclopropyl, —CF₂-cyclobutyl, —SO₂-pyrrolidinyl, —CO-pyrrolidinyl, pyrrolidinyl optionally substituted by ═O, —CH₂-pyrrolidinyl optionally substituted by ═O, —CH₂-pyrazolyl, -furanyl, -pyrazolyl substituted by methyl, -thienyl optionally substituted by methyl, -oxadiazolyl optionally substituted by methyl, -benzofuranyl, -tetrazolyl, —OCH₃, —OCF₃, —CN, —SO₂CH₃, —SO₂CH₂CH₃, —SO₂—CH₂CH(CH₃)₂, —SO₂—CH₂-phenyl, —SO₂NHCH₃, —SO₂N(CH₃)₂, —SO₂NHCH(CH₃)₂), —C(═O)OCH₃, —C(═O)NHCH₃, —C(═O)N(CH₃)₂, —NHS(O)₂CH₃, —NH₂.

In one alternative embodiment, the compound of formula (I) is a compound of formula (Ig)$^a$ or (Ig)$^b$:
wherein;
A is selected from CH and C—Cl;
W is selected from CH and N;
U is selected from CR⁸ and N;
V is selected from CR⁹ and N;
R¹ represents —CH₃, —CF₃ or —CH₂F.
R$^{3a}$ represents hydrogen, methyl, ethyl, CH(CH₃)₂, —CH₂O—CH₃, —CH₂OH, —CH₂—NHC(═O)CH₃, —C(═O)NHCH₃, —C(═O)N(CH₃)₂, —CH₂-(pyrazol-1-yl), —C(═O)-azetidinyl or —C(═O)-morpholinyl;
R⁶ and R⁷ independently represent hydrogen, methyl, CH₂-phenyl, —CH₂—O—CH₂-phenyl, or R⁶ and R⁷ groups, together with the carbon atom to which they are attached, join to form cyclopropyl, cyclobutyl, cyclopentyl, azetidine, piperidine, or indanyl, wherein said azetidinyl and piperidinyl groups are substituted by —C(═O)CH₃, or said piperidinyl group is substituted —C(═O)O—CH₂-phenyl;
R⁸ is selected from hydrogen, bromine, fluorine, ═O and —O—CH₃;
R⁹ is independently selected from hydrogen, bromine, chlorine, fluorine, methyl, isopropyl, isobutyl, isopentyl, —CF₃, -phenyl, fluorochlorophenyl (e.g. 2-fluoro-5-chlorophenyl), —CH₂-phenyl, —CH₂-nitrophenyl (—CH₂-3-nitrophenyl), —CH₂-fluorophenyl (e.g. —CH₂-2-fluorophenyl, —CH₂-3-fluorophenyl, —CH₂-4-fluorophenyl), —CH₂-difluorophenyl (—CH₂-2,4-difluorophenyl), —CH₂-chlorophenyl (e.g. —CH₂-2-chlorophenyl, —CH₂-3-chlorophenyl, —CH₂-4-chlorophenyl), —CH₂-methoxyphenyl (e.g. —CH₂-3-methoxyphenyl, —CH₂-4-methoxyphenyl), —CH(CH₃)-phenyl, —C(═CH₂)-phenyl, —NH-phenyl, —N(CH₃)-phenyl, O-phenyl, O-chlorophenyl (e.g. 0-(2-chlorophenyl)), O-methylphenyl (e.g. O-(2-methylphenyl)), —SO₂-phenyl, —SO₂-methoxyphenyl (e.g. —SO₂-(p-methoxyphenyl), —C(═O)-phenyl, —C(═O)-pyrrolidininyl, —CH₂-cyclohexyl, cyclopentenyl, cyclopentyl, cyclohexenyl, —SO₂-cyclopropyl, —SO₂-pyrrolidinyl, pyrrolidinyl optionally substituted by ═O, —CH₂-pyrazolyl, —OCH₃, —OCF₃, —CN, —SO₂CH₃, —SO₂CH₂CH₃, —SO₂—CH₂CH(CH₃)₂, —SO₂—CH₂-phenyl, —SO₂NHCH₃, —SO₂N(CH₃)₂, —SO₂NHCH(CH₃)₂), —C(═O)OCH₃, —C(═O)NHCH₃, —C(═O)N(CH₃)₂, —NHS(O)₂CH₃, —NH₂.

In one embodiment, the compound of formula (I) is a compound of formula (Ih)$^a$ or (Ih)$^b$:

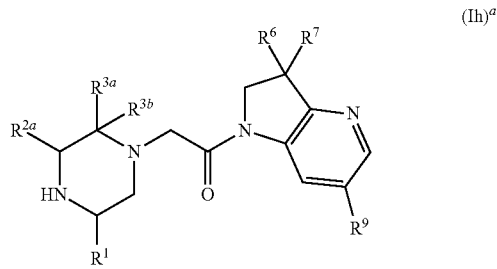

(Ih)$^a$

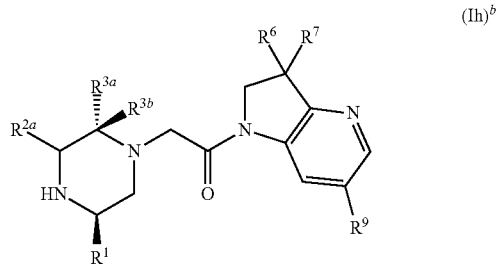

(Ih)$^b$ or tautomeric or stereochemically isomeric forms, N-oxides, pharmaceutically acceptable salts or the solvates thereof; wherein R¹, R$^{2a}$, R$^{3a}$, R$^{3b}$, R⁶, R⁷ and R⁹ are as herein defined or in any of the embodiments.

In one embodiment, the compound of formula (I) is a compound of formula (Ii)$^a$ or (Ii)$^b$:

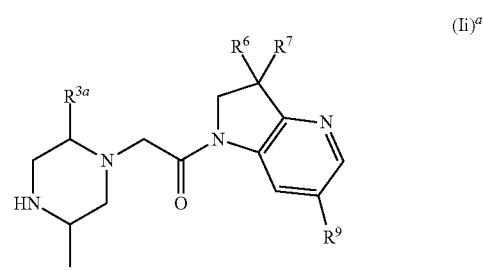

(Ii)$^a$

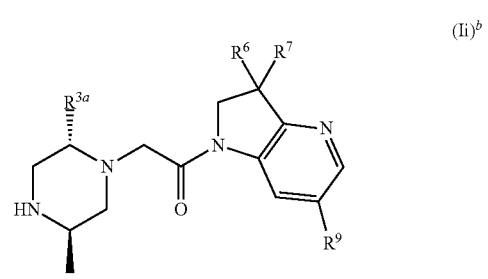

(Ii)$^b$ or tautomeric or stereochemically isomeric forms, N-oxides, pharmaceutically acceptable salts or the solvates thereof; wherein R$^{3a}$, R⁶, R⁷ and R⁹ are as herein defined or in any of the embodiments. In one embodiment R⁶ and R⁷ are both methyl.

In one embodiment, the compound of formula (I) is a compound of formula (Ij)$^a$ or (Ij)$^b$:

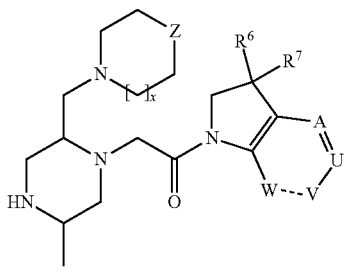

(Ij)$^a$

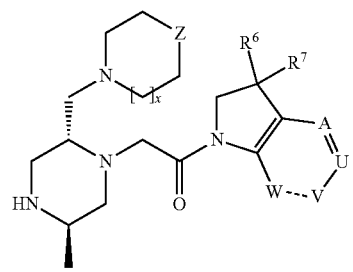

(Ij)$^b$ or tautomeric or stereochemically isomeric forms, N-oxides, pharmaceutically acceptable salts or the solvates thereof; wherein ---- represents a single or double bond, and when ---- represents a double bond then A is selected from CR$^8$ and N,
W is selected from CH and N,
U is selected from CR$^8$ and N, and
V is selected from CR$^9$ and N,
wherein R$^1$, R$^{2a}$, R$^{3a}$, R$^{3b}$, R$^6$, R$^7$, R$^8$ and R$^9$ are as herein defined or in any of the embodiments and wherein z is C, N or O and x is 0, 1, or 2. In one embodiment of formula (Ih) z is 0 and 1.

In one embodiment, the compound of formula (I) is a compound of formula (Ik)$^a$ or (Ik)$^b$:

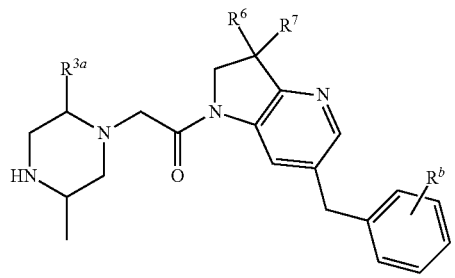

(Ik)$^a$

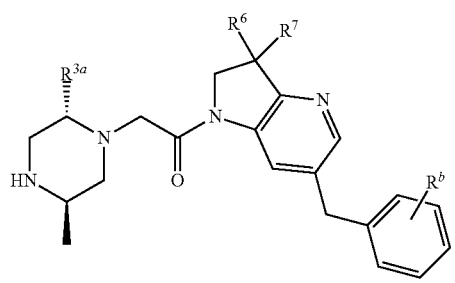

(Ik)$^b$ or tautomeric or stereochemically isomeric forms, N-oxides, pharmaceutically acceptable salts or the solvates thereof; wherein R$^{3a}$, R$^6$, R$^7$ and R$^b$ are as herein defined or in any of the embodiments.

In one embodiment, the compound of formula (I) is a compound of formula (Im) or (In):

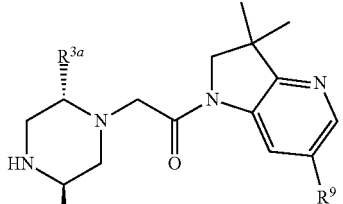

(Im)

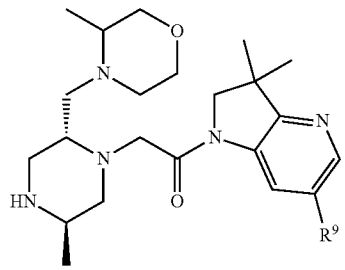

(In)

or tautomeric or stereochemically isomeric forms, N-oxides, pharmaceutically acceptable salts or the solvates thereof; wherein R$^9$ is as herein defined or in any of the embodiments.

In one embodiment, the invention provides a compound of formula (I) which is the free base of a compound of E1-E266 or a tautomeric or stereochemically isomeric form, N-oxide, pharmaceutically acceptable salt or the solvate thereof.

In one particular embodiment which may be mentioned, the invention provides a compound of formula (I) which is the free base of a compound of E1-E116 or a tautomeric or stereochemically isomeric form, N-oxide, pharmaceutically acceptable salt or the solvate thereof.

According to one aspect of the invention, there is provided a compound of formula (I) as hereinbefore defined with the proviso that the compound is other than 1-{6-Benzyl-3,3-dimethyl-1H,2H,3H-pyrrolo[3,2-c]pyridin-1-yl}-2-[3-(trifluoromethyl)piperazin-1-yl]ethan-1-one (E113).

According to one aspect of the invention, there is provided a compound of formula (I) as hereinbefore defined with the proviso that the compound is other than 3,3-Dimethyl-1-[(2S)-2-[(3R)-3-methylpiperazin-1-yl]butanoyl]-2,3-dihydro-1H-indole-6-carbonitrile (E266).

In a further embodiment, the compound of formula (I) comprises a compound of:
1-(6-Benzyl-3,3-dimethyl-2,3-dihydro-pyrrolo[3,2-c]pyridin-1-yl)-2-((2R,5R)-2-methoxymethyl-5-methyl-piperazin-1-yl)-ethanone;
1-{6-Benzyl-3,3-dimethyl-1H,2H,3H-pyrrolo[3,2-c]pyridin-1-yl}-2-[(2R,5R)-5-methyl-2-[(morpholin-4-yl)carbonyl]piperazin-1-yl]ethan-1-one;
1-(6-Benzyl-3,3-dimethyl-2,3-dihydro-indol-1-yl)-2-[(2R,5R)-5-methyl-2-(morpholine-4-carbonyl)-piperazin-1-yl]-ethanone;

1-(6-Benzyl-3,3-dimethyl-2,3-dihydro-pyrrolo[3,2-c]pyridin-1-yl)-2-((2R,5R)-5-methyl-2-pyrazol-1-ylmethyl-piperazin-1-yl)-ethanone (E112);
or a tautomeric or stereochemically isomeric form, N-oxide, pharmaceutically acceptable salt or the solvate thereof, such as:
1-(6-Benzyl-3,3-dimethyl-2,3-dihydro-pyrrolo[3,2-c]pyridin-1-yl)-2-((2R,5R)-2-methoxymethyl-5-methyl-piperazin-1-yl)-ethanone hydrochloride salt (E63);
1-{6-Benzyl-3,3-dimethyl-1H,2H,3H-pyrrolo[3,2-c]pyridin-1-yl}-2-[(2R,5R)-5-methyl-2-[(morpholin-4-yl)carbonyl]piperazin-1-yl]ethan-1-one, hydrochloride salt (E101); or
1-(6-Benzyl-3,3-dimethyl-2,3-dihydro-indol-1-yl)-2-[(2R,5R)-5-methyl-2-(morpholine-4-carbonyl)-piperazin-1-yl]-ethanone, hydrochloride salt (E111).

In one embodiment, the compound of formula (I) is a compound of 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (E259), 1-[6-(1,1-Difluoro-butyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (E260), 1-[6-(2-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (E261), 1-[6-(2,4-Difluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (E264), or a tautomeric or stereochemically isomeric form, N-oxide, pharmaceutically acceptable salt or the solvate thereof, such as 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride (E259), 1-[6-(1,1-Difluoro-butyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride (E260), 1-[6-(2-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride (E261) or 1-[6-(2,4-Difluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride (E264).

In one embodiment, the compound of formula (I) is a compound of 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (E259) or a tautomeric or stereochemically isomeric form, N-oxide, pharmaceutically acceptable salt or the solvate thereof, such as a hydrochloride salt of 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone, i.e. 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride.

For the avoidance of doubt, it is to be understood that each general and specific preference, embodiment and example for one substituent may be combined with each general and specific preference, embodiment and example for one or more, preferably, all other substituents as defined herein and that all such embodiments are embraced by this application.

Salts, Solvates, Tautomers, Isomers, N-Oxides, Esters, Prodrugs and Isotopes

A reference to a compound of the formula (I) and sub-groups thereof also includes ionic forms, salts, solvates, isomers (including geometric and stereochemical isomers), tautomers, N-oxides, esters, prodrugs, isotopes and protected forms thereof, for example, as discussed below; preferably, the salts or tautomers or isomers or N-oxides or solvates thereof; and more preferably, the salts or tautomers or N-oxides or solvates thereof, even more preferably the salts or tautomers or solvates thereof.

Salts

Many compounds of the formula (I) can exist in the form of salts, for example acid addition salts or, in certain cases salts of organic and inorganic bases such as carboxylate, sulfonate and phosphate salts. All such salts are within the scope of this invention, and references to compounds of the formula (I) include the salt forms of the compounds.

The salts of the present invention can be synthesized from the parent compound that contains a basic or acidic moiety by conventional chemical methods such as methods described in *Pharmaceutical Salts: Properties, Selection, and Use*, P. Heinrich Stahl (Editor), Camille G. Wermuth (Editor), ISBN: 3-90639-026-8, Hardcover, 388 pages, August 2002. Generally, such salts can be prepared by reacting the free acid or base forms of these compounds with the appropriate base or acid in water or in an organic solvent, or in a mixture of the two; generally, nonaqueous media such as ether, ethyl acetate, ethanol, isopropanol, or acetonitrile are used.

Acid addition salts (mono- or di-salts) may be formed with a wide variety of acids, both inorganic and organic. Examples of acid addition salts include mono- or di-salts formed with an acid selected from the group consisting of acetic, 2,2-dichloroacetic, adipic, alginic, ascorbic (e.g. L-ascorbic), L-aspartic, benzenesulfonic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, D-gluconic, glucuronic (e.g. D-glucuronic), glutamic (e.g. L-glutamic), α-oxoglutaric, glycolic, hippuric, hydrohalic acids (e.g. hydrobromic, hydrochloric, hydriodic), isethionic, lactic (e.g. (+)-L-lactic, (±)-DL-lactic), lactobionic, maleic, malic, (−)-L-malic, malonic, (±)-DL-mandelic, methanesulfonic, naphthalene-2-sulfonic, naphthalene-1,5-disulfonic, 1-hydroxy-2-naphthoic, nicotinic, nitric, oleic, orotic, oxalic, palmitic, pamoic, phosphoric, propionic, pyruvic, L-pyroglutamic, salicylic, 4-amino-salicylic, sebacic, stearic, succinic, sulfuric, tannic, (+)-L-tartaric, thiocyanic, p-toluenesulfonic, undecylenic and valeric acids, as well as acylated amino acids and cation exchange resins.

One particular group of salts consists of salts formed from acetic, hydrochloric, hydriodic, phosphoric, nitric, sulfuric, citric, lactic, succinic, maleic, malic, isethionic, fumaric, benzenesulfonic, toluenesulfonic, methanesulfonic (mesylate), ethanesulfonic, naphthalenesulfonic, valeric, acetic, propanoic, butanoic, malonic, glucuronic and lactobionic acids. One particular salt is the hydrochloride salt.

If the compound is anionic, or has a functional group which may be anionic (e.g., —COOH may be —COO−), then a salt may be formed with an organic or inorganic base, generating a suitable cation. Examples of suitable inorganic cations include, but are not limited to, alkali metal ions such as $Li^+$, $Na^+$ and $K^+$, alkaline earth metal cations such as $Ca^{2+}$ and $Mg^{2+}$, and other cations such as $Al^{3+}$ or $Zn^+$. Examples of suitable organic cations include, but are not limited to, ammonium ion (i.e., $NH_4^+$) and substituted ammonium ions (e.g., $NH_3R^+$, $NH_2R_2^+$, $NHR_3^+$, $NR_4^+$). Examples of some suitable substituted ammonium ions are those derived from: methylamine, ethylamine, diethylamine, propylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

Where the compounds of the formula (I) contain an amine function, these may form quaternary ammonium salts, for example by reaction with an alkylating agent according to methods well known to the skilled person. Such quaternary ammonium compounds are within the scope of formula (I).

The compounds of the invention may exist as mono- or di-salts depending upon the pKa of the acid from which the salt is formed.

The salt forms of the compounds of the invention are typically pharmaceutically acceptable salts, and examples of pharmaceutically acceptable salts are discussed in Berge et al., 1977, "Pharmaceutically Acceptable Salts," *J. Pharm. Sci.*, Vol. 66, pp. 1-19. However, salts that are not pharmaceutically acceptable may also be prepared as intermediate forms which may then be converted into pharmaceutically acceptable salts. Such non-pharmaceutically acceptable salt forms, which may be useful, for example, in the purification or separation of the compounds of the invention, also form part of the invention.

In one embodiment of the invention, there is provided a pharmaceutical composition comprising a solution (e.g. an aqueous solution) containing a compound of the formula (I) and sub-groups and examples thereof as described herein in the form of a salt in a concentration of greater than 10 mg/ml, typically greater than 15 mg/ml and preferably greater than 20 mg/ml.

N-Oxides

Compounds of the formula (I) containing an amine function may also form N-oxides. A reference herein to a compound of the formula (I) that contains an amine function also includes the N-oxide.

Where a compound contains several amine functions, one or more than one nitrogen atom may be oxidised to form an N-oxide. Particular examples of N-oxides are the N-oxides of a tertiary amine or a nitrogen atom of a nitrogen-containing heterocycle.

N-Oxides can be formed by treatment of the corresponding amine with an oxidizing agent such as hydrogen peroxide or a per-acid (e.g. a peroxycarboxylic acid), see for example *Advanced Organic Chemistry*, by Jerry March, 4th Edition, Wiley Interscience, pages. More particularly, N-oxides can be made by the procedure of L. W. Deady (*Syn. Comm.* 1977, 7, 509-514) in which the amine compound is reacted with m-chloroperoxybenzoic acid (MCPBA), for example, in an inert solvent such as dichloromethane.

Geometric Isomers and Tautomers

Compounds of the formula (I) may exist in a number of different geometric isomeric, and tautomeric forms and references to compounds of the formula (I) include all such forms. For the avoidance of doubt, where a compound can exist in one of several geometric isomeric or tautomeric forms and only one is specifically described or shown, all others are nevertheless embraced by formula (I).

For example, in compounds of the formula (I), ring E can exist in two tautomeric forms as illustrated below. For simplicity, the general formula (I) illustrates one form A but the formula is to be taken as embracing both tautomeric forms.

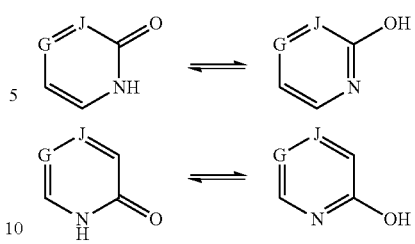

Other examples of tautomeric forms include, for example, keto-, enol-, and enolate-forms, as in, for example, the following tautomeric pairs: keto/enol (illustrated below), imine/enamine, amide/imino alcohol, amidine/enediamines, nitroso/oxime, thioketone/enethiol, and nitro/aci-nitro.

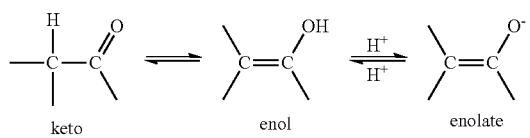

Stereoisomers

Unless otherwise mentioned or indicated, the chemical designation of compounds denotes the mixture of all possible stereochemically isomeric forms.

Stereocentres are illustrated in the usual fashion, using 'hashed' or 'wedged' lines. e.g.

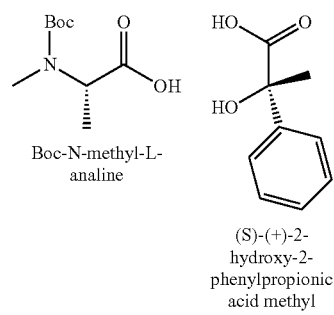

Where a compound is described as a mixture of two diastereoisomers/epimers, the configuration of the stereocentre is not specified and is represented by straight lines.

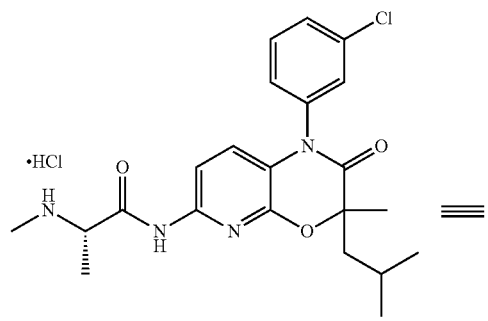

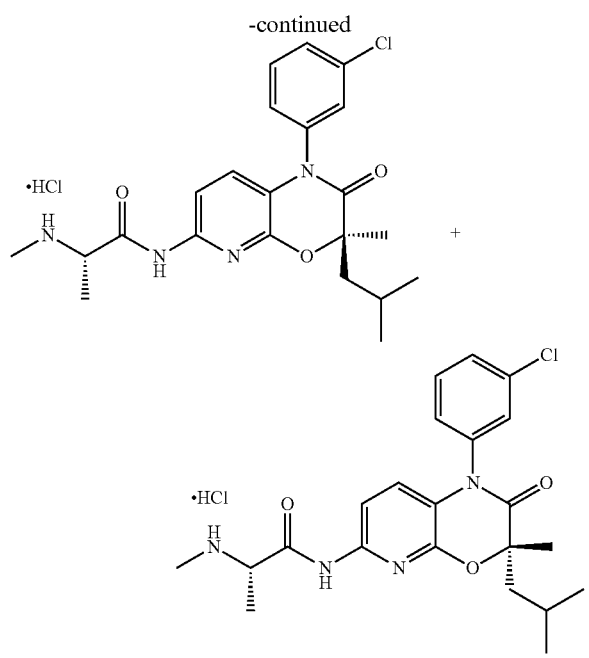

Where compounds of the formula (I) contain one or more chiral centres, and can exist in the form of two or more optical isomers, references to compounds of the formula (I) include all optical isomeric forms thereof (e.g. enantiomers, epimers and diastereoisomers), either as individual optical isomers, or mixtures (e.g. racemic mixtures) or two or more optical isomers, unless the context requires otherwise.

The optical isomers may be characterised and identified by their optical activity (i.e. as + and − isomers, or d and l isomers) or they may be characterised in terms of their absolute stereochemistry using the "R and S" nomenclature developed by Cahn, Ingold and Prelog, see *Advanced Organic Chemistry* by Jerry March, 4$^{th}$ Edition, John Wiley & Sons, New York, 1992, pages 109-114, and see also Cahn, Ingold & Prelog, *Angew. Chem. Int. Ed. Engl.,* 1966, 5, 385-415.

Optical isomers can be separated by a number of techniques including chiral chromatography (chromatography on a chiral support) and such techniques are well known to the person skilled in the art.

As an alternative to chiral chromatography, optical isomers can be separated by forming diastereoisomeric salts with chiral acids such as (+)-tartaric acid, (−)-pyroglutamic acid, (−)-di-toluoyl-L-tartaric acid, (+)-mandelic acid, (−)-malic acid, and (−)-camphorsulfonic acid, separating the diastereoisomers by preferential crystallisation, and then dissociating the salts to give the individual enantiomer of the free base.

Additionally enantiomeric separation can be achieved by covalently linking a enantiomerically pure chiral auxiliary onto the compound and then performing diastereoisomer separation using conventional methods such as chromatography. This is then followed by cleavage of the aforementioned covalent linkage to generate the appropriate enantiomerically pure product.

Where compounds of the formula (I) exist as two or more optical isomeric forms, one enantiomer in a pair of enantiomers may exhibit advantages over the other enantiomer, for example, in terms of biological activity. Thus, in certain circumstances, it may be desirable to use as a therapeutic agent only one of a pair of enantiomers, or only one of a plurality of diastereoisomers. Accordingly, the invention provides compositions containing a compound of the formula (I) having one or more chiral centres, wherein at least 55% (e.g. at least 60%, 65%, 70%, 75%, 80%, 85%, 90% or 95%) of the compound of the formula (I) is present as a single optical isomer (e.g. enantiomer or diastereoisomer). In one general embodiment, 99% or more (e.g. substantially all) of the total amount of the compound of the formula (I) may be present as a single optical isomer (e.g. enantiomer or diastereoisomer).

Compounds encompassing double bonds can have an E (entgegen) or Z (zusammen) stereochemistry at said double bond. Substituents on bivalent cyclic or (partially) saturated radicals may have either the cis- or trans-configuration. The terms cis and trans when used herein are in accordance with Chemical Abstracts nomenclature (J. Org. Chem. 1970, 35 (9), 2849-2867), and refer to the position of the substituents on a ring moiety.

Of special interest are those compounds of formula (I) which are stereochemically pure. When a compound of formula (I) is for instance specified as R, this means that the compound is substantially free of the S isomer. If a compound of formula (I) is for instance specified as E, this means that the compound is substantially free of the Z isomer. The terms cis, trans, R, S, E and Z are well known to a person skilled in the art.

Isotopic Variations

The present invention includes all pharmaceutically acceptable isotopically-labeled compounds of the invention, i.e. compounds of formula (I), wherein one or more atoms are replaced by atoms having the same atomic number, but an atomic mass or mass number different from the atomic mass or mass number usually found in nature.

Examples of isotopes suitable for inclusion in the compounds of the invention comprise isotopes of hydrogen, such as $^{2}$H (D) and $^{3}$H (T), carbon, such as $^{11}$C, $^{13}$C and $^{14}$C, chlorine, such as $^{36}$Cl, fluorine, such as $^{18}$F, iodine, such as $^{123}$I, $^{125}$I and $^{131}$I, nitrogen, such as $^{13}$N and $^{15}$N, oxygen, such as $^{15}$O, $^{17}$O and $^{18}$O, phosphorus, such as $^{32}$P, and sulfur, such as $^{35}$S.

Certain isotopically-labelled compounds of formula (I), for example, those incorporating a radioactive isotope, are useful in drug and/or substrate tissue distribution studies. The compounds of formula (I) can also have valuable diagnostic properties in that they can be used for detecting or identifying the formation of a complex between a labelled compound and other molecules, peptides, proteins, enzymes or receptors. The detecting or identifying methods can use compounds that are labelled with labelling agents such as radioisotopes, enzymes, fluorescent substances, luminous substances (for example, luminol, luminol derivatives, luciferin, aequorin and luciferase), etc. The radioactive isotopes tritium, i.e. $^{3}$H (T), and carbon-14, i.e. $^{14}$C, are particularly useful for this purpose in view of their ease of incorporation and ready means of detection.

Substitution with heavier isotopes such as deuterium, i.e. $^{2}$H (D), may afford certain therapeutic advantages resulting from greater metabolic stability, for example, increased in vivo half-life or reduced dosage requirements, and hence may be preferred in some circumstances. Substitution with positron emitting isotopes, such as $^{11}$C, $^{18}$F, $^{15}$O and $^{13}$N, can be useful in Positron Emission Topography (PET) studies for examining target occupancy.

Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Esters

Esters such as carboxylic acid esters, acyloxy esters and phosphate esters of the compounds of formula (I) bearing a carboxylic acid group or a hydroxyl group are also embraced by Formula (I). Examples of esters are compounds containing the group —C(=O)OR, wherein R is an ester substituent, for example, a $C_{1-7}$ alkyl group, a $C_{3-12}$ heterocyclyl group, or a $C_{5-12}$ aryl group, preferably a $C_{1-6}$ alkyl group. Particular examples of ester groups include, but are not limited to —C(=O)OCH$_3$, —C(=O)OCH$_2$CH$_3$, —C(=O)OC(CH$_3$)$_3$, and —C(=O)OPh. Examples of acyloxy (reverse ester) groups are represented by —OC(=O)R, wherein R is an acyloxy substituent, for example, a $C_{1-6}$ alkyl group, a $C_{3-12}$ heterocyclyl group, or a $C_{5-12}$ aryl group, preferably a $C_{1-6}$ alkyl group. Particular examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph. Examples of phosphate esters are those derived from phosphoric acid.

In one embodiment of the invention, formula (I) includes within its scope esters of compounds of the formula (I) bearing a carboxylic acid group or a hydroxyl group. In another embodiment of the invention, formula (I) does not include within its scope esters of compounds of the formula (I) bearing a carboxylic acid group or a hydroxyl group.

Solvates and Crystalline Forms

Also encompassed by formula (I) are any polymorphic forms of the compounds, and solvates such as hydrates, alcoholates and the like.

The compounds of the invention may form solvates, for example with water (i.e., hydrates) or common organic solvents. As used herein, the term "solvate" means a physical association of the compounds of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include compounds of the invention in combination with water, isopropanol, ethanol, methanol, DMSO, ethyl acetate, acetic acid or ethanolamine and the like. The compounds of the invention may exert their biological effects whilst they are in solution.

Solvates are well known in pharmaceutical chemistry. They can be important to the processes for the preparation of a substance (e.g. in relation to their purification, the storage of the substance (e.g. its stability) and the ease of handling of the substance and are often formed as part of the isolation or purification stages of a chemical synthesis. A person skilled in the art can determine by means of standard and long used techniques whether a hydrate or other solvate has formed by the isolation conditions or purification conditions used to prepare a given compound. Examples of such techniques include thermogravimetric analysis (TGA), differential scanning calorimetry (DSC), X-ray crystallography (e.g. single crystal X-ray crystallography or X-ray powder diffraction) and Solid State NMR (SS-NMR, also known as Magic Angle Spinning NMR or MAS-NMR). Such techniques are as much a part of the standard analytical toolkit of the skilled chemist as NMR, IR, HPLC and MS.

Alternatively the skilled person can deliberately form a solvate using crystallisation conditions that include an amount of the solvent required for the particular solvate. Thereafter the standard methods described above, can be used to establish whether solvates had formed.

Furthermore, the compounds of the present invention may have one or more polymorph or amorphous crystalline forms and as such are intended to be included in the scope of the invention.

Complexes

Formula (I) also includes within its scope complexes (e.g. inclusion complexes or clathrates with compounds such as cyclodextrins, or complexes with metals) of the compounds. Inclusion complexes, clathrates and metal complexes can be formed by means of methods well known to the skilled person.

Prodrugs

Also encompassed by formula (I) are any pro-drugs of the compounds of the formula (I). By "prodrugs" is meant for example any compound that is converted in vivo into a biologically active compound of the formula (I).

For example, some prodrugs are esters of the active compound (e.g., a physiologically acceptable metabolically labile ester). During metabolism, the ester group (—C(=O) OR) is cleaved to yield the active drug. Such esters may be formed by esterification, for example, of any of the carboxylic acid groups (—C(=O)OH) in the parent compound, with, where appropriate, prior protection of any other reactive groups present in the parent compound, followed by deprotection if required.

Examples of such metabolically labile esters include those of the formula —C(=O)OR wherein R is:
$C_{1-7}$alkyl (e.g., -Me, -Et, -nPr, -iPr, -nBu, -sBu, -iBu, -tBu); $C_{1-7}$aminoalkyl (e.g., aminoethyl; 2-(N,N-diethylamino) ethyl; 2-(4-morpholino)ethyl); and acyloxy-$C_{1-7}$alkyl (e.g., acyloxymethyl; acyloxyethyl; pivaloyloxymethyl; acetoxymethyl; 1-acetoxyethyl; 1-(1-methoxy-1-methyl) ethyl-carbonxyloxyethyl; 1-(benzoyloxy)ethyl; isopropoxy-carbonyloxymethyl; 1-isopropoxy-carbonyloxyethyl; cyclohexyl-carbonyloxymethyl; 1-cyclohexyl-carbonyloxyethyl; cyclohexyloxy-carbonyloxymethyl; 1-cyclohexyloxy-carbonyloxyethyl; (4-tetrahydropyranyloxy) carbonyloxymethyl; 1-(4-tetrahydropyranyloxyl)carbonyloxyethyl; (4-tetrahydropyranyl)carbonyloxymethyl; and 1-(4-tetrahydropyranyl)carbonyloxyethyl).

Also, some prodrugs are activated enzymatically to yield the active compound, or a compound which, upon further chemical reaction, yields the active compound (for example, as in antigen-directed enzyme pro-drug therapy (ADEPT), gene-directed enzyme pro-drug therapy (GDEPT), and ligand-directed enzyme pro-drug therapy (LIDEPT), etc.). For example, the prodrug may be a sugar derivative or other glycoside conjugate, or may be an amino acid ester derivative. In one embodiment formula (I) does not include pro-drugs of the compounds of the formula (I) within its scope.

Methods for the Preparation of Compounds of Formula (I)

In this section, as in all other sections of this application unless the context indicates otherwise, references to formula (I) also include all other sub-groups and examples thereof as defined herein.

Compounds of the formula (I) can be prepared in accordance with synthetic methods well known to the skilled person.

According to a further aspect of the invention there is provided a process for preparing a compound of formula (I) as hereinbefore defined which comprises:

(a) (i) reacting a compound of formula (II):

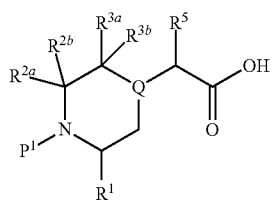

(II)

wherein $R^1$, $R^{2a}$, $R^{2b}$, $R^{3a}$, $R^{3b}$, $R^5$ and Q are as defined hereinbefore for compounds of formula (I) and $P^1$ represents a suitable protecting group such as a tert-butyloxycarbonyl (tBoc) group, with a compound of formula (III):

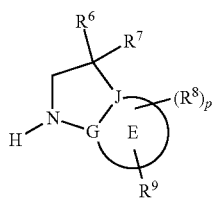

(III)

wherein $R^6$, $R^7$, $R^8$, $R^9$, p, G, J and E are as defined hereinbefore for compounds of formula (I), followed by a deprotection reaction suitable to remove the $P^1$ protecting group; or (ii) for compounds of formula (I) wherein Q represents NH, reacting a compound of formula (III) as defined above with a compound of formula (IV):

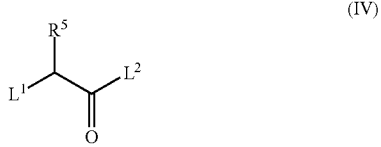

(IV)

wherein $R^5$ is as defined hereinbefore for compounds of formula (I), and $L^1$ and $L^2$ independently represent suitable leaving groups such as halogen, then subsequent reaction with a compound of formula (V):

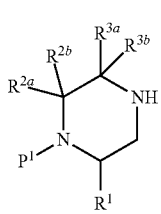

(V)

wherein $R^1$, $R^{2a}$, $R^{2b}$, $R^{3a}$ and $R^{3b}$ are as defined hereinbefore for compounds of formula (I) and $P^1$ represents hydrogen or a suitable protecting group such as a tert-butyloxycarbonyl (tBoc) group, followed by a deprotection reaction suitable to remove the $P^1$ protecting group; and/or (b) deprotection of a protected derivative of a compound of formula (I); and/or (c) interconversion of a compound of formula (I) or protected derivative thereof to a further compound of formula (I) or protected derivative thereof; and (d) optional formation of a pharmaceutically acceptable salt of a compound of formula (I).

Process (a)(i) typically comprises reacting a compound of formula (II) with a compound of formula (III) in a suitable solvent and at a suitable temperature e.g. ambient temperature, in the presence of a suitable base and a reagent capable of activating the carboxylic acid group present in the compound of formula (II). A suitable solvent should be inert toward the reagents used, for example dichloromethane. Examples of suitable bases are triethylamine and N,N-diisopropylethylamine (DIPEA). Examples of suitable activating reagents are bromo-tris-pyrrolidino-phosphonium hexofluorophosphate (PyBrop), O-benzotriazole-N,N,N',N'-tetramethyl-uronium-hexafluoro-phosphate (HBTU), 1,1'-carbonyldiimidazole, 1-ethyl-3-(3'-dimethylaminopropyl)-carbodiimide hydrochloride (EDC) and 2-(7-aza-1H-benzotriazole-1-yl)-1,1,3,3-tetramethyluronium hexafluorophosphate) (HATU). This process may optionally be carried out in the presence of a catalytic or stoichiometric amount of a suitable co-activating reagent such as 1-hydroxybenzotriazole (HOBt) or 1-hydroxyazabenzotriazole (HOAt).

Process (a) may be carried out in accordance with the procedure described herein as General Procedure 1 (PyBrop Coupling), or General Procedure 2 (HBTU coupling), or with the procedure described herein as General Procedure 4 (HATU coupling).

Process (a) (ii) typically comprises dissolving a compound of formula (III) in a suitable solvent such as dichloromethane then treatment with a suitable base such as triethylamine, followed by a compound of formula (IV). The reactive intermediate resulting from reaction of the compounds of formulas (III) and (IV) is then treated with a compound of formula (V) in a suitable solvent such as tetrahydrofuran in the presence of a suitable base such as triethylamine or N,N-diisopropylethylamine. Examples of suitable leaving groups $L^1$ and $L^2$ in the compound of formula (IV) are chloro and bromo.

Process (a) (ii) may be carried out with isolation of the initially formed reactive intermediate, in accordance with the procedures described herein as Preparation 1 and Preparation 6 or Preparation 442 and Preparation 443. In such a two step procedure, the first step may be carried out in the presence of a base such as pyridine, triethylamine or N,N-diisopropylethylamine in a suitable solvent such as diethyl ether or dichloromethane.

Advantageously the first step may be carried out without added base in a solvent chosen such that the first step intermediate precipitates from the reaction mixture as an acid addition salt, for example toluene or acetonitrile. The second step may then be carried out in a suitably inert solvent such as tetrahydrofuran, dichloromethane or acetonitrile, in the presence of a base such as triethylamine or anhydrous potassium carbonate. Where $L^1$ represents chlorine in the compound of formula (IV) the reaction may optionally be accelerated by addition of an iodide salt such as potassium iodide.

This process may also be performed without isolation of the reactive intermediate formed from reaction of the compound of formula (III) with the compound of formula (IV). Thus, a mixture of a compound of formula (III) and a suitable base in excess, such as triethylamine or N,N-diisopropylethylamine, dissolved in a suitably inert solvent such as dichloromethane is treated with a compound of formula (IV) followed, after a suitable time interval, e.g. 1 or 2 hours, with a compound of formula (V).

Process (a) (ii) may be carried out in accordance with the procedures described herein as Preparations 203, 204, 205 and General Procedure 5.

In an alternative process, process (a) (ii) may be carried out in a two step process as described in Preparations 442 and 443.

Process (b) typically comprises any suitable deprotection reaction, the conditions of which will depend upon the nature of the protecting group. When the protecting group represents tBoc, such a deprotection reaction will typically comprise the use of a suitable acid in a suitable solvent. For example, the acid may suitably comprise trifluoroacetic acid or hydrogen chloride and the solvent may suitably comprise dichloromethane ethyl acetate, 1,4-dioxane, methanol or water. Optionally a mixture of solvents may be used, for example aqueous methanol or ethyl acetate/1,4-dioxane.

Process (b) may be carried out in accordance with the procedures described herein as General Procedures for Preparation of Compounds of Formula (I), Methods 1-4.

It will be appreciated that, when the protecting group represents tBoc, deprotection using a suitable acid as described above may generate a compound of formula (I) as a pharmaceutically acceptable salt, which may be isolated directly. Alternatively, the compound of formula (I) may be isolated as the free base using methods well known in the art and thereafter optionally converted to a pharmaceutically acceptable salt according to process (d).

Process (c) typically comprises interconversion procedures known by one skilled in the art. For example, compounds of formula (I) in which $R^8$ or $R^9$ represents a first substituent may be converted by methods known by one skilled in the art into compounds of formula (I) in which $R^8$ or $R^9$ represents a second, alternative substituent. Suitable experimental for such an interconversion reaction is described herein in Preparations 134 to 152. In particular, compounds of formula (I) wherein $R^8$ or $R^9$ represents a halogen atom, such as chlorine or bromine, may be converted to compounds of formula (I) wherein $R^8$ or $R^9$ represents a —Y—$C_{3-12}$ carbocyclyl group, such as a —$CH_2$-phenyl group. Suitable experimental for such an interconversion reaction is described herein as General Procedure 3 (Organozinc halide addition).

Another particular case of process (c) involves reaction of a protected derivative of a compound of formula (I), wherein $R^{3a}$ or $R^{3b}$ represent $C_{1-6}$alkyl substituted with a single group $R^b$ where $R^b$ represents chlorine, bromine or iodine, with a suitable nucleophile for the introduction of an optionally substituted 3-12 membered heterocyclyl group as defined above. Such a process may be carried out in an inert solvent such as acetonitirile in the presence of a suitable base such as potassium carbonate, optionally in the presence of an iodide salt such as potassium iodide. Such a process may be carried out in accordance with the procedure described herein as Preparation 436, 438, 440, or General Procedure 6.

In one embodiment, the interconversion of process (c) comprises the following reaction:

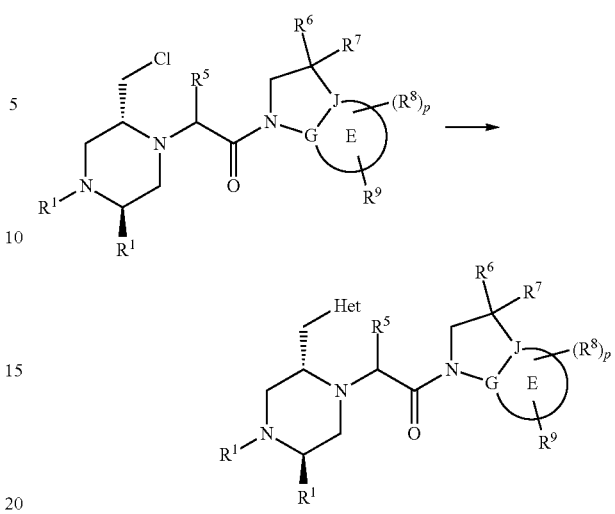

wherein $P^1$ represents a suitable protecting group such as a tert-butyloxycarbonyl (tBoc) group, and Het represents a 3-12 membered heterocyclyl group which may be optionally substituted by one or more $R^b$ groups and wherein $R^b$, $R^1$, $R^5$, $R^6$, $R^7$, $R^8$, $R^9$, G, J, E and p are as defined hereinbefore, followed by a deprotection reaction suitable to remove the $P^1$ protecting group.

Process (d) may be carried out by treatment of a compound of formula (I) in the free base form, dissolved in a suitable solvent, with a stoichiometric amount or an excess of a pharmaceutically acceptable organic or inorganic acid, then isolation of the resulting salt by methods well known in the art, e.g. evaporation of solvent or crystallisation.

If appropriate, the reactions previously described in processes (a), (b) and (c) are followed or preceded by one or more reactions known to the skilled of the art and are performed in an appropriate order to achieve the requisite substitutions on $R^1$, $R^{2a}$, $R^{2b}$, $R^{3a}$, $R^{3b}$, $R^5$, $R^6$, $R^7$, $R^8$ and $R^9$ defined above to afford other compounds of formula (I). Non-limiting examples of such reactions whose conditions can be found in the literature include:
  protection of reactive functions,
  deprotection of reactive functions,
  halogenation,
  dehalogenation,
  dealkylation,
  alkylation and arylation of amine, aniline, alcohol and phenol,
  Mitsunobu reaction on hydroxyl groups,
  cycloaddition reactions on appropriate groups,
  reduction of nitro, esters, cyano, aldehydes,
  transition metal-catalyzed coupling reactions,
  acylation,
  sulfonylation/introduction of sulfonyl groups,
  saponification/hydrolysis of ester groups,
  amidification or transesterification of ester groups,
  esterification or amidification of carboxylic groups,
  halogen exchange,
  nucleophilic substitution with amine, thiol or alcohol,
  reductive amination,
  oxime formation on carbonyl and hydroxylamine groups,
  S-oxidation,
  N-oxidation,
  salification.

Compounds of formula (II) where Q is NH and wherein $R^1$, $R^{2a}$, $R^{2b}$, $R^{3a}$, $R^{3b}$ and $R^5$ are as defined hereinbefore may be prepared by reaction of a compound of formula (V) as defined hereinbefore with a compound of formula (VI)

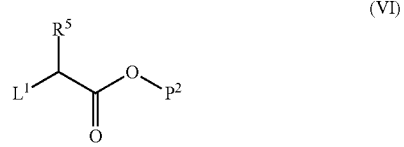

(VI)

Wherein $R^5$ and $L^1$ are as defined hereinbefore and $P^2$ represents a suitable protecting group, followed by the removal of the protecting group $P^2$. Such a reaction may be carried out in a suitably inert solvent such as acetonitrile in the presence of a suitable base such as sodium carbonate or potassium carbonate at a suitable temperature such as ambient temperature or elevated temperature, e.g. under reflux. Advantageously, the group $P^2$ should be removable in such a manner to leave the protecting group $P^1$ intact, hence suitable examples for $P^2$ include optionally substituted benzyl and allyl, where removal may be effected by caltalytic hydrogenolysis or palladium catalysed de-allylation respectively. Alternatively where the group $P^2$ represents lower alkyl, removal may be effected by saponification e.g. hydrolysis using aqueous alkali.

Compounds of formula (III) where J represents C may be prepared from a compound of formula (VII)

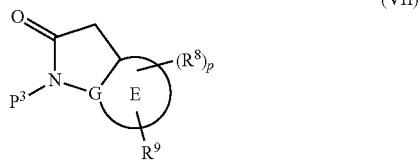

(VII)

wherein $R^8$, $R^9$, p, G and E are as defined hereinbefore for compounds of formula (I) and $P^3$ represents either hydrogen or a suitable protecting group such as tBoc or trimethylsilylethoxymethyl, by treatment with a suitable base and successive reaction with suitable electrophilic reagents for introduction of the groups $R^6$ and $R^7$, for example with compounds of formula $R^6$-$L^3$ and $R^7$-$L^3$, wherein $R^6$ and $R^7$ are as defined hereinbefore and $L^3$ represents a suitable leaving group such as halogen, methylsulfonyloxy or trifluoromethylsulfonyloxy; followed by reduction of the cyclic amide moiety by methods well known in the art. Optionally, functional groups present in $R^6$ and $R^7$ may be interconverted using methods well known in the art; such interconversions may be performed prior to or following the amide reduction step. Examples of suitable bases for the base-mediated introduction of the groups $R^6$ and $R^7$ are alkali metal salts such as sodium carbonate or potassium carbonate and alkylmetal reagents such as butyllithium. Reactions as above involving use of alkali metal salts may be carried out in a compatible solvent such as N,N-dimethylformamide or acetonitrile. Reactions as above involving an alkylmetal reagent as base may be carried out in a suitably inert solvent such as tetrahydrofuran, optionally in conjunction with a suitable additive such as N,N,N',N'-tetramethyethylenediamine (TMEDA) or a lithium halide. It will be appreciated that compounds in which $R^6$ and $R^7$ are joined to form a carbocyle or heterocycle as defined hereinbefore may be prepared in an analogous manner using an appropriate bidentate electrophile, for example 1,2-dibromoethane, 1,3-diiodopropane or 1,4-diiodobutane. Another example of a suitable electrophile for use in the above transformation is a low molecular weight aldehyde e.g. formaldehyde or a compound of formula $C_{1-6}$alkyl-CHO.

For example, use of excess formaldehyde in the presence of an alkali metal salt such as potassium carbonate provides optionally N-protected compounds of formula (III) in which both $R^6$ and $R^7$ represent $CH_2OH$; subsequent functional group interconversion may be carried out, for example conversion of the hydroxyl groups to a suitable leaving group and reaction with a suitable nucleophile or nucleophiles to give optionally protected compounds of formula (III) where $R^6$ and $R^7$ may or may not be connected to form a carbocycle or heterocycle as defined hereinbefore. A particular instance of this generic sequence is described herein for the formation of spiro-azetidine systems using procedures given for Preparations 91-98 inclusive. Suitable reagents for reduction of the cyclic amide moiety include borane-dimethyl sulfide complex or Red-Al® and such reactions may be carried out in a suitably inert solvent such as tetrahydrofuran or toluene.

Compounds of formula (VII) are commercially available, known in the literature or may be prepared from a compound of formula (VIII)

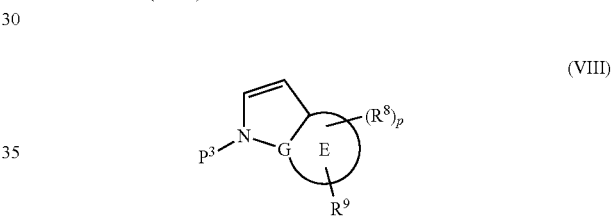

(VIII)

wherein $R^8$, $R^9$, p, G and E are as defined hereinbefore for compounds of formula (I) and $P^3$ represents either hydrogen or a suitable protecting group such as tBoc or trimethylsilylethoxymethyl, using redox methods. For example the compound of formula (VII) may be treated with a brominating agent such as bromine or pyridinium tribromide in a suitable solvent such as 1,4-dioxane followed by hydrolytic work-up; the product, optionally dissolved in an appropriate co-solvent such as tetrahydrofuran, may then be treated with a suitable reducing agent such as a finely divided metal in the presence of an acid, e.g. zinc powder in acetic acid or aqueous ammonium chloride. Such a process may be carried out in an analogous manner to procedures described herein as Preparations 102 and 103.

Compounds of formula (III) as defined hereinbefore wherein $R^6$ and $R^7$ represent hydrogen may be prepared by direct reduction of a compound of formula (VIII) as defined hereinbefore using a suitable reducing agent, for example borane in tetrahydrofuran or sodium cyanoborohydride in the presence of an acid such as acetic acid.

Compounds of formula (VIII) are commercially available, known in the literature, prepared by methods analogous to those in the literature or prepared by methods analogous to those described in the example experimental procedures below. For example see J. Chem. Soc. Perkin Trans. 1, 2000, 1045 for a review of methods known in the art for the synthesis of indoles.

Alternatively, compounds of formula (III) wherein J represents C and $R^7$ represents a group $CHR^{7a}R^{7b}$ (wherein $R^{7a}$ and $R^{7b}$ independently represent $C_{1-7}$alkyl, $C_{1-4}$alkoxy-$C_{1-4}$alkyl, carbocylyl-$C_{1-4}$alkoxy-$C_{1-4}$alkyl, heterocyclyl-$C_{1-4}$alkoxy-$C_{1-4}$alkyl carbocylyl, heterocyclyl, carbocylyl-$C_{1-4}$alkyl, heterocyclyl-$C_{1-4}$alkyl, carbocylyl-oxy or heterocyclyl-oxy; or together may be joined to form a carbocyclyl or heterocyclyl group) may be prepared from a compound of formula (IX)

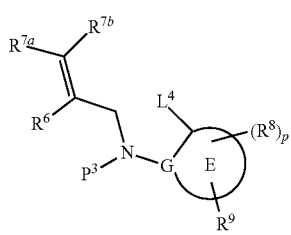

wherein $R^6$, $R^{7a}$, $R^{7b}$, $R^8$, $R^9$, p, G, E and $P^3$ are as defined hereinbefore and $L^4$ represents a suitably reactive group e.g. a leaving group such as halogen or trifluoromethylsulfonyloxy, by cyclisation using an appropriate transition metal catalysed or radical mediated process. For example, this process may be catalysed using cobalt, nickel or palladium and may be carried out in an analogous method to that described in Tetrahedron Letters 1987, 28, 5291-5294, in which case a suitable transition metal source is required such as palladium acetate and $L^4$ advantageously represents iodo. This process requires the presence of a base such as an alkali metal salt such as sodium carbonate or sodium acetate or an organic base such as triethylamine, and may be performed in the presence of a trialkylammonium salt such as tetrabutylammonium chloride. The reaction may be carried out under reducing conditions e.g. in the presence of a salt of formic acid such as sodium formate and optionally in the presence of a suitable ligand such as triphenylphosphine. Suitable solvents for this cyclisation include N,N-dimethylformamide and mixed solvent systems such as toluene-water or dimethyl sulfoxide-water. A particular instance of this cyclisation process is described in Preparations 107-109, and in Preparation 236. For radical cyclisation, a suitable reagent is required for radical generation is required such as an organotin reagent, e.g. tributylstannane. An example of a radical-mediated cyclisation according to this process is described in J. Amer. Chem. Soc. 1992, 114, 9318-9327.

Compounds of formula (IX) can be prepared by reaction of a compound of formula (X)

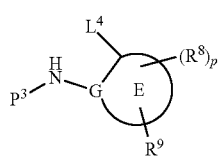

wherein $R^8$, $R^9$, p, G, E, $L^4$ and $P^3$ are as defined hereinbefore, with a compound of formula (XI)

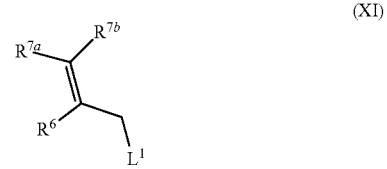

wherein $R^6$, $R^{7a}$, $R^{7b}$ and $L^1$ are as defined hereinbefore. This process is carried out in the presence of a base such as potassium tert-butoxide in a suitable solvent such as tetrahydrofuran.

Alternatively, compounds of formula (III) where G and J both represent C and ring E is phenylene may be prepared by reaction of a compound of formula (XII)

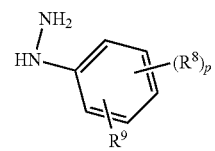

wherein $R^8$, $R^9$ and p are defined hereinbefore, with a compound of formula $R^6R^7CHCHO$, wherein $R^6$ and $R^7$ are defined hereinbefore, to form a hydrazone, then subsequent cyclisation form the desired substituted indoline. Such a process is typically accomplished using acidic conditions, for example using acetic acid as solvent or using an appropriate acid in an inert solvent such as toluene. It will be appreciated that, for certain combinations of $R^8$ and $R^9$, this sequence will result in production of a mixture of regioisomers and that separation of these may be carried out by standard methods known by one skilled in the art e.g. column chromatography. Such a separation may be facilitated by N-acylation of the product from this process e.g. using chloroacetyl chloride or N-protection using, for example a tBoc protecting group after which the compound of formula (III) may optionally be re-generated by deprotection using standard conditions, e.g. for a tBoc protected compound, treatment with an appropriate acid such as HCl.

Compounds of formula (III) wherein J is N may be prepared from a compound of formula (XIII)

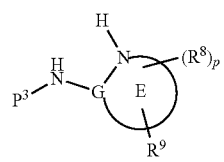

$R^8$, $R^9$, p, G, E, and $P^3$ are as defined hereinbefore, and a compound of formula (XIV)

wherein $R^6$, $R^7$, $L^1$ and $L^2$ are as defined hereinbefore. Such a process may be carried out in the presence of a suitable base such as an alkali metal salt such as potassium carbonate in a suitable solvent such as N,N-dimethylformamide or acetonitrile.

Certain compounds of formulas (III), (VII) and (VIII) may be prepared by functional group interconversions on other compounds of formulas (III), (VII) and (VIII) or suitably protected derivatives thereof and, optionally, subsequent deprotection as appropriate. Examples of functional group interconversions include C-arylation, C-alkylation or C-amination using transition metal mediated methods, chlorosulfonylation and subsequent transformation into sulfones and sulfonamides, de-halogenation using reductive methods such as catalytic hydrogenation, conversion of an aryl halide to an aryl ketone (e.g. by metal-halogen exchange and quench with an appropriate acylating agent), conversion of a ketone group into a difluoromethylene moiety using an appropriate fluorinating agent, and conversion of a carboxylic acid derivative into an amide. Several illustrative methods are given herein (see example experimental procedures below).

Alternatively, compounds of formula (III) where G and J both represent C and ring E is phenylene may be prepared according to the following scheme:

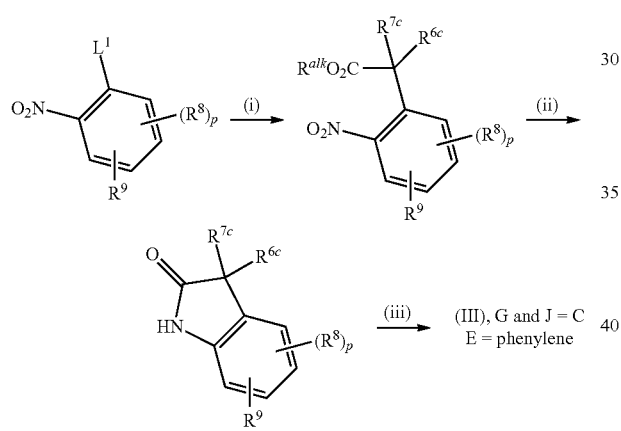

wherein $R^8$, $R^9$, p and $L^1$ are as defined above, $R^{alk}$ represents a $C_{1-4}$ alkyl group or optionally substituted benzyl, $R^{6c}$ is as defined for $R^6$ or may be converted to $R^6$ by functional group interconversions such as those defined above, and $R^{7c}$ is as defined for $R^7$ or a hydrogen atom. Stage (i) involves reaction with a compound $R^{alk}O_2CCH(R^{6c}R^{7c})$ in the presence of a base such as sodium hydride in a suitable solvent such as N,N-dimethylformamide. In this process, $L^1$ is advantageously a lower halogen such as fluorine. The transformation $R^{7c}$=H to $R^{7c}$=$R^7$ may optionally carried out at this stage by reaction with a compound $R^7L^3$ (wherein $L^3$ is as defined above) using a suitable base such as sodium hydride in a suitable solvent such as N,N-dimethylformamide. Stage (ii) may be carried out using suitable reducing conditions e.g. hydrogenation or an appropriate metal such as iron in the presence of an acid such as acetic acid. Stage (iii) may be carried out using a suitable reducing agent e.g. borane-methyl sulfide complex in a suitable solvent such as tetrahydrofuran. Optionally, functional group interconversions may be performed on the groups $R^{6c}$, $R^{7c}$, $R^8$ and $R^9$ on intermediates derived from stages (i) and (ii) using methods well known in the art.

Compounds of formula (III) wherein where G and J both represent C and ring E is a pyridine ring may be prepared from an appropriately substituted halo-nitropyridine in an analogous fashion to that shown in the above scheme.

Certain compounds of formula (V) are commercially available or known in the literature. Other compounds of formula (V) wherein $R^{2a}$ and $R^{2b}$ represent hydrogen may be prepared by reduction of a compound of formula (XV)

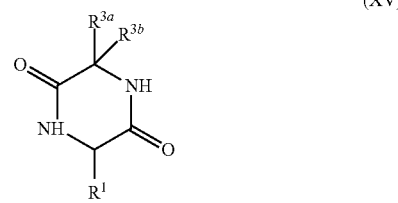

wherein $R^1$, $R^{3a}$ and $R^{3b}$ are as defined hereinbefore. Suitable reagents for the reduction of compounds of formula (XV) include metal hydrides such as lithium aluminium hydride or boron hydrides such as borane and such reactions are typically carried out in an suitably inert solvent such as tetrahydrofuran or diethyl ether.

Compounds of formula (XV) may be prepared by cyclisation of a compound of formula (XVI)

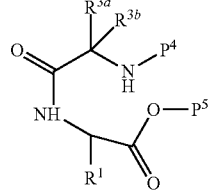

wherein $R^1$, $R^{3a}$ and $R^{3b}$ are as defined hereinbefore and $P^4$ and $P^5$ independently represent hydrogen or a suitable protecting group, for example $P^4$ may represent tBoc or Cbz and $P^5$ may represent a $C^{1-4}$ alkyl group. Such a process may be effected using methods well known in the art for amide bond formation, e.g. using similar methods to those described for process (a) above. In certain circumstances, cyclisation may proceed concomitantly on removal of protecting groups $P^4$ or $P^5$, for example as described below in Preparation 3 (see example experimental procedures).

Certain compounds of formula (XVI) are known in the literature and/or may be prepared by coupling of two appropriately protected amino-acid derivatives using methods well known in the art for amide bond formation, for example using a procedure analogous to that described below in Preparation 2 (see example experimental procedures).

Other compounds of formula (V) may be prepared by functional group interconversion of the groups $R^1$, $R^{2a}$, $R^{2b}$, $R^{3a}$ and $R^{3b}$ using methods well known in the art. Such interconversions may be carried out on compounds of formulas (V) or (XV) which may be appropriately protected, e.g. with a tBoc and/or benzyloxycarbonyl (Cbz) group. For example a compound of formula (V) wherein $R^{3a}$ or $R^{3b}$ represent $C_{1-6}$alkyl substituted with a single group $R^b$ where $R^b$ represents chlorine, bromine or iodine, may be treated with a suitable nucleophile for the introduction of an optionally substituted 3-12 membered heterocyclyl group as defined above. Such a process may be carried out in an inert solvent such as acetonitirile or N,N-dimethylformamide, in the presence of a suitable base such as potassium carbonate or sodium hydride, optionally in the presence of an iodide salt such as potassium iodide.

It will be appreciated that compounds of formulas (V), (XV) and (XVI) can exist in different diastereomeric and/or enantiomeric forms and that processes for their preparation may make use of enantiomerically pure synthetic precursors.

Alternatively racemic precursors may be used and the mixtures of diastereoisomers generated in these process may be separated by methods well known to the person skilled in the art, for example using non-chiral or chiral preparative chromatography or resolution using diastereomeric derivatives: for example crystallisation of a salt formed with an enantiomerically pure acid such as L-tartaric acid; or enantiomer separation of a diastereomeric derivative formed by covalently linking a enantiomerically pure chiral auxiliary onto the compound, followed by separation using conventional methods such as chiral chromatography. The aforementioned covalent linkage is then cleaved to generate the appropriate enantiomerically pure product.

Compounds of formula (II) wherein Q represents CH may be prepared by reaction of a compound of formula (XVII)

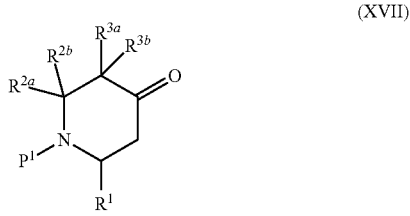

(XVII)

wherein $R^1$, $R^{2a}$, $R^{2b}$, $R^{3a}$, $R^{3b}$ and $P^1$ are as defined hereinbefore; with a compound of formula (XVIII)

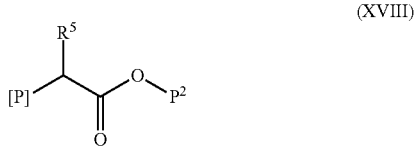

(XVIII)

wherein $R^5$ and $P^2$ are as defined hereinbefore and [P] represents a phosphorus containing residue such as triphenylphosphonium [$Ph_3P^+$] or a dialkylphosphonate [$(alkO)_2P(=O)$ where for example alk represents $C_{1-4}$ alkyl], followed by reduction of the resultant alkene double bond. Reaction between compounds of formulas (XVII) and (XVIII) as defined hereinbefore may be carried out in the presence of a suitable base such as potassium tert-butoxide in a suitably inert solvent such as tetrahydrofuran. The subsequent step may be effected by using methods well known in the art for reduction of alkenes, for example using catalytic hydrogenation.

A wide range of well known functional group interconversions are know by a person skilled in the art for converting a precursor compound to a compound of formula I and are described in *Advanced Organic Chemistry* by Jerry March, 4$^{th}$ Edition, John Wiley & Sons, 1992. For example possible metal catalysed functionalisations such as using organo-tin reagents (the Stille reaction), Grignard reagents and reactions with nitrogen nucleophiles are described in 'Palladium Reagents and Catalysts' [Jiro Tsuji, Wiley, ISBN 0-470-85032-9] and Handbook of OrganoPalladium Chemistry for Organic Synthesis [Volume 1, Edited by Ei-ichi Negishi, Wiley, ISBN 0-471-31506-0].

Compounds (IV), (VI), (X), (XI), (XII), (XIII), (XIV), (XVII) and (XVIII) are commercially available, known in the literature or can be prepared by methods analogous to those described in the literature or by methods similar to that described in the example experimental procedures below.

In a further embodiment the invention provides a novel intermediate. In one embodiment the invention provides a novel intermediate of formula (II) or (III) or (V).

Protecting Groups

In many of the reactions described above, it may be necessary to protect one or more groups to prevent reaction from taking place at an undesirable location on the molecule. Examples of protecting groups, and methods of protecting and deprotecting functional groups, can be found in *Protective Groups in Organic Synthesis* (T. Green and P. Wuts; 3rd Edition; John Wiley and Sons, 1999).

A hydroxy group may be protected, for example, as an ether (—OR) or an ester (—OC(=O)R), for example, as: a t-butyl ether; a tetrahydropyranyl (THP) ether; a benzyl, benzhydryl (diphenylmethyl), or trityl (triphenylmethyl) ether; a trimethylsilyl or t-butyldimethylsilyl ether; or an acetyl ester (—OC(=O)CH$_3$).

An aldehyde or ketone group may be protected, for example, as an acetal (R—CH(OR)$_2$) or ketal (R$_2$C(OR)$_2$), respectively, in which the carbonyl group (>C=O) is treated with, for example, a primary alcohol. The aldehyde or ketone group is readily regenerated by hydrolysis using a large excess of water in the presence of acid.

An amine group may be protected, for example, as an amide (—NRCO—R) or a carbamate (—NRCO—OR), for example, as: a methyl amide (—NHCO—CH$_3$); a benzyl carbamate (—NHCO—OCH$_2$C$_6$H$_5$, —NH-Cbz or NH—Z); as a t-butyl carbamate (—NHCO—OC(CH$_3$)$_3$, —NH-Boc); a 2-biphenyl-2-propyl carbamate (—NHCO—OC(CH$_3$)$_2$C$_6$H$_4$C$_6$H$_5$, —NH-Bpoc), as a 9-fluorenylmethyl carbamate (—NH—Fmoc), as a 6-nitroveratryl carbamate (—NH—Nvoc), as a 2-trimethylsilylethyl carbamate (—NH-Teoc), as a 2,2,2-trichloroethyl carbamate (—NH-Troc), as an allyl carbamate (—NH-Alloc), or as a 2(-phenylsulfonyl)ethyl carbamate (—NH—Psec).

For example, in compounds of formula II contains an amino group, the amino group can be protected by means of a protecting group as hereinbefore defined, one preferred group being the tert-butyloxycarbonyl (Boc) group while the additional funactionalisation is introduced. Where no subsequent modification of the amino group is required, the protecting group can be carried through the reaction sequence to give an N-protected form of a compound of the formula (I) which can then be de-protected by standard methods (e.g. treatment with acid in the case of the Boc group) to give the compound of formula (I).

Other protecting groups for amines, such as cyclic amines and heterocyclic N—H groups, include toluenesulfonyl (tosyl) and methanesulfonyl (mesyl) groups, benzyl groups such as a para-methoxybenzyl (PMB) group and tetrahydropyranyl (THP) groups.

A carboxylic acid group may be protected as an ester for example, as: an C$_{1-7}$ alkyl ester (e.g., a methyl ester; a t-butyl ester); a C$_{1-7}$ haloalkyl ester (e.g., a C$_{1-7}$ trihaloalkyl ester); a triC$_{1-7}$ alkylsilyl-C$_{1-7}$alkyl ester; or a C$_{5-20}$ aryl-C$_{1-7}$ alkyl ester (e.g., a benzyl ester; a nitrobenzyl ester; para-methoxybenzyl ester. A thiol group may be protected, for example, as a thioether (—SR), for example, as: a benzyl thioether; an acetamidomethyl ether (—S—CH$_2$NHC(=O)CH$_3$).

Isolation and Purification of the Compounds of the Invention

The compounds of the invention can be isolated and purified according to standard techniques well known to the person skilled in the art and examples of such methods include chromatographic techniques such as column chromatography (e.g. flash chromatography) and HPLC. One technique of particular usefulness in purifying the compounds is preparative liquid chromatography using mass spectrometry as a means of detecting the purified compounds emerging from the chromatography column.

Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.;* 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.;* 2003; 5(3); 322-9. An example of such a system for purifying compounds via preparative LC-MS is described below in the Examples section of this application (under the heading "Mass Directed Purification LC-MS System").

Methods of recrystallisation of compounds of formula (I) and salt thereof can be carried out by methods well known to the skilled person—see for example (P. Heinrich Stahl (Editor), Camille G. Wermuth (Editor), ISBN: 3-90639-026-8, Handbook of Pharmaceutical Salts: Properties, Selection, and Use, Chapter 8, Publisher Wiley-VCH). Products obtained from an organic reaction are seldom pure when isolated directly from the reaction mixture. If the compound (or a salt thereof) is solid, it may be purified and/or crystallized by recrystallisation from a suitable solvent. A good recrystallisation solvent should dissolve a moderate quantity of the substance to be purified at elevated temperatures but only a small quantity of the substance at lower temperature. It should dissolve impurities readily at low temperatures or not at all. Finally, the solvent should be readily removed from the purified product. This usually means that it has a relatively low boiling point and a person skilled in the art will know recrystallising solvents for a particular substance, or if that information is not available, test several solvents. To get a good yield of purified material, the minimum amount of hot solvent to dissolve all the impure material is used. In practice, 3-5% more solvent than necessary is used so the solution is not saturated. If the impure compound contains an impurity which is insoluble in the solvent it may then be removed by filtration and then allowing the solution to crystallize. In addition, if the impure compound contains traces of coloured material that are not native to the compound, it may be removed by adding a small amount of decolorizing agent e.g. activating charcoal to the hot solution, filtering it and then allowing it to crystallize. Usually crystallization spontaneously occurs upon cooling the solution. If it is not, crystallization may be induced by cooling the solution below room temperature or by adding a single crystal of pure material (a seed crystal). Recrystallisation can also be carried out and/or the yield optimized by the use of an anti-solvent or co-solvent. In this case, the compound is dissolved in a suitable solvent at elevated temperature, filtered and then an additional solvent in which the required compound has low solubility is added to aid crystallization. The crystals are then typically isolated using vacuum filtration, washed and then dried, for example, in an oven or via desiccation.

Other examples of methods for purification include sublimation, which includes an heating step under vacuum for example using a cold finger, and crystallization from melt (Crystallization Technology Handbook 2nd Edition, edited by A. Mersmann, 2001).

Biological Effects

The compounds of the invention, subgroups and examples thereof, are antagonists of inhibitor of apoptosis protein (IAP), and which may be useful in preventing or treating disease states or conditions described herein. In addition the compounds of the invention, and subgroups thereof, will be useful in preventing or treating diseases or condition mediated by IAP. References to the preventing or prophylaxis or treatment of a disease state or condition such as cancer include within their scope alleviating or reducing the incidence of cancer.

Thus, for example, it is envisaged that the compounds of the invention will be useful in alleviating or reducing the incidence of cancer.

The compounds of the present invention may be useful for the treatment of the adult population. The compounds of the present invention may be useful for the treatment of the pediatric population.

More particularly, the compounds of the formula (I) and sub-groups thereof are antagonists of IAP. For example, compounds of the invention have affinity against XIAP, cIAP1 and/or cIAP2, and in particular an IAP selected from XIAP and cIAP1.

Preferred compounds are compounds that have affinity for one or more IAP selected from XIAP, cIAP1 and cIAP2. Preferred compounds of the invention are those having IC$_{50}$ values of less than 0.1 µM.

The antagonist compounds of formula (I) are capable of binding to IAP and exhibiting potency for IAP. In one embodiment the antagonist compounds of formula (I) exhibit selectivity for one or more IAP over other IAP family members, and may be capable of binding to and/or exhibiting affinity for XIAP and/or cIAP in preference to binding to and/or exhibiting affinity for other of the IAP family members.

In addition many of the compounds of the invention exhibit selectivity for the XIAP compared to cIAP or vice versa, selectivity for the cIAP compared to XIAP (in particular cIAP1), and such compounds represent one embodiment of the invention. In particular compounds of the invention may have at least 10 times greater affinity against one or more IAP family member in particular XIAP, cIAP1 and/or cIAP2 than other IAP family members. This can be determined using the methods described herein. In a further embodiment compounds of the invention may have equivalent affinity for XIAP, cIAP1 and/or cIAP2, in particular equivalent affinity (i.e. less than 10-fold difference in affinity) for XIAP and cIAP1.

Activity against XIAP and cIAP may be particularly advantageous. Antagonising XIAP and cIAP1/2 with equipotency should enable triggering of apoptosis via activation of caspase-8 and the switch away from pro-survival NF-kappaB signalling towards apoptosis; and potent antagonism of XIAP will ensure that apoptosis is achieved before any inherent resistance mechanism is upregulated to block the process. On depletion of cIAP1/2 via autoubiquitination and proteasomal degradation there is a temporary upregulation of NF-kappaB signalling that is responsible for expression of TNF-alpha in sensitive cell lines—this is also responsible for upregulation of anti-apoptotic factors such as cIAP2 and c-FLIP. Hence the need for potent XIAP antagonism to potentiate effector caspase activation and cell death, rather than allowing cIAP1/2 antagonism-mediated resistance to build up. It is generally believed that toxicities that arise on dosing these compounds in vivo will arise from the temporary induction of NFkappaB signalling and resultant upregulation of pro-inflammatory cytokines, which is mediated solely by cIAP1/2 antagonism. Therefore dual potency should enable a therapeutic window to be achieved before dose-limiting toxicities are achieved.

IAP function in controlling programmed cell death has also been implicated in many diseases, including disorders associated with cell accumulation (e.g. cancer, autoimmune disorders, inflammation and restenosis), disorders where excessive apoptosis results in cell loss (e.g. stroke, heart failure, neurodegeneration such as Alzheimers' disease, Parkinson's disease, Huntington's disease, amyotrophic lateral sclerosis, AIDS, ischemia (stroke, myocardial infarction) and osteoporosis or treating autoimmune diseases such as multiple sclerosis (MS).

Therefore, it is also envisaged that the compounds of the invention may be useful in treating other conditions such as inflammation, hepatitis, ulcerative colitis, gastritis, autoimmunity, inflammation, restenosis, stroke, heart failure, neurodegenerative conditions such as Alzheimers' disease, Parkinson's disease, Huntington's disease, myotonic dystrophy, and amyotrophic lateral sclerosis, AIDS, ischemia such as traumatic brain injury, spinal cord injury, cerebral ischemia, cerebral ischemia/reperfusion (I/R) injury, acute and chronic CNS injury ischemia, stroke or myocardial infarction, degenerative diseases of the musculoskeletal system such as osteoporosis, autoimmune diseases such as multiple sclerosis (MS) and Type I diabetes, and eye diseases such as retinal degeneration which result from loss of control of programmed cell death.

As a consequence of their affinity for IAP, the compounds will be useful in providing a means of controlling programmed cell death. It is therefore anticipated that the compounds may prove useful in treating or preventing proliferative disorders such as cancers. In addition, the compounds of the invention may be useful in the treatment of diseases in which there is a disorder associated with cell accumulation or where excessive apoptosis results in cell loss.

Examples of cancers (and their benign counterparts) which may be treated (or inhibited) include, but are not limited to tumours of epithelial origin (adenomas and carcinomas of various types including adenocarcinomas, squamous carcinomas, transitional cell carcinomas and other carcinomas) such as carcinomas of the bladder and urinary tract, breast, gastrointestinal tract (including the esophagus, stomach (gastric), small intestine, colon, rectum and anus), liver (hepatocellular carcinoma), gall bladder and biliary system, exocrine pancreas, kidney, lung (for example adenocarcinomas, small cell lung carcinomas, non-small cell lung carcinomas, bronchioalveolar carcinomas and mesotheliomas), head and neck (for example cancers of the tongue, buccal cavity, larynx, pharynx, nasopharynx, tonsil, salivary glands, nasal cavity and paranasal sinuses), ovary, fallopian tubes, peritoneum, vagina, vulva, penis, cervix, myometrium, endometrium, thyroid (for example thyroid follicular carcinoma), adrenal, prostate, skin and adnexae (for example melanoma, basal cell carcinoma, squamous cell carcinoma, keratoacanthoma, dysplastic naevus); haematological malignancies (i.e. leukemias, lymphomas) and pre-malignant haematological disorders and disorders of borderline malignancy including haematological malignancies and related conditions of lymphoid lineage (for example acute lymphocytic leukemia [ALL], chronic lymphocytic leukemia [CLL], B-cell lymphomas such as diffuse large B-cell lymphoma [DLBCL], follicular lymphoma, Burkitt's lymphoma, mantle cell lymphoma, T-cell lymphomas and leukaemias, natural killer [NK] cell lymphomas, Hodgkin's lymphomas, hairy cell leukaemia, monoclonal gammopathy of uncertain significance, plasmacytoma, multiple myeloma, and post-transplant lymphoproliferative disorders), and haematological malignancies and related conditions of myeloid lineage (for example acute myelogenous leukemia [AML], chronic myelogenous leukemia [CML], chronic myelomonocytic leukemia [CMML], hypereosinophilic syndrome, myeloproliferative disorders such as polycythaemia vera, essential thrombocythaemia and primary myelofibrosis, myeloproliferative syndrome, myelodysplastic syndrome, and promyelocytic leukemia); tumours of mesenchymal origin, for example sarcomas of soft tissue, bone or cartilage such as osteosarcomas, fibrosarcomas, chondrosarcomas, rhabdomyosarcomas, leiomyosarcomas, liposarcomas, angiosarcomas, Kaposi's sarcoma, Ewing's sarcoma, synovial sarcomas, epithelioid sarcomas, gastrointestinal stromal tumours, benign and malignant histiocytomas, and dermatofibrosarcoma protuberans; tumours of the central or peripheral nervous system (for example astrocytomas, gliomas and glioblastomas, meningiomas, ependymomas, pineal tumours and schwannomas); endocrine tumours (for example pituitary tumours, adrenal tumours, islet cell tumours, parathyroid tumours, carcinoid tumours and medullary carcinoma of the thyroid); ocular and adnexal tumours (for example retinoblastoma); germ cell and trophoblastic tumours (for example teratomas, seminomas, dysgerminomas, hydatidiform moles and choriocarcinomas); and paediatric and embryonal tumours (for example medulloblastoma, neuroblastoma, Wilms tumour, and primitive neuroectodermal tumours); or syndromes, congenital or otherwise, which leave the patient susceptible to malignancy (for example Xeroderma Pigmentosum).

Growth of cells is a closely controlled function. Cancer, a condition of abnormal cell growth, results when cells replicate in an uncontrolled manner (increasing in number), uncontrollably grow (getting larger) and/or experience reduced cell death by apoptosis (programmed cell death), necrosis, or annoikis. In one embodiment abnormal cell growth is selected from uncontrolled cell proliferation, excessive cell growth or reduced programmed cell death. In particular, the condition or disease of abnormal cell growth is a cancer. Thus, in the pharmaceutical compositions, uses or methods of this invention for treating a disease or condition comprising abnormal cell growth (i.e. uncontrolled and/or rapid cell growth), the disease or condition comprising abnormal cell growth in one embodiment is a cancer.

In one embodiment the haematological malignancies is leukaemia. In another embodiment the haematological malignancies is lymphoma.

Many diseases are characterized by persistent and unregulated angiogenesis. Chronic proliferative diseases are often accompanied by profound angiogenesis, which can contribute to or maintain an inflammatory and/or proliferative state, or which leads to tissue destruction through the invasive proliferation of blood vessels. Tumour growth and metastasis have been found to be angiogenesis-dependent. Compounds of the invention may therefore be useful in preventing and disrupting initiation of tumour angiogenesis. In particular, the compounds of the invention may be useful in the treatment of metastasis and metastatic cancers.

Metastasis or metastatic disease is the spread of a disease from one organ or part to another non-adjacent organ or part. The cancers which can be treated by the compounds of the invention include primary tumours (i.e. cancer cells at the originating site), local invasion (cancer cells which penetrate and infiltrate surrounding normal tissues in the local area), and metastatic (or secondary) tumours ie. tumours that have formed from malignant cells which have circulated through the bloodstream (haematogenous spread) or via lymphatics or across body cavities (trans-coelomic) to other sites and tissues in the body.

Particular cancers include hepatocellular carcinoma, melanoma, oesophageal, renal, colon, colorectal, lung e.g. mesothelioma or lung adenocarcinoma, breast, bladder, gastrointestinal, ovarian and prostate cancers.

Particular cancers include renal, melanoma, colon, lung, breast, ovarian and prostate cancers. In one embodiment the cancer is selected from melanoma, colon, breast and ovarian. In one embodiment the cancer is melanoma. In one embodiment the cancer is infammatory breast cancer.

A further aspect of the invention includes a compound of the invention for use in the prophylaxis or treatment of cancer in a patient selected from a sub-population possessing cancers with a high inflammatory component. Such cancers are also known as "inflammatory phenotype" and include tumours with elevated cytokine signalling (e.g. TNF). In one embodiment the cancer is an inflammatory tumour, for example, melanoma, colon, breast and ovarian, in particular, melanoma.

In one embodiment the disease to be treated is leukaemia, such as acute and chronic leukaemias, acute myeloid leukaemia (AML), and chronic lymphocytic leukaemia (CLL). In one embodiment the leukaemia is refractory DLBCL.

In one embodiment the cancer is mesothelioma including malignant peritoneal mesothelioma or malignant pleural mesothelioma.

Certain cancers are resistant to treatment with particular drugs. This can be due to the type of the tumour (most common epithelial malignancies are inherently chemoresistant) or resistance can arise spontaneously as the disease progresses or as a result of treatment. In this regard, references to mesothelioma includes mesothelioma with resistance towards topoisomerase poisons, alkylating agents, antitubulines, antifolates, platinum compounds and radiation therapy, in particular cisplatin-resistant mesothelioma. Similarly references to multiple myeloma includes bortezomib-sensitive multiple myeloma or refractory multiple myeloma and references to chronic myelogenous leukemia includes imitanib-sensitive chronic myelogenous leukemia and refractory chronic myelogenous leukemia.

The cancers may be cancers which are sensitive to antagonism of any one or more IAP selected from XIAP, cIAP1, cIAP2, NAIP, ILP2, ML-IAP, survivin and BRUCE, more preferably XIAP, cIAP1, cIAP2, ML-IAP, most preferably XIAP.

It is further envisaged that the compounds of the invention, and in particular those compounds having IAP affinity will be particularly useful in the treatment or prevention of cancers of a type associated with or characterised by the presence of elevated levels of IAP or amplification of 11q22 for example the cancers referred to in this context in the introductory section of this application.

Elevated levels of IAP due to overexpression of IAP is found in many cancers and is associated with a poor prognosis. In addition, cancers with the 11q22 amplification may also be sensitive to an IAP antagonist. The elevated levels of IAP and amplification of 11q22 can be identified by the techniques outlined herein. Whether a particular cancer is one which is sensitive to IAP function, may be determined by a method as set out in the section headed "Methods of Diagnosis".

A further aspect provides the use of a compound for the manufacture of a medicament for the treatment of a disease or condition as described herein, in particular cancer.

The compounds may also be useful in the treatment of tumour growth, pathogenesis, resistance to chemo- and radio-therapy by sensitising cells to chemotherapy and as an anti-metastatic agent.

Therapeutic anticancer interventions of all types necessarily increase the stresses imposed on the target tumour cells. In mitigating the deleterious effects of such stresses, IAPs are directly implicated in resisting the effects of cancer drugs and treatment regimens. Thus, antagonists of IAP represent a class of chemotherapeutics with the potential for: (i) sensitizing malignant cells to anticancer drugs and/or treatments; (ii) alleviating or reducing the incidence of resistance to anticancer drugs and/or treatments; (iii) reversing resistance to anticancer drugs and/or treatments; (iv) potentiating the activity of anticancer drugs and/or treatments; (v) delaying or preventing the onset of resistance to anticancer drugs and/or treatments.

As a consequence of their affinity for IAP, the compounds will be useful in providing a means of controlling programmed cell death. Therefore, it is also envisaged that the compounds of the invention may be useful in treating other conditions such as inflammatory disorders such as hepatitis, ulcerative colitis, and gastritis; neurodegenerative conditions such as Alzheimers' disease, Parkinson's disease, Huntington's disease, myotonic dystrophy, and amyotrophic lateral sclerosis; AIDS, ischemia such as restenosis, traumatic brain injury, spinal cord injury, cerebral ischemia, cerebral ischemia/reperfusion (I/R) injury, acute and chronic CNS injury ischemia, stroke or myocardial infarction; degenerative diseases of the musculoskeletal system such as osteoporosis; autoimmune diseases such as multiple sclerosis (MS) and Type I diabetes, and eye diseases such as retinal degeneration.

The affinity of the compounds of the invention as antagonists of IAP can be measured using the biological and biophysical assays set forth in the examples herein and the level of affinity exhibited by a given compound can be defined in terms of the $IC_{50}$ value. Preferred compounds of the present invention are compounds having an $IC_{50}$ value of less than 1 µM, more preferably less than 0.1 µM.

In one embodiment the invention provides a compound for use in the treatment of a disease or condition which is mediated by IAP (e.g. XIAP and/or cIAP e.g. cIAP1). In a further embodiment the invention provides a compound for use in the treatment of a disease or condition which over-expresses IAP (e.g. XIAP and/or cIAP e.g. cIAP1).

In one embodiment the invention provides a compound for use in the treatment of a disease or condition which is mediated by IAP, wherein the compound is an antagonist of IAP having an $IC_{50}$ of less than 50 µM in at least one assay (e.g. a displacement binding) against an IAP. In particular the IAP is XIAP, cIAP1 and/or cIAP2. In a further embodiment the disease or condition which is mediated by IAP is a cancer which is characterised by overexpression of at least one IAP and/or amplification of 11q22.

In one embodiment the invention provides a compound for use in the treatment of a disease or condition which is mediated by IAP, wherein the compound has an $IC_{50}$ of less than 10 µM against at least one IAP in an assay (e.g. displacement binding) against IAP.

A further aspect provides the use of a compound for the manufacture of a medicament for the treatment of a disease or condition which is mediated by IAP, wherein the compound is an antagonist of IAP having an $IC_{50}$ of less than 50 µM against at least one IAP in an assay (e.g. a displacement binding).

Methods of Diagnosis

Prior to administration of a compound of the formula (I), a patient may be screened to determine whether a disease or condition from which the patient is or may be suffering is one which would be susceptible to treatment with a compound having affinity for IAP. The term 'patient' includes human and veterinary subjects.

For example, a biological sample taken from a patient may be analysed to determine whether a condition or disease, such as cancer, that the patient is or may be suffering from is one which is characterised by a genetic abnormality or abnormal protein expression which leads to up-regulation of the levels of IAP or to sensitisation of a pathway to normal IAP function or to upregulation of a biochemical pathway downstream of IAP activation.

Examples of such abnormalities that result in activation or sensitisation of the IAP, loss of, or inhibition of apoptotic pathways, up-regulation of the receptors or ligands, cytogenetic aberrations or presence of mutant variants of the receptors or ligands. Tumours with up-regulation of IAP, in particular over-expression of IAP, may be particularly sensitive to IAP antagonists. For example, overexpression of XIAP and cIAP has been identified in a range of cancers as discussion in the Background section.

Amplification of chromosome 11q22 has been detected in cell lines and primary tumours from squamous cell carcinomas of the esophagus (Imoto et al., 2001) and cervix (Imoto et al., 2002) as well as in primary lung cancers/cell lines (Dai et al., 2003). Immunohistochemistry and western blot analysis have identified cIAP1 and cIAP2 as potential oncogenes in this region as both are overexpressed in cancers in which this rare amplification arises.

The term up-regulation includes elevated expression or over-expression, including gene amplification (i.e. multiple gene copies), cytogenetic aberration and increased expression by a transcriptional effect. Thus, the patient may be subjected to a diagnostic test to detect a marker characteristic of up-regulation of IAP. The term diagnosis includes screening. By marker we include genetic markers including, for example, the measurement of DNA composition to identify presence of mutations of IAP or 11q22 amplification. The term marker also includes markers which are characteristic of up regulation of IAP, including protein levels, protein state and mRNA levels of the aforementioned proteins.

The diagnostic tests and screens are typically conducted on a biological sample (i.e. body tissue or body fluids) selected from tumour biopsy samples, blood samples (isolation and enrichment of shed tumour cells), cerebrospinal fluid, plasma, serum, saliva, stool biopsies, sputum, chromosome analysis, pleural fluid, peritoneal fluid, buccal spears, skin biopsy or urine.

Methods of identification and analysis of cytogenetic aberration, genetic amplification, mutations and up-regulation of proteins are known to a person skilled in the art. Screening methods could include, but are not limited to, standard methods such as reverse-transcriptase polymerase chain reaction (RT-PCR) or in-situ hybridization such as fluorescence in situ hybridization (FISH).

In screening by RT-PCR, the level of mRNA in the tumour is assessed by creating a cDNA copy of the mRNA followed by amplification of the cDNA by PCR. Methods of PCR amplification, the selection of primers, and conditions for amplification, are known to a person skilled in the art. Nucleic acid manipulations and PCR are carried out by standard methods, as described for example in Ausubel, F. M. et al., eds. (2004) Current Protocols in Molecular Biology, John Wiley & Sons Inc., or Innis, M. A. et al., eds. (1990) PCR Protocols: a guide to methods and applications, Academic Press, San Diego. Reactions and manipulations involving nucleic acid techniques are also described in Sambrook et al., (2001), $3^{rd}$ Ed, Molecular Cloning: A Laboratory Manual, Cold Spring Harbor Laboratory Press. Alternatively a commercially available kit for RT-PCR (for example Roche Molecular Biochemicals) may be used, or methodology as set forth in U.S. Pat. Nos. 4,666,828; 4,683,202; 4,801,531; 5,192,659, 5,272,057, 5,882,864, and 6,218,529 and incorporated herein by reference.

An example of an in-situ hybridisation technique for assessing mRNA expression would be fluorescence in-situ hybridisation (FISH) (see Angerer (1987) Meth. Enzymol., 152: 649).

Generally, in situ hybridization comprises the following major steps: (1) fixation of tissue to be analyzed; (2) prehybridization treatment of the sample to increase accessibility of target nucleic acid, and to reduce nonspecific binding; (3) hybridization of the mixture of nucleic acids to the nucleic acid in the biological structure or tissue; (4) post-hybridization washes to remove nucleic acid fragments not bound in the hybridization, and (5) detection of the hybridized nucleic acid fragments. The probes used in such applications are typically labelled, for example, with radio-isotopes or fluorescent reporters. Preferred probes are sufficiently long, for example, from about 50, 100, or 200 nucleotides to about 1000 or more nucleotides, to enable specific hybridization with the target nucleic acid(s) under stringent conditions. Standard methods for carrying out FISH are described in Ausubel, F. M. et al., eds. (2004) Current Protocols in Molecular Biology, John Wiley & Sons Inc and Fluorescence In Situ Hybridization: Technical Overview by John M. S. Bartlett in Molecular Diagnosis of Cancer, Methods and Protocols, 2nd ed.; ISBN: 1-59259-760-2; March 2004, pps. 077-088; Series: Methods in Molecular Medicine.

Methods for gene expression profiling are described by (DePrimo et al. (2003), BMC Cancer, 3:3). Briefly, the protocol is as follows: double-stranded cDNA is synthesized from total RNA using a (dT) 24 oligomer for priming first-strand cDNA synthesis, followed by second strand cDNA synthesis with random hexamer primers. The double-stranded cDNA is used as a template for in vitro transcription of cRNA using biotinylated ribonucleotides. cRNA is chemically fragmented according to protocols described by Affymetrix (Santa Clara, Calif., USA), and then hybridized overnight on Human Genome Arrays.

Alternatively, the protein products expressed from the mRNAs may be assayed by immunohistochemistry of tumour samples, solid phase immunoassay with microtitre plates, Western blotting, 2-dimensional SDS-polyacrylamide gel electrophoresis, ELISA, flow cytometry and other methods known in the art for detection of specific proteins.

Detection methods would include the use of site specific antibodies. The skilled person will recognize that all such well-known techniques for detection of upregulation of IAP, detection of IAP variants or mutants, or detection of 11 q22 amplification could be applicable in the present case.

Abnormal levels of proteins such as IAP can be measured using standard protein assays, for example, those assays described herein. Elevated levels or overexpression could also be detected in a tissue sample, for example, a tumour tissue by measuring the protein levels with an assay such as that from Chemicon International. The protein of interest would be immunoprecipitated from the sample lysate and its levels measured.

Alternative methods for the measurement of the over expression or elevation of IAPs including the isoforms thereof, include the measurement of microvessel density. This can for example be measured using methods described by Orre and Rogers (Int J Cancer (1999), 84(2), 101-8). Assay methods also include the use of markers.

Therefore all of these techniques could also be used to identify tumours particularly suitable for treatment with the compounds of the invention.

Therefore in a further aspect of the invention includes use of a compound according to the invention for the manufacture of a medicament for the treatment or prophylaxis of a disease state or condition in a patient who has been screened and has been determined as suffering from, or being at risk of suffering from, a disease or condition which would be susceptible to treatment with a compound having affinity for IAP (i.e. an IAP antagonist).

Another aspect of the invention includes a compound of the invention for use in the prophylaxis or treatment of cancer in a patient selected from a sub-population possessing overexpression of one or more of the IAP family members (e.g. cIAP and/or XIAP).

Another aspect of the invention includes a compound of the invention for use in the prophylaxis or treatment of cancer in a patient selected as possessing a cytogenetic abherration that results in overexpression of IAPs, for example, a patient selected as possessing the 11q22 amplification.

MRI determination of vessel normalization (e.g. using MRI gradient echo, spin echo, and contrast enhancement to measure blood volume, relative vessel size, and vascular permeability) in combination with circulating biomarkers may also be used to identify for treatment with a compound of the invention.

Thus a further aspect of the invention is a method for the diagnosis and treatment of a disease state or condition mediated by a IAP, which method comprises (i) screening a patient to determine whether a disease or condition from which the patient is or may be suffering is one which would be susceptible to treatment with a compound having affinity for IAP; and (ii) where it is indicated that the disease or condition from which the patient is thus susceptible, thereafter administering to the patient a compound of formula (I) and sub-groups or examples thereof as defined herein.

Pharmaceutical Formulations

While it is possible for the active compound to be administered alone, it is preferable to present it as a pharmaceutical composition (e.g. formulation.

Thus, the present invention further provides pharmaceutical compositions, as defined above, and methods of making a pharmaceutical composition comprising (e.g admixing) at least one compound of formula (I) (and sub-groups thereof as defined herein), together with one or more pharmaceutically acceptable excipients and optionally other therapeutic or prophylactic agents, as described herein.

The pharmaceutically acceptable excipient(s) can be selected from, for example, carriers (e.g. a solid, liquid or semi-solid carrier), adjuvants, diluents, fillers or bulking agents, granulating agents, coating agents, release-controlling agents, binding agents, disintegrants, lubricating agents, preservatives, antioxidants, buffering agents, suspending agents, thickening agents, flavouring agents, sweeteners, taste masking agents, stabilisers or any other excipients conventionally used in pharmaceutical compositions. Examples of excipients for various types of pharmaceutical compositions are set out in more detail below.

The term "pharmaceutically acceptable" as used herein pertains to compounds, materials, compositions, and/or dosage forms which are, within the scope of sound medical judgment, suitable for use in contact with the tissues of a subject (e.g. human) without excessive toxicity, irritation, allergic response, or other problem or complication, commensurate with a reasonable benefit/risk ratio. Each carrier, excipient, etc. must also be "acceptable" in the sense of being compatible with the other ingredients of the formulation.

Pharmaceutical compositions containing compounds of the formula (I) can be formulated in accordance with known techniques, see for example, Remington's Pharmaceutical Sciences, Mack Publishing Company, Easton, Pa., USA.

The pharmaceutical compositions can be in any form suitable for oral, parenteral, topical, intranasal, intrabronchial, sublingual, ophthalmic, otic, rectal, intra-vaginal, or transdermal administration. Where the compositions are intended for parenteral administration, they can be formulated for intravenous, intramuscular, intraperitoneal, subcutaneous administration or for direct delivery into a target organ or tissue by injection, infusion or other means of delivery. The delivery can be by bolus injection, short term infusion or longer term infusion and can be via passive delivery or through the utilisation of a suitable infusion pump or syringe driver.

Pharmaceutical formulations adapted for parenteral administration include aqueous and non-aqueous sterile injection solutions which may contain anti-oxidants, buffers, bacteriostats, co-solvents, surface active agents, organic solvent mixtures, cyclodextrin complexation agents, emulsifying agents (for forming and stabilizing emulsion formulations), liposome components for forming liposomes, gellable polymers for forming polymeric gels, lyophilisation protectants and combinations of agents for, interalia, stabilising the active ingredient in a soluble form and rendering the formulation isotonic with the blood of the intended recipient. Pharmaceutical formulations for parenteral administration may also take the form of aqueous and non-aqueous sterile suspensions which may include suspending agents and thickening agents (R. G. Strickly, Solubilizing Excipients in oral and injectable formulations, Pharmaceutical Research, Vol 21(2) 2004, p 201-230).

The formulations may be presented in unit-dose or multi-dose containers, for example sealed ampoules, vials and prefilled syringes, and may be stored in a freeze-dried (lyophilised) condition requiring only the addition of the sterile liquid carrier, for example water for injections, immediately prior to use.

The pharmaceutical formulation can be prepared by lyophilising a compound of formula (I), or sub-groups thereof. Lyophilisation refers to the procedure of freeze-drying a composition. Freeze-drying and lyophilisation are therefore used herein as synonyms.

Extemporaneous injection solutions and suspensions may be prepared from sterile powders, granules and tablets.

Pharmaceutical compositions of the present invention for parenteral injection can also comprise pharmaceutically acceptable sterile aqueous or non-aqueous solutions, dispersions, suspensions or emulsions as well as sterile powders for reconstitution into sterile injectable solutions or dispersions just prior to use.

Examples of suitable aqueous and nonaqueous carriers, diluents, solvents or vehicles include water, ethanol, polyols (such as glycerol, propylene glycol, polyethylene glycol, and the like), carboxymethylcellulose and suitable mixtures thereof, vegetable oils (such as sunflower oil, safflower oil, corn oil or olive oil), and injectable organic esters such as ethyl oleate. Proper fluidity can be maintained, for example, by the use of thickening or coating materials such as lecithin, by the maintenance of the required particle size in the case of dispersions, and by the use of surfactants.

The compositions of the present invention may also contain adjuvants such as preservatives, wetting agents, emulsifying agents, and dispersing agents. Prevention of the action of microorganisms may be ensured by the inclusion of various antibacterial and antifungal agents, for example, paraben, chlorobutanol, phenol, sorbic acid, and the like. It may also be desirable to include agents to adjust tonicity such as sugars, sodium chloride, and the like. Prolonged absorption of the injectable pharmaceutical form may be brought about by the inclusion of agents which delay absorption such as aluminum monostearate and gelatin.

In one preferred embodiment of the invention, the pharmaceutical composition is in a form suitable for i.v. administration, for example by injection or infusion. For intravenous administration, the solution can be dosed as is, or can be injected into an infusion bag (containing a pharmaceutically acceptable excipient, such as 0.9% saline or 5% dextrose), before administration.

In another preferred embodiment, the pharmaceutical composition is in a form suitable for subcutaneous (s.c.) administration.

Pharmaceutical dosage forms suitable for oral administration include tablets (coated or uncoated), capsules (hard or soft shell), caplets, pills, lozenges, syrups, solutions, powders, granules, elixirs and suspensions, sublingual tablets, wafers or patches such as buccal patches.

Thus, tablet compositions can contain a unit dosage of active compound together with an inert diluent or carrier such as a sugar or sugar alcohol, eg; lactose, sucrose, sorbitol or mannitol; and/or a non-sugar derived diluent such as sodium carbonate, calcium phosphate, calcium carbonate, or a cellulose or derivative thereof such as microcrystalline cellulose (MCC), methyl cellulose, ethyl cellulose, hydroxypropyl methyl cellulose, and starches such as corn starch. Tablets may also contain such standard ingredients as binding and granulating agents such as polyvinylpyrrolidone, disintegrants (e.g. swellable crosslinked polymers such as crosslinked carboxymethylcellulose), lubricating agents (e.g. stearates), preservatives (e.g. parabens), antioxidants (e.g. BHT), buffering agents (for example phosphate or citrate buffers), and effervescent agents such as citrate/bicarbonate mixtures. Such excipients are well known and do not need to be discussed in detail here.

Tablets may be designed to release the drug either upon contact with stomach fluids (immediate release tablets) or to release in a controlled manner (controlled release tablets) over a prolonged period of time or with a specific region of the GI tract.

Capsule formulations may be of the hard gelatin or soft gelatin variety and can contain the active component in solid, semi-solid, or liquid form. Gelatin capsules can be formed from animal gelatin or synthetic or plant derived equivalents thereof.

The solid dosage forms (eg; tablets, capsules etc.) can be coated or un-coated. Coatings may act either as a protective film (e.g. a polymer, wax or varnish) or as a mechanism for controlling drug release or for aesthetic or identification purposes. The coating (e.g. a Eudragit™ type polymer) can be designed to release the active component at a desired location within the gastro-intestinal tract. Thus, the coating can be selected so as to degrade under certain pH conditions within the gastrointestinal tract, thereby selectively release the compound in the stomach or in the ileum, duodenum, jejenum or colon.

Instead of, or in addition to, a coating, the drug can be presented in a solid matrix comprising a release controlling agent, for example a release delaying agent which may be adapted to release the compound in a controlled manner in the gastrointestinal tract. Alternatively the drug can be presented in a polymer coating e.g. a polymethacrylate polymer coating, which may be adapted to selectively release the compound under conditions of varying acidity or alkalinity in the gastrointestinal tract. Alternatively, the matrix material or release retarding coating can take the form of an erodible polymer (e.g. a maleic anhydride polymer) which is substantially continuously eroded as the dosage form passes through the gastrointestinal tract. In another alternative, the coating can be designed to disintegrate under microbial action in the gut. As a further alternative, the active compound can be formulated in a delivery system that provides osmotic control of the release of the compound. Osmotic release and other delayed release or sustained release formulations (for example formulations based on ion exchange resins) may be prepared in accordance with methods well known to those skilled in the art.

The compound of formula (I) may be formulated with a carrier and administered in the form of nanoparticles, the increased surface area of the nanoparticles assisting their absorption. In addition, nanoparticles offer the possibility of direct penetration into the cell. Nanoparticle drug delivery systems are described in "Nanoparticle Technology for Drug Delivery", edited by Ram B Gupta and Uday B. Kompella, Informa Healthcare, ISBN 9781574448573, published 13 Mar. 2006. Nanoparticles for drug delivery are also described in J. Control. Release, 2003, 91 (1-2), 167-172, and in Sinha et al., Mol. Cancer Ther. Aug. 1, (2006) 5, 1909.

The pharmaceutical compositions typically comprise from approximately 1% (w/w) to approximately 95% (w/w) active ingredient and from 99% (w/w) to 5% (w/w) of a pharmaceutically acceptable excipient or combination of excipients. Preferably, the compositions comprise from approximately 20% (w/w) to approximately 90%,% (w/w) active ingredient and from 80% (w/w) to 10% of a pharmaceutically acceptable excipient or combination of excipients. The pharmaceutical compositions comprise from approximately 1% to approximately 95%, preferably from approximately 20% to approximately 90%, active ingredient. Pharmaceutical compositions according to the invention may be, for example, in unit dose form, such as in the form of ampoules, vials, suppositories, pre-filled syringes, dragées, tablets or capsules.

The pharmaceutically acceptable excipient(s) can be selected according to the desired physical form of the formulation and can, for example, be selected from diluents (e.g solid diluents such as fillers or bulking agents; and liquid diluents such as solvents and co-solvents), disintegrants, buffering agents, lubricants, flow aids, release controlling (e.g. release retarding or delaying polymers or waxes) agents, binders, granulating agents, pigments, plasticizers, antioxidants, preservatives, flavouring agents, taste masking agents, tonicity adjusting agents and coating agents.

The skilled person will have the expertise to select the appropriate amounts of ingredients for use in the formulations. For example tablets and capsules typically contain 0-20% disintegrants, 0-5% lubricants, 0-5% flow aids and/or 0-99% (w/w) fillers/or bulking agents (depending on drug dose). They may also contain 0-10% (w/w) polymer binders, 0-5% (w/w) antioxidants, 0-5% (w/w) pigments. Slow release tablets would in addition contain 0-99% (w/w) release-controlling (e.g. delaying) polymers (depending on dose). The film coats of the tablet or capsule typically contain 0-10% (w/w) polymers, 0-3% (w/w) pigments, and/or 0-2% (w/w) plasticizers.

Parenteral formulations typically contain 0-20% (w/w) buffers, 0-50% (w/w) cosolvents, and/or 0-99% (w/w) Water for Injection (WFI) (depending on dose and if freeze dried). Formulations for intramuscular depots may also contain 0-99% (w/w) oils.

Pharmaceutical compositions for oral administration can be obtained by combining the active ingredient with solid carriers, if desired granulating a resulting mixture, and processing the mixture, if desired or necessary, after the addition of appropriate excipients, into tablets, dragee cores or capsules. It is also possible for them to be incorporated into a polymer or waxy matrix that allow the active ingredients to diffuse or be released in measured amounts.

The compounds of the invention can also be formulated as solid dispersions. Solid dispersions are homogeneous extremely fine disperse phases of two or more solids. Solid solutions (molecularly disperse systems), one type of solid dispersion, are well known for use in pharmaceutical technology (see (Chiou and Riegelman, J. Pharm. Sci., 60, 1281-1300 (1971)) and are useful in increasing dissolution rates and increasing the bioavailability of poorly water-soluble drugs.

This invention also provides solid dosage forms comprising the solid solution described above. Solid dosage forms include tablets, capsules, chewable tablets and dispersible or effervescent tablets. Known excipients can be blended with the solid solution to provide the desired dosage form. For example, a capsule can contain the solid solution blended with (a) a disintegrant and a lubricant, or (b) a disintegrant, a lubricant and a surfactant. In addition a capsule can contain a bulking agent, such as lactose or microcrystalline cellulose. A tablet can contain the solid solution blended with at least one disintegrant, a lubricant, a surfactant, a bulking agent and a glidant. A chewable tablet can contain the solid solution blended with a bulking agent, a lubricant, and if desired an additional sweetening agent (such as an artificial sweetener), and suitable flavours. Solid solutions may also be formed by spraying solutions of drug and a suitable polymer onto the surface of inert carriers such as sugar beads ('non-pareils'). These beads can subsequently be filled into capsules or compressed into tablets.

The pharmaceutical formulations may be presented to a patient in "patient packs" containing an entire course of treatment in a single package, usually a blister pack. Patient packs have an advantage over traditional prescriptions, where a pharmacist divides a patient's supply of a pharmaceutical from a bulk supply, in that the patient always has access to the package insert contained in the patient pack, normally missing in patient prescriptions. The inclusion of a package insert has been shown to improve patient compliance with the physician's instructions.

Compositions for topical use and nasal delivery include ointments, creams, sprays, patches, gels, liquid drops and inserts (for example intraocular inserts). Such compositions can be formulated in accordance with known methods.

Examples of formulations for rectal or intra-vaginal administration include pessaries and suppositories which may be, for example, formed from a shaped moldable or waxy material containing the active compound. Solutions of the active compound may also be used for rectal administration.

Compositions for administration by inhalation may take the form of inhalable powder compositions or liquid or powder sprays, and can be administrated in standard form using powder inhaler devices or aerosol dispensing devices. Such devices are well known. For administration by inhalation, the powdered formulations typically comprise the active compound together with an inert solid powdered diluent such as lactose.

The compounds of the formula (I) will generally be presented in unit dosage form and, as such, will typically contain sufficient compound to provide a desired level of biological activity. For example, a formulation may contain from 1 nanogram to 2 grams of active ingredient, e.g. from 1 nanogram to 2 milligrams of active ingredient. Within these ranges, particular sub-ranges of compound are 0.1 milligrams to 2 grams of active ingredient (more usually from 10 milligrams 15 to 1 gram, e.g. 50 milligrams to 500 milligrams), or 1 microgram to 20 milligrams (for example 1 microgram to 10 milligrams, e.g. 0.1 milligrams to 2 milligrams of active ingredient).

For oral compositions, a unit dosage form may contain from 1 milligram to 2 grams, more typically 10 milligrams to 1 gram, for example 50 milligrams to 1 gram, e.g. 100 miligrams to 1 gram, of active compound.

The active compound will be administered to a patient in need thereof (for example a human or animal patient) in an amount sufficient to achieve the desired therapeutic effect.

Methods of Treatment

The compounds of the formula (I) and sub-groups as defined herein may be useful in the prophylaxis or treatment of a range of disease states or conditions mediated by IAP. Examples of such disease states and conditions are set out above.

The compounds are generally administered to a subject in need of such administration, for example a human or animal patient, preferably a human.

The compounds will typically be administered in amounts that are therapeutically or prophylactically useful and which generally are non-toxic. However, in certain situations (for example in the case of life threatening diseases), the benefits of administering a compound of the formula (I) may outweigh the disadvantages of any toxic effects or side effects, in which case it may be considered desirable to administer compounds in amounts that are associated with a degree of toxicity.

The compounds may be administered over a prolonged term to maintain beneficial therapeutic effects or may be administered for a short period only. Alternatively they may be administered in a continuous manner or in a manner that provides intermittent dosing (e.g. a pulsatile manner).

A typical daily dose of the compound of formula (I) can be in the range from 100 picograms to 100 milligrams per kilogram of body weight, more typically 5 nanograms to 25 milligrams per kilogram of bodyweight, and more usually 10 nanograms to 15 milligrams per kilogram (e.g. 10 nanograms to 10 milligrams, and more typically 1 microgram per kilogram to 20 milligrams per kilogram, for example 1 microgram to 10 milligrams per kilogram) per kilogram of bodyweight although higher or lower doses may be administered where required. The compound of the formula (I) can be administered on a daily basis or on a repeat basis every 2, or 3, or 4, or 5, or 6, or 7, or 10 or 14, or 21, or 28 days for example.

The compounds of the invention may be administered orally in a range of doses, for example 1 to 1500 mg, 2 to 800 mg, or 5 to 500 mg, e.g. 2 to 200 mg or 10 to 1000 mg, particular examples of doses including 10, 20, 50 and 80 mg. The compound may be administered once or more than once each day. The compound can be administered continuously (i.e. taken every day without a break for the duration of the treatment regimen). Alternatively, the compound can be administered intermittently (i.e. taken continuously for a given period such as a week, then discontinued for a period such as a week and then taken continuously for another period such as a week and so on throughout the duration of the treatment regimen). Examples of treatment regimens involving intermittent administration include regimens wherein administration is in cycles of one week on, one week off; or two weeks on, one week off; or three weeks on, one week off; or two weeks on, two weeks off; or four weeks on two weeks off; or one week on three weeks off—for one or more cycles, e.g. 2, 3, 4, 5, 6, 7, 8, 9 or 10 or more cycles.

In one particular dosing schedule, a patient will be given an infusion of a compound of the formula (I) for periods of one hour daily for up to ten days in particular up to five days for one week, and the treatment repeated at a desired interval such as two to four weeks, in particular every three weeks.

More particularly, a patient may be given an infusion of a compound of the formula (I) for periods of one hour daily for 5 days and the treatment repeated every three weeks.

In another particular dosing schedule, a patient is given an infusion over 30 minutes to 1 hour followed by maintenance infusions of variable duration, for example 1 to 5 hours, e.g. 3 hours.

In a further particular dosing schedule, a patient is given a continuous infusion for a period of 12 hours to 5 days, an in particular a continuous infusion of 24 hours to 72 hours.

Ultimately, however, the quantity of compound administered and the type of composition used will be commensurate with the nature of the disease or physiological condition being treated and will be at the discretion of the physician.

It has been discovered that IAP antagonists can be used as a single agent or in combination with other anticancer agents. For example, it may be beneficial to combine an antagonist that induces apoptosis with another agent which acts via a different mechanism to regulate cell growth thus treating two of the characteristic features of cancer development. Combination experiments can be performed, for example, as described in Chou T C, Talalay P. Quantitative analysis of dose-effect relationships: the combined effects of multiple drugs or enzyme inhibitors. Adv Enzyme Regulat 1984; 22: 27-55.

The compounds as defined herein can be administered as the sole therapeutic agent or they can be administered in combination therapy with one of more other compounds (or therapies) for treatment of a particular disease state, for example a neoplastic disease such as a cancer as hereinbefore defined. For the treatment of the above conditions, the compounds of the invention may be advantageously employed in combination with one or more other medicinal agents, more particularly, with other anti-cancer agents or adjuvants (supporting agents in the therapy) in cancer therapy. Examples of other therapeutic agents or treatments that may be administered together (whether concurrently or at different time intervals) with the compounds of the formula (I) include but are not limited to:

Topoisomerase I inhibitors
Antimetabolites
Tubulin targeting agents
DNA binder and topoisomerase II inhibitors
Alkylating Agents
Monoclonal Antibodies.
Anti-Hormones
Signal Transduction Inhibitors
Proteasome Inhibitors
DNA methyl transferases
Cytokines and retinoids
Chromatin targeted therapies
Radiotherapy, and,
Other therapeutic or prophylactic agents.

Particular examples of anti-cancer agents or adjuvants (or salts thereof), include but are not limited to any of the agents selected from groups (i)-(xlvi), and optionally group (xlvii), below:

(i) Platinum compounds, for example cisplatin (optionally combined with amifostine), carboplatin or oxaliplatin;

(ii) Taxane compounds, for example paclitaxel, paclitaxel protein bound particles (Abraxane™), docetaxel, cabazitaxel or larotaxel;

(iii) Topoisomerase I inhibitors, for example camptothecin compounds, for example camptothecin, irinotecan (CPT11), SN-38, or topotecan;

(iv) Topoisomerase II inhibitors, for example anti-tumour epipodophyllotoxins or podophyllotoxin derivatives for example etoposide, or teniposide;

(v) Vinca alkaloids, for example vinblastine, vincristine, liposomal vincristine (Onco-TCS), vinorelbine, vindesine, vinflunine or vinvesir;

(vi) Nucleoside derivatives, for example 5-fluorouracil (5-FU, optionally in combination with leucovorin), gemcitabine, capecitabine, tegafur, UFT, S1, cladribine, cytarabine (Ara-C, cytosine arabinoside), fludarabine, clofarabine, or nelarabine;

(vii) Antimetabolites, for example clofarabine, aminopterin, or methotrexate, azacitidine, cytarabine, floxuridine, pentostatin, thioguanine, thiopurine, 6-mercaptopurine, or hydroxyurea (hydroxycarbamide);

(viii) Alkylating agents, such as nitrogen mustards or nitrosourea, for example cyclophosphamide, chlorambucil, carmustine (BCNU), bendamustine, thiotepa, melphalan, treosulfan, lomustine (CCNU), altretamine, busulfan, dacarbazine, estramustine, fotemustine, ifosfamide (optionally in combination with mesna), pipobroman, procarbazine, streptozocin, temozolomide, uracil, mechlorethamine, methylcyclohexylchloroethylnitrosurea, or nimustine (ACNU);

(ix) Anthracyclines, anthracenediones and related drugs, for example daunorubicin, doxorubicin (optionally in combination with dexrazoxane), liposomal formulations of doxorubicin (eg. Caelyx™, Myocet™, Doxil™), idarubicin, mitoxantrone, epirubicin, amsacrine, or valrubicin;

(x) Epothilones, for example ixabepilone, patupilone, BMS-310705, KOS-862 and ZK-EPO, epothilone A, epothilone B, desoxyepothilone B (also known as epothilone D or KOS-862), aza-epothilone B (also known as BMS-247550), aulimalide, isolaulimalide, or luetherobin;

(xi) DNA methyl transferase inhibitors, for example temozolomide, azacytidine or decitabine;

(xii) Antifolates, for example methotrexate, pemetrexed disodium, or raltitrexed;

(xiii) Cytotoxic antibiotics, for example antinomycin D, bleomycin, mitomycin C, dactinomycin, carminomycin, daunomycin, levamisole, plicamycin, or mithramycin;

(xiv) Tubulin-binding agents, for example combrestatin, colchicines or nocodazole;

(xv) Signal Transduction inhibitors such as Kinase inhibitors (e.g. EGFR (epithelial growth factor receptor) inhibitors, VEGFR (vascular endothelial growth factor receptor) inhibitors, PDGFR (platelet-derived growth factor receptor) inhibitors, MTKI (multi target kinase inhibitors), Raf inhibitors, mTOR inhibitors for example imatinib mesylate, erlotinib, gefitinib, dasatinib, lapatinib, dovotinib, axitinib, nilotinib, vandetanib, vatalinib, pazopanib, sorafenib, sunitinib, temsirolimus, everolimus (RAD 001), or vemurafenib (PLX4032/RG7204);

(xvi) Aurora kinase inhibitors for example AT9283, barasertib (AZD1152), TAK-901, MK0457 (VX680), cenisertib (R-763), danusertib (PHA-739358), alisertib (MLN-8237), or MP-470;

(xvii) CDK inhibitors for example AT7519, roscovitine, seliciclib, alvocidib (flavopiridol), dinaciclib (SCH-727965), 7-hydroxy-staurosporine (UCN-01), JNJ-7706621, BMS-387032 (a.k.a. SNS-032), PHA533533, PD332991, ZK-304709, or AZD-5438;

(xviii) PKA/B inhibitors and PKB (akt) pathway inhibitors for example AT13148, AZ-5363, Semaphore, SF1126 and MTOR inhibitors such as rapamycin analogues, AP23841 and AP23573, calmodulin inhibitors (forkhead translocation inhibitors), API-2/TCN (triciribine), RX-0201, enzastaurin HCl (LY317615), NL-71-101, SR-13668, PX-316, or KRX-0401 (perifosine/NSC 639966);

(xix) Hsp90 inhibitors for example AT13387, herbimycin, geldanamycin (GA), 17-allylamino-17-desmethoxygeldanamycin (17-AAG) e.g. NSC-330507, Kos-953 and CNF-1010, 17-dimethylaminoethylamino-17-demethoxygeldanamycin hydrochloride (17-DMAG) e.g. NSC-707545 and Kos-1022, NVP-AUY922 (VER-52296), NVP-BEP800, CNF-2024 (BIIB-021 an oral purine), ganetespib (STA-9090), SNX-5422 (SC-102112) or IPI-504;

(xx) Monoclonal Antibodies (unconjugated or conjugated to radioisotopes, toxins or other agents), antibody derivatives and related agents, such as anti-CD, anti-VEGFR, anti-HER2 or anti-EGFR antibodies, for example rituximab (CD20), ofatumumab (CD20), ibritumomab tiuxetan (CD20), GA101 (CD20), tositumomab (CD20), epratuzumab (CD22), lintuzumab (CD33), gemtuzumab ozogamicin (CD33), alemtuzumab (CD52), galiximab (CD80), trastuzumab (HER2 antibody), pertuzumab (HER2), trastuzumab-DM1 (HER2), ertumaxomab (HER2 and CD3), cetuximab (EGFR), panitumumab (EGFR), necitumumab (EGFR), nimotuzumab (EGFR), bevacizumab (VEGF), ipilimumab (CTLA4), catumaxumab (EpCAM and CD3), abagovomab (CA125), farletuzumab (folate receptor), elotuzumab (CS1), denosumab (RANK ligand), figitumumab (IGF1R), CP751,871 (IGF1R), mapatumumab (TRAIL receptor), metMAB (met), mitumomab (GD3 ganglioside), naptumomab estafenatox (5T4), or siltuximab (IL6);

(xxi) Estrogen receptor antagonists or selective estrogen receptor modulators (SERMs) or inhibitors of estrogen synthesis, for example tamoxifen, fulvestrant, toremifene, droloxifene, faslodex, or raloxifene;

(xxii) Aromatase inhibitors and related drugs, such as exemestane, anastrozole, letrazole, testolactone aminoglutethimide, mitotane or vorozole;

(xxiii) Antiandrogens (i.e. androgen receptor antagonists) and related agents for example bicalutamide, nilutamide, flutamide, cyproterone, or ketoconazole;

(xxiv) Hormones and analogues thereof such as medroxyprogesterone, diethylstilbestrol (a.k.a. diethylstilboestrol) or octreotide;

(xxv) Steroids for example dromostanolone propionate, megestrol acetate, nandrolone (decanoate, phenpropionate), fluoxymestrone or gossypol, (xxvi) Steroidal cytochrome P450 17alpha-hydroxylase-17, 20-lyase inhibitor (CYP17), e.g. abiraterone;

(xxvii) Gonadotropin releasing hormone agonists or antagonists (GnRAs) for example abarelix, goserelin acetate, histrelin acetate, leuprolide acetate, triptorelin, buserelin, or deslorelin;

(xxviii) Glucocorticoids, for example prednisone, prednisolone, dexamethasone;

(xxix) Differentiating agents, such as retinoids, rexinoids, vitamin D or retinoic acid and retinoic acid metabolism blocking agents (RAMBA) for example accutane, alitretinoin, bexarotene, or tretinoin;

(xxx) Farnesyltransferase inhibitors for example tipifarnib;

(xxxi) Chromatin targeted therapies such as histone deacetylase (HDAC) inhibitors for example sodium butyrate, suberoylanilide hydroxamide acid (SAHA), depsipeptide (FR 901228), dacinostat (NVP-LAQ824), R306465/JNJ-16241199, JNJ-26481585, trichostatin A, vorinostat, chlamydocin, A-173, JNJ-MGCD-0103, PXD-101, or apicidin;

(xxxii) Proteasome Inhibitors for example bortezomib, carfilzomib, CEP-18770, MLN-9708, or ONX-0912;

(xxxiii) Photodynamic drugs for example porfimer sodium or temoporfin;

(xxxiv) Marine organism-derived anticancer agents such as trabectidin;

(xxxv) Radiolabelled drugs for radioimmunotherapy for example with a beta particle-emitting isotope (e.g., Iodine-131, Yittrium-90) or an alpha particle-emitting isotope (e.g., Bismuth-213 or Actinium-225) for example ibritumomab or Iodine tositumomab;

(xxxvi) Telomerase inhibitors for example telomestatin;

(xxxvii) Matrix metalloproteinase inhibitors for example batimastat, marimastat, prinostat or metastat;

(xxxviii) Recombinant interferons (such as interferon-γ and interferon α) and interleukins (e.g. interleukin 2), for example aldesleukin, denileukin diftitox, interferon alfa 2a, interferon alfa 2b, or peginterferon alfa 2b;

(xxxix) Selective immunoresponse modulators for example thalidomide, or lenalidomide;

(xl) Therapeutic Vaccines such as sipuleucel-T (Provenge) or OncoVex;

(xli) Cytokine-activating agents include Picibanil, Romurtide, Sizofiran, Virulizin, or Thymosin;

(xlii) Arsenic trioxide;

(xliii) Inhibitors of G-protein coupled receptors (GPCR) for example atrasentan;

(xliv) Enzymes such as L-asparaginase, pegaspargase, rasburicase, or pegademase;

(xlv) DNA repair inhibitors such as PARP inhibitors for example, olaparib, velaparib, iniparib, INO-1001, AG-014699, or ONO-2231;

(xlvi) Agonists of Death receptor (e.g. TNF-related apoptosis inducing ligand (TRAIL) receptor), such as mapatumumab (formerly HGS-ETR1), conatumumab (formerly AMG 655), PRO95780, lexatumumab, dulanermin, CS-1008, apomab or recombinant TRAIL ligands such as recombinant Human TRAIL/Apo2 Ligand;

(xlvii) Prophylactic agents (adjuncts); i.e. agents that reduce or alleviate some of the side effects associated with chemotherapy agents, for example
anti-emetic agents,
agents that prevent or decrease the duration of chemotherapy-associated neutropenia and prevent complications that arise from reduced levels of platelets, red blood cells or white blood cells, for example interleukin-11 (e.g. oprelvekin), erythropoietin (EPO) and analogues thereof (e.g. darbepoetin alfa), colony-stimulating factor analogs such as granulocyte macrophage-colony stimulating factor (GM-CSF) (e.g. sargramostim), and granulocyte-colony stimulating factor (G-CSF) and analogues thereof (e.g. filgrastim, pegfilgrastim),
agents that inhibit bone resorption such as denosumab or bisphosphonates e.g. zoledronate, zoledronic acid, pamidronate and ibandronate,
agents that suppress inflammatory responses such as dexamethasone, prednisone, and prednisolone,
agents used to reduce blood levels of growth hormone and IGF-I (and other hormones) in patients with acromegaly or other rare hormone-producing tumours, such as synthetic forms of the hormone somatostatin e.g. octreotide acetate,
antidote to drugs that decrease levels of folic acid such as leucovorin, or folinic acid,
agents for pain e.g. opiates such as morphine, diamorphine and fentanyl,
non-steroidal anti-inflammatory drugs (NSAID) such as COX-2 inhibitors for example celecoxib, etoricoxib and lumiracoxib,
agents for mucositis e.g. palifermin,
agents for the treatment of side-effects including anorexia, cachexia, oedema or thromoembolic episodes, such as megestrol acetate.

Each of the compounds present in the combinations of the invention may be given in individually varying dose schedules and via different routes. As such, the posology of each of the two or more agents may differ: each may be administered at the same time or at different times. A person skilled in the art would know through his or her common general knowledge the dosing regimes and combination therapies to use. For example, the compound of the invention may be using in combination with one or more other agents which are administered according to their existing combination regimen. Examples of standard combination regimens are provided below.

The taxane compound is advantageously administered in a dosage of 50 to 400 mg per square meter (mg/m$^2$) of body surface area, for example 75 to 250 mg/m$^2$, particularly for paclitaxel in a dosage of about 175 to 250 mg/m$^2$ and for docetaxel in about 75 to 150 mg/m$^2$ per course of treatment.

The camptothecin compound is advantageously administered in a dosage of 0.1 to 400 mg per square meter (mg/m$^2$) of body surface area, for example 1 to 300 mg/m$^2$, particularly for irinotecan in a dosage of about 100 to 350 mg/m$^2$ and for topotecan in about 1 to 2 mg/m$^2$ per course of treatment.

The anti-tumour podophyllotoxin derivative is advantageously administered in a dosage of 30 to 300 mg per square meter (mg/m$^2$) of body surface area, for example 50 to 250 mg/m$^2$, particularly for etoposide in a dosage of about 35 to 100 mg/m$^2$ and for teniposide in about 50 to 250 mg/m$^2$ per course of treatment.

The anti-tumour vinca alkaloid is advantageously administered in a dosage of 2 to 30 mg per square meter (mg/m$^2$) of body surface area, particularly for vinblastine in a dosage of about 3 to 12 mg/m$^2$, for vincristine in a dosage of about 1 to 2 mg/m$^2$, and for vinorelbine in dosage of about 10 to 30 mg/m$^2$ per course of treatment.

The anti-tumour nucleoside derivative is advantageously administered in a dosage of 200 to 2500 mg per square meter (mg/m$^2$) of body surface area, for example 700 to 1500 mg/m$^2$, particularly for 5-FU in a dosage of 200 to 500 mg/m$^2$, for gemcitabine in a dosage of about 800 to 1200 mg/m$^2$ and for capecitabine in about 1000 to 2500 mg/m$^2$ per course of treatment.

The alkylating agents such as nitrogen mustard or nitrosourea is advantageously administered in a dosage of 100 to 500 mg per square meter (mg/m$^2$) of body surface area, for example 120 to 200 mg/m$^2$, particularly for cyclophosphamide in a dosage of about 100 to 500 mg/m$^2$, for chlorambucil in a dosage of about 0.1 to 0.2 mg/kg, for carmustine in a dosage of about 150 to 200 mg/m$^2$, and for lomustine in a dosage of about 100 to 150 mg/m$^2$ per course of treatment.

The anti-tumour anthracycline derivative is advantageously administered in a dosage of 10 to 75 mg per square meter (mg/m$^2$) of body surface area, for example 15 to 60 mg/m$^2$, particularly for doxorubicin in a dosage of about 40 to 75 mg/m$^2$, for daunorubicin in a dosage of about 25 to 45 mg/m$^2$, and for idarubicin in a dosage of about 10 to 15 mg/m$^2$ per course of treatment.

The antiestrogen agent is advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

Antibodies are advantageously administered in a dosage of about 1 to 5 mg per square meter (mg/m$^2$) of body surface area, or as known in the art, if different. Trastuzumab is advantageously administered in a dosage of 1 to 5 mg per square meter (mg/m$^2$) of body surface area, particularly 2 to 4 mg/m$^2$ per course of treatment.

Where the compound of the formula (I) is administered in combination therapy with one, two, three, four or more other therapeutic agents (preferably one or two, more preferably one), the compounds can be administered simultaneously or sequentially. In the latter case, the two or more compounds will be administered within a period and in an amount and manner that is sufficient to ensure that an advantageous or synergistic effect is achieved. When administered sequentially, they can be administered at closely spaced intervals (for example over a period of 5-10 minutes) or at longer intervals (for example 1, 2, 3, 4 or more hours apart, or even longer periods apart where required), the precise dosage regimen being commensurate with the properties of the therapeutic agent(s). These dosages may be administered for example once, twice or more per course of treatment, which may be repeated for example every 7, 14, 21 or 28 days.

It will be appreciated that the preferred method and order of administration and the respective dosage amounts and regimes for each component of the combination will depend on the particular other medicinal agent and compound of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compound according to the present invention and the one or more other anticancer agent(s) when given as a combination may be determined by the person skilled in the art. Said ratio and the exact dosage and frequency of administration depends on the particular compound according to the invention and the other anticancer agent(s) used, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the compounds of the instant invention. A particular weight ratio for the present compound of formula (I) and another anticancer agent may range from 1/10 to 10/1, more in particular from 1/5 to 5/1, even more in particular from 1/3 to 3/1.

The compounds of the invention may also be administered in conjunction with non-chemotherapeutic treatments such as radiotherapy, photodynamic therapy, gene therapy; surgery and controlled diets.

The compounds of the present invention also have therapeutic applications in sensitising tumour cells for radiotherapy and chemotherapy. Hence the compounds of the present invention can be used as "radiosensitizer" and/or "chemosensitizer" or can be given in combination with another "radiosensitizer" and/or "chemosensitizer". In one embodiment the compound of the invention is for use as chemosensitiser.

The term "radiosensitizer" is defined as a molecule administered to patients in therapeutically effective amounts to increase the sensitivity of the cells to ionizing radiation and/or to promote the treatment of diseases which are treatable with ionizing radiation.

The term "chemosensitizer" is defined as a molecule administered to patients in therapeutically effective amounts to increase the sensitivity of cells to chemotherapy and/or promote the treatment of diseases which are treatable with chemotherapeutics.

Many cancer treatment protocols currently employ radiosensitizers in conjunction with radiation of x-rays. Examples of x-ray activated radiosensitizers include, but are not limited to, the following: metronidazole, misonidazole, desmethylmisonidazole, pimonidazole, etanidazole, nimorazole, mitomycin C, RSU 1069, SR 4233, EO9, RB 6145, nicotinamide, 5-bromodeoxyuridine (BUdR), 5-iododeoxyuridine (IUdR), bromodeoxycytidine, fluorodeoxyuridine (FudR), hydroxyurea, cisplatin, and therapeutically effective analogs and derivatives of the same.

Photodynamic therapy (PDT) of cancers employs visible light as the radiation activator of the sensitizing agent. Examples of photodynamic radiosensitizers include the following, but are not limited to: hematoporphyrin derivatives, Photofrin, benzoporphyrin derivatives, tin etioporphyrin, pheoborbide-a, bacteriochlorophyll-a, naphthalocyanines, phthalocyanines, zinc phthalocyanine, and therapeutically effective analogs and derivatives of the same.

Radiosensitizers may be administered in conjunction with a therapeutically effective amount of one or more other compounds, including but not limited to: compounds which promote the incorporation of radiosensitizers to the target cells; compounds which control the flow of therapeutics, nutrients, and/or oxygen to the target cells; chemotherapeutic agents which act on the tumour with or without additional radiation; or other therapeutically effective compounds for treating cancer or other diseases.

Chemosensitizers may be administered in conjunction with a therapeutically effective amount of one or more other compounds, including but not limited to: compounds which promote the incorporation of chemosensitizers to the target cells; compounds which control the flow of therapeutics, nutrients, and/or oxygen to the target cells; chemotherapeutic agents which act on the tumour or other therapeutically effective compounds for treating cancer or other disease. Calcium antagonists, for example verapamil, are found useful in combination with antineoplastic agents to establish chemosensitivity in tumor cells resistant to accepted chemotherapeutic agents and to potentiate the efficacy of such compounds in drug-sensitive malignancies.

For use in combination therapy with another chemotherapeutic agent, the compound of the formula (I) and one, two, three, four or more other therapeutic agents can be, for example, formulated together in a dosage form containing two, three, four or more therapeutic agents i.e. in a unitary pharmaceutical composition containing all components. In an alternative embodiment, the individual therapeutic agents may be formulated separately and presented together in the form of a kit, optionally with instructions for their use.

In one embodiment is provided a combination of a compound of formula (I) with one or more (e.g. 1 or 2) other therapeutic agents (e.g. anticancer agents as described above).

In another embodiment is provided a compound of formula (I) in combination with one or more (e.g. 1 or 2) other therapeutic agents (e.g. anticancer agents) for use in therapy, such as in the prophylaxis or treatment of cancer.

In one embodiment the pharmaceutical composition comprises a compound of formula (I) together with a pharmaceutically acceptable carrier and optionally one or more therapeutic agent(s).

In another embodiment the invention relates to the use of a combination according to the invention in the manufacture of a pharmaceutical composition for inhibiting the growth of tumour cells.

In a further embodiment the invention relates to a product containing a compound of formula (I) and one or more anticancer agent, as a combined preparation for simultaneous, separate or sequential use in the treatment of patients suffering from cancer.

EXAMPLES

The invention will now be illustrated, but not limited, by reference to the specific embodiments described in the following examples. Compounds are named using an automated naming package such as AutoNom (MDL) or are as named by the chemical supplier.

The following synthetic procedures are provided for illustration of the methods used; for a given preparation or step the precursor used may not necessarily derive from the individual batch synthesised according to the step in the description given. In the examples, the following abbreviations are used.

AcOH acetic acid
Boc tert-butyloxycarbonyl
Boc-Abu-OH (S)-2-(Boc-amino)butyric acid
BuLi butyllithium
CDI 1,1-carbonyldiimidazole
DCM dichloromethane
DIPEA N-ethyl-N-(1-methylethyl)-2-propylamine
DMC dimethyl carbonate
DMF N,N-dimethylformamide
DMSO dimethyl sulfoxide
EDC 1-ethyl-3-(3'-dimethylaminopropyl)-carbodiimide hydrochloride
Et$_3$N triethylamine
EtOAc ethyl acetate
EtOH ethanol
Et$_2$O diethyl ether
HATU 2-(7-aza-1H-benzotriazole-1-yl)-1,1,3,3-tetramethyluronium hexafluorophosphate)
HBTU O-benzotriazole-N,N,N',N'-tetramethyl-uronium-hexafluoro-phosphate
HCl hydrochloric acid
HOAc acetic acid
HOAt 1-hydroxyazabenzotriazole
HOBt 1-hydroxybenzotriazole
HPLC high pressure liquid chromatography
IPA isopropyl alcohol
KHMDS potassium hexamethyldisilazide
LiHMDS lithium bis(trimethylsilyl)amide
MeCN acetonitrile
MeOH methanol
mins. minutes
MS mass spectrometry
NaBH(OAc)$_3$ sodium triacetoxyborohydride
NaOtBu potassium tert-butoxide
NMP N-methyl-2-pyrrolidinone
NMR nuclear magnetic resonance spectroscopy
Pd$_2$(dba)$_3$ tris(dibenzylideneacetone)dipalladium (o)
Pd(OAc)$_2$ palladium (2) acetate
Pd(PPh$_3$)$_4$ tetrakis(triphenylphosphine)palladium (0)
petrol petroleum ether fraction with boiling point range 40-60° C.
PyBrop bromo-tris-pyrrolidino-phosphonium hexafluorophosphate
RT room temperature
SiO$_2$ silica
TBABr tetrabutylammonium bromide
TBAF tetrabutylammonium fluoride
TBTU N,N, N, N'-tetramethyl-O-(benzotriazol-1-yl)uronium tetrafluoroborate
TEA triethylamine
TFA trifluoroacetic acid
THF tetrahydrofuran
TMEDA N,N,N,N-tetramethylethylenediamine
NMR Data:

Unless indicated, $^1$H NMR spectra were recorded at 25° C. on a Bruker Avance I spectrometer operating at 400 MHz. The data were processed and analysed using Topspin 2.1 software. For NMR data, where the number of protons assigned is less than the theoretical number of protons in the molecule, it is assumed that the apparently missing signal(s) is/are obscured by solvent and/or water peaks. In addition, where spectra were obtained in protic NMR solvents, exchange of NH and/or OH protons with solvent occurs and hence such signals are normally not observed.

IR Data:

IR Spectra were recorded using Bruker Alpha P IR spectrometer.

Analytical and Preparative LC-MS Systems

Analytical LC-MS System and Method Description

In the following examples, compounds were characterised by mass spectroscopy using the systems and operating conditions set out below. Where atoms with different isotopes are present and a single mass quoted, the mass quoted for the compound is the monoisotopic mass (i.e. $^{35}$Cl; $^{79}$Br etc.).

Waters Platform LC-MS System:
HPLC System: Waters 2795
Mass Spec Detector: Micromass Platform LC
PDA Detector: Waters 2996 PDA
Platform MS Conditions:
Capillary voltage: 3.6 kV (3.40 kV on ES negative)
Cone voltage: 30 V
Source Temperature: 120° C.
Scan Range: 125-800 amu
Ionisation Mode: ElectroSpray Positive or
  ElectroSpray Negative or
  ElectroSpray Positive & Negative
Waters Fractionlynx LC-MS System:
HPLC System: 2767 autosampler—2525 binary gradient pump
Mass Spec Detector: Waters ZQ
PDA Detector: Waters 2996 PDA
Fractionlynx MS Conditions:
Capillary voltage: 3.5 kV (3.25 kV on ES negative)
Cone voltage: 40 V (25 V on ES negative)
Source Temperature: 120° C.
Scan Range: 125-800 amu
Ionisation Mode: ElectroSpray Positive or
  ElectroSpray Negative or
  ElectroSpray Positive & Negative
Agilent 1200SL-6140 LC-MS System—RAPID:
HPLC System: Agilent 1200 series SL
Mass Spec Detector: Agilent 6140 single quadrupole
Second Detector: Agilent 1200 MWD SL
Agilent MS Conditions:
Capillary voltage: 4000V on ES pos (3500V on ES Neg)
Fragmentor/Gain: 100
Gain: 1
Drying gas flow: 7.0 L/min
Gas Temperature: 345° C.
Nebuliser Pressure: 35 psig
Scan Range: 125-800 amu
Ionisation Mode: ElectroSpray Positive-Negative switching
Preparative LC-MS System and Method Description Preparative LC-MS is a standard and effective method used for the purification of small organic molecules such as the compounds described herein. The methods for the liquid chromatography (LC) and mass spectrometry (MS) can be varied to provide better separation of the crude materials and improved detection of the samples by MS. Optimisation of the preparative gradient LC method will involve varying columns, volatile eluents and modifiers, and gradients. Methods are well known in the art for optimising preparative LC-MS methods and then using them to purify compounds. Such methods are described in Rosentreter U, Huber U.; Optimal fraction collecting in preparative LC/MS; *J Comb Chem.*; 2004; 6(2), 159-64 and Leister W, Strauss K, Wisnoski D, Zhao Z, Lindsley C., Development of a custom high-throughput preparative liquid chromatography/mass spectrometer platform for the preparative purification and analytical analysis of compound libraries; *J Comb Chem.*; 2003; 5(3); 322-9.

Several systems for purifying compounds via preparative LC-MS are described below although a person skilled in the art will appreciate that alternative systems and methods to those described could be used. From the information provided herein, or employing alternative chromatographic systems, a person skilled in the art could purify the compounds described herein by preparative LC-MS.

Waters Fractionlynx System:
Hardware:
2767 Dual Loop Autosampler/Fraction Collector
2525 preparative pump
CFO (column fluidic organiser) for column selection
RMA (Waters reagent manager) as make up pump
Waters ZQ Mass Spectrometer
Waters 2996 Photo Diode Array detector
Waters ZQ Mass Spectrometer
Waters MS Running Conditions:
Capillary voltage: 3.5 kV (3.2 kV on ES Negative)
Cone voltage: 25 V
Source Temperature: 120° C.
Scan Range: 125-800 amu
Ionisation Mode: ElectroSpray Positive or ElectroSpray Negative Agilent 1100 LC-MS Preparative System:
Hardware:
Autosampler: 1100 series "prepALS"
Pump: 1100 series "PrepPump" for preparative flow gradient and 1100 series "QuatPump" for pumping modifier in prep flow
UV detector: 1100 series "MWD" Multi Wavelength Detector
MS detector: 1100 series "LC-MSD VL"
Fraction Collector: 2×"Prep-FC"
Agilent Active Splitter
Agilent MS Running Conditions:
Capillary voltage: 4000 V (3500 V on ES Negative)
Fragmentor/Gain: 150/1
Drying gas flow: 12.0 L/min
Gas Temperature: 350° C.
Nebuliser Pressure: 50 psig
Scan Range: 125-800 amu
Ionisation Mode: ElectroSpray Positive or ElectroSpray Negative Columns:
A range of commercially available columns—both achiral and chiral—may be used such that, in conjunction with the changes in mobile phase, organic modifier and pH, they enabled the greatest cover in terms of a broad range of selectivity. All columns were used in accordance with the manufacturers recommended operating conditions. Typically 5 micron particle sized columns were used where available. For example, columns from Waters (including but not limited to XBridge™ Prep OBD™ C18 and Phenyl, Atlantis® Prep T3 OBD™ and Sunfire™ Prep OBD C18 5 μm 19×100 mm), Phenomenex (including but not limited to Synergy MAX-RP and LUX™ Cellulose-2), Astec (Chirobiotic™ columns including but not limited to V, V2 and T2) and Diacel® (including but not limited to Chiralpak® AD-H) were available for screening.

Eluents:
Mobile phase eluent was chosen in conjunction with column manufacturers recommended stationary phase limitations in order to optimise a columns separation performance.

Methods:
Achiral Preparative Chromatoqraphy
The compound examples described have undergone HPLC purification, where indicated, using methods developed following recommendations as described in Snyder L. R., Dolan J. W., High-Performance Gradient Elution The Practical Application of the Linear-Solvent-Strength Model, Wiley, Hoboken, 2007.

Chiral Preparative Chromatography
Preparative separations using Chiral Stationary Phases (CSPs) are the natural technique to apply to the resolution of enantiomeric mixtures. Equally, it can be applied to the separation of diastereomers and achiral molecules. Methods are well known in the art for optimising preparative chiral separations on CSPs and then using them to purify compounds. Such methods are described in Beesley T. E., Scott R. P. W.; Chiral Chromatography; Wiley, Chichester, 1998.

Preparation 1: 2-Chloro-1-(6-chloro-3,3-dimethyl-2,3-dihydro-indol-1-yl)-ethanone Hydrazine hydrochloride (5.0 g, 28 mmol) and isobutyraldehyde (2.56 mL, 28 mmol) in glacial acetic acid (93 mL) were heated to 60° C. for 3 h. The reaction was cooled with a cold water bath and diluted with 1,2-dichloroethane (93 mL). NaBH(OAc)$_3$ (3.96 g, 18.7 mmol) was added in portions over 15 min and the reaction allowed to stir for 30 min. The solvent was removed in vacuo and the residue diluted with EtOAc (200 mL) and saturated sodium carbonate (200 mL). The mixture was extracted with EtOAc (200 mL) and the combined organics were washed with saturated brine solution (400 mL), dried over sodium sulfate, filtered and the solvent evaporated in vacuo. Chromatography on silica gel (gradient elution, 0-0% 0-50%, EtOAc/petrol) gave (2.65 g) as a yellow oil (a mixture of the 4 and 6-chloro isomers). The mixture (2.65 g, 14.6 mmol) was dissolved in Et$_2$O (73 mL) cooled to −20° C. (acetone/dry ice). Pyridine (1.18 mL, 14.6 mmol) and bromoacetyl chloride (1.46 mL, 17.5 mmol) were added. The reaction was allowed to warm gently to ambient temperature over 18 h. Water (50 mL) was added and the organic layer separated and the remaining aqueous phase extracted with Et$_2$O (2×60 mL). Combined organic extracts were dried over sodium sulfate and filtered. The crude oil was purified by column chromatography on silica gel (gradient elution, 0-30% EtOAc/petrol), to give the title compound (353 mg, 26%) as a red/pink solid. $^1$H NMR (Me-d3-OD): 8.11 (1H, dd), 7.22 (1H, d), 7.16-7.06 (1H, m), 4.39 (1H, s), 4.13 (1H, s), 4.00 (2H, d), 1.38 (6H, d).

Preparation 2: (R)-2-((S)-2-Benzyloxycarbonylamino-3-hydroxy-propionyl-amino)-propionic acid methyl ester Diisopropylethylamine (375 mL) was added dropwise to a cooled mixture of (R)-2-amino-propionic acid methyl ester hydrochloride (100 g, 0.716 mol), EDC (165 g, 0.86 mol), carbobenzyloxy-L-serine (171.4 g, 0.716 mol) and DCM (3.6 L). The resulting mixture was stirred under nitrogen at ambient temperature for 16 h. After removing solvent in vacuo at 40° C., the residue was diluted with saturated sodium carbonate (1 L), water (1 L) and extracted with EtOAc (2 L, 2×1 L). The combined organic phases were washed with 2 M hydrochloric acid (1 L), saturated brine solution (1 L), dried over magnesium sulfate and concentrated in vacuo at 40° C., to give the title compound (172 g) as a colourless solid. $^1$H NMR (Me-d3-OD): 7.44-7.28 (6H, m), 5.13 (2H, s), 4.46 (1H, d), 4.43 (1H, d), 4.25 (1H, t), 3.82-3.68 (5H, m), 1.39 (3H, d).

Preparation 3: (3S,6R)-3-Hydroxymethyl-6-methyl-piperazine-2,5-dione

To (R)-2-((S)-2-benzyloxycarbonylamino-3-hydroxy-propionylamino)-propionic acid methyl ester (172 g, 0.53 mol) was added 10% Pd/C (8.6 g), MeOH (530 mL) and cyclohexene (344 mL) under nitrogen. The mixture was heated to reflux for 17 h. MeOH (500 mL) was added and the reflux continued for 1 h. The hot reaction mixture was filtered through a pad of celite, cake washing with hot MeOH (2×500 mL). The combined filtrates were concentrated. The resulting solid was slurried in 2-butanone (400 mL) and petrol (400 mL) was added gradually over 10 min. After stirring for 30 min, the solids were filtered, cake washed with 2:1 petrol/2-butanone (300 mL). The filter cake was dried in vacuo at 40° C., to give the title compound (68.3 g) as an off white solid. $^1$H NMR (DMSO-d6): 8.08 (1H, s), 7.90 (1H, s), 5.11 (1H, t), 3.92 (1H, q), 3.80-3.71 (1H, m), 3.71-3.60 (1H, m), 3.58-3.47 (1H, m), 1.24 (3H, d).

Preparation 4:
((2R,5R)-5-Methyl-piperazin-2-yl)-methanol hydrochloride

To (3S,6R)-3-hydroxymethyl-6-methyl-piperazine-2,5-dione (34 g, 0.215 mol) was added a solution of borane in THF (1 M, 1.6 L, 1.6 mol) and the mixture was heated to 70° C. for 18 h.

The solution was cooled in ice, then MeOH (425 mL) was gradually added, followed by 5 M hydrochloric acid (113 mL). The mixture was heated to 70° C. for 2 h and then cooled to ambient temperature. The resulting solid was filtered, cake washed with THF (200 mL) and dried in vacuo at 40° C., to give the title compound (39.3 g) as a colourless solid. $^1$H NMR (DMSO-d6): 9.79 (3H, s), 5.59 (1H, s), 3.76-3.40 (5H, m), 3.19-2.94 (2H, m), 1.28 (3H, d).

Preparation 5: (2R,5R)-5-Hydroxymethyl-2-methyl-piperazine-1-carboxylic acid tert-butyl ester To the piperazine dihydrochloride (20 g, 119 mmol) in MeOH (96 mL) at 0° C. (ice bath) was added triethylamine (48.7 mL, 357 mmol). tert-Butyl dicarbonate (61 g, 280 mmol) in MeOH (145 mL) was added over 30 min. The reaction temperature was maintained at <10° C. for 1 h, warmed to ambient temperature over 1 h and then heated to 50° C. for 18 h. The reaction was concentrated and the residue dissolved in ethanol (397 mL). A solution of NaOH (23.8 g, 595 mmol) in water (397 mL) was added and the reaction heated to 100° C. for 18 h, then cooled to ambient temperature. Mixture was neutralised with 1M HCl (~300 mL) to pH 9 (using a pH meter), then extracted with chloroform (3×700 mL), dried over sodium sulfate, filtered and concentrated. The residue was redissolved in MeOH and concentrated, then dried in vacuo at 40° C., to give the title compound (21 g, 75%) as a colourless solid. $^1$H NMR (Me-d3-OD): 4.20-4.07 (1H, m), 3.79 (1H, dd), 3.71-3.58 (2H, m), 3.54 (1H, dd), 3.24 (1H, dd), 3.18-3.01 (1H, m), 3.01-2.89 (1H, m), 2.55 (1H, dd), 1.48 (9H, s), 1.25 (3H, s).

Preparation 6: (2R,5R)-4-[2-(6-Chloro-3,3-dimethyl-2,3-dihydro-indol-1-yl)-2-oxo-ethyl]-5-hydroxymethyl-2-methyl-piperazine-1-carboxylic acid tert-butyl ester To 2-chloro-1-(6-chloro-3,3-dimethyl-2,3-dihydro-indol-1-yl)-ethanone (397 mg, 1.31 mmol) in anhydrous THF (1.23 mL) was added triethylamine (366 μL, 2.60 mmol) and a solution of (2R,5R)-5-hydroxymethyl-2-methyl-piperazine-1-carboxylic acid tert-butyl ester (380 mg, 1.6 mmol) in anhydrous THF (730 μL). The reaction was heated to 65° C. for 3 h, cooled to ambient temperature and the solvent removed in vacuo. The residue was purified by column chromatography on silica gel (gradient elution, 0-80%, EtOAc/petrol), to give the title compound (447 mg, 75%) as a colourless solid. $^1$H NMR (Me-d3-OD): 8.15 (1H, d), 7.20 (1H, d), 7.09 (1H, dd), 5.51 (2H, s), 4.23-4.13 (1H, m), 4.09-3.96 (3H, m), 3.81-3.65 (2H, m), 3.64-3.47 (2H, m), 2.97-2.82 (2H, m), 2.67 (1H, dd), 1.48 (9H, s), 1.37 (6H, s), 1.26-1.22 (3H, m).

Preparation 7: (2R,5R)-4-[2-(6-Chloro-3,3-dimethyl-2,3-dihydro-indol-1-yl)-2-oxo-ethyl]-5-methoxymethyl-2-methyl-piperazine-1-carboxylic acid tert-butyl ester To a cooled solution of (2R,5R)-4-[2-(6-chloro-3,3-dimethyl-2,3-dihydro-indol-1-yl)-2-oxo-ethyl]-5-hydroxymethyl-2-methyl-piperazine-1-carboxylic acid tert-butyl ester (100 mg, 0.22 mmol) in DMF (1.1 mL) at 0° C. (ice bath) was added sodium hydride (60%, 10 mg, 0.24 mmol). After stirring for 1 h, methyl iodide (15 μL, 0.24 mmol) was added and the reaction stirred for 30 mins. Reaction was allowed to warm gently to ambient temperature over 18 h. The solvent was removed in vacuo and residue was purified by column chromatography on silica gel (gradient elution, 0-100% EtOAc/petrol), to give the title compound (20 mg, 19%) as a colourless oil. $^1$H NMR (Me-d3-OD): 8.14 (1H, s), 7.27-7.13 (1H, m), 7.09 (1H, dd), 4.19 (1H, dd), 4.13-3.84 (3H, m), 3.78-3.44 (3H, m), 3.44-3.38 (1H, m), 3.36 (3H, s), 3.29 (1H, d), 3.07-2.94 (1H, m), 2.94-2.81 (1H, m), 2.66 (1H, dd), 1.48 (9H, s), 1.37 (6H, s), 1.34-1.20 (3H, m).

Preparation 8: (2R,5R)-5-Azidomethyl-4-[2-(6-chloro-3,3-dimethyl-2,3-dihydro-indol-1-yl)-2-oxo-ethyl]-2-methyl-piperazine-1-carboxylic acid tert-butyl ester (2R,5R)-4-[2-(6-Chloro-3,3-dimethyl-2,3-dihydro-indol-1-yl)-2-oxo-ethyl]-5-hydroxymethyl-2-methyl-piperazine-1-carboxylic acid tert-butyl ester (175 mg, 0.39 mmol) was dissolved in anhydrous DCM (3.87 mL) and cooled in an ice bath. Triethylamine (0.27 mL, 1.94 mmol) was added followed by toluene-4-sulfonyl chloride (148 mg, 0.77 mmol). Reaction was stirred for 1 h at 0° C. (ice bath) and gently warmed to ambient temperature over 18 h. The solvent was removed in vacuo and residue purified by column chromatography on silica gel (0-50%, EtOAc/petrol). The product (117 mg, 0.25 mmol) was dissolved in DMF (2.5 mL) and sodium azide (24 mg, 0.37 mmol) added. The reaction was heated to 65° C. for 18 h, then cooled to ambient temperature and the solvent removed in vacuo. The residue was slurried in Et$_2$O, filtered and the filtrate evaporated in vacuo. The resulting oil was purified by column chromatography on silica gel (gradient elution, 0-75%, EtOAc/petrol), to give the title compound (81 mg, 44%) as a colourless oil. $^1$H NMR (Me-d3-OD): 8.14 (1H, d), 7.21 (1H, d), 7.09 (1H, dd), 4.26-4.15 (1H, m), 4.10-3.97 (3H, m), 3.76-3.46 (3H, m), 3.46-3.36 (1H, m), 3.05-2.91 (1H, m), 2.85 (1H, dd), 2.70 (1H, dd), 1.50 (9H, s), 1.38 (6H, s), 1.24 (3H, d).

Preparation 9: (2R,5S)-5-(Acetylamino-methyl)-4-[2-(6-chloro-3,3-dimethyl-2,3-dihydro-indol-1-yl)-2-oxo-ethyl]-2-methyl-piperazine-1-carboxylic acid tert-butyl ester (2R,5R)-5-Azidomethyl-4-[2-(6-chloro-3,3-dimethyl-2,3-dihydro-indol-1-yl)-2-oxo-ethyl]-2-methyl-piperazine-1-carboxylic acid tert-butyl ester (81 mg, 0.17 mmol) was dissolved in thioacetic acid (459 μL) and left to stir for 18.5 h, then concentrated. The crude oil was purified by column chromatography on silica gel (gradient elution, 0-100%, EtOAc/petrol) to give the title compound (47 mg, 56%) as a colourless solid. $^1$H NMR (Me-d3-OD): 8.15 (1H, d), 7.21 (1H, d), 7.09 (1H, dd), 4.24-4.14 (1H, m), 4.06-3.96 (2H, m), 3.84 (1H, d), 3.71 (1H, d), 3.56 (1H, d), 3.48-3.40 (1H, m), 3.25-3.13 (1H, m), 3.04-2.96 (1H, m), 2.92 (1H, dd), 2.65 (1H, dd), 1.97 (3H, s), 1.49 (9H, s), 1.38 (6H, s), 1.32-1.19 (3H, m).

Preparation 10: (2R,5R)-2-Hydroxymethyl-5-methyl-piperazine-1,4-dicarboxylic acid 1-benzyl ester 4-tert-butyl ester To (2R,5R)-5-hydroxymethyl-2-methyl-piperazine-1-carboxylic acid tert-butyl ester (21 g, 90 mmol) in THF (210 mL) at 3-4° C. (ice bath) was added 1 M aqueous NaOH (99.5 mL) and benzyl chloroformate (12.9 mL, 90.43 mmol). After stirring for 1 h at the same temperature, the mixture was left to stir for another 1 h and then warmed to RT. The organic layer was separated and the aqueous phase extracted with EtOAc (2×50 mL). The combined organic extracts were washed with saturated brine solution (150 mL), then dried over sodium sulfate, filtered and concentrated. The crude oil was purified by column chromatography on silica gel (gradient elution, 0-100%, EtOAc/petrol), to give the title compound (26 g) as a pale yellow oil, used directly in Preparation 11. $^1$H NMR (Me-d3-OD): 7.47-7.15 (5H, m), 5.26-5.07 (2H, m), 4.25 (2H, s), 4.04-3.88 (1H, m), 3.83 (1H, d), 3.61 (2H, bs), 3.31-3.09 (2H, m), 1.48 (9H, s), 1.14 (3H, t).

Preparation 11: (2R,5R)-2-Methoxymethyl-5-methyl-piperazine-1,4-dicarboxylic acid 1-benzyl ester 4-tert-butyl ester (2R,5R)-2-Hydroxymethyl-5-methyl-piperazine-1,4-dicarboxylic acid 1-benzyl ester 4-tert-butyl ester (25 g, 68 mmol) in DCM (823 mL) was cooled to 4° C. (ice bath). 1,8-bis(dimethylamino)naphthalene (72 g, 337 mmol) was added in one portion followed by trimethyl oxonium tetrfluoroborate (50 g, 337 mmol) portionwise over 5 min. The mixture was stirred for 35 min at 5° C., the ice bath removed, then warmed from 5-17° C. over 1 h. After stirring for a further 20 min., saturated aqueous ammonium chloride (300 mL) was added slowly and reaction stirred for 10 min. The organic layer was separated and the aqueous phase extracted with DCM (2×300 mL). The combined organic extracts were washed with 1.0 M HCl (3×1.5 L), saturated sodium bicarbonate solution (3×1.5 L), dried over sodium sulfate, filtered and concentrated. The oil was dissolved in DCM and petrol added until precipitation of 1,8-bis(dimethylamino)naphthalene occurred. Purification by column chromatography (silica gel, 0-0%, 0-100%, EtOAc/petrol) gave an oil which contained 1,8-bis(dimethylamino)naphthalene as a contaminant. The remaining 1,8-bis(dimethylamino)naphthalene was captured during filtration through a SCX-2 column eluting with MeOH, to give the title compound (18 g, 52% over two steps) as a pale yellow oil. $^1$H NMR (Me-d$_3$-OD): 7.46-7.26 (5H, m), 5.26-5.07 (2H, m), 4.31 (2H, d), 4.04-3.85 (1H, m), 3.79 (1H, d), 3.46 (2H, s), 3.28-3.09 (2H, m), 1.48 (9H, s), 1.15 (3H, dd).

Preparation 12: (2R,5R)-5-Methoxymethyl-2-methyl-piperazine-1-carboxylic acid tert-butyl ester 10% Pd/C (5.05 g, 4.76 mmol) and (2R,5R)-2-methoxymethyl-5-methyl-piperazine-1,4-dicarboxylic acid 1-benzyl ester 4-tert-butyl ester (18 g, 48 mmol) were mixed with MeOH (190 mL) at ambient temperature and the mixture was hydrogenated at ambient temperature and ~1 bar for 3 h. The mixture was filtered through celite and the filtrate concentrated, to give the title compound (11 g, 99%) as a colourless oil. $^1$H NMR (Me-d3-OD): 4.16 (1H, dd), 3.80 (1H, d), 3.71-3.47 (1H, m), 3.47-3.40 (1H, m), 3.39 (3H, s), 3.30-3.17 (2H, m), 3.17-3.00 (2H, m), 2.60 (1H, dd), 1.48 (9H, s), 1.25 (3H, d).

Preparation 13: (2R,5R)-4-Benzyloxycarbonylmethyl-5-methoxymethyl-2-methyl-piperazine-1-carboxylic acid tert-butyl ester To a stirred suspension of (2R,5R)-5-methoxymethyl-2-methyl-piperazine-1-carboxylic acid tert-butyl ester (11 g, 45 mmol), potassium carbonate (6.79 g, 49.14 mmol) and acetonitrile (48 mL) was added benzyl bromoacetate (7.08 mL, 44.67 mmol) dropwise at ambient temperature. The reaction was stirred for 18 h at ambient temperature, then diluted with chloroform (150 mL), filtered and the filtrate concentrated. The crude oil was purified by column chromatography on silica gel (gradient elution, 0-70%, EtOAc/petrol), to give the title compound (16 g, 92%) as a pale yellow oil. $^1$H NMR (Me-d3-OD): 7.45-7.22 (5H, m), 5.21-5.12 (2H, m), 4.84 (2H, s), 4.16-4.03 (1H, m), 3.91 (1H, d), 3.62 (1H, d), 3.56-3.40 (2H, m), 3.31-3.19 (3H, m), 3.04-2.92 (1H, m), 2.80 (1H, dd), 2.68 (1H, dd), 1.48 (9H, s), 1.19 (3H, d).

Preparation 14: (2R,5R)-4-Carboxymethyl-5-methoxymethyl-2-methyl-piperazine-1-carboxylic acid tert-butyl ester Prepared using a hydrogenolysis method analogous to that described in Preparation 12; stirring for 2 h. $^1$H NMR (Me-d3-OD): 4.35-4.17 (1H, m), 4.01 (1H, d), 3.85-3.55 (3H, m), 3.55-3.34 (6H, m), 3.21-2.94 (2H, m), 1.50 (9H, s), 1.28 (3H, d).

Preparation 15: (R)-4-Carboxymethyl-2-methyl-piperazine-1-carboxylic acid tert-butyl ester Prepared from (R)-2-methyl-piperazine-1-carboxylic acid tert-butyl ester in an analogous manner to that described for (2R,5R)-4-carboxymethyl-5-methoxymethyl-2-methyl-piperazine-1-carboxylic acid tert-butyl ester in Preparations 13 and 14. $^1$H NMR (Me-d3-OD): 4.51-4.42 (1H, m), 4.10-3.99

(1H, m), 3.58 (1H, d), 3.53-3.39 (2H, m), 3.28 (1H, s), 2.99-2.82 (2H, m), 1.49 (9H, s), 1.36 (3H, d).

Preparation 16:
(2R,5R)-5-Methyl-piperazine-1,2,4-tricarboxylic acid 1-benzyl ester 4-tert-butyl ester To sodium periodate (1.76 g, 8.24 mol) dissolved in water (10.3 mL) and dimethyl carbonate/acetonitrile (1:1, 5.5 mL) was added $RuCl_3$ (7 mg, 0.05 mol) and (2R,5R)-2-hydroxymethyl-5-methyl-piperazine-1,4-dicarboxylic acid 1-benzyl ester 4-tert-butyl ester (1.5 g, 4.12 mmol) in a 1:1 mixture of DMC/MeCN (15 mL). The reaction was stirred for 1.5 h at ambient temperature. Water (20 mL) was added and the reaction was extracted with EtOAc (3×30 mL); the combined organics were washed with saturated brine solution (100 mL), dried over sodium sulfate and filtered through a plug of celite eluting with EtOAc. The solvent was removed in vacuo and residue dissolved in $Et_2O$, evaporated and the resulting solid triturated with petrol, to give the title compound (1.21 g, 78%) as a beige solid. $^1$H NMR (Me-d3-OD): 7.45-7.27 (5H, m), 5.26-5.10 (2H, m), 4.70 (1H, s), 4.55-4.18 (2H, m), 3.83-3.66 (1H, m), 3.52-3.36 (2H, m), 1.46 (9H, s), 1.18 (3H, t).

Preparation 17: (2R,5R)-2-Methyl-5-methylcarbamoyl-piperazine-1,4-dicarboxylic acid 4-benzyl ester 1-tert-butyl ester (2R,5R)-5-Methyl-piperazine-1,2,4-tricarboxylic acid 1-benzyl ester 4-tert-butyl ester (200 mg, 0.53 mmol) was dissolved in anhydrous DMF (2.65 mL). HATU (221 mg, 0.58 mol) was added and the reaction stirred for 20 min. DIPEA (184 µL, 1.06 mmol) and methylamine in THF (2.0M, 0.53 mL, 1.06 mmol) were added and the reaction stirred for 2 h. Water (10 mL) was added and aqueous phase extracted with EtOAc (3×5.0 mL). The combined organic extracts were washed with saturated aqueous sodium bicarbonate (3×15 mL), brine (3×15 mL), dried over sodium sulfate, filtered and concentrated. Column chromatography on silica gel (gradient elution, 0-100% EtOAc/petrol), gave the title compound (0.12 g, 58%) as a colourless oil. $^1$H NMR (Me-d3-OD): 7.48-7.26 (5H, m), 5.30-5.04 (2H, m), 4.44 (1H, d), 4.21 (2H, s), 3.64 (2H, d), 3.44 (1H, d), 2.72 (3H, d), 1.46 (9H, s), 1.16 (3H, dd).

Preparation 18: (2R,5R)-2-Methyl-5-methylcarbamoyl-piperazine-1-carboxylic acid tert-butyl ester Prepared by a method analogous to that described in Preparation 12, starting with (2R,5R)-2-methyl-5-methylcarbamoyl-piperazine-1,4-dicarboxylic acid 4-benzyl ester 1-tert-butyl ester. $^1$H NMR (Me-d3-OD): 4.23 (1H, dd), 4.09-3.94 (1H, m), 3.46 (1H, d), 3.28 (1H, dd), 2.98 (1H, dd), 2.78 (3H, s), 2.66 (1H, dd), 1.46 (9H, s), 1.18 (3H, d).

Preparation 19: (2R,5R)-4-Benzyloxycarbonylmethyl-2-methyl-5-methylcarbamoyl-piperazine-1-carboxylic acid tert-butyl ester Prepared by a method analogous to that described in Preparation 13, starting with (2R,5R)-4-benzyloxycarbonyl-methyl-2-methyl-5-methylcarbamoyl-piperazine-1-carboxylic acid tert-butyl ester. $^1$H NMR (Me-d3-OD): 7.45-7.29 (5H, m), 5.19 (2H, s), 4.19-4.03 (2H, m), 3.58-3.35 (4H, m), 3.01-2.89 (1H, m), 2.89-2.67 (4H, m), 1.43 (9H, s), 1.10 (3H, d).

Preparation 20: (2R,5R)-4-Carboxymethyl-2-methyl-5-methylcarbamoyl-piperazine-1-carboxylic acid tert-butyl ester Method analogous to that described in Preparation 14, starting with (2R,5R)-4-benzyloxycarbonylmethyl-2-methyl-5-methylcarbamoyl-piperazine-1-carboxylic acid tert-butyl ester. $^1$H NMR (Me-d3-OD): 4.30-4.05 (2H, m), 3.62-3.38 (4H, m), 3.05-2.82 (2H, m), 2.82-2.68 (3H, m), 1.45 (9H, s), 1.14 (3H, d).

Preparation 21: (R)-2-Benzylamino-propionic acid methyl ester

A suspension of D-alanine methyl ester hydrochloride (5.0 g, 36 mmol) and benzaldehyde (3.8 g, 36 mmol) in anhydrous DCM (60 mL) were stirred for 18 h at ambient temperature. Sodium triacetoxyborohydride was added in portions over 0.5 h and the reaction stirred for 18 h at ambient temperature. The solvent was removed in vacuo and the residue partitioned between EtOAc (20 mL) and 1 M hydrochloric acid (80 mL). The aqueous phase was separated and washed with EtOAc (2×30 mL), then was basified to pH 10 with 1 M aqueous NaOH and extracted with EtOAc (3×50 mL) and washed with brine (50 mL). The combined organic extracts were dried over sodium sulfate, filtered and the solvent removed in vacuo, to give the title compound (5.3 g, 77%) as a pale yellow oil. $^1$H NMR (Me-d3-OD): 7.43-7.19 (4H, m), 3.85-3.44 (5H, m), 3.39 (1H, q), 3.33 (1H, s), 1.32 (3H, d).

Preparation 22: (3S,6R)-1-Benzyl-3-ethyl-6-methyl-piperazine-2,5-dione

To a solution of (R)-2-benzylamino-propionic acid methyl ester (3.5 g, 18.1 mmol) and EDC (3.65 g, 19.0 mmol) in anhydrous DCM (30 mL) was added Boc-Abu-OH (3.68 g, 18.1 mmol). The reaction was stirred for 18 h, then additional Boc-Abu-OH (0.74 mmol, 3.62 mmol), EDC (1.35 g 7.1 mmol) and DMF (2.4 mL) were added to the reaction, followed by stirring for 18 h. The solvent was removed in vacuo and the resulting oil was dissolved in EtOAc (50 mL) and washed with 1 M hydrochloric acid (50 mL×3), 1 M aqueous NaOH (50 mL×3), brine (50 mL), dried over sodium sulfate, filtered and concentrated, to give (R)-2-[benzyl-((S)-2-tert-butoxycarbonylamino-butyryl)-amino]-propionic acid methyl ester (6.0 g, 87%) as a pale colourless oil. An aliquot (3.9 g, 10.3 mmol) was dissolved in DCM (52 mL) and HCl gas was bubbled through the reaction for 30 min at ambient temperature. The reaction was stirred for an additional hour and then solvent removed in vacuo. The resultant solid was triturated with $Et_2O$, to give (R)-2-[((S)-2-amino-butyryl)-benzyl-amino]-propionic acid methyl ester hydrochloride (3.0 g, 93%) as a colourless solid. This material was slurried in EtOAc (47 mL) at ambient temperature and saturated aqueous sodium bicarbonate (14 mL) added. After stirring for 18 h, the organic layer was separated and washed with brine, dried over sodium sulfate, filtered and concentrated, to give the title compound (1.68 g, 72%) as a colourless oil. $^1$H NMR (Me-d3-OD): 7.44-7.23 (5H, m), 5.19 (1H, d), 4.28-4.08 (2H, m), 3.86 (1H, q), 2.18-1.99 (1H, m), 1.96-1.79 (1H, m), 1.46 (3H, d), 0.95 (3H, t).

Preparation 23: (2R,5S)-4-Carboxymethyl-5-ethyl-2-methyl-piperazine-1-carboxylic acid tert-butyl ester Step 1: A solution of borane in THF (1 M, 197 mL) was slowly added to (3S,6R)-1-benzyl-3-ethyl-6-methyl-piperazine-2,5-dione (4.9 g, 19.7 mmol) over 15 min under nitrogen. The reaction mixture was then stirred at 70° C. for 72 h. The resulting solution was cooled to 0° C. and MeOH (60 mL) and 5 M hydrochloric acid (16 mL) were slowly added, then the solution was heated at 70° C. with stirring for 2 h. The solvent was removed in vacuo, and the residue was partitioned between water and Et$_2$O. 1 M aqueous NaOH was added to give pH 12 and the product was extracted with EtOAc (3×). The organic phase was dried (MgSO$_4$), filtered and concentrated to give (2R,5S)-1-benzyl-5-ethyl-2-methyl-piperazine (3.5 g) as a yellow liquid. MS: [M+H]$^+$=219.

Step 2: Benzyl bromoacetate (2.6 mL, 16 mmol) was added to a solution of (2R,5S)-1-benzyl-5-ethyl-2-methyl-piperazine (3.5 g, 16 mmol) in acetonitrile (20 mL) containing K$_2$CO$_3$ (2.4 g, 17.6 mmol). The reaction mixture was stirred at ambient temperature overnight. The suspension was diluted with CHCl$_3$ and the solid was filtered off. Filtrate was evaporated in vacuo and the residue was purified by SiO$_2$ chromatography (EtOAc:petrol 4:6) to give ((2S,5R)-4-benzyl-2-ethyl-5-methyl-piperazin-1-yl)-acetic acid benzyl ester (3.4 g) as a pale yellow oil. $^1$H NMR (CDCl$_3$): 7.46-7.14 (10H, m), 5.18 (2H, d), 4.10 (1H, d), 3.49 (1H, d), 3.32 (1H, d), 3.17 (1H, d), 2.91-2.79 (1H, m), 2.73 (1H, dd), 2.60-2.42 (3H, m), 2.01-1.79 (1H, m), 1.60-1.44 (1H, m), 1.41-1.23 (1H, m), 1.14 (3H, d), 0.77 (3H, t).

Step 3: A solution of ((2S,5R)-4-benzyl-2-ethyl-5-methyl-piperazin-1-yl)-acetic acid benzyl ester (3.4 g, 9.3 mmol) in MeOH (93 mL) containing Pd/C (10%, 985 mg) and acetic acid (1.57 mL) was stirred overnight under H$_2$ (3.5 bar). The mixture was filtered through Celite and the solvent was removed in vacuo to give ((2S,5R)-2-ethyl-5-methyl-piperazin-1-yl)-acetic acid, (1.87 g) as a white solid. The compound was directly used in the next step without further purification.

Step 4: tert-Butyl dicarbonate (2.1 g, 9.6 mmol) and triethylamine (6.7 mL, 48.4 mmol) were added to a suspension of ((2S,5R)-2-ethyl-5-methyl-piperazin-1-yl)-acetic acid (1.8 g, 9.6 mmol) in DCM. The resulting solution was stirred at room temperature for 24 h. The solvent was removed in vacuo to give (2R,5S)-4-carboxymethyl-5-ethyl-2-methyl-piperazine-1-carboxylic acid tert-butyl ester triethylamine salt (3.8 g) as a yellow gum. $^1$H NMR (CDCl$_3$): 11.73-9.75 ($^1$H, m), 4.20 (1H, s), 3.86 (1H, d), 3.34-3.07 (3H, m), 2.97 (6H, q, triethylamine), 2.77-2.65 (2H, m), 2.60 (1H, dd), 1.47-1.36 (11H, m), 1.26 (3H, d), 1.24-1.14 (9H, m, triethylamine), 0.87 (3H, t).

Step 5: Cs$_2$CO$_3$ (3.4 g, 10.5 mmol) was added to a solution of (2R,5S)-4-carboxymethyl-5-ethyl-2-methyl-piperazine-1-carboxylic acid tert-butyl ester triethylamine salt (3.9 g, 9.6 mmol) in DMF (20 mL). After stirring for 2 h at room temperature, a solution of benzyl bromide (1.25 mL, 10.5 mmol) in DMF (10 mL) was added over 30 minutes. The reaction mixture was stirred overnight at room temperature and the resulting solid was filtered off and the filtrate was evaporated in vacuo. The residue was dissolved in EtOAc and washed with water. The organic phase was dried (MgSO$_4$), filtered and concentrated and the residue was purified by SiO$_2$ chromatography (EtOAc:Petrol 1:1) to give (2R,5S)-4-benzyloxycarbonylmethyl-5-ethyl-2-methyl-piperazine-1-carboxylic acid tert-butyl ester (2.8 g) as a pale yellow oil. $^1$H NMR (CDCl$_3$): 7.45-7.29 (5H, m), 5.26-5.08 (2H, m), 4.27-4.08 (1H, m), 3.89 (1H, d), 3.52-3.22 (3H, m), 2.75 (1H, dd), 2.68-2.40 (2H, m), 1.47 (11H, d), 1.26 (3H, d), 0.90 (3H, t).

Step 6: Pd/C (10%, 810 mg) was added to a solution of (2R,5S)-4-benzyloxycarbonylmethyl-5-ethyl-2-methyl-piperazine-1-carboxylic acid tert-butyl ester (2.8 g, 7.6 mmol) in MeOH (50 mL). The suspension was stirred overnight under H$_2$. and catalyst was removed via filtration through Celite and the filtrate was evaporated in vacuo to give the title compound (1.7 g) as a pale yellow solid. $^1$H NMR (DMSO-d6): 4.41-3.89 (1H, m), 3.89-3.64 (1H, m), 3.37-3.21 (1H, m), 3.21-3.05 (2H, m), 2.71-2.55 (2H, m), 2.54-2.42 (3H, m), 1.45-1.36 (9H, m), 1.16 (3H, d), 0.83 (3H, t). MS: [M+H]$^+$=287.

Preparation 24: (2R,5S)-4-Carboxymethyl-5-isopropyl-2-methyl-piperazine-1-carboxylic acid tert-butyl ester triethylamine salt Prepared using an analogous procedure to that described in Preparations 22 and 23 starting with Boc-valine instead of Boc-Abu-OH and omitting steps 5 and 6 from Preparation 23. $^1$H NMR (Me-d3-OD): 4.11 (1H, dd), 3.96 (1H, d), 3.56-3.35 (3H, m), 3.19 (9H, q, triethylamine), 3.16-3.04 (1H, m), 3.04-2.82 (1H, m), 2.82-2.60 (1H, m), 1.48 (9H, s) 1.32 (14H, t, triethylamine), 1.22 (3H, d), 1.02 (6H, dd).

Preparation 25: 6-Chloro-3,3-dimethyl-2,3-dihydro-1H-indole and 4-chloro-3,3-dimethyl-2,3-dihydro-1H-indole Step 1 of the synthesis of 2-chloro-1-(6-chloro-3,3-dimethyl-2,3-dihydro-indol-1-yl)-ethanone (Preparation 1) was repeated, using 3-chlorophenylhydrazine (1.0 g, 5.6 mmol) and the two isomers separated by chromatography on silica gel (gradient elution, 0-60% EtOAc/petrol then 0-100% Et$_2$O/petrol), to give 6-chloro-3,3-dimethyl-2,3-dihydro-1H-indole (38 mg, 4%) as a yellow oil, $^1$H NMR (CDCl$_3$): 6.93 (1H, d), 6.71 (1H, dd), 6.61 (1H, d), 3.34 (2H, s), 1.31 (6H, s) and 4-chloro-3,3-dimethyl-2,3-dihydro-1H-indole (146 mg, 14%), as a yellow oil, 1H NMR (Me-d3-OD): 6.93 (1H, t), 6.58 (1H, d), 6.53 (1H, d), 3.27 (2H, s), 1.43 (6H, s).

Preparation 26: 6-Benzyl-2,3-dihydro-1H-indole

Pd(PPh$_3$)$_4$ (108 mg, 0.1 mmol), indole-6-boronic acid (300 mg, 1.9 mmol), benzyl bromide (333 µL, 2.8 mmol), THF (3.73 mL) and 2.0 M aqueous K$_2$CO$_3$ solution (2.80 mL, 5.6 mmol) was added to a microwave tube. The reaction was degassed with nitrogen and heated to 80° C. for 4 h under microwave irradiation. The organic layer was separated and concentrated. Purification by column chromatography on silica gel (gradient elution, 0-20% EtOAc/petrol), gave a yellow oil (0.27 g). The crude oil (242 mg) was dissolved in 1.0 M BH$_3$ in THF (1.75 mL) at 0° C. and stirred for 30 min. TFA (1.75 mL) was added dropwise and the solution stirred at 0° C. for 30 min. 6 M aqueous NaOH solution was added until the solution was made basic (pH 11). The aqueous solution was extracted with DCM (3×25 mL), dried over sodium sulfate, filtered and concentrated. Chromatography on silica gel (gradient elution, 0-100%, EtOAc/petrol), gave the title compound (139 mg), MS: [M+H]$^+$ 210.

Preparation 27:
5-Bromo-2,3-dihydro-1H-indole-6-sulfonic acid methylamide

To a slurry of 1-acetyl-5-bromo-2,3-dihydro-1H-indole-6-sulfonyl chloride (see Preparation 43) (0.40 g, 1.2 mmol) in THF (3.38 mL) was added triethylamine (0.660 mL, 4.73 mmol) and 40% methylamine in water (0.18 mL, 2.4 mmol). The reaction was heated to reflux and stirred for 1.5 h, then cooled and concentrated. The residue was slurried in hot MeOH and filtered under vacuum washing with MeOH. The solid was dried in vacuo at 40° C., to give 1-acetyl-5-bromo-2,3-dihydro-1H-indole-6-sulfonic acid methylamide (0.33 g, 85%) as a colourless solid. This product (320 mg, 1.0 mmol) was slurried in 1,4-dioxane (0.98 mL) and concentrated hydrochloric acid (0.72 mL), heated to 100° C. for 1.5 h, then cooled to ambient temperature solvent removed in vacuo. The pH was adjusted to ~7 with 1 M aqueous NaOH and the resulting precipitate collected by vacuum filtration, washed with water and dried in vacuo at 40° C., to give the title compound (0.176 g, 62%) as a beige solid; MS: [M+H]$^+$ 291

Preparation 28:
5-Bromo-2,3-dihydro-1H-indole-6-sulfonic acid dimethylamide

Starting with dimethylamine and 1-acetyl-5-bromo-2,3-dihydro-1H-indole-6-sulfonyl chloride, the title compound was prepared by using similar methods to those described for Preparation 27. $^1$H NMR (DMSO-d6): 7.40 (1H, s), 7.01 (1H, s), 3.51 (2H, t), 3.01 (2H, t), 2.77 (6H, s).

Preparation 29: 6-Chloro-1,2-dihydrospiro[indole-3,4'-piperidine]-1'-carboxylic acid, benzyl ester Starting with 3-chloro-hydrazine hydrochloride and 4-formyl-piperidine-1-carboxylic acid benzyl ester, the title compound was prepared by using similar methods to those described for Preparation 25. $^1$H NMR (CDCl$_3$): 7.46-7.31 (5H, m), 6.92 (1H, d), 6.71 (1H, dd), 6.62 (1H, d), 5.25-5.11 (2H, m), 4.16 (2H, d), 3.94-3.70 (1H, m), 3.00 (2H, s), 1.70 (6H, d).

Preparation 30: 6-Chloro-2,3-dihydro-1H-indole

6-Chloroindole (1.0 g, 6.6 mmol) was dissolved in a solution of borane in THF (1 M, 9.83 mmol) at 0° C. and stirred for 30 min. TFA (9.83 mL) was added dropwise and the solution stirred at 0° C. for 30 min. 6 M aqueous NaOH was added until the solution was basic (pH 11). The aqueous solution was extracted with DCM (3×25 mL), dried over sodium sulfate, filtered and concentrated to give the title compound (864 mg, 86%) as a yellow oil. $^1$H NMR (Me-d3-OD): 6.99 (1H, d), 6.64-6.55 (2H, m), 3.50 (2H, t), 2.95 (2H, t).

Preparation 31: 6-Methyl-2,3-dihydro-1H-indole

6-Methyl indole (0.50 g, 3.8 mmol) was dissolved in glacial acetic acid (19.1 mL) and cooled to 0° C. Sodium cyanoborohydride (0.48 g, 7.6 mmol) was added portionwise and the mixture warmed to ambient temperature and stirred for 2 h. The reaction was diluted with water (8.0 mL), made alkaline with 40% aqueous NaOH and extracted with EtOAc (3×10 mL). The combined organic extracts were washed with brine (3×30 mL), dried over sodium sulfate, filtered and concentrated. Purification by column chromatography on silica gel (gradient elution, 0-100% EtOAc/petrol), gave the title compound (0.256 g, 51%) as a purple oil. $^1$H NMR (Me-d3-OD): 6.96 (1H, d), 6.53 (2H, d), 3.44 (2H, t), 2.94 (2H, t), 2.23 (3H, s).

Preparation 32: 6-Methoxy-2,3-dihydro-1H-indole

Starting with 6-methoxy indole, the title compound was prepared by using similar methods to those described for Preparation 31. $^1$H NMR (Me-d3-OD): 6.96 (1H, d), 6.37-6.18 (2H, m), 3.72 (3H, s), 3.47 (2H, t), 2.91 (2H, t).

Preparation 33:
6-Trifluoromethyl-2,3-dihydro-1H-indole

Starting with 6-trifluoromethyl indole, the title compound was prepared by using similar methods to those described for Preparation 31. $^1$H NMR (Me-d3-OD): 7.19 (1H, d), 6.89 (1H, d), 6.81 (1H, s), 3.55 (2H, t), 3.05 (2H, t).

Preparation 34: 2,3-Dihydro-1H-indole-6-carboxylic acid methyl ester

Starting with methyl 6-indolecarboxylate, the title compound was prepared by using similar methods to those described for Preparation 31. $^1$H NMR (Me-d3-OD): 7.37 (1H, dd), 7.24 (1H, d), 7.16 (1H, d), 3.86 (3H, s), 3.53 (2H, t), 3.04 (2H, t).

Preparation 35:
6-Chloro-2,3-dihydro-1H-pyrrolo[3,2-c]pyridine

Under nitrogen, 6-chloro-5-aza indole (500 mg, 3.29 mmol) was dissolved in 2.0 M BH$_3$.SMe$_2$ in THF (6.6 mL, 13.16 mmol) and heated gently to 68° C. for 2 h. After cooling to ambient temperature, MeOH (6.0 mL) was added slowly over 20 min. Once bubbling had stopped, the reaction was heated to 68° C. for 30 min, then cooled to ambient temperature and concentrated in vacuo. Chromatography on silica gel (gradient elution, 0-60% EtOAc/petrol), gave the title compound (209 mg, 41%) as colourless oil. $^1$H NMR (CDCl$_3$): 7.86 (1H, s), 6.43 (1H, s), 4.33 (1H, s), 3.80-3.65 (2H, m), 3.05 (2H, t).

Preparation 36:
5-Fluoro-6-phenyl-2,3-dihydro-1H-indole

A mixture of 6-bromo-5-fluoro-1H-indole (0.214 g, 1 mmol), phenylboronic acid (0.171 g, 1.4 mmol), sodium carbonate (1.06 g, 10 mmol), Pd(PPh$_3$)$_4$ (0.116 g, 0.1 mmol), 1,2-dimethoxyethane (5 mL) and water (5 mL) was stirred under nitrogen at 85° C. for 18 h. The mixture was partitioned between water (20 mL) and DCM (2×30 mL) and the combined extracts were dried (Na$_2$SO$_4$) and evaporated in vacuo to give an oil. Chromatography (SiO$_2$; gradient elution with 0-50% Et$_2$O in petrol) gave 5-fluoro-6-phenyl-1H-indole (0.202 g, 95%) as a pale green solid. MS: [M+H]$^+$=212. A solution of borane in THF (1 M, 1.42 mL) was added to 5-fluoro-6-phenyl-1H-indole (0.20 g, 0.95 mmol) under nitrogen with external cooling using an ice-MeOH bath. The resulting mixture was stirred at 0° C. for 0.5 h, then TFA was added dropwise over 0.1 h. The mixture was stirred at 0° C. for 1 h then a solution of sodium hydroxide (0.8 g, 20 mmol) and water (5 mL) was added dropwise over 0.1 h. The resulting mixture was partitioned between water (20 mL) and DCM (2×30 mL) and the combined organic extracts were dried (Na$_2$SO$_4$) and evaporated in vacuo to give an oil. Chromatography (SiO$_2$; gradient elution with 0-100% Et$_2$O in petrol) gave the title compound (0.17 g, 85%) as an oil. MS: [M+H]$^+$=214.

Preparation 37:
6-Trifluoromethoxy-2,3-dihydro-1H-indole

Prepared from 6-trifluoromethoxy-1H-indole in an analogous manner to that used in Preparation 30. MS: [M+H]$^+$=204.

Preparation 38: 6-Methylsulfonyl-2,3-dihydro-1H-indole

Prepared from 6-methylsulfonyl-1H-indole in an analogous manner to that used in Preparation 30. MS: [M+H]$^+$=198.

Preparation 39: 6-Bromo-1-triisopropylsilanyl-1H-indole

To a stirred solution of 6-bromo-1H-indole (2.04 g, 1.04 mmol) in THF under nitrogen at 0° C. was added sodium hydride (60%, 1.25 g 31.2 mmol), portionwise over 0.2 h. The mixture was stirred at 0-20° C. for 1 h then was cooled in an ice-MeOH bath, whereupon triisopropylsilyl trifluoromethylsulfonate (3.83 g, 12.5 mmol) was added dropwise over 3 h. The resulting mixture was stirred at −0° C. for 1 h then at 20° C. for 72 h. The mixture was quenched (caution!) with a mixture of THF (30 mL) and water (1 mL) with external ice cooling and the resulting clear solution was partitioned between water (100 mL) and DCM (3×50 mL). The combined organic extracts were dried (Na$_2$SO$_4$) and evaporated in vacuo to give an oil. Chromatography (SiO$_2$; gradient elution with 0-40% Et$_2$O in petrol) gave the title compound (3.48 g) as a colourless oil. $^1$H NMR (CDCl$_3$): 7.66-7.64 (1H, m), 7.50 (1H, d), 7.25-7.21 (2H, m), 6.61 (1H, d), 1.76-1.64 (3H, m), 1.17 (18H, d).

Preparation 40: 6-Phenylsulfonyl-1-triisopropylsilanyl-1H-indole

To as stirred solution of 6-bromo-1-triisopropylsilanyl-1H-indole (0.687 g, 1.95 mmol) in THF (12 mL) at −78° C. under nitrogen was added, dropwise over 0.3 h, a solution of tert-butyllithium in pentane (1.7 M, 2.52 mL, 4.29 mmol) (internal temperature was kept below −70° C.). The mixture was stirred at −78° C. for 0.1 h then phenylsulfonyl fluoride (0.26 mL, 0.343 g, 2.15 mmol) was added dropwise. The mixture was stirred at −78° C. then warmed to 20° C. and stirred thus for 1 h. Excess tert-butyllithium was quenched by addition of ice and the resulting mixture was partitioned between water (100 mL) and EtOAc (3×50 mL). The combined organic extracts were dried (Na$_2$SO$_4$) and evaporated in vacuo to give semi-solid. Chromatography (SiO$_2$; gradient elution with 0-40% Et$_2$O in petrol) gave the title compound (0.365 g, 45%). $^1$H NMR (CDCl$_3$): 8.21 (1H, s), 8.00-7.89 (2H, m), 7.70 (1H, d), 7.63 (1H, dd), 7.57-7.41 (4H, m), 6.69 (1H, d), 1.82-1.65 (3H, m), 1.16 (18H, d).

Preparation 41: 6-Phenylsulfonyl-1H-indole

To a solution of 6-phenylsulfonyl-1-triisopropylsilanyl-1H-indole 0.365 g, 0.88 mmol) in THF (10 mL) was added a solution of TBAF in THF (1 M, 1 mL) followed by a solution of boric acid (0.062 g, 1 mmol) in water (1 mL) and stirring was carried out for 2 h. The mixture was partitioned between water (50 mL) and DCM (3×30 mL) and the combined organic extracts were dried (Na$_2$SO$_4$) and evaporated in vacuo to give an oil. Chromatography (SiO$_2$; gradient elution with 0-40% EtOAc in petrol) gave the title compound (0.21 g) as a colourless solid. MS: [M+H]$^+$=258.

Preparation 42: 6-Phenylsulfonyl-2,3-dihydro-1H-indole

Prepared from 6-phenylsulfonyl-1H-indole in an analogous manner to that used in Preparation 30. MS: [M+H]$^+$=260.

Preparation 43: 1-Acetyl-5-bromo-2,3-dihydro-1H-indole-6-sulfonyl chloride 1-(5-Bromo-2,3-dihydro-indol-1-yl)-ethanone (0.249 g, 1.04 mmol) was added portionwise to chlorosulfonic acid (1 mL) at 20° C. with stirring and mixture was stirred for 26 h, then poured onto crushed ice. The resulting solid was collected by filtration and dried in vacuo. The filtrate was extracted with EtOAc and the organic phase was dried (Na$_2$SO$_4$) and evaporated in vacuo to give further solid. The two batches of solid were combined to give the title compound (0.25 g) which was used in the next stage without further purification. MS: [M−H]$^−$=336.

Preparation 44: 1-[5-Bromo-6-(pyrrolidine-1-sulfonyl)-2,3-dihydro-indol-1-yl]-ethanone A mixture of 1-acetyl-5-bromo-2,3-dihydro-1H-indole-6-sulfonyl chloride (0.25 g, 0.74 mmol), pyrrolidine (0.156 g, 2.2 mmol) and THF (10 mL) was stirred at 20° C. for 18 h then was partitioned between water (50 mL) and EtOAc (2×50 mL). The combined organic extracts were dried (Na$_2$SO$_4$) and evaporated in vacuo to give a solid. Chromatography (SiO$_2$; gradient elution with 50-100% EtOAc in petrol) gave the title compound (0.206 g) as a colourless solid.

MS: [M+H]$^+$=373.

Preparation 45: 5-Bromo-6-(pyrrolidine-1-sulfonyl)-2,3-dihydro-1H-indole

A mixture of 1-[5-bromo-6-(pyrrolidine-1-sulfonyl)-2,3-dihydro-indol-1-yl]-ethanone (0.203 g, 0.54 mmol), concentrated hydrochloric acid (2 mL) and 1,4-dioxane (5 mL) was heated at 100° C. in a sealed vessel for 2 h. The mixture was cooled then neutralised with saturated aqueous sodium hydrogen carbonate and resulting solid collected by filtration to give the title compound (0.13 g, 72%). MS: [M+H]$^+$=331.

Preparation 46: 5-Methoxy-2,3-dihydro-pyrrolo[2,3-c]pyridine-1-carboxylic acid tert-butyl ester A mixture of 5-methoxy-1H-pyrrolo[2,3-c]pyridine (0.536 g, 3.6 mmol) and a solution of borane dimethyl sulfide complex in THF (2 M, 18 mL) was heated at reflux under nitrogen for 6 h, then was cooled to 20° C. and left thus for 16 h. MeOH (4 mL) was added dropwise with external ice bath cooling (caution!) over 0.3 h, and the resulting clear solution was heated at reflux for 1 h.

Excess solvent was then evaporated in vacuo. A mixture of this residue with di-tert-butyl dicarbonate (0.865 g, 4 mmol) and DCM (20 mL) was stirred at 20° C. for 2 h then was evaporated in vacuo to give a semi-solid. Chromatography (SiO$_2$; gradient elution with 0-50% EtOAc in petrol) gave the title compound (0.429 g, ~47%). MS: [M+H]$^+$=251.

Preparation 47: 6-Benzyl-5-oxo-2,3,5,6-tetrahydro-pyrrolo[2,3-c]pyridine-1-carboxylic acid tert-butyl ester A mixture of 5-methoxy-2,3-dihydro-pyrrolo[2,3-c]pyridine-1-carboxylic acid tert-butyl ester (0.065 g, 0.26 mmol), benzyl bromide (0.053 g, 0.31 mmol), sodium iodide (0.077 g, 0.52 mmol) and acetonitrile (2 mL) was stirred at 60° C. for 40 h. The mixture was poured into a mixture of water (10 mL) and saturated aqueous sodium thiosulfate (10 mL) and extracted with DCM (3×20 mL). The combined organic extracts were dried ($Na_2SO_4$) and evaporated in vacuo to give a brown oil. Chromatography ($SiO_2$; gradient elution with 0-100% EtOAc in petrol) gave the title compound (0.054 g, ~64%) as a colourless oil. MS: $[M+H]^+=327$.

Preparation 48: 6-Benzyl-1,2,3,6-tetrahydro-pyrrolo[2,3-c]pyridin-5-one, hydrochloride A mixture of 6-benzyl-5-oxo-2,3,5,6-tetrahydro-pyrrolo[2,3-c]pyridine-1-carboxylic acid tert-butyl ester (0.050 g, 0.15 mmol), 1,4-dioxane (1 mL) and a solution of hydrogen chloride in 1,4-dioxane (4 M, 0.5 mL) was stirred at 20° C. for 18 h, then was evaporated in vacuo. The residue was dissolved in MeOH then re-evaporated and the azeotrope process repeated to give the title compound as a pale green glass, used without further purification. MS: $[M+H]^+=227$.

Preparation 49: 1-Benzenesulfonyl-3-fluoro-benzene

A mixture of 1-fluoro-3-iodobenzene (2.22 g, 10 mmol), sodium phenylsulfinate (2.16 g, 13 mmol), copper (1) trifluoromethylsulfonate-benzene complex (0.15 g, 0.3 mmol), N, N'-dimethylethylenediamine (0.95 g, 1.09 mmol) and dimethyl sulfoxide (20 mL) was heated at 90° C. under nitrogen with stirring for 2 h then at 115° C. for 18 h. Mixture was cooled then partitioned between water (150 mL) and 1:1 $Et_2O$-EtOAc (100 mL) and the organic phase was washed with water (3×100 mL), dried ($Na_2SO_4$) and evaporated in vacuo to give a beige solid. Chromatography ($SiO_2$; gradient elution with 0-40% $Et_2O$ in petrol) gave the title compound (1.725 g, 73%) as a colourless solid. $^1H$ NMR (CDCl3): 8.02-7.93 (2H, m), 7.81-7.71 (1H, m), 7.71-7.46 (5H, m), 7.28 (1H, m).

Preparation 50: (3-Benzenesulfonyl-phenyl)-hydrazine

A mixture of 1-benzenesulfonyl-3-fluoro-benzene (1.34 g, 5.7 mmol), hydrazine hydrate (1.4 mL) and dimethyl sulfoxide (2 mL) was stirred at 118° C. for 18 h, then cooled and poured into water (100 mL). The resulting colourless crystals were collected by filtration to give the title compound (1.34 g, 95%). $^1H$ NMR (DMSO-d6): 7.95-7.84 (2H, m), 7.73-7.56 (3H, m), 7.37-7.21 (3H, m), 7.06 (1H, d), 6.96 (1H, dd), 4.14 (2H, br m).

Preparation 51: 6-Benzenesulfonyl-3,3-dimethyl-2,3-dihydro-1H-indole

A mixture of (3-benzenesulfonyl-phenyl)-hydrazine (0.824 g, 3.3 mmol), isobutyraldehyde (0.245 g, 3.4 mmol) and toluene (12 mL) was stirred at 20° C. for 2 h. Acetic acid (12 mL) was added, followed by a solution of HCl in 1,4-dioxane (4 M, 0.83 mL, 3.3 mmol) and stirring was continued for 2 h. 1,2-Dichloroethane (12 mL) was added followed by sodium triacetoxyborohydride (1.05 g, 5 mmol) and stirring was continued for 1 h. The mixture was concentrated to ~5 mL in vacuo and residue partitioned between saturated aqueous sodium hydrogen carbonate (200 mL) and DCM (3×60 mL). The combined organic extracts were dried ($Na_2SO_4$) and evaporated in vacuo to give an orange oil. Chromatography ($SiO_2$; gradient elution with 0-30% $Et_2O$ in petrol) gave the title compound (0.044 g). MS: $[M+H]^+=288$.

Preparation 52: 4,6-Dichloro-3,3-dimethyl-2,3-dihydro-1H-indole

Prepared from 3,5-dichlorophenylhydrazine hydrochloride in an analogous manner to that described for 6-chloro-3,3-dimethyl-2,3-dihydro-1H-indole (Preparation 25). MS: $[M+H]^+=216$.

Preparation 53: 6' Chloro-spiro[cyclopentane-1,3'-[3H]indol]-2'(1'H)-one

To a stirred solution of 6-chloro-1,3-dihydro-indol-2-one (1.0 g, 6 mmol) in THF (20 mL) at −25 30° C. under nitrogen was added, dropwise over 0.15 h, a solution of butyllithium in hexanes (1.6 M, 7.5 mL, 12 mmol). Tetramethylethylenediamine (1.39 g, 12 mmol) was added dropwise over 0.02 h and the resulting brown suspension was stirred for 0.5 h at −25° C. 1,4-Diiodobutane was then added over 0.02 h and the resulting mixture slowly warmed to 20° C. and stirred thus for 18 h. The mixture was then quenched with saturated aqueous ammonium chloride then partitioned between water (100 mL) and EtOAc (100 mL). The organic phase was washed with aqueous HCl (2 M, 100 mL), water (100 mL) then dried ($Na_2SO_4$) and evaporated in vacuo. Chromatography ($SiO_2$; gradient elution with 0-40% EtOAc in petrol) gave the title compound (0.509 g). MS: $[M+H]^+=222$.

Preparation 54: 6'-Chloro-1',2'-dihydro-spiro[cyclopentane-1,3'-[3H]indole]

A solution of borane-dimethyl sulfide complex in THF (2 M, 3.75 mL) was added to 6' chloro-spiro[cyclopentane-1,3'-[3H]indol]-2'(1'H)-one under nitrogen and the resulting solution stirred at 20° C. for 0.2 h then at reflux for 1 h. The mixture was cooled then MeOH (3 mL) was added slowly (caution!) and reflux resumed for 1 h. Excess solvent was evaporated in vacuo and chromatography of the residue ($SiO_2$; gradient elution with 0-40% $Et_2O$ in petrol) gave the title compound (0.335 g, 88%). MS: $[M+H]^+=208$.

Preparation 55: 6-Chloro-2-oxo-2,3-dihydro-indole-1-carboxylic acid tert-butyl ester A mixture of 6-chloro-1,3-dihydro-indol-2-one (11.35 g, 67.7 mmol), sodium carbonate (35.9 g, 338.5 mmol), tert-butyl dicarbonate (36.7 g, 168.2 mmol) and THF (300 mL) was stirred at 20° C. for 88 h then solids were removed by filtration and the filtrate evaporated in vacuo to give an oil. Chromatography ($SiO_2$; gradient elution with 5-25% EtOAc in petrol) gave the title compound (8.746 g) as an oil. MS: $[M−H]^−=266$.

Preparation 56: 6' Chloro-spiro[cyclopropane-1,3'-[3H]indol]-2'(1'H)-one-1-carboxylic acid tert-butyl ester A mixture of 6-chloro-2-oxo-2,3-dihydro-indole-1-carboxylic acid tert-butyl ester (2.00 g, 7.5 mmol), potassium carbonate (2.18 g, 15.8 mmol), 1,2-dibromoethane (1.56 g, 8.3 mmol) and DMF (20 mL) was stirred at 20° C. for 18 h then partitioned between water (100 mL) and EtOAc (100 mL). The organic phase was washed with water (100 mL) and brine (50 mL) then was dried ($Na_2SO_4$) and evaporated in vacuo. Chromatography ($SiO_2$; gradient elution with 0-100% EtOAc in petrol) gave the title compound (0.594 g).

¹H NMR (CDCl₃): 8.00 (1H, d), 7.13 (1H, dd), 6.74 (1H, d), 1.90-1.80 (2H, m), 1.67 (9H, s), 1.58-1.55 (2H, m).

Preparation 57: 6' Chloro-spiro[cyclopropane-1,3'-[3H]indol]-2'(1'H)-one

A mixture of 6' chloro-spiro[cyclopropane-1,3'-[3H]indol]-2'(1'H)-one-1-carboxylic acid tert-butyl ester (0.70 g, 2.4 mmol), DCM (5 mL) and TFA (2.5 mL) was stirred at 0° C. for 1 h then was evaporated in vacuo to give a solid. Chromatography (SiO₂; gradient elution with 10-30% EtOAc in petrol) gave the title compound (0.359 g) as a beige solid. MS: [M+H]⁺=194.

Preparation 58: 6'-Chloro-1',2'-dihydro-spiro[cyclopropane-1,3'-[3H]indole]

A mixture of 6' chloro-spiro[cyclopropane-1,3'-[3H]indol]-2'(1'H)-one (0.291 g, 1.5 mmol) and borane-dimethyl sulfide complex in THF (2 M, 3.0 mL) was heated at reflux under nitrogen for 2 h. The mixture was cooled and MeOH (3 mL) was added dropwise (caution!). The resulting mixture was heated at reflux for 2 h, then was cooled and solvent evaporated in vacuo. Chromatography (SiO₂; gradient elution with 0-100% Et₂O in petrol) gave the title compound (0.142 g). MS: [M+H]⁺=180.

Preparation 59 6' Chloro-spiro[cyclobutane-1,3'-[3H]indol]-2'(1'H)-one

Prepared in an analogous manner to that described in Preparation 53, using 1,3-diiodopropane instead of 1,4-diiodobutane. MS: [M+H]⁺=208.

Preparation 60: 6'-Chloro-1',2'-dihydro-spiro[cyclobutane-1,3'-[3H]indole]

Prepared in an analogous manner to that described for in Preparation 54 using 6' chloro-spiro[cyclobutane-1,3'-[3H]indol]-2'(1'H)-one as starting material. MS: [M+H]⁺=194.

Preparation 61: 1-(5-Bromo-3,3-dimethyl-2,3-dihydro-indol-1-yl)-ethanone and 5-Bromo-3,3-dimethyl-2,3-dihydro-1H-indole The title compounds were prepared starting from 4-bromophenylhydrazine hydrochloride (4 g, 17.9 mmol) and isobutyraldehyde (1.6 mL, 17.9 mmol) following similar methods to those described in Preparation 25 to give 1-(5-bromo-3,3-dimethyl-2,3-dihydro-indol-1-yl)-ethanone (2.0 g) as a dark orange oil [¹H NMR (CDCl₃): 8.09 (1H, d), 7.32 (1H, dd), 7.23 (1H, d), 3.80 (2H, s), 2.23 (3H, s), 1.37 (6H, s). MS: [M+H]⁺ 268] and 5-bromo-3,3-dimethyl-2,3-dihydro-1H-indole (1.3 g) as an orange liquid. [MS: [M+H]⁺ 226].

Preparation 62: 1-(5-Bromo-3,3-dimethyl-2,3-dihydro-indol-1-yl)-ethanone

To a solution of 5-bromo-3,3-dimethyl-2,3-dihydro-1H-indole (1.6 g, 7.1 mmol) in DCM (40 mL) and pyridine (1.1 mL, 14.2 mmol) was added acetic anhydride (1 mL, 11 mmol). The reaction was stirred at room temperature overnight, then solvent was removed in vacuo and the residue partitioned between water and saturated aqueous NH₄Cl. The organic phase was separated, dried (MgSO₄), filtered and concentrated to give the title compound (1.8 g), used without further purification. Analytical data were consistent with those reported in Preparation 61.

Preparation 63: 1-Acetyl-5-bromo-3,3-dimethyl-2,3-dihydro-1H-indole-6-sulfonyl chloride 1-(5-Bromo-3,3-dimethyl-2,3-dihydro-indol-1-yl)-ethanone (2.0 g, 7.5 mmol) was slowly added to chlorosulfonic acid (20 mL) and the resulting solution was stirred at room temperature for 3 days. The mixture was then carefully poured over ice and the resulting solid filtered, washed with water and dried in vacuo to give the title compound (2.7 g) as a pale brown solid. ¹H NMR (Acetone-d₆): 9.02 (1H, s), 7.89 (1H, s), 4.11 (2H, s), 2.26 (3H, s), 1.49 (6H, s).

Preparation 64: 1-(5-Bromo-6-ethanesulfonyl-3,3-dimethyl-2,3-dihydro-indol-1-yl)-ethanone A suspension of 1-acetyl-5-bromo-3,3-dimethyl-2,3-dihydro-1H-indole-6-sulfonyl chloride (300 mg, 0.81 mmol), Na₂SO₃ (206 mg, 1.6 mmol) and NaHCO₃ (134 mg, 1.6 mmol) in water (5 mL) was stirred at 105° C. for 1.5 h. The resulting solution was cooled to 70° C., then TBABr (1.5 mg, 0.005 mmol) and iodoethane (323 µL, 4 mmol) were added and the stirring maintained at the same temperature for 4 h. The reaction mixture was cooled to ambient temperature, diluted with water (15 mL) and extracted with DCM (3×). The organic phase was dried (MgSO₄), filtered and concentrated and the crude material was purified using SiO₂ chromatography (50% EtOAc/Petrol) to give the title compound (0.21 g) as a pale yellow oil. ¹H NMR (CDCl₃): 8.92 (1H, s), 7.45 (1H, s), 3.87 (2H, s), 3.43 (2H, q), 2.23 (3H, s), 1.39 (6H, s), 1.33-1.26 (3H, m).

Preparation 65: 1-(6-Ethanesulfonyl-3,3-dimethyl-2,3-dihydro-indol-1-yl)-ethanone To a solution of 1-(5-bromo-6-ethanesulfonyl-3,3-dimethyl-2,3-dihydro-indol-1-yl)-ethanone (180 mg, 0.5 mmol) in THF (5 mL) containing saturated aqueous NH₄Cl (1 mL), zinc dust (325 mg, 5 mmol) was added. The suspension was stirred at room temperature for 3 days and then partitioned between water and EtOAc. The aqueous phase was extracted twice with EtOAc. The organic extracts were filtered through a plug of Celite and the filtrate was evaporated in vacuo to give the title compound (130 mg) as a colourless gum which was used in the next step without further purification. MS: [M+H]⁺=282.

Preparation 66: 6-Ethanesulfonyl-3,3-dimethyl-2,3-dihydro-1H-indole 1-(6-Ethanesulfonyl-3,3-dimethyl-2,3-dihydro-indol-1-yl)-ethanone (130 mg, 0.46 mmol) was dissolved in MeOH (7 mL) and 5 M hydrochloric acid (920 µL, 4.6 mmol) was added. The solution was stirred at 90° C. for 1.5 h then solvent was removed in vacuo. The residue was quenched with saturated aqueous NaHCO₃ and the product extracted with EtOAc. The organic phase was dried (MgSO₄), filtered and concentrated to give the title compound (60 mg), used without further purification. MS: [M+H]⁺=240.

Preparation 67: 3,3-Dimethyl-6-(2-methyl-propane-1-sulfonyl)-2,3-dihydro-1H-indole The title compound was prepared following similar methods to those described in Preparations 64-66 using 1-bromo-2-methyl-propane instead of iodoethane. MS: [M+H]⁺=268.

Preparation 68: 3,3-Dimethyl-6-phenylmethanesulfonyl-2,3-dihydro-1H-indole

The title compound was prepared following similar methods to those described in Preparations 64-66 using benzyl bromide instead of iodoethane. MS: [M+H]$^+$=302.

Preparation 69: 1-Acetyl-5-bromo-3,3-dimethyl-2,3-dihydro-1H-indole-6-sulfonic acid methylamide Methylamine (2 M solution in THF, 2.4 mL, 4.9 mmol) was added to a solution of 1-acetyl-5-bromo-3,3-dimethyl-2,3-dihydro-1H-indole-6-sulfonyl chloride (300 mg, 0.82 mmol) in THF (10 mL). The solution was stirred at room temperature for 30 minutes then the solvent was removed in vacuo and the residue partitioned between water and EtOAc. The organic phase was dried (MgSO$_4$), filtered and concentrated to give the title compound (271 mg) as a yellow solid. $^1$H NMR (CDCl$_3$): 8.93 (1H, s), 7.44 (1H, s), 5.07 (1H, s), 3.88 (2H, s), 2.68 (3H, d), 2.25 (3H, s), 1.48-1.22 (6H, s).

Preparation 70: 1-Acetyl-3,3-dimethyl-2,3-dihydro-1H-indole-6-sulfonic acid methylamide 1-Acetyl-5-bromo-3,3-dimethyl-2,3-dihydro-1H-indole-6-sulfonic acid methylamide (270 mg, 0.75 mmol), Pd/C (10%, 79 mg) and triethylamine (209 μL, 1.5 mmol) were suspended in MeOH (10 mL). The reaction was stirred under a hydrogen atmosphere for 1 h, then the mixture was filtered through Celite and filtrate was evaporated in vacuo to give the title compound (160 mg) as a white solid. $^1$H NMR (CDCl$_3$): 8.65 (1H, s), 7.62 (1H, d), 7.26 (1H, d), 4.52 (1H, s), 3.88 (2H, s), 2.70 (3H, d), 2.26 (3H, s), 1.40 (6H, s). MS: [M+H]$^+$=283.

Preparation 71: 3,3-Dimethyl-2,3-dihydro-1H-indole-6-sulfonic acid methylamide 1-Acetyl-3,3-dimethyl-2,3-dihydro-1H-indole-6-sulfonic acid methylamide (160 mg, 0.56 mmol) was processed in an analogous manner to Preparation 66. The title compound (91 mg) was obtained as a colourless gum. MS: [M+H]$^+$=241.

Preparation 72: 3,3-Dimethyl-2,3-dihydro-1H-indole-6-sulfonic acid dimethylamide The title compound was prepared following similar methods to those described in Preparations 69-71 using dimethylamine instead of methylamine. $^1$H NMR (CDCl$_3$): 7.14 (2H, s), 6.97 (1H, s), 3.41 (2H, s), 2.74 (6H, s), 1.35 (6H, s).

Preparation 73: 3,3-Dimethyl-2,3-dihydro-1H-indole-6-sulfonic acid isopropylamide The title compound was prepared following similar methods to those described in Preparations 69-71 using isopropylamine instead of methylamine. $^1$H NMR (CDCl$_3$): 7.23 (1H, dd), 7.15-7.00 (2H, m), 4.60 (1H, d), 3.54-3.40 (1H, m), 3.37 (2H, s), 1.32 (6H, s), 1.09 (6H, d).

Preparation 74: 5-Fluoro-3,3-dimethyl-2,3-dihydro-1H-indole

The title compound (1.6 g) was prepared following an analogous procedure to that in Preparation 25 using 4-fluorophenylhydrazine hydrochloride (8.0 g) instead of 3-chlorophenylhydrazine hydrochloride. 1H NMR (DMSO-d6): 6.85 (1H, dd), 6.77-6.62 (1H, m), 6.44 (1H, dd), 5.32 (1H, s), 3.18 (2H, s), 1.21 (6H, s). 1-(5-Fluoro-3,3-dimethyl-2,3-dihydro-indol-1-yl)-ethanone (3.1 g) was also isolated. $^1$H NMR (DMSO-d6): 8.01 (1H, dd), 7.25-7.10 (1H, m), 7.05-6.90 (1H, m), 3.87 (2H, s), 2.15 (3H, s), 1.30 (6H, s).

Preparation 75: Bromo-5-fluoro-3,3-dimethyl-2,3-dihydro-1H-indole

To a solution of 5-fluoro-3,3-dimethyl-2,3-dihydro-1H-indole (1.6 g, 9.6 mmol) in 98% H$_2$SO$_4$ (20 mL), Ag$_2$SO$_4$ (1.6 g, 5.1 mmol) was added and the suspension was stirred under nitrogen for 30 minutes. The mixture was then cooled to −5° C., Br$_2$ (508 μL, 9.9 mmol) was slowly added over 15 minutes and stirring maintained at the same temperature for 1 h. The reaction mixture was slowly poured over 200 mL of water/ice and subsequently filtered through Celite. 50% aqueous NaOH was added to the resulting solution (to pH=9-10) and the product was extracted with EtOAc (3×). The organic phase was dried (MgSO$_4$), filtered and concentrated to give the title compound (1.58 g) as a dark oil. $^1$H NMR (DMSO-d6): 7.03 (1H, d), 6.64 (1H, d), 5.59 (1H, s), 3.20 (2H, s), 1.25-1.15 (6H, m). MS: [M+H]$^+$=244.

Preparation 76: 6-Bromo-5-fluoro-3,3-dimethyl-1-triisopropylsilanyl-2,3-dihydro-1H-indole Triisopropylsilyltrifluoromethanesulfonate (3.5 mL, 13.0 mmol) and DIPEA (3.2 mL, 19.5 mmol) were added to a solution of 6-bromo-5-fluoro-3,3-dimethyl-2,3-dihydro-1H-indole (1.5 g, 6.5 mmol) in DCM (50 mL). The reaction mixture was stirred at room temperature overnight then quenched with saturated aqueous NaHCO$_3$ and extracted with DCM (×3). The organic phase was dried (MgSO$_4$), filtered and concentrated. The crude material was purified by SiO$_2$ chromatography (10% EtOAc in petrol) to give the title compound (1.8 g) as a white solid. $^1$H NMR (DMSO-d6): 7.07 (1H, d), 6.65 (1H, d), 3.44 (2H, s), 1.64-1.33 (3H, m), 1.33-1.17 (6H, m), 1.10 (18H, d).

Preparation 77: 6-Benzenesulfonyl-5-fluoro-3,3-dimethyl-1-triisopropylsilanyl-2,3-dihydro-1H-indole BuLi (2.2 M solution in Et$_2$O. 2.4 mL, 5.4 mmol) was slowly added to a solution of 6-bromo-5-fluoro-3,3-dimethyl-1-triisopropylsilanyl-2,3-dihydro-1H-indole (1.8 g, 4.5 mmol) in THF (20 mL) at −78° C. under nitrogen. The solution was stirred for 15 minutes at −78° C. and then phenylsulfonyl fluoride (541 μL, 4.5 mmol) was slowly added. Stirring was maintained for 1 h at the same temperature. The reaction was quenched by adding saturated aqueous NH$_4$Cl and the product was extracted with EtOAc. The organic phase was dried (MgSO$_4$), filtered and concentrated. The crude material was purified by SiO$_2$ chromatography (10% EtOAc in petrol) to give the title compound (1.4 g) as a yellow solid. $^1$H NMR (CDCl3): 7.98 (2H, d), 7.64-7.56 (1H, m), 7.56-7.48 (2H, m), 7.23 (1H, d), 6.68 (1H, d), 3.50 (2H, s), 1.55-1.45 (3H, m), 1.24 (6H, s), 1.21-1.11 (18H, m).

Preparation 78: 6-Benzenesulfonyl-5-fluoro-3,3-dimethyl-2,3-dihydro-1H-indole 6-Benzenesulfonyl-5-fluoro-3,3-dimethyl-1-triisopropylsilanyl-2,3-dihydro-1H-indole (1.43 mg, 3.1 mmol) was treated with TBAF (1M solution in THF, 4.0 mL) in dry THF (20 mL) and the resulting solution stirred at room temperature for 1.5 hours. The reaction was quenched with saturated aqueous NH$_4$Cl and extracted with EtOAc. The crude material was purified by chromatography (petrol: EtOAc 1:1) to give the title compound (810 mg) as a colourless oil. MS: [M+H]$^+$=306.

Preparation 79: 4-Methoxy-benzenesulfonyl fluoride

To a solution of 4-methoxy-benzenesulfonyl chloride (1.0 g, 4.8 mmol) in acetonitrile (20 mL) was added KF (563 mg, 9.7 mmol) and the resulting mixture was stirred for 16 h at room temperature. The solid was filtered off and the filtrate was concentrated in vacuo. The residue was dissolved in EtOAc and washed with water. The organic phase was dried (MgSO$_4$) and concentrated in vacuo to give the title compound (780 mg) as a colourless oil. $^1$H NMR (CDCl$_3$): 7.97 (2H, d), 7.09 (2H, d), 3.94 (3H, s).

Preparation 80: 5-Fluoro-6-(4-methoxy-benzenesulfonyl)-3,3-dimethyl-1-triisopropylsilanyl-2,3-dihydro-1H-indole The title compound was prepared starting from 6-bromo-5-fluoro-3,3-dimethyl-1-triisopropylsilanyl-2,3-dihydro-1H-indole (400 mg, 1.0 mmol) and 4-methoxy-benzenesulfonyl fluoride (190 mg, 1.0 mmol) following similar methods to those Preparation 77 to give the title compound (270 mg) as a yellow oil. $^1$H NMR (CDCl$_3$): 7.92 (2H, dd), 7.20 (1H, d), 7.01-6.94 (2H, m), 6.67 (1H, d), 3.87 (3H, s), 3.49 (2H, s), 1.56-1.43 (3H, m), 1.25-1.21 (6H, m), 1.17 (18H, d).

Preparation 81: 5-Fluoro-6-(4-methoxy-benzenesulfonyl)-3,3-dimethyl-2,3-dihydro-1H-indole 5-Fluoro-6-(4-methoxy-benzenesulfonyl)-3,3-dimethyl-1-triisopropylsilanyl-2,3-dihydro-1H-indole (250 mg, 0.51 mmol) was treated with TBAF following similar methods to those described in Preparation 78 to give the title compound (110 mg) as a pale yellow oil. $^1$H NMR (CDCl$_3$): 7.99-7.81 (2H, m), 7.21 (1H, d), 7.04-6.92 (2H, m), 6.73 (1H, d), 3.87 (3H, s), 3.35 (2H, s), 1.27 (6H, s).

Preparation 82: 1-Acetyl-5-fluoro-3,3-dimethyl-2,3-dihydro-1H-indole-6-sulfonyl chloride 1-(5-Fluoro-3,3-dimethyl-2,3-dihydro-indol-1-yl)-ethanone (1.1 g, 6.0 mmol) was treated with chlorosulfonic acid (10 mL) following similar methods to those described in Preparation 63) to give the desired compound (900 mg) as a grey solid. $^1$H NMR (Acetone-d$_6$): 8.76 (1H, d), 7.54 (1H, d), 4.10 (2H, s), 2.32-2.23 (3H, m), 1.48 (6H, s).

Preparation 83: 1-[5-Fluoro-3,3-dimethyl-6-(pyrrolidine-1-sulfonyl)-2,3-dihydro-indol-1-yl]-ethanone The title compound was prepared starting from 1-acetyl-5-fluoro-3,3-dimethyl-2,3-dihydro-1H-indole-6-sulfonyl chloride (400 mg, 1.3 mmol) and pyrrolidine (650 μL, 7.87 mmol) following similar methods to those described in Preparation 69 to give the title compound (287 mg) as a dark orange solid. MS: [M+H]$^+$=341.

Preparation 84: 5-Fluoro-3,3-dimethyl-6-(pyrrolidine-1-sulfonyl)-2,3-dihydro-1H-indole The title compound was prepared by treating 1-[5-Fluoro-3,3-dimethyl-6-(pyrrolidine-1-sulfonyl)-2,3-dihydro-indol-1-yl]-ethanone (287 mg, 0.84 mmol) with hydrochloric acid (5 M, 1.7 mL) following similar methods to those described in Preparation 66 to give the title compound (145 mg) as a light brown oil. $^1$H NMR (DMSO-d6): 7.13 (1H, d), 6.79 (1H, d), 5.79 (1H, d), 3.25 (2H, s), 3.23-3.11 (4H, m), 1.83-1.68 (4H, m), 1.25 (6H, s).

Preparation 85: 1-(6-Ethanesulfonyl-5-fluoro-3,3-dimethyl-2,3-dihydro-indol-1-yl)-ethanone The title compound was prepared from 1-acetyl-5-fluoro-3,3-dimethyl-2,3-dihydro-1H-indole-6-sulfonyl chloride (300 mg, 0.98 mmol), iodoethane (396 μL, 4.9 mmol), Na$_2$SO$_3$ (236 mg, 1.87 mmol), NaHCO$_3$ (165 mg, 1.96 mmol) and TBABr (2 mg, 0.006 mmol) following similar methods to those described in Prep 64, to give the title compound (160 mg). $^1$H NMR (CDCl$_3$): 8.67 (1H, d), 6.98 (1H, d), 3.86 (2H, s), 3.38-3.19 (2H, m), 2.22 (3H, s), 1.38 (6H, s), 1.34-1.27 (3H, m).

Preparation 86: 6-Ethanesulfonyl-5-fluoro-3,3-dimethyl-2,3-dihydro-1H-indole 1-(6-Ethanesulfonyl-5-fluoro-3,3-dimethyl-2,3-dihydro-indol-1-yl)-ethanone (160 mg, 0.53 mmol) was treated with hydrochloric acid (5 M, 1.1 mL) following similar methods to those described in Preparation 66 to give the title compound (80 mg). MS: [M+H]$^+$ 258.

Preparation 87: 5-Fluoro-3,3-dimethyl-6-(propane-2-sulfonyl)-2,3-dihydro-1H-indole Prepared following similar methods to those described in Preparations 85 and 86 using 2-iodopropane instead of iodoethane. MS: [M+H]$^+$=272.

Preparation 88: 1-[6-(3-Chloro-propane-1-sulfonyl)-5-fluoro-3,3-dimethyl-2,3-dihydro-indol-1-yl]-ethanone Prepared from 1-acetyl-5-fluoro-3,3-dimethyl-2,3-dihydro-1H-indole-6-sulfonyl chloride (500 mg, 1.64 mmol) and 1-chloro-3-iodo-propane (863 μL, 8.2 mmol) following similar methods to those described in Preparation 64. The title compound (502 mg) was obtained as a pale yellow oil. $^1$H NMR (CDCl$_3$): 8.72 (1H, d), 7.01 (1H, d), 3.88 (2H, s), 3.75-3.57 (2H, m), 3.57-3.35 (2H, m), 2.37-2.18 (5H, m), 1.41 (6H, s).

Preparation 89: 1-(6-Cyclopropanesulfonyl-5-fluoro-3,3-dimethyl-2,3-dihydro-indol-1-yl)-ethanone To a solution of 1-[6-(3-chloro-propane-1-sulfonyl)-5-fluoro-3,3-dimethyl-2,3-dihydro-indol-1-yl]-ethanone (502 mg, 1.44 mmol) at −78° C. in THF (30 mL) under N$_2$, KHMDS (0.5 M in toluene, 3 mL) was slowly added. The solution was stirred for 10 minutes at the same temperature and then 30 minutes at ambient temperature then quenched with 1 M hydrochloric acid and extracted with EtOAc. The organic phase was dried (MgSO$_4$), filtered and concentrated. The crude material was purified by SiO$_2$ chromatography (EtOAc: Petrol 1:1) to give the title compound (310 mg). MS: [M+H]$^+$=312.

Preparation 90: 6-Cyclopropanesulfonyl-5-fluoro-3,3-dimethyl-2,3-dihydro-1H-indole 1-(6-Cyclopropanesulfonyl-5-fluoro-3,3-dimethyl-2,3-dihydro-indol-1-yl)-ethanone (310 mg, 0.99 mmol) was processed in a manner similar to that described in Preparation 66 to give the title compound (106 mg), used without further purification. MS: [M+H]$^+$=270.

Preparation 91: 6-Chloro-3,3-bis-hydroxymethyl-2-oxo-2,3-dihydro-indole-1-carboxylic acid tert-butyl ester A mixture of 6-chloro-2-oxo-2,3-dihydro-indole-1-carboxylic acid tert-butyl ester (2.7 g, 10.1 mmol), potassium carbonate (4.2 g, 30.3 mmol), THF (150 mL) and paraformaldehyde (7.2 g, 0.24 mol) was stirred at 20° C. for 2 h then was poured onto ice (100 g) and saturated aqueous NaHCO$_3$ (100 mL) and extracted with EtOAc (4×100 mL). The combined organic extracts were dried (Na$_2$SO$_4$) and evaporated in vacuo. Chromatography (SiO$_2$; gradient elution with 30-100% EtOAc in petrol) gave an orange solid (3.7 g). Crystallisation from EtOAc and petrol gave the title compound (1.23 g). Chromatography of the mother liquor gave further product (0.978 g). MS: [M-tert-Bu]$^+$=272 (fragment ion).

Preparation 92: 6-Chloro-3,3-bis-hydroxymethyl-1,3-dihydro-indol-2-one

A mixture of 6-chloro-3,3-bis-hydroxymethyl-2-oxo-2,3-dihydro-indole-1-carboxylic acid tert-butyl ester (1.9 g, 5.8 mmol), DCM (50 mL) and TFA (10 mL) was stirred at 20° C. for 5 h then evaporated in vacuo to give a semi-solid. Azeotrope with THF was performed to give the title compound (2.5 g). MS: [M+H]$^+$=228.

Preparation 93: (6-Chloro-3-hydroxymethyl-2,3-dihydro-1H-indol-3-yl)-methanol A mixture of 6-chloro-3,3-bis-hydroxymethyl-1,3-dihydro-indol-2-one (5.8 mmol), THF (10 mL) and a solution of borane-dimethylsulfide complex in THF (2 M, 30 mL) was heated at 70° C. for 3 h, then cooled to 20° C. MeOH (30 mL) was added dropwise (caution!) over 0.2 h, then mixture was heated at reflux for 2 h. Resulting mixture was cooled then evaporated in vacuo to give an oily residue. Chromatography (SiO$_2$; gradient elution with 20-100% EtOAc in petrol) gave the title compound (1.15 g) as an oil which crystallised. MS: [M+H]$^+$=214.

Preparation 94: 6-Chloro-3,3-bis-hydroxymethyl-2,3-dihydro-indole-1-carboxylic acid tert-butyl ester A mixture of (6-chloro-3-hydroxymethyl-2,3-dihydro-1H-indol-3-yl)-methanol (1.1 g, 5.15 mmol), di-tert-butyl dicarbonate (1.24 g, 5.67 mmol) and THF (20 mL) was stirred at 20° C. for 24 h then at −40° C. for 1 h, then was evaporated in vacuo to give an oil. Chromatography (SiO$_2$; gradient elution with 0-100% EtOAc in petrol) gave the title compound (1.15 g) as an oil which later solidified. MS: [M−H]$^−$=312.

Preparation 95: 1-Diphenylmethyl-6'-chloro-1',2'-dihydrospiro[azetidine-3,3'-indole]-1'-yl-carboxylic acid tert-butyl ester To a stirred mixture of 6-chloro-3,3-bis-hydroxymethyl-2,3-dihydro-indole-1-carboxylic acid tert-butyl ester (0.31 g, 1 mmol), DIPEA (0.645 g, 5 mmol) and acetonitrile (5 mL) at −25° C. under nitrogen was added a solution of trifluoromethylsulfonic anhydride in DCM (1 M, 2.1 mL) dropwise over 0.3 h (T<−20° C.) and resulting mixture was stirred at −20° C. for 1 h), then a solution of C,C-diphenyl-methylamine (0.179 g, 0.98 mmol) in acetonitrile (2 mL) was added (T<−20° C.) and stirring continued for 0.5 h. Mixture was warmed slowly to 20° C. and left thus for 16 h, heated at 75° C. for 8 h and then evaporated in vacuo. Chromatography (SiO$_2$; gradient elution with 0-40% Et$_2$O in petrol) gave the title compound (0.273 g). $^1$H NMR (CDCl$_3$): 7.47 (4H, d), 7.35-7.27 (6H, m), 7.22 (2H, t), 7.05 (1H, dd), 4.41 (1H, s), 4.15-4.10 (2H, m), 3.37 (2H, d), 3.30 (2H, d), 1.64-1.55 (9H, m).

Preparation 96: 6'-Chloro-1',2'-dihydrospiro[azetidine-3,3'-indole]-1'-yl-carboxylic acid tert-butyl ester 1-Diphenylmethyl-6'-chloro-1',2'-dihydrospiro[azetidine-3,3'-indole]-1'-yl-carboxylic acid tert-butyl ester (0.10 g, 0.22 mmol) was dissolved in DCM (2 mL) and then cooled in an ice-water bath under N$_2$. Pre-mixed 1-chloroethyl chloroformate (26 uL, 0.24 mmol) and DIPEA (76 uL, 0.43 mmol) in DCM (1 mL) was added dropwise. The reaction was stirred for 15 minutes and then stirred at room temperature for 2 hours. MeOH (10 mL) was added and the mixture was heated to reflux for 30 minutes. The mixture was concentrated in vacuo and used without further purification. MS: [M+H]$^+$=295.

Preparation 97: 1-Acetyl-6'-chloro-1',2'-dihydrospiro[azetidine-3,3'-indole]-1'-yl-carboxylic acid tert-butyl ester To a stirred solution of AcOH (19 uL, 0.33 mmol) in DCM (2.2 mL) under N$_2$, was added EDC (63 mg, 0.33 mmol), HOAt (46 mg, 0.33 mmol) and DIPEA (173 uL, 0.99 mmol) sequentially. After 10 minutes the amine was added and the reaction was stirred for 16 h then quenched by adding saturated aqueous NaHCO$_3$ followed by extraction with DCM (×3). The combined organic layers were washed with water, brine and dried over MgSO$_4$. then concentrated in vacuo to yield the title compound. MS: [M+H]$^+$=337.

Preparation 98: 1-Acetyl-6'-chloro-1',2'-dihydrospiro[azetidine-3,3'-indole]hydrochloride 1-Acetyl-6'-chloro-1',2'-dihydrospiro[azetidine-3,3'-indole]-1'-yl-carboxylic acid tert-butyl ester was (56 mg) was taken up in saturated HCl in EtOAc (5 mL). The reaction was stirred for 1 hour at ambient temperature and then concentrated in vacuo. The residue was taken up in MeOH and concentrated in vacuo again to yield the title compound. MS: [M+H]$^+$=237.

Preparation 99: 1-Acetyl-6'-benzyl-1',2'-dihydrospiro[azetidine-3,3'-indole]-1'-yl-carboxylic acid tert-butyl ester (1,3-Diisopropylimidazol-2-ylidene)(3-chloropyridyl) palladium (II) dichloride (2 mg, 10 mol %) and LiBr (41 mg, 0.47 mmol) were dissolved in dry NMP and the solution was degassed with N$_2$ for 5 minutes. Then 1-acetyl-6'-chloro-1',2'-dihydrospiro[azetidine-3,3'-indole]-1'-yl-carboxylic acid tert-butyl ester (100 mg, 0.29 mmol) and benzylzinc bromide (0.5M solution in toluene, 950 µL, 0.475 mmol) were added. The reaction mixture was stirred under N$_2$ for 4 h. A second aliquot of catalyst (2 mg) and benzylzinc bromide (950 µL) were added and stirring maintained for 4 h. The reaction was quenched with water and extracted with EtOAc. The organic phase was dried (MgSO$_4$), filtered and concentrated. The crude material was purified by column chromatography (EtOAc:petrol 1:1 to EtOAc 100%) to give the title compound (200 mg) as a pale yellow oil (ca. 50% pure by NMR, contaminated with NMP), used without further purification. MS: [M+H]$^+$=393.

Preparation 100: 1-Acetyl-6'-benzyl-1',2'-dihydrospiro[azetidine-3,3'-indole]hydrochloride 1-Acetyl-6'-benzyl-1',2'-dihydrospiro[azetidine-3,3'-indole]-1'-yl-carboxylic acid tert-butyl ester was taken up in saturated HCl in EtOAc (5 mL). The reaction was stirred for 1 h at ambient temperature and then concentrated in vacuo. The residue was taken up in MeOH and concentrated in vacuo again to yield the title compound. MS: [M+H]$^+$=293.

Preparation 101: 6-Chloro-1-(2-trimethylsilanyl-ethoxymethyl)-1H-pyrrolo[3,2-c]pyridine Sodium hydride (60%, 1.40 g, 35.0 mmol) was added in portions over 20 min to a solution of 6-chloro-5-aza-indole (4.45 g, 29.1 mmol) in DMF (17.2 mL) at 0° C. (ice bath). The mixture was stirred for 1 h. (2-Chloromethoxy-ethyl)-trimethyl-silane (5.83 g, 35.0 mmol) was then added over 15 min. After stirring for 1 h, the reaction was quenched with water (100 mL) and the mixture extracted with DCM (3×100 mL). The combined organic extracts were washed with brine (3×300 mL), dried over Na$_2$SO$_4$, filtered and concentrated. Chromatography on silica gel (gradient elution, 0-100%, EtOAc/petrol 40-60° C.), gave the title compound (6.7 g, 82%) as a yellow oil. $^1$H NMR (Me-d3-OD): 8.61 (1H, s), 7.63 (1H, s), 7.50 (1H, d), 6.71 (1H, d), 5.57 (2H, s), 3.53 (2H, t), 0.88 (2H, t), −0.04--0.16 (9H, m).

Preparation 102: 3,3-Dibromo-6-chloro-1-(2-trimethylsilanyl-ethoxymethyl)-1,3-dihydro-pyrrolo[3,2-c]pyridin-2-one A solution of 6-chloro-1-(2-trimethylsilanyl-ethoxymethyl)-1H-pyrrolo[3,2-c]pyridine (6.70 g, 23.8 mmol) in anhydrous 1,4-dioxane (41 mL) was added to a solution of pyridium hydrobromide perbromide (38.0 g, 119 mmol) in anhydrous 1,4-dioxane (41 mL) over 30 min. After stirring for 1 h, water (100 mL) was added and the reaction stirred for 10 min, the extracted with EtOAc (100 mL×3), washed with water (3×100 mL) and brine (3×100 mL), then dried over Na$_2$SO$_4$, filtered and concentrated, to give the title compound (10.3 g) as a red oil. $^1$H NMR (CDCl$_3$): 8.56 (1H, s), 7.07 (1H, s), 5.21 (2H, s), 3.62 (2H, t), 0.99-0.92 (2H, m), 0.02--0.01 (9H, m). MS: [M+H]$^+$=456.

Preparation 103: 6-Chloro-1-(2-trimethylsilanyl-ethoxymethyl)-1,3-dihydro-pyrrolo[3,2-c]pyridin-2-one Zinc powder (14.8 g, 226 mmol) was added to a biphasic mixture of 3,3-dibromo-6-chloro-1-(2-trimethylsilanyl-ethoxymethyl)-1,3-dihydro-pyrrolo[3,2-c]pyridin-2-one (10.3 g, 22.6 mmo) in THF (129 mL) and saturated ammonium chloride solution (33 mL). Due to delayed exotherm, the reaction was cooled in ice. The reaction was stirred for 3 h at ambient temperature, filtered and the filtrate concentrated. The residue was dissolved in EtOAc (20 mL) and water (20 mL) and passed through a short plug of celite, washing with EtOAc. The organic layer was separated and the aqueous phase extracted with EtOAc (2×20 mL). The combined organic solutions were washed with brine, dried over magnesium sulfate, filtered and concentrated. Chromatography on silica gel (gradient elution, 0-100%, EtOAc/petrol), gave the title compound (5.08 g, 75%) as a pale yellow oil. $^1$H NMR (Me-d3-OD): 8.14 (1H, s), 7.18 (1H, s), 5.17 (2H, s), 3.63 (2H, t), 0.94 (2H, t), 0.18-0.18 (9H, m).

Preparation 104: 6-Chloro-3,3-dimethyl-1-(2-trimethylsilanyl-ethoxymethyl)-1,3-dihydro-pyrrolo[3,2-c]pyridin-2-one 6-Chloro-1-(2-trimethylsilanyl-ethoxymethyl)-1,3-dihydro-pyrrolo[3,2-c]pyridin-2-one (5.08 g, 17.05 mmol) in anhydrous THF (85 mL) was cooled to −78° C. 1 M LiHMDS in THF (37.5 mL) was added dropwise over 10 min and the reaction stirred for 30 min. Methyl iodide (3.18 mL, 51.1 mol) was added and the reaction stirred for 30 min then warmed to ambient temperature over 1.5 h and quenched with saturated aqueous ammonium chloride (50 mL), then extracted with EtOAc (3×50 mL). The combined organic extracts were washed with water (3×150 mL), brine (3×150 mL), dried over sodium sulfate, filtered and concentrated. Chromatography on silica gel (gradient elution 0-70%, EtOAc/petrol), gave the title compound (2.83 g, 51%) as a pale yellow oil; $^1$H NMR (Me-d3-OD): 8.22 (1H, s), 7.22 (1H, s), 5.19 (2H, s), 3.60 (2H, t), 1.44 (6H, s), 0.93 (2H, t), 0.16-0.20 (9H, m).

Preparation 105: 6-Chloro-3,3-dimethyl-1,3-dihydro-pyrrolo[3,2-c]pyridin-2-one

To a solution of 6-chloro-3,3-dimethyl-1-(2-trimethylsilanyl-ethoxymethyl)-1,3-dihydro-pyrrolo[3,2-c]pyridin-2-one (7.25 g, 22.2 mmol) in DCM (50 mL) was added TFA (50 mL) and resulting mixture was stirred at 20° C. for 1 h. The solution was evaporated in vacuo and the residue dissolved in MeOH and solvent re-evaporated to give a solid. To an aliquot of this material (2.40 g) in THF (53 mL) was added piperazine (4.56 g, 52.9 mmol). After stirring for 1 h, water (30 mL) and EtOAc (30 mL) were added and the organic layer separated. The organic layer was washed with water (30 mL×2) and brine (30 mL), dried over Na$_2$SO$_4$, filtered and concentrated in vacuo. Chromatography on silica gel (gradient elution, 0-100% EtOAc/petrol), gave the title compound (1.4 g, 67%) as a colourless solid. $^1$H NMR (Me-d3-OD): 8.12 (1H, s), 6.99 (1H, s), 1.41 (6H, s).

Preparation 106: 6-Chloro-3,3-dimethyl-2,3-dihydro-1H-pyrrolo[3,2-c]pyridine

6-Chloro-3,3-dimethyl-1,3-dihydro-pyrrolo[3,2-c]pyridin-2-one (1.4 g, 7.14 mmol) was dissolved in a solution of borane-dimethyl sulfide complex in THF (2 M, 36 mL, 71.4 mmol) and heated to 65° C. for 3 h, then cooled to ambient temperature. MeOH was added and the reaction heated at reflux for 1.5 h. After stirring overnight, the solvent was removed in vacuo. Column chromatography on silica gel (gradient elution, 0-100% EtOAc/petrol), gave the title compound (1.23 g, 95%) as a colourless solid. $^1$H NMR (Me-d3-OD): 7.65 (1H, s), 6.42 (1H, s), 3.43 (2H, s), 1.34 (6H, s).

6-Chloro-3,3-dimethyl-2,3-dihydro-1H-pyrrolo[3,2-c]pyridine (alternative synthesis)

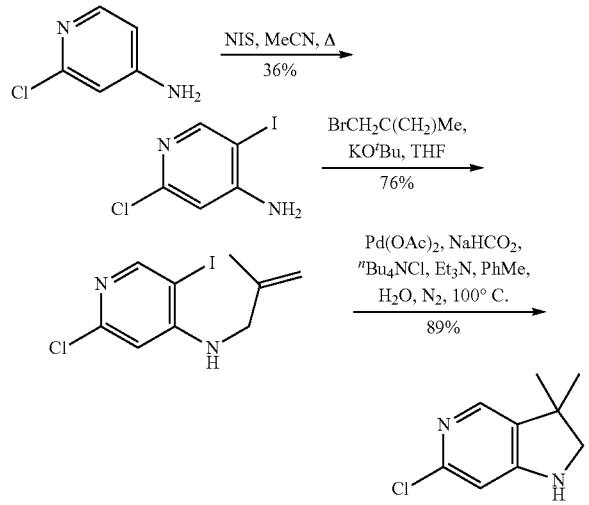

Preparation 107: 2-Chloro-5-iodo-pyridin-4-ylamine

N-Iodosuccinimide (24.75 g, 110.0 mmol) was added to a solution of 2-chloro-pyridin-4-ylamine (12.85 g, 100.0 mmol) in acetonitrile (400 mL) and the mixture stirred and held at reflux overnight. Upon cooling to room temperature the solvent was removed in vacuo and residue partitioned between EtOAc (250 mL), saturated sodium thiosulfate (100 mL) and water (250 mL). The organic layer was separated, washed with water (2×250 mL), separated and the solvent removed in vacuo to afford an orange oil that was subjected to column chromatography on silica. Gradient elution with 30-50% EtOAc in petrol afforded a pale orange solid that was rinsed with 25% EtOAc in petrol (80 mL). Solids were collected by filtration and sucked dry to afford the title compound (7.32 g) as an off-white solid. The mother liquors were concentrated to dryness in vacuo and the residues subjected to column chromatography on silica. Elution with 30-50% EtOAc in petrol afforded further pure material (1.90 g). Combined yield: (9.22 g, 36%) $^1$H NMR (DMSO-$d_6$) 8.20 (1H, s), 6.64 (1H, s), 6.50 (2H, br s). MS: [M+H]$^+$ 255.

Preparation 108: (2-Chloro-5-iodo-pyridin-4-yl)-(2-methyl-allyl)-amine

Potassium tert-butoxide (4.56 g, 40.73 mmol) was added to a stirred solution of 2-chloro-5-iodo-pyridin-4-ylamine (8.62 g, 33.94 mmol) in anhydrous THF (140 mL) and the mixture was stirred at room temperature for 0.25 h. 3-Bromo-2-methyl-propene (5.51 g, 40.73 mmol) was added and the mixture was stirred at room temperature overnight. The solvent was removed in vacuo and the residues partitioned between DCM (100 mL) and water (100 mL). The organic layer was separated, the solvent removed in vacuo and the residues subjected to column chromatography on silica. Gradient elution with 5-20% EtOAc in petrol afforded the title compound (7.93 g, 76%) as a pale yellow oil. $^1$H NMR (DMSO-$d_6$) 8.24 (1H, s), 6.50 (1H, br t), 6.39 (1H, s), 4.84 (1H, d), 4.73 (1H, d), 3.83 (2H, d), 1.70 (3H, s). MS: [M+H]$^+$ 309.

Preparation 109: 6-Chloro-3,3-dimethyl-2,3-dihydro-1H-pyrrolo[3,2-c]pyridine

Palladium (II) acetate (300 mg, 1.34 mmol), sodium formate (2.40 g, 30.53 mmol), tetra-n-butyl-ammonium chloride (8.48 g, 30.53 mmol) and triethylamine (10.6 mL, 76.32 mmol) were added to a solution of (2-chloro-5-iodo-pyridin-4-yl)-(2-methyl-allyl)-amine (7.85 g, 25.44 mmol) in toluene (200 mL) and water (10 mL) and the mixture was stirred and held at 100° C. under a nitrogen atmosphere overnight. The mixture was filtered whilst hot and the solids rinsed with toluene (50 mL), water (50 mL) and EtOAc (50 mL). The organic solvent was removed in vacuo, the aqueous residues were diluted with water (100 mL) and extracted with EtOAc (2×200 mL). The organic layer was separated, the solvent was removed in vacuo and the residues subjected to column chromatography on silica. Elution with 30-100% EtOAc in petrol afforded the title compound (4.12 g, 89%) as a colourless solid. $^1$H NMR (DMSO-$d_6$) 7.72 (1H, s), 6.75 (1H, br s), 6.33 (1H, s), 3.32 (2H, d), 1.25 (6H, s). MS: [M+H]$^+$ 183.

Preparation 110: 6-Chloro-3,3-dimethyl-2,3-dihydro-pyrrolo[3,2-c]pyridine-1-carboxylic acid tert-butyl ester To a solution of 6-chloro-3,3-dimethyl-2,3-dihydro-1H-pyrrolo[3,2-c]pyridine (1.3 g, 7.4 mmol) in THF (20 mL) were added tert-butyl dicarbonate (4.1 g, 18.6 mmol) and dimethyl-pyridin-4-yl-amine (2.22 g, 18.6 mmol) and the solution was stirred for 2 h. Water (60 mL) was added and the product was extracted with EtOAc. The organic phase was washed with brine, dried (MgSO$_4$), filtered and evaporated. Chromatography (SiO$_2$, eluted with petrol-EtOAc 0-40%) gave the title compound (1.04 g). $^1$H NMR (Me-d3-OD): 8.04 (1H, s), 7.60 (1H, s), 3.81 (2H, s), 1.59 (9H, s), 1.40 (6H, s). MS: [M+H]$^+$=283.

Alternative procedure: Potassium tert-butoxide (600 mg, 5.36 mmol) was added to a stirred solution of 6-chloro-3,3-dimethyl-2,3-dihydro-1H-pyrrolo[3,2-c]pyridine (800 mg, 4.38 mmol) in anhydrous THF (15 mL) and the mixture was stirred at room temperature for 10 minutes. A solution of di-tert-butyl dicarbonate (1.07 g, 4.89 mmol) in anhydrous THF (15 mL) was added and the mixture was stirred at room temperature overnight. The organic solvent was removed in vacuo, the aqueous residues were diluted with water (100 mL) and extracted with EtOAc (2×200 mL). The organic layers were combined and the solvent was removed in vacuo to afford the title compound (1.19 g, 96%), NMR data consistent with those previously obtained.

Preparation 111: 3,3-Dimethyl-6-phenylamino-2,3-dihydro-pyrrolo[3,2-c]pyridine-1-carboxylic acid tert-butyl ester A vessel containing 6-chloro-3,3-dimethyl-2,3-dihydro-pyrrolo[3,2-c]pyridine-1-carboxylic acid tert-butyl ester (100 mg, 0.35 mmol), aniline (64 uL, 0.71 mmol), 2-(dicyclohexylphosphino)-3,6-dimethoxy-2'-4'-6'-tri-i-propyl-1,1'-biphenyl (19 mg, 0.035 mmol), Pd$_2$(dba)$_3$ (16 mg, 0.018 mmol) and NaOtBu (51 mg, 0.53 mmol) in toluene (2 mL) was evacuated and flushed with nitrogen.

The mixture was stirred at 110° C. overnight, then was allowed to cool and then partitioned between EtOAc and water. The organic extract was washed with brine, dried (Na$_2$SO$_4$) and evaporated in vacuo. Chromatography (SiO$_2$;

gradient elution with 50-100% EtOAc in petrol) gave the title compound (60 mg, 50%) as a colourless solid. MS: [M+H]⁺=340.

Preparation 112: (3,3-Dimethyl-2,3-dihydro-1H-pyrrolo[3,2-c]pyridin-6-yl)-phenyl-amine hydrochloride 3,3-Dimethyl-6-phenylamino-2,3-dihydro-pyrrolo[3,2-c]pyridine-1-carboxylic acid tert-butyl ester (60 mg, 0.18 mmol) was treated with HCl (saturated solution in EtOAc) and stirred for 4 h. The mixture was then evaporated to dryness in vacuo to give a colourless gum which was used without further purification. MS: [M+H]⁺=240.

Preparation 113: 3,3-Dimethyl-6-o-tolyloxy-2,3-dihydro-pyrrolo[3,2-c]pyridine-1-carboxylic acid tert-butyl ester A vessel containing 6-chloro-3,3-dimethyl-2,3-dihydro-pyrrolo[3,2-c]pyridine-1-carboxylic acid tert-butyl ester (100 mg, 0.35 mmol), 2-methyl-phenol (38 mg, 0.42 mmol), 2-di-tert-butylphosphino-2',4',6'-triisopropylbiphenyl (tBuXPhos) (5 mg, 0.01 mmol), Pd(OAc)₂ (1.6 mg, 0.007 mmol) and potassium phosphate (150 mg, 0.70 mmol) in toluene (2 mL) was evacuated and flushed with nitrogen. The mixture was stirred at 110° C. overnight then were allowed to cool and then partitioned between EtOAc and water. The organic extract was washed with brine, dried (Na₂SO₄) and evaporated in vacuo. Chromatography (SiO₂; gradient elution with 0-10% EtOAc in petrol) gave title compound (89 mg) {MS: [M+H]⁺=355} as an inseparable mixture with starting material.

Preparation 114: 3,3-Dimethyl-6-o-tolyloxy-2,3-dihydro-1H-pyrrolo[3,2-c]pyridine hydrochloride The product from Preparation 113 (89 mg) was treated with HCl (saturated solution in EtOAc) and stirred for 5 h. The mixture was then evaporated to dryness in vacuo to give a colourless gum which was used directly in the next step without further purification.

Preparation 115: 3,3-Dimethyl-6-(methyl-phenyl-amino)-2,3-dihydro-pyrrolo[3,2-c]pyridine-1-carboxylic acid tert-butyl ester A solution of 6-chloro-3,3-dimethyl-2,3-dihydro-pyrrolo[3,2-c]pyridine-1-carboxylic acid tert-butyl ester (116 mg, 0.41 mmol), N-methylaniline (89 µL, 0.82 mmol), RuPhos (20 mg, 0.041 mmol), chloro(2-dicyclohexylphosphino-2',6'-di-iso-propoxy-1,-1'-biphenyl)[2-(2-aminoethylphenyl) palladium(II), methyl-tert-butylether adduct (33 mg, 0.041 mmol) and NaO^tBu (99 mg, 1.8 mmol) in toluene (2 mL) was evacuated and flushed with nitrogen. The mixture was stirred at 110° C. for 5 h. The mixtures was allowed to cool and then partitioned between EtOAc and water. The organic extract was washed with brine, dried (Na₂SO₄) and evaporated in vacuo. Chromatography (SiO₂; gradient elution with 5-20% EtOAc in petrol) gave the title compound (112 mg, 56%) as a colourless solid. MS: [M+H]⁺=354.

Preparation 116: (3,3-Dimethyl-2,3-dihydro-1H-pyrrolo[3,2-c]pyridin-6-yl)-methyl-phenyl-amine 3,3-Dimethyl-6-(methyl-phenyl-amino)-2,3-dihydro-pyrrolo[3,2-c]pyridine-1-carboxylic acid tert-butyl ester (112 mg, 0.32 mmol) was treated with HCl (saturated solution in EtOAc) and stirred for 4 h. The mixture was then evaporated to dryness in vacuo to give a colourless gum which was used directly in the next step without further purification.

Preparation 117: 6-Benzyl-3,3-dimethyl-2,3-dihydro-pyrrolo[3,2-c]pyridine-1-carboxylic acid tert-butyl ester To a nitrogen-degassed mixture of 6-chloro-3,3-dimethyl-2,3-dihydro-pyrrolo[3,2-c]pyridine-1-carboxylic acid tert-butyl ester (1.12 g, 4 mmol), lithium bromide (1.39 g, 16 mmol), (1,3-diisopropylimidazol-2-ylidene)(3-chloropyridyl)palladium (II) dichloride (0.056 g, 0.08 mmol), 1-methyl-2-pyrrolidinone (10 mL) and THF (10 mL) was added a solution of benzylzinc bromide in THF (0.5 M, 32 mL) and resulting mixture was stirred at 20° C. for 24 h. The mixture was poured into water (100 mL) and 5% aqueous citric acid (30 mL) and the resulting mixture extracted with 1:1 EtOAc-petrol. The organic phase was washed with water (3×50 mL), dried (Na₂SO₄) and evaporated in vacuo to give an oil. Chromatography (SiO₂, eluted with petrol-Et₂O 0-80%) gave the title compound (1.1 g) as an oil. ¹H NMR (CDCl₃): 8.20 (1H, s), 7.32 (4H, d), 7.27-7.03 (2H, m), 4.13 (2H, s), 3.71 (2H, s), 1.51 (9H, s), 1.37 (6H, s).

Preparation 118: 6-(2-Fluoro-benzyl)-3,3-dimethyl-2,3-dihydro-pyrrolo[3,2-c]pyridine-1-carboxylic acid tert-butyl ester Starting with 6-chloro-3,3-dimethyl-2,3-dihydro-pyrrolo[3,2-c]pyridine-1-carboxylic acid tert-butyl ester, the title compound was prepared by using similar methods to those described in Preparation 117 using 2-fluorobenzylzinc chloride instead of benzylzinc chloride. ¹H NMR (Me-d3-OD): 8.15 (1H, s), 7.64-7.20 (3H, m), 7.20-7.03 (2H, m), 4.12 (2H, s), 3.74 (2H, s), 1.50 (9H, s), 1.37 (6H, s). MS: [M+H]⁺=357.

Preparation 119: 6-(2-Fluoro-benzyl)-3,3-dimethyl-2,3-dihydro-1H-pyrrolo[3,2-c]pyridine hydrochloride Prepared from 6-(2-fluoro-benzyl-3,3-dimethyl-2,3-dihydro-pyrrolo[3,2-c]pyridine-1-carboxylic acid tert-butyl ester using similar methods to those described in Preparation 116. MS: [M+H]⁺=257.

Preparation 120: 6-(2-Chloro-benzyl)-3,3-dimethyl-2,3-dihydro-1H-pyrrolo[3,2-c]pyridine hydrochloride Prepared in an analogous manner to 6-(2-fluoro-benzyl)-3,3-dimethyl-2,3-dihydro-1H-pyrrolo[3,2-c]pyridine hydrochloride (Preparation 119) using 2-chlorobenzylzinc chloride instead of 2-fluorobenzylzinc chloride. MS: [M+H]⁺=273.

Preparation 121: 6-Cyclohexylmethyl-3,3-dimethyl-2,3-dihydro-1H-pyrrolo[3,2-c]pyridine hydrochloride Prepared in an analogous manner to 6-(2-fluoro-benzyl)-3,3-dimethyl-2,3-dihydro-1H-pyrrolo[3,2-c]pyridine hydrochloride (Preparation 119) using cyclohexylmethylzinc bromide instead of 2-fluorobenzylzinc chloride. MS: [M+H]⁺=245.

Preparation 122: 6-(3-Cyano-benzyl)-3,3-dimethyl-2,3-dihydro-1H-pyrrolo[3,2-c]pyridine hydrochloride Prepared in an analogous manner to 6-(2-fluoro-benzyl)-3,3-dimethyl-2,3-dihydro-1H-pyrrolo[3,2-c]pyridine hydrochloride (Preparation 119) using 3-cyanobenzylzinc bromide instead of 2-fluorobenzylzinc chloride. MS: [M+H]$^+$=264.

Preparation 123: 6-(4-Chloro-benzyl)-3,3-dimethyl-2,3-dihydro-1H-pyrrolo[3,2-c]pyridine hydrochloride Prepared in an analogous manner to 6-(2-fluoro-benzyl)-3,3-dimethyl-2,3-dihydro-1H-pyrrolo[3,2-c]pyridine hydrochloride (Preparation 119) using 4-chlorobenzylzinc chloride instead of 2-fluorobenzylzinc chloride. MS: [M+H]$^+$=273.

Preparation 124: (6-Methoxy-4-methyl-pyridin-3-yl)-carbamic acid tert-butyl ester To 5-amino-2-methoxy-4-picoline (5.0 g, 36.2 mmol) and di-tert-butyl dicarbonate (7.9 g, 36.2 mol) in THF (80 mL) was added saturated aqueous Na$_2$CO$_3$ (21 mL). The reaction was stirred over night at ambient temperature then was concentrated in vacuo and the residue partitioned between DCM and water. The product was extracted with DCM (×3). The combined organic layers were washed with brine and dried over MgSO$_4$. The product was filtered and concentrated in vacuo to give the title compound (8.6 g, >90% pure). as a red solid. $^1$H NMR (Me-d$_3$-OD): 7.97 (1H, s), 6.69 (1H, s), 3.88 (3H, s), 2.25 (3H, s), 1.51 (9H, s). MS: [M+H]$^+$=239.

Preparation 125: (5-tert-Butoxycarbonylamino-2-methoxy-pyridin-4-yl)-acetic acid s-BuLi (2.2 eq., 1.4 M in cyclohexane (59 mL)) was added slowly to a vigorously stirred solution of (6-methoxy-4-methyl-pyridin-3-yl)-carbamic acid tert-butyl ester (10.0 g, 37.8 mmol) in THF (315 mL) at −78° C. under N$_2$. After 10 minutes, CO$_2$ was bubbled through from a solid source via cannula for 1 h, while being allowed to warm slowly to room temperature. The reaction was carefully quenched with 2 M hydrochloric acid until pH2, adjusted to pH 4 with aqueous NaOH (1 M), and extracted with EtOAc (×3). The combined organic layers were washed with water, brine and dried over MgSO$_4$. The product was filtered and concentrated in vacuo to give the title compound (10.8 g. >85% pure) as a red oil, used without further purification. A sample was purified by prep HPLC. $^1$H NMR (Me-d$_3$-OD): 8.26 (1H, br s), 6.74 (1H, s), 3.88 (3H, s), 3.48 (2H, s), 1.52 (9H, s). MS: [M+H]$^+$=283.

Preparation 126: 5-Methoxy-2-oxo-2,3-dihydro-pyrrolo[2,3-c]pyridine-1-carboxylic acid tert-butyl ester (5-tert-Butoxycarbonylamino-2-methoxy-pyridin-4-yl)-acetic acid (10 g, 35.4 mmol) was dissovled in DCM (142 mL) and EDC (7.5 g, 39 mmol), HOAt (5.4 g, 39 mmol) and DIPEA (15 mL, 85.7 mmol) were sequentially added, under N$_2$. The reaction was stirred for 2 h at ambient temperature then quenched by addition of saturated aqueous NaHCO$_3$ and extracted with DCM (×3). The combined organic extracts were washed with water and brine then dried over MgSO$_4$ and concentrated in vacuo. The product was purified by column chromatography to yield the title compound (9.5 g) as a pale brown solid. $^1$H NMR DMSO-d$_6$): 8.38 (1H, s), 6.83 (1H, s), 3.84 (3H, s), 3.77 (2H, s), 1.57 (9H, s). MS: [M+H]$^+$=265.

Preparation 127: 5-Methoxy-3,3-dimethyl-2-oxo-2,3-dihydro-pyrrolo[2,3-c]pyridine-1-carboxylic acid tert-butyl ester 5-Methoxy-2-oxo-2,3-dihydro-pyrrolo[2,3-c]pyridine-1-carboxylic acid tert-butyl ester (5.8 g, 22.0 mmol) was dissolved in acetone (73 mL) and K$_2$CO$_3$ (10.6 g, 46.1 mmol) and then MeI (7.8 g, 55.9 mmol) were added, under N$_2$. The reaction was heated at reflux overnight, allowed to cool and then filtered. The filtrate was concentrated in vacuo and the product purified by column chromatography (100% DCM, Rf 0.21) to yield the title compound. $^1$H NMR (Me-d$_3$-OD): 8.53 (1H, s), 6.86 (1H, s), 3.92 (3H, s), 1.66 (9H, s), 1.44 (6H, s). MS: [M+H]$^+$=293.

Preparation 128: 3,3-Dimethyl-6-(2-methyl-allyl)-2,5-dioxo-2,3,5,6-tetrahydro-pyrrolo[2,3-c]pyridine-1-carboxylic acid tert-butyl ester 5-Methoxy-3,3-dimethyl-2-oxo-2,3-dihydro-pyrrolo[2,3-c]pyridine-1-carboxylic acid tert-butyl ester was heated with 3-bromo-2-methylpropene (4 eq.) at 100° C. for 4 h in a reactivial and then allowed to cool. Saturated HCl in EtOAc ~10 vol) was added and the reaction was stirred for 30 minutes at room temperature. The reaction was then concentrated in vacuo to give the title compound, used without further purification. MS: [M+H]$^+$=333.

Preparation 129: 6-Isobutyl-3,3-dimethyl-2,5-dioxo-2,3,5,6-tetrahydro-pyrrolo[2,3-c]pyridine-1-carboxylic acid tert-butyl ester 3,3-Dimethyl-6-(2-methyl-allyl)-1,6-dihydro-3H-pyrrolo[2,3-c]pyridine-2,5-dione was taken up in MeOH (0.10 M) and 10% Pd/C (0.15 eq.) was added. The reaction was shaken under H$_2$ for 16 hours then filtered and concentrated in vacuo. The product was purified by column chromatography to yield the title compound. MS: [M+H]$^+$=335.

Preparation 130: 6-Isobutyl-3,3-dimethyl-1,2,3,6-tetrahydro-pyrrolo[2,3-c]pyridin-5-one 6-Isobutyl-3,3-dimethyl-2,5-dioxo-2,3,5,6-tetrahydro-pyrrolo[2,3-c]pyridine-1-carboxylic acid tert-butyl ester was treated with saturated HCl in EtOAc over 1 h, then the reaction mixture was evaporated in vacuo. The residue was dissolved in MeOH and solvent re-evaporated to give 6-isobutyl-3,3-dimethyl-1,6-dihydro-3H-pyrrolo[2,3-c]pyridine-2,5-dione. Red-Al (1.5 eq., 67% in toluene) was added to this material in toluene (0.20 M) at 80° C. under N$_2$. The reaction was held at 80° C. for 1.5 hours. More Red-Al was added as required to drive the reaction to completion. The reaction was then allowed to cool and was quenched carefully with NaOH (1 M, aq.) in an ice bath. The mixture was further diluted with water and the product was extracted with CHCl$_3$:IPA (3:1, ×3). The combined organic layers were washed with water, brine and dried over MgSO$_4$ then concentrated in vacuo to yield the title compound, used without further purification. MS: [M+H]⁺=221.

Preparation 131: 5-Methoxy-3,3-dimethyl-2,3-dihydro-1H-pyrrolo[2,3-c]pyridine

Prepared from 5-methoxy-3,3-dimethyl-2-oxo-2,3-dihydro-pyrrolo[2,3-c]pyridine-1-carboxylic acid tert-butyl ester (Preparation 126) by deprotection and reduction using methods analogous to those of Preparations 116 and 130. MS: [M+H]⁺=179

Preparation 132: 3,3,6-Trimethyl-1,2,3,6-tetrahydropyrrolo[2,3-c]pyridin-5-one

Prepared in an analogous method to 6-isobutyl-3,3-dimethyl-1,2,3,6-tetrahydro-pyrrolo[2,3-c]pyridin-5-one using iodomethane instead of 3-bromo-2-methylpropene and omitting the hydrogenation step (see Preparations 128 and 130).

Preparation 133: 6-Benzyl-3,3-dimethyl-1,2,3,6-tetrahydro-pyrrolo[2,3-c]pyridin-5-one Prepared in an analogous method to 6-isobutyl-3,3-dimethyl-1,2,3,6-tetrahydro-pyrrolo[2,3-c]pyridin-5-one using benzyl bromide instead of 3-bromo-2-methylpropene and omitting the hydrogenation step (see Preparations 128 and 130).

General Procedure 1 (PyBrop Coupling): (R)-4-[2-(6-Bromo-2,3-dihydro-indol-1-yl)-2-oxo-ethyl]-2-methyl-piperazine-1-carboxylic acid tert-butyl ester

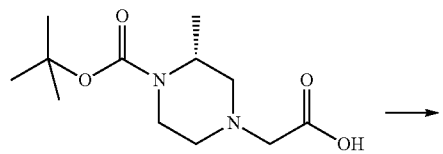

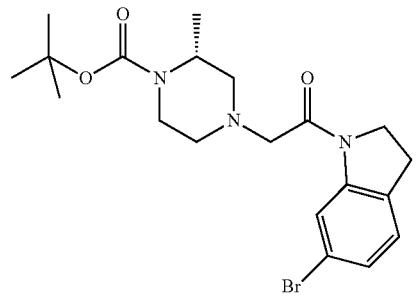

(R)-4-Carboxymethyl-2-methyl-piperazine-1-carboxylic acid tert-butyl ester (100 mg, 0.39 mmol), 6-bromo indoline (100 mg, 0.43 mmol) and triethylamine (0.148 mL, 1.06 mmol) were dissolved in DCM (1.94 mL) at ambient temperature. PyBrop (199 mg, 0.43 mmol) was added and the reaction stirred for 18 h. The solvent was removed in vacuo and the residue purified by column chromatography on silica gel (gradient elution, 0-100% EtOAc/petrol), to give the title compound (97 mg, 52%) as a pale yellow oil. ¹H NMR (Me-d3-OD): 8.32 (1H, s), 7.24-7.10 (2H, m), 5.50 (1H, s), 4.38-4.17 (3H, m), 3.83 (1H, d), 3.31 (1H, s), 3.17 (2H, t), 2.91 (1H, d), 2.81 (1H, d), 2.33 (1H, dd), 2.20-2.09 (1H, m), 1.48 (9H, s), 1.30 (3H, d).

Compounds of Table 1 below were prepared using procedures analogous to that described above, starting from the appropriate substituted 2,3-dihydroindole or dihydro-pyrrolopyridine and substituted carboxymethylpiperazine (synthesised as described above, Preparation reference numbers listed where appropriate).

TABLE 1

| Compound Name | Characterising data (¹H NMR Me-d3-OD unless indicated) | Prep nos. |
|---|---|---|
| (R)-4-[2-(6-Nitro-2,3-dihydro-indol-1-yl)-2-oxo-ethyl]-2-methyl-piperazine-1-carboxylic acid tert-butyl ester | MS: [M + H]⁺ = 405. | 15 |
| (R)-4-{2-[5-Bromo-6-(pyrrolidine-1-sulfonyl)-2,3-dihydro-indol-1-yl]-2-oxo-ethyl}-2-methyl-piperazine-1-carboxylic acid tert-butyl ester | MS: [M + H]⁺ = 571. | 15, 45 |
| (R)-4-[2-(4-Chloro-2,3-dihydro-pyrrolo[3,2-c]pyridin-1-yl)-2-oxo-ethyl]-2-methyl-piperazine-1-carboxylic acid tert-butyl ester | 8.23 (1H, d), 8.04 (1H, d), 4.60 (1H, s), 4.51-4.28 (2H, m), 4.28-4.14 (3H, m), 3.76-3.61 (1H, m), 3.61-3.39 (2H, m), 3.31-3.12 (2H, m), 1.51 (9H, s), 1.45 (3H, d). | 15 |
| (R)-4-[2-(6-Chloro-2,3-dihydro-indol-1-yl)-2-oxo-ethyl]-2-methyl-piperazine-1-carboxylic acid tert-butyl ester | 8.16 (1H, s), 7.21 (1H, d), 7.05 (1H, dd), 4.37-4.17 (3H, m), 3.83 (1H, d), 3.25-3.07 (3H, m), 2.92 (1H, d), 2.82 (1H, d), 2.34 (1H, dd), 2.23-2.10 (1H, m), 1.48 (9H, s), 1.29 (3H, d). | 15, 30 |
| (R)-4-[2-(6-Methoxy-2,3-dihydro-indol-1-yl)-2-oxo-ethyl]-2-methyl-piperazine-1-carboxylic acid tert-butyl ester | 8.77 (1H, s), 7.75 (1H, dd), 7.34 (1H, d), 4.32 (2H, t), 4.23 (1H, s), 3.91 (3H, s), 3.83 (1H, d), 3.31-3.21 (2H, m), 3.21-3.07 (1H, m), 2.97-2.77 (2H, m), 2.34 (1H, dd), 2.26-2.10 (1H, m), 1.48 (9H, s), 1.31 (3H, d). | 15, 32 |
| (R)-2-Methyl-4-[2-(6-methyl-2,3-dihydro-indol-1-yl)-2-oxo-ethyl]-piperazine-1-carboxylic acid tert-butyl ester | 8.00 (1H, s), 7.12 (1H, d), 6.89 (1H, d), 4.35-4.18 (3H, m), 3.83 (1H, d), 3.30 (2H, s), 3.27-2.99 (3H, m), 2.87 (2H, dd), 2.42-2.26 (4H, m), 2.26-2.08 (1H, m), 1.48 (9H, s), 1.30 (3H, d). | 15, 31 |

TABLE 1-continued

| Compound Name | Characterising data ($^1$H NMR Me-d3-OD unless indicated) | Prep nos. |
|---|---|---|
| (R)-4-[2-(5-Fluoro-2,3-dihydro-indol-1-yl)-2-oxo-ethyl]-2-methyl-piperazine-1-carboxylic acid tert-butyl ester | 8.12 (1H, dd), 7.01 (1H, d), 6.97-6.84 (1H, m), 4.40-4.07 (3H, m), 3.82 (1H, d), 3.30 (2H, s), 3.29-3.17 (3H, m), 2.86 (2H, dd), 2.38-2.07 (2H, m), 1.48 (9H, s), 1.29 (3H, d). | 15 |
| (R)-4-[2-(6-Fluoro-2,3-dihydro-indol-1-yl)-2-oxo-ethyl]-2-methyl-piperazine-1-carboxylic acid tert-butyl ester | 7.88 (1H, dd), 7.20 (1H, t), 6.83-6.71 (1H, m), 4.40-4.09 (3H, m), 3.83 (1H, d), 3.25-2.98 (3H, m), 2.87 (2H, dd), 2.39-2.22 (1H, m), 2.22-2.09 (1H, m), 1.48 (9H, s), 1.29 (3H, d). | 15 |
| (R)-4-[2-(5-Bromo-2,3-dihydro-indol-1-yl)-2-oxo-ethyl]-2-methyl-piperazine-1-carboxylic acid tert-butyl ester | 8.04 (1H, d), 7.39 (1H, s), 7.31 (1H, d), 4.37-4.06 (3H, m), 3.82 (1H, d), 3.30 (2H, s), 3.28-3.17 (3H, m), 2.86 (2H, dd), 2.38-2.08 (2H, m), 1.47 (9H, s), 1.30 (3H, d). | 15 |
| (2R,5S)-4-[2-(6-Bromo-2,3-dihydro-indol-1-yl)-2-oxo-ethyl]-5-isopropyl-2-methyl-piperazine-1-carboxylic acid tert-butyl ester | MS: [M + H]$^+$ = 481. | 24 |
| 1-[2-((R)-4-tert-Butoxycarbonyl-3-methyl-piperazin-1-yl)-acetyl]-2,3-dihydro-1H-indole-6-carboxylic acid methyl ester | 8.77 (1H, s), 7.75 (1H, dd), 7.34 (1H, d), 4.32 (2H, t), 4.23 (1H, s), 3.91 (3H, s), 3.83 (1H, d), 3.31-3.21 (2H, m), 3.21-3.07 (1H, m), 2.93 (1H, d), 2.83 (1H, d), 2.34 (1H, dd), 2.26-2.10 (1H, m), 1.48 (9H, s), 1.31 (3H, d). | 15, 34 |
| (R)-4-[2-(4-Chloro-3,3-dimethyl-2,3-dihydro-indol-1-yl)-2-oxo-ethyl]-2-methyl-piperazine-1-carboxylic acid tert-butyl ester | 8.14 (1H, d), 7.19 (1H, t), 7.05 (1H, d), 4.31-4.18 (1H, m), 4.18-3.95 (2H, m), 3.83 (1H, d), 3.29 (2H, s), 3.17 (1H, t), 2.91 (1H, d), 2.81 (1H, d), 2.33 (1H, dd), 2.23-2.08 (1H, m), 1.53 (6H, s), 1.48 (9H, s), 1.30 (3H, d). | 15, 25 |
| (R)-4-[2-(6-Chloro-3,3-dimethyl-2,3-dihydro-indol-1-yl)-2-oxo-ethyl]-2-methyl-piperazine-1-carboxylic acid tert-butyl ester | 8.14 (1H, d), 7.21 (1H, d), 7.09 (1H, dd), 4.31-4.20 (1H, m), 4.11-3.98 (2H, m), 3.84 (1H, d), 3.29 (2H, s), 3.24-3.04 (1H, m), 2.91 (1H, d), 2.81 (1H, d), 2.33 (1H, dd), 2.25-2.06 (1H, m), 1.48 (9H, s), 1.37 (6H, s), 1.30 (3H, d). | 15, 25 |
| (R)-2-Methyl-4-[2-oxo-2-(6-trifluoromethyl-2,3-dihydro-indol-1-yl)-ethyl]-piperazine-1-carboxylic acid tert-butyl ester | 8.45 (1H, s), 7.42 (1H, d), 7.35 (1H, d), 4.43-4.29 (2H, m), 4.24 (1H, s), 3.83 (1H, d), 3.29 (2H, d), 3.25-3.00 (1H, m), 2.93 (1H, d), 2.83 (1H, d), 2.34 (1H, dd), 2.26-2.10 (1H, m), 1.48 (9H, s), 1.31 (3H, d). | 15, 33 |
| 6-Chloro-1-{2-[(3R)-4-tert-butoxycarbonyl-3-methylpiperazin-1-yl]acetyl}-1,2-dihydrospiro[indole-3,4'-piperidine]-1'-carboxylic acid, benzyl ester | 8.18 (1H, d), 7.44-7.31 (5H, m), 7.21 (1H, d), 7.10 (1H, dd), 5.17 (2H, s), 4.31 (1H, d), 4.28-4.15 (4H, m), 3.84 (1H, d), 3.23-3.01 (3H, m), 2.94 (1H, d), 2.84 (1H, d), 2.34 (1H, dd), 2.21-2.12 (1H, m), 1.94-1.78 (2H, m), 1.71 (2H, d), 1.48 (9H, s), 1.29 (3H, d). | 15, 29 |
| (R)-4-[2-(5-Fluoro-6-phenyl-2,3-dihydro-indol-1-yl)-2-oxo-ethyl]-2-methyl-piperazine-1-carboxylic acid tert-butyl ester | MS: [M + H]$^+$ = 454. | 15, 36 |
| (R)-4-[2-(5-Bromo-6-methylsulfamoyl-2,3-dihydro-indol-1-yl)-2-oxo-ethyl]-2-methyl-piperazine-1-carboxylic acid tert-butyl ester | 8.87 (1H, s), 7.66 (1H, s), 4.34 (2H, t), 4.23 (1H, s), 3.82 (1H, d), 3.72 (1H, s), 3.31-3.14 (3H, m), 2.92 (1H, d), 2.82 (1H, d), 2.57 (3H, s), 2.41-2.08 (3H, m), 1.48 (9H, s), 1.31 (3H, d). | 15, 27 |
| (R)-4-[2-(5-Bromo-6-dimethylsulfamoyl-2,3-dihydro-indol-1-yl)-2-oxo-ethyl]-2-methyl-piperazine-1-carboxylic acid tert-butyl ester | 8.79 (1H, s), 7.67 (1H, s), 4.35 (2H, t), 4.23 (1H, s), 3.82 (1H, d), 3.29 (2H, d), 3.25-3.05 (1H, m), 3.05-2.86 (7H, m), 2.82 (1H, d), 2.34 (1H, dd), 2.24-2.11 (1H, m), 1.48 (9H, s), 1.31 (3H, d). | 15, 28 |
| (R)-2-Methyl-4-[2-oxo-2-(6-trifluoromethoxy-2,3-dihydro-indol-1-yl)-ethyl]-piperazine-1-carboxylic acid tert-butyl ester | MS: [M + H]$^+$ = 444. | 15, 37 |
| (R)-4-[2-(6-Benzyl-2,3-dihydro-indol-1-yl)-2-oxo-ethyl]-2-methyl-piperazine-1-carboxylic acid tert-butyl ester | 8.05 (1H, s), 7.34-7.11 (6H, m), 6.92 (1H, d), 4.32-4.08 (3H, m), 3.95 (2H, s), 3.81 (1H, d), 3.28 (2H, s), 3.24-3.03 (3H, m), 2.90 (1H, d), 2.80 (1H, d), 2.31 (1H, dd), 2.20-2.00 (1H, m), 1.47 (9H, s), 1.33-1.27 (3H, m). | 15, 26 |
| (R)-4-[2-(6-Methanesulfonyl-2,3-dihydro-indol-1-yl)-2-oxo-ethyl]-2-methyl-piperazine-1-carboxylic acid tert-butyl ester | MS: [M + H]$^+$ = 438. | 15, 38 |
| (R)-4-[2-(6-Benzenesulfonyl-2,3-dihydro-indol-1-yl)-2-oxo-ethyl]-2-methyl-piperazine-1-carboxylic acid tert-butyl ester | MS: [M + H]$^+$ = 500. | 15, 42 |
| (R)-4-[2-(6-Chloro-2,3-dihydro-pyrrolo[3,2-c]pyridin-1-yl)-2-oxo- | 8.12 (1H, s), 8.06-7.99 (1H, m), 4.35 (2H, t), 4.31-4.19 (1H, m), 3.83 (1H, d), | 15, 35 |

TABLE 1-continued

| Compound Name | Characterising data (¹H NMR Me-d3-OD unless indicated) | Prep nos. |
|---|---|---|
| ethyl]-2-methyl-piperazine-1-carboxylic acid tert-butyl ester | 3.30-3.09 (4H, m), 2.91 (1H, d), 2.82 (1H, d), 2.36 (1H, dd), 2.25-2.14 (1H, m), 1.48 (9H, s), 1.30 (3H, d). | |
| (R)-4-[2-(2,3-Dihydro-pyrrolo[2,3-b]pyridin-1-yl)-2-oxo-ethyl]-2-methyl-piperazine-1-carboxylic acid tert-butyl ester | 8.12 (1H, d), 7.60 (1H, d), 6.98 (1H, dd), 4.30-4.15 (1H, m), 4.12-4.06 (2H, m), 4.06-3.86 (2H, m), 3.79 (1H, d), 3.30-3.04 (3H, m), 2.97 (1H, d), 2.91 (1H, d), 2.38 (1H, dd), 2.33-2.16 (1H, m), 1.47 (9H, s), 1.25 (3H, d). | 15 |
| (R)-4-[2-(6-Benzyl-5-oxo-2,3,5,6-tetrahydro-pyrrolo[2,3-c]pyridin-1-yl)-2-oxo-ethyl]-2-methyl-piperazine-1-carboxylic acid tert-butyl ester | MS: [M + H]⁺ = 467. | 15, 48 |
| (R)-4-[2-(6-Benzenesulfonyl-3,3-dimethyl-2,3-dihydro-indol-1-yl)-2-oxo-ethyl]-2-methyl-piperazine-1-carboxylic acid tert-butyl ester | MS: [M + H]⁺ = 528. | 15, 51 |
| (R)-4-[2-(4,6-Dichloro-3,3-dimethyl-2,3-dihydro-indol-1-yl)-2-oxo-ethyl]-2-methyl-piperazine-1-carboxylic acid tert-butyl ester | MS: [M + H]⁺ = 456. | 15, 52 |
| (R)-4-[2-(6-Benzenesulfonyl-5-fluoro-3,3-dimethyl-2,3-dihydro-indol-1-yl)-2-oxo-ethyl]-2-methyl-piperazine-1-carboxylic acid tert-butyl ester | MS: [M + H]⁺ = 546. | 15, 78 |
| (2R,5S)-4-[2-(6-Benzenesulfonyl-5-fluoro-3,3-dimethyl-2,3-dihydro-indol-1-yl)-2-oxo-ethyl]-5-ethyl-2-methyl-piperazine-1-carboxylic acid tert-butyl ester | MS: [M + H]⁺ = 574. | 23, 78 |
| (R)-4-{2-[5-Fluoro-3,3-dimethyl-6-(pyrrolidine-1-sulfonyl)-2,3-dihydro-indol-1-yl]-2-oxo-ethyl}-2-methyl-piperazine-1-carboxylic acid tert-butyl ester | (CDCl3): 8.64 (1H, d), 6.97 (1H, d), 4.25 (1H, s), 4.11-3.96 (2H, m), 3.96-3.78 (1H, m), 3.40 (4H, t), 3.18 (3H, d), 2.87 (1H, d), 2.72 (1H, d), 2.36 (1H, dd), 2.25-2.11 (1H, m), 1.96-1.81 (4H, m), 1.46 (9H, s), 1.37 (6H, s), 1.26 (3H, d). | 15, 84 |
| 1-{6'-Chloro-1',2'-dihydrospiro[cyclopentane-1,3'-indole]-1'-yl}-2-[(3R)-4-tert-butoxycarbonyl-3-methylpiperazin-1-yl]ethan-1-one | MS: [M + H]⁺ = 448. | 15, 54 |
| (R)-4-[2-(6-Ethanesulfonyl-5-fluoro-3,3-dimethyl-2,3-dihydro-indol-1-yl)-2-oxo-ethyl]-2-methyl-piperazine-1-carboxylic acid tert-butyl ester | 8.65 (1H, d), 7.33 (1H, d), 4.24 (1H, s), 4.20-4.13 (2H, m), 3.83 (1H, d), 3.41-3.32 (4H, m), 3.26-3.09 (1H, m), 2.92 (1H, d), 2.82 (1H, d), 2.40-2.23 (1H, m), 2.23-2.07 (1H, m), 1.48 (9H, s), 1.43 (6H, s), 1.38-1.21 (6H, m). | 15, 86 |
| (R)-4-{2-[5-Fluoro-3,3-dimethyl-6-(propane-2-sulfonyl)-2,3-dihydro-indol-1-yl]-2-oxo-ethyl}-2-methyl-piperazine-1-carboxylic acid tert-butyl ester | MS: [M + H]⁺ = 512. | 15, 87 |
| 1-{6'-Chloro-1',2'-dihydrospiro[cyclopropane-1,3'-indole]-1'-yl}-2-[(3R)-4-tert-butoxycarbonyl-3-methylpiperazin-1-yl]ethan-1-one | MS: [M + H]⁺ = 420. | 15, 58 |
| (2R,5R)-4-[2-(6-Chloro-3,3-dimethyl-2,3-dihydro-indol-1-yl)-2-oxo-ethyl]-2-methyl-5-methylcarbamoyl-piperazine-1-carboxylic acid tert-butyl ester | 8.15 (1H, d), 7.21 (1H, d), 7.09 (1H, dd), 4.24-4.14 (1H, m), 4.06-3.96 (2H, m), 3.84 (1H, d), 3.71 (1H, d), 3.56 (1H, d), 3.48-3.40 (1H, m), 3.25-3.13 (1H, m), 3.04-2.96 (1H, m), 2.92 (1H, dd), 2.65 (1H, dd), 1.97 (3H, s), 1.49 (9H, s), 1.38 (6H, s), 1.32-1.24 (3H, m). | 20, 25 |
| 1-{6'-Chloro-1',2'-dihydrospiro[cyclobutane-1,3'-indole]-1'-yl}-2-[(3R)-4-tert-butoxycarbonyl-3-methylpiperazin-1-yl]ethan-1-one | MS: [M + H]⁺ = 434. | 15, 60 |
| (2R,5R)-4-[2-(6-Benzenesulfonyl-5-fluoro-3,3-dimethyl-2,3-dihydro-indol-1-yl)-2-oxo-ethyl]-2-methyl-5-methylcarbamoyl-piperazine-1-carboxylic acid tert-butyl ester | MS: [M + H]⁺ = 603. | 20, 78 |
| (R)-4-[2-(6-Cyclopropanesulfonyl-5-fluoro-3,3-dimethyl-2,3-dihydro- | 8.66-8.54 (1H, m), 7.40-7.27 (1H, m), 4.41-4.20 (1H, m), 4.20-4.13 (2H, m), | 15, 90 |

TABLE 1-continued

| Compound Name | Characterising data ($^1$H NMR Me-d3-OD unless indicated) | Prep nos. |
|---|---|---|
| indol-1-yl)-2-oxo-ethyl]-2-methyl-piperazine-1-carboxylic acid tert-butyl ester | 3.88-3.77 (1H, m), 3.30 (2H, d), 3.25-3.09 (1H, m), 2.98-2.72 (3H, m), 2.39-2.29 (1H, m), 2.22-2.09 (1H, m), 1.62-1.46 (9H, m), 1.43 (7H, s), 1.38-1.23 (6H, m), 1.17-1.08 (2H, m). | |
| (2R,5R)-4-[2-(6-Benzenesulfonyl-5-fluoro-3,3-dimethyl-2,3-dihydro-indol-1-yl)-2-oxo-ethyl]-5-methoxymethyl-2-methyl-piperazine-1-carboxylic acid tert-butyl ester | 8.83 (1H, d), 7.99 (2H, d), 7.70 (1H, t), 7.62 (2H, t), 7.18 (1H, d), 4.25-4.16 (1H, m), 4.10-3.93 (3H, m), 3.71 (1H, d), 3.63 (1H, dd), 3.54 (1H, d), 3.43-3.36 (4H, m), 3.04 (1H, s), 2.89 (1H, dd), 2.70 (1H, dd), 1.49 (9H, s), 1.37 (6H, s), 1.27-1.23 (3H, m). | 14, 78 |
| (2R,5R)-4-[2-(6-Ethanesulfonyl-3,3-dimethyl-2,3-dihydro-indol-1-yl)-2-oxo-ethyl]-5-methoxymethyl-2-methyl-piperazine-1-carboxylic acid tert-butyl ester | MS: [M + H]$^+$ = 524. | 14, 66 |
| (2R,5R)-4-{2-[5-Fluoro-6-(4-methoxy-benzenesulfonyl)-3,3-dimethyl-2,3-dihydro-indol-1-yl]-2-oxo-ethyl}-5-methoxymethyl-2-methyl-piperazine-1-carboxylic acid tert-butyl ester | 8.80 (1H, d), 7.90 (2H, d), 7.15 (1H, d), 7.09 (2H, d), 4.29-4.16 (1H, m), 4.06 (1H, d), 4.03-3.94 (1H, m), 3.88 (3H, s), 3.71 (1H, d), 3.63 (1H, dd), 3.54 (1H, d), 3.43-3.32 (6H, m), 3.03 (1H, s), 2.87 (1H, dd), 2.75-2.51 (1H, m), 1.49 (9H, s), 1.36 (6H, s), 1.26 (3H, s). | 14, 81 |
| (2R,5R)-4-[2-(3,3-Dimethyl-6-methylsulfamoyl-2,3-dihydro-indol-1-yl)-2-oxo-ethyl]-5-methoxymethyl-2-methyl-piperazine-1-carboxylic acid tert-butyl ester | 8.62 (1H, s), 7.58 (1H, dd), 7.44 (1H, d), 4.24-4.15 (1H, m), 4.09-4.02 (2H, m), 3.97 (1H, d), 3.71 (1H, d), 3.63 (1H, dd), 3.55 (1H, d), 3.40 (1H, d), 3.36 (3H, s), 3.32-3.22 (1H, m), 3.03 (1H, s), 2.87 (1H, dd), 2.69 (1H, dd), 2.55 (3H, s), 1.49 (9H, s), 1.41 (6H, s), 1.26 (3H, d). | 14, 71 |
| (2R,5R)-4-[2-(6-Chloro-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]$^+$ = 467. | 14, 106 |
| (2R,5R)-4-{2-[3,3-Dimethyl-6-(2-methyl-propane-1-sulfonyl)-2,3-dihydro-indol-1-yl]-2-oxo-ethyl}-5-methoxymethyl-2-methyl-piperazine-1-carboxylic acid tert-butyl ester | MS: [M + H]$^+$ = 552. | 14, 67 |
| (2R,5R)-4-[2-(6-Dimethylsulfamoyl-3,3-dimethyl-2,3-dihydro-indol-1-yl)-2-oxo-ethyl]-5-methoxymethyl-2-methyl-piperazine-1-carboxylic acid tert-butyl ester | MS: [M + H]$^+$ = 539. | 14, 72 |
| (2R,5R)-4-[2-(6-Isopropylsulfamoyl-3,3-dimethyl-2,3-dihydro-indol-1-yl)-2-oxo-ethyl]-5-methoxymethyl-2-methyl-piperazine-1-carboxylic acid tert-butyl ester | MS: [M + H]$^+$ = 553. | 14, 73 |
| (2R,5R)-4-[2-(3,3-Dimethyl-6-phenylmethanesulfonyl-2,3-dihydro-indol-1-yl)-2-oxo-ethyl]-5-methoxymethyl-2-methyl-piperazine-1-carboxylic acid tert-butyl ester | MS: [M + H]$^+$ = 586. | 14, 68 |
| 1-{1-Acetyl-6'-benzyl-1',2'-dihydrospiro[azetidine-3,3'-indole]-1'-yl}-2-[(2R,5R)-4-tert-butoxycarbonyl-2-(methoxymethyl)-5-methylpiperazin-1-yl]ethan-1-one | MS: [M + H]$^+$ = 577. | 14, 100 |
| (2R,5R)-4-{2-[6-(2-Fluoro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]$^+$ = 541. | 14, 119 |
| (2R,5R)-4-{2-[6-(2-Chloro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]$^+$ = 557. | 14, 120 |

TABLE 1-continued

| Compound Name | Characterising data ($^1$H NMR Me-d3-OD unless indicated) | Prep nos. |
|---|---|---|
| (2R,5R)-4-[2-(6-Cyclohexylmethyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]$^+$ = 529. | 14, 121 |
| (2R,5R)-4-{2-[6-(3-Cyano-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]$^+$ = 548. | 14, 122 |
| (2R,5R)-4-[2-(3,3-Dimethyl-6-phenylamino-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]$^+$ = 524. | 14, 112 |
| (2R,5R)-4-{2-[6-(4-Chloro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]$^+$ = 557. | 14, 123 |
| (2R,5R)-4-[2-(3,3-Dimethyl-6-o-tolyloxy-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]$^+$ = 539. | 14, 114 |
| (2R,5R)-4-{2-[3,3-Dimethyl-6-(methyl-phenyl-amino)-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]$^+$ = 538. | 14, 116 |
| (R)-4-[2-(2,3-Dihydro-indol-1-yl)-2-oxo-ethyl]-2-methyl-piperazine-1-carboxylic acid tert-butyl ester | MS: [M + H]+ = 360 | 15 |
| (2R,5R)-4-{2-[6-(3-Chloro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 557 | 14, 154 |
| (2R,5R)-4-{2-[3,3-Dimethyl-6-(1-phenyl-ethyl)-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 537 | 14, 155 |
| (2R,5R)-4-{2-[6-(4-Fluoro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 541 | 14, 156 |
| (2R,5R)-4-{2-[6-(3-Methoxy-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 553 | 14, 157 |
| (2R,5R)-4-[2-(6-Cyclopent-1-enyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]+ = 499 | 14, 162 |
| (2R,5S)-4-[2-(6-Benzyl-3,3-dimethyl-2,3-dihydro-pyrrolo[3,2-c]pyridin-1-yl)-2-oxo-ethyl]-5-ethyl-2-methyl-piperazine-1-carboxylic acid tert-butyl ester | MS: [M + H]+ = 507 | 23, 153 |
| (2R,5R)-4-{2-[3,3-Dimethyl-6-(1-phenyl-vinyl)-2,3-dihydro-pyrrolo[3,2-c]pyridin-1-yl]-2-oxo- | MS: [M + H]+ = 535 | 14, 165 |

TABLE 1-continued

| Compound Name | Characterising data ($^1$H NMR Me-d3-OD unless indicated) | Prep nos. |
|---|---|---|
| ethyl}-5-methoxymethyl-2-methyl-piperazine-1-carboxylic acid tert-butyl ester | | |
| (2R,5S)-4-[2-(3,3-Dimethyl-6-pyrazol-1-ylmethyl-2,3-dihydro-pyrrolo[3,2-c]pyridin-1-yl)-2-oxo-ethyl]-5-ethyl-2-methyl-piperazine-1-carboxylic acid tert-butyl ester | MS: [M + H]+ = 497 | 23, 176 |
| (2R,5R)-4-[2-(6-Benzoyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]+ = 537 | 14, 167 |
| (2R,5R)-4-{2-[6-(3-Fluoro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 541 | 14, 158 |
| (2R,5R)-4-{2-[6-(4-Methoxy-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 553 | 14, 159 |
| (2R,5R)-4-{2-[3,3-Dimethyl-6-(2-oxo-pyrrolidin-1-yl)-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 516 | 14, 189 |
| (2R,5R)-4-[2-(6-Cyano-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]+ = 458 | 14, 177 |
| (2R,5R)-4-{2-[6-(2,4-Difluoro-benzyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 559 | 14, 160 |
| (2R,5R)-4-[2-(6-Cyclohex-1-enyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: [M + H]+ = 513 | 14, 169 |
| (2R,5R)-4-[2-(3-Benzyl-6-chloro-3-methyl-2,3-dihydro-indol-1-yl)-2-oxo-ethyl]-5-methoxymethyl-2-methyl-piperazine-1-carboxylic acid tert-butyl ester | MS: [M + H]+ = 542 | 14, 187 |
| (2R,5R)-4-{2-[6-(2-Chloro-phenoxy)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | MS: [M + H]+ = 559 | 14, |

General Procedure 2 (HBTU Coupling)

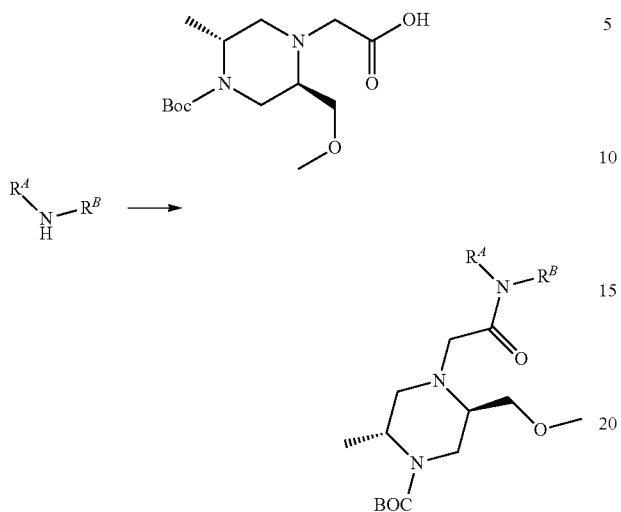

The starting amine was dissolved in DCM (0.1 M) and treated successively with HBTU (1.5 eq.), (2R,5R)-4-carboxymethyl-5-methoxymethyl-2-methyl-piperazine-1-carboxylic acid tert-butyl ester (1.3 eq.) and then DIPEA (3.0 eq.) under $N_2$. The reaction was stirred at room temperature for 16 h. The reaction was quenched by the addition of saturated aqueous $NaHCO_3$. The product was extracted with DCM (×2). The combined organic layers were washed with water, brine and dried over $MgSO_4$ then concentrated in vacuo. The product was purified by HPLC or column chromatography.

The compounds of Table 2 below were prepared using procedures analogous to that described above, starting from the appropriate substituted dihydropyrrolopyridine or tetrahdropyrrolopyridinone or dihydrospiro[azetidine-3,3'-indole] and substituted carboxymethylpiperazine (syntheses as described above, Preparation reference numbers listed where appropriate).

TABLE 2

| Compound Name | MS: [M + H]+ | Prep nos. |
|---|---|---|
| (2R,5R)-4-[2-(5-Methoxy-3,3-dimethyl-2,3-dihydro-pyrrolo[2,3-c]pyridin-1-yl)-2-oxo-ethyl]-5-methoxymethyl-2-methyl-piperazine-1-carboxylic acid tert-butyl ester | 463 | 14, 131 |
| (2R,5R)-5-Methoxymethyl-2-methyl-4-[2-oxo-2-(3,3,6-trimethyl-5-oxo-2,3,5,6-tetrahydro-pyrrolo[2,3-c]pyridin-1-yl)-ethyl]-piperazine-1-carboxylic acid tert-butyl ester | 463 | 14, 132 |
| (2R,5R)-4-[2-(6-Benzyl-3,3-dimethyl-5-oxo-2,3,5,6-tetrahydro-pyrrolo[2,3-c]pyridin-1-yl)-2-oxo-ethyl]-5-methoxymethyl-2-methyl-piperazine-1-carboxylic acid tert-butyl ester | 539 | 14, 133 |
| 1-{1-Acetyl-6'-chloro-1',2'-dihydrospiro[azetidine-3,3'-indole]-1'-yl}-2-[(2R,5R)-4-tert-butoxycarbonyl-2-(methoxymethyl)-5-methylpiperazin-1-yl]ethan-1-one | 521 | 14, 98 |
| (2R,5R)-4-[2-(6-Isobutyl-3,3-dimethyl-5-oxo-2,3,5,6-tetrahydro-pyrrolo[2,3-c]pyridin-1-yl)-2-oxo-ethyl]-5-methoxymethyl-2-methyl-piperazine-1-carboxylic acid tert-butyl ester | 505 | 14, 130 |

Preparation 134: 2-((R)-3-Methyl-piperazin-1-yl)-1-(6-phenylamino-2,3-dihydro-indol-1-yl)-ethanone To $Pd_2(dba)_3$ (4 mg, 0.005 mmol), (2-biphenyl)P(t-Bu)$_2$ (1 mg, 0.005 mmol), and NaO$^t$Bu (31 mg, 0.32 mmol) was added a solution of the aniline (26 mg, 0.27 mmol) in toluene (0.57 mL), followed by (R)-4-[2-(6-bromo-2,3-dihydro-indol-1-yl)-2-oxo-ethyl]-2-methyl-piperazine-1-carboxylic acid tert-butyl ester (50 mg, 0.11 mmol). The mixture was heated to 100° C. for 18 h then filtered and concentrated and the residue purified by preparative HPLC (TFA method), to give the title compound (12 mg, 24%) as a orange/brown solid. $^1$H NMR (Me-d3-OD): 8.05 (1H, dd), 7.30-7.17 (2H, m), 7.13 (1H, d), 7.10-7.02 (2H, m), 6.91-6.81 (2H, m), 4.58 (1H, s), 4.43-4.26 (2H, m), 4.26-4.16 (1H, m), 4.16-4.04 (2H, m), 3.71 (1H, d), 3.58-3.38 (2H, m), 3.29-3.18 (4H, m), 1.51 (9H, s), 1.43 (3H, d).

Preparation 135: 1-[6-(Methyl-phenyl-amino)-2,3-dihydro-indol-1-yl]-2-((R)-3-methyl-piperazin-1-yl)-ethanone Starting with N-methylaniline, the title compound was prepared by using similar methods to those described in Preparation 134 MS: [M+H]+=465.

Preparation 136: (R)-4-[2-(6-Isopropyl-2,3-dihydro-indol-1-yl)-2-oxo-ethyl]-2-methyl-piperazine-1-carboxylic acid tert-butyl ester $Pd(PPh_3)_4$ (32 mg, 0.03 mmol), (R)-4-[2-(6-bromo-2,3-dihydro-indol-1-yl)-2-oxo-ethyl]-2-methyl-piperazine-1-carboxylic acid tert-butyl ester (246 mg, 0.56 mmol) and 2-isopropenyl-4,4,5,5-tetramethyl-1,3,2-dioxaborolane (113 mg, 0.67 mmol) were dissolved in DMF (1.87 mL). $Cs_2CO_3$ (549 mg, 1.7 mmol) dissolved in water (0.37 mL) was added to the DMF solution. The reaction was degassed and heated to 85° C. for 18 h then was filtered and concentrated. Column chromatography on silica gel (gradient elution, 0-100% EtOAc/petrol), gave (R)-4-[2-(6-isopropenyl-2,3-dihydro-indol-1-yl)-2-oxo-ethyl]-2-methyl-piperazine-1-carboxylic acid tert-butyl ester (0.18 g) as a yellow oil. 10% Pd/C (48 mg, 0.05 mmol) and (R)-4-[2-(6-isopropenyl-2,3-dihydro-indol-1-yl)-2-oxo-ethyl]-2-methyl-piperazine-1-carboxylic acid tert-butyl ester (0.18 g) were mixed with MeOH (4.5 mL). The reaction was hydrogenated at ~1 bar for 30 min at ambient temperature then filtered under vacuum and concentrated, to give the title compound (157 mg, 86%) as a colourless oil. $^1$H NMR (Me-d3-OD): 8.08 (1H, s), 7.15 (1H, d), 6.95 (1H, d), 4.35-4.18 (3H, m), 3.83

(1H, d), 3.30 (2H, s), 3.25-3.12 (3H, m), 2.97-2.76 (3H, m), 2.33 (1H, dd), 2.20-2.08 (1H, m), 1.48 (9H, s), 1.31 (3H, d), 1.25 (6H, d).

Preparation 137: (R)-4-[2-(6-Amino-2,3-dihydro-indol-1-yl)-2-oxo-ethyl]-2-methyl-piperazine-1-carboxylic acid tert-butyl ester (R)-2-Methyl-4-[2-(6-nitro-2,3-dihydro-indol-1-yl)-2-oxo-ethyl]-piperazine-1-carboxylic acid tert-butyl ester (390 mg, 0.96 mmol) and 10% Pd/C (0.102 mg, 0.10 mmol) were mixed with MeOH (9.6 mL). The reaction was hydrogenated at −1 bar for 30 min at ambient temperature then filtered under vacuum and concentrated, to give the title compound (360 mg, 100%) as an off white glass. $^1$H NMR (Me-d3-OD): 7.64 (1H, d), 6.97 (1H, d), 6.47 (1H, dd), 4.32-4.17 (3H, m), 3.82 (1H, d), 3.28 (2H, s), 3.24-3.14 (1H, m), 3.07 (2H, t), 2.92 (1H, d), 2.81 (1H, d), 2.32 (1H, dd), 2.24-2.07 (1H, m), 1.48 (9H, s), 1.30 (3H, d).

Preparation 138: (R)-4-[2-(6-Methanesulfonylamino-2,3-dihydro-indol-1-yl)-2-oxo-ethyl]-2-methyl-piperazine-1-carboxylic acid tert-butyl ester R)-4-[2-(6-Amino-2,3-dihydro-indol-1-yl)-2-oxo-ethyl]-2-methyl-piperazine-1-carboxylic acid tert-butyl ester (75 mg, 0.20 mmol) was dissolved in anhydrous DCM (1.0 mL) and triethylamine (43 µL, 0.24 mmol) and methanesulfonyl chloride (17 µL, 0.22 mmol) were added. After stirring for 18 h, additional triethylamine (43 µL) and methane sulfonyl chloride (17 µL) were added. After stirring for 1 h the solvent was removed in vacuo and dissolved in THF (1.0 mL) and H$_2$O (0.6 mL). Sodium hydroxide (24 mg, 0.6 mmol) was added and the reaction stirred for 18 h. Purification by column chromatography on silica gel (gradient elution, 0-100% EtOAc/petrol), gave the title compound (65 mg, 72%) as an off white glass. $^1$H NMR (CDCl3): 8.17 (1H, s), 7.68 (1H, s), 7.19 (2H, s), 4.37-4.19 (3H, m), 3.85 (1H, d), 3.32 (2H, s), 3.29-3.10 (3H, m), 2.94 (3H, s), 2.88 (1H, d), 2.74 (1H, d), 2.41 (1H, d), 2.23 (1H, t), 1.47 (9H, s), 1.28-1.25 (3H, m).

Preparation 139: (R)-4-[2-(2,3-Dihydro-pyrrolo[3,2-c]pyridin-1-yl)-2-oxo-ethyl]-2-methyl-piperazine-1-carboxylic acid tert-butyl ester 10% Pd/C (62 mg, 0.06 mmol) and (R)-4-[2-(4-chloro-2,3-dihydro-pyrrolo[3,2-c]pyridin-1-yl)-2-oxo-ethyl]-2-methyl-piperazine-1-carboxylic acid tert-butyl ester (232 mg, 0.6 mmol) were mixed with THF (5.82 mL) and triethylamine (1.22 mL, 0.87 mmol) was added. The reaction was hydrogenated at −1 bar for 5 h at ambient temperature then filtered under vacuum and the solvent evaporated in vacuo. The residue was dissolved in MeOH and loaded onto SCX column eluting with MeOH then 2 M ammonia in MeOH to release the amine and concentrated, to give the title compound (111 mg, 53%) as a yellow oil, $^1$H NMR (Me-d3-OD): 8.35 (1H, s), 8.31 (1H, d), 8.05 (1H, s), 4.33 (2H, t), 4.28-4.17 (1H, m), 3.83 (1H, d), 3.28 (2H, d), 3.24-3.08 (1H, m), 3.00-2.79 (3H, m), 2.36 (1H, dd), 2.26-2.12 (1H, m), 1.48 (9H, s), 1.31 (3H, d).

Preparation 140: (R)-2-Methyl-4-[2-(6-methylcarbamoyl-2,3-dihydro-indol-1-yl)-2-oxo-ethyl]-piperazine-1-carboxylic acid tert-butyl ester 1-[2-((R)-4-tert-Butoxycarbonyl-3-methyl-piperazin-1-yl)-acetyl]-2,3-dihydro-1H-indole-6-carboxylic acid methyl ester (200 mg, 0.48 mmol) was dissolved in 2.0 M methylamine in MeOH (2.4 mL) and heated under microwave irradiation at 120° C. for 4 h. The solvent was removed in vacuo and the resulting oil was purified by column chromatography on silica gel (gradient elution, 0-100% EtOAc/petrol), to give the title compound (39 mg, 20%) as a colourless solid, $^1$H NMR (Me-d3-OD): 8.58 (1H, s), 7.51 (1H, d), 7.33 (1H, d), 4.39-4.28 (2H, m), 4.23 (1H, d), 3.88-3.77 (1H, m), 3.31-3.14 (3H, m), 2.92 (3H, s), 2.84 (1H, d), 2.39-2.30 (1H, m), 2.24-2.12 (1H, m), 1.48 (9H, s), 1.30 (3H, d).

Preparation 141: 1-[2-((R)-4-tert-Butoxycarbonyl-3-methyl-piperazin-1-yl)-acetyl]-2,3-dihydro-1H-indole-6-carboxylic acid 1-[2-((R)-4-tert-Butoxycarbonyl-3-methyl-piperazin-1-yl)-acetyl]-2,3-dihydro-1H-indole-6-carboxylic acid methyl ester (690 mg, 1.65 mmol) was dissolved in THF/MeOH/H$_2$O (3.3/3.3/1.7 mL) and sodium hydroxide (331 mg, 8.27 mmol) was added. The reaction was stirred for 18 h and neutralised with 2 M hydrochloric acid (4.1 mL). The solvent was removed in vacuo and the residue azeoptroped with MeOH to dryness, to give the title compound (630 mg, 95%) as a red/pink solid. $^1$H NMR (Me-d3-OD): 8.76 (1H, s), 7.71 (1H, dd), 7.27 (1H, d), 4.39-4.28 (2H, m), 4.27-4.10 (1H, m), 3.83 (1H, d), 3.28-3.07 (3H, m), 2.93 (1H, d), 2.84 (1H, d), 2.33 (1H, dd), 2.26-2.08 (1H, m), 1.47 (9H, s), 1.34-1.27 (3H, m).

Preparation 142: (R)-4-[2-(6-Dimethylcarbamoyl-2,3-dihydro-indol-1-yl)-2-oxo-ethyl]-2-methyl-piperazine-1-carboxylic acid tert-butyl ester Starting with dimethylamine and 1-[2-((R)-4-tert-butoxycarbonyl-3-methyl-piperazin-1-yl)-acetyl]-2,3-dihydro-1H-indole-6-carboxylic acid, the title compound was prepared by using similar methods to those described in General Procedure 1. MS: [M+H]$^+$=431.

Preparation 143: (R)-2-Methyl-4-{2-oxo-2-[6-(pyrrolidine-1-carbonyl)-2,3-dihydro-indol-1-yl]-ethyl}-piperazine-1-carboxylic acid tert-butyl ester Starting with pyrrolidine and 1-[2-((R)-4-tert-butoxycarbonyl-3-methyl-piperazin-1-yl)-acetyl]-2,3-dihydro-1H-indole-6-carboxylic acid, the title compound was prepared by using similar methods to those described in General Procedure 1. $^1$H NMR (Me-d3-OD): 8.31 (1H, s), 7.34 (1H, d), 7.22 (1H, dd), 4.32 (2H, t), 4.24 (1H, s), 3.83 (1H, d), 3.67-3.54 (2H, m), 3.54-3.41 (2H, m), 3.31-3.09 (5H, m), 2.93 (1H, d), 2.83 (1H, d), 2.41-2.23 (1H, m), 2.23-2.09 (1H, m), 2.02-1.98 (2H, m), 1.96-1.84 (2H, m), 1.48 (9H, s), 1.30 (3H, d).

Preparation 144: 1-{1'-Acetyl-6-chloro-1,2-dihydrospiro[indole-3,4'-piperidine]-1-yl}-2-[(3R)-4-tert-butoxycarbonyl-3-methylpiperazin-1-yl]ethan-1-one 10% Pd/C (9 mg, 0.01 mmol) and 6-chloro-1-{2-[(3R)-4-tert-butoxycarbonyl-3-methylpiperazin-1-yl]acetyl}-1,2-dihydrospiro[indole-3,4'-piperidine]-1'-carboxylic acid, benzyl ester (51 mg, 0.09 mmol) were mixed with EtOAc (0.34 mL) at ambient temperature and glacial acetic acid (0.02 mL) added. The reaction was hydrogenated at −1 bar for 1 h at ambient temperature, then filtered and concentrated in vacuo. The crude brown oil was purified by preparative HPLC to give product (21 mg). To this material in anhydrous DCM (0.18 mL) was added triethylamine (13 μL, 0.09 mmol) and acetic anhydride (6 μL, 0.06 mmol). After stirring for 2 h at ambient temperature, the solvent was removed in vacuo and the residue dissolved in MeOH and loaded onto SCX column eluting with MeOH and then 2.0 M ammonia in MeOH to release the amine. Solvent was removed in vacuo to give the title compound (21 mg, 92%) as a colourless oil. MS: [M+H]$^+$ 505.

Preparation 145: (R)-2-Methyl-4-[2-(6-methylsulfamoyl-2,3-dihydro-indol-1-yl)-2-oxo-ethyl]-piperazine-1-carboxylic acid tert-butyl ester Starting with (R)-4-[2-(5-bromo-6-methylsulfamoyl-2,3-dihydro-indol-1-yl)-2-oxo-ethyl]-2-methyl-piperazine-1-carboxylic acid tert-butyl ester, the title compound was prepared by using similar methods to those described in Preparation 139. $^1$H NMR (Me-d3-OD): 8.63 (1H, s), 7.55 (1H, dd), 7.44 (1H, d), 4.35 (2H, t), 4.24 (1H, d), 3.83 (1H, d), 3.26-3.12 (1H, m), 2.93 (1H, d), 2.83 (1H, d), 2.55 (3H, s), 2.35 (1H, dd), 2.24-2.12 (1H, m), 1.48 (9H, s), 1.31 (3H, d).

Preparation 146: (R)-4-[2-(6-Dimethylsulfamoyl-2,3-dihydro-indol-1-yl)-2-oxo-ethyl]-2-methyl-piperazine-1-carboxylic acid tert-butyl ester Starting with (R)-4-[2-(5-Bromo-6-dimethylsulfamoyl-2,3-dihydro-indol-1-yl)-2-oxo-ethyl]-2-methyl-piperazine-1-carboxylic acid tert-butyl ester, the title compound was prepared by using similar methods to those described in Preparation 139. $^1$H NMR (Me-d3-OD): 8.56 (1H, s), 7.54-7.42 (2H, m), 4.43-4.18 (3H, m), 3.83 (1H, d), 3.26-3.10 (1H, m), 3.01-2.78 (2H, m), 2.70 (6H, s), 2.35 (1H, dd), 2.24-2.10 (1H, m), 1.48 (9H, s), 1.31 (3H, d).

Preparation 147: (R)-2-Methyl-4-{2-oxo-2-[6-(pyrrolidine-1-sulfonyl)-2,3-dihydro-indol-1-yl]-ethyl}-piperazine-1-carboxylic acid tert-butyl ester Starting with (R)-4-{2-[5-bromo-6-(pyrrolidine-1-sulfonyl)-2,3-dihydro-indol-1-yl]-2-oxo-ethyl}-2-methyl-piperazine-1-carboxylic acid tert-butyl ester, the title compound was prepared by using similar methods to those described in Preparation 139). MS: [M+H]$^+$=493

Preparation 148: (R)-4-[2-(3,3-Dimethyl-2,3-dihydro-indol-1-yl)-2-oxo-ethyl]-2-methyl-piperazine-1-carboxylic acid tert-butyl ester Starting with (R)-4-[2-(4-chloro-3,3-dimethyl-2,3-dihydro-indol-1-yl)-2-oxo-ethyl]-2-methyl-piperazine-1-carboxylic acid tert-butyl ester, the title compound was prepared by using similar methods to those described in Preparation 139. $^1$H NMR (Me-d3-OD): 8.10 (1H, d), 7.36-7.15 (2H, m), 7.15-7.04 (1H, m), 4.24 (1H, s), 4.13-4.01 (2H, m), 3.83 (1H, d), 3.29 (2H, s), 3.23-3.06 (1H, m), 2.96-2.86 (1H, m), 2.82 (1H, d), 2.38-2.23 (1H, m), 2.22-2.08 (1H, m), 1.48 (9H, s), 1.37 (6H, s), 1.30 (3H, d).

Preparation 149: (R)-4-[2-(5-Bromo-6-dimethylsulfamoyl-2,3-dihydro-indol-1-yl)-2-oxo-ethyl]-2-methyl-piperazine-1-carboxylic acid tert-butyl ester Starting with (R)-4-[2-(5-bromo-6-dimethylsulfamoyl-3,3-dimethyl-2,3-dihydro-indol-1-yl)-2-oxo-ethyl]-2-methyl-piperazine-1-carboxylic acid tert-butyl ester, the title compound was prepared by using similar methods to those described in Preparation 139. $^1$H NMR (Me-d3-OD): 8.56 (1H, s), 7.54-7.42 (2H, m), 4.43-4.18 (3H, m), 3.83 (1H, d), 3.26-3.10 (1H, m), 3.01-2.78 (2H, m), 2.70 (6H, s), 2.35 (1H, dd), 2.24-2.10 (1H, m), 1.48 (9H, s), 1.31 (3H, d).

Preparation 150: (2R,5R)-4-[2-(3,3-Dimethyl-6-phenoxy-2,3-dihydro-pyrrolo[3,2-c]pyridin-1-yl)-2-oxo-ethyl]-5-methoxymethyl-2-methyl-piperazine-1-carboxylic acid tert-butyl ester (2R,5R)-4-[2-(6-chloro-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester (100 mg, 0.21 mol), phenol (24 mg, 0.206 mol), K$_3$PO$_4$ (96 mg, 0.43 mmol), 2-di-tert-butylphosphino-2',4',6'-triisopropylbiphenyl (3 mg, 0.01 mmol), Pd(OAc)$_2$ were combined and slurried in toluene (0.714 mL). The reaction was degassed with nitrogen and heated to 100° C. After 18 h the reaction was cooled to RT. MeOH was added and the solution passed through a Phenomenex NH2 column, eluting with MeOH and then 2.0 M ammonia in MeOH to release the amine. The residue was purified by column chromatography on silica gel (gradient elution, 0-100% EtOAc/petrol), to give (75 mg). Further purification by preparative HPLC (basic method), gave the title compound (19 mg, 17%) as a colourless oil. $^1$H NMR (Me-d3-OD): 7.91 (1H, s), 7.51 (1H, s), 7.42 (2H, t), 7.22 (1H, t), 7.10 (2H, d), 4.22-4.12 (1H, m), 4.05 (2H, q), 3.95 (1H, d), 3.70 (1H, d), 3.60 (1H, dd), 3.52 (1H, d), 3.00 (1H, s), 2.85 (1H, dd), 2.64 (1H, dd), 1.48 (9H, s), 1.43 (6H, s), 1.22 (3H, d).

Preparation 151: (R)-4-[2-(6-Benzenesulfonyl-5-fluoro-2,3-dihydro-indol-1-yl)-2-oxo-ethyl]-2-methyl-piperazine-1-carboxylic acid tert-butyl ester A mixture of (R)-4-[2-(6-bromo-5-fluoro-2,3-dihydro-indol-1-yl)-2-oxo-ethyl]-2-methyl-piperazine-1-carboxylic acid tert-butyl ester (0.137 g, 0.30 mmol), sodium phenylsulfinate (0.064 g, 0.39 mmol), copper (1) trifluoromethylsulfonate-benzene complex (0.0045 g, 0.009 mmol), N,N'-dimethylethylenediamine (0.29 g, 0.33 mmol) and dimethyl sulfoxide (1.5 mL) was stirred at 150° C. under nitrogen for 18 h in a sealed vessel. The resulting mixture was partitioned between water (50 mL) and 1:1 Et$_2$O-EtOAc (30 mL) and the organic phase was washed with water (2×20 mL), dried (Na$_2$SO$_4$) and evaporated in vacuo to give a brown oil. Chromatography (SiO$_2$; gradient elution with 0-100% EtOAc in petrol) gave the title compound (0.031 g, ~25%). MS: [M+H]$^+$=518.

Preparation 152: (R)-4-{2-[6-(4-Chloro-2-fluorophenyl)-2,3-dihydro-pyrrolo[3,2-c]pyridin-1-yl]-2-oxo-ethyl}-2-methyl-piperazine-1-carboxylic acid tert-butyl ester (R)-4-[2-(6-Chloro-2,3-dihydro-pyrrolo[3,2-c]pyridin-1-yl)-2-oxo-ethyl]-2-methyl-piperazine-1-carboxylic acid tert-butyl ester, 2-fluoro-5-chloro-phenyl boronic acid, 2.0 M aqueous K$_2$CO$_3$ and 1,4-dioxane were degassed under nitrogen for 5 min. Pd(PPh$_3$)$_4$ was added and the reaction heated to 110° C. for 18 h. After cooling to ambient temperature, the reaction was dissolved in MeOH, filtered and loaded onto an SCX column. Elution with MeOH and then 2.0 M ammonia in MeOH was carried out and the basic eluate was concentrated in vacuo. The resulting brown oil was purified by column chromatography on silica gel (gradient elution, 0-100% EtOAc/petrol). The solid was further purified by preparative HPLC (basic method), to give the title compound (17 mg, 14%) as a colourless oil. $^1$H NMR (Me-d3-OD): 8.46 (2H, s), 7.80 (1H, dd), 7.52-7.41 (1H, m), 7.27 (1H, t), 4.38 (2H, t), 4.24 (1H, s), 3.83 (1H, d), 3.27-3.06 (1H, m), 3.06-2.76 (3H, m), 2.36 (1H, dd), 2.25-2.11 (1H, m), 1.95-1.76 (1H, m), 1.48 (9H, s), 1.30 (3H, d).

General Procedure 3 (Organozinc Halide Addition)

(2R,5R)-4-[2-(6-Benzyl-3,3-di methyl-2,3-dihydro-indol-1-yl)-2-oxo-ethyl]-5-hydroxymethyl-2-methyl-piperazine-1-carboxylic acid tert-butyl ester To a degassed ($N_2$) solution of LiBr (20 mg, 0.2 mmol) and (1,3-diisopropylimidazol-2-ylidene)(3-chloropyridyl)palladium (II) dichloride (1.0 mg, 0.14 mmol) in anhydrous THF/NMP (1:1, 0.48 mL) was added a solution of (2R,5R)-4-[2-(6-chloro-3,3-dimethyl-2,3-dihydro-indol-1-yl)-2-oxo-ethyl]-5-hydroxymethyl-2-methyl-piperazine-1-carboxylic acid tert-butyl ester (65 mg, 0.14 mmol), THF (0.1 mL) and benzylzinc bromide (575 µL, 0.30 mmol). The reaction was stirred for 18 h and diluted with MeOH then loaded onto a SCX column eluting with MeOH and then 2.0 M ammonia-MeOH to release the amine. The solvent was removed in vacuo, to give the title compound (9.0 mg, 12%) as a colourless oil. $^1$H NMR (Me-d3-OD): 8.03 (1H, s), 7.33-7.03 (6H, m), 6.96 (1H, d), 4.15 (1H, d), 4.10-3.93 (5H, m), 3.76 (1H, dd), 3.67 (1H, d), 3.59-3.49 (2H, m), 2.93-2.83 (2H, m), 2.65 (1H, dd), 1.48 (9H, s), 1.35 (6H, s), 1.23 (3H, d).

The compounds of Table 3 below were prepared using procedures analogous to that described above, starting from the appropriate halo substituted dihydroindole or dihydropyrrolopyridine (syntheses as described above).

Preparation 153: 6-Benzyl-3,3-dimethyl-2,3-dihydro-pyrrolo[3,2-c]pyridine, hydrochloride salt Prepared from 6-benzyl-3,3-dimethyl-2,3-dihydro-pyrrolo[3,2-c]pyridine-1-carboxylic acid tert-butyl ester using an analogous method to Preparation 116. MS: $[M+H]^+$=239.

The compounds of Preparations 154-160 below were prepared in two steps from 6-chloro-3,3-dimethyl-2,3-dihydro-pyrrolo[3,2-c]pyridine-1-carboxylic acid tert-butyl ester by (i) reaction with the appropriate arylalkylzinc halide following a procedure analogous to that of Preparation 117 and (ii) deprotection following a procedure analogous to that of Preparation 116.

Preparation 154: 6-(3-Chloro-benzyl)-3,3-dimethyl-2,3-dihydro-1H-pyrrolo[3,2-c]pyridine, hydrochloride salt

MS: $[M+H]^+$=273.

Preparation 155: 3,3-Dimethyl-6-(1-phenyl-ethyl)-2,3-dihydro-1H-pyrrolo[3,2-c]pyridine, hydrochloride salt

MS: $[M+H]^+$=253.

Preparation 156: 6-(4-Fluoro-benzyl)-3,3-dimethyl-2,3-dihydro-1H-pyrrolo[3,2-c]pyridine, hydrochloride salt

MS: $[M+H]^+$=257.

Preparation 157: 6-(3-Methoxy-benzyl)-3,3-dimethyl-2,3-dihydro-1H-pyrrolo[3,2-c]pyridine, hydrochloride salt

MS: $[M+H]^+$=269.

TABLE 3

| Compound Name | Characterising data |
| --- | --- |
| (R)-4-[2-(6-Benzyl-2,3-dihydro-pyrrolo[3,2-c]pyridin-1-yl)-2-oxo-ethyl]-2-methyl-piperazine-1-carboxylic acid tert-butyl ester | MS: $[M + H]^+$ = 451. |
| (2R,5R)-4-[2-(6-Benzyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: $[M + H]^+$ = 523. |
| (2R,5R)-4-[2-(6-Isobutyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | MS: $[M + H]^+$ = 489. |
| (2R,5R)-4-{2-[3,3-Dimethyl-6-(3-methyl-butyl)-2,3-dihydro-pyrrolo[3,2-c]pyridin-1-yl]-2-oxo-ethyl}-5-methoxymethyl-2-methyl-piperazine-1-carboxylic acid tert-butyl ester | $^1$H NMR (CDCl$_3$): 8.34-8.24 (1H, m), 7.96 (1H, s), 4.22 (1H, d), 3.96 (2H, d), 3.86 (1H, d), 3.66 (2H, d), 3.54-3.42 (1H, m), 3.42-3.36 (4H, m), 3.32 (1H, dd), 3.05 (1H, s), 2.86 (1H, dd), 2.83-2.76 (2H, m), 2.71 (1H, dd), 1.70-1.58 (3H, m), 1.49 (9H, s), 1.41 (6H, s), 1.24 (3H, d), 0.96 (6H, d). |
| (2R,5R)-4-[2-(6-Benzyl-3,3-dimethyl-2,3-dihydro-indol-1-yl)-2-oxo-ethyl]-5-methoxymethyl-2-methyl-piperazine-1-carboxylic acid tert-butyl ester | MS: [M + H]+ = 522 |
| (2R,5R)-4-[2-(6-Benzyl-3,3-dimethyl-2,3-dihydro-indol-1-yl)-2-oxo-ethyl]-2-methyl-5-(morpholine-4-carbonyl)-piperazine-1-carboxylic acid tert-butyl ester | MS: [M + H]+ = 591 |

Preparation 158: 6-(3-Fluoro-benzyl)-3,3-dimethyl-2,3-dihydro-1H-pyrrolo[3,2-c]pyridine, hydrochloride salt

MS: [M+H]$^+$=257.

Preparation 159: 6-(4-Methoxy-benzyl)-3,3-dimethyl-2,3-dihydro-1H-pyrrolo[3,2-c]pyridine, hydrochloride salt

MS: [M+H]$^+$=269.

Preparation 160: 6-(2,4-Difluoro-benzyl)-3,3-dimethyl-2,3-dihydro-1H-pyrrolo[3,2-c]pyridine, hydrochloride salt

MS: [M+H]$^+$=275.

Preparation 161: 6-Cyclopent-1-enyl-3,3-dimethyl-2,3-dihydro-pyrrolo[3,2-c]pyridine-1-carboxylic acid tert-butyl ester A mixture of 6-chloro-3,3-dimethyl-2,3-dihydro-pyrrolo[3,2-c]pyridine-1-carboxylic acid tert-butyl ester (340 mg, 1.2 mmol), cyclopenten-1-ylboronic acid (270 mg, 2.4 mmol), potassium carbonate (414 mg, 3.0 mmol) and dichlorobis(tri-o-tolyl-phosphine)palladium(II) (38 mg, 0.04 mmol) in 1,4-dioxane (6 mL) and water (1.5 mL) was degassed and heated in a reaction vial at 90° C. for 2 h. The reaction mixture was cooled, water (20 mL) was added and the product was extracted with EtOAc (2×20 mL). The combined organic layers were dried, filtered and the solvent evaporated. The crude material was purified by column chromatography (SiO$_2$, petrol-EtOAc 0-60%) to afford the title compound (213 mg, 57%). MS: [M+H]$^+$=315.

Preparation 162: 6-Cyclopent-1-enyl-3,3-dimethyl-2,3-dihydro-1H-pyrrolo[3,2-c]pyridine, hydrochloride salt Prepared from 6-cyclopent-1-enyl-3,3-dimethyl-2,3-dihydro-pyrrolo[3,2-c]pyridine-1-carboxylic acid tert-butyl ester using a procedure analogous to that of Preparation 116. MS: [M+H]$^+$=215.

Preparation 163: (2R,5R)-4-[2-(6-Cyclopentyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester To a solution of (2R,5R)-4-[2-(6-cyclopent-1-enyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester (see Table 1) (60 mg, 0.12 mmol) in THF (5 mL) and MeOH (5 mL) was added palladium on carbon (10%, 10 mg) and the mixture was hydrogenated for 2 h. The catalyst was filtered and the filtrate evaporated to afford the title compound (52 mg, 87%) as a white solid. MS [M+H]$^+$=501.

Preparation 164: 3,3-Dimethyl-6-(1-phenyl-vinyl)-2,3-dihydro-1H-pyrrolo[3,2-c]pyridine-1-carboxylic acid tert-butyl ester The title compound was prepared using an analogous procedure to that of Preparation 161 using 1-phenylvinylboronic acid instead of cyclopenten-1-ylboronic acid; reaction was heated at 90° C. overnight. MS: [M+H]$^+$=351.

Preparation 165: 3,3-Dimethyl-6-(1-phenyl-vinyl)-2,3-dihydro-1H-pyrrolo[3,2-c]pyridine, hydrochloride salt Prepared from 3,3-dimethyl-6-(1-phenyl-vinyl)-2,3-dihydro-pyrrolo[3,2-c]pyridine-1-carboxylic acid tert-butyl ester using a procedure analogous to that of Preparation 116. MS: [M+H]$^+$=251.

Preparation 166: 6-Benzoyl-3,3-dimethyl-2,3-dihydro-pyrrolo[3,2-c]pyridine-1-carboxylic acid tert-butyl ester To a solution of 3,3-dimethyl-6-(1-phenyl-vinyl)-2,3-dihydro-pyrrolo[3,2-c]pyridine-1-carboxylic acid tert-butyl ester (914 mg, 2.6 mmol) in THF (10 mL), acetone (5 mL) and water (5 mL) was added NaIO$_4$ (2.8 g, 13.05 mmol), then OsO$_4$ (2 mL of 4% solution in water, 0.3 mmol) and the reaction mixture was stirred at room temperature for 24 h. The reaction mixture was concentrated in vacuo, water (20 mL) was added and the product was extracted with EtOAc (2×20 mL). The organic phase was washed with brine, dried (MgSO$_4$), filtered and the solvent evaporated. The crude product was purified by column chromatography on silica, eluted with petrol-EtOAc 0-40% to afford the title compound (654 mg, 65%). MS: [M+H]$^+$=353.

Preparation 167: 6-Benzoyl-3,3-dimethyl-2,3-dihydro-1H-pyrrolo[3,2-c]pyridine, hydrochloride salt Prepared from 6-benzoyl-3,3-dimethyl-2,3-dihydro-pyrrolo[3,2-c]pyridine-1-carboxylic acid tert-butyl ester using a procedure analogous to that of Preparation 116. MS: [M+H]$^+$=253.

Preparation 168: 6-Cyclohex-1-enyl-3,3-dimethyl-2,3-dihydro-pyrrolo[3,2-c]pyridine-1-carboxylic acid tert-butyl ester The title compound was prepared using an analogous method to that of Preparation 161, using cyclohexen-1-ylboronic acid was used instead of cyclopenten-1-ylboronic acid; reaction was heated at 90° C. overnight. MS: [M+H]$^+$=329.

Preparation 169: 6-Cyclohex-1-enyl-3,3-dimethyl-2,3-dihydro-1H-pyrrolo[3,2-c]pyridine, hydrochloride salt Prepared from 6-cyclohex-1-enyl-3,3-dimethyl-2,3-dihydro-pyrrolo[3,2-c]pyridine-1-carboxylic acid tert-butyl ester using a procedure analogous to that of Preparation 116. MS: [M+H]$^+$=229.

Preparation 170: 3,3,6-Trimethyl-2,3-dihydro-pyrrolo[3,2-c]pyridine-1-carboxylic acid tert-butyl ester Prepared from 6-chloro-3,3-dimethyl-2,3-dihydro-pyrrolo[3,2-c]pyridine-1-carboxylic acid tert-butyl ester by a method analogous to that of Preparation 117 using methyl zinc chloride (2.0 M in THF, 9.75 mmol), to give the title compound (510 mg, 55%) as a colourless oil. MS: [M+H]$^+$=263.

Preparation 171: 3,3,6-Trimethyl-2,3-dihydro-pyrrolo[3,2-c]pyridine-1-carboxylic acid, 5-oxide, tert-butyl ester To 3,3,6-trimethyl-2,3-dihydro-pyrrolo[3,2-c]pyridine-1-carboxylic acid tert-butyl ester (0.4 g, 1.53 mmol), in DCM (3.2 mL) was added 3-chloroperbenzoic acid (0.29 g, 1.7 mmol) at ambient temperature. The reaction was stirred for 18 h at ambient temperature. More 3-chloroperbenzoic acid was added (750 mg) and the reaction stirred for 6 h. DCM (5.0 mL) was added and the organic solution washed with saturated aqueous sodium bicarbonate (3×5.0 mL), dried over sodium sulfate, filtered and the solvent removed in vacuo. Chromatography ($SiO_2$, gradient elution, 0-100%, EtOAc/petrol then $SiO_2$, gradient elution, 0-10%, MeOH/DCM) gave the title compound (0.38 g, 90%) as a pale yellow foam. MS: $[M+H]^+=279$.

Preparation 172: 6-Acetoxymethyl-3,3-dimethyl-2,3-dihydro-pyrrolo[3,2-c]pyridine-1-carboxylic acid tert-butyl ester 3,3,6-Trimethyl-2,3-dihydro-pyrrolo[3,2-c]pyridine-1-carboxylic acid, 5-oxide, tert-butyl ester (0.375 g, 1.34 mmol) was dissolved in acetic anhydride (1.68 mL) and heated to 125° C. for 1 h. The reaction was cooled to ambient temperature and concentrated in vacuo. Chromatography ($SiO_2$, gradient elution, 0-100%, EtOAc/petrol), gave the title compound (0.280 mg, 65%) as a yellow oil. MS: $[M+H]^+=321$.

Preparation 173: 6-Hydroxymethyl-3,3-dimethyl-2,3-dihydro-pyrrolo[3,2-c]pyridine-1-carboxylic acid tert-butyl ester To 6-acetoxymethyl-3,3-dimethyl-2,3-dihydro-pyrrolo[3,2-c]pyridine-1-carboxylic acid tert-butyl ester (0.261 g, 0.82 mmol), in MeOH (8.2 mL) was added potassium carbonate (0.45 g, 3.3 mmol) at ambient temperature. The reaction was stirred for 2 h at ambient temperature. Water (10 mL) was added and the reaction extracted with EtOAc (3×10 mL). The combined organic extracts were washed with brine (30 mL), dried over sodium sulfate, filtered and concentrated to give the title compound (0.268 g) as a pale yellow oil, used without further purification. MS: $[M+H]^+=279$.

Preparation 174: 6-Methanesulfonyloxymethyl-3,3-dimethyl-2,3-dihydro-pyrrolo[3,2-c]pyridine-1-carboxylic acid tert-butyl ester To 6-hydroxymethyl-3,3-dimethyl-2,3-dihydro-pyrrolo[3,2-c]pyridine-1-carboxylic acid tert-butyl ester (0.268 g, 0.96 mmol) and triethylamine (0.417 mL, 3 mmol) in EtOAc (4.8 mL) was added methanesulfonyl chloride (0.224 mL, 2.9 mmol) at 0° C. The reaction was stirred at the same temperature for 1 h. Water (5 mL) was added and the aqueous mixture extracted with EtOAc (3×5.0 mL). The combined organic extracts were washed with brine (20 mL), dried over sodium sulfate, filtered and the solvent removed in vacuo to give the title compound (0.279 g,) as a pale yellow oil. MS: $[M+H]^+=357$.

Preparation 175: 3,3-Dimethyl-6-pyrazol-1-ylmethyl-2,3-dihydro-pyrrolo[3,2-c]pyridine-1-carboxylic acid tert-butyl ester To a solution of potassium tert-butoxide (0.090 g, 0.80 mmol) in anhydrous THF (4.0 mL) was added pyrazole (0.104 g, 1.52 mmol). The reaction was stirred for 30 min. 6-Methanesulfonyloxymethyl-3,3-dimethyl-2,3-dihydro-pyrrolo[3,2-c]pyridine-1-carboxylic acid tert-butyl ester (0.271 g, 0.76 mmol) was added at ambient temperature and the reaction was stirred for 1 h. A second equivalent of pyrazole (104 mg) was added, followed by potassium tert-butoxide (90 mg) and the reaction stirred for 1 h. Water (4.0 mL) was added and the reaction extracted with EtOAc (3×5.0 mL), washed with saturated brine solution (15 mL), dried over sodium sulfate, filtered and concentrated. Chromatography ($SiO_2$, gradient elution, 0-100%, EtOAc/petrol then $SiO_2$, gradient elution, 0-5%, MeOH/DCM). gave the title compound (0.13 g, 52%) as a pale yellow oil MS: $[M+H]^+=329$.

Preparation 176: 3,3-Dimethyl-6-pyrazol-1-ylmethyl-2,3-dihydro-pyrrolo[3,2-c]pyridine Prepared from 3,3-Dimethyl-6-pyrazol-1-ylmethyl-2,3-dihydro-pyrrolo[3,2-c]pyridine-1-carboxylic acid tert-butyl ester using a procedure analogous to that of Preparation 116. MS: $[M+H]^+=229$

Preparation 177: 3,3-Dimethyl-2,3-dihydro-1H-pyrrolo[3,2-c]pyridine-6-carbonitrile A mixture of 6-chloro-3,3-dimethyl-2,3-dihydro-pyrrolo[3,2-c]pyridine-1-carboxylic acid tert-butyl ester (0.405 g, 1.43 mmol), $K_4[Fe(CN)_6]$ (1.21 g, 2.86 mmol), $Pd(OAc)_2$ (16 mg, 0.07 mmol), butyl di-1-adamantylphoshine (77 mg, 0.21 mmol) and sodium carbonate (0.304 g, 2.86 mmol) was slurried in NMP (14.3 mL) at ambient temperature. The reaction was heated under microwave irradiation at 185° C. for 2 h. The reaction was cooled to ambient temperature and filtered. The filtrate was dissolved in water and extracted with diethyl ether/petrol (1:1, 3×). The combined organic extracts were washed with brine (3×), dried over sodium sulfate, and solvent removed in vacuo. Chromatography ($SiO_2$, gradient elution, 0-100%, EtOAc/petrol) gave the title compound (36 mg, 15%) as a colourless solid. MS: $[M+H]^+=174$

Preparation 178: (2-Chloromethyl-allyloxymethyl)-benzene

Benzyl alcohol (3.5 mL, 33.6 mmol) and DMF (8 mL) were added to a suspension of NaH (60% suspension in mineral oil, 1.8 g, 43.7 mmol, washed with hexane before use) in THF (35 mL). The resulting mixture was stirred for 30 minutes at room temperature and then 1 h at reflux. The mixture was cooled to room temperature and slowly added over 1 h to a solution of 3-chloro-2-chloromethyl-propene (4.2 g, 33.6 mmol) in THF (40 mL). The reaction was stirred at room temperature for 18 h, quenched with brine/water (1:1) and extracted with $Et_2O$. The organic phase was dried ($MgSO_4$), filtered and concentrated. Chromatography ($SiO_2$, EtOAc:Petrol 1:9) to give the title compound (3.1 g) as a colourless oil. $^1H$ NMR ($CDCl_3$): 7.46-7.29 (5H, m), 5.35 (1H, s), 5.30 (1H, d), 4.56 (2H, s), 4.24-4.06 (4H, m).

Preparation 179: (2-Bromomethyl-allyloxymethyl)-benzene

LiBr (2.7 g, 31.6 mmol) was flame dried under vacuum and then cooled to room temperature. TBABr (255 mg, 0.79 mmol), (2-chloromethyl-allyloxymethyl)-benzene (3.1 g, 15.8 mmol) and THF (5 mL) were then added and the suspension was stirred at 60° C. for 2 h. The mixture was filtered through Celite and the solvent was removed in vacuo to give the title compound (3.4 g) as a colourless oil which was used in the next step without further purification. $^1$H NMR (CDCl$_3$): 7.47-7.30 (5H, m), 5.47-5.33 (1H, m), 5.30 (1H, q), 4.56 (2H, s), 4.19 (2H, s), 4.08 (2H, s).

Preparation 180: (2-Benzyloxymethyl-allyl)-(2-chloro-5-iodo-pyridin-4-yl)-amine The title compound was prepared from 2-chloro-5-iodo-pyridin-4-yl-amine and (2-bromomethyl-allyloxymethyl)-benzene following a similar method to that described in Preparation 108. The reaction was stirred at 55° C. for 3 h. MS: [M+H]$^+$=415.

Preparation 181: 3-Benzyloxymethyl-6-chloro-3-methyl-2,3-dihydro-1H-pyrrolo[3,2-c]pyridine The title compound was obtained from (2-benzyloxymethyl-allyl)-(2-chloro-5-iodo-pyridin-4-yl)-amine by palladium catalysed cyclisation following a similar method to that described in Preparation 109 to give the title compound as a pale yellow solid. MS: [M+H]$^+$=289.

Preparation 182: 3-Benzyloxymethyl-6-chloro-3-methyl-2,3-dihydro-pyrrolo[3,2-c]pyridine-1-carboxylic acid tert-butyl ester The title compound was prepared from 3-benzyloxymethyl-6-chloro-3-methyl-2,3-dihydro-1H-pyrrolo[3,2-c]pyridine (500 mg, 1.74 mmol) following a similar method to that described in Preparation 110. MS: [M+H]$^+$=389.

Preparation 183: 6-Benzyl-3-benzyloxymethyl-3-methyl-2,3-dihydro-pyrrolo[3,2-c]pyridine-1-carboxylic acid tert-butyl ester The title compound was prepared from 3-benzyloxymethyl-6-chloro-3-methyl-2,3-dihydro-pyrrolo[3,2-c]pyridine-1-carboxylic acid tert-butyl ester (520 mg) following a similar method to that described for Preparation 117. [M+H]$^+$=445.

Preparation 184: 6-Benzyl-3-benzyloxymethyl-3-methyl-2,3-dihydro-1H-pyrrolo[3,2-c]pyridine hydrochloride salt The title compound was prepared from 6-benzyl-3-benzyloxymethyl-3-methyl-2,3-dihydro-pyrrolo[3,2-c]pyridine-1-carboxylic acid tert-butyl ester (82 mg) following a similar method to that described in Preparation 116. MS: [M+H]$^+$=345.

Preparation 185: 6-Chloro-3-methyl-1,3-dihydro-indol-2-one

To a cooled (−78° C.) solution of 6-chloro-1,3-dihydro-indol-2-one (4.0 g, 24 mmol) and TMEDA (11.2 mL, 79 mmol) in THF (100 mL) was slowly added BuLi (2.2 M solution in cyclohexane, 22 mL, 48 mmol). The solution was stirred for 30 minutes at the same temperature and then iodomethane (2.2 mL, 36 mmol) was slowly added. The reaction was stirred at −20° C. for 1.5 h. The reaction was quenched with saturated aqueous NH$_4$Cl and extracted with EtOAc. The organic phase was dried (MgSO$_4$), filtered and concentrated in vacuo. Chromatography (SiO$_2$, EtOAc/Petrol 2:8) gave the title compound (2.7 g) as a pale pink solid. MS: [M+H]$^+$=182.

Preparation 186: 3-Benzyl-6-chloro-3-methyl-1,3-dihydro-indol-2-one

The title compound was prepared from 6-chloro-3-methyl-1,3-dihydro-indol-2-one (700 mg) following similar methods to those described in Preparation 185 using benzyl bromide instead of iodomethane to give the title compound (641 mg) as a white solid. MS: [M+H]$^+$=272.

Preparation 187: 3-Benzyl-6-chloro-3-methyl-2,3-dihydro-1H-indole

3-Benzyl-6-chloro-3-methyl-1,3-dihydro-indol-2-one (641 mg) was reduced with BH$_3$.Me$_2$S following a similar method to that described in Preparation 54 to give title compound (410 mg) as a colourless gum. MS: [M+H]$^+$=258.

Preparation 188: 3,3-Dimethyl-6-(2-oxo-pyrrolidin-1-yl)-2,3-dihydro-pyrrolo[3,2-c]pyridine-1-carboxylic acid tert-butyl ester A vessel containing a solution of 6-chloro-3,3-dimethyl-2,3-dihydro-pyrrolo[3,2-c]pyridine-1-carboxylic acid tert-butyl ester (150 mg, 0.53 mmol), 2-pyrrolidinone (68 mg, 0.80 mmol), 9,9-dimethyl-4,5-bis(diphenylphosphino)xanthene (Xantphos) (46 mg, 0.079 mmol), Pd$_2$(dba)$_3$ (50 mg, 0.052 mmol) and cesium carbonate (260 mg, 0.79 mmol) in 1,4-dioxane (3 mL) was evacuated and flushed with nitrogen. The mixture was stirred at 110° C. overnight. The mixture was allowed to cool and then partitioned between EtOAc and water. The organic extract was washed with brine, dried (MgSO$_4$) and evaporated in vacuo. Chromatography (SiO$_2$; gradient elution with 50-100% EtOAc in petrol) gave the title compound (102 mg). MS: [M+H]$^+$=332.

Preparation 189: 1-(3,3-Dimethyl-2,3-dihydro-1H-pyrrolo[3,2-c]pyridin-6-yl)-pyrrolidin-2-one hydrochloride salt 3,3-Dimethyl-6-(2-oxo-pyrrolidin-1-yl)-2,3-dihydro-pyrrolo[3,2-c]pyridine-1-carboxylic acid tert-butyl ester (100 mg) was treated with HCl (saturated solution in EtOAc) and stirred for 4 h. The mixture was then evaporated to dryness in vacuo to give the title compound as a pale yellow solid. MS: [M+H]$^+$=232.

Preparation 190: 6-Bromo-3,3-dimethyl-2,3-dihydro-pyrrolo[3,2-c]pyridine-1-carboxylic acid tert-butyl ester

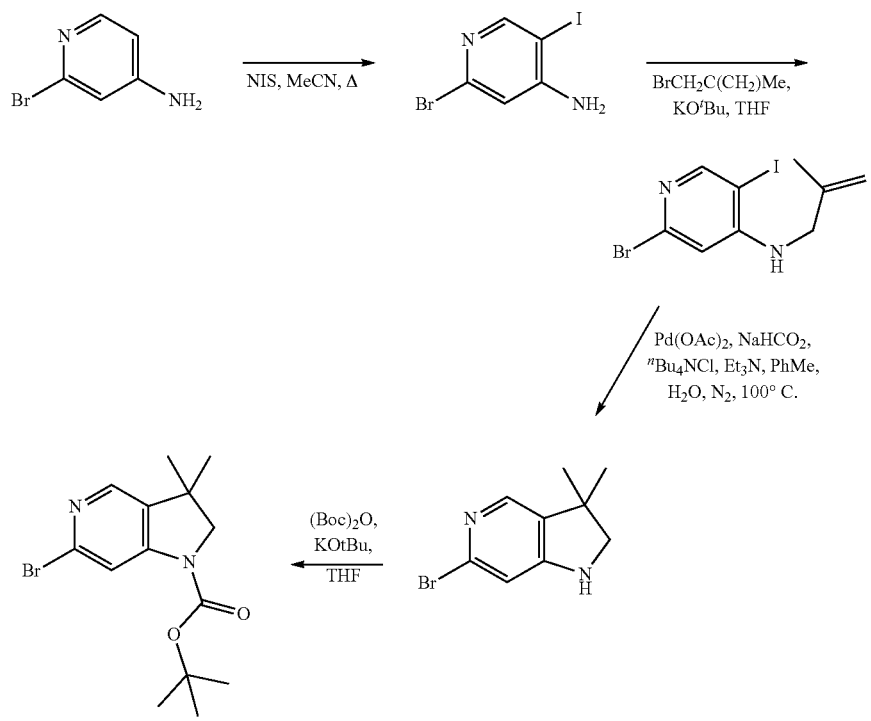

The title compound was prepared from 2-bromo-pyridin-4-ylamine using analogous methods to those outlined above for 6-chloro-3,3-dimethyl-2,3-dihydro-pyrrolo[3,2-c]pyridine-1-carboxylic acid tert-butyl ester (Preparations 107-110). Colourless solid. $^1$H NMR (CDCl$_3$) 8.00 (1H, s), 7.87 (1H, br s), 3.75 (2H, s), 1.59 (9H, br s), 1.39 (6H, s). MS: [M+H-$^t$Bu]$^+$ 271, 273. Synthetic intermediates isolated in this process were as follows: 2-Bromo-5-iodo-pyridin-4-ylamine (pale orange solid, $^1$H NMR (DMSO-d$_6$) 8.18 (1H, s), 6.78 (1H, s), 6.48 (2H, br s); MS: [M+H]$^+$ 299, 301); (2-Bromo-5-iodo-pyridin-4-yl)-(2-methyl-allyl)-amine (pale orange oil, $^1$H NMR (DMSO-d$_6$) 8.20 (1H, s), 6.52 (1H, s), 6.47 (1H, br t), 4.85 (1H, d), 4.74 (1H, d), 3.82 (2H, d), 1.68 (3H, s); MS: [M+H]$^+$ 353, 355); 6-Bromo-3,3-dimethyl-2,3-dihydro-1H-pyrrolo[3,2-c]pyridine (colourless solid, $^1$H NMR (DMSO-d$_6$) 7.70 (1H, s), 6.73 (1H, br s), 6.47 (1H, s), 3.30 (2H, d), 1.26 (6H, s); MS: [M+H]$^+$ 227, 229).

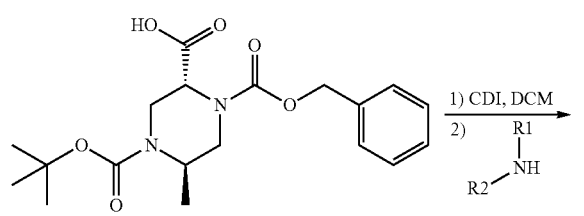

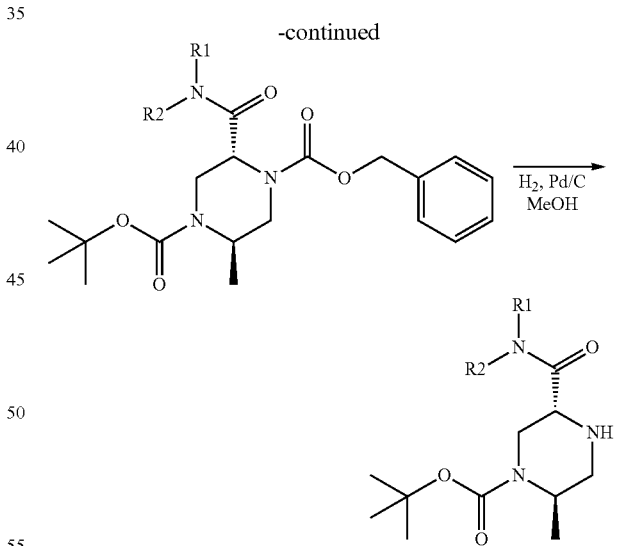

General Method for Synthesis of Protected Amido-Substituted Piperazines

Step 1: 1,1'-Carbonyldiimidazole (490 mg, 3.0 mmol) was added to a stirred solution of (2R,5R)-5-methyl-piperazine-1,2,4-tricarboxylic acid 1-benzyl ester 4-tert-butyl ester (950 mg, 2.5 mmol) in dichloromethane (20 mL) and the mixture was stirred at room temperature for 3 hours whereupon the secondary amine (3.75 mmol) was added and the mixture stirred at room temperature for 16-48 hours. Hydrochloric acid (2 M, 20 mL) was added and the mixture stirred at room temperature for 30 minutes. The organic layer was separated and evaporated to dryness in vacuo to afford the crude product which was used without further purification. The compounds of Preparations 191-196 were prepared by such means with the appropriate secondary amine reagent indicated:

Preparation 191: (2R,5R)-2-Dimethylcarbamoyl-5-methyl-piperazine-1,4-dicarboxylic acid 1-benzyl ester 4-tert-butyl ester Using dimethylamine (40 wt % in water; 2 mL). MS: [M+H-$^t$Bu]$^+$ 350.

Preparation 192: (2R,5R)-2-(Azetidine-1-carbonyl)-5-methyl-piperazine-1,4-dicarboxylic acid 1-benzyl ester 4-tert-butyl ester Using azetidine. MS: [M+H-$^t$Bu]$^+$ 362.

Preparation 193: (2R,5R)-2-Methyl-5-(morpholine-4-carbonyl)-piperazine-1,4-dicarboxylic acid 4-benzyl ester 1-tert-butyl ester Using morpholine. MS: [M+H-$^t$Bu]$^+$ 392.

Preparation 194: (2R,5R)-2-Diethylcarbamoyl-5-methyl-piperazine-1,4-dicarboxylic acid 1-benzyl ester 4-tert-butyl ester Using diethylamine. MS: [M+H]$^+$ 434.

Preparation 195: (2R,5R)-2-Methyl-5-(pyrrolidine-1-carbonyl)-piperazine-1,4-dicarboxylic acid 4-benzyl ester 1-tert-butyl ester Using pyrrolidine. MS: [M+H]$^+$ 432.

Preparation 196: (2R,5R)-2-Methyl-5-(piperidine-1-carbonyl)-piperazine-1,4-dicarboxylic acid 4-benzyl ester 1-tert-butyl ester Using piperidine. MS: [M+H]$^+$ 446.

Step 2: 10% Palladium on carbon (200 mg) was added to a solution of the benzyloxycarbonyl protected piperazine derivative (2.5 mmol) in methanol (40 mL) and the mixture was stirred at ambient temperature under an atmosphere of hydrogen for 16-48 hours. The solids were removed by filtration under gravity and rinsed with methanol (10 mL). The combined filtrates were evaporated to dryness in vacuo to afford the crude product which was used without further purification. The compounds of Preparations 197-202 were prepared by such means, with appropriate precursor indicated:

Preparation 197: (2R,5R)-5-Dimethylcarbamoyl-2-methyl-piperazine-1-carboxylic acid tert-butyl ester From (2R,5R)-2-dimethylcarbamoyl-5-methyl-piperazine-1,4-dicarboxylic acid 1-benzyl ester 4-tert-butyl ester. MS: [M+H]$^+$ 272

Preparation 198: (2R,5R)-5-(Azetidine-1-carbonyl)-2-methyl-piperazine-1-carboxylic acid tert-butyl ester From (2R,5R)-2-(azetidine-1-carbonyl)-5-methyl-piperazine-1,4-dicarboxylic acid 1-benzyl ester 4-tert-butyl ester. MS: [M+H]$^+$ 284

Preparation 199: (2R,5R)-2-Methyl-5-(morpholine-4-carbonyl)-piperazine-1-carboxylic acid tert-butyl ester From (2R,5R)-2-methyl-5-(morpholine-4-carbonyl)-piperazine-1,4-dicarboxylic acid 4-benzyl ester 1-tert-butyl ester. MS: [M+H]$^+$ 314

Preparation 200: (2R,5R)-5-Diethylcarbamoyl-2-methyl-piperazine-1-carboxylic acid tert-butyl ester From (2R,5R)-2-diethylcarbamoyl-5-methyl-piperazine-1,4-dicarboxylic acid 1-benzyl ester 4-tert-butyl ester. MS: [M+H]$^+$ 300.

Preparation 201: (2R,5R)-2-Methyl-5-(pyrrolidine-1-carbonyl)-piperazine-1-carboxylic acid tert-butyl ester From (2R,5R)-2-methyl-5-(pyrrolidine-1-carbonyl)-piperazine-1,4-dicarboxylic acid 4-benzyl ester 1-tert-butyl ester. MS: [M+H]$^+$ 298

Preparation 202: (2R,5R)-2-Methyl-5-(piperidine-1-carbonyl)-piperazine-1-carboxylic acid tert-butyl ester From (2R,5R)-2-methyl-5-(piperidine-1-carbonyl)-piperazine-1,4-dicarboxylic acid 4-benzyl ester 1-tert-butyl ester. MS: [M+H]$^+$ 312.

General Method for the Synthesis of Protected Coupled Products

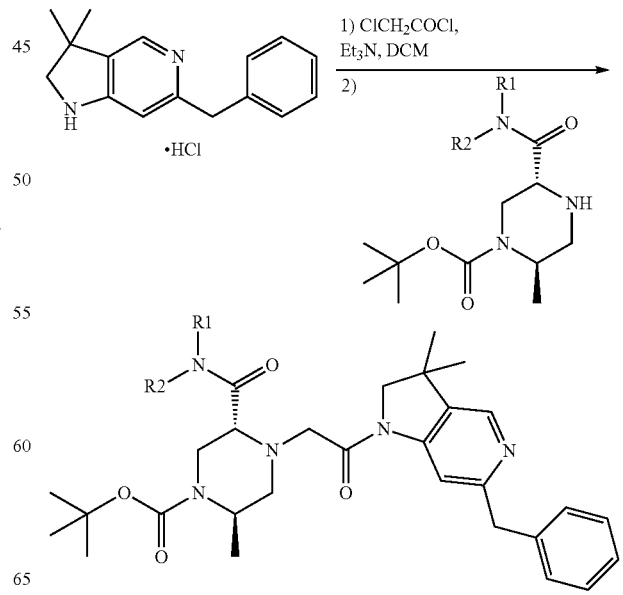

Triethylamine (0.230 mL, 1.65 mmol) was added to a stirred solution of 6-benzyl-3,3-dimethyl-2,3-dihydro-1H-pyrrolo[3,2-c]pyridine hydrochloride (137 mg, 0.5 mmol) in anhydrous DCM (2.5 mL) and the mixture was stirred at room temperature for 10 minutes. Chloroacetyl chloride (0.044 mL, 0.55 mmol) was added and the mixture was stirred at room temperature for 3 hours The substituted piperazine derivative (0.6 mmol) was added and the mixture was stirred at room temperature overnight. The mixture was partitioned between DCM (20 mL) and water (20 mL), the organic layer was separated and the solvent removed in vacuo. Chromatography ($SiO_2$, 20-100% EtOAc in petrol afforded the product as a colourless solid. The compounds of Preparations 203-205 were prepared by such means, with the appropriate substituted piperazine indicated:

Preparation 203: (2R,5R)-4-[2-(6-Benzyl-3,3-dimethyl-2,3-dihydro-pyrrolo[3,2-c]pyridin-1-yl)-2-oxo-ethyl]-5-dimethylcarbamoyl-2-methyl-piperazine-1-carboxylic acid tert-butyl ester From (2R,5R)-5-dimethylcarbamoyl-2-methyl-piperazine-1-carboxylic acid tert-butyl ester. MS: $[M+H]^+$ 550.

Preparation 204: (2R,5R)-5-(Azetidine-1-carbonyl)-4-[2-(6-benzyl-3,3-dimethyl-2,3-dihydro-pyrrolo[3,2-c]pyridin-1-yl)-2-oxo-ethyl]-2-methyl-piperazine-1-carboxylic acid tert-butyl ester From (2R,5R)-5-(azetidine-1-carbonyl)-2-methyl-piperazine-1-carboxylic acid tert-butyl ester. MS: $[M+H]^+$ 562.

Preparation 205: (2R,5R)-4-[2-(6-Benzyl-3,3-dimethyl-2,3-dihydro-pyrrolo[3,2-c]pyridin-1-yl)-2-oxo-ethyl]-2-methyl-5-(morpholine-4-carbonyl)-piperazine-1-carboxylic acid tert-butyl ester From (2R,5R)-2-methyl-5-(morpholine-4-carbonyl)-piperazine-1-carboxylic acid tert-butyl ester. MS: $[M+H]^+$ 592.

Preparation 206: (2R,5R)-4-[2-(6-Benzyl-3-benzyloxymethyl-3-methyl-2,3-dihydro-pyrrolo[3,2-c]pyridin-1-yl)-2-oxo-ethyl]-5-dimethylcarbamoyl-2-methyl-piperazine-1-carboxylic acid tert-butyl ester The title compound (40 mg) was prepared from 6-benzyl-3-benzyloxymethyl-3-methyl-2,3-dihydro-1H-pyrrolo[3,2-c]pyridine hydrochloride salt (60 mg, 0.15 mmol), chloroacetyl chloride (18 µL, 0.22 mmol), TEA (75 µL, 0.54 mmol) and (2R,5R)-5-dimethylcarbamoyl-2-methyl-1-piperazine-1-carboxylic acid tert-butyl ester (59 mg, 0.22 mmol) prepared following a similar method to that described in Preparation 203. MS: $[M+H]^+$=656.

Preparation 207:
(1,4-Dibenzyl-piperazin-2-yl)-methanol

To a stirred solution of lithium aluminium hydride in THF (1 M, 49.6 mL, 49.6 mmol) at −5° C. under nitrogen was added, dropwise over 0.5 h, a solution of (1,4-dibenzyl-piperazin-2-yl)-carboxylic acid, ethyl ester (8.4 g, 24.8 mmol) in THF (30 mL), internal temperature kept <5° C. Resulting mixture was stirred at 0° C. for 1 h then at 20° C. for 18 h, then was quenched by addition of a mixture of water (4 mL) and THF (100 mL) with external cooling in an ice-methanol bath. The resulting suspension was treated with saturated aqueous potassium sodium tartrate (~50 mL) and mixture was allowed to stir at 0° C. for 1 h. The supernatant liquid was decanted and evaporated in vacuo. The resulting oil was dissolved in dichloromethane and the solution dried ($Na_2SO_4$) and evaporated in vacuo to give the title compound (8.04 g) as an oil. MS: $[M+H]^+$=297.

Preparation 208:
1,4-Dibenzyl-2-fluoromethyl-piperazine

To a stirred solution of diethylaminosulfur trifluoride (0.89 g, 5.53 mmol) in DCM (4 mL) at −78° C. under nitrogen was added a solution of (1,4-dibenzyl-piperazin-2-yl)-methanol (1.364 g, 4.61 mmol) in DCM (6 mL), dropwise over 0.2 h (internal temperature <−65° C.). Resulting solution was stirred at −78° C. for 1 h then warmed slowly to 20° C. and stirred thus for 16 h. The mixture was cooled in an ice-methanol bath then ice was added with stirring. The mixture was poured into saturated aqueous $NaHCO_3$ (100 mL) and extracted with DCM (3×30 mL). The combined organic extracts were dried ($Na_2SO_4$) and evaporated in vacuo to give an oil. Chromatography ($SiO_2$; gradient elution with 0-25% diethyl ether in 40-60 petroleum ether) gave the title compound (0.471 g) as an oil. $^1$H NMR ($CDCl_3$): 7.38-7.23 (10H, m), 4.93-4.64 (1H, m), 4.55 (1H, ddd), 4.03 (1H, d), 3.52 (3H, d), 2.91 (1H, d), 2.84-2.64 (2H, m), 2.56 (1H, s), 2.48-2.21 (3H, m).

Preparation 209: 2-Fluoromethyl-piperazine, diacetate salt

A mixture of 1,4-dibenzyl-2-fluoromethyl-piperazine (0.47 g, 1.6 mmol), ethanol (20 mL), acetic acid (0.4 mL) and 10% palladium on carbon (0.2 g) was hydrogenated at 20° C. and 4 bar for 72 h. Solids were removed by filtration and the filtrate evaporated in vacuo to give a colourless solid. Trituration (twice) with ether gave the title compound (0.332 g) as a colourless solid. $^1$H NMR (DMSO-d6): 7.38-5.74 (4H, m), 4.40-4.27 (1H, m), 4.27-4.14 (1H, m), 2.94-2.69 (4H, m), 2.69-2.58 (1H, m), 2.58-2.52 (1H, m), 2.32 (1H, dd), 1.87 (6H, s).

Preparation 210: (2R,5R)-4-[2-(6-Chloro-3,3-dimethyl-2,3-dihydro-indol-1-yl)-2-oxo-ethyl]-2-methyl-5-(morpholine-4-carbonyl)-piperazine-1-carboxylic acid tert-butyl ester Prepared from 6-chloro-3,3-dimethyl-2,3-dihydro-1H-indole and (2R,5R)-2-methyl-5-(morpholine-4-carbonyl)-piperazine-1-carboxylic acid tert-butyl ester using an analogous procedure to that of Preparation 203. MS: $[M+H]^+$=535.

Preparation 211: (1'-tert-Butyloxycarbonyl-6'-chloro)-1,1',2',3-tetrahydrospiro[indene-2,3'-indole]

To 6-chloro-2-oxo-2,3-dihydro-indole-1-carboxylic acid tert-butyl ester (2.5 g, 9.36 mmol) and $K_2CO_3$ (2.85 g, 20.6 mmol) in DMF (25 mL) was added o-xylylene dibromide (5.98 g, 22.7 mmol) at ambient temperature. The reaction was stirred at ambient temperature for 18 h. Water (150 mL) was added and the reaction extracted with DCM (3×). The organic layers were combined and washed with brine, dried with sodium sulfate, and the solvent removed in vacuo. The crude product was purified by column chromatography on silica gel (gradient elution, 0-100%, EtOAc/petrol) a second column, (gradient elution, 0-100%, DCM/petrol), to give the title compound (541 mg, 30%) as a colourless solid. MS: [M+H]=314 (M-tBu).

Preparation 212: (6'-Chloro)-1,1',2',3-tetrahydrospiro[indene-2,3'-indole]

(1'-tert-Butyloxycarbonyl-6'-chloro)-1,1',2',3-tetrahydrospiro[indene-2,3'-indole](0.541 g, 1.5 mmol) was dissolved in 50% TFA in DCM (7.3 mL) at ambient temperature and the reaction was stirred at 1 h for ambient temperature. Solvent was removed in vacuo and residue was dissolved in toluene and evaporated. Chromatography on silica gel (gradient elution, 0-50%, EtOAc/petrol) gave a colourless solid. MS: [M+H]=270. A solution of this material (0.226 g, 0.84 mmol) in 2.0M BH$_3$.SMe$_2$ in THF (4.2 mL) was heated to 75° C. for 3 h then cooled to ambient temperature. MeOH (4 mL) was added and the reaction heated to reflux for 1 h then was concentrated in vacuo. Chromatography on silica gel (gradient elution, 0-50%, EtOAc/petrol), gave the title compound (0.17 g, 80%) as a colourless solid. MS: [M+H]=256.

Preparation 213: 1,1',2',3-Tetrahydrospiro[indene-2,3'-indole]-6'-carbonitrile (6'-Chloro)-1,1',2',3-tetrahydrospiro[indene-2,3'-indole (348 mg, 1.92 mmol), Zn(CN)$_2$ (0.257 mg, 2.19 mmol), Pd$_2$(dba)$_3$ (35 mg, 0.15 mmol), Sphos (0126 mg, 0.31 mmol) were combined and dissolved in NMP (9.6 mL). The suspension was degassed (N$_2$) for 5 min. The reaction was heated under microwave irradiation for 2 h at 180° C. then cooled to ambient temperature. Additional reagents were added: Zn(CN)$_2$ (0.257 mg, 2.19 mmol), Pd$_2$(dba)$_3$ (35 mg, 0.15 mmol), Sphos (126 mg, 0.31 mmol) and, reaction heated to 185° C. for 1 h. The reaction was diluted with water and extracted with diethyl ether/petrol (1:1) (3×). The combined organic extracts were washed with water and brine, dried over sodium sulfate and concentrated in vacuo. Chromatography on silica gel (gradient elution, 0-100%, EtOAc/petrol), to give the title compound (0.06 g, 18%) as pale yellow solid. MS: [M+H]=247.

Preparation 214: 1'-{2-[(2R,5R)-4-(tert-Butyloxycarbonyl)-5-methyl-2-[(morpholin-4-yl)carbonyl]piperazin-1-yl]acetyl}-1,1',2',3-tetrahydrospiro[indene-2,3'-indole]-6'-carbonitrile The title compound was prepared following similar methods to those described in Preparation 203: reaction mixture was heated to 50° C. for 2 h. MS: [M+H]=600.

Preparation 215: 6-(2-Chloro-phenoxy)-3,3-dimethyl-2,3-dihydro-pyrrolo[3,2-c]pyridine-1-carboxylic acid tert-butyl ester A solution of 6-bromo-3,3-dimethyl-2,3-dihydro-pyrrolo[3,2-c]pyridine-1-carboxylic acid tert-butyl ester (150 mg, 0.46 mmol), 2-chlorophenol (0.071 mL, 0.69 mmol), CuI (17 mg, 0.046 mmol), picolinic acid (23 mg, 0.092 mmol) and potassium phosphate (195 mg, 0.92 mmol) in DMSO (1 mL) was stirred at 85° C. overnight. The mixture was allowed to cool and then partitioned between EtOAc and water. The organic extract was washed with brine, dried (MgSO$_4$) and evaporated in vacuo. Chromatography (SiO$_2$; gradient elution with 2-10% ethyl acetate in petrol) gave the title compound (143 mg). MS: [M+H]$^+$=375.

Preparation 216: 6-(2-Chloro-phenoxy)-3,3-dimethyl-2,3-dihydro-1H-pyrrolo[3,2-c]pyridine hydrochloride 6-(2-Chloro-phenoxy)-3,3-dimethyl-2,3-dihydro-pyrrolo[3,2-c]pyridine-1-carboxylic acid tert-butyl ester (143 mg) was treated with HCl (saturated solution in ethyl acetate) and stirred for 4 hours.

The mixture was then evaporated to dryness in vacuo to give a colourless solid used directly in the next step without further purification. MS: [M+H]$^+$=275.

Preparation 217: (2R,5R)-4-Benzyl-5-hydroxymethyl-2-methyl-piperazine-1-carboxylic acid tert-butyl ester

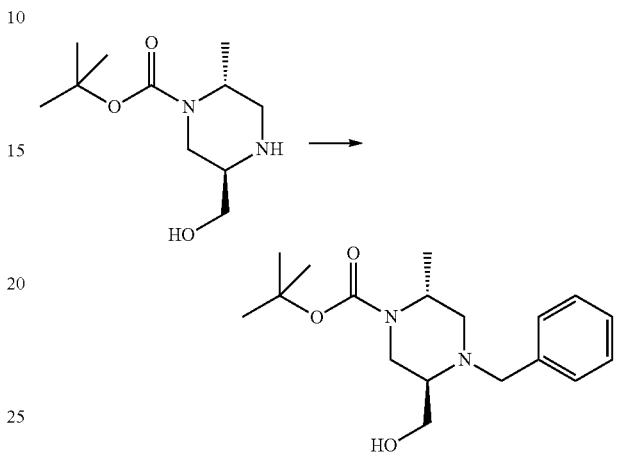

A mixture of (2R,5R)-2-hydroxymethyl-5-methyl-piperazine-1,4-dicarboxylic acid 1-benzyl ester 4-tert-butyl ester (3.48 g, 15.1 mmol), benzaldehyde (1.76 g, 16.6 mmol), sodium triacetoxyborohydride (3.84 g, 18.1 mmol) and 1,2-dichloroethane (30 mL) was stirred at 20° C. for 18 h, then partitioned between saturated aqueous NaHCO$_3$ (150 mL) and DCM (3×50 mL). Combined organic extracts were dried (Na$_2$SO$_4$) then evaporated in vacuo to give an oil. Chromatography (SiO$_2$, 0-30% EtOAc in petrol) gave the title compound (4.588 g, 74%) as a colourless solid. MS: [M+H]$^+$=321.

Preparation 218: (2R,5R)-4-Benzyl-2-methyl-5-pyrazol-1-ylmethyl-piperazine-1-carboxylic acid tert-butyl ester To a stirred solution of (2R,5R)-4-benzyl-5-hydroxymethyl-2-methyl-piperazine-1-carboxylic acid tert-butyl ester (0.96 g, 3 mmol) in DCM (10 mL) externally cooled in an ice-methanol bath was added triethylamine (0.91 g, 1.25 mL, 9 mmol) followed, dropwise over 0.05 h, methylsulfonyl chloride (0.38 g, 0.26 mL, 3.3 mmol). The mixture was stirred at 0-20° C. for 2 h, then pyrazole (0.27 g, 4 mmol) was added in one portion and stirring continued at 20° C. for 7 days. Mixture was poured into saturated aqueous NaHCO$_3$ and extracted with DCM (3×20 mL). Combined organic extracts were dried (Na$_2$SO$_4$) then evaporated in vacuo to give an oil. Chromatography (SiO$_2$, 0-100% Et$_2$O in petrol) gave the title compound (0.24 g). MS: [M+H]$^+$=371.

Preparation 219: (2R,5R)-2-Methyl-5-pyrazol-1-ylmethyl-piperazine-1-carboxylic acid tert-butyl ester (2R,5R)-4-Benzyl-2-methyl-5-pyrazol-1-ylmethyl-piperazine-1-carboxylic acid tert-butyl ester (0.24 g, 0.65 mmol) was hydrogenated over 10% palladium on carbon at 4 bar using a similar procedure to that described in Preparation 209. The crude product was dissolved in methanol and

Preparation 220: (2R,5R)-4-[2-(6-Benzyl-3,3-dimethyl-2,3-dihydro-pyrrolo[3,2-c]pyridin-1-yl)-2-oxo-ethyl]-2-methyl-5-pyrazol-1-ylmethyl-piperazine-1-carboxylic acid tert-butyl ester Prepared from (2R,5R)-2-methyl-5-pyrazol-1-ylmethyl-piperazine-1-carboxylic acid tert-butyl ester (0.103 g, 0.37 mmol) and 6-benzyl-3,3-dimethyl-2,3-dihydro-pyrrolo[3,2-c]pyridine, hydrochloride salt (0.101 g, 0.37 mmol) using an analogous procedure to that of Preparation 203, except that chloroform (10 mL) was added to the reaction mixture following reagent addition and mixture was heated at reflux for 7 days. The title compound (0.019 g) was obtained as an oil. MS: [M+H]$^+$=559.

Preparation 221: 3,3-Dimethyl-2,3-dihydro-1H-indole-6-carbonitrile

6-Chloro-3,3-dimethyl-2,3-dihydro-1H-indole (1 g, 5.5 mmol), zinc cyanide (0.74 g, 6.3 mmol), tris(dibenzylideneacetone)dipalladium (0) (0.2 g, 0.9 mmol) and 2-dicyclohexylphosphino-2',6'-dimethoxybiphenyl (0.4 g, 1.1 mmol) were combined and dissolved in N-methyl-pyrrolidinone (27.6 mL). The suspension was degassed with nitrogen for 5 minutes. The reaction was heated under microwave irradiation for 2 h at 185° C. then cooled to room temperature and the reaction was diluted with water and extracted with diethyl ether/petrol (1:1) (3×). The combined organic extracts were washed with water and brine, dried over sodium sulfate and concentrated in vacuo. Chromatography (silica gel, gradient elution, 0-100%, EtOAc in petrol 40-60) gave the title compound (0.14 g, 15%) as pale yellow solid. MS: [M+H]$^+$=173.

Preparation 222: 1-(2-Chloro-acetyl)-3,3-dimethyl-2,3-dihydro-1H-indole-6-carbonitrile To a solution of 3,3-dimethylindoline-6-carbonitrile (0.35 g, 2.0 mmol) and triethylamine (0.56 mL, 4.0 mmol) in DCM (10 mL) at 0° C. was added chloroacetyl chloride (0.16 mL, 2.0 mmol) dropwise. The reaction was warmed to room temperature and stirred overnight. The reaction mixture was then diluted with water. The organic phase was then separated, dried over magnesium sulfate and concentrated to give the title compound (0.39 g). $^1$H NMR (CDCl$_3$): 8.47 (s, 1H), 7.40 (d, 1H), 7.24 (d, 1H), 4.14 (s, 2H), 3.94 (s, 2H), 1.42 (s, 6H).

Preparation 223: (R)-4-[2-(6-Cyano-3,3-dimethyl-2,3-dihydro-indol-1-yl)-2-oxo-ethyl]-2-methyl-piperazine-1-carboxylic acid tert-butyl ester To a solution of 1-(2-chloroacetyl)-3,3-dimethylindoline-6-carbonitrile (0.10 g, 0.40 mmol) and (R)-tert-butyl 2-methylpiperazine-1-carboxylate (0.088 g, 0.41 mmol) in acetonitrile (1.5 mL) was added triethylamine (0.083 mL, 0.6 mmol). The reaction mixture was heated at 50° C. for 3 h. The reaction mixture was then cooled and concentrated. The reaction was repeated on a 0.6 mmol scale and the combined crude material was purified by flash column chromatography, eluting with 20% EtOAc in heptane, to give the title compound (0.29 g) [M+H]$^+$=413.

Preparation 224: (R)-4-[(S)-2-(6-Cyano-3,3-dimethyl-2,3-dihydro-indol-1-yl)-1-methyl-2-oxo-ethyl]-2-methyl-piperazine-1-carboxylic acid tert-butyl ester To a stirred solution of 2-chloro-1-propionic acid (0.11 mL, 1.16 mmol) in DCM (20 mL) was added O-benzotriazole-N,N,N',N'-tetramethyl-uronium-hexafluoro-phosphate (0.55 g, 1.45 mmol). The mixture was stirred for 30 minutes then triethylamine (0.48 mL, 3.44 mmol), 3,3-dimethyl-2,3-dihydro-1H-indole-6-carbonitrile (0.2 g, 1.16 mmol) and a drop of DMF was added and the resulting mixture was stirred overnight. The reaction mixture was then diluted with DCM and washed with water. The organic phases were separated, dried with Na$_2$SO$_4$ and concentrated. The crude product was washed with diethyl ether and the filtrate was concentrated and purified by flash column chromatography eluting with 10% EtOAc in heptane to give (R)-1-(2-chloropropanoyl)-3,3-dimethylindoline-6-carbonitrile (0.133 g) [M+H]$^+$=263. A solution of this material, (R)-2-methyl-piperazine-1-carboxylic acid tert-butyl ester (0.13 g, 0.51 mmol) and potassium carbonate (0.10 g, 0.51 mmol) in acetonitrile (2.5 mL) was heated at 60° C. for 48 h. The reaction mixture was then diluted with EtOAc and washed with water. The organic phase was separated, dried with Na$_2$SO$_4$ and concentrated. The residue was purified by flash column chromatography eluting with 15% EtOAc in heptane to give the title compound (33.5 mg), [M+H]$^+$=427.

Preparation 225: 3,3,6-Trimethyl-2,3-dihydro-indole-1-carboxylic acid tert-butyl ester The title compound was prepared from 6-chloro-3,3-dimethyl-2,3-dihydro-indole-1-carboxylic acid tert-butyl ester and methylzinc chloride following similar methods to those described in Preparation 117, MS: [M+H]$^+$=206 (−tBu).

Preparation 226: 5-Bromo-6-bromomethyl-3,3-dimethyl-2,3-dihydro-indole-1-carboxylic acid tert-butyl ester To 3,3,6-trimethyl-2,3-dihydro-indole-1-carboxylic acid tert-butyl ester (1.25 g, 1 mmol) in carbon tetrachloride (58.2 mL) was added dibenzoyl peroxide (0.02 g, 0.1 mmol), 2,2'-azobis(2-methylpropionitrile) (17 mg, 0.10 mmol) and N-bromosuccinimide (0.93 g, 5.2 mmol) at room temperature. The reaction was stirred for 1 h at reflux. The reaction was cooled to room temperature, filtered and concentrated. Chromatography (silica gel, gradient elution, 0-20%, EtOAc in petrol 40-60), gave the title compound, $^1$H NMR (CDCl$_3$): 7.83 (1H, s), 7.22 (1H, s), 3.71 (2H, s), 2.38 (2H, s), 1.58 (9H, s), 1.38-1.28 (6H, m).

Preparation 227: 5-Bromo-3,3-dimethyl-6-(2-oxo-pyrrolidin-1-ylmethyl)-2,3-dihydro-indole-1-carboxylic acid tert-butyl ester To 2-pyrrolidinone (0.8 g, 9.4 mmol) in THF (15.6 mL) was added potassium tert-butoxide (1.05 g, 9.4 mmol) and the mixture was stirred for 30 minutes at room temperature. 5-Bromo-6-bromomethyl-3,3-dimethyl-2,3-dihydro-indole-1-carboxylic acid tert-butyl ester was added in one portion and the reaction stirred for 2 h at room temperature. Saturated aqueous ammonium chloride (15 mL) was added and the mixture extracted with EtOAc. The organic layer was washed with brine, dried with sodium sulfate, filtered and concentrated. Chromatography (silica gel, gradient elution, 0-100%, EtOAc in petrol 40-60) gave the title compound (0.17 g) MS: [M+H]$^+$=424.

Preparation 228: 1-(5-Bromo-3,3-dimethyl-2,3-di-hydro-1H-indol-6-ylmethyl)-pyrrolidin-2-one The title compound was prepared following similar methods to those described in Preparation 116. The crude product was applied to an SCX column, amine released with 2M ammonia in methanol, MS: [M+H]$^+$=324.

Preparation 229: 3,3,5-Trimethyl-2,3-dihydro-1H-indole

The title compound was prepared following similar methods to those described in Preparation 25, MS: [M+H]$^+$=162

Preparation 230: 6-Bromo-3,3,5-trimethyl-2,3-dihydro-1H-indole 3,3,5-Trimethyl-2,3-dihydro-1H-indole (1.84 g, 11.43 mmol) was dissolved in concentrated sulfuric acid (25 mL) and silver sulfate (1.90 g, 6.06 mmol) added. The reaction was stirred for 1 h and bromine (0.6 mL, 11.77 mmol) was added over 5 minutes. The reaction was stirred at this temperature for 1 h and very slowly quenched by slow addition to 50% aqueous sodium hydroxide (100 mL) with ice cooling (CAUTION!). Further aqueous sodium hydroxide was added to adjust pH to basic. The resulting mixture was extracted with diethyl ether (3×) and the organic phase dried over sodium sulfate, filtered and concentrated. Chromatography (silica gel, gradient elution, 0-50%, EtOAc in petrol 40-60), to give the title compound (1.30 g), MS: [M+H]$^+$=241.

Preparation 231: 3,3,5-Trimethyl-2,3-dihydro-1H-indole-6-carbonitrile

6-Bromo-3,3,5-trimethyl-2,3-dihydro-1H-indole (1.0 g, 4.17 mmol), zinc cyanide (0.563 g, 4.79 mmol), tris(dibenzylideneacetone)dipalladium (0.094 g, 0.42 mmol), 1,1'-bisdiphenylphosphino)ferrocene (0.462 g, 0.83 mmol) and powdered zinc (0.054 g, 0.83 mmol) were combined and dissolved in dimethylacetamide (20.8 mL). The reaction was degassed under nitrogen for 5 minutes, then heated with microwave irradiation for 30 minutes at 150° C. The reaction was cooled to room temperature and water was added. The mixture was extracted with diethyl ether (3×). The combined organic extracts were dried over sodium sulfate, filtered and concentrated. Chromatography (silica gel, gradient elution, 0-20%, EtOAc in petrol 40-60), gave the title compound (110 mg) MS: [M+H]$^+$=185.

Preparation 232: (6-Chloro-3-iodo-pyridin-2-yl)-(2-methyl-allyl)-amine

The title compound was prepared following similar methods to those described in Preparation 108, $^1$H NMR (270 MHz, CDCl$_3$): 7.72-7.68 (1H, d), 6.36-6.33 (1H, d), 5.10 (1H, bs), 4.89-4.86 (2H, m), 4.02-4.00 (2H, m), 1.79 (3H, s).

Preparation 233: 6-Chloro-3,3-dimethyl-2,3-di-hydro-1H-pyrrolo[2,3-b]pyridine

The title compound was prepared following similar methods to those described in Preparation 109, MS: [M+H]$^+$=183.

Preparation 234: 5-Bromo-2-iodo-pyridin-3-ylamine

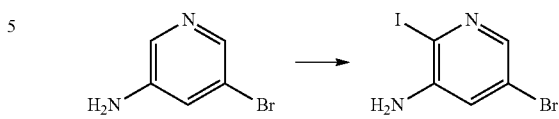

3-Amino-5-bromopyridine (13.8 g, 79.8 mmol) was dissolved in acetic acid (440 mL) and placed under a nitrogen atmosphere. N-Iodosuccinimide (16.15 g, 71.8 mmol) was charged to the reaction which was stirred at room temperature overnight. The reaction was concentrated and the residue partitioned between EtOAc (200 mL) and saturated aqueous sodium hydrogen carbonate (200 mL). The layers were separated and the organic phase was washed with saturated aqueous sodium hydrogen carbonate (200 mL). The aqueous phase was extracted with EtOAc (3×200 mL). The organic extracts were dried over magnesium sulfate, filtered and concentrated. Chromatography (silica; 1.4 Kg packed in 70% DCM:30% heptane, eluting with 70-100% DCM in heptane) gave the title compound (11.5 g). $^1$H NMR (270 MHz, CDCl$_3$): 7.83 (1H, m), 7.04 (1H, m), 4.33 (2H, br s).

Preparation 235: (5-Bromo-2-iodo-pyridin-3-yl)-(2-methyl-allyl)-amine

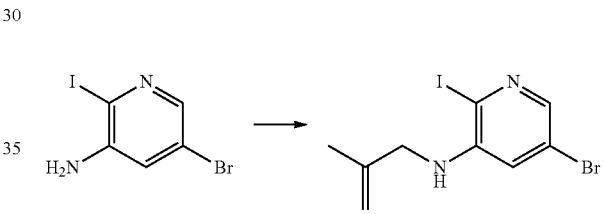

The title compound was prepared following similar methods to those described in Preparation 108, except using 5-bromo-2-iodopyridinyl-3-amine, potassium tert-butoxide (1.1 eq) and 3-bromo-2-methylpropane (1.1 eq), $^1$H NMR (270 MHz, CDCl$_3$): 7.76 (1H, d), 6.72 (1H, d), 4.92 (2H, m), 4.61 (1H, s), 3.70 (2H, d), 1.69 (3H, s).

Preparation 236: 6-Bromo-3,3-dimethyl-2,3-di-hydro-1H-pyrrolo[3,2-b]pyridine

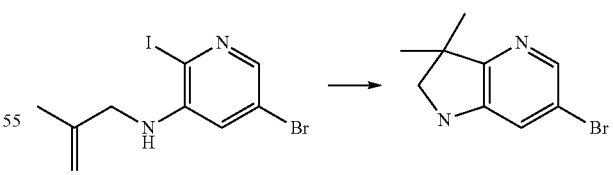

A mixture of (5-bromo-2-iodo-pyridin-3-yl)-(2-methyl-allyl)-amine (10.2 g, 28.9 mmol), tetrabutylammonium chloride (9.64 g, 34.7 mmol), sodium formate (2.36 g, 34.7 mmol), palladium acetate (0.97 g, 4.3 mmol), triethylamine (8.76 g, 86.7 mmol), water (12.1 mL) and dimethyl sulfoxide (255 mL) was stirred at 100° C. under nitrogen for 1 h. The mixture was cooled by the addition of ice (100 g) then was diluted with water (200 mL) with stirring. The mixture was partitioned between water (1 L) and a mixture of toluene (600 mL) and EtOAc (50 mL). The organic phase was washed with water (4×250 mL), dried (Na₂SO₄) and evaporated in vacuo to give a brown oil. Chromatography (SiO₂, gradient elution with 0-100% diethyl ether in 40-60 petroleum ether) gave the title compound (2.84 g) as a yellow solid. MS: [M+H]⁺=227, 229.

Preparation 237: 6-Bromo-3,3-dimethyl-2,3-dihydro-pyrrolo[3,2-b]pyridine-1-carboxylic acid tert-butyl ester

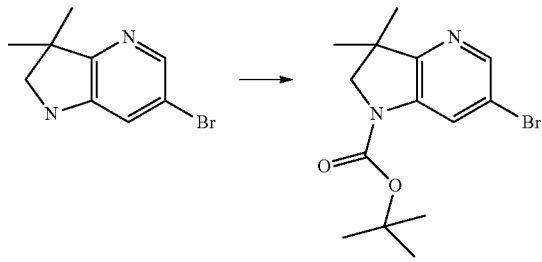 [SMILES: CC1(C)CNc2cc(Br)cnc21 ; CC(C)(C)OC(=O)N1CC(C)(C)c2ncc(Br)cc21]

6-Bromo-2,3-dihydro-3,3-dimethyl-1H-pyrrolo[2,3-b]pyridine (2.45 g, 10.8 mmol) was dissolved in THF (44 mL) and placed under a nitrogen atmosphere. Potassium tert-butoxide (1.2 g, 10.8 mmol) was added to the reaction which was stirred at room temperature for 10 minutes. Di-tert-butyldicarbonate (2.73 mL, 11.9 mmol) was charged to the reaction which was stirred for 1 h. An additional charge of di-tert-butyldicarbonate (0.25 mL, 1.0 mmol) was added to the reaction. After a further 45 minutes the reaction was concentrated. The residue was partitioned between water (50 mL) and DCM (50 mL). The layers were separated and the aqueous was extracted with DCM (2×50 mL). The organic extracts were dried over magnesium sulfate, filtered and concentrated. Chromatography (silica; 250 g packed in heptane, eluting with 5% EtOAc:heptane) gave the title compound (2.3 g), MS: [M+H]⁺=327.

Preparation 238: 6-Benzyl-3,3-dimethyl-2,3-dihydro-pyrrolo[3,2-b]pyridine-1-carboxylic acid tert-butyl ester The title compound was prepared following similar methods to those described in Preparation 117, ¹H NMR (270 MHz, CDCl₃): 8.00 (1H, s), 7.39-7.18 (6H, m), 3.91 (2H, s), 3.70 (2H, s), 1.50 (9H, s) and 1.34 (6H, s).

Preparation 239: 6-Benzyl-3,3-dimethyl-2,3-dihydro-1H-pyrrolo[3,2-b]pyridine

6-Benzyl-3,3-dimethyl-2,3-dihydro-pyrrolo[3,2-b]pyridine-1-carboxylic acid tert-butyl ester (1.66 g, 4.9 mmol) was dissolved in methanol (16 mL) and placed under a nitrogen atmosphere. 4M HCl in 1,4-dioxane (18.5 mL, 74 mmol) was added and the reaction was stirred at room temperature overnight. The reaction was concentrated in vacuo giving a sticky gum. The residue was stripped down from diethyl ether (2×30 mL) giving a sticky solid. The solid was dissolved in DCM (25 mL) and concentrated, to give the title compound (1.2 g), MS: [M+H]⁺=239.

Preparation 240: (3,6-Dichloro-pyridazin-4-yl)-(2-methyl-allyl)-amine

Potassium tert-butoxide (157.5 g) was charged portionwise to a stirred solution of 3,6-dichloro-pyridazin-4-ylamine (210 g) in THF (3.36 L). After 15 minutes, 3-bromo-2-methylpropene (141.8 mL) was added dropwise over a period of 30 minutes, maintaining the temperature <25° C. The solution was allowed to stir at room temperature for 16 h, after which time the reaction was concentrated and the residue partitioned between DCM (6 L) and water (6 L). The aqueous phase was extracted with DCM (2×5 L). The combined organic phases were washed (brine, 5 L), dried with magnesium sulfate, filtered and concentrated. Chromatography (Silica gel, eluting with 70:30 Heptane:—EtOAc) gave the title compound (211.7 g). ¹H NMR (270 MHz, CDCl₃): 6.49 (1H, s), 5.48 (1H, br s), 5.00 (1H, s), 4.91 (1H, s), 3.81 (2H, d, J=6 Hz), 1.80 (3H, s).

Preparation 241: (3,6-Dichloro-pyridazin-4-yl)-(2-methyl-allyl)-carbamic acid tert-butyl ester Di-tert-butyldicarbonate (267.5 mL) was charged to a stirred solution of (3,6-dichloro-pyridazin-4-yl)-(2-methyl-allyl)-amine (211.7 g) and 4-(dimethylamino)pyridine (23.65 g) in THF (4.54 L). After the addition, the solution was warmed to 60° C. and allowed to stir for 2 h. After this time, the solvent was removed in vacuo and the residue purified by column chromatography, eluting with 75:25 Heptane:EtOAc, to give the title compound (296.9 g). MS: [M+H]⁺=318.

Preparation 242: 3-Chloro-7,7-dimethyl-6,7-dihydro-pyrrolo[3,2-c]pyridazine-5-carboxylic acid tert-butyl ester (3,6-Dichloro-pyridazin-4-yl)-(2-methyl-allyl)-carbamic acid tert-butyl ester (239 g), Bu₄NCl (251.8 g), sodium formate (64.2 g), Et₃N (354 mL) and Pd(OAc)₂ (13 g) were dissolved in DMSO (6 L) and water (354 mL). The reaction mixture was heated to 100° C. and held at temperature for 10 minutes, after which time the reaction was complete and the mixture was allowed to cool to room temperature. The mixture was diluted with water (9 L) and extracted with EtOAc (4×3 L). The combined organic extracts were washed with brine (3 L). The emulsion was allowed to separate overnight and the interface back extracted with EtOAc (3 L). The combined organic extracts were dried with magnesium sulfate, filtered and concentrated. Chromatography on silica, eluting with a solvent gradient of 10% EtOAc in heptane to 20% EtOAc in heptane, gave the title compound (118 g) [M+H]⁺=284.

Preparation 243: 3-Chloro-7,7-dimethyl-6,7-dihydro-5H-pyrrolo[3,2-c]pyridazine

3-Chloro-7,7-dimethyl-6,7-dihydro-pyrrolo[3,2-c]pyridazine-5-carboxylic acid tert-butyl ester (75 mg) suspended in EtOAc (0.5 mL) was stirred under a N₂ atmosphere. 4M HCl/EtOAc (5 mL) was added slowly and after complete addition the mixture was stirred for 8 h. LC analysis indicated 10% starting material remaining. The reaction mixture was concentrated in vacuo and the following morning taken up in 4M HCl/EtOAc (5 mL). The solution was stirred for 1 h after which point LC analysis indicated complete consumption of the starting material. The reaction mixture was concentrated in vacuo and azeotroped with MeOH (2×5 mL) to provide the title compound (61 mg) as a white solid. ¹H NMR (270 MHz, D₄-MeOH): 6.92 (1H, s), 3.79 (2H, s) and 1.44 (6H, s). MS: [M+H]⁺=184.

Preparation 244: 5-Bromo-6-chloro-3,3-dimethyl-2,3-dihydro-indole-1-carboxylic acid tert-butyl ester To 6-chloro-3,3-dimethyl-2,3-dihydro-indole-1-carboxylic acid tert-butyl-ester (0.500 g, 2.75 mmol) in MeCN (3.78 mL) was added N-bromosuccinimide (0.492 g, 2.76 mmol) at room temperature. The reaction was stirred for 1 h at room temperature and concentrated. Chromatography (silica gel, gradient elution, 0-40%, EtOAc in petrol 40-60) gave the title compound (356 mg), 1H NMR (Me-d3-OD): 7.80 (1H, s), 7.43 (1H, s), 3.73 (2H, s), 1.66-1.51 (9H, m), 1.32 (6H, s).

Preparation 245: 6-Chloro-3,3-dimethyl-2,3-dihydro-indole-1,5-dicarboxylic acid 1-tert-butyl ester 5-Bromo-6-chloro-3,3-dimethyl-2,3-dihydro-indole-1-carboxylic acid tert-butyl ester (0.336 g, 0.93 mmol) was dissolved in THF (3.73 mL) and cooled to −78° C. under nitrogen. Butyllithium (2.5 M in hexanes, 0.411 mL, 1.03 mmol) was added dropwise. The reaction was stirred for 20 minutes and carbon dioxide gas was bubbled through the reaction and the temperature allowed to warm gently to room temperature. Water was added and the organic layer separated and extracted with 2 M aqueous NaOH (3×), The combined aqueous layers were washed with EtOAc (3×), acidified to pH 4 with 2M HCl. Extracted with EtOAc (3×) and the combined organic extracts washed with brine, dried with sodium sulfate and concentrated, to give the title compound (67 mg), MS: $[M+H]^+=326$.

Preparation 246: 6-Chloro-3,3-dimethyl-5-(3-methyl-[1,2,4]oxadiazol-5-yl)-2,3-dihydro-indole-1-carboxylic acid tert-butyl ester To 6-chloro-3,3-dimethyl-2,3-dihydro-indole-1,5-dicarboxylic acid 1-tert-butyl ester (0.067 g, 0.21 mmol) in DMF (1.03 mL) was added N,N-diisopropylethylamine (0.126 uL, 0.72 mmol) and O-(7-azabenzotriazol-1-yl)-N,N,N',N'-tetramethyluronium hexafluorophosphate (0.08 g, 0.21 mmol) at room temperature. After stirring for 10 minutes, N-hydroxyacetamidine (0.015 g, 0.41 mmol) was added and the reaction stirred for 18 h. DMF (3.44 mL) was added and the reaction heated to 120° C. for 3 h. Water was added and the mixture extracted with diethyl ether (3×). The combined organic extracts were dried over sodium sulfate, filtered and concentrated. Chromatography (silica gel, gradient elution, 0-60%, EtOAc in petrol 40-60) gave the title compound (36 mg). MS: $[M+H]^+=364$.

Preparation 247: 6-Chloro-3,3-dimethyl-5-(3-methyl-[1,2,4]oxadiazol-5-yl)-2,3-dihydro-1H-indole 6-Chloro-3,3-dimethyl-5-(3-methyl-[1,2,4]oxadiazol-5-yl)-2,3-dihydro-indole-1-carboxylic acid tert-butyl ester (36 mg, 0.11 mmol) was dissolved in 50% TFA in DCM (0.534 mL) and the mixture was stirred for 30 minutes and concentrated. The residue was dissolved in methanol, loaded onto an SCX column and eluted with methanol then 2.0M ammonia in methanol to release the amine and fractions concentrated, to give the title compound (26 mg), MS: $[M+H]^+=264$.

Preparation 248: 3,3-Dimethyl-6-propionyl-2,3-dihydro-pyrrolo[3,2-b]pyridine-1-carboxylic acid tert-butyl ester 6-Bromo-3,3-dimethyl-2,3-dihydro-pyrrolo[3,2-b]pyridine-1-carboxylic acid tert-butyl ester (1.33 g, 4.07 mmol) in THF (20.3 mL) was cooled to −78° C. under nitrogen and butyllithium (2.5 M in hexanes, 3.75 mL, 9.4 mmol) added. The reaction was stirred at this temperature for 30 minutes. To this was added N-methoxy-N-methyl-propionamide (0.71 g, 6.1 mmol) and the reaction was stirred for 1 h. Water and EtOAc were added and the organic layer separated, washed with brine (3×) and dried with sodium sulfate, filtered and concentrated. Chromatography (silica gel, gradient elution, 0-60%, EtOAc in petrol 40-60) gave the title compound (0.823 g), MS: $[M+H]^+=305$, as a 2:1 mixture with 3,3-dimethyl-2,3-dihydro-pyrrolo[3,2-b]pyridine-1-carboxylic acid tert-butyl ester.

Preparation 249: 6-(1,1-Difluoro-propyl)-3,3-dimethyl-2,3-dihydro-pyrrolo[3,2-b]pyridine-1-carboxylic acid tert-butyl ester The product mixture from Preparation 248 (0.50 g) was dissolved in a THF solution of Deoxo-Fluor (50%, 1.64 g, 7.4 mmol) and was heated at 90° C. for 18 h. The reaction was cooled to room temperature and poured into saturated aqueous sodium carbonate. The mixture was extracted with DCM (3×), dried with sodium sulfate, filtered and concentrated. Chromatography (silica gel, gradient elution, 0-25%, EtOAc/petrol 40-60) gave the title compound (0.25 g). MS: $[M+H]^+=327$.

Preparation 250: 6-(1,1-Difluoro-propyl)-3,3-dimethyl-2,3-dihydro-1H-pyrrolo[3,2-b]pyridine 6-(1,1-Difluoro-propyl)-3,3-dimethyl-2,3-dihydro-pyrrolo[3,2-b]pyridine-1-carboxylic acid tert-butyl ester (0.245 g, 0.75 mmol) was dissolved in 5M aqueous HCl and MeOH (1:1, 10 mL) and the reaction was stirred at room temperature for 18 h. The solvent was removed in vacuo, to give the title compound (0.178 g) MS: $[M+H]^+=227$.

Preparation 251: 3-(2,4-Difluoro-benzyl)-7,7-dimethyl-6,7-dihydro-pyrrolo[3,2-c]pyridazine-5-carboxylic acid tert-butyl ester The title compound was prepared following similar methods to those described in Preparation 117, MS: $[M+H]^+=376$.

Preparation 252: 3-(2,4-Difluoro-benzyl)-7,7-dimethyl-6,7-dihydro-5H-pyrrolo[3,2-c]pyridazine The title compound was prepared following similar methods to those described Preparation 116. The crude product was loaded onto SCX column eluting with methanol then 2.0 M ammonia in methanol to release the amine. Relevant fractions concentrated, MS: $[M+H]+=276$.

Preparation 253: (2R,5R)-2-Formyl-5-methyl-piperazine-1,4-dicarboxylic acid di-tert-butyl ester To (2R,5R)-2-hydroxymethyl-5-methyl-piperazine-1,4-dicarboxylic acid di-tert-butyl ester (1.42 g, 4.3 mmol) in DCM (18.7 mL) was added Dess-Martin periodinane (1.83 g, 4.3 mmol) at room temperature. The reaction was stirred at this temperature for 1 h. Saturated aqueous sodium hydrogen carbonate and sodium thiosulfate (1:1) was added and the solution extracted with ethyl acetate (3×). The combined organic extracts were washed with saturated aqueous hydrogen carbonate and sodium thiosulfate (1:1) (3×), dried over sodium sulfate, filtered and concentrated to give the title compound (1.71 g, 96%) as a pale yellow solid, used without further purification. $^1$H NMR (CDCl$_3$): 9.58 (1H, s), 4.78-4.08 (3H, m), 3.73 (1H, m), 3.39-3.06 (2H, m), 1.53-1.41 (18H, m), 1.18 (3H, t).

Preparation 254: (2R,5R)-2-(Hydroxy-thiazol-2-yl-methyl)-5-methyl-piperazine-1,4-dicarboxylic acid di-tert-butyl ester 2-Bromothiazole (0.500 g, 3.05 mmol) was dissolved in anhydrous THF (7.62 mL) and cooled to 4° C. (ice bath) under nitrogen. i-PrMgCl.LiCl in THF (2.0 M, 1.52 mL, 3.05 mmol) was added and the reaction stirred at this temperature for 30 minutes. The ice bath was removed and the reaction stirred for 30 minutes at room temperature. (2R,5R)-2-Formyl-5-methyl-piperazine-1,4-dicarboxylic acid di-tert-butyl ester (0.500 g, 1.52 mmol) was added and the reaction stirred for 2 h. The reaction mixture was quenched with water and extracted with DCM (3×). The combined organic extracts were dried with sodium sulfate, filtered and concentrated. Chromatography (silica gel, gradient elution, 0-100%, EtOAc in petrol 40-60) gave the title compound (473 mg). MS: [M+H]$^+$=414.

Preparation 255: (2R,5R)-5-(Hydroxy-thiazol-2-yl-methyl)-2-methyl-piperazine-1-carboxylic acid tert-butyl ester Sodium hydride (60% in mineral oil, 0.08 g, 1.9 mmol) was added to (2R,5R)-2-(hydroxy-thiazol-2-yl-methyl)-5-methyl-piperazine-1,4-dicarboxylic acid di-tert-butyl ester (0.393 g, 0.95 mmol) in THF (4.8 mL) at 0° C. (ice bath) under nitrogen. The reaction was heated to 70° C. for 18 h. The reaction was cooled to room temperature and saturated aqueous ammonium chloride was added and the mixture extracted with EtOAc (3×). The combined organic extracts were dried with sodium sulfate, filtered and concentrated. Chromatography (silica gel, gradient elution, 0-100%, EtOAc in petrol 40-60) gave the title compound (0.111 g) MS: [M+H]$^+$=314.

Preparation 256: (2R,5R)-4-{2-[6-(1,1-Difluoro-butyl)-3,3-dimethyl-2,3-dihydro-pyrrolo[3,2-c]pyridin-1-yl]-2-oxo-ethyl}-5-(hydroxy-thiazol-2-yl-methyl)-2-methyl-piperazine-1-carboxylic acid tert-butyl ester To 6-(1,1-difluoro-butyl)-3,3-dimethyl-2,3-dihydro-1H-pyrrolo[3,2-c]pyridine (0.252 g, 1.05 mmol) and N,N-diisopropylethylamine (0.28 g, 2.2 mmol) in DCM (4.2 mL) cooled with an ice bath under nitrogen was added chloroacetyl chloride (0.09 g, 0.8 mmol), dropwise. After stirring at this temperature for 1.5 h, (2R,5R)-5-(hydroxy-thiazol-2-yl-methyl)-2-methyl-piperazine-1-carboxylic acid tert-butyl ester (0.18 g, 0.6 mmol) in DCM (0.5 mL) was added. The reaction was stirred at room temperature for 18 h, then saturated aqueous sodium bicarbonate was added and the mixture extracted with DCM (3×). The combined organic extracts were filtered and concentrated. Chromatography (silica gel, gradient elution, 0-100%, EtOAc in petrol 40-60) gave the title compound (0.076 g). MS: [M+H]$^+$=594.

Preparation 257: (2R,5R)-5-(Chloro-thiazol-2-yl-methyl)-4-{2-[6-(1,1-difluoro-butyl)-3,3-dimethyl-2,3-dihydro-pyrrolo[3,2-c]pyridin-1-yl]-2-oxo-ethyl}-2-methyl-piperazine-1-carboxylic acid tert-butyl ester To (2R,5R)-4-{2-[6-(1,1-difluoro-butyl)-3,3-dimethyl-2,3-dihydro-pyrrolo[3,2-c]pyridin-1-yl]-2-oxo-ethyl}-5-(hydroxy-thiazol-2-yl-methyl)-2-methyl-piperazine-1-carboxylic acid tert-butyl ester (0.076 g, 0.13 mmol) and triethylamine (36 uL, 0.3 mmol) in DCM (0.6 mL) cooled with an ice bath under nitrogen was added methanesulfonyl chloride (12 μL, 0.2 mmol). The reaction was stirred at this temperature for 1 h and then warmed room temperature for 18 h. Saturated aqueous sodium bicarbonate was added and the mixture extracted with EtOAc. The combined organics were washed with brine, dried with sodium sulfate, filtered and concentrated. Chromatography (silica gel, gradient elution, 0-100%, EtOAc in petrol 40-60) gave the title compound (0.03 g). MS: [M+H]$^+$=612.

Preparation 258: (2R,5S)-4-{2-[6-(1,1-Difluoro-butyl)-3,3-dimethyl-2,3-dihydro-pyrrolo[3,2-c]pyridin-1-yl]-2-oxo-ethyl}-2-methyl-5-thiazol-2-ylm-ethyl-piperazine-1-carboxylic acid tert-butyl ester (2R,5R)-5-(Chloro-thiazol-2-yl-methyl)-4-{2-[6-(1,1-difluoro-butyl)-3,3-dimethyl-2,3-dihydro-pyrrolo[3,2-c]pyridin-1-yl]-2-oxo-ethyl}-2-methyl-piperazine-1-carboxylic acid tert-butyl ester (0.03 g, 0.05 mmol), Pd/C (0.01 g, 0 mmol), triethylamine (0.01 g, 0.1 mmol) were dissolved in EtOAc (0.2 mL) and hydrogenated at room temperature and 1 bar for 30 minutes, followed by hydrogenation at 40 psi in a Parr hydrogenator for 1 h. The reaction was filtered and solids washed with EtOAc. The filtrate was concentrated and the crude product was purified by column chromatography (silica gel, gradient elution, 0-100%, EtOAc in petrol 40-60), to give the title compound (0.011 g). MS: [M+H]$^+$=578.

Preparation 259: (2R,5S)-4-Benzyl-2-methyl-5-(2-oxo-pyrrolidin-1-ylmethyl)-piperazine-1-carboxylic acid tert-butyl ester Three separate reaction flasks were each charged with sodium hydride (60% in mineral oil, 0.486 g, 12.16 mmol) and anydrous DMF (40.5 mL). To these, pyrrolidinone (0.924 mL, 12.16 mmol) was added dropwise. After stirring at this temperature for 30 minutes, (2R,5R)-4-benzyl-5-chloromethyl-2-methyl-piperazine-1-carboxylic acid tert-butyl ester (2.74 g, 8.11 mmol) was added to each at room temperature. The reactions were stirred at 80° C. for 4 h. The reactions were combined and saturated aqueous sodium bicarbonate was added and the mixture extracted with diethyl ether (3×). The combined organic layers were washed with brine, dried with sodium sulfate, filtered and concentrated. Chromatography (silica gel, gradient elution, 0-100%, EtOAc in petrol 40-60) gave the title compound (5.9 g), MS: [M+H]$^+$=388.

Preparation 260: (2R,5S)-2-Methyl-5-(2-oxo-pyrrolidin-1-ylmethyl)-piperazine-1-carboxylic acid tert-butyl ester (2R,5S)-4-Benzyl-2-methyl-5-(2-oxo-pyrrolidin-1-ylmethyl)-piperazine-1-carboxylic acid tert-butyl ester (5.9 g, 15.25 mmol) and 10% Pd/C (2.13 g, 1.5 mmol) were dissolved in glacial acetic acid/ethanol (27.2 mL/72.6 mL) and stirred under hydrogen at 1 bar for 1 h. The mixture was filtered and the filtrate concentrated. Saturated aqueous sodium hydrogen carbonate and EtOAc were added. The EtOAc layer was separated and the aqueous phase extracted with DCM (3×). The combined DCM layers were dried with sodium sulfate, filtered and concentrated. The residue was azeotroped with toluene, to give the title compound (3.9 g), ¹H NMR (CDCl₃): 4.23-4.08 (1H, m), 3.95-3.77 (1H, m), 3.69 (1H, d), 3.59-3.46 (1H, m), 3.46-3.34 (1H, m), 3.34-3.07 (3H, m), 3.07-2.89 (1H, m), 2.55-2.39 (3H, m), 2.15-1.92 (2H, m), 1.48 (9H, s), 1.23 (3H, d).

Preparation 261: (2R,5S)-4-Benzyloxycarbonylmethyl-2-methyl-5-(2-oxo-pyrrolidin-1-ylmethyl)-piperazine-1-carboxylic acid tert-butyl ester To (2R,5S)-2-methyl-5-(2-oxo-pyrrolidin-1-ylmethyl)-piperazine-1-carboxylic acid tert-butyl ester (2.73 g, 9.19 mmol) and potassium carbonate (1.4 g, 10.1 mmol) in MeCN (9.8 mL) was added benzyl bromoacetate (2.11 g, 9.2 mmol) at room temperature. The reaction was stirred at this temperature for 18 h then diluted with chloroform, filtered and the filtrate concentrated. Chromatography (silica gel, gradient elution, 0-60%, EtOAc in petrol 40-60) gave the title compound (4 g). MS: [M+H]⁺=446.

Preparation 262: (2R,5S)-4-Carboxymethyl-2-methyl-5-(2-oxo-pyrrolidin-1-ylmethyl)-piperazine-1-carboxylic acid tert-butyl ester (2R,5S)-4-Benzyloxycarbonylmethyl-2-methyl-5-(2-oxo-pyrrolidin-1-ylmethyl)-piperazine-1-carboxylic acid tert-butyl ester (4.29 g, 9.64 mmol) and 10% Pd/C (1.35 g, 1 mmol) in EtOAc (45.9 mL) were hydrogenated at room temperature and 1 bar. After stirring for 30 minutes, the reaction was filtered and solids washed with EtOAc. The filtrate was evaporated in vacuo and the residue azeotroped with toluene to give the title compound (2.9 g,). MS: [M+H]⁺=356.

Preparation 263: 6-Butyryl-3,3-dimethyl-2,3-dihydro-pyrrolo[3,2-b]pyridine-1-carboxylic acid tert-butyl ester Butyllithium (12.0 mL, 2.5 M solution in hexanes, 30 mmol) was added dropwise to a solution of 6-bromo-3,3-dimethyl-2,3-dihydro-pyrrolo[3,2-b]pyridine-1-carboxylic acid tert-butyl ester (8.0 g, 24.5 mmol) in diethyl ether (80 mL) at −78° C. The resulting orange slurry was stirred 30 minutes at this temperature before a solution of N-methoxy-N-methylbutyramide (prepared in a manner similar to that described in US2010/060696) (5.3 g, 36.6 mmol) in diethyl ether (40 mL) was added dropwise over 1 h. The reaction was allowed to warm to room temperature and stirred 1 h further, then quenched with saturated aqueous ammonium chloride and the two layers were separated. The aqueous fraction was further extracted with EtOAc (2×50 mL). The combined organic fractions were dried over MgSO₄, filtered and concentrated. Chromatography (0-30% EtOAc/petrol) gave the title compound (5.6 g, 72%) as a yellow solid. MS: [M+H]⁺=319.

Preparation 264: 6-(1,1-Difluoro-butyl)-3,3-dimethyl-2,3-dihydro-pyrrolo[3,2-b]pyridine-1-carboxylic acid tert-butyl ester A mixture of 6-butyryl-3,3-dimethyl-2,3-dihydro-pyrrolo[3,2-b]pyridine-1-carboxylic acid tert-butyl ester (1.43 g, 4.49 mmol) and deoxo-fluor (9.9 mL, 50% solution in THF, 22.5 mmol) was heated at 70° C. for 18 h. The reaction was cooled in ice and treated cautiously with saturated aqueous sodium carbonate until it became pH10. EtOAc (20 mL) was added and the layers separated. The aqueous fraction was further extracted with EtOAc (50 mL). The combined organic fractions were dried over MgSO₄, filtered and concentrated. Chromatography (0-25% EtOAc/petrol) gave the title compound (0.47 g, 31%) as a yellow solid. MS: [M+H]⁺=341. Further elution yielded the starting ketone (0.30 g).

Preparation 265: 6-(1,1-Difluoro-butyl)-3,3-dimethyl-2,3-dihydro-1H-pyrrolo[3,2-b]pyridine Prepared from 6-(1,1-difluoro-butyl)-3,3-dimethyl-2,3-dihydro-pyrrolo[3,2-b]pyridine-1-carboxylic acid tert-butyl ester using an analogous procedure to Preparation 116. MS: [M+H]⁺=241.

Preparation 266: N-Methoxy-3-N-dimethyl-butyramide

A solution of ethyl-iso-valerate (3.01 mL, 20 mmol) and N,O-dimethyl hydroxylamine hydrochloride (2.93 g, 30 mmol) in THF (40 mL) was cooled to −20° C. under nitrogen. iso-Propyl magnesium chloride (30 mL of a 2M solution in THF, 60 mmol) was added dropwise and the reaction was stirred at this temperature for 40 min before being quenched with saturated aqueous ammonium chloride and allowed to warm to room temperature. The layers were separated and the aqueous fraction further extracted with EtOAc (3×20 mL) and the combined organic fractions were washed with brine, dried over MgSO₄, filtered and concentrated to give the title compound (2.84 g, 98%) which was used without further purification. ¹H NMR (CDCl₃): 3.69 (3H, s), 3.19 (3H, s), 2.32 (2H, d), 2.27-2.11 (1H, m), 0.98 (6H, d).

Preparation 267: 6-(1,1-Difluoro-3-methyl-butyl)-3,3-dimethyl-2,3-dihydro-1H-pyrrolo[3,2-b]pyridine Prepared starting from N-Methoxy-3,N-dimethyl-butyramide in an analogous fashion to 6-(1,1-difluoro-butyl)-3,3-dimethyl-2,3-dihydro-1H-pyrrolo[3,2-b]pyridine (see Preparations 264 and 116. MS: [M+H]⁺ =255.

Preparation 268: (2R,5R)-4-Benzyl-5-hydroxymethyl-2-methyl-piperazine-1-carboxylic acid tert-butyl ester A mixture of (2R,5R)-5-hydroxymethyl-2-methyl-piperazine-1-carboxylic acid tert-butyl ester (14.58 g, 63 mmol), benzaldehyde (7.39 g, 70 mmol), sodium triacetoxyborohydride (16.0 g, 76 mmol) and 1,2-dichloroethane (100 mL) was stirred at 20° C. then quenched with saturated aqueous sodium hydrogen carbonate (500 mL). The mixture was extracted with DCM (3×100 mL) and the combined organic extracts dried (Na₂SO₄) and evaporated in vacuo to give an oil. Chromatography (SiO₂; gradient elution with 0-25% EtOAc in 40-60 petroleum ether) gave the title compound (15.4 g, 76%) as an oil. MS: [M+H]⁺=321. 1H NMR (CDCl₃): 7.42-7.12 (5H, m), 4.12-3.88 (2H, m), 3.85-3.55 (4H, m), 3.27 (1H, dd), 2.91-2.79 (1H, m), 2.73 (1H, dd), 2.63 (1H, s), 2.33 (1H, dd), 1.49 (9H, s), 1.21 (3H, d).

Preparation 269: (2R,5R)-4-Benzyl-5-fluoromethyl-2-methyl-piperazine-1-carboxylic acid tert-butyl ester To a stirred solution of diethylaminosulfur trifluoride (0.32 mL, 0.393 g, 2.44 mmol) in DCM (2 mL) at −78° C. under nitrogen was added a solution of (2R,5R)-4-benzyl- 5-hydroxymethyl-2-methyl-piperazine-1-carboxylic acid tert-butyl ester (0.651 g, 2.03 mmol) in DCM (6 mL). Mixture was stirred at −78° C. for 0.5 h then at 20° C. for 3 h. Mixture was poured into saturated aqueous sodium hydrogen carbonate (100 mL) and ice (20 g) then extracted with DCM (3×50 mL). Combined organic extracts were dried (Na$_2$SO$_4$) and evaporated in vacuo to give an oil. Chromatography (SiO$_2$; gradient elution with 0-40% Et$_2$O in 40-60 petroleum ether) gave the title compound (0.393 g) as an oil. MS: [M+H]$^+$=323.

Preparation 270: (2R,5R)-5-Fluoromethyl-2-methyl-piperazine-1-carboxylic acid tert-butyl ester, acetate A mixture of (2R,5R)-4-benzyl-5-fluoromethyl-2-methyl-piperazine-1-carboxylic acid tert-butyl ester (0.627 g, 1.95 mmol), ethanol (20 mL), acetic acid (0.5 mL) and 10% palladium on carbon (0.30 g) was hydrogenated at 20° C. and 3 bar for 4 h. Catalyst was removed by filtration and the filtrate evaporated in vacuo with toluene azeotrope (×2). Residue was dried in vacuo at 40° C. to give the title compound (0.52 g). MS: [M+H]$^+$=233.

Preparation 271: (2R,5R)-4-Benzyloxycarbonylmethyl-5-fluoromethyl-2-methyl-piperazine-1-carboxylic acid tert-butyl ester A mixture of (2R,5R)-5-fluoromethyl-2-methyl-piperazine-1-carboxylic acid tert-butyl ester (0.371 g, 1.27 mmol), potassium carbonate (0.70 g, 5.1 mmol), benzyl bromoacetate (0.38 g, 1.65 mmol) and acetonitrile (10 mL) was stirred at 20° C. for 18 h. Mixture was poured into water (50 mL) and extracted with DCM (3×30 mL). Combined organic extracts were dried (Na$_2$SO$_4$) and evaporated in vacuo to give an oil. Chromatography (SiO$_2$; gradient elution with 0-100% Et$_2$O in 40-60 petroleum ether) gave the title compound (0.424 g, 87%) as an oil. MS [M+H]$^+$=381.

Preparation 272: (2R,5R)-4-Carboxymethyl-5-fluoromethyl-2-methyl-piperazine-1-carboxylic acid tert-butyl ester A mixture of (2R,5R)-4-benzyloxycarbonylmethyl-5-fluoromethyl-2-methyl-piperazine-1-carboxylic acid tert-butyl ester (0.42 g, 1.1 mmol), methanol (20 mL) and 10% palladium on carbon (0.14 g) was hydrogenated at 20° C. and 1 bar for 18 h. Catalyst was removed by filtration and the filtrate evaporated in vacuo to give the title compound (0.289 g) as an oil. MS: [M+H]$^+$=291.

Preparation 273: (2R,5R)-4-Benzyl-5-formyl-2-methyl-piperazine-1-carboxylic acid tert-butyl ester To a solution of oxalyl chloride in DCM (2 M, 3 mL, 6 mmol) and DCM (5 mL) at −78° C. under nitrogen was added, dropwise with stirring, a solution of DMSO (1.0 mL, 1.09 g, 14 mmol) in DCM (5 mL) and mixture was stirred at −78° C. for 0.4 h. A solution of (2R,5R)-4-benzyl-5-hydroxymethyl-2-methyl-piperazine-1-carboxylic acid tert-butyl ester (1.12 g, 3.5 mmol) in DCM (5 mL) was added dropwise over 0.2 h and mixture stirred at −78° C. for 0.6 h. Triethylamine (3.9 mL, 2.83 g, 28 mmol) was added dropwise over 0.2 h and stirring was continued for a further 0.3 h. Water (10 mL) was added and mixture was warmed slowly to 20° C. over 16 h. Organic phase was separated and aqueous phase was extracted with DCM (2×10 mL). Combined organic extracts were dried (Na$_2$SO$_4$) and evaporated in vacuo to give a paste. This was partitioned between 1:1 Et$_2$O+40-60 petroleum ether (50 mL) and water (3×50 mL) and organic phase was dried (Na$_2$SO$_4$) and evaporated in vacuo to give an oil. Chromatography (SiO$_2$; gradient elution with 0-20% EtOAc in 40-60 petroleum ether) gave the title compound (0.275 g) as an oil. MS: [M+H]$^+$=319.

Preparation 274: (2R,5R)-4-Benzyl-5-difluoromethyl-2-methyl-piperazine-1-carboxylic acid tert-butyl ester Prepared from (2R,5R)-4-benzyl-5-formyl-2-methyl-piperazine-1-carboxylic acid tert-butyl ester using a procedure similar to that of Preparation 269. MS: [M+H]$^+$=341.

Preparation 275: (2R,5R)-5-Difluoromethyl-2-methyl-piperazine-1-carboxylic acid tert-butyl ester Prepared from (2R,5R)-4-benzyl-5-difluoromethyl-2-methyl-piperazine-1-carboxylic acid tert-butyl ester ester using a procedure similar to that of Preparation 270. $^1$H NMR (Me-d3-OD): 5.91 (1H, dt), 4.26-4.08 (1H, m), 4.04-3.88 (1H, m), 3.31-3.17 (1H, m), 3.15-2.94 (2H, m), 2.61 (1H, dd), 1.48 (9H, d), 1.24 (3H, d).

Preparation 276: (2R,5R)-4-Benzyloxycarbonylmethyl-5-difluoromethyl-2-methyl-piperazine-1-carboxylic acid tert-butyl ester Prepared from (2R,5R)-5-difluoromethyl-2-methyl-piperazine-1-carboxylic acid tert-butyl ester using a procedure similar to that of Preparation 271. MS: [M+H]$^+$=399.

Preparation 277: (2R,5R)-4-Carboxymethyl-5-difluoromethyl-2-methyl-piperazine-1-carboxylic acid tert-butyl ester Prepared from (2R,5R)-4-benzyloxycarbonylmethyl-5-difluoromethyl-2-methyl-piperazine-1-carboxylic acid tert-butyl ester using a procedure similar to that of Preparation 272. MS: [M−H]$^-$=307.

Preparation 278: (2R,5R)-4-Benzyl-2-methyl-5-pyrazol-1-ylmethyl-piperazine-1-carboxylic acid tert-butyl ester (alternative procedure)

A solution of methanesulfonic anhydride (0.65 g, 3.72 mmol) in DCM (5 mL) was added slowly to a solution of (2R,5R)-4-benzyl-5-hydroxymethyl-2-methyl-piperazine-1-carboxylic acid tert-butyl ester (1.08 g, 3.38 mmol) and triethylamine (1.42 mL, 1.02 g, 10.1 mmol) in DCM (10 mL) with stirring under nitrogen and external ice bath cooling. Stirring was continued at 0° C. for 2 h then pyrazole (0.3 g, 4.4 mmol) was added in one portion. Stirring at 20° C. was continued for 18 h, then mixture was partitioned between saturated aqueous NaHCO$_3$ (40 mL) and DCM (3×20 mL). Combined organic extracts were dried (Na$_2$SO$_4$) and evaporated in vacuo to give an oil. Chromatography (SiO$_2$; gradient elution with 0-40% Et$_2$O in 40-60 petroleum ether) gave the title compound (0.811 g) as an oil. MS: [M+H]$^+$=371.

Preparation 279: (2R,5R)-4-Benzyloxycarbonylmethyl-2-methyl-5-pyrazol-1-ylmethyl-piperazine-1-carboxylic acid tert-butyl ester Prepared from (2R,5R)-2-methyl-5-pyrazol-1-ylmethyl-piperazine-1-carboxylic acid tert-butyl ester (see preparation 219) using a similar procedure to Preparation 271. MS: [M+H]$^+$=429.

Preparation 280: (2R,5R)-4-Carboxymethyl-2-methyl-5-pyrazol-1-ylmethyl-piperazine-1-carboxylic acid tert-butyl ester Prepared from (2R,5R)-4-benzyloxycarbonylmethyl-2-methyl-5-pyrazol-1-ylmethyl-piperazine-1-carboxylic acid tert-butyl ester using a similar procedure to Preparation 272. MS: $[M+H]^+=339$.

Preparation 281: (2R,5R)-4-Benzyl-2-methyl-5-(4-methyl-pyrazol-1-ylmethyl)-piperazine-1-carboxylic acid tert-butyl ester Prepared from 4-methylpyrazole using a similar method to Preparation 278. MS: $[M+H]^+=385$.

Preparation 282: (2R,5R)-2-Methyl-5-(4-methyl-pyrazol-1-ylmethyl)-piperazine-1-carboxylic acid tert-butyl ester, acetate Prepared from (2R,5R)-4-benzyl-2-methyl-5-(4-methyl-pyrazol-1-ylmethyl)-piperazine-1-carboxylic acid tert-butyl ester using a similar method to Preparation 270. MS: $[M+H]^+=295$.

Preparation 283: (2R,5R)-4-Benzyloxycarbonylmethyl-2-methyl-5-(4-methyl-pyrazol-1-ylmethyl)-piperazine-1-carboxylic acid tert-butyl ester Prepared from (2R,5R)-2-methyl-5-(4-methyl-pyrazol-1-ylmethyl)-piperazine-1-carboxylic acid tert-butyl ester using a similar method to Preparation 271. MS: $[M+H]^+=443$.

Preparation 284: (2R,5R)-4-Carboxymethyl-2-methyl-5-(4-methyl-pyrazol-1-ylmethyl)-piperazine-1-carboxylic acid tert-butyl ester Prepared from (2R,5R)-4-Benzyloxycarbonylmethyl-2-methyl-5-(4-methyl-pyrazol-1-ylmethyl)-piperazine-1-carboxylic acid tert-butyl ester using a similar method to Preparation 272. MS: $[M+H]^+=353$.

Preparation 285: (2R,5R)-4-Benzyl-5-(4-fluoro-pyrazol-1-ylmethyl)-2-methyl-piperazine-1-carboxylic acid tert-butyl ester Prepared from 4-fluoropyrazole (see England et al., Tetrahedron Letters 2010 51 2849-2851) using a similar method to Preparation 278. $^1$H NMR (Me-d3-OD): 7.63 (1H, d), 7.45-7.20 (6H, m), 4.31 (1H, dd), 4.27-4.08 (2H, m), 3.81 (1H, d), 3.65 (2H, d), 3.31-3.20 (2H, m), 2.84 (1H, dd), 2.38 (1H, dd), 1.57-1.45 (9H, m), 1.19 (3H, d).

Preparation 286: (2R,5R)-5-(4-Fluoro-pyrazol-1-ylmethyl)-2-methyl-piperazine-1-carboxylic acid tert-butyl ester, acetate Prepared from (2R,5R)-4-benzyl-5-(4-fluoro-pyrazol-1-ylmethyl)-2-methyl-piperazine-1-carboxylic acid tert-butyl ester using a similar method to Preparation 270. MS: $[M+H]^+=299$.

Preparation 287: (2R,5R)-4-Benzyloxycarbonylmethyl-5-(4-fluoro-pyrazol-1-ylmethyl)-2-methyl-piperazine-1-carboxylic acid tert-butyl ester Prepared from (2R,5R)-5-(4-fluoro-pyrazol-1-ylmethyl)-2-methyl-piperazine-1-carboxylic acid tert-butyl ester using a similar method to Preparation 271. MS: $[M+H]^+=447$.

Preparation 288: (2R,5R)-4-Carboxymethyl-5-(4-fluoro-pyrazol-1-ylmethyl)-2-methyl-piperazine-1-carboxylic acid tert-butyl ester Prepared from (2R,5R)-4-benzyloxycarbonylmethyl-5-(4-fluoro-pyrazol-1-ylmethyl)-2-methyl-piperazine-1-carboxylic acid tert-butyl ester using a similar method to Preparation 272. MS: $[M+H]^+=357$.

Preparation 289: 6-(Difluoro-phenyl-methyl)-3,3-dimethyl-2,3-dihydro-pyrrolo[3,2-c]pyridine-1-carboxylic acid tert-butyl ester To a stirred solution of diethylaminosulfur trifluoride (14.8 mL, 18 g, 112.5 mmol) in DCM (20 mL) at −78° C. under nitrogen was added a solution of 6-benzoyl-3,3-dimethyl-2,3-dihydro-pyrrolo[3,2-c]pyridine-1-carboxylic acid tert-butyl ester (9.9 g, 28.1 mmol) in DCM (30 mL) and resulting solution was stirred at −78° C. for 1 h then at 20° C. for 6 days. Mixture was cooled to −78° C. and a solution of ethanol in DCM (2 mL) was added and the resulting solution stirred at 20° C. for 11 days. The reaction mixture was slowly added to a mixture of ice (200 g) and saturated aqueous NaHCO$_3$ (300 mL) and the resulting mixture was extracted with DCM (5×100 mL). Combined organic extracts were dried (Na$_2$SO$_4$) and evaporated in vacuo to give an oil. Chromatography (SiO$_2$; gradient elution with 10-40% Et$_2$O in 40-60 petroleum ether) gave a yellow solid. Crystallisation from EtOAc and 40-60 petroleum ether gave the title compound (6.22 g) as a colourless solid. MS: $[M+H]^+=375$.

Preparation 290: 6-(Difluoro-phenyl-methyl)-3,3-dimethyl-2,3-dihydro-1H-pyrrolo[3,2-c]pyridine hydrochloride A mixture of 6-(difluoro-phenyl-methyl)-3,3-dimethyl-2,3-dihydro-pyrrolo[3,2-c]pyridine-1-carboxylic acid tert-butyl ester (6.22 g, 16.6 mmol), methanol (30 mL) and hydrochloric acid (5 M, 30 mL) was stirred at 20° C. for 3 h, at 35° C. for 4 h, then left at 20° C. for 14 h. Mixture was evaporated in vacuo and the residue azeotroped with toluene (×3), isopropanol and methanol (×3). Residue was dried in vacuo at 50° C. for 4 h to give the title compound. MS: $[M+H]^+=275$.

Preparation 291: 3,3-Dimethyl-6-(1-methylene-propyl)-2,3-dihydro-pyrrolo[3,2-c]pyridine-1-carboxylic acid tert-butyl ester A mixture of 4,4,5,5-tetramethyl-2-(1-methylene-propyl)-[1,3,2]dioxaborolane (0.793 g, 4.36 mmol), 6-chloro-3,3-dimethyl-2,3-dihydro-1H-pyrrolo[3,2-c]pyridine-1-carboxylic acid tert-butyl ester (0.821 g, 2.9 mmol), potassium carbonate (1.20 g, 8.7 mmol), tris(dibenzylideneacetone)-dipalladium (0) (0.133 g, 0.145 mmol), 2-dicyclohexylphosphino-2',6'-dimethoxybiphenyl (SPhos, 0.060 g, 0.145 mmol), 1,4-dioxane (18 mL) and water (45 mL) was heated at 94° C. for 18 h, then poured into saturated aqueous NaHCO$_3$ (100 mL) and extracted with DCM (3×50 mL). Combined organic extracts were dried (Na$_2$SO$_4$) and evaporated in vacuo to give an oil. Chromatography (SiO$_2$; gradient elution with 0-25% Et$_2$O in 40-60 petroleum ether) gave the title compound (0.487 g) as an oil. MS: [M+H]$^+$=303. Further chromatography of mixed fractions gave further title compound (0.20 g).

Preparation 292: 3,3-Dimethyl-6-propionyl-2,3-dihydro-pyrrolo[3,2-c]pyridine-1-carboxylic acid tert-butyl ester A mixture of 3,3-dimethyl-6-(1-methylene-propyl)-2,3-dihydro-pyrrolo[3,2-c]pyridine-1-carboxylic acid tert-butyl ester (0.65 g, 2.15 mmol), sodium periodate (1.89 g, 8.61 mmol), 4% aqueous osmium tetroxide (1.65 mL, 0.26 mmol), THF (16 mL), acetone (8 mL) and water (16 mL) was stirred at 20° C. for 4 h then partitioned between water (50 mL) and DCM (3×50 mL). Combined organic extracts were dried (Na$_2$SO$_4$) and evaporated in vacuo to give an oil. Chromatography (SiO$_2$; gradient elution with 0-30% Et$_2$O in 40-60 petroleum ether) gave a solid, which was triturated with 40-60 petroleum ether to give a solid (0.25 g). The mother liquors were concentrated and purified by chromatography as above to give further solid (0.27 g). The two batches of solid were combined to give the title compound (0.52 g). MS [M+H]$^+$=305.

Preparation 293: 6-(1,1-Difluoro-propyl)-3,3-dimethyl-2,3-dihydro-pyrrolo[3,2-c]pyridine-1-carboxylic acid tert-butyl ester To a stirred solution of diethylaminosulfur trifluoride (0.53 mL, 0.64 g, 4 mmol) in DCM (3 mL) at −78° C. under nitrogen was added, dropwise over 0.2 h, a solution of 3,3-dimethyl-6-propionyl-2,3-dihydro-pyrrolo[3,2-c]pyridine-1-carboxylic acid tert-butyl ester (0.52 g, 1.7 mmol) in DCM (7 mL). Mixture was stirred at −78° C. for 1 h then at 20° C. for 16 h. Mixture was poured into ice (30 g) and saturated aqueous NaHCO$_3$ (30 mL) and extracted with DCM (3×20 mL). Combined organic extracts were dried (Na$_2$SO$_4$) and evaporated in vacuo to give an oil. Chromatography (SiO$_2$; gradient elution with 0-30% Et$_2$O in 40-60 petroleum ether) gave the title compound (0.398 g) as a solid. $^1$H NMR (Me-d3-OD): 8.30 (1H, s), 7.91 (1H, s), 3.87-3.76 (2H, m), 2.37-2.18 (2H, m), 1.60 (9H, s), 1.43 (6H, s), 0.98 (3H, t).

Preparation 294: 6-(1,1-Difluoro-propyl)-3,3-dimethyl-2,3-dihydro-1H-pyrrolo[3,2-c]pyridine hydrochloride A mixture of 6-(1,1-difluoro-propyl)-3,3-dimethyl-2,3-dihydro-pyrrolo[3,2-c]pyridine-1-carboxylic acid tert-butyl ester (0.398 g, 1.2 mmol), hydrochloric acid (5 M, 12 mL) and methanol (12 mL) was stirred at 20° C. for 16 h then evaporated in vacuo. The residue was azeotroped with methanol (×3) and toluene (×2) to give the title compound (0.3 g) as a solid. MS: [M+H]$^+$=227.

Preparation 295: 6-(1-Hydroxy-2-methyl-propyl)-3,3-dimethyl-2,3-dihydro-pyrrolo[3,2-c]pyridine-1-carboxylic acid tert-butyl ester To a stirred solution of 6-formyl-3,3-dimethyl-2,3-dihydro-pyrrolo[3,2-c]pyridine-1-carboxylic acid tert-butyl ester (0.65 g, 2.36 mmol), in THF (20 mL) at −78° C. under nitrogen was added, dropwise over 0.1 h, a solution of isopropylmagnesium chloride-lithium chloride complex in THF (1.3 M, 2.7 mL, 3.53 mmol). Resulting solution was stirred at −78° C. then was quenched with aqueous citric acid (5%, 30 mL) and extracted with DCM (4×50 mL). Combined organic extracts were dried (Na$_2$SO$_4$) and evaporated in vacuo to give a foam. Chromatography (SiO$_2$; gradient elution with 0-100% EtOAc in 40-60 petroleum ether) gave the title compound (0.398 g). $^1$H NMR (Me-d3-OD): 8.15 (1H, s), 8.08-7.45 (1H, m), 4.41 (1H, d), 3.78 (2H, s), 2.10-1.97 (1H, m), 1.60 (9H, s), 1.40 (6H, d), 0.92 (6H, t).

Preparation 296: 6-Isobutyryl-3,3-dimethyl-2,3-dihydro-pyrrolo[3,2-c]pyridine-1-carboxylic acid tert-butyl ester A mixture of 6-(1-hydroxy-2-methyl-propyl)-3,3-dimethyl-2,3-dihydro-pyrrolo[3,2-c]pyridine-1-carboxylic acid tert-butyl ester (0.366 g, 1.14 mmol), DCM (50 mL) and manganese (IV) oxide (9.6 g, 110 mmol) was stirred at 20° C. for 18 h, then solids were removed by filtration and the filtrate evaporated in vacuo to give a solid. Chromatography (SiO$_2$; gradient elution with 0-40% EtOAc in 40-60 petroleum ether) gave the title compound (0.299 g) as a colourless solid. MS: [M+H]$^+$=319.

Preparation 297: 6-(1,1-Difluoro-2-methyl-propyl)-3,3-dimethyl-2,3-dihydro-pyrrolo[3,2-c]pyridine-1-carboxylic acid tert-butyl ester Prepared from 6-isobutyryl-3,3-dimethyl-2,3-dihydro-pyrrolo[3,2-c]pyridine-1-carboxylic acid tert-butyl ester using a procedure similar to Preparation 293. MS: [M+H]$^+$=341.

Preparation 298: 6-(1,1-Difluoro-2-methyl-propyl)-3,3-dimethyl-2,3-dihydro-1H-pyrrolo[3,2-c]pyridine hydrochloride Prepared from 6-(1,1-difluoro-2-methyl-propyl)-3,3-dimethyl-2,3-dihydro-pyrrolo[3,2-c]pyridine-1-carboxylic acid tert-butyl ester using a similar method to Preparation 294. MS: [M+H]$^+$=241.

Preparation 299: 6-(Cyclopropyl-hydroxy-methyl)-3,3-dimethyl-2,3-dihydro-pyrrolo[3,2-c]pyridine-1-carboxylic acid tert-butyl ester Prepared following a similar method to that of Preparation 295, using cyclopropylmagnesium chloride. MS: [M+H]$^+$=319.

Preparation 300: 6-Cyclopropanecarbonyl-3,3-dimethyl-2,3-dihydro-pyrrolo[3,2-c]pyridine-1-carboxylic acid tert-butyl ester Prepared from 6-(cyclopropyl-hydroxy-methyl)-3,3-dimethyl-2,3-dihydro-pyrrolo[3,2-c]pyridine-1-carboxylic acid tert-butyl ester using a similar procedure to Preparation 296. MS: [M+H]$^+$=317.

Preparation 301: 6-(Cyclopropyl-difluoro-methyl)-3,3-dimethyl-2,3-dihydro-pyrrolo[3,2-c]pyridine-1-carboxylic acid tert-butyl ester A mixture of 6-cyclopropanecarbonyl-3,3-dimethyl-2,3-dihydro-pyrrolo[3,2-c]pyridine-1-carboxylic acid tert-butyl ester (0.21 g, 0.66 mmol), THF (2 mL) and deoxofluor (50% in THF, 1.4 mL, 1.5 g, 3.3 mmol) was heated at 80° C. for 18 h then cooled and partitioned between ice (20 g), saturated aqueous NaHCO₃ (30 mL) and DCM (3×30 mL). Combined organic extracts were dried (Na₂SO₄) and evaporated in vacuo to give an oil. Chromatography (SiO₂; gradient elution with 0-25% EtOAc in 40-60 petroleum ether) gave the title compound (0.189 g) as an oil which solidified. MS: [M+H]⁺=339.

Preparation 302: 6-(Cyclopropyl-difluoro-methyl)-3, 3-dimethyl-2,3-dihydro-1H-pyrrolo[3,2-c]pyridine Prepared from 6-(cyclopropyl-difluoro-methyl)-3,3-dimethyl-2,3-dihydro-pyrrolo[3,2-c]pyridine-1-carboxylic acid tert-butyl ester using a similar method to Preparation 294. The residue from evaporation was converted to the free base by partion between DCM and aqueous sodium hydrogen carbonate then purified by silica chromatography to give the title compound (0.085 g). MS: [M+H]⁺=239.

Preparation 303: 3,3-Dimethyl-6-(3-methyl-butyl)-2,3-dihydro-pyrrolo[3,2-c]pyridine-1-carboxylic acid tert-butyl ester Prepared following an analogous method to Preparation 117, using 3-methylbutylzinc bromide. MS: [M+H]⁺=319.

Preparation 304: 3,3-Dimethyl-6-(3-methyl-butyl)-5-oxy-2,3-dihydro-pyrrolo[3,2-c]pyridine-1-carboxylic acid tert-butyl ester A mixture of 3,3-dimethyl-6-(3-methyl-butyl)-2,3-dihydro-pyrrolo[3,2-c]pyridine-1-carboxylic acid tert-butyl ester (1.77 g, 5.57 mmol), DCM (20 mL) and 3-chloroperbenzoic acid (1.37 g, 6.12 mmol) was stirred at 20° C. for 3 h. Mixture was applied directly to a silica cartridge and elution carried out with 20-100% EtOAc in 40-60 petroleum ether, followed by 0-20% MeOH in EtOAc to give the title compound (1.596 g) as a solid. MS: [M+H]⁺=335.

Preparation 305: 6-(1-Hydroxy-3-methyl-butyl)-3,3-dimethyl-2,3-dihydro-pyrrolo[3,2-c]pyridine-1-carboxylic acid tert-butyl ester A mixture of 3,3-dimethyl-6-(3-methyl-butyl)-5-oxy-2,3-dihydro-pyrrolo[3,2-c]pyridine-1-carboxylic acid tert-butyl ester (1.6 g, 4.8 mmol) and acetic anhydride (10 mL) was heated at 100° C. for 2 h then poured into ice-water (50 g) and stirred for 1 h. Mixture was neutralised with NaHCO₃ then extracted with DCM (3×50 mL). Combined organic extracts were dried (Na₂SO₄) and evaporated in vacuo to give an oil (2.096 g). This material was mixed with methanol (20 mL), sodium hydroxide (0.25 g, 6.13 mmol) and water (1 mL) and stirred at 100° C. for 1 h. The mixture was poured into brine and extracted with DCM (3×50 mL). Combined organic extracts were dried (Na₂SO₄) and evaporated in vacuo. Chromatography of the residue (SiO₂; gradient elution with 0-100% EtOAc in 40-60 petroleum ether) gave the title compound (1.757 g) as a colourless foam. MS: [M+H]⁺=335.

Preparation 306: 3,3-Dimethyl-6-(3-methyl-butyryl)-2,3-dihydro-pyrrolo[3,2-c]pyridine-1-carboxylic acid tert-butyl ester Prepared from 6-(1-hydroxy-3-methyl-butyl)-3,3-dimethyl-2,3-dihydro-pyrrolo[3,2-c]pyridine-1-carboxylic acid tert-butyl ester using a method similar to that of Preparation 296. [M+H]⁺=333.

Preparation 307: 6-(1,1-Difluoro-3-methyl-butyl)-3,3-dimethyl-2,3-dihydro-pyrrolo[3,2-c]pyridine-1-carboxylic acid tert-butyl ester Prepared from 3,3-dimethyl-6-(3-methyl-butyryl)-2,3-dihydro-pyrrolo[3,2-c]pyridine-1-carboxylic acid tert-butyl ester using a method similar to that of Preparation 293. MS: [M+H]⁺=355.

Preparation 308: 6-(1,1-Difluoro-3-methyl-butyl)-3,3-dimethyl-2,3-dihydro-1H-pyrrolo[3,2-c]pyridine Prepared from 6-(1,1-difluoro-3-methyl-butyl)-3,3-dimethyl-2,3-dihydro-pyrrolo[3,2-c]pyridine-1-carboxylic acid tert-butyl ester using a method similar to that of Preparation 294. The residue from evaporation was converted to the free base by partion between DCM and aqueous sodium hydrogen carbonate to give the title compound (0.795 g) as an off-white solid. MS: [M+H]⁺=255.

Preparation 309: 6-Butyl-3,3-dimethyl-2,3-dihydro-pyrrolo[3,2-c]pyridine-1-carboxylic acid tert-butyl ester Prepared following an analogous method to Prep 117 using butylzinc bromide. MS [M+H]⁺ 305.

Preparation 310: 6-Butyl-3,3-dimethyl-5-oxy-2,3-dihydro-pyrrolo[3,2-c]pyridine-1-carboxylic acid tert-butyl ester To a cooled solution (ice bath 3-4° C.) of 6-butyl-3,3-dimethyl-2,3-dihydro-pyrrolo[3,2-c]pyridine-1-carboxylic acid tert-butyl ester (13.4 g, 44.08 mmol) in DCM (490 mL) was added 3-chloroperbenzoic acid (10.37 g, 46.28 mmol) portionwise over 0.25 h. The temperature was kept below 5° C. during addition, then mixture was warmed gently overnight to 20° C. The organic layer was washed with saturated aqueous sodium bicarbonate (3×500 mL), dried (Na₂SO₄) and evaporated in vacuo. Chromatography (SiO₂ gradient elution, 0-20%, MeOH in EtOAc) gave the title compound (12 g, 85%) as a pale yellow solid. MS: [M+H]⁺=321.

Preparation 311: 6-(1-Hydroxy-butyl)-3,3-dimethyl-2,3-dihydro-pyrrolo[3,2-c]pyridine-1-carboxylic acid tert-butyl ester Prepared from 6-butyl-3,3-dimethyl-5-oxy-2,3-dihydro-pyrrolo[3,2-c]pyridine-1-carboxylic acid tert-butyl ester using an analogous method to Preparation 305. MS: [M+H]⁺=321.

Preparation 312: 6-Butyryl-3,3-dimethyl-2,3-dihydro-pyrrolo[3,2-c]pyridine-1-carboxylic acid tert-butyl ester Prepared from 6-(1-hydroxy-butyl)-3,3-dimethyl-2,3-dihydro-pyyrrolo[3,2-c]pyridine-1-carboxylic acid tert-butyl ester using an analogous method to Preparation 296. MS: [M+H]⁺=319.

Preparation 313: 6-(1,1-Difluoro-butyl)-3,3-dimethyl-2,3-dihydro-pyrrolo[3,2-c]pyridine-1-carboxylic acid tert-butyl ester Prepared from 6-butyryl-3,3-dimethyl-2,3-dihydro-pyrrolo[3,2-c]pyridine-1-carboxylic acid tert-butyl ester using an analogous method to Preparation 293. MS: [M+H]$^+$=341.

Preparation 314: 6-(1,1-Difluoro-butyl)-3,3-dimethyl-2,3-dihydro-1H-pyrrolo[3,2-c]pyridine Prepared from 6-(1,1-difluoro-butyl)-3,3-dimethyl-2,3-dihydro-pyrrolo[3,2-c]pyridine-1-carboxylic acid tert-butyl ester using an analogous method to Preparation 294. The residue from evaporation was converted to the free base by partion between DCM and aqueous sodium hydrogen carbonate to give the title compound (0.799 g) as an oil. MS: [M+H]$^+$=241.

Preparation 315: (2R,5R)-4-{2-[6-(2-Fluoro-benzyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester Prepared from (2R,5R)-5-hydroxymethyl-2-methyl-piperazine-1-carboxylic acid tert-butyl ester, chloroacetyl chloride and 6-(2-fluoro-benzyl)-3,3-dimethyl-2,3-dihydro-1H-pyrrolo[3,2-c]pyridine using an analogous method to Preparation 203, but with DIPEA as base instead of triethylamine and heating carried out at 40° C. (See also General Procedure 5, below). MS: [M+H]$^+$=527.

Preparation 316: (2R,5R)-5-Chloromethyl-4-{2-[6-(2-fluoro-benzyl)-3,3-dimethyl-2,3-dihydro-pyrrolo[3,2-c]pyridin-1-yl]-2-oxo-ethyl}-2-methyl-piperazine-1-carboxylic acid tert-butyl ester To a stirred solution of (2R,5R)-4-{2-[6-(2-fluoro-benzyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester (0.572 g, 0.97 mmol) and triethylamine (0.22 mL, 0.157 g, 1.55 mmol) in DCM (10 mL) at −10° C. under nitrogen was added a solution of methanesulfonyl chloride (0.09 mL, 0.133 g, 1.2 mmol) in DCM (5 mL). Mixture was stirred at 20° C. for 18 h then partitioned between saturated aqueous NaHCO$_3$ (50 mL) and DCM (3×30 mL) and combined organic extracts were dried (Na$_2$SO$_4$) and evaporated in vacuo to give the title compound (0.576 g) as an oil, used without further purification. MS: [M+H]$^+$=545.

Preparation 317: 6-(2,6-Dimethyl-phenoxy)-3,3-dimethyl-2,3-dihydro-1H-pyrrolo[3,2-c]pyridine hydrochloride Prepared from 2,6-dimethylphenol using analogous methods to Preparations 215 and 216. MS: [M+H]$^+$=269.

Preparation 318: 6-(2,6-Difluoro-phenoxy)-3,3-dimethyl-2,3-dihydro-1H-pyrrolo[3,2-c]pyridine hydrochloride Prepared from 2,6-difluorophenol using analogous methods to Preparations 215 and 216. MS: [M+H]$^+$=277.

Preparation 319: 6-(2-Chloro-6-methyl-phenoxy)-3,3-dimethyl-2,3-dihydro-1H-pyrrolo[3,2-c]pyridine hydrochloride Prepared from 2-chloro-6-methylphenol using analogous methods to Preparations 215 and 216. MS: [M+H]$^+$=289.

Preparation 320: 6-Formyl-3,3-dimethyl-2,3-dihydro-pyrrolo[3,2-c]pyridine-1-carboxylic acid tert-butyl ester 6-Chloro-3,3-dimethyl-2,3-dihydro-pyrrolo[3,2-c]pyridine-1-carboxylic acid tert-butyl ester (1 g, 3.5 mmol), potassium vinyltrifluoroborate (950 mg, 7 mmol), triethylamine (986 uL, 7 mmol) and PdCl$_2$(dppf)$_2$.DCM were dissolved in EtOH and heated at 100° C. for 11 hours. The mixture was allowed to cool and then concentrated in vacuo. The residue was partitioned between DCM and water. The DCM layer was washed with brine and dried (MgSO$_4$). Purification by alumina chromatography (eluting with DCM) gave the product as a yellow oil (842 mg, 87%). MS: m/z=275 [M+H]$^+$. This material (842 mg, 3.07 mmol) was dissolved in a THF/acetone/water mixture (2:2:1; 25 mL) and then treated with NaIO$_4$ (3.27 g, 15.3 mmol) and OsO$_4$ (2 mL, 4% in H$_2$O; ~0.01 mol eq.). The mixture was stirred overnight and then partitioned between EtOAc and water. The aqueous layer was extracted twice with EtOAc. The combined organic fraction was washed with brine, dried (MgSO$_4$) and concentrated in vacuo. Purification by SiO$_2$ chromatography (eluting with 20-40% EtOAc-hexanes) gave the title compound (500 mg, 59%). MS: [M+H]$^+$=277.

Preparation 321: 6-Chloro-3-methyl-1,3-dihydro-indol-2-one

BuLi (2.2 M in cyclohexane, 22 mL, 48 mmol) was added dropwise at −78° C. to a solution of 6-chloro-1,3-dihydro-indol-2-one (4 g, 24 mmol) and TMEDA (11.2 mL, 79 mmol) in THF (100 mL) under N$_2$. The solution was stirred for 30 minutes at the same temperature and then MeI (2.2 mL, 36 mmol) was added. The reaction mixture was warmed to −20° C. and stirred at this temperature for 1.5 h. The reaction was quenched with saturated aqueous NH$_4$Cl and extracted with EtOAc. The organic phase was dried over MgSO$_4$, filtered and concentrated in vacuo. Chromatography gave the title compound (2.7 g) as a pale pink solid. MS: [M+H]$^+$=182.

Preparation 322: 6-Chloro-3-ethyl-3-methyl-1,3-dihydro-indol-2-one

The title compound was prepared following similar methods to those described in Preparation 321 using 6-chloro-3-methyl-1,3-dihydro-indol-2-one (500 mg, 2.76 mmol) and EtI (242 uL, 3 mmol) to give the title compound (250 mg) as a white solid. MS: [M+H]$^+$=210.

Preparation 323: 6-Chloro-3-ethyl-3-methyl-2,3-dihydro-1H-indole BH$_3$-Me$_2$S (2 M in THF, 5.7 mL, 11.5 mmol) was added to a solution of 6-chloro-3-ethyl-3-methyl-1,3-dihydro-indol-2-one (240 mg, 1.1 mmol) in THF (10 mL)

The reaction mixture was stirred at 70° C. for 3 h. The reaction was cooled to room temperature and MeOH (ca. 20 mL) was carefully added. The resulting solution was heated at reflux for 2 h. The solvents were then removed in vacuo

Preparation 324: 2-(4-Bromo-2-nitro-phenyl)-malonic acid dimethyl ester

To a cooled (0° C.) solution of dimethylmalonate (16.7 mL, 146 mmol) in DMF (100 mL) were added 4-bromo-1-fluoro-2-nitro-benzene (21.4 g, 97.3 mmol) and $K_2CO_3$ (40 g, 291 mmol). The reaction mixture was stirred overnight at room temperature and then poured into 2 M aqueous HCl/ice. More 2 M aqueous HCl was added until precipitation of the product was completed. The solid formed was filtered, washed with water and dried in vacuo to give the title compound (24 g) as an off-white solid. MS: $[M+H]^+=332$.

Preparation 325: 2-(4-Bromo-2-nitro-phenyl)-2-methyl-malonic acid dimethyl ester Following similar methods to those described in Preparation 324 using 2-(4-bromo-2-nitro-phenyl)-malonic acid dimethyl ester (10 g, 30 mmol), MeI (2 mL, 33 mmol) and $K_2CO_3$ (4.6 g, 33 mmol) gave the title compound (9.4 g) as a yellow solid. MS: $[M+H]^+=346$.

Preparation 326: 6-Bromo-3-methyl-2-oxo-2,3-dihydro-1H-indole-3-carboxylic acid methyl ester A mixture of 2-(4-bromo-2-nitro-phenyl)-2-methyl-malonic acid dimethyl ester (5 g, 14.4 mmol) in AcOH (30 mL) containing iron powder (2.4 g, 43.3 mmol) was stirred at 95° C. for 1 h. After that time a second aliquot of iron powder was added (803 mg, 14.4 mmol) and the stirring was maintained for an additional hour. The solvent was then removed in vacuo and the residue dissolved in EtOAc. The solid was collected by filtration and dissolved in 2 M aqueous HCl (20 mL). The mixture was stirred for 1 h at room temperature and the product was then extracted with DCM (3×). The organic phase was dried over $MgSO_4$ and concentrated in vacuo to give the title compound (2.7 g) as a white solid. MS: $[M+H]^+=284$.

Preparation 327: (6-Bromo-3-methyl-2,3-dihydro-1H-indol-3-yl)-methanol

Following similar methods to those described in Preparation 323 using 6-bromo-3-methyl-2-oxo-2,3-dihydro-1H-indole-3-carboxylic acid methyl ester (500 mg, 1.76 mmol) and $BH_3\cdot Me_2S$ (2M in THF, 8.8 mL, 17.6 mmol) gave the title compound (279 mg) as a white semi-solid. MS: $[M+H]^+=242$.

Preparation 328: 6-Bromo-3-hydroxymethyl-3-methyl-2,3-dihydro-indole-1-carboxylic acid tert-butyl ester Di-tert-butyl dicarbonate (271 mg, 1.24 mmol) and DIPEA (226 μL, 1.3 mmol) were added to a solution of (6-bromo-3-methyl-2,3-dihydro-1H-indol-3-yl)-methanol (279 mg, 1.15 mmol) in DCM (5 mL) and the mixture was stirred overnight at room temperature. The reaction was partitioned between saturated aqueous $NaHCO_3$ and DCM, the organic phase was dried over $MgSO_4$ and concentrated in vacuo to give the title compound (360 mg) as a white semi-solid, MS: $[M-{}^tBu]+=286$.

Preparation 329: 6-Bromo-3-methoxymethyl-3-methyl-2,3-dihydro-indole-1-carboxylic acid tert-butyl ester NaH (60% dispersion in mineral oil, 60 mg, 1.5 mmol) was added to a solution of 6-bromo-3-hydroxymethyl-3-methyl-2,3-dihydro-indole-1-carboxylic acid tert-butyl ester (360 mg, 1.05 mmol) in dry DMF (5 mL). After 10 minutes MeI (66 μL, 1.1 mmol) was added and the stirring was maintained for 2 h. The reaction was quenched with water and extracted with EtOAc. The organic phase was dried over $MgSO_4$ and concentrated in vacuo. Chromatography (20% EtOAc in 40-60 petroleum ether) gave the title compound (300 mg) as a colourless liquid. MS: $[M-{}^tBu]^+=300$.

Preparation 330: 6-Bromo-3-methoxymethyl-3-methyl-2,3-dihydro-1H-indole hydrochloride salt Saturated HCl in EtOAc (10 mL) was added to 6-bromo-3-methoxymethyl-3-methyl-2,3-dihydro-indole-1-carboxylic acid tert-butyl ester (300 mg, 0.84 mmol) and the mixture was stirred at room temperature for 1 h. The solvent was removed in vacuo, the solid was washed with $Et_2O$ and dried in vacuo to give the title compound (220 mg) as a yellow semi-solid. MS: $[M+H]^+=256$.

Preparation 331: 6-Bromo-3-methyl-2,3-dihydro-1H-indole-3-carboxylic acid methyl ester To a solution of 6-bromo-3-methyl-2-oxo-2,3-dihydro-1H-indole-3-carboxylic acid methyl ester (200 mg, 0.7 mmol) in toluene under $N_2$ were added $Fe_3(CO)_{12}$ (14 mg, 0.028 mmol) and $PhSiH_3$ (33 μL) and the mixture was stirred at 100° C. for 16 h. The resulting mixture was filtered through Celite (wash with EtOAc). The solvent was removed in vacuo to give the title compound (70 mg) as a colourless gum. MS: $[M+H]^+=270$.

Preparation 332: 2-(4-Bromo-2-nitro-phenyl)-2-phenyl-propionic acid methyl ester A solution of phenyl-acetic acid methyl ester (4 g, 27.3 mmol) and 4-bromo-1-fluoro-2-nitro-benzene (5 g, 22.7 mmol) in DMF (30 mL) was slowly added to a suspension of NaH (60% in mineral oil, 3 g, 77.1 mmol) in DMF (80 mL) at 0° C. under $N_2$. The reaction was then stirred for 3 h at room temperature. MeI (5.6 mL, 91 mmol) was then added and the reaction was stirred overnight at the same temperature. The reaction was quenched with saturated aqueous $NaHCO_3$ and extracted with EtOAc. The organic phase was dried over $MgSO_4$ and concentrated in vacuo. Chromatography (10% EtOAc in 40-60 petroleum ether) gave the title compound (2.6 g) as an orange semi-solid. $^1H$ NMR (DMSO-d6): 8.21-8.14 (1H, m), 7.86-7.77 (1H, m), 7.44-7.36 (5H, m), 6.84 (1H, d), 3.53 (3H, s), 2.06 (3H, s).

Preparation 333: 6-Bromo-3-methyl-3-phenyl-1,3-dihydro-indol-2-one

Following similar methods to those described in Preparation 326 starting from 2-(4-bromo-2-nitro-phenyl)-2-phenyl-propionic acid methyl ester (1.3 g, 4.9 mmol) and iron powder (890 mg, 15 mmol) gave the title compound (875 mg) as a yellow solid. MS: [M+H]$^+$=302.

Preparation 334: 6-Bromo-3-methyl-3-phenyl-2,3-dihydro-1H-indole

Following similar methods to those described in Preparation 323 using 6-bromo-3-methyl-3-phenyl-1,3-dihydro-indol-2-one (875 mg, 2.89 mmol) and BH$_3$-Me$_2$S (2M in THF, 14.58 mL, 28.9 mmol) gave the title compound (600 mg) as a colourless oil. MS: [M+H]$^+$=288.

Preparation 335: 1-(6-Bromo-3-methyl-3-phenyl-2,3-dihydro-indol-1-yl)-ethanone

Acetyl chloride (163 uL, 2.29 mmol) and TEA (313 µL, 2.29 mmol) were added to a solution of 6-bromo-3-methyl-3-phenyl-2,3-dihydro-1H-indole (600 mg, 2.1 mmol) in DCM (20 mL) at 0° C. The reaction was stirred for 45 minutes at room temperature and then quenched with 1 M aqueous HCl and extracted with EtOAc. The organic phase was dried over MgSO$_4$ and concentrated in vacuo to give the title compound (660 mg) as a yellow solid. MS: [M+H]$^+$=330.

Preparation 336: 1-Acetyl-3-methyl-3-phenyl-2,3-dihydro-1H-indole-6-carbonitrile CuCN (179 mg, 2 mmol) was added to a solution of 1-(6-bromo-3-methyl-3-phenyl-2,3-dihydro-indol-1-yl)-ethanone (330 mg, 1 mmol) in NMP (5 mL). The reaction was stirred at 175° C. for 16 h. Et$_2$O was added to the mixture and the solid was filtered off. The filtrate was washed with 2 M aqueous HCl and saturated aqueous NaHCO$_3$. The solvent was removed in vacuo to give the title compound (250 mg) as a brown solid. MS: [M+H]$^+$=277.

Preparation 337: 3-Methyl-3-phenyl-2,3-dihydro-1H-indole-6-carbonitrile

5 M aqueous HCl (3 mL) was added to a solution of 1-acetyl-3-methyl-3-phenyl-2,3-dihydro-1H-indole-6-carbonitrile (250 mg, 0.9 mmol) in acetonitrile (10 mL). The solution was stirred at reflux for 1 h and then cooled to room temperature. Saturated aqueous NaHCO$_3$ was then added to the reaction mixture until the pH of the solution reached 8 and the product was then extracted with EtOAc. The organic phase was dried over MgSO$_4$ and concentrated in vacuo to give the title compound (200 mg) as a light brown gum. MS: [M+H]$^+$=235.

Preparation 338: 2-(4-Bromo-2-nitro-phenyl)-2-pyridin-2-yl-propionic acid ethyl ester Following similar methods to those described in Preparation 332 starting from 4-bromo-1-fluoro-2-nitro-benzene (5 g, 22.7 mmol), pyridin-2-yl-acetic acid ethyl ester (4.5 g, 27.3 mmol), MeI (5.6 mL, 91 mmol) and NaH (60% in mineral oil, 3 g, 77.1 mmol) gave the title compound (7.2 g) as a yellow solid. MS: [M+H]$^+$=379.

Preparation 339: 6-Bromo-3-methyl-3-pyridin-2-yl-1,3-dihydro-indol-2-one

Following similar methods to those described in Preparation 326 using 2-(4-bromo-2-nitro-phenyl)-2-pyridin-2-yl-propionic acid ethyl ester (4 g, 10.5 mmol) and Fe(0) powder (1.76 g, 31.6 mmol) gave the title compound (2.8 g) as a pale brown semi-solid. MS: [M−H]$^-$=302.

Preparation 340: 6-Bromo-3-methyl-3-pyridin-2-yl-2,3-dihydro-1H-indole

Following similar methods to those described in Preparation 323 using 6-bromo-3-methyl-3-pyridin-2-yl-1,3-dihydro-indol-2-one (1.4 g, 4.6 mmol) and BH$_3$-Me$_2$S (2M in THF, 23 mL, 46 mmol) gave the title compound (1.2 g) as a yellow gum. MS: [M+H]$^+$=289.

Preparation 341: 1-(6-Bromo-3-methyl-3-pyridin-2-yl-2,3-dihydro-indol-1-yl)-ethanone Following similar methods to those described in Preparation 335 using 6-bromo-3-methyl-3-pyridin-2-yl-2,3-dihydro-1H-indole (1.2 g, 4.1 mmol), acetyl chloride (360 µL, 5 mmol) and TEA (721 µL, 5 mmol) gave the title compound as a pale yellow oil. MS: [M+H]$^+$=331.

Preparation 342: 1-(6-Benzyl-3-methyl-3-pyridin-2-yl-2,3-dihydro-indol-1-yl)-ethanone To a degassed solution of LiBr (165 mg, 1.9 mmol) and (1,3-diisopropylimidazol-2-ylidene)(3-chloropyridyl)palladium (II) dichloride (8 mg, 0.012 mmol) in NMP (3 mL) under N$_2$ were added a solution of 1-(6-bromo-3-methyl-3-pyridin-2-yl-2,3-dihydro-indol-1-yl)-ethanone (400 mg, 1.2 mmol) in THF (3 mL) and benzylzinc bromide (0.5 M in THF, 3.8 mL, 1.9 mmol). The reaction mixture was stirred at room temperature for 16 h and then partitioned between brine and EtOAc. The organic phase was separated, dried over MgSO$_4$, filtered and concentrated in vacuo. Chromatography (50% EtOAc in Petrol) gave the title compound (350 mg) as a colourless gum. MS: [M+H]$^+$=343.

Preparation 343: 6-Benzyl-3-methyl-3-pyridin-2-yl-2,3-dihydro-1H-indole

Prepared following similar methods to those described in Preparation 337. MS: [M+H]$^+$=301.

Preparation 344: 1-Acetyl-3-methyl-3-pyridin-2-yl-2,3-dihydro-1H-indole-6-carbonitrile Prepared following similar methods to those described in Preparation 336 starting from 1-(6-bromo-3-methyl-3-pyridin-2-yl-2,3-dihydro-indol-1-yl)-ethanone. MS: [M+H]$^+$=278.

Preparation 345: 3-Methyl-3-pyridin-2-yl-2,3-dihydro-1H-indole-6-carbonitrile

Prepared following similar methods to those described in Preparation 337 starting from 1-acetyl-3-methyl-3-pyridin-2-yl-2,3-dihydro-1H-indole-6-carbonitrile. MS: [M+H]$^+$=236.

Preparation 346: Pyridin-3-yl-acetic acid methyl ester

A solution of pyridin-3-yl-acetic acid hydrochloride (10 g, 57.6 mmol) in MeOH (30 mL) was treated with thionyl chloride (4.2 mL, 57.6 mmol) and the mixture was stirred at room temperature for 2 h. Solvent was removed in vacuo and the residue was partitioned between saturated aqueous NaHCO$_3$ and EtOAc. The organic phase was collected, dried over MgSO$_4$ and evaporated to give the title compound (7.9 g) as a colourless oil. $^1$H NMR (CDCl$_3$): 8.53 (2H, m), 7.64 (1H, d), 7.33-7.20 (1H, m), 3.72 (3H, s), 3.64 (2H, s).

Preparation 347: 6-Benzyl-3-methyl-3-pyridin-3-yl-2,3-dihydro-1H-indole

Following methods similar to those described in Preparations 338-343 starting from 4-bromo-1-fluoro-2-nitrobenzene and pyridin-3-yl-acetic acid methyl ester gave the title compound (117 mg) as a pale yellow gum. MS: [M+H]$^+$=301.

Preparation 348: 6-Benzyl-3-methyl-3-(3-methyl-isoxazol-5-yl)-2,3-dihydro-1H-indole Following methods similar to those described in Preparations 338-343 starting from 4-bromo-1-fluoro-2-nitrobenzene and (3-methyl-isoxazol-5-yl)-acetic acid methyl ester (prepared from the corresponding acid using a similar method to Preparation 346) gave the title compound (370 mg) as a pale yellow gum. MS: [M+H]$^+$=305.

Preparation 349: 6-Chloro-3,3-diethyl-1,3-dihydro-indol-2-one

Following similar methods to those described in Preparation 321 starting from 6-chloro-1,3-dihydro-indol-2-one (4 g, 25 mmol), TMEDA (11.2 mL, 79 mmol), BuLi (1.6M in hexane, 30 mL, 48 mmol) and EtI (2.9 mL, 36 mmol) gave the title compound (1.3 g). MS: [M+H]$^+$=224.

Preparation 350: 6-Chloro-3,3-diethyl-2,3-dihydro-1H-indole

Following similar methods to those described in Preparation 323 starting from 6-chloro-3,3-diethyl-1,3-dihydro-indol-2-one (1.3 g, 5.8 mmol) and BH$_3$-Me$_2$S (2M in THF, 29 mL, 58 mmol) gave the title compound. MS: [M+H]$^+$=210.

Preparation 351: (2R,5R)-4-Benzyl-5-chloromethyl-2-methyl-piperazine-1-carboxylic acid tert-butyl ester Methanesulfonyl chloride (570 µL, 7.35 mmol) was added to a solution of (2R,5R)-4-benzyl-5-hydroxymethyl-2-methyl-piperazine-1-carboxylic acid tert-butyl ester (1.9 g, 6.12 mmol) containing TEA (2.6 mL, 18.4 mmol) in DCM (30 mL) at 0° C. The solution was stirred at room temperature for 18 h. The reaction was partitioned between aqueous NH$_4$Cl and DCM. The organic phase was collected, dried over MgSO$_4$, filtered and concentrated in vacuo. Chromatography (30% EtOAc in petrol) gave the title compound (1.6 g) as a white solid. MS: [M+H]$^+$=339.

Preparation 352: (2R,5S)-4-Benzyl-2-methyl-5-(2-oxo-oxazolidin-3-ylmethyl)-piperazine-1-carboxylic acid tert-butyl ester K$_2$CO$_3$ (610 mg, 4.4 mmol), KI (730 mg, 4.4 mmol) and oxazolidinone (170 mg, 2.2 mmol) were added to a solution of (2R,5R)-4-benzyl-5-chloromethyl-2-methyl-piperazine-1-carboxylic acid tert-butyl ester (500 mg, 1.47 mmol) in acetonitrile (10 mL). The reaction was stirred at 60° C. for 3 days. The solids were filtered off and the solvent was removed in vacuo. Chromatography (40% EtOAc in petrol) gave the title compound (450 mg) as a white solid, MS: [M+H]$^+$=390.

Preparation 353: (2R,5S)-2-Methyl-5-(2-oxo-oxazolidin-3-ylmethyl)-piperazine-1-carboxylic acid tert-butyl ester, acetate salt Acetic acid (1.5 mL) and Pd/C (400 mg) were added to a solution of (2R,5S)-4-benzyl-2-methyl-5-(2-oxo-oxazolidin-3-ylmethyl)-piperazine-1-carboxylic acid tert-butyl ester (450 mg, 1.15 mmol) in EtOH (20 mL) and the resulting mixture was reacted under H$_2$ (1 bar) for 3 h. The catalyst was removed by filtration through a plug of Celite and the solvent was removed in vacuo to give the title compound (530 mg) as a colourless gum. MS: [M+H]$^+$=300.

Preparation 354: (2R,5S)-4-Benzyloxycarbonylmethyl-2-methyl-5-(2-oxo-oxazolidin-3-ylmethyl)-piperazine-1-carboxylic acid tert-butyl ester The title compound was prepared following similar methods to those described in Preparation 13 using (2R,5S)-2-methyl-5-(2-oxo-oxazolidin-3-ylmethyl)-piperazine-1-carboxylic acid tert-butyl ester (530 mg), benzylbromoacetate (183 µL) and K$_2$CO$_3$ (467 mg) to give the title compound (265 mg). MS: [M+H]$^+$=448.

Preparation 355: (2R,5S)-4-Carboxymethyl-2-methyl-5-(2-oxo-oxazolidin-3-ylmethyl)-piperazine-1-carboxylic acid tert-butyl ester Following similar methods to those described in Preparation 12, starting from (2R,5S)-4-benzyloxycarbonylmethyl-2-methyl-5-(2-oxo-oxazolidin-3-ylmethyl)-piperazine-1-carboxylic acid tert-butyl ester (265 mg), and Pd/C (65 mg) gave the title compound (189 mg) as a white solid. MS: [M+H]$^+$=358.

Preparation 356: (2R,5S)-4-Benzyl-2-methyl-5-(3-oxo-morpholin-4-ylmethyl)-piperazine-1-carboxylic acid tert-butyl ester Morpholin-3-one (896 mg, 8.87 mmol) was added to a slurry of NaH (60% in mineral oil, 355 mg, 8.87 mmol) in DMF (10 mL) under N$_2$. The suspension was stirred for 30 minutes at room temperature and then a solution of (2R,5R)-4-benzyl-5-chloromethyl-2-methyl-piperazine-1-carboxylic acid tert-butyl ester (2.0 g, 5.9 mmol) in DMF (10 mL) was slowly added. The resulting mixture was stirred at 65° C. for 2 h. The reaction was cooled to room temperature and partitioned between EtOAc and saturated aqueous NaHCO$_3$. The organic phase was dried over MgSO$_4$ and concentrated in vacuo. Chromatography (50% EtOAc in petrol) gave the title compound (1.76 g) as a pale yellow gum. MS: [M+H]$^+$=404.

Preparation 357: (2R,5S)-2-Methyl-5-(3-oxo-morpholin-4-ylmethyl)-piperazine-1-carboxylic acid tert-butyl ester Prepared from (2R,5S)-4-benzyl-2-methyl-5-(3-oxo-morpholin-4-ylmethyl)-piperazine-1-carboxylic acid tert-butyl ester (1.75 g), acetic acid (8 mL) and Pd/C (1.3 g) using an analogous method to that of Preparation 353. The catalyst was removed by filtration and the solvent was removed in vacuo. The crude material was partitioned between DCM and saturated aqueous NaHCO$_3$. The organic phase was dried over MgSO$_4$ and concentrated in vacuo to give the title compound (870 mg) as a colourless gum. $^1$H NMR (CDCl$_3$): 4.18 (3H, d), 4.00 (1H, dd), 3.90 (2H, t), 3.70 (1H, d), 3.55-3.37 (2H, m), 3.37-3.16 (3H, m), 3.08 (1H, dd), 2.51 (1H, dd), 2.38-1.78 (1H, m), 1.47 (9H, s), 1.22 (3H, d).

Preparation 358: (2R,5S)-4-Benzyl-2-methyl-5-(2-oxo-piperidin-1-ylmethyl)-piperazine-1-carboxylic acid tert-butyl ester The title compound was prepared following similar methods to those described in Preparation 356 starting from piperidin-2-one. MS: [M+H]$^+$=402.

Preparation 359: (2R,5S)-2-Methyl-5-(2-oxo-piperidin-1-ylmethyl)-piperazine-1-carboxylic acid tert-butyl ester The title compound was prepared following similar methods to those described in Preparation 357 starting from (2R,5S)-4-benzyl-2-methyl-5-(2-oxo-piperidin-1-ylmethyl)-piperazine-1-carboxylic acid tert-butyl ester. $^1$H NMR (CDCl$_3$): 4.24-4.05 (1H, m), 4.05-3.78 (1H, m), 3.66 (1H, d), 3.46-3.34 (1H, m), 3.34-3.15 (4H, m), 3.03-2.92 (1H, m), 2.48 (1H, dd), 2.44-2.32 (2H, m), 2.07 (2H, s), 1.97-1.72 (3H, m), 1.45 (9H, s), 1.21 (3H, d).

Preparation 360: (2R,5S)-4-Benzyl-2-methyl-5-(3-methyl-2-oxo-imidazolidin-1-ylmethyl)-piperazine-1-carboxylic acid tert-butyl ester The title compound was prepared following similar methods to those described in Preparation 356 starting from 1-methyl-imidazolidin-2-one. MS: [M+H]$^+$=403.

Preparation 361: (2R,5S)-2-Methyl-5-(3-methyl-2-oxo-imidazolidin-1-ylmethyl)-piperazine-1-carboxylic acid tert-butyl ester The title compound was prepared following similar methods to those described in Preparation 357 starting from (2R,5S)-4-Benzyl-2-methyl-5-(3-methyl-2-oxo-imidazolidin-1-ylmethyl)-piperazine-1-carboxylic acid tert-butyl ester. $^1$H NMR (CDCl$_3$): 4.17 (1H, t), 3.82 (1H, dd), 3.71 (1H, d), 3.57-3.41 (1H, m), 3.41-3.19 (5H, m), 3.19-3.08 (1H, m), 2.87-2.76 (4H, m), 2.48 (1H, dd), 1.92 (1H, s), 1.47 (9H, s), 1.24 (3H, d).

Preparation 362: (2R,5S)-4-Benzyl-5-((S)-3-fluoro-pyrrolidin-1-ylmethyl)-2-methyl-piperazine-1-carboxylic acid tert-butyl ester The title compound was prepared following similar methods to those described in Preparation 352 starting from (2R,5R)-4-benzyl-5-chloromethyl-2-methyl-piperazine-1-carboxylic acid tert-butyl ester (300 mg, 0.88 mmol) and (S)-3-fluoro-pyrrolidine (165 mg, 1.32 mmol). MS: [M+H]$^+$=392.

Preparation 363: (2R,5S)-5-((S)-3-Fluoro-pyrrolidin-1-ylmethyl)-2-methyl-piperazine-1-carboxylic acid tert-butyl ester The title compound was prepared following similar methods to those described in Preparation 357 starting from (2R,5S)-4-benzyl-5-((S)-3-fluoro-pyrrolidin-1-ylmethyl)-2-methyl-piperazine-1-carboxylic acid tert-butyl ester. $^1$H NMR (CDCl$_3$): 5.30-5.01 (1H, m), 4.28-3.98 (1H, m), 3.69 (1H, d), 3.42-3.25 (1H, m), 3.11 (1H, dd), 3.05-2.63 (5H, m), 2.63-2.32 (2H, m), 2.32-1.83 (4H, m), 1.47 (9H, s), 1.27 (3H, d).

Preparation 364: (2R,5S)-4-Benzyl-5-((R)-3-fluoro-pyrrolidin-1-ylmethyl)-2-methyl-piperazine-1-carboxylic acid tert-butyl ester The title compound was prepared following similar methods to those described in Preparation 352 starting from (2R,5R)-4-benzyl-5-chloromethyl-2-methyl-piperazine-1-carboxylic acid tert-butyl ester and (R)-3-fluoro-pyrrolidine. MS: [M+H]$^+$=392.

Preparation 365: (2R,5S)-5-((R)-3-Fluoro-pyrrolidin-1-ylmethyl)-2-methyl-piperazine-1-carboxylic acid tert-butyl ester The title compound was prepared following similar methods to those described in Preparation 357. $^1$H NMR (CDCl$_3$): 5.28-5.01 (1H, m), 4.25-3.95 (1H, m), 3.70 (1H, d), 3.31 (1H, dd), 3.11 (1H, dd), 3.06-2.68 (5H, m), 2.68-2.35 (2H, m), 2.35-1.82 (4H, m), 1.48 (9H, s), 1.28 (3H, d).

Preparation 366: (2R,5S)-4-Benzyl-5-(2,5-dioxo-pyrrolidin-1-ylmethyl)-2-methylpiperazine-1-carboxylic acid tert-butyl ester The title compound was prepared following similar methods to those described in Preparation 356 starting from (2R,5R)-4-benzyl-5-chloromethyl-2-methyl-piperazine-1-carboxylic acid tert-butyl ester and pyrrolidine-2,5-dione. $^1$H NMR (CDCl$_3$): 7.37-7.01 (5H, m), 4.24-4.06 (1H, m), 3.89 (1H, d), 3.80-3.47 (4H, m), 3.22 (2H, d), 3.09-2.78 (1H, m), 2.70-2.55 (4H, m), 2.33 (1H, dd), 1.48 (9H, s), 1.19 (3H, d).

Preparation 367: (2R,5S)-5-(2,5-Dioxo-pyrrolidin-1-ylmethyl)-2-methyl-piperazine-1-carboxylic acid tert-butyl ester The title compound was prepared following similar methods to those described in Preparation 357. $^1$H NMR (CDCl$_3$): 4.21-4.06 (1H, m), 3.96 (1H, dd), 3.68 (1H, d), 3.39 (1H, dd), 3.29 (2H, dd), 3.15 (1H, dd), 2.72 (4H, s), 2.38 (1H, dd), 1.81 (1H, s), 1.46 (9H, s), 1.17 (3H, d).

Preparation 368: (2R,5R)-4-{2-[6-(1,1-Difluoro-ethyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester The title compound was prepared following methods similar to those described in Preparation 203 starting from (2R,5R)-5-hydroxymethyl-2-methyl-piperazine-1-carboxylic acid tert-butyl ester (1.74 g, 7.5 mmol), 6-(1,1-difluoro-ethyl)-3,3-dimethyl-2,3-dihydro-1H-pyrrolo[3,2-b]pyridine (1.1 g, 5.0 mmol), chloroacetyl chloride (490 μL, 6.1 mmol) and DIPEA (3 mL, 16.6 mmol) to give the title compound (1.47 g) as an orange semi-solid. MS: [M+H]$^+$=483.

Preparation 369: (2R,5R)-5-Chloromethyl-4-{2-[6-(1,1-difluoro-ethyl)-3,3-dimethyl-2,3-dihydro-pyrrolo[3,2-b]pyridin-1-yl]-2-oxo-ethyl}-2-methyl-piperazine-1-carboxylic acid tert-butyl ester The title compound was prepared following methods similar to those described in Preparation 351 starting from (2R,5R)-4-{2-[6-(1,1-difluoro-ethyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester. MS: [M+H]$^+$=501.

Preparation 370: (2R,5R)-4-{2-[6-(Difluoro-phenyl-methyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester The title compound was prepared following methods similar to those described in Preparation 203 starting from (2R,5R)-5-hydroxymethyl-2-methyl-piperazine-1-carboxylic acid tert-butyl ester (1.1 g, 3.2 mmol), 6-(difluoro-phenyl-methyl)-3,3-dimethyl-2,3-dihydro-1H-pyrrolo[3,2-c]pyridine hydrochloride (1.0 g, 3.55 mmol), chloroacetyl chloride (282 µL, 3.55 mmol) and DIPEA (2 mL, 11.3 mmol) to give the title compound (1.37 g) as an orange gum. MS: [M+H]$^+$=545.

Preparation 371: (2R,5R)-5-Chloromethyl-4-{2-[6-(difluoro-phenyl-methyl)-3,3-dimethyl-2,3-dihydro-pyrrolo[3,2-c]pyridin-1-yl]-2-oxo-ethyl}-2-methyl-piperazine-1-carboxylic acid tert-butyl ester The title compound was prepared following methods similar to those described in Preparation 351 starting from (2R,5R)-4-{2-[6-(difluoro-phenyl-methyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester (1.37 g, 2.5 mmol), methanesulfonyl chloride (234 µL, 3.0 mmol) and TEA (582 uL, 4.0 mmol) to give the title compound (1.0 g) as a pale yellow gum. MS: [M+H]$^+$=563.

Preparation 372: (2R,5S)-4-Benzyl-2-methyl-5-((R)-3-methyl-morpholin-4-ylmethyl)-piperazine-1-carboxylic acid tert-butyl ester

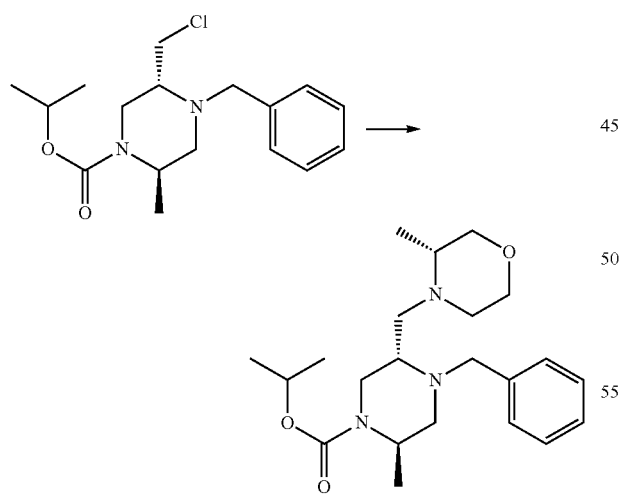

K$_2$CO$_3$ (81.6 g, 591 mmol) and KI (73.6 g, 443 mmol) were added to a solution of (2R,5R)-4-benzyl-5-chloromethyl-2-methyl-piperazine-1-carboxylic acid tert-butyl ester (50 g, 147.9 mmol) in acetonitrile (400 mL) followed by (R)-3-methyl-morpholine hydrochloride (26.4 g, 192 mmol). The reaction was stirred at 70° C. for 18 h. The solid was then removed by filtration and the solvent removed in vacuo. The crude material was purified by chromatography using a pad of silica (20% EtOAc in Petrol) to give the title compound (41.3 g) as a white solid. MS: [M+H]$^+$=404.

Preparation 373: (2R,5S)-2-Methyl-5-((R)-3-methyl-morpholin-4-ylmethyl)-piperazine-1-carboxylic acid tert-butyl ester

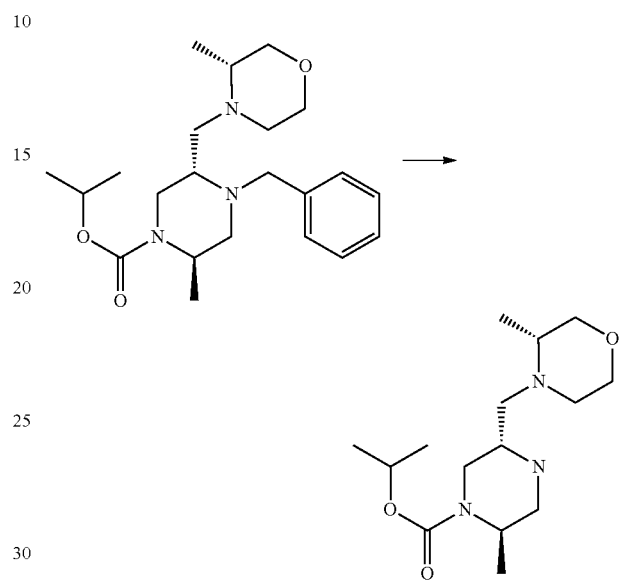

Pd/C (33 g) and acetic acid (220 mL) were added to a solution of (2R,5S)-4-benzyl-2-methyl-5-((R)-3-methyl-morpholin-4-ylmethyl)-piperazine-1-carboxylic acid tert-butyl ester (41.3 g, 102 mmol) in EtOH (300 mL). The mixture was stirred under H$_2$ (1 atmosphere) at room temperature for 18 h. The reaction mixture was then filtered through a pad of Celilte to remove the catalyst and the solvent was removed in vacuo. The crude material was partitioned between saturated aqueous NaHCO$_3$ and DCM and the product extracted with DCM (3×). The organic phase was dried over MgSO$_4$, filtered and concentrated in vacuo to give the title compound (30.5 g) as a pale yellow oil. $^1$H NMR (CDCl$_3$): 4.43-3.87 (1H, m), 3.78 (1H, d), 3.73-3.55 (3H, m), 3.32 (1H, dd), 3.22 (1H, dd), 3.16-2.93 (3H, m), 2.93-2.72 (1H, m), 2.55-2.35 (2H, m), 2.35-2.15 (2H, m), 1.89 (1H, dd), 1.45 (9H, s), 1.26 (3H, d), 0.96 (3H, d).

Preparation 374: (2R,5S)-4-Benzyloxycarbonylmethyl-2-methyl-5-((R)-3-methyl-morpholin-4-ylmethyl)-piperazine-1-carboxylic acid tert-butyl ester

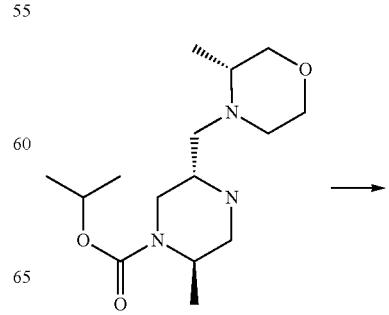

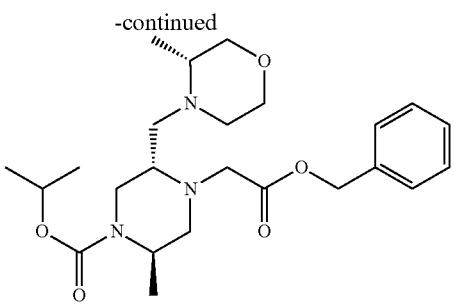

Benzyl bromoacetate (25.2 mL, 126 mmol) and K₂CO₃ (50 g, 389 mmol) were added to a solution of (2R,5S)-2-methyl-5-((R)-3-methyl-morpholin-4-ylmethyl)-piperazine-1-carboxylic acid tert-butyl ester (30.5 g, 97.4 mmol) in acetonitrile (300 mL) and the reaction was stirred at room temperature for 18 h. The solid was removed by filtration and the solvent was removed in vacuo. The crude material was purified by chromatography using a pad of silica eluting with EtOAc/Petrol (1/9 to 4/6) to give the title compound (39 g). MS: [M+H]⁺=462.

Preparation 375: (2R,5S)-4-Carboxymethyl-2-methyl-5-((R)-3-methyl-morpholin-4-ylmethyl)-piperazine-1-carboxylic acid tert-butyl ester

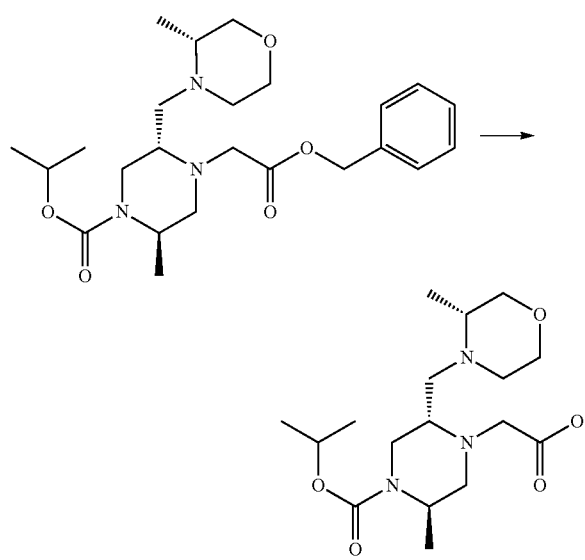

(2R,5S)-4-Benzyloxycarbonylmethyl-2-methyl-5-((R)-3-methyl-morpholin-4-ylmethyl)-piperazine-1-carboxylic acid tert-butyl ester (39 g, 84.6 mmol) in EtOH (200 mL) was hydrogenated (1 atmosphere H₂) in the presence of Pd/C (8.9 g) at room temperature for 2 h. The reaction mixture was filtered through Celite and the solvent was removed in vacuo to give the title compound (28 g) as a pale yellow solid. ¹H NMR (CDCl₃): 4.21-4.05 (1H, m), 4.05-3.83 (3H, m), 3.83-3.55 (4H, m), 3.55-3.27 (4H, m), 3.27-3.13 (1H, m), 3.05 (1H, s), 2.87 (1H, s), 2.64 (1H, dd), 2.50 (1H, d), 1.48 (9H, s), 1.37-1.06 (6H, m). MS: [M+H]⁺=372.

Preparation 376: 6-(2,4-Difluoro-benzyl)-3,3-dimethyl-2,3-dihydro-1H-pyrrolo[3,2-c]pyridine 5-oxide 3-Chloroperbenzoic acid (895 mg, 3.58 mmol) was added to a solution of 6-(2,4-difluoro-benzyl)-3,3-dimethyl-2,3-dihydro-pyrrolo[3,2-c]pyridine-1-carboxylic acid tert-butyl ester (895 mg, 2.39 mmol) in DCM (45 mL) and the mixture was stirred at room temperature for 3 hours. The mixture was washed twice with saturated aqueous sodium hydrogen carbonate, the organic layer was separated and the solvent removed in vacuo to afford 6-(2,4-difluoro-benzyl)-3,3-dimethyl-5-oxy-2,3-dihydro-pyrrolo[3,2-c]pyridine-1-carboxylic acid tert-butyl ester as a pale yellow oil that was used immediately without further purification. MS: [M+H]⁺ 391. A stirred solution of this material in ethyl acetate (10 mL) was treated with 4 M hydrogen chloride in 1,4-dioxane (5 mL) and the resulting mixture was stirred at room temperature overnight. The mixture was evaporated to dryness in vacuo and partitioned between ethyl acetate and 2 M sodium hydroxide. The organic layer was separated and the solvent removed in vacuo to afford a pale yellow solid that was rinsed with petroleum ether, filtered and sucked dry under reduced pressure to afford the title compound (570 mg, 82%) as a pale yellow solid. ¹H NMR (DMSO-d₆) 7.90 (1H, s), 7.40 (1H, m), 7.23 (1H, td), 7.06 (1H, td), 6.38 (1H, br s), 6.08 (1H, s), 3.98 (2H, s), 3.27 (2H, s), 1.26 (6H, s). MS: [M+H]⁺=291.

Preparation 377: (2R,5R)-5-Chloromethyl-4-{2-[6-(2,4-difluoro-benzyl)-3,3-dimethyl-2,3-dihydro-pyrrolo[3,2-c]pyridin-1-yl]-2-oxo-ethyl}-2-methyl-piperazine-1-carboxylic acid tert-butyl ester Chloroacetyl chloride (0.995 mL, 12.0 mmol) was added dropwise to a stirred solution of 6-(2,4-difluoro-benzyl)-3,3-dimethyl-2,3-dihydro-1H-pyrrolo[3,2-c]pyridine hydrochloride (3.10 g, 10.0 mmol) and triethylamine (4.6 mL, 33.0 mmol) in anhydrous DCM (50 mL) and the mixture was stirred at room temperature for 16 hours. (2R,5R)-5-Hydroxymethyl-2-methyl-piperazine-1-carboxylic acid tert-butyl ester (2.76 g, 12.0 mmol) was added and the mixture was stirred at room temperature for a further 16 hours. Further triethylamine (1 mL) and (2R,5R)-5-hydroxymethyl-2-methyl-piperazine-1-carboxylic acid tert-butyl ester (700 mg) were added and the mixture stirred for a further 16 hours. The mixture was diluted with DCM, washed with water, the organic layer separated and the solvent removed in vacuo. Chromatography (silica, elution with 30-100% ethyl acetate in petroleum ether) afforded (2R,5R)-4-{2-[6-(2,4-difluoro-benzyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester (4.36 g, 80%) as a pale tan foam. MS: [M+H]⁺ 545. Methanesulfonyl chloride (0.78 mL, 10.0 mmol) was added dropwise to a stirred solution of (2R,5R)-4-{2-[6-(2,4-difluoro-benzyl)-3,3-dimethyl-2,3-dihydro-pyrrolo[3,2-c]pyridin-1-yl]-2-oxo-ethyl}-5-hydroxymethyl-2-methyl-piperazine-1-carboxylic acid tert-butyl ester (4.36 g, 8.0 mmol) and triethylamine (1.67 mL, 12.0 mmol) in anhydrous DCM (40 mL) and the mixture was stirred at room temperature for 16 hours. The mixture was diluted with DCM, washed successively with saturated aqueous sodium hydrogen carbonate and then water. The organic layer was separated and the solvent removed in vacuo to afford the title compound (4.0 g, 71%) as a pale yellow foam. MS: [M+H]⁺=563, 565.

Preparation 378: (2R,5R)-4-[2-(6-Cyclohexyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester To a solution of (2R,5R)-4-[2-(6-cyclohex-1-enyl-3,3-dimethyl-2,3-dihydro-pyrrolo[3,2-c]pyridin-1-yl)-2-oxoethyl]-5-methoxymethyl-2-methyl-piperazine-1-carboxylic acid tert-butyl ester (see Table 1) (65 mg, 0.13 mmol) in EtOH (5 mL) was added palladium on carbon (10%, 20 mg) and the mixture was hydrogenated for 2 h. The catalyst was filtered and the filtrate evaporated to afford the title compound (60 mg, 92%) as a white solid. MS: [M+H]$^+$=515.

Preparation 379: 3,3-Dimethyl-6-(1-methyl-1H-pyrazol-4-yl)-2,3-dihydro-pyrrolo[3,2-c]pyridine-1-carboxylic acid tert-butyl ester A mixture of 1-methyl-4-(4,4,5,5-tetramethyl-[1,3,2]dioxaborolan-2-yl)-1H-pyrazole (0.609 g, 3.0 mmol), 6-chloro-3,3-dimethyl-2,3-dihydro-pyrrolo[3,2-c]pyridine-1-carboxylic acid tert-butyl ester (0.282 g, 1.0 mmol), potassium carbonate (0.414 g, 3.0 mmol), tris(dibenzylideneacetone)-dipalladium (0) (0.091 g, 0.1 mmol) and 2-dicyclohexylphosphino-2',6'-dimethoxybiphenyl (SPhos, 0.041 g, 0.1 mmol), 1,4-dioxane (6 mL) and water (1.5 mL) was heated at 90° C. for 18 h. The solvent was evaporated, water (30 mL) was added and the product extracted with EtOAc (3×20 mL). Combined organic extracts were dried (MgSO$_4$) and evaporated in vacuo to give an oil. Chromatography (SiO$_2$; gradient elution with 0-100% EtOAc in 40-60 petroleum ether) gave the title compound (0.267 g) as an oil. MS: [M+H]$^+$=329.

Preparation 380: 3,3-Dimethyl-6-(1-methyl-1H-pyrazol-4-yl)-2,3-dihydro-pyrrolo[3,2-c]pyridine Prepared from 3,3-dimethyl-6-(1-methyl-1H-pyrazol-4-yl)-2,3-dihydro-pyrrolo[3,2-c]pyridine-1-carboxylic acid tert-butyl ester using a procedure analogous to Prep 116. MS [M+H]$^+$ 229.

Preparation 381: 3,3-Dimethyl-6-thiophen-3-yl-2,3-dihydro-pyrrolo[3,2-c]pyridine-1-carboxylic acid tert-butyl ester Prepared from 6-chloro-3,3-dimethyl-2,3-dihydro-pyrrolo[3,2-c]pyridine-1-carboxylic acid tert-butyl ester and thiophen-3-boronic acid using a procedure similar to Prep 379. MS [M+H]$^+$ 331.

Preparation 382: 3,3-Dimethyl-6-thiophen-3-yl-2,3-dihydro-1H-pyrrolo[3,2-c]pyridine Prepared from 3,3-dimethyl-6-thiophen-3-yl-2,3-dihydro-pyrrolo[3,2-c]pyridine-1-carboxylic acid tert-butyl ester using a procedure analogous to that of Preparation 116. MS: [M+H]$^+$=231.

Preparation 383: 6-(Hydroxy-phenyl-methyl)-3,3-dimethyl-2,3-dihydro-pyrrolo[3,2-c]pyridine-1-carboxylic acid tert-butyl ester To a solution of 6-benzoyl-3,3-dimethyl-2,3-dihydro-pyrrolo[3,2-c]pyridine-1-carboxylic acid tert-butyl ester (0.35 g, 1.0 mmol) in methanol (10 mL) was added sodium borohydride (0.114 g, 3.0 mmol) and the reaction mixture was stirred for 1 hour. Water (5 mL) was added and the reaction mixture was concentrated. Water was added and the product was extracted with EtOAc. The combined organic phase was dried (MgSO$_4$) and evaporated in vacuo to give an oil. Chromatography (SiO$_2$; gradient elution with 0-60% EtOAc in 40-60 petroleum ether) gave the title compound (0.26 g, 73%) as an oil. MS: [M+H]$^+$=355.

Preparation 384: 6-(Methoxy-phenyl-methyl)-3,3-dimethyl-2,3-dihydro-pyrrolo[3,2-c]pyridine-1-carboxylic acid tert-butyl ester To a solution of 6-(hydroxy-phenyl-methyl)-3,3-dimethyl-2,3-dihydro-pyrrolo[3,2-c]pyridine-1-carboxylic acid tert-butyl ester (0.15 g, 0.42 mmol) in THF (5 mL) was added sodium hydride (60%, 0.02 g, 0.50 mmol) and the mixture was stirred for 1 h. Methyl iodide (52 uL, 0.84 mmol) was added and the reaction mixture was stirred for 18 h at ambient temperature. Water (10 mL) was added and the product was extracted with EtOAc (2×10 mL). The combined organic phase was dried (MgSO$_4$) and evaporated in vacuo to give an oil. Chromatography (SiO$_2$; gradient elution with 0-70% EtOAc in 40-60 petroleum ether) gave the title compound (0.11 g, 70%) as an oil. MS: [M+H]$^+$=369.

Preparation 385: 6-(Methoxy-phenyl-methyl)-3,3-dimethyl-2,3-dihydro-pyrrolo[3,2-c]pyridine Prepared from 6-(methoxy-phenyl-methyl)-3,3-dimethyl-2,3-dihydro-pyrrolo[3,2-c]pyridine-1-carboxylic acid tert-butyl ester using a procedure analogous to Prep 116. MS [M+H]$^+$ 269.

Preparation 386: 6-Furan-3-yl-3,3-dimethyl-2,3-dihydro-pyrrolo[3,2-c]pyridine-1-carboxylic acid tert-butyl ester Prepared from 6-chloro-3,3-dimethyl-2,3-dihydro-pyrrolo[3,2-c]pyridine-1-carboxylic acid tert-butyl ester and furan-3-boronic acid using an analogous procedure to that of Preparation 161. MS: [M+H]$^+$=315.

Preparation 387: 6-Furan-3-yl-3,3-dimethyl-2,3-dihydro-1H-pyrrolo[3,2-c]pyridine Prepared from 6-furan-3-yl-3,3-dimethyl-2,3-dihydro-pyrrolo[3,2-c]pyridine-1-carboxylic acid tert-butyl ester using a procedure analogous to that of Preparation 116. MS: [M+H]$^+$=215.

Preparation 388: 3,3-Dimethyl-6-(5-methyl-thiophen-2-yl)-2,3-dihydro-pyrrolo[3,2-c]pyridine-1-carboxylic acid tert-butyl ester Prepared from 6-chloro-3,3-dimethyl-2,3-dihydro-pyrrolo[3,2-c]pyridine-1-carboxylic acid tert-butyl ester and 4,4,5,5-tetramethyl-2-(5-methyl-thiophen-2-yl)-[1,3,2]dioxaborolane using a procedure similar to Preparation 379. MS: [M+H]$^+$=345.

Preparation 389: 3,3-Dimethyl-6-(5-methyl-thiophen-2-yl)-2,3-dihydro-1H-pyrrolo[3,2-c]pyridine Prepared from 3,3-dimethyl-6-(5-methyl-thiophen-2-yl)-2,3-dihydro-pyrrolo[3,2-c]pyridine-1-carboxylic acid tert-butyl ester using a procedure analogous to that of Preparation 116. MS: [M+H]$^+$=245.

Preparation 390: 6-Benzofuran-2-yl-3,3-dimethyl-2,3-dihydro-pyrrolo[3,2-c]pyridine-1-carboxylic acid tert-butyl ester Prepared from 6-chloro-3,3-dimethyl-2,3-dihydro-pyrrolo[3,2-c]pyridine-1-carboxylic acid tert-butyl ester and benzofuran-2-boronic acid using an analogous procedure to that of Preparation 161. MS: [M+H]$^+$=365.

Preparation 391: 6-Benzofuran-2-yl-3,3-dimethyl-2,3-dihydro-1H-pyrrolo[3,2-c]pyridine Prepared from 6-benzofuran-2-yl-3,3-dimethyl-2,3-dihydro-pyrrolo[3,2-c]pyridine-1-carboxylic acid tert-butyl ester using a procedure analogous to that of Preparation 116. MS: [M+H]$^+$=265.

Preparation 392: 6-Isopropenyl-3,3-dimethyl-2,3-dihydro-pyrrolo[3,2-c]pyridine-1-carboxylic acid tert-butyl ester Prepared from 6-chloro-3,3-dimethyl-2,3-dihydro-1H-pyrrolo[3,2-c]pyridine-1-carboxylic acid tert butyl ester and 2-isopropenyl-4,4,5,5-tetramethyl-[1,3,2]dioxaborolane using a procedure analogous to that of Preparation 379. MS: [M+H]$^+$=289.

Preparation 393: 6-Acetyl-3,3-dimethyl-2,3-dihydro-pyrrolo[3,2-c]pyridine-1-carboxylic acid tert-butyl ester Prepared from 6-isopropenyl-3,3-dimethyl-2,3-dihydro-pyrrolo[3,2-c]pyridine-1-carboxylic acid tert-butyl ester using a procedure analogous to that of Preparation 166. MS: [M+H]$^+$=291.

Preparation 394: 6-(1,1-Difluoro-ethyl)-3,3-dimethyl-2,3-dihydro-pyrrolo[3,2-c]pyridine-1-carboxylic acid tert-butyl ester Prepared from 6-acetyl-3,3-dimethyl-2,3-dihydro-pyrrolo[3,2-c]pyridine-1-carboxylic acid tert-butyl ester using a procedure analogous to that of Preparation 293. MS: [M+H]$^+$=313.

Preparation 395: 6-(1,1-Difluoro-ethyl)-3,3-dimethyl-2,3-dihydro-1H-pyrrolo[3,2-c]pyridine Prepared from 6-(1,1-difluoro-ethyl)-3,3-dimethyl-2,3-dihydro-pyrrolo[3,2-c]pyridine-1-carboxylic acid tert-butyl ester using a procedure analogous to that of Preparation 116. MS: [M+H]$^+$=213.

Preparation 396: 6-Benzoyl-3,3-dimethyl-2,3-dihydro-pyrrolo[3,2-b]pyridine-1-carboxylic acid tert-butyl ester n-Butyl lithium (5.0 mL of a 2.5 M solution in hexanes, 12 mmol) was added dropwise to a solution of 6-bromo-3,3-dimethyl-2,3-dihydro-pyrrolo[3,2-b]pyridine-1-carboxylic acid tert-butyl ester (3.27 g, 10.0 mmol) in diethyl ether (20 mL) at −78° C. The resulting orange slurry was stirred 30 minutes at this temperature, then a solution of N-methoxy-N-methyl-benzamide (2.3 mL, 15.0 mmol) in diethyl ether (10 mL) was added dropwise. The reaction was allowed to warm to room temperature and stirred 1 h further, then quenched with saturated aqueous ammonium chloride and the two layers were separated. The aqueous fraction was further extracted with EtOAc (2×20 mL). The combined organic fractions were dried over MgSO$_4$, filtered and concentrated. The residue was purified by column chromatography (0-30% EtOAc/petrol) to give the title compound (2.4 g, 67%) as a yellow solid. MS: [M+H]$^+$=353.

Preparation 397: 6-Benzoyl-3,3-dimethyl-2,3-dihydro-1H-pyrrolo[3,2-b]pyridine Prepared from 6-benzoyl-3,3-dimethyl-2,3-dihydro-pyrrolo[3,2-c]pyridine-1-carboxylic acid tert-butyl ester using a procedure analogous to that of Preparation 116. MS: [M+H]$^+$=253.

Preparation 398: 6-Acetyl-3,3-dimethyl-2,3-dihydro-pyrrolo[3,2-b]pyridine-1-carboxylic acid tert-butyl ester Prepared from 6-bromo-3,3-dimethyl-2,3-dihydro-pyrrolo[3,2-b]pyridine-1-carboxylic acid tert-butyl ester and N-methoxy-N-methyl-acetamide using a procedure analogous to that of Preparation 263. MS: [M+H]$^+$=291.

Preparation 399: 6-(1,1-Difluoro-ethyl)-3,3-dimethyl-2,3-dihydro-pyrrolo[3,2-b]pyridine-1-carboxylic acid tert-butyl ester Prepared from 6-acetyl-3,3-dimethyl-2,3-dihydro-pyrrolo[3,2-b]pyridine-1-carboxylic acid tert-butyl ester using a procedure analogous to that of Preparation 264. MS: [M+H]$^+$=313.

Preparation 400: 6-(1,1-Difluoro-ethyl)-3,3-dimethyl-2,3-dihydro-1H-pyrrolo[3,2-b]pyridine Prepared from 6-(1,1-difluoro-ethyl)-3,3-dimethyl-2,3-dihydro-pyrrolo[3,2-b]pyridine-1-carboxylic acid tert-butyl ester using a procedure analogous to that of Preparation 116. MS: [M+H]$^+$=213.

Preparation 401: 6-(2,4-Difluoro-benzyl)-3,3-dimethyl-2,3-dihydro-pyrrolo[3,2-b]pyridine-1-carboxylic acid tert-butyl ester To a nitrogen-degassed mixture of 6-bromo-3,3-dimethyl-2,3-dihydro-pyrrolo[3,2-b]pyridine-1-carboxylic acid tert-butyl ester (4.90 g, 15.0 mmol), lithium bromide (3.87 g, 45.0 mmol), (1,3-diisopropylimidazol-2-ylidene)(3-chloropyridyl)palladium (II) dichloride (0.2 g, 0.3 mmol), 1-methyl-2-pyrrolidinone (40 mL) and THF (40 mL) was added a solution of 2,4-difluoro-benzylzinc bromide in THF (0.5 M, 60 mL, 30 mmol) and resulting mixture was stirred at 20° C. for 1 h. The mixture was poured into water (200 mL) and 5% aqueous citric acid (50 mL) and the resulting mixture extracted with Et$_2$O (3×100 mL). The organic phase was washed with water (100 mL), brine (3×100 mL), dried (MgSO$_4$) and evaporated in vacuo to give an oil. Chromatography (SiO$_2$, eluted with petrol-EtOAc 0-30%) gave the title compound (5.7 g, 100%) as an oil. MS: [M+H]$^+$=375.

Preparation 402: 6-(2,4-Difluoro-benzyl)-3,3-dimethyl-2,3-dihydro-1H-pyrrolo[3,2-b]pyridine Prepared from 6-(2,4-difluoro-benzyl)-3,3-dimethyl-2,3-dihydro-pyrrolo[3,2-b]pyridine-1-carboxylic acid tert-butyl ester using a procedure analogous to that of Preparation 116. MS: [M+H]$^+$=275.

Preparation 403: 6-(4-Fluoro-benzyl)-3,3-dimethyl-2,3-dihydro-pyrrolo[3,2-b]pyridine-1-carboxylic acid tert-butyl ester

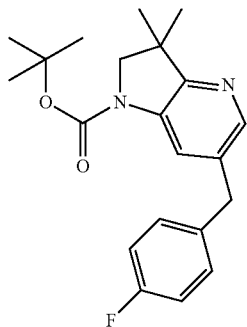 [SMILES: CC(C)(C)OC(=O)N1CC(C)(C)c2ncc(Cc3ccc(F)cc3)cc21]

To a nitrogen-degassed mixture of 6-bromo-3,3-dimethyl-2,3-dihydro-pyrrolo[3,2-b]pyridine-1-carboxylic acid tert-butyl ester (3.27 g, 10.0 mmol), lithium bromide (2.58 g, 30.0 mmol), (1,3-diisopropylimidazol-2-ylidene)(3-chloropyridyl)palladium (II) dichloride (0.136 g, 0.2 mmol), 1-methyl-2-pyrrolidinone (30 mL) and THF (30 mL) was added a solution of 4-fluoro-benzylzinc chloride in THF (0.5 M, 40 mL, 20 mmol) and resulting mixture was stirred at 20° C. for 3 h. The mixture was poured into water (150 mL) and 5% aqueous citric acid (30 mL) and the resulting mixture extracted with Et$_2$O (3×70 mL). The organic phase was washed with water (100 mL), brine (3×100 mL), dried (MgSO$_4$) and evaporated in vacuo to give an oil. Chromatography (SiO$_2$, eluted with petrol-EtOAc 0-30%) gave the title compound (3.5 g, 99%) as an oil. MS: [M+H]$^+$=357.

Preparation 404: 6-(4-Fluoro-benzyl)-3,3-dimethyl-2,3-dihydro-1H-pyrrolo[3,2-b]pyridine

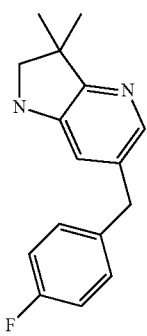 [SMILES: CC1(C)CNc2cc(Cc3ccc(F)cc3)cnc21]

A solution of 6-(4-fluoro-benzyl)-3,3-dimethyl-2,3-dihydro-pyrrolo[3,2-b]pyridine-1-carboxylic acid tert-butyl ester (9.0 g, 25 mmol) in methanol (62.5 mL) was treated with 5 M hydrochloric acid (62.5 mL) and the mixture stirred at 20° C. for 18 h then heated at 50° C. for 2 h. Solvent was evaporated and the residue was partitioned between water (200 mL) and EtOAc (3×). The aqueous phase was slowly poured into saturated aqueous NaHCO3 and the resulting solid collected by filtration to afford the title compound (3.45 g). 1H NMR (CDCl$_3$): 7.81 (1H, s), 7.16 (2H, dd), 6.99 (2H, t), 6.58 (1H, d), 3.84 (2H, s), 3.38 (2H, s), 1.36 (6H, s). MS: [M+H]$^+$=257. Further title compound (1.5 g) was obtained by aqueous acid extraction of the combined organic extracts and subsequent basificatioin of the combined aqueous extracts.

Preparation 405: 6-(Difluoro-phenyl-methyl)-3,3-dimethyl-2,3-dihydro-pyrrolo[3,2-b]pyridine-1-carboxylic acid tert-butyl ester Prepared from 6-benzoyl-3,3-dimethyl-2,3-dihydro-pyrrolo[3,2-b]pyridine-1-carboxylic acid tert-butyl ester using a procedure analogous to that of Preparation 264. MS: [M+H]$^+$=375.

Preparation 406: 6-(Difluoro-phenyl-methyl)-3,3-dimethyl-2,3-dihydro-1H-pyrrolo[3,2-b]pyridine Prepared from 6-(difluoro-phenyl-methyl)-3,3-dimethyl-2,3-dihydro-pyrrolo[3,2-b]pyridine-1-carboxylic acid tert-butyl ester using a procedure analogous to that of Preparation 116. MS: [M+H]$^+$=275.

Preparation 407: Cyclobutanecarboxylic acid methoxy-methyl-amide

To an ice-cooled suspension of N,O-dimethoxyhydroxylamine hydrochloride (1.95 g, 20 mmol) in DCM (50 mL) was added DIPEA (7.0 mL, 40.0 mmol) and cyclobutanecarboxylic acid (1.9 mL, 20 mmmol). After stirring for 5 min, EDC (4.2 g, 22.0 mmol) was added and the reaction mixture was stirred overnight while allowing it to warm to room temperature. The mixture was diluted with DCM (50 mL) and was transferred to a separatory funnel. The organic layer was washed with saturated aqueous NaHCO$_3$ (2×50 mL), water (1×50 mL), brine (50 mL), dried (MgSO$_4$) and concentrated. Chromatography (SiO$_2$, eluted with petrol-EtOAc 0-40%) gave the title compound (1.9 g, 67%) as an oil. MS: [M+H]$^+$=144.

Preparation 408: 6-Cyclobutanecarbonyl-3,3-dimethyl-2,3-dihydro-pyrrolo[3,2-b]pyridine-1-carboxylic acid tert-butyl ester Prepared from 6-bromo-3,3-dimethyl-2,3-dihydro-pyrrolo[3,2-b]pyridine-1-carboxylic acid tert-butyl ester and cyclobutanecarboxylic acid methoxy-methyl-amide using a procedure analogous to that of Preparation 263. MS: [M+H]$^+$=331.

Preparation 409: 6-(Cyclobutyl-difluoro-methyl)-3,3-dimethyl-2,3-dihydro-pyrrolo[3,2-b]pyridine-1-carboxylic acid tert-butyl ester Prepared from 6-cyclobutanecarbonyl-3,3-dimethyl-2,3-dihydro-pyrrolo[3,2-b]pyridine-1-carboxylic acid tert-butyl ester using a procedure analogous to that of Preparation 264. MS: [M+H]$^+$=353.

Preparation 410: 6-(Cyclobutyl-difluoro-methyl)-3,3-dimethyl-2,3-dihydro-1H-pyrrolo[3,2-b]pyridine Prepared from 6-(cyclobutyl-difluoro-methyl)-3,3-dimethyl-2,3-dihydro-pyrrolo[3,2-b]pyridine-1-carboxylic acid tert-butyl ester using a procedure analogous to that of Preparation 116. The hydrochloride salt initially obtained was partitioned between saturated aqueous NaHCO$_3$ and EtOAc to give the title compound. MS: [M+H]$^+$=253.

Preparation 411: 2-Cyclopropyl-N-methoxy-N-methyl-acetamide

Prepared from cyclopropyl acetic acid in an analogous fashion to Prep 407 MS [M+H]⁺=144.

Preparation 412: 6-(2-Cyclopropyl-acetyl)-3,3-dimethyl-2,3-dihydro-pyrrolo[3,2-b]pyridine-1-carboxylic acid tert-butyl ester Prepared from 6-bromo-3,3-dimethyl-2,3-dihydro-pyrrolo[3,2-b]pyridine-1-carboxylic acid tert-butyl ester and 2-cyclopropyl-N-methoxy-N-methyl-acetamide using a procedure analogous to that of Preparation 263. MS: [M+H]⁺=331.

Preparation 413: 6-(2-Cyclopropyl-1,1-difluoro-ethyl)-3,3-dimethyl-2,3-dihydro-pyrrolo[3,2-b]pyridine-1-carboxylic acid tert-butyl ester Prepared from 6-(2-cyclopropyl-acetyl)-3,3-dimethyl-2,3-dihydro-pyrrolo[3,2-b]pyridine-1-carboxylic acid tert-butyl ester using a procedure analogous to that of Preparation 264. MS: [M+H]⁺=353.

Preparation 414: 6-(2-Cyclopropyl-1,1-difluoro-ethyl)-3,3-dimethyl-2,3-dihydro-1H-pyrrolo[3,2-b]pyridine Prepared from 6-(2-cyclopropyl-1,1-difluoro-ethyl)-3,3-dimethyl-2,3-dihydro-pyrrolo[3,2-b]pyridine-1-carboxylic acid tert-butyl ester using a procedure analogous to that of Preparation 116. The hydrochloride salt initially obtained was partitioned between saturated aqueous NaHCO₃ and EtOAc to give the title compound. MS: [M+H]⁺=253.

Preparation 415: (2R,5S)-4-Benzyl-2-methyl-5-morpholin-4-ylmethyl-piperazine-1-carboxylic acid tert-butyl ester K₂CO₃ (12.4 g, 90.0 mmol), KI (8.29 g, 51.0 mmol) and morpholine (3.9 mL, 45.0 mmol) were added to a solution of (2R,5R)-4-benzyl-5-chloromethyl-2-methyl-piperazine-1-carboxylic acid tert-butyl ester (10.0 g, 30.0 mmol) in acetonitrile (150 mL). The reaction was stirred at 70° C. for 18 h. The solids were filtered off and the solvent was removed in vacuo. The residue was partitioned between DCM (150 mL) and water (150 mL). The organic phase was dried (MgSO₄) and evaporated. Chromatography (SiO₂, eluted with petrol-EtOAc 0-50%) gave the title compound (9.0 g, 77%) as a white solid. MS: [M+H]⁺=390.

Preparation 416: (2R,5S)-2-Methyl-5-morpholin-4-ylmethyl-piperazine-1-carboxylic acid tert-butyl ester Acetic acid (30.0 mL) and Pd/C (10%, 6.0 g) were added to a solution of (2R,5S)-4-benzyl-2-methyl-5-morpholin-4-ylmethyl-piperazine-1-carboxylic acid tert-butyl ester (9.0 g, 23.1 mmol) in EtOH (240 mL) and the resulting mixture was hydrogenated at 1 bar for 3 h. The catalyst was removed by filtration and the solvent was removed in vacuo. The residue was dissolved in DCM (150 mL), the organic solution was washed with saturated aqueous NaHCO₃ (150 mL), water (150 mL), dried (MgSO₄) and evaporated to give the title compound as a colourless gum (6.57 g, 95%). ¹H NMR (CDCl₃): 4.32-3.90 (1H, m), 3.77-3.64 (5H, m), 3.30 (1H, dd), 3.16-2.82 (2H, m), 2.67 (1H, dd), 2.59-2.49 (2H, m), 2.47-2.30 (2H, m), 2.21 (1H, dd), 2.17-2.07 (2H, m), 1.47 (9H, s), 1.27 (3H, d).

Preparation 417: (2R,5S)-4-Benzyloxycarbonylmethyl-2-methyl-5-morpholin-4-ylmethyl-piperazine-1-carboxylic acid tert-butyl ester Following similar methods to those described in Preparation 13 using (2R,5S)-2-methyl-5-morpholin-4-ylmethyl-piperazine-1-carboxylic acid tert-butyl ester (3.13, 10.5 mmol), benzylbromoacetate (2.16 m, 13.69 mmol) and K₂CO₃ (4.33 g, 31.5 mmol), gave the title compound (4.28 g, 91%). MS: [M+H]⁺=448.

Preparation 418: (2R,5S)-4-Carboxymethyl-2-methyl-5-morpholin-4-ylmethyl-piperazine-1-carboxylic acid tert-butyl ester Following similar methods to those described in Preparation 14, starting from (2R,5S)-4-benzyloxycarbonylmethyl-2-methyl-5-morpholin-4-ylmethyl)-piperazine-1-carboxylic acid tert-butyl ester (4.28 g, 9.57 mmol), and Pd/C (0.5 g), gave the title compound (3.2 g 94%) as a white solid. ¹H NMR (CDCl₃): 4.13 (2H, s), 3.96-3.78 (4H, m), 3.73 (1H, d), 3.59 (2H, d), 3.34 (1H, dd), 3.20 (1H, dd), 2.99 (1H, d), 2.84-2.74 (2H, m), 2.74-2.63 (2H, m), 2.55 (1H, dd), 2.38 (1H, dd), 1.56-1.37 (9H, m), 1.25 (3H, d).

Preparation 419: (2R,5R)-4-{2-[6-(4-Fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester Following methods similar to those described in Preparation 203 or General Procedure 5, starting from (2R,5R)-5-hydroxymethyl-2-methyl-piperazine-1-carboxylic acid tert-butyl ester (1.38 g, 6.0 mmol), 6-(4-fluoro-benzyl)-3,3-dimethyl-2,3-dihydro-1H-pyrrolo[3,2-b]pyridine hydrochloride (1.17 g, 4.0 mmol) using DIPEA as base gave the title compound (1.34 g, 64%) as an orange semi-solid. MS: [M+H]⁺=527.

Preparation 420: (2R,5R)-5-Chloromethyl-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester Following methods similar to those described in Preparation 316 starting from (2R,5R)-4-{2-[6-(4-fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester (1.38 g, 2.6 mmol), gave the title compound (1.11 g, 78%) as an orange semi-solid. MS: [M+H]⁺=545.

Preparation 421: (2R,5R)-4-{2-[6-(1,1-Difluoro-butyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester Following methods similar to those described in Preparation 203 or General Procedure 5, starting from (2R,5R)-5-hydroxymethyl-2-methyl-piperazine-1-carboxylic acid tert-butyl ester (0.69 g, 3.0 mmol), 6-(1,1-difluoro-butyl)-3,3-dimethyl-2,3-dihydro-1H-pyrrolo[3,2-b]pyridine, chloroacetyl chloride (185 µL, 2.3 mmol) and DIPEA (1.42 mL, 8.4 mmol), gave the title compound (0.61 g, 60%). MS: [M+H]$^+$=511.

Preparation 422: (2R,5R)-5-Chloromethyl-4-{2-[6-(1,1-difluoro-butyl)-3,3-dimethyl-2,3-dihydro-pyrrolo[3,2-b]pyridin-1-yl]-2-oxo-ethyl}-2-methyl-piperazine-1-carboxylic acid tert-butyl ester Following methods similar to those described in Preparation 316, starting from (2R,5R)-4-{2-[6-(1,1-difluoro-butyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester (0.61 g, 1.2 mmol), gave the title compound (0.7 g, 100%) as a brown semi-solid. MS: [M+H]$^+$=529.

Preparation 423: 6-(2-Fluoro-benzyl)-3,3-dimethyl-2,3-dihydro-pyrrolo[3,2-b]pyridine-1-carboxylic acid tert-butyl ester To a nitrogen-degassed mixture of 6-bromo-3,3-dimethyl-2,3-dihydro-pyrrolo[3,2-b]pyridine-1-carboxylic acid tert-butyl ester (4.09 g, 12.5 mmol), lithium bromide (3.22 g, 37.5 mmol), (1,3-diisopropylimidazol-2-ylidene)(3-chloropyridyl)palladium (II) dichloride (0.17 g, 0.25 mmol), 1-methyl-2-pyrrolidinone (30 mL) and THF (30 mL) was added a solution of 2-fluoro-benzylzinc chloride in THF (0.5 M, 40 mL, 20 mmol) and resulting mixture was stirred at 20° C. for 3 h. The mixture was poured into water (150 mL) and 5% aqueous citric acid (30 mL) and the resulting mixture extracted with Et$_2$O (3×70 mL). The organic phase was washed with water (100 mL), brine (3×100 mL), dried (MgSO$_4$) and evaporated in vacuo to give an oil. Chromatography (SiO$_2$, eluted with petrol-EtOAc 0-30%) gave the title compound (4.29 g 96%) as an oil. MS: [M+H]$^+$=357.

Preparation 424: 6-(4-Fluoro-benzyl)-3,3-dimethyl-2,3-dihydro-1H-pyrrolo[3,2-b]pyridine Prepared from 6-(2-fluoro-benzyl)-3,3-dimethyl-2,3-dihydro-pyrrolo[3,2-b]pyridine-1-carboxylic acid tert-butyl ester (3.69 g, 10.3 mmol) using a procedure analogous to that of Preparation 404 to afford the title compound (2.33 g, 88%) as an off-white solid. [M+H]$^+$=257.

Preparation 425: (2R,5R)-4-{2-[6-(2-Fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester Following methods similar to those described in Preparation 203 or General Procedure 5, starting from (2R,5R)-5-hydroxymethyl-2-methyl-piperazine-1-carboxylic acid tert-butyl ester (0.69 g, 3.0 mmol) and 6-(2-fluoro-benzyl)-3,3-dimethyl-2,3-dihydro-1H-pyrrolo[3,2-b]pyridine (0.55 g, 2.0 mmol) using DIPEA as base, gave the title compound (0.92 g, 87%) as an orange semi-solid. MS: [M+H]$^+$=527.

Preparation 426: (2R,5R)-5-Chloromethyl-4-{2-[6-(2-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester Following methods similar to those described in Preparation 316, starting from (2R,5R)-4-{2-[6-(2-fluoro-benzyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester (0.92 g, 1.74 mmol), gave the title compound (0.8 g, 84%) as an orange semi-solid. MS: [M+H]$^+$=545.

Preparation 427: (2R,5R)-4-{2-[6-(1,1-Difluoro-propyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester Following methods similar to those described in Prep 203 or General Procedure 5, starting from (2R,5R)-5-hydroxymethyl-2-methyl-piperazine-1-carboxylic acid tert-butyl ester (0.35 g, 3.0 mmol) and 6-(1,1-difluoro-propyl)-3,3-dimethyl-2,3-dihydro-1H-pyrrolo[3,2-b]pyridine (0.23 g, 1.0 mmol) using DIPEA as base, gave the title compound (0.33 g, 66%). MS [M+H]$^+$=497.

Preparation 428: (2R,5R)-5-Chloromethyl-4-{2-[6-(1,1-difluoro-propyl)-3,3-dimethyl-2,3-dihydro-pyrrolo[3,2-b]pyridin-1-yl]-2-oxo-ethyl}-2-methyl-piperazine-1-carboxylic acid tert-butyl ester Following methods similar to those described in Preparation 316, starting from (2R,5R)-4-{2-[6-(1,1-difluoro-propyl)-3,3-dimethyl-2,3-dihydro-pyrrolo[3,2-b]pyridin-1-yl]-2-oxo-ethyl}-5-hydroxymethyl-2-methyl-piperazine-1-carboxylic acid tert-butyl ester (0.32 g, 0.65 mmol), gave the title compound (0.33 g, 100%) as a tan solid. MS: [M+H]$^+$=515.

Preparation 429: (2R,5S)-4-Benzyloxycarbonylmethyl-5-((R)-3-fluoro-pyrrolidin-1-ylmethyl)-2-methyl-piperazine-1-carboxylic acid tert-butyl ester Prepared from (2R,5S)-5-((R)-3-fluoro-pyrrolidin-1-ylmethyl)-2-methyl-piperazine-1-carboxylic acid tert-butyl ester in an analogous manner to that described in Prep 13. MS: [M+H]$^+$=450

Preparation 430: (2R,5S)-4-Carboxymethyl-5-((R)-3-fluoro-pyrrolidin-1-ylmethyl)-2-methyl-piperazine-1-carboxylic acid tert-butyl ester Prepared from (2R,5S)-4-benzyloxycarbonylmethyl-5-((R)-3-fluoro-pyrrolidin-1-ylmethyl)-2-methyl-piperazine-1-carboxylic acid tert-butyl ester using a similar method to that described in Preparation 272 (EtOH used as solvent). $^1$H NMR (CDCl$_3$): 10.12-9.12 (1H, br s), 5.27 (1H, d), 4.17-3.89 (1H, m), 3.81-3.45 (3H, m), 3.45-2.78 (8H, m), 2.78-2.43 (2H, m), 2.42-1.99 (2H, m), 1.47 (9H, s), 1.23 (3H, d).

Compounds of Table 4 below were prepared using procedures analogous to that described in General Procedure 1 (see above), starting from the appropriate substituted 2,3-dihydroindole or dihydro-pyrrolopyridine and substituted carboxymethylpiperazine (synthesised as described above, Preparation reference numbers and significant differences from the general procedure are listed where appropriate).

TABLE 4

| Name | Characterising Data (MS or NMR) | Prep. No. |
|---|---|---|
| (2R,5R)-4-[2-(6-Cyano-3,3-dimethyl-2,3-dihydro-indol-1-yl)-2-oxo-ethyl]-5-methoxymethyl-2-methyl-piperazine-1-carboxylic acid tert-butyl ester | m/z: 457 | 14, 221 |
| (2R,5R)-4-{2-[6-(2,6-Dimethyl-phenoxy)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 553 | 14, 317 |
| (2R,5R)-4-(2-{6'-Chloro-1,1',2',3-tetrahydrospiro[indene-2,3'-indole]-1'-yl}-2-oxoethyl)-5-(methoxymethyl)-2-methylpiperazine-1-carboxylic acid tert-butyl ester | m/z: 540 | 14, 212 |
| (2R,5R)-4-[2-(6-Benzyl-3,3-dimethyl-2,3-dihydro-pyrrolo[3,2-c]pyridin-1-yl)-2-oxo-ethyl]-5-fluoromethyl-2-methyl-piperazine-1-carboxylic acid tert-butyl ester | m/z: 511 | 272, 153 |
| (2R,5R)-4-[2-(6-Benzyl-3,3-dimethyl-2,3-dihydro-pyrrolo[3,2-c]pyridin-1-yl)-2-oxo-ethyl]-5-difluoromethyl-2-methyl-piperazine-1-carboxylic acid tert-butyl ester | 529 | 277, 153 |
| (2R,5R)-4-[2-(6-Chloro-3-ethyl-3-methyl-2,3-dihydro-indol-1-yl)-2-oxo-ethyl]-5-methoxymethyl-2-methyl-piperazine-1-carboxylic acid tert-butyl ester | m/z: 480 | 14, 323[a] |
| (2R,5R)-4-{2-[3,3-Dimethyl-6-(1-methyl-1H-pyrazol-4-yl)-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 513 | 14, 380 |
| (2R,5R)-4-{2-[5-Bromo-3,3-dimethyl-6-(2-oxo-pyrrolidin-1-ylmethyl)-2,3-dihydro-indol-1-yl]-2-oxo-ethyl}-5-methoxymethyl-2-methyl-piperazine-1-carboxylic acid tert-butyl ester | m/z: 608 | 14, 228 |
| (2R,5R)-4-[2-(3,3-Dimethyl-6-thiophen-3-yl-2,3-dihydro-pyrrolo[3,2-c]pyridin-1-yl)-2-oxo-ethyl]-5-methoxymethyl-2-methyl-piperazine-1-carboxylic acid tert-butyl ester | m/z: 515 | 14, 382 |
| (2R,5R)-4-[2-(6-Bromo-3-methoxymethyl-3-methyl-2,3-dihydro-indol-1-yl)-2-oxo-ethyl]-5-methoxymethyl-2-methyl-piperazine-1-carboxylic acid tert-butyl ester | m/z: 540 | 14, 330[a] |
| (2R,5R)-4-{2-[6-(2,6-Difluoro-phenoxy)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 561 | 14, 318 |
| 6-Bromo-1-[2-((2R,5R)-4-tert-butoxycarbonyl-2-methoxymethyl-5-methyl-piperazin-1-yl)-acetyl]-3-methyl-2,3-dihydro-1H-indole-3-carboxylic acid methyl ester | m/z: 554 | 14, 331[a] |
| (2R,5R)-4-{2-[6-(2-Chloro-6-methyl-phenoxy)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 573 | 14, 319 |
| (2R,5R)-4-[2-(6-Chloro-3,3-dimethyl-2,3-dihydro-pyrrolo[2,3-b]pyridin-1-yl)-2-oxo-ethyl]-5-methoxymethyl-2-methyl-piperazine-1-carboxylic acid tert-butyl ester | $^1$H NMR (270 MHz, CDCl$_3$): 7.33 (1H, d, J = 7.8 Hz), 6.91 (1H, d), 4.30 (1H, d), 4.17-4.13 (1H, m), 3.85-4.01 (2H, m), 3.75-3.84 (2H, m), 3.60 (1H, dd), 3.28-3.41 (4H, m), 3.10-3.26 (2H, m), 2.65-2.86 (2H, m), 1.44 (9H, s), 1.31-1.29 (6H, d), 1.10- (3H, d | 14, 233 |
| (2R,5R)-5-Methoxymethyl-4-{2-[6-(methoxy-phenyl-methyl)-3,3-dimethyl-2,3-dihydro-pyrrolo[3,2-c]pyridin-1-yl]-2-oxo-ethyl}-2-methyl-piperazine-1-carboxylic acid tert-butyl ester | m/z: 553 | 14, 385 |
| (2R,5R)-4-[2-(6-Cyano-3,3,5-trimethyl-2,3-dihydro-indol-1-yl)-2-oxo-ethyl]-5-methoxymethyl-2-methyl-piperazine-1-carboxylic acid tert-butyl ester | m/z: 471 | 14, 231 |
| (2R,5R)-4-[2-(6-Cyano-3-methyl-3-phenyl-2,3-dihydro-indol-1-yl)-2-oxo-ethyl]-5-methoxymethyl-2-methyl-piperazine-1-carboxylic acid tert-butyl ester | m/z: 519 | 14, 337[a] |
| (2R,5R)-4-[2-(6-Bromo-3,3-dimethyl-2,3-dihydro-pyrrolo[3,2-b]pyridin-1-yl)-2-oxo-ethyl]-5-methoxymethyl-2-methyl-piperazine-1-carboxylic acid tert-butyl ester | $^1$H NMR (270 MHz, CDCl$_3$): 8.55-8.54 (1H, d), 8.25-8.24 (1H, d), 4.20-4.15 (1H, m), 4.02-3.86 (3H, m), 3.65-3.60 (2H, m), 3.45-3.24 (6H, m), 3.02-2.98 (1H, m), 2.85-2.79 (1H, dd), 2.67-2.61 (1H, dd), 2.03 (1H, s), 1.62 (1H, s), 1.45 (9H, s) and 1.37 (7H, s). MS: [M + H] 511 | 14, 236 |

TABLE 4-continued

| Name | Characterising Data (MS or NMR) | Prep. No. |
|---|---|---|
| (2R,5R)-4-[2-(6-Chloro-3,3-dimethyl-2,3-dihydro-indol-1-yl)-2-oxo-ethyl]-2-methyl-5-pyrazol-1-ylmethyl-piperazine-1-carboxylic acid tert-butyl ester | m/z: 502 | 280, 25 |
| (2R,5R)-4-{2-[6-Chloro-3,3-dimethyl-5-(3-methyl-[1,2,4]oxadiazol-5-yl)-2,3-dihydro-indol-1-yl]-2-oxo-ethyl}-5-methoxymethyl-2-methyl-piperazine-1-carboxylic acid tert-butyl ester | m/z: 548 | 14, 247 |
| (2R,5R)-4-(2-{6'-Chloro-1,1',2',3-tetrahydrospiro[indene-2,3'-indole]-1'-yl}-2-oxoethyl)-2-methyl-5-(1H-pyrazol-1-ylmethyl)piperazine-1-carboxylic acid tert-butyl ester | m/z: 576 | 280, 212 |
| (2R,5R)-4-[2-(6-Cyano-3-methyl-3-phenyl-2,3-dihydro-indol-1-yl)-2-oxo-ethyl]-2-methyl-5-pyrazol-1-ylmethyl-piperazine-1-carboxylic acid tert-butyl ester | m/z: 555 | 280, 337[a] |
| (2R,5R)-4-[2-(6-Benzyl-3-methyl-3-pyridin-2-yl-2,3-dihydro-indol-1-yl)-2-oxo-ethyl]-5-methoxymethyl-2-methyl-piperazine-1-carboxylic acid tert-butyl ester | m/z: 585 | 14, 343[a] |
| (2R,5R)-4-[2-(6-Benzyl-3,3-dimethyl-2,3-dihydro-pyrrolo[3,2-c]pyridin-1-yl)-2-oxo-ethyl]-2-methyl-5-(4-methyl-pyrazol-1-ylmethyl)-piperazine-1-carboxylic acid tert-butyl ester | m/z: 573 | 284, 153 |
| (2R,5R)-4-[2-(6-Cyano-3-methyl-3-pyridin-2-yl-2,3-dihydro-indol-1-yl)-2-oxo-ethyl]-5-methoxymethyl-2-methyl-piperazine-1-carboxylic acid tert-butyl ester | $^1$H NMR (Me-d3-OD): 8.59-8.42 (2H, m), 7.99 (1H, s), 7.85-7.71 (1H, m), 7.51-7.19 (3H, m), 4.57-4.19 (2H, m), 3.95 (2H, t), 3.83-3.65 (1H, m), 3.65-3.42 (5H, m), 3.29-3.10 (2H, m), 2.86-2.72 (2H, m), 2.72-2.46 (1H, m), 1.56-1.39 (12H, m), 1.39-1.17 (3H, m). | 14, 345[a] |
| (2R,5R)-4-[2-(6-Benzyl-3,3-dimethyl-2,3-dihydro-pyrrolo[3,2-c]pyridin-1-yl)-2-oxo-ethyl]-5-(4-fluoro-pyrazol-1-ylmethyl)-2-methyl-piperazine-1-carboxylic acid tert-butyl ester | 577 | 288, 153 |
| (2R,5R)-4-(2-{6'-Cyano-1,1',2',3-tetrahydrospiro[indene-2,3'-indole]-1'-yl}-2-oxoethyl)-2-methyl-5-[(4-methyl-1H-pyrazol-1-yl)methyl]piperazine-1-carboxylic acid, tert-butyl ester | m/z: 581 | 284, 213 |
| (2R,5R)-4-[2-(6-Benzyl-3-methyl-3-pyridin-3-yl-2,3-dihydro-indol-1-yl)-2-oxo-ethyl]-5-methoxymethyl-2-methyl-piperazine-1-carboxylic acid tert-butyl ester | m/z: 585 | 14, 347[a] |
| (2R,5R)-4-[2-(6-Benzyl-3,3-dimethyl-2,3-dihydro-pyrrolo[3,2-b]pyridin-1-yl)-2-oxo-ethyl]-5-(4-fluoro-pyrazol-1-ylmethyl)-2-methyl-piperazine-1-carboxylic acid tert-butyl ester | m/z: 577 | 288, 239 |
| (2R,5R)-4-{2-[6-Benzyl-3-methyl-3-(3-methyl-isoxazol-5-yl)-2,3-dihydro-indol-1-yl]-2-oxo-ethyl}-5-methoxymethyl-2-methyl-piperazine-1-carboxylic acid tert-butyl ester | m/z: 589 | 14, 348[a] |
| (2R,5R)-4-{2-[6-(Difluoro-phenyl-methyl)-3,3-dimethyl-2,3-dihydro-pyrrolo[3,2-c]pyridin-1-yl]-2-oxo-ethyl}-5-(4-fluoro-pyrazol-1-ylmethyl)-2-methyl-piperazine-1-carboxylic acid tert-butyl ester | m/z: 613 | 288, 290 |
| (2R,5R)-4-{2-[6-(2-Chloro-phenoxy)-3,3-dimethyl-2,3-dihydro-pyrrolo[3,2-c]pyridin-1-yl]-2-oxo-ethyl}-5-(4-fluoro-pyrazol-1-ylmethyl)-2-methyl-piperazine-1-carboxylic acid tert-butyl ester | m/z: 613 | 288, 216 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 612 | 262, 160 |
| (2R,5S)-4-{2-[6-(2-Chloro-phenoxy)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 612 | 262, 216 |
| (2R,5R)-4-[2-(3-Chloro-7,7-dimethyl-6,7-dihydro-pyrrolo[3,2-c]pyridazin-5-yl)-2-oxo-ethyl]-5-methoxymethyl-2-methyl-piperazine-1-carboxylic acid tert-butyl ester | $^1$H NMR (Me-d3-OD): 8.00 (1H, s), 4.23-4.06 (3H, m), 3.96 (1H, d), 3.84-3.69 (1H, m), 3.69-3.58 (2H, m), 3.09-2.98 (1H, m), 2.88 (1H, dd), 2.68 (1H, dd), 1.51 (6H, d), 1.49 (9H, s), 1.24 (3H, d). | 14, 243 |

TABLE 4-continued

| Name | Characterising Data (MS or NMR) | Prep. No. |
|---|---|---|
| (2R,5S)-4-{2-[6-(2-Fluoro-benzyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 594 | 262, 119 |
| (2R,5S)-4-{2-[6-(2-Fluoro-benzyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 594 | 262, 424 |
| (R)-4-{2-[6-(4-Fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester | m/z: 497 | 15, 156 |

Note:
[a] DIPEA used as base instead of TEA

General Procedure 4 (Amide Coupling Using HATU)

(2R,5S)-4-{2-[6-(1,1-Difluoro-propyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester

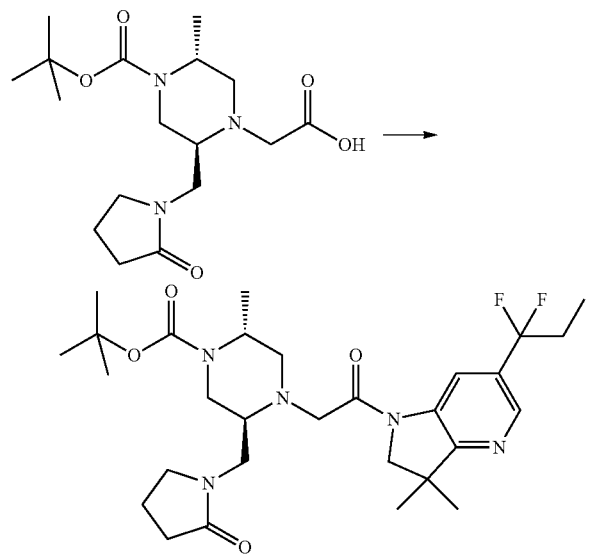

(2R,5S)-4-Carboxymethyl-2-methyl-5-(2-oxo-pyrrolidin-1-ylmethyl)-piperazine-1-carboxylic acid tert-butyl ester (0.20 g, 0.56 mmol) and 6-(1,1-difluoro-propyl)-3,3-dimethyl-2,3-dihydro-1H-pyrrolo[3,2-b]pyridine (0.15 g, 0.6 mmol) were dissolved in DMF (2.8 mL). N,N-Diisopropylethylamine (0.36 g, 2.8 mmol) and O-(7-azabenzotriazol-1-yl)-N,N,N',N'-tetramethyluronium hexafluorophosphate (0.43 g, 1.1 mmol) were added and the reaction stirred at room temperature for 18 h. Saturated aqueous sodium bicarbonate (10 mL) was added and the aqueous phase extracted with EtOAc (3×10 mL). The combined organic extracts were diluted with petroleum spirit (20 mL), washed with water (3×), dried with sodium sulfate, filtered and concentrated. Chromatography (silica gel, gradient elution, 0-5%, methanol in EtOAc) gave the title compound (0.178 g), MS: $[M+H]^+=564$.

Compounds of Table 5 below were prepared using procedures analogous to that described in General Procedure 4 above, starting from the appropriate substituted 2,3-dihydroindole or dihydro-pyrrolopyridine and substituted carboxymethylpiperazine (synthesised as described above, Preparation reference numbers are listed where appropriate).

TABLE 5

| Name | MS Data | Prep. Nos |
|---|---|---|
| (2R,5R)-4-[2-(6-Furan-3-yl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | m/z: 499 | 14, 387 |
| (2R,5R)-4-{2-[6-(Difluoro-phenyl-methyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 559 | 14, 290 |
| (2R,5R)-4-{2-[3,3-Dimethyl-6-(5-methyl-thiophen-2-yl)-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 529 | 14, 389 |
| (2R,5R)-4-[2-(6-Benzofuran-2-yl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester | m/z: 549 | 14, 391 |

TABLE 5-continued

| Name | MS Data | Prep. Nos |
|---|---|---|
| (2R,5R)-4-{2-[6-(1,1-Difluoro-ethyl)-3,3-dimethyl-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 497 | 14, 395 |
| (2R,5S)-4-{2-[6-(1,1-Difluoro-ethyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 550 | 262, 395 |
| (2R,5S)-4-[2-(6-Benzoyl-3,3-dimethyl-2,3-dihydro-pyrrolo[3,2-b]pyridin-1-yl)-2-oxo-ethyl]-2-methyl-5-(2-oxo-pyrrolidin-1-ylmethyl)-piperazine-1-carboxylic acid tert-butyl ester | m/z: 590 | 262, 397 |
| (2R,5S)-4-{2-[6-(1,1-Difluoro-ethyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 550 | 262, 400 |
| (2R,5S)-4-{2-[6-(2-Chloro-phenoxy)-3,3-dimethyl-2,3-dihydro-pyrrolo[3,2-c]pyridin-1-yl]-2-oxo-ethyl}-2-methyl-5-(2-oxo-oxazolidin-3-ylmethyl)-piperazine-1-carboxylic acid tert-butyl ester | m/z: 614 | 355, 216 |
| (2R,5S)-4-{2-[6-(1,1-Difluoro-propyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 564 | 262, 250 |
| (2R,5S)-4-{2-[6-(1,1-Difluoro-propyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 564 | 262, 294 |
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 612 | 262, 402 |
| (2R,5S)-4-{2-[6-(Difluoro-phenyl-methyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 612 | 262, 406 |
| (2R,5S)-4-{2-[6-(1,1-Difluoro-2-methyl-propyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 578 | 262, 298 |
| (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 594 | 262, 404 |
| (2R,5S)-4-{2-[6-(1,1-Difluoro-3-methyl-butyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 592 | 262, 267 |
| (2R,5S)-4-{2-[6-(1,1-Difluoro-butyl)-3,3-dimethyl-2,3-dihydro-pyrrolo[3,2-b]pyridin-1-yl]-2-oxoethyl}-2-methyl-5-(2-oxo-pyrrolidin-1-ylmethyl)-piperazine-1-carboxylic acid tert-butyl ester | m/z: 578 | 262, 265 |
| (2R,5S)-4-{2-[6-(1,1-Difluoro-butyl)-3,3-dimethyl-2,3-dihydro-pyrrolo[3,2-b]pyridin-1-yl]-2-oxo-ethyl}-5-((R)-3-fluoro-pyrrolidin-1-ylmethyl)-2-methyl-piperazine-1-carboxylic acid tert-butyl ester | m/z: 582 | 430, 265 |
| (2R,5S)-4-{2-[6-(1,1-Difluoro-butyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 578 | 262, 314 |
| (2R,5S)-4-{2-[6-(2-Cyclopropyl-1,1-difluoro-ethyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 592 | 418, 414 |
| (2R,5S)-4-{2-[6-(Difluoro-phenyl-methyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 614 | 418, 406 |
| (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 596 | 418, 404 |
| (2R,5S)-4-{2-[6-(1,1-Difluoro-3-methyl-butyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 594 | 418, 267 |
| (2R,5S)-4-{2-[6-(1,1-Difluoro-butyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 580 | 418, 265 |
| (2R,5S)-4-{2-[6-(2-Fluoro-benzyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 596 | 418, 424 |
| (2R,5S)-4-{2-[6-(4-Fluoro-benzyl)-3,3-dimethyl-2,3-dihydro-pyrrolo[3,2-c]pyridin-1-yl]-2-oxo-ethyl}-2-methyl-5-((R)-3-methyl-morpholin-4-ylmethyl)-piperazine-1-carboxylic acid tert-butyl ester | m/z: 610 | 375, 156 |
| (2R,5S)-4-{2-[6-(1,1-Difluoro-butyl)-3,3-dimethyl-2,3-dihydro-pyrrolo[3,2-c]pyridin-1-yl]-2-oxo-ethyl}-2-methyl-5-((R)-3-methyl-morpholin-4-ylmethyl)-piperazine-1-carboxylic acid tert-butyl ester | m/z: 594 | 375, 314 |
| (2R,5S)-4-{2-[6-(1,1-Difluoropropyl)-3,3-dimethyl-1H,2H,3H-pyrrolo[3,2-b]pyridin-1-yl]-2-oxoethyl}-2-methyl-5-{[(3R)-3-methylmorpholin-4-yl]methyl}piperazine-1-carboxylic acid tert-butyl ester | m/z: 580 | 375, 250 |

General Procedure 5 (3 Component Coupling)

(2R,5S)-4-{2-[6-(4-Fluoro-benzyl)-3,3-dimethyl-2,3-dihydro-pyrrolo[3,2-c]pyridin-1-yl]-2-oxo-ethyl}-2-methyl-5-morpholin-4-ylmethyl-piperazine-1-carboxylic acid tert-butyl ester To a stirred solution of 6-(4-fluoro-benzyl)-3,3-dimethyl-2,3-dihydro-1H-pyrrolo[3,2-c]pyridine (0.11 g, 0.43 mmol) and diisopropylethylamine (0.082 mL, 0.061 g, 0.47 mmol) in DCM (3 mL) at 0° C. under nitrogen was added chloroacetyl chloride (0.036 mL, 0.051 g, 0.45 mmol) and the mixture was stirred at 20° C. for 1 h. Further diisopropylethylamine (0.22 mL, 0.166 g, 1.29 mmol) was added, followed by a solution of (2R,5S)-4-carboxymethyl-2-methyl-5-morpholin-4-ylmethyl-piperazine-1-carboxylic acid tert-butyl ester (0.141 g, 0.47 mmol) in DCM (2 mL). The mixture was stirred at 35° C. for 64 h, then the mixture was partitioned between saturated aqueous NaHCO$_3$ and DCM (×3) and combined organic extracts were dried and evaporated. Chromatography (SiO$_2$, gradient elution with 0-100% EtOAc in 40-60 PE) gave the title compound (0.184 g) as an oil. MS: [M+H]$^+$=596.

Compounds of Table 6 below were prepared using procedures analogous to that described in General Procedure 5 above, starting from the appropriate substituted 2,3-dihydroindole or dihydro-pyrrolopyridine and substituted piperazine (synthesised as described above). In cases where the alkylation step was slow, gentle heating of the reaction mixture was carried out (as in the above illustration), otherwise reactions were run at room temperature. Preparation reference numbers and significant differences from the general procedure are listed where appropriate.

TABLE 6

| Name | MS data | Comments | Prep No. |
|---|---|---|---|
| (2R,5R)-4-[2-(6-Benzyl-3,3-dimethyl-2,3-dihydro-pyrrolo[3,2-c]pyridin-1-yl)-2-oxo-ethyl]-2-methyl-5-(pyrrolidine-1-carbonyl)-piperazine-1-carboxylic acid tert-butyl ester | m/z: 576 | TEA used as base | 201, 153 |
| (2R,5R)-4-[2-(6-Benzyl-3,3-dimethyl-2,3-dihydro-pyrrolo[3,2-c]pyridin-1-yl)-2-oxo-ethyl]-2-methyl-5-(piperidine-1-carbonyl)-piperazine-1-carboxylic acid tert-butyl ester | m/z: 590 | TEA used as base | 202, 153 |
| (2R,5R)-4-[2-(6-Chloro-3,3-diethyl-2,3-dihydro-indol-1-yl)-2-oxo-ethyl]-2-methyl-5-(morpholine-4-carbonyl)-piperazine-1-carboxylic acid tert-butyl ester | m/z: 563 | TEA used as base | 199, 350 |
| (2R,5R)-4-[2-(6-Cyano-3-methyl-3-phenyl-2,3-dihydro-indol-1-yl)-2-oxo-ethyl]-2-methyl-5-(morpholine-4-carbonyl)-piperazine-1-carboxylic acid tert-butyl ester | m/z: 588 | TEA used as base | 199, 337 |
| (2R,5R)-4-{2-[6-(2-Chloro-phenoxy)-3,3-dimethyl-2,3-dihydro-pyrrolo[3,2-c]pyridin-1-yl]-2-oxo-ethyl}-5-dimethylcarbamoyl-2-methyl-piperazine-1-carboxylic acid tert-butyl ester | m/z: 586 | TEA used as base | 197, 216 |
| (2R,5R)-4-{2-[6-(Difluoro-phenyl-methyl)-3,3-dimethyl-2,3-dihydro-pyrrolo[3,2-c]pyridin-1-yl]-2-oxo-ethyl}-5-dimethylcarbamoyl-2-methyl-piperazine-1-carboxylic acid tert-butyl ester | m/z: 586 | TEA used as base | 197, 290 |
| (2R,5R)-4-{2-[6-(Difluoro-phenyl-methyl)-3,3-dimethyl-2,3-dihydro-pyrrolo[3,2-c]pyridin-1-yl]-2-oxo-ethyl}-2-methyl-5-(4-methyl-pyrazol-1-ylmethyl)-piperazine-1-carboxylic acid tert-butyl ester | m/z: 609 | TEA used as base | 282, 290 |
| (2R,5R)-4-[2-(6-Benzyl-3,3-dimethyl-2,3-dihydro-pyrrolo[3,2-b]pyridin-1-yl)-2-oxo-ethyl]-2-methyl-5-(morpholine-4-carbonyl)-piperazine-1-carboxylic acid tert-butyl ester | m/z: 592 | TEA used as base | 199, 239 |
| (2R,5R)-4-{2-[6-(2,4-Difluoro-benzyl)-3,3-dimethyl-2,3-dihydro-pyrrolo[3,2-c]pyridin-1-yl]-2-oxo-ethyl}-5-dimethylcarbamoyl-2-methyl-piperazine-1-carboxylic acid tert-butyl ester | m/z: 586 | TEA used as base | 197, 160 |
| (2R,5R)-4-{2-[6-(2-Chloro-phenoxy)-3,3-dimethyl-2,3-dihydro-pyrrolo[3,2-c]pyridin-1-yl]-2-oxo-ethyl}-2-methyl-5-(morpholine-4-carbonyl)-piperazine-1-carboxylic acid tert-butyl ester | m/z: 628 | TEA used as base | 199, 216 |
| (2R,5R)-4-{2-[6-(2,4-Difluoro-benzyl)-3,3-dimethyl-5-oxy-2,3-dihydro-pyrrolo[3,2-c]pyridin-1-yl]-2-oxo-ethyl}-5-methoxymethyl-2-methyl-piperazine-1-carboxylic acid tert-butyl ester | m/z: 575 | TEA used as base | 14, 376 |
| (2R,5R)-4-{2-[6-(2,4-Difluoro-benzyl)-3,3-dimethyl-5-oxy-2,3-dihydro-pyrrolo[3,2-c]pyridin-1-yl]-2-oxo-ethyl}-5-dimethylcarbamoyl-2-methyl-piperazine-1-carboxylic acid tert-butyl ester | m/z: 602 | TEA used as base | 197, 376 |
| (2R,5R)-4-[2-(6-Benzyl-3,3-dimethyl-2,3-dihydro-pyrrolo[3,2-b]pyridin-1-yl)-2-oxo-ethyl]-5-dimethylcarbamoyl-2-methyl-piperazine-1-carboxylic acid tert-butyl ester | m/z: 550 | TEA used as base | 197, 239 |
| (2R,5S)-4-[2-(6-Benzyl-3,3-dimethyl-2,3-dihydro-pyrrolo[3,2-c]pyridin-1-yl)-2-oxo-ethyl]-2-methyl-5-(2-oxo-pyrrolidin-1-ylmethyl)-piperazine-1-carboxylic acid tert-butyl ester | m/z: 576 | TEA used as base | 260, 153 |
| (2R,5S)-4-{2-[6-(Difluoro-phenyl-methyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 612 | TEA used as base | 260, 290 |
| (2R,5R)-4-{2-[6-(Difluoro-phenyl-methyl)-3,3-dimethyl-2,3-dihydro-pyrrolo[3,2-c]pyridin-1-yl]-2-oxo-ethyl}-2-methyl-5-(morpholine-4-carbonyl)-piperazine-1-carboxylic acid tert-butyl ester | m/z: 628 | TEA used as base | 199, 290 |

TABLE 6-continued

| Name | MS data | Comments | Prep No. |
|---|---|---|---|
| (2R,5S)-4-[2-(6-Benzyl-3,3-dimethyl-2,3-dihydro-pyrrolo[3,2-b]pyridin-1-yl)-2-oxo-ethyl]-2-methyl-5-(2-oxo-pyrrolidin-1-ylmethyl)-piperazine-1-carboxylic acid tert-butyl ester | m/z: 576 | TEA used as base | 260, 239 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(3-oxo-morpholin-4-ylmethyl)-piperazine-1-carboxylic acid tert-butyl ester | m/z: 628 | TEA used as base | 357, 160 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(2-oxo-piperidin-1-ylmethyl)-piperazine-1-carboxylic acid tert-butyl ester | m/z: 626 | TEA used as base | 359, 160 |
| (2R,5S)-4-{2-[6-(Difluoro-phenyl-methyl)-3,3-dimethyl-2,3-dihydro-pyrrolo[3,2-c]pyridin-1-yl]-2-oxo-ethyl}-2-methyl-5-(3-methyl-2-oxo-imidazolidin-1-ylmethyl)-piperazine-1-carboxylic acid tert-butyl ester | m/z: 627 | TEA used as base | 361, 290 |
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-2-methyl-5-(2-oxo-oxazolidin-3-ylmethyl)-piperazine-1-carboxylic acid tert-butyl ester | m/z: 614 | TEA used as base | 353, 402 |
| (2R,5S)-4-{2-[3-(2,4-Difluoro-benzyl)-7,7-dimethyl-6,7-dihydro-pyrrolo[3,2-c]pyridazin-5-yl]-2-oxo-ethyl}-2-methyl-5-(2-oxo-pyrrolidin-1-ylmethyl)-piperazine-1-carboxylic acid tert-butyl ester | m/z: 613 | bromoacetyl bromide used instead of chloroacetyl chloride | 260, 252 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-5-((S)-3-fluoro-pyrrolidin-1-ylmethyl)-2-methyl-piperazine-1-carboxylic acid tert-butyl ester | m/z: 616 | TEA used as base | 363, 160 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-5-((R)-3-fluoro-pyrrolidin-1-ylmethyl)-2-methyl-piperazine-1-carboxylic acid tert-butyl ester | m/z: 616 | TEA used as base | 365, 160 |
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-5-((S)-3-fluoro-pyrrolidin-1-ylmethyl)-2-methyl-piperazine-1-carboxylic acid tert-butyl ester | m/z: 616 | TEA used as base | 363, 402 |
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-5-((R)-3-fluoro-pyrrolidin-1-ylmethyl)-2-methyl-piperazine-1-carboxylic acid tert-butyl ester | m/z: 616 | | 365, 402 |
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-2-methyl-5-(2-oxo-oxazolidin-3-ylmethyl)-piperazine-1-carboxylic acid tert-butyl ester | m/z: 614 | TEA used as base | 353, 160 |
| (2R,5S)-4-{2-[6-(Cyclopropyl-difluoro-methyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 576 | bromoacetyl bromide used instead of chloroacetyl chloride | 260, 302 |
| (2R,5S)-4-{2-[6-(Difluoro-phenyl-methyl)-3,3-dimethyl-2,3-dihydro-pyrrolo[3,2-c]pyridin-1-yl]-2-oxo-ethyl}-5-((R)-3-fluoro-pyrrolidin-1-ylmethyl)-2-methyl-piperazine-1-carboxylic acid tert-butyl ester | m/z: 616 | TEA used as base | 365, 290 |
| (2R,5S)-4-{2-[6-(1,1-Difluoro-propyl)-3,3-dimethyl-2,3-dihydro-pyrrolo[3,2-c]pyridin-1-yl]-2-oxo-ethyl}-5-((R)-3-fluoro-pyrrolidin-1-ylmethyl)-2-methyl-piperazine-1-carboxylic acid tert-butyl ester | m/z: 568 | bromoacetyl bromide used instead of chloroacetyl chloride | 365, 294 |
| (2R,5S)-4-{2-[6-(Difluoro-phenyl-methyl)-3,3-dimethyl-2,3-dihydro-pyrrolo[3,2-c]pyridin-1-yl]-2-oxo-ethyl}-5-(2,5-dioxo-pyrrolidin-1-ylmethyl)-2-methyl-piperazine-1-carboxylic acid tert-butyl ester | m/z: 626 | TEA used as base | 367, 290 |
| (2R,5S)-4-{2-[6-(Difluoro-phenyl-methyl)-3,3-dimethyl-2,3-dihydro-pyrrolo[3,2-b]pyridin-1-yl]-2-oxo-ethyl}-5-((R)-3-fluoro-pyrrolidin-1-ylmethyl)-2-methyl-piperazine-1-carboxylic acid tert-butyl ester | m/z: 616 | TEA used as base | 365, 406 |
| (2R,5S)-4-{2-[6-(1,1-Difluoro-3-methyl-butyl)-3,3-dimethyl-2,3-dihydro-pyrrolo[3,2-c]pyridin-1-yl]-2-oxo-ethyl}-2-methyl-5-(2-oxo-pyrrolidin-1-ylmethyl)-piperazine-1-carboxylic acid tert-butyl ester | m/z: 592 | | 260, 308 |
| (2R,5S)-4-{2-[6-(Cyclobutyl-difluoro-methyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 590 | TEA used as base | 260, 410 |
| (2R,5S)-4-{2-[6-(1,1-Difluoro-3-methyl-butyl)-3,3-dimethyl-2,3-dihydro-pyrrolo[3,2-c]pyridin-1-yl]-2-oxo-ethyl}-2-methyl-5-morpholin-4-ylmethyl-piperazine-1-carboxylic acid tert-butyl ester | m/z: 594 | TEA used as base | 416, 308 |
| (2R,5S)-4-{2-[6-(2-Cyclopropyl-1,1-difluoro-ethyl)-3,3-dimethyl-2,3-dihydro-pyrrolo[3,2-b]pyridin-1-yl]-2-oxo-ethyl}-2-methyl-5-(2-oxo-pyrrolidin-1-ylmethyl)-piperazine-1-carboxylic acid tert-butyl ester | m/z: 590 | TEA used as base | 260, 414 |

TABLE 6-continued

| Name | MS data | Comments | Prep No. |
|---|---|---|---|
| (2R,5S)-4-{2-[6-(2,4-Difluoro-benzyl)-3,3-dimethyl-2,3-dihydro-pyrrolo[3,2-b]pyridin-1-yl]-2-oxo-ethyl}-2-methyl-5-morpholin-4-ylmethyl-piperazine-1-carboxylic acid tert-butyl ester | m/z: 614 | | 416, 402 |
| (2R,5S)-4-{2-[6-(2-Fluoro-benzyl)-3,3-dimethyl-2,3-dihydro-pyrrolo[3,2-b]pyridin-1-yl]-2-oxo-ethyl}-5-((R)-3-fluoro-pyrrolidin-1-ylmethyl)-2-methyl-piperazine-1-carboxylic acid tert-butyl ester | m/z: 598 | | 365, 424 |

General Procedure 6 (Alkylation Using Coupled Chloromethylpiperazines)

(2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(2-oxo-2H-pyrimidin-1-ylmethyl)-piperazine-1-carboxylic acid tert-butyl ester

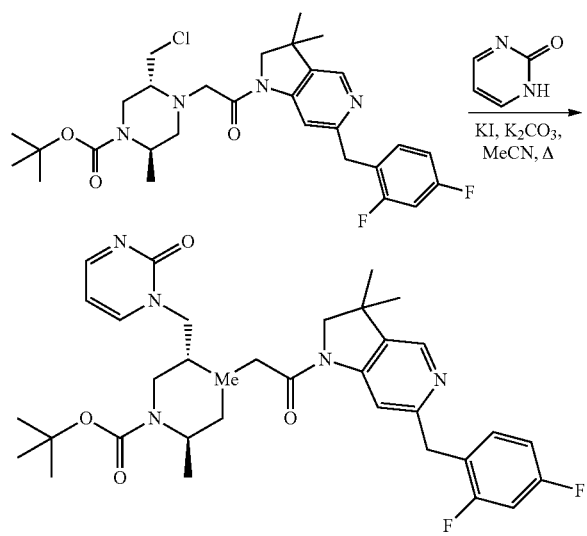

A mixture of (2R,5R)-5-chloromethyl-4-{2-[6-(2,4-difluoro-benzyl)-3,3-dimethyl-2,3-dihydro-pyrrolo[3,2-c]pyridin-1-yl]-2-oxo-ethyl}-2-methyl-piperazine-1-carboxylic acid tert-butyl ester (124 mg, 0.23 mmol), potassium iodide (83 mg, 0.5 mmol), anhydrous potassium carbonate (276 mg, 2.0 mmol) and 1H-pyrimidin-2-one (48 mg, 0.5 mmol) in acetonitrile (5 mL) was stirred and held at reflux in a sealed tube for 16 hours. Upon cooling to room temperature the solvent was removed in vacuo and the residues partitioned between DCM and water. The organic layer was separated, the solvent removed in vacuo and the residues were purified by column chromatography (silica, elution with 30-100% ethyl acetate in petroleum ether then 0-50% methanol in ethyl acetate) to give (2R,5S)-4-{2-[6-(2,4-difluoro-benzyl)-3,3-dimethyl-2,3-dihydro-pyrrolo[3,2-c]pyridin-1-yl]-2-oxo-ethyl}-2-methyl-5-(2-oxo-2H-pyrimidin-1-ylmethyl)-piperazine-1-carboxylic acid tert-butyl ester (70 mg, 49%) as a colourless solid. MS: $[M+H]^+$=623.

Compounds of Table 7 below were prepared using procedures analogous to that described in General Procedure 6 above, by reaction of the appropriate nucleophile with the appropriate substituted halopiperazine-amide (synthesised as described above, Preparation reference number given).

TABLE 7

| Name | MS Data | Prep. Nos |
|---|---|---|
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(2-oxo-2H-pyridin-1-ylmethyl)-piperazine-1-carboxylic acid tert-butyl ester | m/z: 622 | 377 |
| (2R,5R)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(6-oxo-6H-pyridazin-1-ylmethyl)-piperazine-1-carboxylic acid tert-butyl ester | m/z: 623 | 377 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(2-oxo-2H-pyrazin-1-ylmethyl)-piperazine-1-carboxylic acid tert-butyl ester | m/z: 623 | 377 |
| (2R,5R)-4-{2-[6-(2,4-Difluoro-benzyl)-3,3-dimethyl-2,3-dihydro-pyrrolo[3,2-c]pyridin-1-yl]-2-oxo-ethyl}-5-(3,5-dimethyl-[1,2,4]triazol-1-ylmethyl)-2-methyl-piperazine-1-carboxylic acid tert-butyl ester | m/z: 624 | 377 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-(3-oxo-pyrrolidin-1-ylmethyl)-piperazine-1-carboxylic acid tert-butyl ester | m/z: 612 | 377 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-5-(3,3-difluoro-pyrrolidin-1-ylmethyl)-2-methyl-piperazine-1-carboxylic acid tert-butyl ester | m/z: 634 | 377 |
| (2R,5S)-4-{2-[6-(2,4-Difluoro-benzyl)-3,3-dimethyl-2,3-dihydro-pyrrolo 3,2-c]pyridin-1-yl]-2-oxo-ethyl}-2-methyl-5-morpholin-4-ylmethyl-piperazine-1-carboxylic acid tert-butyl ester | m/z: 614 | 377 |
| (2R,5S)-4-{2-[6-(2,4-Difluoro-benzyl)-3,3-dimethyl-2,3-dihydro-pyrrolo[3,2-c]pyridin-1-yl]-2-oxo-ethyl}-2-methyl-5-pyrrolidin-1-ylmethyl-piperazine-1-carboxylic acid tert-butyl ester | m/z: 598 | 377 |

TABLE 7-continued

| Name | MS Data | Prep. Nos |
|---|---|---|
| (2R,5S)-4-{2-[6-(1,1-Difluoro-ethyl)-3,3-dimethyl-2,3-dihydro-pyrrolo[3,2-b]pyridin-1-yl]-2-oxo-ethyl}-5-(2,3-dihydro-pyrrolo[2,3-b]pyridin-1-ylmethyl)-2-methyl-piperazine-1-carboxylic acid tert-butyl ester | m/z: 585 | 369 |
| (2R,5S)-4-{2-[6-(Difluoro-phenyl-methyl)-3,3-dimethyl-2,3-dihydro-pyrrolo[3,2-c]pyridin-1-yl]-2-oxo-ethyl}-2-methyl-5-morpholin-4-ylmethyl-piperazine-1-carboxylic acid tert-butyl ester | m/z: 614 | 371 |
| (2R,5S)-4-{2-[6-(1,1-Difluoro-ethyl)-3,3-dimethyl-2,3-dihydro-pyrrolo[3,2-b]pyridin-1-yl]-2-oxo-ethyl}-2-methyl-5-(4-methyl-3-oxo-piperazin-1-ylmethyl)-piperazine-1-carboxylic acid tert-butyl ester | m/z: 579 | 369 |
| (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((S)-3-methyl-morpholin-4-ylmethyl)-piperazine-1-carboxylic acid tert-butyl ester | m/z: 610 | 420 |
| (2R,5S)-4-{2-[6-(4-Fluoro-benzyl)-3,3-dimethyl-2,3-dihydro-pyrrolo[3,2-b]pyridin-1-yl]-2-oxo-ethyl}-5-((R)-3-fluoro-pyrrolidin-1-ylmethyl)-2-methyl-piperazine-1-carboxylic acid tert-butyl ester | m/z: 598 | 420 |
| (2R,5S)-5-((2R,6S)-2,6-Dimethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester | m/z: 624 | 420 |
| (2R,5S)-4-{2-[6-(2-Fluoro-benzyl)-3,3-dimethyl-2,3-dihydro-pyrrolo[3,2-c]pyridin-1-yl]-2-oxo-ethyl}-2-methyl-5-((R)-3-methyl-morpholin-4-ylmethyl)-piperazine-1-carboxylic acid tert-butyl ester | m/z: 610 | 316 |
| (2R,5S)-4-{2-[6-(2-Fluoro-benzyl)-3,3-dimethyl-2,3-dihydro-pyrrolo[3,2-c]pyridin-1-yl]-2-oxo-ethyl}-2-methyl-5-morpholin-4-ylmethyl-piperazine-1-carboxylic acid tert-butyl ester | m/z: 596 | 316 |
| (2R,5S)-4-{2-[6-(1,1-Difluoro-butyl)-3,3-dimethyl-2,3-dihydro-pyrrolo[3,2-b]pyridin-1-yl]-2-oxo-ethyl}-5-((2R,6S)-2,6-dimethyl-morpholin-4-ylmethyl)-2-methyl-piperazine-1-carboxylic acid tert-butyl ester | m/z: 608 | 422 |
| (2R,5S)-4-{2-[6-(1,1-Difluoro-butyl)-3,3-dimethyl-2,3-dihydro-pyrrolo[3,2-b]pyridin-1-yl]-2-oxo-ethyl}-5-((R)-3-ethyl-morpholin-4-ylmethyl)-2-methyl-piperazine-1-carboxylic acid tert-butyl ester | m/z: 608 | 422 |
| (2R,5S)-4-{2-[6-(1,1-Difluoro-ethyl)-3,3-dimethyl-2,3-dihydro-pyrrolo[3,2-b]pyridin-1-yl]-2-oxo-ethyl}-5-((R)-3-ethyl-morpholin-4-ylmethyl)-2-methyl-piperazine-1-carboxylic acid tert-butyl ester | m/z: 580 | 369 |
| (2R,5S)-5-((R)-3-Ethyl-morpholin-4-ylmethyl)-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester | m/z: 624 | 420 |
| (2R,5S)-4-{2-[6-(1,1-Difluoro-propyl)-3,3-dimethyl-2,3-dihydro-pyrrolo[3,2-b]pyridin-1-yl]-2-oxo-ethyl}-5-((R)-3-ethyl-morpholin-4-ylmethyl)-2-methyl-piperazine-1-carboxylic acid tert-butyl ester | m/z: 594 | 428 |
| (2R,5S)-4-{2-[6-(1,1-Difluoro-propyl)-3,3-dimethyl-2,3-dihydro-pyrrolo[3,2-b]pyridin-1-yl]-2-oxo-ethyl}-5-((R)-3-methoxymethyl-morpholin-4-ylmethyl)-2-methyl-piperazine-1-carboxylic acid tert-butyl ester | m/z: 610 | 428 |

Preparation 431: (2R,5R)-4-{2-[3,3-Dimethyl-6-(2-oxo-pyrrolidin-1-ylmethyl)-2,3-dihydro-indol-1-yl]-2-oxo-ethyl}-5-methoxymethyl-2-methyl-piperazine-1-carboxylic acid tert-butyl ester 10% Pd/C (12 mg, 0.1 mmol) and (2R,5R)-4-{2-[5-bromo-3,3-dimethyl-6-(2-oxo-pyrrolidin-1-ylmethyl)-2,3-dihydro-indol-1-yl]-2-oxo-ethyl}-5-methoxymethyl-2-methyl-piperazine-1-carboxylic acid tert-butyl ester (66 mg, 0.1 mmol) were dissolved in methanol (0.44 mL) and triethylamine (23 µL, 0.16 mmol) was added. The reaction was hydrogenated at 1 bar for 1 h at ambient temperature then filtered under vacuum and concentrated. Residue was dissolved in methanol, loaded onto SCX column eluting with methanol then 2.0 M ammonia in methanol to release the amine and the relevant fractions concentrated. Chromatography (silica gel, gradient elution, 0-100%, EtOAc in petrol 40-60) gave the title compound (60 mg), MS: [M+H]$^+$=529.

Preparation 432: (2R,5R)-4-[2-(6-Benzyl-3,3-dimethyl-2,3-dihydro-pyrrolo[2,3-b]pyridin-1-yl)-2-oxo-ethyl]-5-methoxymethyl-2-methyl-piperazine-1-carboxylic acid tert-butyl ester The title compound was prepared following similar methods to those described in General Procedure 3, MS: [M+H]$^+$=523

Preparation 433: (2R,5R)-4-[2-(6-Benzyl-3,3-dimethyl-2,3-dihydro-pyrrolo[3,2-b]pyridin-1-yl)-2-oxo-ethyl]-5-methoxymethyl-2-methyl-piperazine-1-carboxylic acid tert-butyl ester The title compound was prepared following similar methods to those described in General Procedure 3, MS: [M+H]$^+$=523.

Preparation 434: (2R,5S)-4-{2-[6-(1,1-Difluoro-butyl)-3,3-dimethyl-2,3-dihydro-pyrrolo[3,2-c]pyridin-1-yl]-2-oxo-ethyl}-2-methyl-5-morpholin-4-ylmethyl-piperazine-1-carboxylic acid tert-butyl ester A stirred solution of 6-(1,1-difluoro-butyl)-3,3-dimethyl-2,3-dihydro-1H-pyrrolo[3,2-c]pyridine (100 mg, 0.42 mmol) in DCM (5 mL) and pyridine (0.5 mL) at 0° C. was treated with chloroacetyl chloride (0.036 mL, 0.46 mmol). After 2 h the solution was treated with (2R,5S)-2-methyl-5-morpholin-4-ylmethyl-piperazine-1-carboxylic acid tert-butyl ester (124 mg, 0.42 mmol) and further pyridine (0.5 mL). After overnight stirring at room temperature no coupling had occurred: the mixture was concentrated in vacuo, diluted with DMF (3 mL), treated with DMAP (1 mg) and heated to 75° C. After 6 h, LC/MS showed ~80% progression. The mixture was cooled and partitioned between DCM and water. The aqueous phase was extracted with DCM. The combined organic phases were dried (Na$_2$SO$_4$), filtered and concentrated to dryness. Purification by preparative HPLC gave a pale brown glass (30 mg, 12%). MS: [M+H]$^+$=580

Preparation 435: (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester

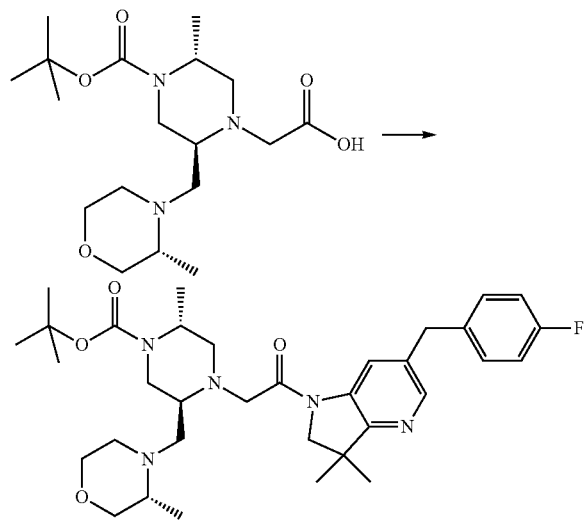

To (2R,5S)-4-carboxymethyl-2-methyl-5-((R)-3-methyl-morpholin-4-ylmethyl)-piperazine-1-carboxylic acid tert-butyl ester (1.5 g, 4.04 mmol) and 6-(4-fluoro-benzyl)-3,3-dimethyl-2,3-dihydro-1H-pyrrolo[3,2-b]pyridine (1.14 g, 4.4 mmol) in DMF (20.2 mL) were added O-(7-azabenzotriazol-1-yl)-N,N,N',N'-tetramethyluronium hexafluorophosphate (2.31 g, 6.1 mmol) and N,N-diisopropylethylamine (1.41 mL, 8.1 mmol) at room temperature. The reaction was stirred at room temperature for 18 h, then saturated aqueous sodium hydrogen carbonate was added and the mixture extracted with diethyl ether (3 x). The combined organic extracts were washed with water (3×) and brine (3×), then dried with sodium sulfate, filtered and concentrated. Chromatography (silica gel, gradient elution, 0-100%, EtOAc in petrol 40-60) gave the title compound (1.9 g, 77%), MS: [M+H]$^+$=610.

Preparation 436: (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-yl methyl)-piperazine-1-carboxylic acid tert-butyl ester, Alternative Procedure Prepared from (2R,5R)-5-chloromethyl-4-{2-[6-(4-fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester (see Preparation 420) and (R)-3-methyl-morpholine in a similar manner to General Procedure 6. MS: [M+H]$^+$=610.

Preparation 437: (2R,5S)-4-{2-[6-(1,1-Difluoro-butyl)-3,3-dimethyl-2,3-dihydro-pyrrolo[3,2-b]pyridin-1-yl]-2-oxo-ethyl}-2-methyl-5-((R)-3-methyl-morpholin-4-yl methyl)-piperazine-1-carboxylic acid tert-butyl ester HATU (3.8 g, 9.9 mmol) and DIPEA (2.4 mL, 13.3 mmol) were added to a solution of (2R,5S)-4-carboxymethyl-2-methyl-5-((R)-3-methyl-morpholin-4-ylmethyl)-piperazine-1-carboxylic acid tert-butyl ester (1.7 g, 6.7 mmol) and 6-(1,1-difluoro-butyl)-3,3-dimethyl-2,3-dihydro-1H-pyrrolo[3,2-b]pyridine (1.6 g, 6.7 mmol) in DMF (10 mL). The reaction was stirred at room temperature for 16 h and then partitioned between saturated aqueous NaHCO$_3$ and EtOAc. The organic phase was separated, washed with brine (3×), dried over MgSO$_4$ and concentrated in vacuo. Chromatography (70% EtOAc in Petrol) gave the title compound (2.1 g) as a yellow solid. MS: [M+H]$^+$=594.

Preparation 438: (2R,5S)-4-{2-[6-(1,1-Difluoro-butyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester, Alternative Procedure Prepared from (2R,5R)-5-chloromethyl-4-{2-[6-(1,1-difluoro-butyl)-3,3-dimethyl-2,3-dihydro-pyrrolo[3,2-b]pyridin-1-yl]-2-oxo-ethyl}-2-methyl-piperazine-1-carboxylic acid tert-butyl ester and (R)-3-methyl-morpholine in a similar manner to General Procedure 6. MS: [M+H]$^+$=594.

Preparation 439: (2R,5S)-4-{2-[6-(2-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester To (2R,5S)-4-carboxymethyl-2-methyl-5-((R)-3-methyl-morpholin-4-ylmethyl)-piperazine-1-carboxylic acid tert-butyl ester (1.5 g, 4.04 mmol) and 6-(2-fluoro-benzyl)-3,3-dimethyl-2,3-dihydro-1H-pyrrolo[3,2-b]pyridine (1.14 g, 4.45 mmol) in DMF (20.2 mL) were added O-(7-azabenzotriazol-1-yl)-N,N,N',N'-tetramethyluronium hexafluorophosphate (2.31 g, 6.1 mmol) and N,N-diisopropylethylamine (1.41 mL, 8.1 mmol) at room temperature. The reaction was stirred at room temperature for 18 h. Saturated aqueous sodium hydrogen carbonate was added and the mixture extracted with diethyl ether (3×). The combined organic extracts were washed with water (3×) and brine (3×) then dried with sodium sulfate, filtered and concentrated. Chromatography (silica gel, gradient elution, 0-100%, EtOAc in petrol 40-60) gave the title compound (1.43 g), MS: [M+H]$^+$=610.

Preparation 440: (2R,5S)-4-{2-[6-(2-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester, Alternative Procedure Prepared from (2R,5R)-5-chloromethyl-4-{2-[6-(2-fluoro-benzyl)-3,3-dimethyl-2,3-dihydro-pyrrolo[3,2-b]

pyridin-1-yl]-2-oxo-ethyl}-2-methyl-piperazine-1-carboxylic acid tert-butyl ester and (R)-3-methyl-morpholine in a similar manner to General Procedure 6. MS: [M+H]⁺=610.

Preparation 441: (2R,5S)-4-{2-[6-(2,4-Difluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester A mixture of (2R,5S)-4-carboxymethyl-2-methyl-5-((R)-3-methyl-morpholin-4-ylmethyl)-piperazine-1-carboxylic acid tert-butyl ester (0.12 g, 0.32 mmol), 1,1'-carbonyldiimidazole (0.057 g, 0.35 mmol) and DCM (5 mL) was stirred at 20° C. for 24 h. 6-(2,4-Difluoro-benzyl)-3,3-dimethyl-2,3-dihydro-1H-pyrrolo[3,2-b]pyridine (0.088 g, 0.32 mmol) was added and the mixture heated at 35° C. for 24 h. Solvent was evaporated and the residue dissolved in 1,2-dichloroethane and the mixture was heated to 60° C. for 24 h. Mixture was partitioned between saturated aqueous NaHCO₃ (30 mL) and DCM (3×20 mL) and combined organic extracts were dried and evaporated to give an oil. Chromatography (SiO₂, gradient elution, 0-100% EtOAc in petrol 40-60) gave the title compound (0.103 g) as an oil. MS: [M+H]⁺=628.

Preparation 442: 2-Chloro-1-[6-(4-fluoro-benzyl)-3,3-dimethyl-2,3-dihydro-pyrrolo[3,2-b]pyridin-1-yl]-ethanone hydrochloride

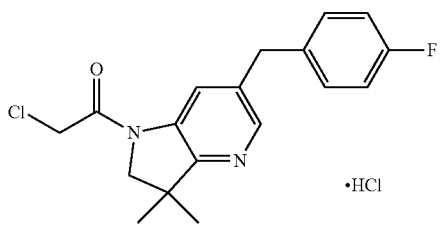 [SMILES: CC1(C)CN(C(=O)CCl)c2cc(Cc3ccc(F)cc3)cnc21 ; Cl]

To a stirred suspension of 6-(4-fluoro-benzyl)-3,3-dimethyl-2,3-dihydro-1H-pyrrolo[3,2-b]pyridine (6.68 g, 26 mol) in acetonitrile (20 mL) at 20° C. was added, steadily over 0.2 h, a solution of chloroacetyl chloride (3.83 g, 2.7 mL, 33.9 mmol) in acetonitrile (10 mL), maintaining the reaction mixture at or below 20° C. using an external ice-methanol bath. A clear solution resulted then, as the internal temperature reached 0° C., a solid began to crystallize from the reaction mixture. Stirring at 20° C. was continued for 1 h then toluene (20 mL) and 40-60 petroleum ether (20 mL) were added slowly and stirring continued for 0.2 h. The resulting colourless solid was collected by filtration to give the title compound (8.0 g, 83%). 1H NMR (Me-d3-OD): 8.81 (1H, s), 8.31 (1H, s), 7.39-7.29 (2H, m), 7.16-7.04 (2H, m), 4.45 (2H, s), 4.19 (4H, s), 1.58 (6H, s). MS: [M+H]⁺=333.

Preparation 443: (2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester

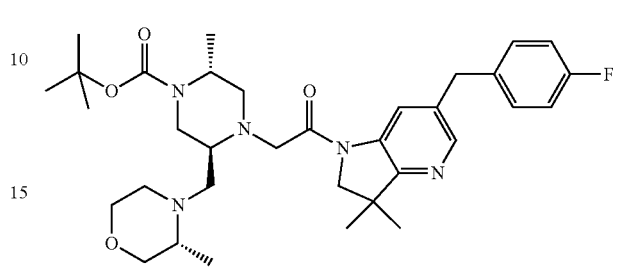

A mixture of 2-chloro-1-[6-(4-fluoro-benzyl)-3,3-dimethyl-2,3-dihydro-pyrrolo[3,2-b]pyridin-1-yl]-ethanone hydrochloride (6.63 g, 17.96 mmol), (2R,5S)-2-methyl-5-((R)-3-methyl-morpholin-4-ylmethyl)-piperazine-1-carboxylic acid tert-butyl ester (5.62 g, 17.96 mmol), potassium carbonate (9.95 g, 72 mmol) and finely ground potassium iodide (5.98 g, 36 mmol) in acetonitrile (40 mL) was stirred at 20° C. for 1 h. Water (200 mL) was added and mixture stirred for 0.2 h, then the mixture was extracted with EtOAc (200 mL). The organic phase was dried (Na₂SO₄) and evaporated in vacuo to give the title compound (11.3 g) as an oil, used without further purification. ¹H NMR (Me-d3-OD): 8.28-8.19 (1H, m), 8.13-8.04 (1H, m), 7.25 (2H, dd), 7.04 (2H, t), 4.23-4.13 (1H, m), 4.13-4.04 (2H, m), 4.04-3.95 (3H, m), 3.81-3.58 (4H, m), 3.54 (1H, d), 3.25 (2H, dd), 3.01-2.66 (4H, m), 2.62-2.42 (2H, m), 2.42-2.17 (2H, m), 1.47 (9H, s), 1.43-1.37 (6H, m), 1.29-1.21 (3H, m), 1.01 (3H, d). MS: [M+H]⁺=610. IR: $v_{C=O}$ 1685, 1653 cm⁻¹.

General Procedures for Preparations of Compounds of Formula (I)

As understood by a person skilled in the art, compounds synthesised using the protocols as indicated may exist as a solvate e.g. hydrate, and/or contain residual solvent or minor impurities. Compounds isolated as a salt form, may be integer stoichiometric i.e. mono- or di-salts, or of intermediate stoichiometry.

The following procedures are illustrative for general methods used in the preparation of Examples 1-112 listed in Table 8 below.

Method 1

1-[2-((R)-3-Methyl-piperazin-1-yl)-acetyl]-2,3-dihydro-1H-indole-6-sulfonic acid methylamide (Example 27)

(R)-2-Methyl-4-[2-(6-methylsulfamoyl-2,3-dihydro-indol-1-yl)-2-oxo-ethyl]-piperazine-1-carboxylic acid tert-butyl ester (65 mg, 0.14 mmol) was dissolved in TFA (0.72 mL) and stirred at ambient temperature for 30 min. The solvent was removed in vacuo. The residue was dissolved in MeOH and loaded onto SCX column eluting with MeOH and then 2.0 M NH₃ MeOH to release the amine. The solvent was removed in vacuo, to give the title compound (47 mg, 93%) as a colourless solid.

Method 2

1-(2,3-Dihydro-pyrrolo[2,3-b]pyridin-1-yl)-2-((R)-3-methyl-piperazin-1-yl)-ethanone, hydrochloride salt (Example 36)

(R)-4-[2-(2,3-Dihydro-pyrrolo[2,3-b]pyridin-1-yl)-2-oxo-ethyl]-2-methyl-piperazine-1-carboxylic acid tert-butyl ester (300 mg, 0.83 mmol) was dissolved in saturated HCl in EtOAc (20.8 mL) stirred at ambient temperature for 1 h. The solvent was removed in vacuo. The residue was dissolved in MeOH and concentrated and the residue dried at 40° C. in vacuo, to give the title compound (241 mg) as a beige solid.

Method 3

1-(5-Fluoro-6-phenyl-2,3-dihydro-indol-1-yl)-2-((R)-3-methyl-piperazin-1-yl)-ethanone hydrochloride salt (Example 24)

A mixture of (R)-4-[2-(5-fluoro-6-phenyl-2,3-dihydro-indol-1-yl)-2-oxo-ethyl]-2-methyl-piperazine-1-carboxylic acid tert-butyl ester (0.138 g), HCl in 1,4-dioxane (4 M, 2 mL) and MeOH (2 mL) was stirred at 20° C. for 3 h and resulting solid was collected by filtration to give the title compound (0.076 g).

Method 4

1-(6-Benzyl-3,3-dimethyl-2,3-dihydro-pyrrolo[3,2-c]pyridin-1-yl)-2-((2R,5R)-2-methoxymethyl-5-methyl-piperazin-1-yl)-ethanone hydrochloride salt (Example 63)

A mixture of (2R,5R)-4-[2-(6-benzyl-3,3-dimethyl-2,3-dihydro-pyrrolo[3,2-c]pyridin-1-yl)-2-oxo-ethyl]-5-methoxymethyl-2-methyl-piperazine-1-carboxylic acid tert-butyl ester (0.17 g, 0.33 mmol), MeOH (5 mL) and hydrochloric acid (5 M, 5 mL) was stirred at 20° C. for 4 h then at 40° C. for 0.5 h and the mixture evaporated in vacuo. The residue was re-dissolved in MeOH and re-evaporated in vacuo. This azeotrope procedure with MeOH was repeated 4 times to give the title compound (0.145 g) as a colourless solid.

Examples 1-112

By following methods similar and/or analogous to those described above, the compounds set out in Table 8 were prepared from the corresponding N-Boc protected derivatives, with any significant variations indicated below except where otherwise stated. The title compounds were either isolated directly as the free base or appropriate salt without further purification, or purified for example using mass-directed preparative HPLC, crystallization or trituration.

TABLE 8

| Ex. | Structure | Compound Name | $^1$H NMR Data (Me-d3-OD, unless indicated) | MS Data [M + H]$^+$ | Method |
|---|---|---|---|---|---|
| 1 | 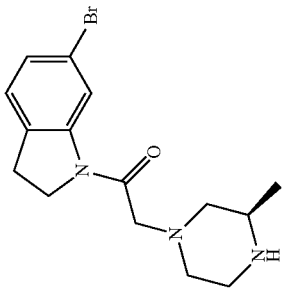 | 1-(6-Bromo-2,3-dihydro-indol-1-yl)-2-((R)-3-methyl-piperazin-1-yl)-ethanone | 8.33 (1H, s), 7.24-7.10 (2H, m), 4.22 (2H, t), 3.37 (1H, s), 3.16 (2H, t), 3.04-2.77 (6H, m), 2.32-2.17 (1H, m), 1.93 (1H, t), 1.09 (3H, d). | 339 | 1 |
| 2 | 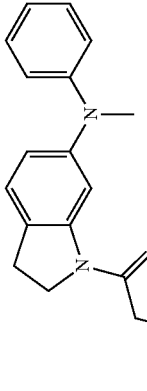 | 1-[6-(Methyl-phenyl-amino)-2,3-dihydro-indol-1-yl]-2-((R)-3-methyl-piperazin-1-yl)-ethanone Trifluoroacetate salt | 7.92 (1H, d), 7.33-7.19 (2H, m), 7.15 (1H, d), 6.98 (2H, d), 6.91 (1H, t), 6.75 (1H, dd), 4.16 (2H, t), 3.58 (2H, s), 3.53-3.36 (2H, m), 3.28 (3H, s), 3.25-3.02 (4H, m), 2.72 (1H, d), 2.51 (1H, d), 1.33 (3H, d). | | 1, Purified by preparative HPLC; TFA method |
| 3 | 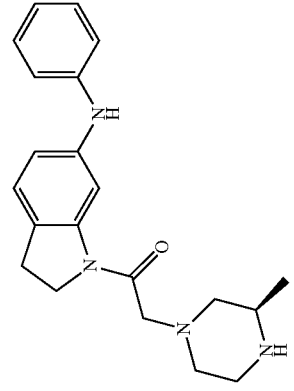 | 2-((R)-3-Methyl-piperazin-1-yl)-1-(6-phenylamino-2,3-dihydro-indol-1-yl)-ethanone Trifluoroacetate salt | 8.07 (1H, s), 7.30-7.16 (2H, m), 7.16-7.02 (3H, m), 6.91-6.74 (2H, m), 5.50 (1H, s), 4.14 (2H, t), 3.78 (2H, s), 3.64-3.43 (2H, m), 3.16 (2H, t), 2.92 (1H, s), 2.72 (1H, t), 1.35 (3H, d). | 351 | 1, Purified by preparative HPLC; TFA method |

TABLE 8-continued

| Ex. | Structure | Compound Name | 1H NMR Data (Me-d3-OD, unless indicated) | MS Data [M + H]+ | Method |
|---|---|---|---|---|---|
| 4 | 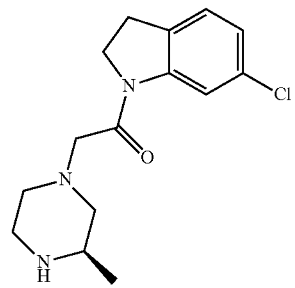 [SMILES: C[C@@H]1CN(CC(=O)N2CCc3ccc(Cl)cc32)CCN1] | 1-(6-Chloro-2,3-dihydro-indol-1-yl)-2-((R)-3-methyl-piperazin-1-yl)-ethanone | 8.16 (1H, s), 7.19 (1H, d), 7.03 (1H, dd), 4.22 (2H, t), 3.18 (2H, t), 3.06-2.73 (6H, m), 2.30-2.14 (1H, m), 1.90 (1H, t), 1.07 (3H, d). | 294 | 1 |
| 5 | 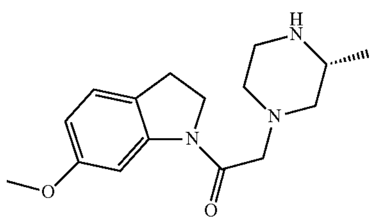 | 1-(6-Methoxy-2,3-dihydro-indol-1-yl)-2-((R)-3-methyl-piperazin-1-yl)-ethanone | 7.82 (1H, d), 7.11 (1H, d), 6.62 (1H, dd), 4.19 (2H, t), 3.78 (3H, s), 3.12 (2H, t), 3.03-2.82 (6H, m), 2.29-2.14 (1H, m), 1.89 (1H, t), 1.07 (3H, d). | 290 | 1 |
| 6 | 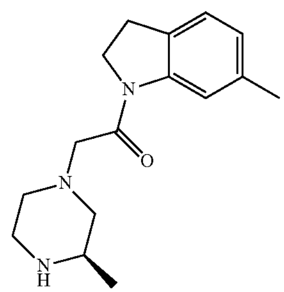 [SMILES: Cc1ccc2c(c1)N(C(=O)CN1CCN[C@H](C)C1)CC2] | 1-(6-Methyl-2,3-dihydro-indol-1-yl)-2-((R)-3-methyl-piperazin-1-yl)-ethanone | 8.01 (1H, s), 7.11 (1H, d), 6.88 (1H, d), 4.18 (2H, t), 3.26-3.01 (2H, m), 3.00-2.83 (6H, m), 2.33 (3H, s), 2.28-2.13 (1H, m), 1.89 (1H, t), 1.07 (3H, d). | 274 | 1 |

TABLE 8-continued

| Ex. | Structure | Compound Name | ¹H NMR Data (Me-d3-OD, unless indicated) | MS Data [M + H]⁺ | Method |
|---|---|---|---|---|---|
| 7 | 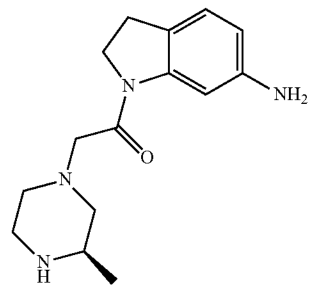 [SMILES: C[C@@H]1CN(CC(=O)N2CCc3ccc(N)cc32)CCN1] | 1-(6-Amino-2,3-dihydro-indol-1-yl)-2-((R)-3-methyl-piperazin-1-yl)-ethanone | 7.65 (1H, d), 6.97 (1H, d), 6.47 (1H, dd), 4.14 (2H, t), 3.37 (1H, s), 3.27-2.90 (8H, m), 2.47-2.33 (1H, m), 2.13 (1H, q), 1.19 (3H, d). | 275 | 1 |
| 8 | 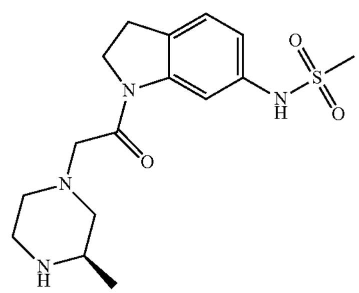 [SMILES: C[C@@H]1CN(CC(=O)N2CCc3ccc(NS(C)(=O)=O)cc32)CCN1] | N-{1-[2-((R)-3-Methyl-piperazin-1-yl)-acetyl]-2,3-dihydro-1H-indol-6-yl}-methanesulfonamide | 8.13 (1H, s), 7.20 (1H, d), 6.99 (1H, dd), 4.22 (2H, t), 3.27-3.12 (2H, m), 3.04-2.89 (8H, m), 2.31-2.20 (2H, m), 1.94 (1H, t), 1.09 (3H, d). | 353 | 1 |
| 9 | 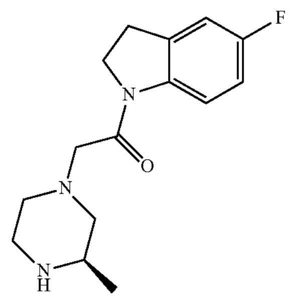 [SMILES: C[C@@H]1CN(CC(=O)N2CCc3cc(F)ccc32)CCN1] | 1-(5-Fluoro-2,3-dihydro-indol-1-yl)-2-((R)-3-methyl-piperazin-1-yl)-ethanone | 8.13 (1H, dd), 7.00 (1H, d), 6.95-6.83 (1H, m), 4.22 (2H, t), 3.21 (2H, t), 3.01-2.72 (6H, m), 2.29-2.13 (1H, m), 1.89 (1H, t), 1.07 (3H, d). | 278 | 1 |

TABLE 8-continued
| Ex. | Structure | Compound Name | 1H NMR Data (Me-d3-OD, unless indicated) | MS Data [M + H]+ | Method |
|---|---|---|---|---|---|
| 10 | 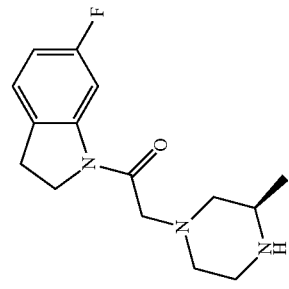 | 1-(6-Fluoro-2,3-dihydro-indol-1-yl)-2-((R)-3-methyl-piperazin-1-yl)-ethanone | 7.89 (1H, dd), 7.19 (1H, t), 6.82-6.70 (1H, m), 4.24 (2H, t), 3.17 (2H, t), 3.04-2.73 (6H, m), 2.30-2.14 (1H, m), 1.90 (1H, t), 1.07 (3H, d). | 278 | 1 |
| 11 | 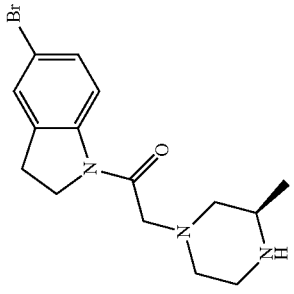 | 1-(5-Bromo-2,3-dihydro-indol-1-yl)-2-((R)-3-methyl-piperazin-1-yl)-ethanone | 8.05 (1H, d), 7.39 (1H, s), 7.31 (1H, d), 4.21 (2H, t), 3.27-3.03 (2H, m), 3.03-2.73 (6H, m), 2.29-2.14 (1H, m), 1.89 (1H, t), 1.07 (3H, d). | 338 | 1 |
| 12 | 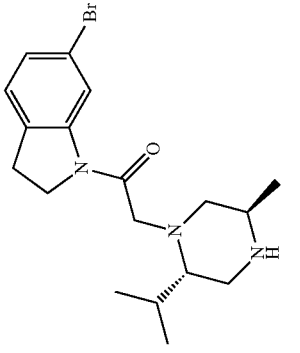 | 1-(6-Bromo-2,3-dihydro-indol-1-yl)-2-((2S,5R)-2-isopropyl-5-methyl-piperazin-1-yl)ethanone | 8.32 (1H, s), 7.35-7.09 (2H, m), 4.34-4.12 (2H, m), 3.73 (1H, d), 3.17 (2H, t), 3.03-2.93 (3H, m), 2.71-2.59 (2H, m), 2.41 (1H, t), 2.23-2.14 (1H, m), 1.10 (3H, d), 0.99 (3H, d), 0.91 (3H, d). | 381 | 1 |

TABLE 8-continued

| Ex. | Structure | Compound Name | ¹H NMR Data (Me-d3-OD, unless indicated) | MS Data [M + H]⁺ | Method |
|---|---|---|---|---|---|
| 13 | 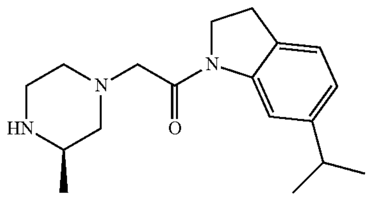 [SMILES: CC(C)c1ccc2c(c1)N(C(=O)CN1CCN[C@H](C)C1)CC2] | 1-(6-Isopropyl-2,3-dihydro-indol-1-yl)-2-((R)-3-methyl-piperazin-1-yl)-ethanone | 8.10 (1H, s), 7.15 (1H, d), 6.94 (1H, d), 4.19 (2H, t), 3.25-3.02 (2H, m), 3.02-2.74 (6H, m), 2.30-2.15 (1H, m), 1.91 (1H, t), 1.25 (6H, d), 1.08 (3H, d). | 302 | 1 |
| 14 | 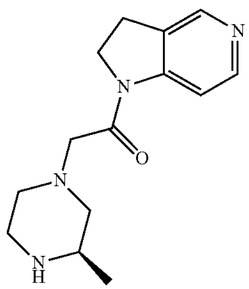 [SMILES: C[C@@H]1CN(CC(=O)N2CCc3cnccc32)CCN1] | 1-(2,3-Dihydro-pyrrolo[3,2-c]pyridin-1-yl)-2-((R)-3-methyl-piperazin-1-yl)ethanone | 8.34 (1H, s), 8.30 (1H, d), 8.06 (1H, s), 4.26 (2H, t), 3.28 (2H, t), 3.17-2.76 (6H, m), 2.33-2.18 (1H, m), 1.94 (1H, t), 1.08 (4H, d). | 261 | 1 |
| 15 | 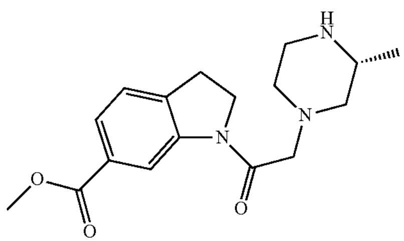 | 1-[2-((R)-3-Methyl-piperazin-1-yl)-acetyl]-2,3-dihydro-1H-indole-6-carboxylic acid methyl ester | 8.79 (1H, s), 7.75 (1H, dd), 7.35 (1H, d), 4.25 (2H, dd), 3.91 (3H, s), 3.39-3.35 (2H, m), 3.31-3.22 (2H, m), 3.03-2.91 (5H, m), 2.33-2.19 (1H, m), 2.02-1.88 (1H, m), 1.09 (3H, d). | 318 | 1 |
| 16 | 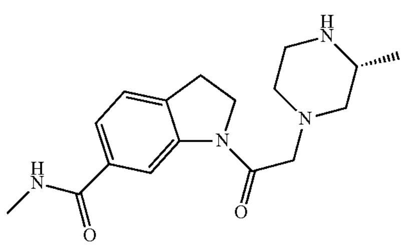 | 1-[2-((R)-3-Methyl-piperazin-1-yl)-acetyl]-2,3-dihydro-1H-indole-6-carboxylic acid methylamide | 8.59 (1H, s), 7.50 (1H, dd), 7.32 (1H, d), 4.25 (2H, dd), 3.44-3.37 (2H, m), 3.26 (2H, t), 3.02-2.96 (5H, m), 2.92 (3H, s), 2.35-2.16 (1H, m), 2.04-1.90 (1H, m), 1.11 (3H, d). | 317 | 1 |

TABLE 8-continued

| Ex. | Structure | Compound Name | ¹H NMR Data (Me-d3-OD, unless indicated) | MS Data [M + H]⁺ | Method |
|---|---|---|---|---|---|
| 17 | 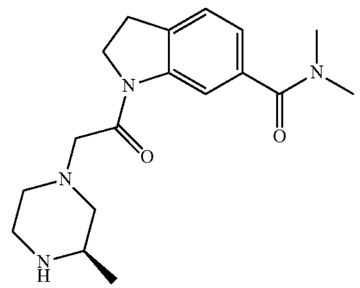 [SMILES: C[C@@H]1CN(CC(=O)N2CCc3ccc(C(=O)N(C)C)cc32)CCN1] | 1-[2-((R)-3-Methyl-piperazin-1-yl)-acetyl]-2,3-dihydro-1H-indole-6-carboxylic acid dimethylamide | 8.23 (1H, s), 7.33 (1H, d), 7.11 (1H, dd), 4.24 (2H, t), 3.26 (2H, t), 3.11 (3H, d), 3.08-2.82 (9H, m), 2.40-2.21 (1H, m), 2.03 (1H, t), 1.13 (3H, d). | 331 | 1 |
| 18 | 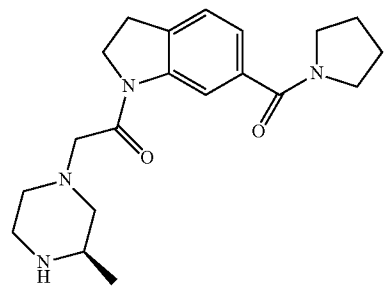 [SMILES: C[C@@H]1CN(CC(=O)N2CCc3ccc(C(=O)N4CCCC4)cc32)CCN1] | 2-((R)-3-Methyl-piperazin-1-yl)-1-[6-(pyrrolidine-1-carbonyl)-2,3-dihydro-indol-1-yl]-ethanone | 8.32 (1H, s), 7.33 (1H, d), 7.21 (1H, dd), 4.24 (2H, t), 3.60 (2H, t), 3.48 (2H, t), 3.26 (2H, t), 3.09-2.86 (6H, m), 2.39-2.22 (1H, m), 2.09-1.83 (6H, m), 1.13 (3H, d). | 357 | 1 |
| 19 | 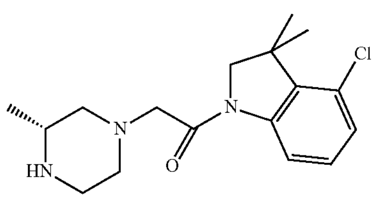 [SMILES: C[C@@H]1CN(CC(=O)N2CC(C)(C)c3c(Cl)cccc32)CCN1] | 1-(4-Chloro-3,3-dimethyl-2,3-dihydro-indol-1-yl)-2-((R)-3-methyl-piperazin-1-yl)-ethanone | 8.15 (1H, d), 7.19 (1H, t), 7.04 (1H, d), 3.99 (2H, s), 3.00-2.84 (5H, m), 2.30-2.16 (1H, m), 1.92 (1H, t), 1.52 (6H, s), 1.08 (3H, d). | 322 | 1 |

TABLE 8-continued

| Ex. | Structure | Compound Name | ¹H NMR Data (Me-d3-OD, unless indicated) | MS Data [M + H]⁺ | Method |
|---|---|---|---|---|---|
| 20 | 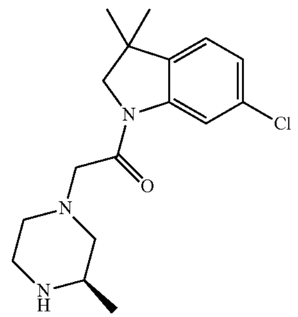 [SMILES: C[C@@H]1CN(CC(=O)N2CC(C)(C)c3ccc(Cl)cc32)CCN1] | 1-(6-Chloro-3,3-dimethyl-2,3-dihydro-indol-1-yl)-2-((R)-3-methyl-piperazin-1-yl)ethanone | 8.14 (1H, s), 7.20 (1H, d), 7.08 (1H, dd), 3.99 (2H, s), 3.04-2.76 (6H, m), 2.32-2.18 (1H, m), 1.94 (1H, t), 1.36 (6H, s), 1.09 (3H, d). | 322 | 1 |
| 21 | 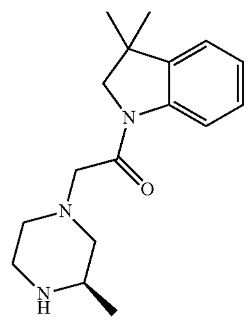 [SMILES: C[C@@H]1CN(CC(=O)N2CC(C)(C)c3ccccc32)CCN1] | 1-(3,3-Dimethyl-2,3-dihydro-indol-1-yl)-2-((R)-3-methyl-piperazin-1-yl)ethanone | 8.11 (1H, d), 7.31-7.13 (2H, m), 7.10 (1H, t), 3.97 (2H, s), 3.04-2.85 (6H, m), 2.31-2.17 (1H, m), 1.93 (1H, t), 1.37 (6H, s), 1.09 (3H, d). | 288 | 1 |
| 22 | 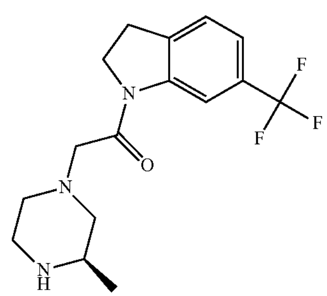 [SMILES: C[C@@H]1CN(CC(=O)N2CCc3ccc(C(F)(F)F)cc32)CCN1] | 2-((R)-3-Methyl-piperazin-1-yl)-1-(6-trifluoromethyl-2,3-dihydro-indol-1-yl)-ethanone | 8.46 (1H, s), 7.41 (1H, d), 7.34 (1H, d), 4.27 (2H, dd), 3.37-3.36 (2H, m), 3.32-3.25 (2H, m), 2.94 (5H, m), 2.31-2.14 (1H, m), 1.98-1.85 (1H, m), 1.08 (3H, d). | 328 | 1 |

TABLE 8-continued

| Ex. | Structure | Compound Name | ¹H NMR Data (Me-d3-OD, unless indicated) | MS Data [M + H]⁺ | Method |
|---|---|---|---|---|---|
| 23 | 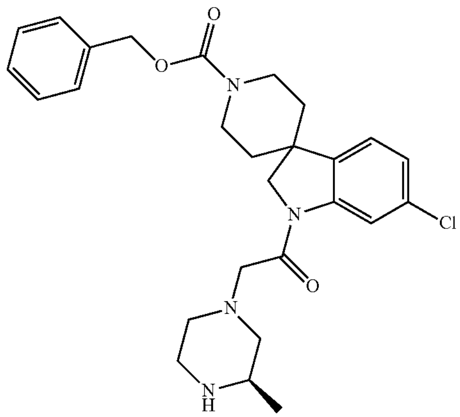 | Benzyl 6-chloro-1-{2-[(3R)-3-methylpiperazin-1-yl]acetyl}-1,2-dihydrospiro[indole-3,4'-piperidine]-1'-carboxylate hydrochloride salt | 8.19 (1H, d), 7.47-7.31 (5H, m), 7.27 (1H, d), 7.16 (1H, dd), 5.18 (2H, s), 4.53 (2H, s), 4.30-4.18 (2H, m), 4.14 (2H, s), 3.93-3.68 (4H, m), 3.68-3.47 (2H, m), 3.45-3.35 (1H, m), 3.22-3.00 (2H, m), 1.97-1.82 (2H, m), 1.74 (2H, d), 1.47 (3H, d). | 497 | 2 |
| 24 | 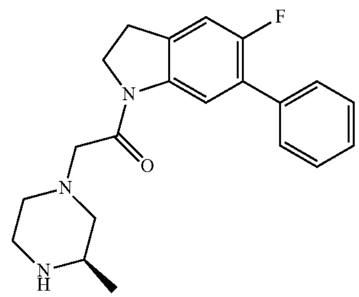 | 1-(5-Fluoro-6-phenyl-2,3-dihydro-indol-1-yl)-2-((R)-3-methyl-piperazin-1-yl)-ethanone hydrochloride salt | 8.29 (1H, d), 7.56-7.34 (5H, m), 7.17 (1H, d), 4.45 (2H, s), 4.21 (2H, t), 3.95-3.70 (4H, m), 3.66-3.47 (2H, m), 3.43-3.34 (3H, m), 1.47 (3H, d). | 354 | 3 |
| 25 | 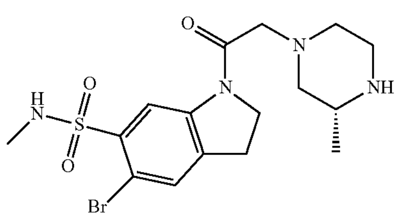 | 5-Bromo-1-[2-((R)-3-methyl-piperazin-1-yl)-acetyl]-2,3-dihydro-1H-indole-6-sulfonic acid methylamide hydrochloride salt | 8.90 (1H, s), 7.73 (1H, s), 4.31 (2H, s), 4.23 (2H, t), 3.83-3.68 (5H, m), 3.56-3.48 (1H, m), 3.39 (2H, s), 2.54 (3H, s), 1.45 (4H, d). | 431 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 26 | 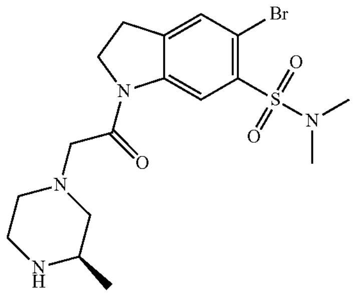 | 5-Bromo-1-[2-((R)-3-methyl-piperazin-1-yl-acetyl]-2,3-dihydro-1H-indole-6-sulfonic acid dimethylamide hydrochloride salt | 8.80 (1H, s), 7.74 (1H, s), 4.57-4.41 (2H, m), 4.24 (2H, t), 3.98-3.81 (3H, m), 3.81-3.70 (2H, m), 3.70-3.46 (2H, m), 3.38 (2H, t), 2.88 (6H, s), 1.48 (3H, d). | 445 | 2 |
| 27 | 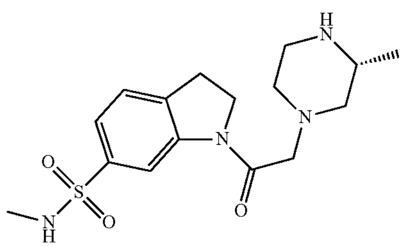 | 1-[2-((R)-3-Methyl-piperazin-1-yl)-acetyl]-2,3-dihydro-1H-indole-6-sulfonic acid methylamide | 8.64 (1H, s), 7.54 (1H, d), 7.43 (1H, d), 4.28 (2H, t), 3.04-2.89 (6H, m), 2.54 (3H, s), 2.34-2.21 (1H, m), 1.96 (1H, t), 1.10 (3H, d). | 353 | 1 |
| 28 | 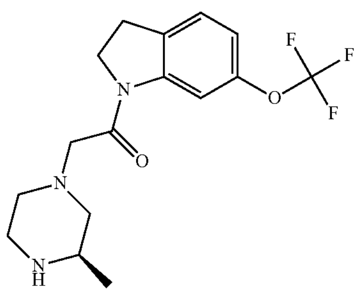 | 2-((R)-3-Methyl-piperazin-1-yl)-1-(6-trifluoromethoxy-2,3-dihydro-indol-1-yl)-ethanone hydrochloride salt | 8.10 (1H, s), 7.36 (1H, d), 7.03 (1H, d), 4.48 (2H, s), 4.22 (2H, t), 3.94-3.80 (3H, m), 3.80-3.72 (1H, m), 3.66-3.54 (2H, m), 3.40 (1H, t), 1.48 (3H, d). | 344 | 3, Isolated by evaporation and purified by trituration of residue with 1,4-dioxane then Et₂O |

TABLE 8-continued

| Ex. | Structure | Compound Name | 1H NMR Data (Me-d3-OD, unless indicated) | MS Data [M + H]+ | Method |
|---|---|---|---|---|---|
| 29 | (structure with benzyl-indoline, methylpiperazine, ·HCl) | 1-(6-Benzyl-2,3-dihydro-indol-1-yl)-2-((R)-3-methyl-piperazin-1-yl)-ethanone hydrochloride salt | 8.04 (1H, s), 7.33-7.11 (6H, m), 7.00 (1H, d), 4.50 (2H, s), 4.12 (2H, t), 4.03-3.81 (5H, m), 3.77 (1H, d), 3.63 (2H, d), 3.45 (1H, t), 3.25 (2H, t), 1.48 (3H, d) | 350 | 2 |
| 30 | (structure with methanesulfonyl-indoline, methylpiperazine, ·HCl) | 1-(6-Methanesulfonyl-2,3-dihydro-indol-1-yl)-2-((R)-3-methyl-piperazin-1-yl)-ethanone hydrochloride salt | (DMSO-d6): 8.53 (1H, s), 7.57 (1H, dd), 7.51 (1H, d), 4.18 (2H, t), 3.47 (2H, s), 3.31-3.22 (4H, m), 3.13 (3H, s), 3.07-2.94 (3H, m), 2.65 (1H, t), 2.45 (1H, t), 1.19 (3H, d) | 338 | 3, Isolated by evaporation and purified by trituration of residue with Et2O then MeOH |
| 31 | (spiro structure with chloro, acetyl-piperidine, methylpiperazine, ·HCl) | 1-{1'-Acetyl-6-chloro-1,2-dihydrospiro[indole-3,4'-piperidine]-1-yl}-2-[(3R)-3-methylpiperazin-1-yl]ethan-1-one hydrochloride salt | 8.21 (1H, d), 7.30 (1H, d), 7.18 (1H, dd), 4.81-4.68 (2H, m), 4.68-4.56 (1H, m), 4.28-4.13 (2H, m), 4.11-3.87 (4H, m), 3.82 (1H, d), 3.79-3.68 (2H, m), 3.61-3.51 (1H, m), 3.51-3.37 (1H, m), 2.92 (1H, t), 2.21 (3H, s), 2.05-1.92 (1H, m), 1.92-1.73 (3H, m), 1.50 (3H, d). | 405 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 32 | 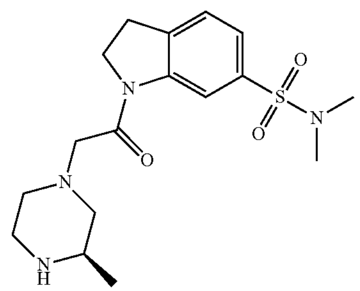 [SMILES: C[C@@H]1CN(CC(=O)N2CCc3ccc(S(=O)(=O)N(C)C)cc32)CCN1] | 1-[2-((R)-3-Methyl-piperazin-1-yl)-acetyl]-2,3-dihydro-1H-indole-6-sulfonic acid dimethylamide | 8.57 (1H, s), 7.54-7.42 (2H, m), 4.28 (2H, t), 3.39 (2H, s), 3.11-2.83 (5H, m), 2.70 (6H, s), 2.36-2.22 (1H, m), 1.98 (1H, t), 1.11 (3H, d). | 367 | 1 |
| 33 | 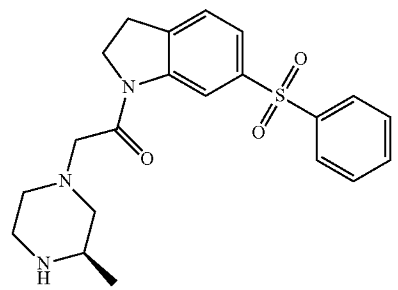 | 1-(6-Benzenesulfonyl-2,3-dihydro-indol-1-yl)-2-((R)-3-methyl-piperazin-1-yl)-ethanone hydrochloride salt | 8.68 (1H, d), 8.00-7.88 (2H, m), 7.73 (1H, dd), 7.69-7.62 (1H, m), 7.58 (2H, t), 7.49 (1H, d), 4.41 (2H, s), 4.19 (2H, t), 3.89-3.80 (3H, m), 3.77-3.72 (1H, m), 3.66-3.47 (2H, m), 1.47 (3H, d). | 400 | 3, Isolated by evaporation and purified by trituration of residue with isopropanol |
| 34 | 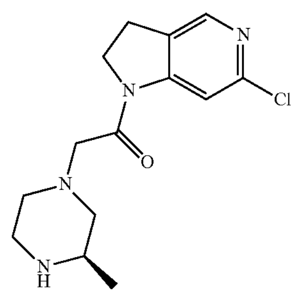 | 1-(6-Chloro-2,3-dihydro-pyrrolo[3,2-c]pyridin-1-yl)-2-((R)-3-methyl-piperazin-1-yl)-ethanone hydrochloride salt | 8.25 (1H, s), 8.11 (1H, s), 4.39 (2H, s), 4.35-4.22 (2H, m), 3.86-3.68 (4H, m), 3.62-3.41 (2H, m), 1.45 (3H, d). | 295 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 35 | 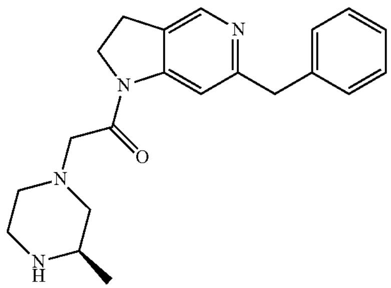 | 1-(6-Benzyl-2,3-dihydro-pyrrolo[3,2-c]pyridin-1-yl)-2-((R)-3-methyl-piperazin-1-yl)-ethanone hydrochloride salt | 8.48 (1H, s), 8.26 (1H, s), 7.46-7.28 (5H, m), 4.47 (2H, s), 4.44-4.32 (4H, m), 3.87-3.65 (4H, m), 3.61-3.52 (1H, m), 3.46 (3H, t), 3.27 (1H, t), 1.44 (3H, d). | 351 | 2 |
| 36 | 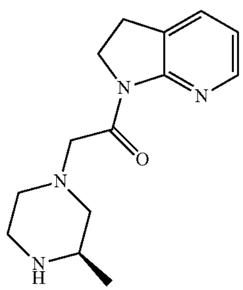 | 1-(2,3-Dihydro-pyrrolo[2,3-b]pyridin-1-yl)-2-((R)-3-methyl-piperazin-1-yl)-ethanone dihydrochloride salt | (DMSO-d6): 10.45 (1H, s), 10.33 (1H, s), 8.19 (1H, d), 7.75 (1H, d), 7.16-7.08 (1H, m), 4.87 (2H, s), 4.06 (2H, t), 3.94-3.30 (7H, m), 1.34 (3H, d). | 261 | 2 |
| 37 | 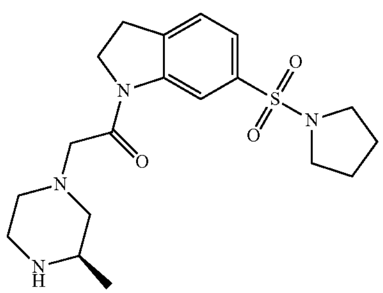 | 2-((R)-3-Methyl-piperazin-1-yl)-1-[6-(pyrrolidine-1-sulfonyl)-2,3-dihydro-indol-1-yl]-ethanone hydrochloride salt | 8.60 (1H, d), 7.60 (1H, dd), 7.52 (1H, d), 4.52 (1H, d), 4.50 (1H, d), 4.23 (2H, t), 4.00-3.84 (3H, m), 3.82-3.72 (1H, m), 3.72-3.54 (2H, m), 3.46-3.37 (3H, m), 3.24 (4H, t), 1.83-1.68 (4H, m), 1.48 (3H, d). | 393 | 4, Purified by crystallisation of crude product from isopropanol |

TABLE 8-continued

| Ex. | Structure | Compound Name | ¹H NMR Data (Me-d3-OD, unless indicated) | MS Data [M + H]⁺ | Method |
|---|---|---|---|---|---|
| 38 | 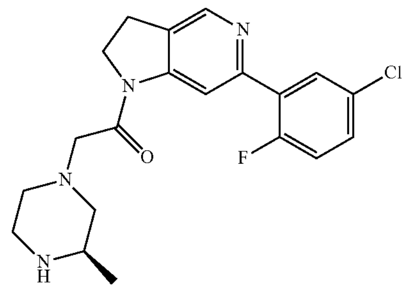 | 1-[6-(5-Chloro-2-fluoro-phenyl)-2,3-dihydro-pyrrolo[3,2-c]pyridin-1-yl]-2-((R)-3-methyl-piperazin-1-yl)-ethanone hydrochloride salt | 8.68 (1H, s), 8.63 (1H, s), 7.86 (1H, dd), 7.83-7.71 (1H, m), 7.49 (1H, t), 4.59 (2H, s), 4.49 (2H, t), 3.94-3.69 (4H, m), 3.64-3.47 (4H, m), 1.47 (3H, d). | 389 | 2 |
| 39 | 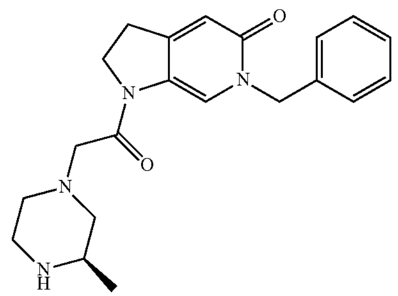 | 6-Benzyl-1-[2-((R)-3-methyl-piperazin-1-yl)-acetyl]-1,2,3,6-tetrahydro-pyrrolo[2,3-c]pyridin-5-one hydrochloride salt | 8.36 (1H, s), 7.42-7.25 (5H, m), 6.60 (1H, s), 5.21 (2H, s), 4.21 (2H, s), 4.12 (2H, t), 3.80-3.61 (4H, m), 3.55-3.45 (1H, m), 3.31-3.26 (2H, m), 3.26-3.02 (2H, m), 1.42 (3H, d). | 367 | 4 |
| 40 | 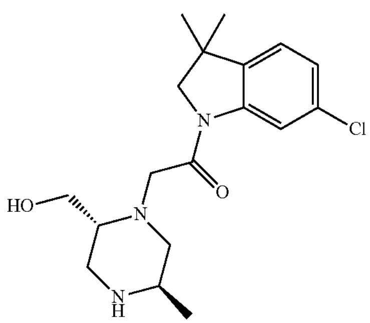 | 1-(6-Chloro-3,3-dimethyl-2,3-dihydro-indol-1-yl)-2-((2R,5R)-2-hydroxymethyl-5-methyl-piperazin-1-yl)-ethanone hydrochloride salt | 8.17 (1H, d), 7.26 (1H, d), 7.16 (1H, dd), 4.60-4.40 (2H, m), 4.11-3.98 (2H, m), 3.96 (2H, s), 3.84 (3H, d), 3.74 (1H, d), 3.67-3.52 (2H, m), 1.45 (3H, d), 1.41 (6H, s). | 352 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 41 | 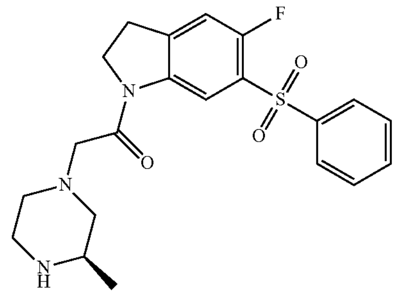 [SMILES: C[C@@H]1CN(CC(=O)N2CCc3cc(F)c(S(=O)(=O)c4ccccc4)cc32)CCN1] | 1-(6-Benzenesulfonyl-5-fluoro-2,3-dihydro-indol-1-yl)-2-((R)-3-methyl-piperazin-1-yl)ethanone | 8.85 (1H, d), 7.98 (2H, d), 7.69 (1H, t), 7.61 (2H, t), 7.14 (1H, d), 4.27 (2H, t), 3.37 (2H, d), 3.31-3.19 (2H, m), 2.97 (5H, d), 2.33-2.21 (1H, m), 1.95 (1H, t), 1.10 (3H, d). | 418 | 4, Purified by preparative HPLC, basic method |
| 42 | 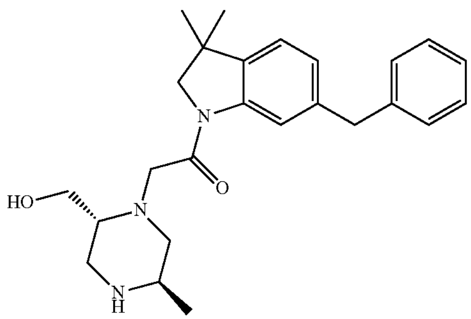 | 1-(6-Benzyl-3,3-dimethyl-2,3-dihydro-indol-1-yl)-2-((2R,5R)-2-hydroxymethyl-5-methyl-piperazin-1-yl)ethanone trifluoroacetate salt | 8.01 (1H, s), 7.33-7.11 (6H, m), 6.99 (1H, dd), 4.01 (1H, d), 3.95 (2H, s), 3.92-3.85 (3H, m), 3.84-3.76 (1H, m), 3.71 (1H, dd), 3.59-3.45 (2H, m), 3.45-3.38 (1H, m), 3.22 (1H, t), 3.11 (1H, t), 2.08-1.99 (1H, m), 1.39-1.31 (9H, m). | | 2, Purified by preparative HPLC, TFA method |
| 43 | 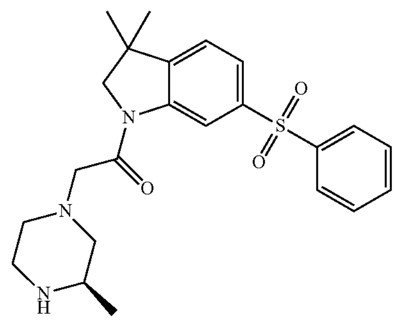 | 1-(6-Benzenesulfonyl-3,3-dimethyl-2,3-dihydro-indol-1-yl)-2-((R)-3-methyl-piperazin-1-yl)-ethanone hydrochloride salt | 8.68 (1H, d), 7.97-7.90 (2H, m), 7.78 (1H, dd), 7.70-7.63 (1H, m), 7.58 (2H, t), 7.51 (1H, d), 4.60-4.45 (2H, m), 4.02-3.83 (5H, m), 3.83-3.70 (1H, m), 3.70-3.55 (2H, m), 3.44 (1H, t), 1.49 (3H, d), 1.42 (6H, s). | 428 | 4 |

TABLE 8-continued

| Ex. | Structure | Compound Name | ¹H NMR Data (Me-d3-OD, unless indicated) | MS Data [M + H]⁺ | Method |
|---|---|---|---|---|---|
| 44 | 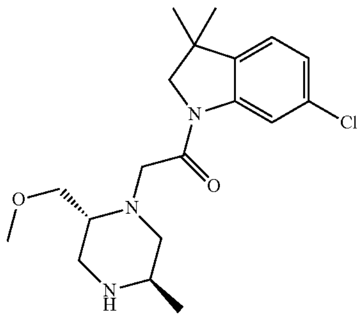 | 1-(6-Chloro-3,3-dimethyl-2,3-dihydro-indol-1-yl)-2-((2R,5R)-2-methoxymethyl-5-methyl-piperazin-1-yl)-ethanone hydrochloride salt | 8.18 (1H, d), 7.27 (1H, d), 7.16 (1H, dd), 4.60-4.41 (2H, m), 4.16 (1H, s), 4.01-3.46 (11H, m), 1.50-1.40 (9H, m). | 366 | 2 |
| 45 | 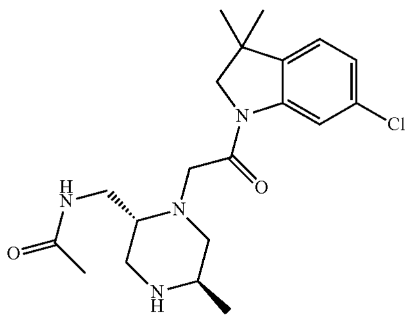 | N-{[(2R,5R)-1-[2-(6-Chloro-3,3-dimethyl-2,3-dihydro-indol-1-yl)-2-oxo-ethyl]-5-methyl-piperazin-2-ylmethyl]}-acetamide hydrochloride salt | 8.16 (1H, d), 7.25 (1H, d), 7.13 (1H, d), 4.27-4.14 (1H, m), 4.13-4.03 (1H, m), 3.93 (2H, s), 3.58 (6H, m), 3.28-3.12 (2H, m), 1.97 (3H, s), 1.46-1.34 (9H, m). | 393 | 2 |
| 46 | 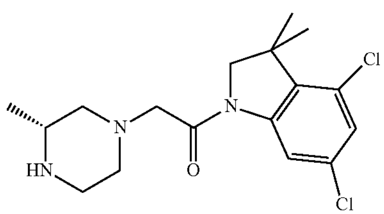 | 1-(4,6-Dichloro-3,3-dimethyl-2,3-dihydro-indol-1-yl)-2-((R)-3-methyl-piperazin-1-yl)-ethanone hydrochloride salt | 8.21 (1H, d), 7.17 (1H, d), 4.52 (2H, s), 3.96 (2H, s), 3.89 (3H, s), 3.82-3.71 (1H, m), 3.64 (2H, d), 3.46 (1H, t), 1.57 (6H, s), 1.48 (3H, d). | 356 | 4 |

TABLE 8-continued

| Ex. | Structure | Compound Name | 1H NMR Data (Me-d3-OD, unless indicated) | MS Data [M + H]+ | Method |
|---|---|---|---|---|---|
| 47 | (structure) ·2HCl | 1-(6-Benzenesulfonyl-5-fluoro-3,3-dimethyl-2,3-dihydro-indol-1-yl)-2-((R)-3-methyl-piperazin-1-yl)-ethanone dihydrochloride salt | (DMSO-d6): 10.21-9.80 (2H, bs), 8.70 (1H, d), 7.92 (2H, d), 7.76 (1H, t), 7.68 (2H, t), 7.54 (1H, d), 4.72-4.09 (4H, m), 3.80-3.21 (7H, m), 1.43-1.13 (9H, m). | 446 | 2 |
| 48 | (structure) ·2HCl | 1-(6-Benzenesulfonyl-5-fluoro-3,3-dimethyl-2,3-dihydro-indol-1-yl)-2-((2S,5R)-2-ethyl-5-methyl-piperazin-1-yl)-ethanone dihydrochloride salt | (DMSO-d6): 10.61-9.62 (2H, m), 8.70 (1H, d), 7.92 (2H, d), 7.76 (1H, t), 7.68 (2H, t), 7.54 (1H, d), 4.77-4.04 (4H, m), 3.87-3.14 (7H, m), 1.32 (9H, d), 1.11-0.72 (4H, m). | 474 | 2 |
| 49 | (structure) ·2HCl | 1-[5-Fluoro-3,3-dimethyl-6-(pyrrolidine-1-sulfonyl)-2,3-dihydro-indol-1-yl]-2-((R)-3-methyl-piperazin-1-yl)-ethanone dihydrochloride salt | 8.64 (1H, d), 7.35 (1H, d), 4.47 (2H, s), 3.99 (2H, s), 3.95-3.69 (4H, m), 3.69-3.40 (3H, m), 3.40-3.22 (4H, m), 1.93-1.79 (4H, m), 1.53-1.26 (9H, m). | 439 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 50 | 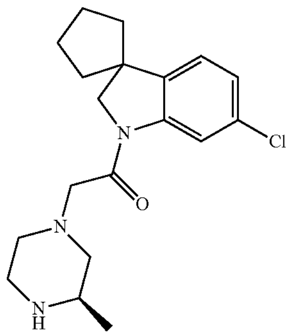 | 1-{6-Chloro-1',2'-dihydrospiro[cyclopentane-1,3'-indole]-1'-yl]-2-[(3R)-3-methylpiperazin-1-yl]ethan-1-one hydrochloride salt | 8.16 (1H, d), 7.26 (1H, d), 7.15 (1H, dd), 4.66 (2H, s), 4.23-3.91 (5H, m), 3.91-3.67 (3H, m), 3.59 (1H, t), 2.03-1.80 (8H, m), 1.51 (3H, d). | 348 | 4 |
| 51 | 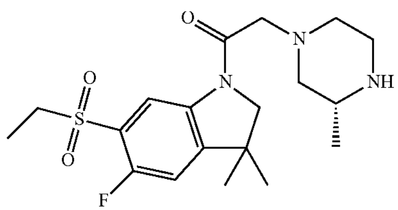 | 1-(6-Ethanesulfonyl-5-fluoro-3,3-dimethyl-2,3-dihydro-indol-1-yl)-2-((R)-3-methyl-piperazin-1-yl)-ethanone dihydrochloride salt | 8.65 (1H, d), 7.41 (1H, d), 4.55 (2H, s), 4.01 (2H, s), 3.98-3.82 (3H, m), 3.81-3.72 (1H, m), 3.72-3.56 (2H, m), 3.47 (1H, t), 3.42-3.35 (2H, m), 1.67-1.40 (9H, m), 1.26 (3H, t). | 398 | 2 |
| 52 | 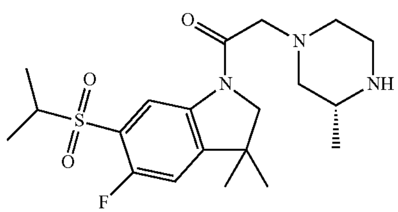 | 1-[5-Fluoro-3,3-dimethyl-6-(propane-2-sulfonyl)-2,3-dihydro-indol-1-yl]-2-((R)-3-methyl-piperazin-1-yl)-ethanone dihydrochloride salt | 8.64 (1H, d), 7.40 (1H, d), 4.57 (2H, s), 4.01 (2H, s), 3.92 (3H, d), 3.85-3.74 (1H, m), 3.73-3.61 (2H, m), 3.61-3.43 (2H, m), 1.68-1.44 (9H, m), 1.30 (6H, d). | 412 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 53 | 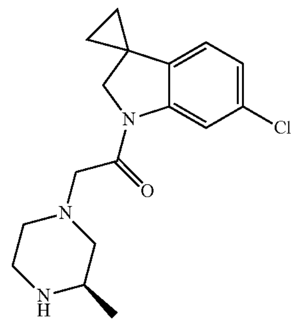 | 1-{6-Chloro-1',2'-dihydrospiro[cyclopropane-1,3'-indole]-1'-yl}-2-[(3R)-3-methylpiperazin-1-yl]ethan-1-one hydrochloride salt | 8.17 (1H, d), 7.09 (1H, d), 6.80 (1H, dd), 4.43 (2H, s), 4.18 (2H, s), 3.99-3.69 (4H, m), 3.69-3.51 (2H, m), 3.41 (1H, t), 1.48 (3H, d), 1.25-1.19 (2H, m), 1.19-1.13 (2H, m). | 320 | 4 |
| 54 | 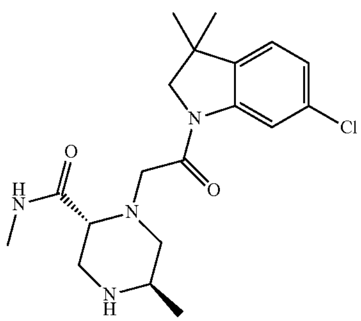 | (2R,5R)-1-[2-(6-Chloro-3,3-dimethyl-2,3-dihydro-indol-1-yl)-2-oxo-ethyl]-5-methyl-piperazine-2-carboxylic acid methylamide hydrochloride salt | 8.18 (1H, d), 7.25 (1H, d), 7.14 (1H, dd), 4.52 (1H, d), 4.23 (2H, s), 3.97-3.89 (2H, m), 3.88-3.76 (3H, m), 3.56-3.43 (2H, m), 2.84 (3H, s), 1.45 (3H, d), 1.39 (6H, d). | 379 | 2 |
| 55 | 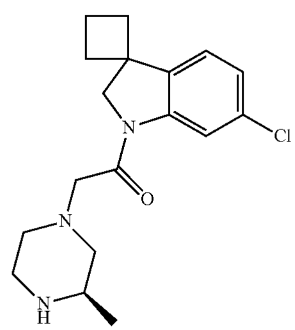 | 1-{6-Chloro-1',2'-dihydrospiro[cyclobutane-1,3'-indole]-1'-yl}-2-[(3R)-3-methylpiperazin-1-yl]ethan-1-one hydrochloride salt | 8.13 (1H, d), 7.55 (1H, d), 7.21 (1H, dd), 4.61 (2H, s), 4.29 (2H, s), 3.94 (3H, dd), 3.84-3.62 (3H, m), 3.53 (1H, t), 2.61-2.30 (4H, m), 2.30-2.03 (2H, m), 1.50 (3H, d). | 334 | 4 |

TABLE 8-continued

| Ex. | Structure | Compound Name | 1H NMR Data (Me-d3-OD, unless indicated) | MS Data [M + H]+ | Method |
|---|---|---|---|---|---|
| 56 | (structure) ·HCl | (2R,5R)-1-[2-(6-Benzenesulfonyl-5-fluoro-3,3-dimethyl-2,3-dihydro-indol-1-yl)-2-oxo-ethyl]-5-methyl-piperazine-2-carboxylic acid methylamide hydrochloride salt | 8.86 (1H, d), 7.97 (2H, d), 7.71 (1H, t), 7.62 (2H, t), 7.21 (1H, d), 4.09 (1H, d), 4.06-3.89 (3H, m), 3.89-3.78 (1H, m), 3.63 (2H, d), 3.52 (1H, d), 3.18-3.04 (1H, m), 2.82 (3H, s), 1.42-1.36 (9H, m). | 503 | 2 |
| 57 | (structure) ·2HCl | 1-(6-Cyclopropanesulfonyl-5-fluoro-3,3-dimethyl-2,3-dihydro-indol-1-yl)-2-((R)-3-methyl-piperazin-1-yl)-ethanone dihydrochloride salt | 8.66-8.55 (1H, m), 7.40 (1H, d), 4.55 (2H, s), 4.00 (2H, s), 3.98-3.83 (3H, m), 3.83-3.71 (1H, m), 3.71-3.57 (2H, m), 3.47 (1H, t), 2.94-2.81 (1H, m), 1.66-1.41 (9H, m), 1.41-1.19 (2H, m), 1.19-1.01 (2H, m). | 410 | 2 |
| 58 | (structure) ·HCl | 1-(6-Benzenesulfonyl-5-fluoro-3,3-dimethyl-2,3-dihydro-indol-1-yl)-2-((2R,5R)-2-methoxymethyl-5-methyl-piperazin-1-yl)-ethanone hydrochloride salt | 8.85 (1H, d), 7.97 (2H, d), 7.71 (1H, t), 7.62 (2H, t), 7.24 (1H, d), 4.47-4.22 (2H, m), 4.13-3.91 (3H, m), 3.91-3.61 (6H, m), 3.61-3.38 (3H, m), 1.50-1.39 (9H, m). | 490 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 59 | 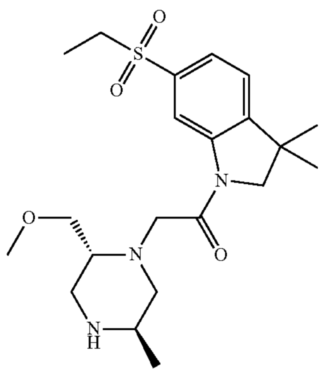 | 1-(6-Ethanesulfonyl-3,3-dimethyl-2,3-dihydro-indol-1-yl)-2-((2R,5R)-2-methoxymethyl-5-methyl-piperazin-1-yl)-ethanone dihydrochloride salt | 8.67 (1H, d), 7.72 (1H, dd), 7.58 (1H, d), 4.61-4.36 (2H, m), 4.22-4.08 (1H, m), 4.08-3.98 (2H, m), 3.93-3.80 (3H, m), 3.80-3.51 (4H, m), 3.35 (3H, s), 3.27-3.14 (2H, m), 1.65-1.30 (9H, m), 1.30-1.18 (3H, m). | 424 | 2 |
| 60 | 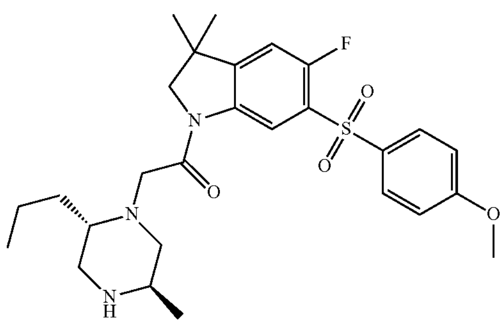 | 1-[5-Fluoro-6-(4-methoxy-benzenesulfonyl)-3,3-dimethyl-2,3-dihydro-indol-1-yl]-2-((2R,5R)-2-methoxymethyl-5-methyl-piperazin-1-yl)-ethanone dihydrochloride salt | 8.81 (1H, d), 7.88 (2H, d), 7.23 (1H, d), 7.11 (2H, d), 4.56-4.34 (2H, m), 4.10 (1H, d), 4.04-3.99 (2H, m), 3.89 (3H, s), 3.88-3.69 (5H, m), 3.64-3.49 (2H, m), 3.36 (3H, s), 1.46 (3H, d), 1.41 (6H, s). | 520 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 61 | 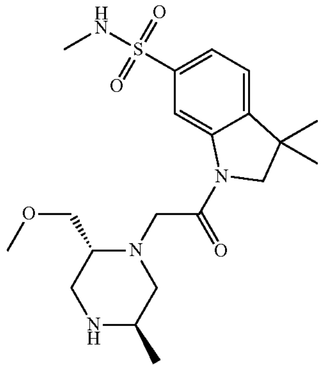 | 1-[2-((2R,5R)-2-Methoxymethyl-5-methyl-piperazin-1-yl)-acetyl]-3,3-dimethyl-2,3-dihydro-1H-indole-6-sulfonic acid methylamide dihydrochloride salt | 8.64 (1H, d), 7.64 (1H, dd), 7.50 (1H, d), 4.60-4.44 (2H, m), 4.23-4.08 (1H, m), 4.02 (2H, s), 3.96-3.79 (3H, m), 3.79-3.69 (2H, m), 3.69-3.55 (2H, m), 3.34 (3H, s), 2.55 (3H, s), 1.55-1.25 (9H, m). | 425 | 2 |
| 62 | 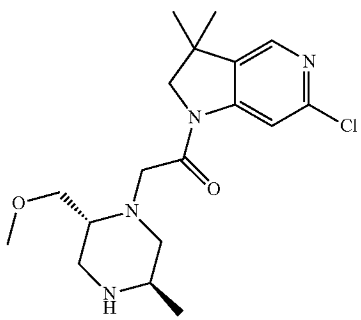 | 1-(6-Chloro-3,3-dimethyl-2,3-dihydro-pyrrolo[3,2-c]pyridin-1-yl)-2-((2R,5R)-2-methoxymethyl-5-methyl-piperazin-1-yl)ethanone hydrochloride salt | 8.44 (1H, s), 8.25 (1H, s), 4.62 (1H, d), 4.55 (1H, d), 4.36-4.02 (3H, m), 3.92-3.68 (5H, m), 3.68-3.51 (2H, m), 3.35 (3H, s), 1.53 (6H, s), 1.46 (3H, d). | 367 | 4 |
| 63 | 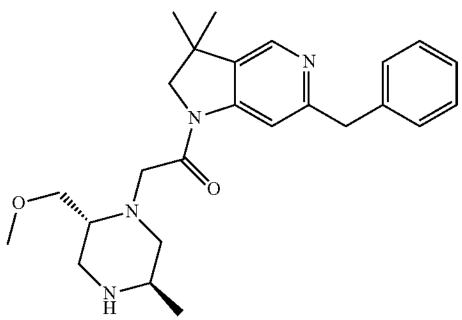 | 1-(6-Benzyl-3,3-dimethyl-2,3-dihydro-pyrrolo[3,2-c]pyridin-1-yl)-2-((2R,5R)-2-methoxymethyl-5-methyl-piperazin-1-yl)-ethanone hydrochloride salt | 8.60 (1H, s), 8.26 (1H, s), 7.48-7.26 (5H, m), 4.58-4.31 (4H, m), 4.31-4.08 (2H, m), 4.08-3.91 (1H, m), 3.90-3.71 (2H, m), 3.71-3.58 (3H, m), 3.58-3.40 (2H, m), 1.54 (6H, s), 1.41 (3H, d). | 423 | 4 |

TABLE 8-continued

| Ex. | Structure | Compound Name | ¹H NMR Data (Me-d3-OD, unless indicated) | MS Data [M + H]⁺ | Method |
|---|---|---|---|---|---|
| 64 | 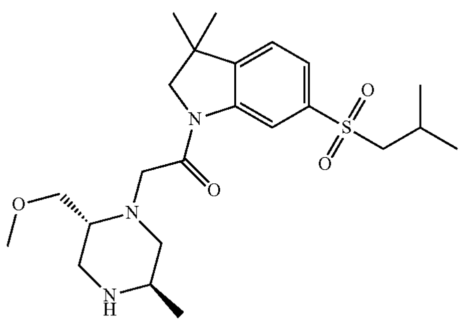 | 1-[3,3-Dimethyl-6-(2-methyl-propane-1-sulfonyl)-2,3-dihydro-indol-1-yl]-2-((2R,5R)-2-methoxymethyl-5-methyl-piperazin-1-yl)-ethanone dihydrochloride salt | 8.68 (1H, d), 7.72 (1H, dd), 7.56 (1H, d), 4.47-4.27 (2H, m), 4.08-3.93 (3H, m), 3.88-3.62 (5H, m), 3.58-3.40 (2H, m), 3.34 (3H, s), 3.11 (2H, d), 2.20-2.07 (1H, m), 1.47 (6H, s), 1.43 (3H, d), 1.06 (6H, d). | 452 | 2 |
| 65 | 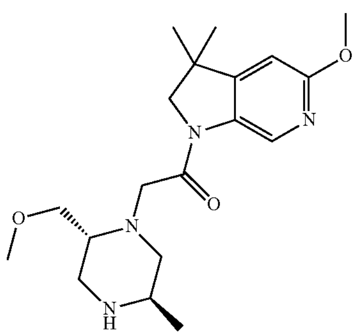 | 1-(5-Methoxy-3,3-dimethyl-2,3-dihydro-pyrrolo[2,3-c]pyridin-1-yl)-2-((2R,5R)-2-methoxymethyl-5-methyl-piperazin-1-yl)ethanone hydrochloride salt | 8.78 (1H, s), 7.59 (1H, s), 4.38-4.26 (2H, m), 4.23 (3H, s), 4.15-4.08 (2H, m), 3.97-3.81 (2H, m), 3.80-3.55 (7H, m), 3.43 (2H, d), 1.55 (6H, s), 1.41 (3H, d). | 363 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 66 | 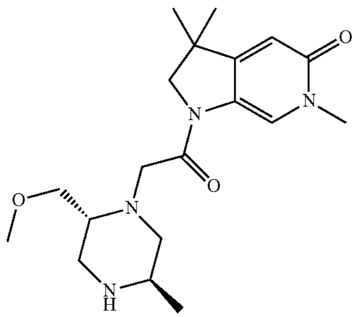 | 1-[2-((2R,5R)-2-Methoxymethyl-5-methyl-piperazin-1-yl)-acetyl]-3,3,6-trimethyl-1,2,3,6-tetrahydro-pyrrolo[2,3-c]pyridin-5-one hydrochloride salt | 8.41 (1H, s), 6.56 (1H, s), 4.08-3.85 (4H, m), 3.66-3.47 (9H, m), 3.40-3.36 (3H, m), 3.23-3.08 (2H, m), 1.46-1.38 (6H, m), 1.35 (3H, d). | 363 | 2 |
| 67 | 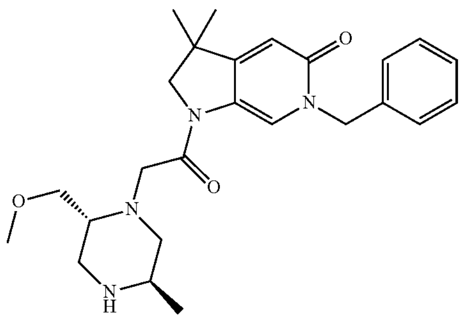 | 6-Benzyl-1-[2-((2R,5R)-2-methoxymethyl-5-methyl-piperazin-1-yl)-acetyl]-3,3-dimethyl-1,2,3,6-tetrahydro-pyrrolo[2,3-c]pyridin-5-one hydrochloride salt | 8.38 (1H, s), 7.40-7.28 (5H, m), 6.57 (1H, s), 5.23 (2H, s), 4.21-3.99 (2H, m), 3.94-3.86 (2H, m), 3.76-3.36 (11H, m), 1.43 (6H, s), 1.36 (3H, d). | 439 | 2 |
| 68 | 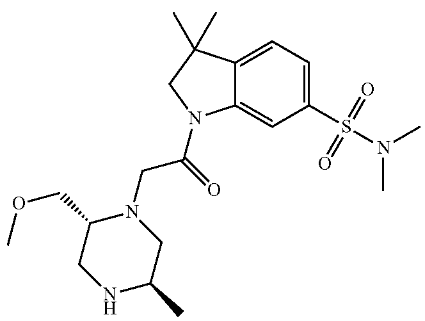 | 1-[2-((2R,5R)-2-Methoxymethyl-5-methyl-piperazin-1-yl)-acetyl]-3,3-dimethyl-2,3-dihydro-1H-indole-6-sulfonic acid dimethylamide dihydrochloride salt | 8.57 (1H, d), 7.59 (1H, dd), 7.55 (1H, d), 4.63-4.38 (2H, m), 4.23-4.09 (1H, m), 4.03 (2H, s), 3.96-3.80 (3H, m), 3.80-3.69 (2H, m), 3.69-3.54 (2H, m), 3.35 (3H, s), 2.71 (6H, s), 1.69-1.25 (9H, m). | 439 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 69 | 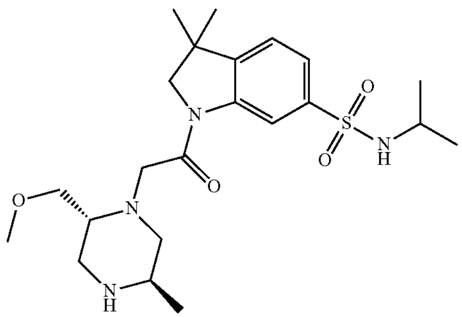 | 1-[2-((2R,5R)-2-Methoxymethyl-5-methyl-piperazin-1-yl)-acetyl]-3,3-dimethyl-2,3-dihydro-1H-indole-6-sulfonic acid isopropylamide dihydrochloride salt | 8.67 (1H, d), 7.67 (1H, dd), 7.49 (1H, d), 4.66-4.41 (2H, m), 4.27-4.11 (1H, m), 4.02 (2H, s), 3.96-3.58 (7H, m), 3.43-3.35 (1H, m), 3.35 (3H, m), 1.65-1.43 (9H, m), 1.05 (6H, d). | 453 | 2 |
| 70 | 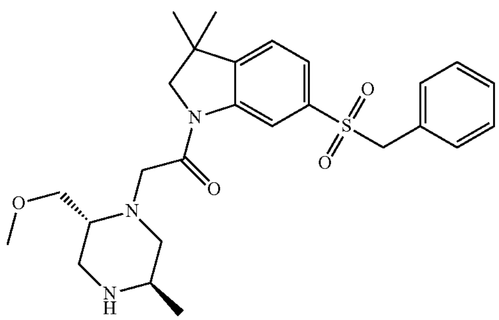 | 1-(3,3-Dimethyl-6-phenylmethanesulfonyl-2,3-dihydro-indol-1-yl)-2-((2R,5R)-2-methoxymethyl-5-methyl-piperazin-1-yl)-ethanone dihydrochloride salt | 8.48 (1H, s), 7.52-7.43 (2H, m), 7.34-7.22 (3H, m), 7.16 (2H, d), 4.55-4.31 (4H, m), 4.10-3.93 (3H, m), 3.93-3.76 (2H, m), 3.76-3.66 (3H, m), 3.66-3.46 (2H, m), 3.31 (3H, s), 1.52-1.39 (9H, m). | 486 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 71 | 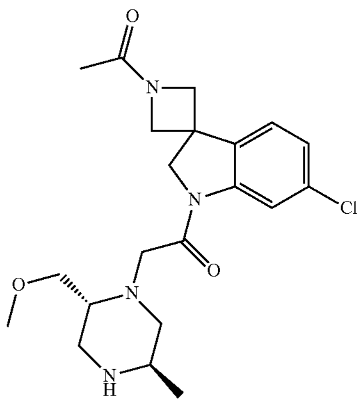 | 1-{1-Acetyl-6-chloro-1',2'-dihydrospiro[azetidine-3,3'-indole]-1'-yl]-2-[(2R,5R)-2-(methoxymethyl)-5-methylpiperazin-1-yl]ethan-1-one hydrochloride salt | 8.19 (1H, d), 7.61 (1H, d), 7.27 (1H, dd), 4.53 (1H, d), 4.50-4.38 (4H, m), 4.38-4.31 (1H, m), 4.28 (1H, d), 4.20 (1H, dd), 4.05-3.95 (1H, m), 3.86-3.63 (5H, m), 3.55-3.42 (2H, m), 3.35 (3H, s), 1.98 (3H, s), 1.42 (3H, d). | 421 | 2 |
| 72 | 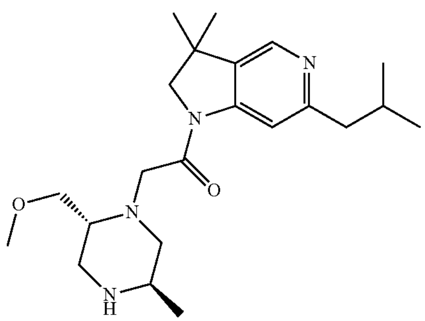 [SMILES: COC[C@H]1CN[C@H](C)CN1CC(=O)N1CC(C)(C)c2cnc(CC(C)C)cc21] | 1-(6-Isobutyl-3,3-dimethyl-2,3-dihydro-pyrrolo[3,2-c]pyridin-1-yl)-2-((2R,5R)-2-methoxymethyl-5-methyl-piperazin-1-yl)-ethanone | 8.21 (1H, s), 7.93 (1H, s), 4.06-3.89 (2H, m), 3.79 (1H, d), 3.58-3.42 (2H, m), 3.42-3.35 (3H, m), 3.21 (3H, s), 2.91 (3H, dd), 2.81-2.50 (5H, m), 2.38 (1H, t), 2.11-1.96 (1H, m), 1.07 (3H, d), 0.94 (6H, d). | 389 | 2, Purified by preparative HPLC, basic method |

TABLE 8-continued

| Ex. | Structure | Compound Name | 1H NMR Data (Me-d3-OD, unless indicated) | MS Data [M + H]+ | Method |
|---|---|---|---|---|---|
| 73 | (isobutyl-dimethyl-pyrrolopyridinone with (2R,5R)-methoxymethyl-methylpiperazinyl-acetyl substituent) · HCl | 6-Isobutyl-1-[2-((2R,5R)-2-methoxymethyl-5-methyl-piperazin-1-yl)-acetyl]-3,3-dimethyl-1,2,3,6-tetrahydro-pyrrolo[2,3-c]pyridin-5-one hydrochloride salt | 8.36 (1H, s), 6.57 (1H, s), 4.31-4.15 (2H, m), 3.94 (2H, dd), 3.87 (2H, d), 3.78-3.54 (8H, m), 2.22-2.10 (1H, m), 1.44 (6H, s), 1.40 (3H, d), 0.96 (6H, d). | 405 | 2 |
| 74 | (dimethyl-phenoxy-dihydropyrrolopyridine with (2R,5R)-methoxymethyl-methylpiperazinyl-ethanone substituent) · HCl | 1-(3,3-Dimethyl-6-phenoxy-2,3-dihydro-pyrrolo[3,2-c]pyridin-1-yl)-2-((2R,5R)-2-methoxymethyl-5-methyl-piperazin-1-yl)-ethanone hydrochloride salt | 8.36 (1H, s), 7.66-7.53 (3H, m), 7.49 (1H, t), 7.38 (2H, d), 4.31 (2H, s), 4.21-4.09 (2H, m), 3.82 (1H, s), 3.72-3.41 (6H, m), 3.29 (3H, s), 1.54 (6H, s), 1.36 (3H, d). | 425 | 2 |
| 75 | (dimethyl-isopentyl-dihydropyrrolopyridine with (2R,5R)-methoxymethyl-methylpiperazinyl-ethanone substituent) | 1-[3,3-Dimethyl-6-(3-methyl-butyl)-2,3-dihydro-pyrrolo[3,2-c]pyridin-1-yl]-2-((2R,5R)-2-methoxymethyl-5-methyl-piperazin-1-yl)-ethanone | (CDCl3): 8.25 (1H, s), 8.05-7.81 (1H, m), 3.95 (1H, d), 3.84-3.70 (2H, m), 3.48 (1H, dd), 3.44-3.31 (2H, m), 3.27 (3H, s), 3.01-2.85 (1H, s), 2.85-2.67 (4H, m), 2.50-2.28 (1H, m), 1.41 (6H, d), 1.05 (3H, d), 0.96 (6H, d). | 403 | 4, Purified by preparative HPLC, basic method |

TABLE 8-continued

| Ex. | Structure | Compound Name | ¹H NMR Data (Me-d3-OD, unless indicated) | MS Data [M + H]⁺ | Method |
|---|---|---|---|---|---|
| 76 | 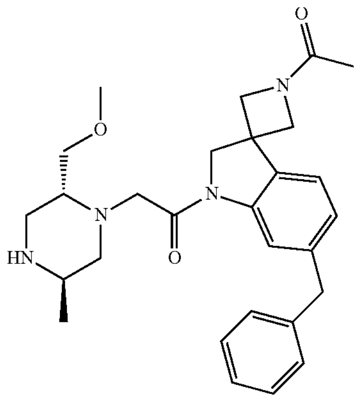 | 1-{1-Acetyl-6'-benzyl-1',2'-dihydrospiro[azetidine-3,3'-indole]-1'-yl}-2-[(2R,5R)-2-(methoxymethyl)-5-methylpiperazin-1-yl]ethan-1-one hydrochloride salt | 8.06 (1H, s), 7.63-7.50 (1H, m), 7.39-7.22 (2H, m), 7.22-7.10 (4H, m), 4.76-4.36 (6H, m), 4.30 (2H, d), 4.21 (1H, dd), 4.07-3.86 (5H, m), 3.86-3.64 (6H, m), 3.60-3.46 (1H, m), 2.02-1.97 (3H, m), 1.46 (3H, d). | 477 | 2 |
| 77 | 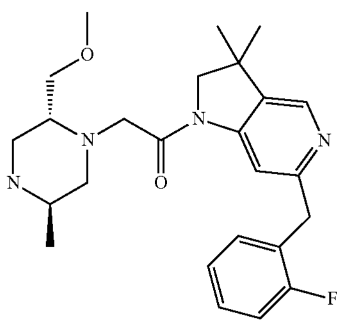 [SMILES: COC[C@H]1CN[C@H](C)CN1CC(=O)N1CC(C)(C)c2cnc(Cc3ccccc3F)cc21] | 1-{6-[(2-Fluorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one | 8.22 (1H, s), 7.92 (1H, s), 7.33-7.21 (2H, m), 7.17-7.02 (2H, m), 4.14 (2H, s), 3.99 (1H, d), 3.91 (1H, d), 3.74 (1H, d), 3.45-3.35 (2H, m), 3.15 (3H, s), 2.93-2.77 (3H, m), 2.74-2.55 (2H, m), 2.30 (1H, t), 1.41 (6H, s), 1.04 (3H, d). | 441 | 2, Purified by preparative HPLC, basic method |

TABLE 8-continued

| Ex. | Structure | Compound Name | ¹H NMR Data (Me-d3-OD, unless indicated) | MS Data [M + H]⁺ | Method |
|---|---|---|---|---|---|
| 78 | 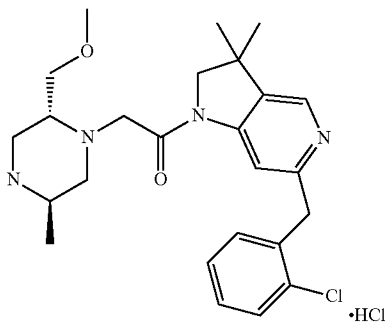 [SMILES: COC[C@H]1CN[C@H](C)CN1CC(=O)N1CC(C)(C)c2cnc(Cc3ccccc3Cl)cc21 ; Cl] | 1-{6-[(2-Chlorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one hydrochloride salt | 8.61 (1H, s), 8.09 (1H, s), 7.55-7.46 (2H, m), 7.46-7.37 (2H, m), 4.50 (2H, s), 4.16 (4H, d), 3.75-3.65 (1H, m), 3.64-3.38 (5H, m), 3.29-3.14 (5H, m), 1.53 (6H, s), 1.35 (3H, d). | 457 | 2 |
| 79 | 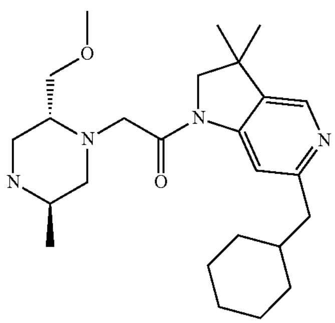 [SMILES: COC[C@H]1CN[C@H](C)CN1CC(=O)N1CC(C)(C)c2cnc(CC3CCCCC3)cc21] | 1-[6-(Cyclohexylmethyl)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one | 8.20 (1H, s), 7.92 (1H, s), 4.02 (1H, d), 3.97-3.70 (2H, m), 3.55-3.36 (3H, m), 3.20 (3H, s), 2.97-2.81 (3H, m), 2.81-2.55 (4H, m), 2.34 (1H, t), 1.80-1.52 (6H, m), 1.42 (6H, s), 1.32-1.15 (3H, m), 1.15-0.86 (5H, m). | 429 | 2, Purified by preparative HPLC, basic method |

TABLE 8-continued

| Ex. | Structure | Compound Name | ¹H NMR Data (Me-d3-OD, unless indicated) | MS Data [M + H]⁺ | Method |
|---|---|---|---|---|---|
| 80 | 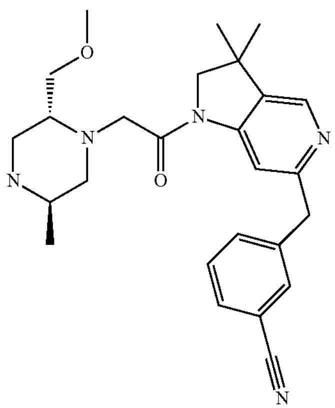 | 3-[(1-{2-[(2R,5R)-2-(Methoxymethyl)-5-methylpiperazin-1-yl]acetyl}-3,3-dimethyl-1H,2H,3H-pyrrolo[3,2-c]pyridin-6-yl)methyl]benzonitrile hydrochloride salt | 8.58 (1H, s), 8.23 (1H, s), 7.80-7.65 (3H, m), 7.61 (1H, t), 4.45 (2H, s), 4.21-4.03 (5H, m), 3.55-3.40 (3H, m), 3.28 (3H, s), 3.25-3.07 (3H, m), 1.52 (6H, s), 1.35 (3H, d). | 448 | 2 |
| 81 | 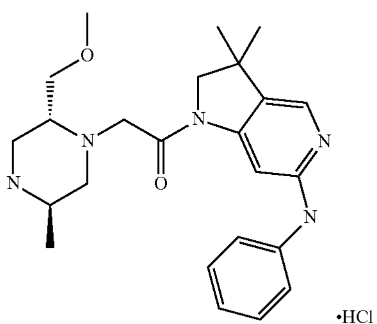 [SMILES: COC[C@H]1CN[C@H](C)CN1CC(=O)N1CC(C)(C)c2cnc(Nc3ccccc3)cc21 ; Cl] | 1-(3,3-Dimethyl-6-phenylamino-2,3-dihydro-pyrrolo[3,2-c]pyridin-1-yl)-2-((2R,5R)-2-methoxymethyl-5-methyl-piperazin-1-yl)-ethanone hydrochloride salt | 7.83 (1H, s), 7.74-7.56 (5H, m), 6.09 (1H, s), 4.04 (1H, d), 3.89 (1H, d), 3.85-3.75 (1H, m), 3.68-3.49 (7H, m), 3.42-3.29 (4H, m), 3.17 (1H, t), 1.42 (6H, s), 1.37 (3H, d). | 424 | 2, Purified by trituration with EtOAc |

TABLE 8-continued

| Ex. | Structure | Compound Name | ¹H NMR Data (Me-d3-OD, unless indicated) | MS Data [M + H]⁺ | Method |
|---|---|---|---|---|---|
| 82 | 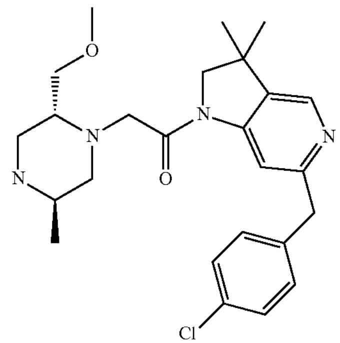 [SMILES: COC[C@H]1CN[C@H](C)CN1CC(=O)N1CC(C)(C)c2cnc(Cc3ccc(Cl)cc3)cc21] | 1-[6-(4-Chloro-benzyl)-3,3-dimethyl-2,3-dihydro-pyrrolo[3,2-c]pyridin-1-yl]-2-((2R,5R)-2-methoxymethyl-5-methyl-piperazin-1-yl)ethanone | 8.23 (1H, s), 7.92 (1H, s), 7.34-7.19 (4H, m), 4.09 (2H, s), 3.99 (1H, d), 3.91 (1H, d), 3.76 (1H, d), 3.48-3.39 (2H, m), 3.17 (3H, s), 2.96-2.79 (3H, m), 2.79-2.57 (2H, m), 2.35 (1H, t), 1.40 (6H, s), 1.05 (3H, d). | 457 | 2, Purified by preparative HPLC, basic method |
| 83 | 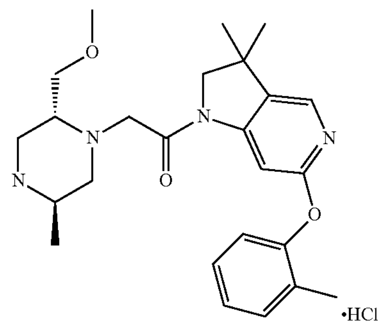 [SMILES: COC[C@H]1CN[C@H](C)CN1CC(=O)N1CC(C)(C)c2cnc(Oc3ccccc3C)cc21 ; Cl] | 1-(3,3-Dimethyl-6-o-tolyloxy-2,3-dihydro-pyrrolo[3,2-c]pyridin-1-yl)-2-((2R,5R)-2-methoxymethyl-5-methyl-piperazin-1-yl)ethanone hydrochloride salt | 8.35 (1H, s), 7.53-7.32 (4H, m), 7.32-7.23 (1H, m), 4.20-4.02 (4H, m), 3.74-3.41 (5H, m), 3.38-3.08 (6H, m), 2.26 (3H, s), 1.52 (6H, s), 1.32 (3H, d). | 439 | 2 |
| 84 | 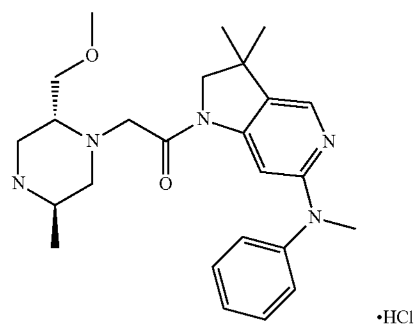 [SMILES: COC[C@H]1CN[C@H](C)CN1CC(=O)N1CC(C)(C)c2cnc(N(C)c3ccccc3)cc21 ; Cl] | 1-[3,3-Dimethyl-6-(methyl-phenyl-amino)-2,3-dihydro-pyrrolo[3,2-c]pyridin-1-yl]-2-((2R,5R)-2-methoxymethyl-5-methyl-piperazin-1-yl)-ethanone hydrochloride salt | 7.79 (1H, s), 7.74-7.37 (6H, m), 4.55-4.25 (2H, m), 4.09-4.01 (2H, m), 3.88 (1H, s), 3.78-3.27 (13H, m), 1.55-1.44 (6H, m), 1.38 (3H, d). | 438 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 85 | 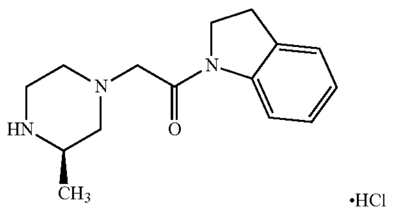 [SMILES: C[C@@H]1CN(CC(=O)N2CCc3ccccc32)CCN1 ; Cl] | 1-(2,3-Dihydro-1H-indol-1-yl)-2-[(3R)-3-methylpiperazin-1-yl]ethan-1-one, hydrochloride salt | 8.16 (1H, d), 7.30 (1H, d), 7.22 (1H, t), 7.12 (1H, t), 4.55 (2H, s), 4.14 (2H, s), 3.93 (3H, d), 3.79 (1H, d), 3.65 (2H, s), 3.48 (1H, s), 3.34-3.32 (2H, m), 1.49 (3H, d). | 260 | 2 |
| 86 | 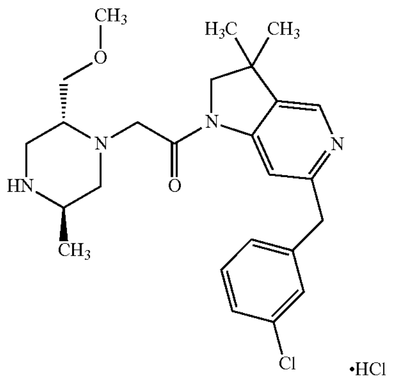 [SMILES: COC[C@H]1CN[C@H](C)CN1CC(=O)N1CC(C)(C)c2cnc(Cc3cccc(Cl)c3)cc21 ; Cl] | 1-{6-[(3-Chlorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.57 (1H, s), 8.24 (1H, s), 7.45-7.33 (3H, m), 7.33-7.25 (1H, m), 4.37 (2H, s), 4.18-4.05 (5H, m), 3.67-3.55 (3H, m), 3.54-3.40 (2H, m), 3.29-3.06 (5H, m), 1.52 (6H, s), 1.34 (3H, d). | 457 | 2 |
| 87 | 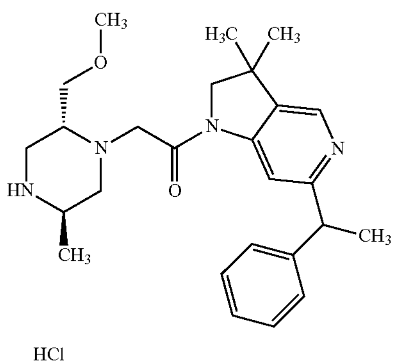 [SMILES: COC[C@H]1CN[C@H](C)CN1CC(=O)N1CC(C)(C)c2cnc(C(C)c3ccccc3)cc21 ; Cl] | 1-[3,3-Dimethyl-6-(1-phenylethyl)-1H,2H,3H-pyrrolo[3,2-c]pyridin-1-yl]-2-[(2R,5R)-2-(methoxymethyl)-5-methylpiperazin-1-yl]ethan-1-one, hydrochloride salt | 8.51 (1H, s), 8.35 (1H, s), 7.46-7.28 (5H, m), 4.57 (1H, q), 4.22-4.06 (5H, m), 3.74-3.45 (6H, m), 1.80 (3H, d), 1.51 (6H, d), 1.36 (3H, d). | 437 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 88 | 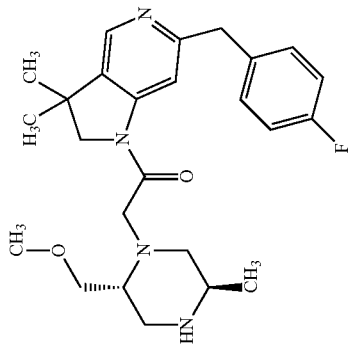 | 1-{6-[(4-Fluorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.55 (1H, s), 8.20 (1H, s), 7.37 (2H, dd), 7.20-7.09 (2H, m), 4.36 (2H, s), 4.06 (2H, s), 3.62-3.53 (3H, m), 3.50-3.39 (3H, m), 3.29-3.04 (7H, m), 1.51 (6H, s), 1.34 (3H, d). | 441 | 2 |
| 89 | 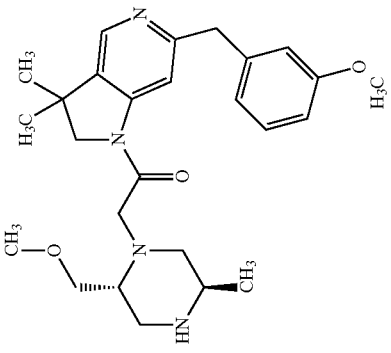 | 2-[(2R,5R)-2-(Methoxymethyl)-5-methylpiperazin-1-yl]-1-{6-[(3-methoxyphenyl)methyl]-3,3-dimethyl-1H,2H,3H-pyrrolo[3,2-c]pyridin-1-yl}ethan-1-one, hydrochloride salt | 8.56 (1H, s), 8.25 (1H, s), 7.36-7.26 (1H, m), 6.96-6.84 (3H, m), 4.33 (2H, s), 4.19 (2H, s), 4.17-4.07 (2H, m), 3.81 (3H, s), 3.78-3.67 (1H, m), 3.67-3.37 (5H, m), 3.30-3.12 (5H, m), 1.52 (6H, s), 1.36 (3H, d). | 453 | 2 |

TABLE 8-continued

| Ex. | Structure | Compound Name | 1H NMR Data (Me-d3-OD, unless indicated) | MS Data [M + H]+ | Method |
|---|---|---|---|---|---|
| 90 | 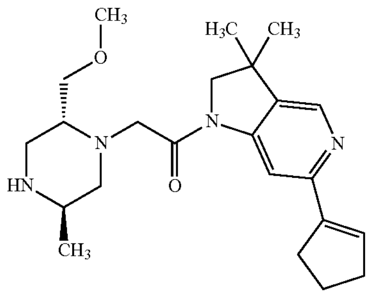 | 1-{6-(Cyclopent-1-en-1-yl)-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.45 (2H, s), 7.03 (1H, s), 4.41-4.25 (2H, m), 4.19 (2H, s), 3.84 (1H, d), 3.78-3.61 (3H, m), 3.61-3.45 (2H, m), 2.87 (2H, s), 2.75 (2H, s), 2.26-2.10 (2H, m), 1.55 (6H, s), 1.40 (4H, d). | 399 | 2 |
| 91 | 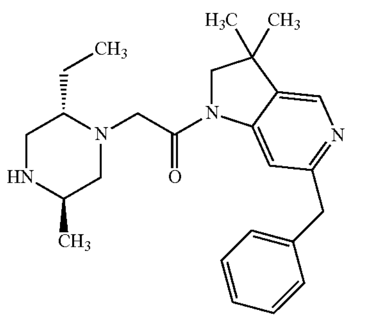 | 1-{6-Benzyl-3,3-dimethyl-1H,2H,3H-pyrrolo[3,2-c]pyridin-1-yl}-2-[(2S,5R)-2-ethyl-5-methylpiperazin-1-yl]ethan-1-one, hydrochloride salt | 8.62 (1H, s), 8.26 (1H, s), 7.46-7.26 (5H, m), 4.69 (1H, d), 4.47 (1H, d), 4.39 (2H, s), 4.26 (1H, d), 4.20 (1H, d), 3.98-3.73 (4H, m), 3.59-3.40 (2H, m), 2.08-1.87 (1H, m), 1.85-1.67 (1H, m), 1.62-1.47 (6H, m), 1.42 (3H, d), 1.08 (3H, t). | 407 | 4 |
| 92 | 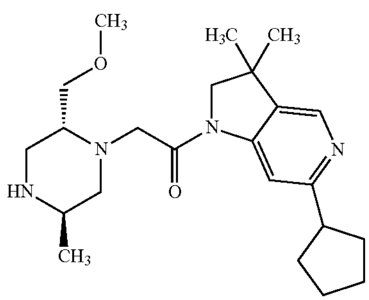 | 1-{6-Cyclopentyl-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.50 (1H, s), 8.39 (1H, s), 4.39-4.25 (2H, m), 4.25-4.05 (2H, m), 3.91-3.76 (1H, m), 3.75-3.38 (7H, m), 2.36-2.14 (2H, m), 1.99-1.63 (6H, m), 1.53 (6H, s), 1.45-1.33 (3H, m). | 401 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 93 | 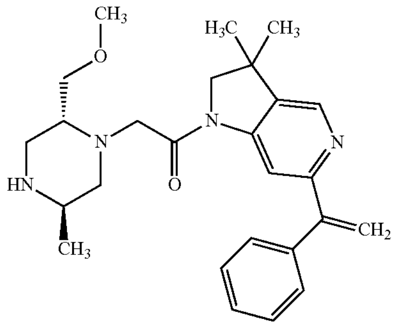 | 1-[3,3-Dimethyl-6-(1-phenylethenyl)-1H,2H,3H-pyrrolo[3,2-c]pyridin-1-yl]-2-[(2R,5R)-2-(methoxymethyl)-5-methylpiperazin-1-yl]ethan-1-one, hydrochloride salt | 8.61 (1H, s), 8.34 (1H, s), 7.46 (6H, d), 6.19-6.09 (1H, m), 6.01 (1H, s), 4.34 (2H, s), 4.23 (2H, s), 3.83 (1H, s), 3.76-3.44 (6H, m), 1.70-1.50 (6H, m), 1.39 (3H, s). | 435 | 2 |
| 94 | 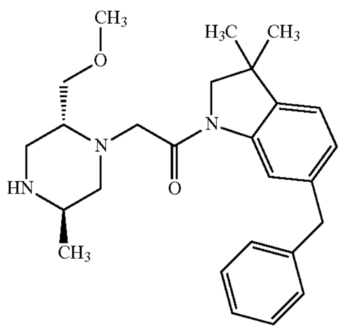 | 1-(6-Benzyl-3,3-dimethyl-2,3-dihydro-1H-indol-1-yl)-2-[(2R,5R)-2-(methoxymethyl)-5-methylpiperazin-1-yl]ethan-1-one, hydrochloride salt | 8.03 (1H, s), 7.32-7.12 (6H, m), 7.04 (1H, d), 4.51-4.30 (2H, m), 4.07 (1H, s), 3.97 (2H, s), 3.90 (2H, s), 3.85-3.67 (5H, m), 3.64-3.47 (2H, m), 3.31 (3H, s), 1.43 (3H, d), 1.40 (6H, s). | 422 | 2 |
| 95 | 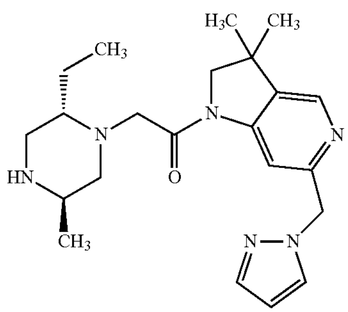 [SMILES: CC[C@H]1CN[C@H](C)CN1CC(=O)N1CC(C)(C)c2cnc(Cn3cccn3)cc21] | 1-[3,3-Dimethyl-6-(1H-pyrazol-1-ylmethyl)-1H,2H,3H-pyrrolo[3,2-c]pyridin-1-yl]-2-[(2S,5R)-2-ethyl-5-methylpiperazin-1-yl]ethan-1-one | 8.30 (1H, s), 7.77 (1H, d), 7.56 (1H, s), 7.71 (1H, s), 5.44 (2H, s), 4.07 (1H, d), 6.38 (1H, t), 3.78 (1H, d), 3.19 (1H, d), 3.96 (1H, d), 2.95-2.80 (2H, m), 2.63-2.50 (1H, m), 2.48-2.35 (1H, m), 2.16 (1H, t), 1.78-1.62 (1H, m), 1.42 (6H, d), 1.39-1.30 (1H, m), 1.03 (3H, d), 0.90 (3H, t). | 397 | 2, Purified by preparative HPLC, basic method |

TABLE 8-continued

| Ex. | Compound Name | ¹H NMR Data (Me-d3-OD, unless indicated) | MS Data [M + H]⁺ | Method |
|---|---|---|---|---|
| 96 | 1-{6-Benzoyl-3,3-dimethyl-1H,2H,3H-pyrrolo[3,2-c]pyridin-1-yl]-2-[(2R,5R)-2-(methoxymethyl)-5-methylpiperazin-1-yl]ethan-1-one, dihydrochloride salt | (DMSO-d6): 10.21-9.83 (1H, m), 9.57 (1H, s), 8.66 (1H, s), 8.50-8.43 (1H, m), 8.00-7.91 (2H, m), 7.72-7.64 (1H, m), 7.56 (2H, t), 4.05 (4H, s), 3.83-3.67 (1H, m), 3.67-3.24 (7H, m), 3.22 (3H, s), 3.15-2.92 (1H, m), 1.45 (6H, s), 1.26 (3H, d). | 437 | 2 |
| 97 | 1-{6-[(3-Fluorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.58 (1H, s), 8.25 (1H, s), 7.48-7.37 (1H, m), 7.22-7.04 (3H, m), 4.39 (2H, s), 4.23 (2H, s), 4.19-4.06 (2H, m), 3.82-3.69 (1H, m), 3.69-3.49 (4H, m), 3.49-3.39 (1H, m), 3.30-3.16 (5H, m), 1.53 (6H, s), 1.37 (3H, d). | 441 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 98 | 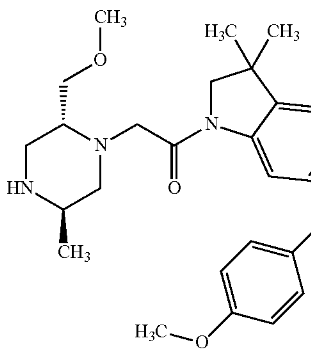 | 2-[(2R,5R)-2-(Methoxymethyl)-5-methylpiperazin-1-yl]-1-{6-[(4-methoxyphenyl)methyl]-3,3-dimethyl-1H,2H,3H-pyrrolo[3,2-c]pyridin-1-yl}ethan-1-one, hydrochloride salt | 8.54 (1H, s), 8.21 (1H, s), 7.25 (2H, d), 7.00-6.90 (2H, m), 4.29 (2H, s), 4.14 (4H, d), 3.81 (3H, s), 3.73-3.65 (1H, m), 3.65-3.43 (4H, m), 3.30-3.24 (4H, m), 3.24-3.12 (2H, m), 1.52 (6H, s), 1.36 (3H, d). | 453 | 2 |
| 99 | 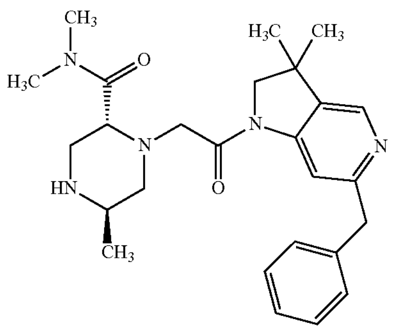 | (2R,5R)-1-(2-{6-Benzyl-3,3-dimethyl-1H,2H,3H-pyrrolo[3,2-c]pyridin-1-yl}-2-oxoethyl)-N,N,5-trimethylpiperazine-2-carboxamide, hydrochloride salt | 8.54 (1H, s), 8.23 (1H, s), 7.40 (2H, m), 7.36 (3H, m), 4.68 (1H, dd), 4.38 (2H, s), 4.16 (1H, d), 4.10 (1H, d), 3.90 (2H, s), 3.58 (2H, dm), 3.41 (1H, dd), 3.23 (1H, dd), 3.21 (3H, s), 3.11 (1H, dd), 2.82 (3H, s), 1.51 (3H, s), 1.50 (3H, s), 1.38 (3H, d) | 450 | 3, EtOAc used as co-solvent |

TABLE 8-continued

| Ex. | Structure | Compound Name | 1H NMR Data (Me-d3-OD, unless indicated) | MS Data [M + H]+ | Method |
|---|---|---|---|---|---|
| 100 | 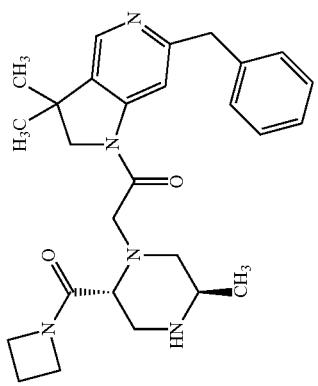 HCl | 2-[(2R,5R)-2-[(Azetidin-1-yl)carbonyl]-5-methylpiperazin-1-yl]-1-{6-benzyl-3,3-dimethyl-1H,2H,3H-pyrrolo[3,2-c]pyridin-1-yl}ethan-1-one, hydrochloride salt | 8.52 (1H, s), 8.24 (1H, s), 7.40 (2H, m), 7.34 (3H, m), 4.37 (3H, m), 4.18 (1H, d), 4.16 (1H, d), 4.04 (1H, dd), 3.97 (1H, m), 3.80-3.70 (3H, m), 3.68 (1H, m), 3.54 (1H, m), 3.50 (1H, m), 3.28 (1H, m), 3.18 (1H, dd), 2.93 (1H, m), 2.30 (2H, m), 1.52 (3H, s), 1.50 (3H, s), 1.33 (3H, d) | 462 | 3, EtOAc used as co-solvent |
| 101 | 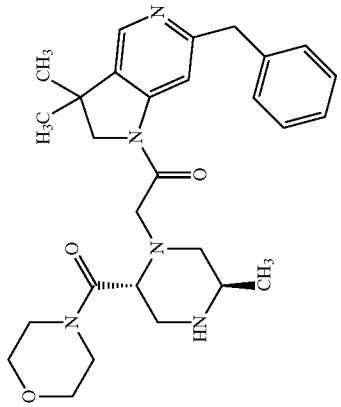 HCl | 1-{6-Benzyl-3,3-dimethyl-1H,2H,3H-pyrrolo[3,2-c]pyridin-1-yl}-2-[(2R,5R)-5-methyl-2-[(morpholin-4-yl)carbonyl]piperazin-1-yl]ethan-1-one, hydrochloride salt | 8.53 (1H, s), 8.22 (1H, s), 7.40 (2H, m), 7.36 (3H, m), 4.62 (1H, dd), 4.37 (2H, s), 4.17 (1H, d), 4.12 (1H, d), 3.88 (2H, d), 3.72 (2H, m), 3.62 (6H, m), 3.50 (2H, dm), 3.38 (1H, dd), 3.30 (1H, d), 3.10 (1H, dd), 1.51 (3H, s), 1.50 (3H, s), 1.36 (3H, d) | 492 | 3, EtOAc used as co-solvent |

TABLE 8-continued

| Ex. | Structure | Compound Name | ¹H NMR Data (Me-d3-OD, unless indicated) | MS Data [M + H]⁺ | Method |
|---|---|---|---|---|---|
| 102 | 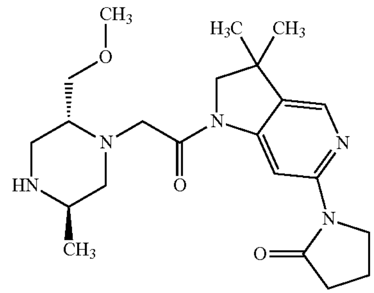 | 1-(1-{2-[(2R,5R)-2-(Methoxymethyl)-5-methylpiperazin-1-yl]acetyl}-3,3-dimethyl-1H,2H,3H-pyrrolo[3,2-c]pyridin-6-yl)pyrrolidin-2-one, hydrochloride salt | 8.20 (1H, s), 8.06 (1H, s), 4.22-3.98 (5H, m), 3.72-3.39 (7H, m), 3.30-3.10 (2H, m), 2.82 (2H, t), 2.40-2.26 (2H, m), 1.52 (6H, s), 1.37 (3H, d). | 416 | 2 |
| 103 | 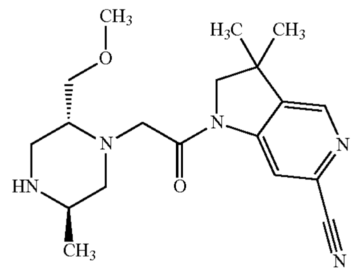 [SMILES: COC[C@H]1CN[C@H](C)CN1CC(=O)N1CC(C)(C)c2cnc(C#N)cc21] | 1-{2-[(2R,5R)-2-(Methoxymethyl)-5-methylpiperazin-1-yl]acetyl}-3,3-dimethyl-1H,2H,3H-pyrrolo[3,2-c]pyridine-6-carbonitrile | 8.49 (1H, s), 8.41 (1H, s), 4.08 (1H, d), 4.01 (1H, d), 3.80 (1H, d), 3.53-3.42 (2H, m), 3.39-3.35 (1H, m), 3.21 (3H, s), 2.96-2.80 (3H, m), 2.80-2.70 (1H, m), 2.64 (1H, t), 2.37 (1H, t), 1.46 (6H, s), 1.06 (3H, d). | 358 | 2, purification by preparative HPLC, basic method |
| 104 | 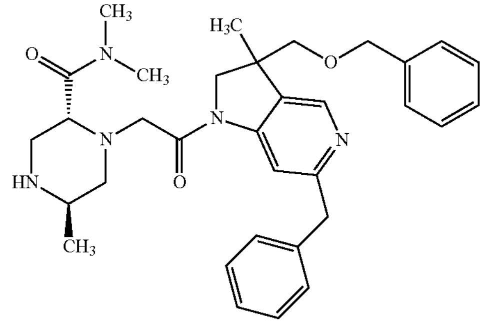 | (2R,5R)-1-(2-{6-Benzyl-3-[(benzyloxy)methyl]-3-methyl-1H,2H,3H-pyrrolo[3,2-c]pyridin-1-yl}-2-oxoethyl)-N,N,5-trimethylpiperazine-2-carboxamide, hydrochloride salt | 8.45 (1H, d), 8.24 (1H, d), 7.47-7.24 (8H, m), 7.24-7.10 (2H, m), 4.74 (1H, t), 4.61-4.43 (2H, m), 4.42-4.22 (3H, m), 4.06 (1H, t), 3.94 (2H, d), 3.69-3.52 (4H, m), 3.43 (1H, d), 3.30-3.21 (2H, m), 3.17 (3H, d), 2.91 (3H, d), 1.51 (3H, d), 1.35 (3H, dd). | 556 | 2 |

TABLE 8-continued

| Ex. | Compound Name | 1H NMR Data (Me-d3-OD, unless indicated) | MS Data [M + H]+ | Method |
|---|---|---|---|---|
| 105 | 1-{6-[(2,4-Difluorophenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one, hydrochloride salt | 8.60 (1H, s), 8.19 (1H, s), 7.56-7.43 (1H, m), 7.13-7.00 (2H, m), 4.46-4.34 (2H, m), 4.27 (2H, d), 4.19-4.12 (2H, m), 3.79 (1H, d), 3.72-3.41 (5H, m), 3.30-3.15 (4H, m), 1.53 (6H, s), 1.37 (3H, d). | 459 | 2 |
| 106 | 1-[6-(Cyclohex-1-en-1-yl)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one, hydrochloride salt | 8.48-8.37 (2H, m), 6.81-6.73 (1H, m), 4.16 (4H, d), 3.75-3.46 (5H, m), 2.56-2.47 (2H, m), 2.47-2.34 (2H, m), 1.96-1.83 (2H, m), 1.83-1.70 (2H, m), 1.53 (6H, s), 1.44-1.26 (3H, m). | 413 | 2 |

TABLE 8-continued

| Ex. | Structure | Compound Name | ¹H NMR Data (Me-d3-OD, unless indicated) | MS Data [M + H]⁺ | Method |
|---|---|---|---|---|---|
| 107 | 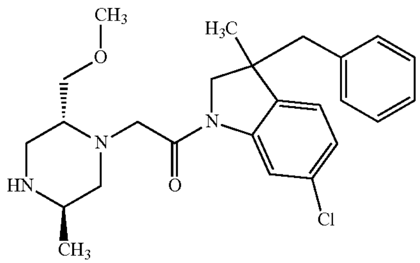 | 1-(3-Benzyl-6-chloro-3-methyl-2,3-dihydro-1H-indol-1-yl)-2-[(2R,5R)-2-(methoxymethyl)-5-methylpiperazin-1-yl]ethan-1-one, hydrochloride salt | 8.04 (1H, d), 7.29-7.16 (5H, m), 7.04-6.94 (2H, m), 4.30 (1H, s), 4.19 (1H, d), 4.14-4.00 (1H, m), 3.86-3.59 (7H, m), 3.59-3.45 (2H, m), 3.31-3.25 (3H, m), 3.00 (1H, d), 2.95 (1H, d), 1.51 (3H, d), 1.46-1.42 (3H, m). | 442 | 2 |
| 108 | 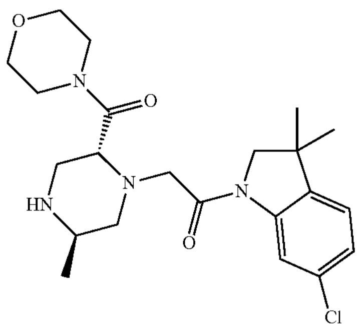 | 1-(6-Chloro-3,3-dimethyl-2,3-dihydro-indol-1-yl)-2-[(2R,5R)-5-methyl-2-(morpholine-4-carbonyl)-piperazin-1-yl]-ethanone, hydrochloride salt | 8.17 (1H, s), 7.26 (1H, d), 7.21-7.10 (1H, m), 5.21 (1H, d), 4.30-4.04 (2H, m), 3.97-3.86 (2H, m), 3.83-3.63 (9H, m), 3.62-3.41 (3H, m), 3.41-3.34 (1H, m), 1.52-1.42 (3H, m), 1.42-1.32 (6H, m). | 435 | 4 |
| 109 | 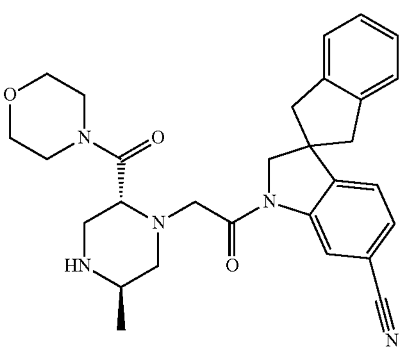 | 1'-{2-[(2R,5R)-5-Methyl-2-[(morpholin-4-yl)carbonyl]piperazin-1-yl]acetyl}-1,1',2',3-tetrahydrospiro[indene-2,3'-indole]-6'-carbonitrile, hydrochloride salt | 8.48 (1H, s), 7.43 (1H, dd), 7.39-7.19 (5H, m), 4.80-4.70 (1H, m), 4.22-4.09 (2H, m), 3.90-3.36 (19H, m), 1.36 (3H, d). | 500 | 3, DCM used as co-solvent instead of methanol: residue from evaporation azeotroped with methanol. |

TABLE 8-continued

| Ex. | Structure | Compound Name | 1H NMR Data (Me-d3-OD, unless indicated) | MS Data [M + H]+ | Method |
|---|---|---|---|---|---|
| 110 | 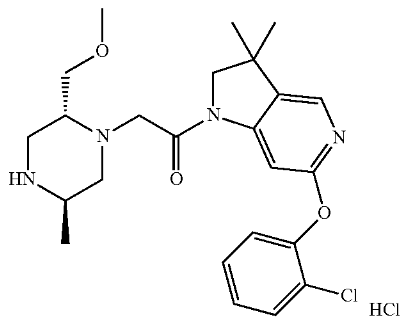 [SMILES: COC[C@H]1CN[C@H](C)CN1CC(=O)N1CC(C)(C)c2cnc(Oc3ccccc3Cl)cc21 ; Cl] | 1-[6-(2-Chloro-phenoxy)-3,3-dimethyl-2,3-dihydro-pyrrolo[3,2-c]pyridin-1-yl]-2-((2R,5R)-2-methoxymethyl-5-methyl-piperazin-1-yl)-ethanone, hydrochloride salt | 8.32 (1H, s), 7.68 (1H, dd), 7.60-7.40 (4H, m), 4.31-3.96 (4H, m), 3.64-3.40 (5H, m), 3.27 (3H, s), 3.24-3.05 (2H, m), 1.52 (6H, s), 1.33 (3H, d). | 459 | 2, Product triturated with EtOAc and collected by filtration) |
| 111 | 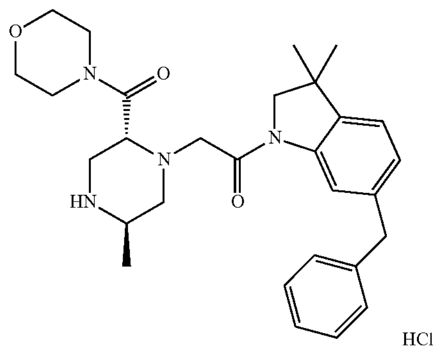 [SMILES: C[C@@H]1CN(CC(=O)N2CC(C)(C)c3ccc(Cc4ccccc4)cc32)[C@@H](C(=O)N2CCOCC2)CN1 ; Cl] | 1-(6-Benzyl-3,3-dimethyl-2,3-dihydro-indol-1-yl)-2-[(2R,5R)-5-methyl-2-(morpholine-4-carbonyl)-piperazin-1-yl]-ethanone, hydrochloride salt | 8.02 (1H, s), 7.30-7.23 (2H, m), 7.23-7.14 (4H, m), 7.03 (1H, d), 5.26 (1H, d), 4.29-4.10 (2H, m), 3.96 (2H, s), 3.90-3.59 (12H, m), 3.58-3.43 (3H, m), 1.44 (3H, d), 1.38 (6H, d). | 491 | 4 |
| 112 | 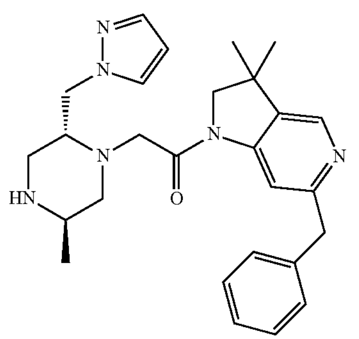 [SMILES: C[C@@H]1CN(CC(=O)N2CC(C)(C)c3cnc(Cc4ccccc4)cc32)[C@@H](Cn2cccn2)CN1] | 1-(6-Benzyl-3,3-dimethyl-2,3-dihydro-pyrrolo[3,2-c]pyridin-1-yl)-2-((2R,5R)-5-methyl-2-pyrazol-1-ylmethyl-piperazin-1-yl)-ethanone | 8.23 (1H, s), 7.91 (1H, s), 7.65 (1H, d), 7.44 (1H, d), 7.35-7.16 (5H, m), 6.23 (1H, t), 4.44 (1H, dd), 4.16-4.03 (3H, m), 3.92 (1H, d), 3.86 (1H, d), 3.79 (1H, d), 3.43 (1H, d), 3.12 (1H, q), 2.95-2.79 (2H, m), 2.70 (1H, dd), 2.64-2.53 (1H, m), 2.30 (1H, t), 1.42 (6H, d), 1.02 (3H, d). | 459 | 4, product purified by preparative HPLC, basic method |

Example 113: 1-{6-Benzyl-3,3-dimethyl-1H,2H,3H-pyrrolo[3,2-c]pyridin-1-yl}-2-[3-(trifluoromethyl)piperazin-1-yl]ethan-1-one

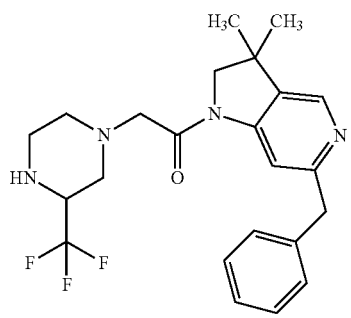 [SMILES: CC1(C)CN(C(=O)CN2CCNC(C(F)(F)F)C2)c2cc(Cc3ccccc3)ncc21]

A solution of bromoacetyl chloride (0.535 g, 3.4 mmol) in DCM (5 mL) was added to a two phase mixture of 6-benzyl-3,3-dimethyl-2,3-dihydro-pyrrolo[3,2-c]pyridine (0.467 g, 1.7 mmol) sodium hydrogen carbonate (1.43 g, 17 mmol), DCM (20 mL) and water (25 mL) with ice cooling over 0.1 h. The mixture was stirred at −0° C. for 2 h then the organic phase was separated and the aqueous phase was extracted with DCM (25 mL). The combined organic phases were dried ($Na_2SO_4$) and evaporated in vacuo to give an oil which was purified by chromatography ($SiO_2$, 20-50% EtOAc in petrol) gave an oil which solidified. A mixture of this material (0.081 g, 0.23 mmol) 2-trifluoromethylpiperazine (0.039 g, 0.25 mmol), potassium carbonate (0.064 g, 0.46 mmol) and acetonitrile (2 mL) was stirred at 20° C. for 4 h. The mixture was partitioned between water (30 mL) and DCM (3×20 mL) and the combined extracts were dried ($Na_2SO_4$) and evaporated in vacuo to give an oil. Chromatography ($SiO_2$, 0-20% MeOH in EtOAc), gave impure product and this was followed by further chromatography ($SiO_2$, 0-5% MeOH in EtOAc) then preparative HPLC (basic method) to give the title compound (0.005 g). $^1$H NMR (Me-d3-OD): 8.24 (1H, s), 7.94 (1H, s), 7.34-7.23 (4H, m), 7.23-7.16 (1H, m), 4.11 (2H, s), 4.03-3.92 (2H, m), 3.45 (3H, s), 3.08 (1H, d), 3.04-2.81 (3H, m), 2.32 (2H, q), 1.42 (6H, s). MS: $[M+H]^+$=433.

Example 114: 1-{6-Benzyl-3,3-dimethyl-1H,2H,3H-pyrrolo[3,2-c]pyridin-1-yl}-2-[3-(fluoromethyl)piperazin-1-yl]ethan-1-one

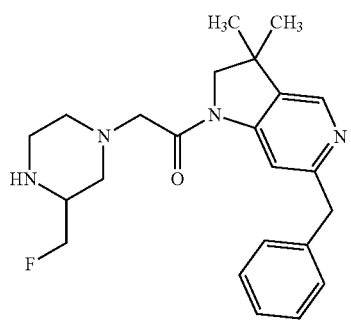 [SMILES: CC1(C)CN(C(=O)CN2CCNC(CF)C2)c2cc(Cc3ccccc3)ncc21]

Prepared in an analogous method to that described in Prep 203 using 6-benzyl-3,3-dimethyl-2,3-dihydro-pyrrolo[3,2-c]pyridine, chloroacetyl chloride and 2-fluoromethyl-piperazine, diacetate salt. The product was purified by preparative HPLC (basic method) to provide the title compound (0.05 g). $^1$H NMR (Me-d3-OD): 8.24 (1H, s), 7.93 (1H, s), 7.36-7.14 (5H, m), 4.53-4.39 (1H, m), 4.39-4.26 (1H, m), 4.10 (2H, s), 4.05-3.66 (3H, m), 3.52-3.37 (2H, m), 3.25-2.76 (5H, m), 2.31 (1H, d), 2.25-2.08 (1H, m), 1.42 (6H, s). MS: $[M+H]^+$ =397.

Example 115: 1-{6-Benzyl-3,3-dimethyl-1H,2H,3H-pyrrolo[3,2-c]pyridin-1-yl}-2-[(3S)-3-(fluoromethyl)piperazin-1-yl]ethan-1-one

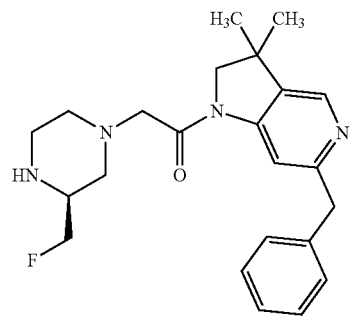 [SMILES: CC1(C)CN(C(=O)CN2CCN[C@H](CF)C2)c2cc(Cc3ccccc3)ncc21]

Prepared by chiral preparative HPLC separation of Example 114: LUX cellulose 2 (Phenomenex), 5 u, 250× 21.2 mm, eluting with heptane-ethanol 80:20, faster eluting isomer. $^1$H NMR (Me-d3-OD): 8.24 (1H, s), 7.93 (1H, s), 7.34-7.15 (5H, m), 4.50-4.38 (1H, m), 4.38-4.25 (1H, m), 4.10 (2H, s), 3.99 (2H, s), 3.40-3.35 (2H, m), 3.11 (1H, d), 3.03-2.77 (4H, m), 2.28 (1H, t), 2.17-2.04 (1H, m), 1.42 (6H, s). MS: $[M+H]^+$ =397.

Example 116: 1-{6-Benzyl-3,3-dimethyl-1H,2H,3H-pyrrolo[3,2-c]pyridin-1-yl}-2-[(3R)-3-(fluoromethyl)piperazin-1-yl]ethan-1-one

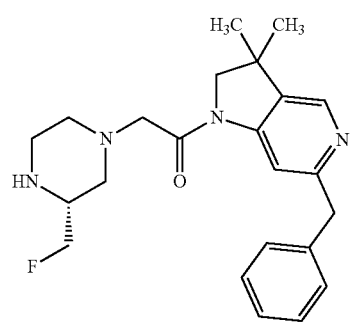 [SMILES: CC1(C)CN(C(=O)CN2CCN[C@@H](CF)C2)c2cc(Cc3ccccc3)ncc21]

Prepared by chiral preparative HPLC separation of Example 113: LUX cellulose 2 (Phenomenex), 5 u, 250× 21.2 mm, eluting with heptane-ethanol 80:20, slower eluting isomer. $^1$H NMR (Me-d3-OD): 8.24 (1H, s), 7.94 (1H, s), 7.39-7.15 (5H, m), 4.50-4.37 (1H, m), 4.37-4.24 (1H, m), 4.10 (2H, s), 3.99 (2H, s), 3.37 (2H, s), 3.12 (1H, s), 3.05-2.73 (4H, m), 2.35-2.21 (1H, m), 2.10 (1H, t), 1.42 (6H, s). MS: $[M+H]^+$ =397.

Examples 117-256

By following methods similar and/or analogous to those described above, the compounds set out in Table 9 were prepared from the corresponding N-Boc protected derivatives, with any significant variations indicated below, except where otherwise stated. The title compounds were either isolated directly as the free base or appropriate salt without further purification, or purified for example using mass-directed preparative HPLC, crystallization or trituration.

Notes:

[a] See General procedures for preparations of compounds of Formula (I), Methods 1-4 above. [b] Conditions for chiral chromatographic separation: Phenomenex LUX-Cellulose 2, 5 µM, 250×21.2 mm eluting with 70/30 heptane-EtOH. [c] Conditions for chiral chromatographic separation: Phenomenex LUX-Cellulose 2, 5 µM, 250×21.2 mm eluting with 50/50 heptane-EtOH.

TABLE 9

| Ex. | Structure | Name | ¹H NMR Data (Me-d3-OD) | MS Data | Method [a] |
|---|---|---|---|---|---|
| 117 | 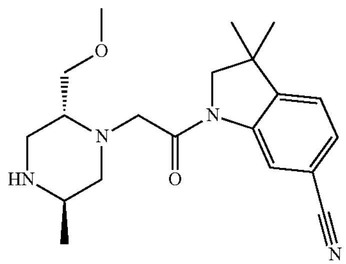 | 1-{2-[(2R,5R)-2-(Methoxymethyl)-5-methylpiperazin-1-yl]acetyl}-3,3-dimethyl-2,3-dihydro-1H-indole-6-carbonitrile hydrochloride | 8.45 (1H, s), 7.52 (1H, d), 7.49 (1H, d), 4.40 (2H, d), 4.00 (3H, s), 3.91-3.63 (7H, m), 3.59-(3H, m), 1.49-1.42 (9H, m). | m/z: 357 | 3, without MeOH co-solvent |
| 118 | 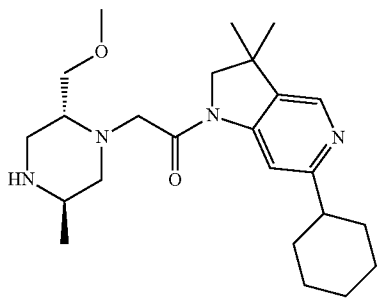 | 1-[6-Cyclohexyl-3,3-dimethyl-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.50 (1H, s), 8.36 (1H, s), 4.24.4.08 (4H, m), 3.78-3.68 (1H, m), 3.68-3.46 (4H, m), 3.46-3.37 (1H, m), 3.04-2.91 (1H, m), 2.09-1.90 (5H, m), 1.85 (1H, d), 1.68-1.42 (10H, m), 1.37 (3H, d). | m/z: 415 | 2 |
| 119 | 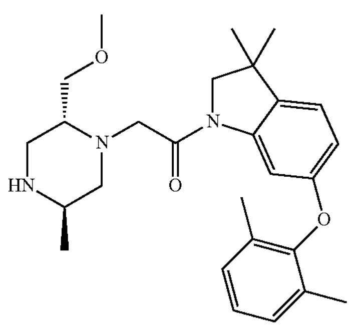 | 1-[6-(2,6-Dimethylphenoxy)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one hydrochloride | 8.39 (1H, s), 7.38 (1H, s), 7.28 (3H, s), 4.31-4.19 (2H, m), 4.19-4.05 (2H, m), 3.79-3.67 (1H, m), 3.66-3.47 (4H, m), 3.41 (1H, dd), 3.31-3.18 (5H, m), 2.21 (6H, s), 1.54 (6H, s), 1.34 (3H, d). | m/z: 453 | 2 |

TABLE 9-continued

| Ex. | Structure | Name | $^1$H NMR Data (Me-d3-OD) | MS Data | Method [a] |
|---|---|---|---|---|---|
| 120 | 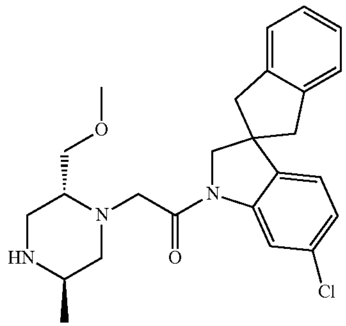 [SMILES: COC[C@H]1CN[C@H](C)CN1CC(=O)N1CC2(Cc3ccccc3C2)c2ccc(Cl)cc21] | 1-{6-Chloro-1,1′:2′,3-tetrahydrospiro[indene-2,3′-indole]-1-yl}-2-[(2R,5R)-2-(methoxymethyl)-5-methylpiperazin-1-yl]ethan-1-one | 8.20 (1H, s), 7.31-7.17 (4H, m), 7.13 (1H, d), 7.03 (1H, dd), 4.32 (1H, d), 4.12 (1H, d), 3.80 (1H, d), 3.31-3.13 (6H, m), 3.10 (3H, s), 2.93-2.78 (3H, m), 2.70-2.53 (2H, m), 2.22 (1H, t), 1.04 (3H, d). | m/z: 440 | 3, no MeOH co-solvent, purification by prep HPLC, basic method |
| 121 | 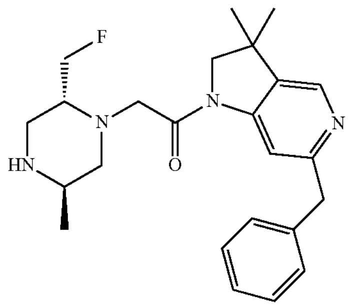 | 1-{6-Benzyl-3,3-dimethyl-1H,2H,3H-pyrrolo[3,2-c]pyridin-1-yl}-2-[(2R,5R)-2-(fluoromethyl)-5-methylpiperazin-1-yl]ethan-1-one hydrochloride | 8.56 (1H, s), 8.25 (1H, s), 7.47-7.26 (5H, m), 4.82-4.52 (2H, m), 4.38 (2H, s), 4.36-4.22 (2H, m), 4.22-4.07 (2H, m), 4.07-3.83 (1H, m), 3.69-3.55 (2H, m), 3.47 (1H, dd), 1.51 (6H, s), 1.38 (3H, d). | m/z: 411 | 4 |
| 122 | 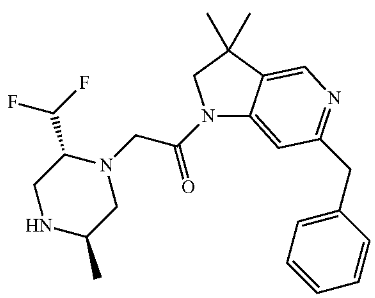 | 1-{6-Benzyl-3,3-dimethyl-1H,2H,3H-pyrrolo[3,2-c]pyridin-1-yl}-2-[(2R,5R)-2-(difluoromethyl)-5-methylpiperazin-1-yl]ethan-1-one hydrochloride | 8.52 (1H, s), 8.28-8.21 (1H, m), 7.44-7.31 (5H, m), 6.47-5.95 (1H, m), 4.35 (2H, s), 4.15-4.06 (2H, m), 4.06-3.83 (3H, m), 3.50 (1H, m), 3.46-3.37 (1H, m), 3.24-3.04 (3H, m), 1.50 (6H, d), 1.33 (3H, d). | m/z: 429 | 4 |

TABLE 9-continued

| Ex. | Structure | Name | ¹H NMR Data (Me-d3-OD) | MS Data | Method[a] |
|---|---|---|---|---|---|
| 123 | 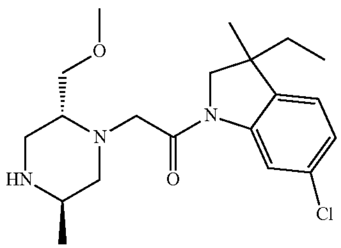 | 1-(6-Chloro-3-ethyl-3-methyl-2,3-dihydro-1H-indol-1-yl)-2-[(2R,5R)-2-(methoxymethyl)-5-methylpiperazin-1-yl]ethan-1-one hydrochloride | 8.19 (1H, d), 7.23 (1H, d), 7.16 (1H, dd), 4.64-4.39 (2H, m), 4.23-4.11 (1H, m), 4.07 (1H, m), 4.00-3.53 (8H, m), 1.83-1.57 (2H, m), 1.46 (3H, d), 1.43-1.36 (3H, m), 0.94-0.72 (3H, m). | m/z: 380 | 2 |
| 124 | 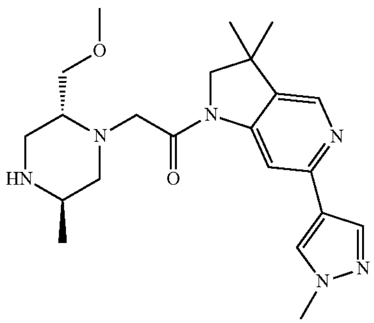 | 1-[3,3-Dimethyl-6-(1-methyl-1H-pyrazol-4-yl)-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.58 (1H, s), 8.55-8.43 (2H, m), 8.19-8.12 (1H, m), 4.28-4.20 (2H, m), 4.20-4.11 (2H, m), 4.09-4.01 (3H, m), 3.82-3.72 (1H, m), 3.72-3.39 (6H m), 1.60-1.49 (6H, m), 1.42-1.27 (3H, m). | m/z: 413 | 2 |
| 125 | 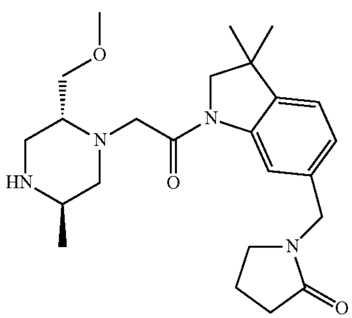 | 1-((1-(2-{[(2R,5R)-2-(Methoxymethyl)-5-methylpiperazin-1-yl]acetyl}-3,3-dimethyl-2,3-dihydro-1H-indol-6-yl)methyl]pyrrolidin-2-one hydrochloride | 8.09 (1H, s), 7.27 (1H, d), 7.08 (1H, d), 4.52-4.30 (4H, m), 4.11-3.99 (1H, m), 3.92 (2H, s), 3.86-3.63 (6H, m), 3.63-3.47 (2H, m), 3.47-3.35 (3H, m), 2.45 (2H, t), 2.11-1.97 (2H, m), 1.44 (3H, d), 1.41 (6H, s). | m/z: 429 | 3, no MeOH co-solvent, purification by prep HPLC, basic method |

TABLE 9-continued

| Ex. | Structure | Name | $^1$H NMR Data (Me-d3-OD) | MS Data | Method [a] |
|---|---|---|---|---|---|
| 126 | 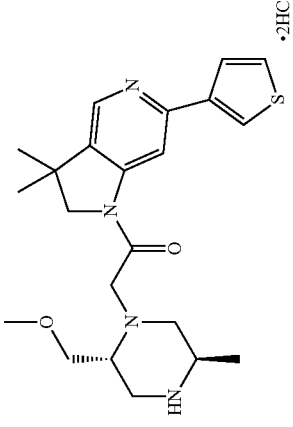 | 1-[3,3-Dimethyl-6-(thiophen-3-yl)-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.70 (1H, s), 8.55 (1H, s), 8.37 (1H, dd), 7.81 (1H, dd), 7.75-7.65 (1H, m), 4.31-4.14 (4H, m), 3.84-3.40 (7H, m), 1.57 (6H, s), 1.39 (3H, d). | m/z: 415 | 2 |
| 127 | 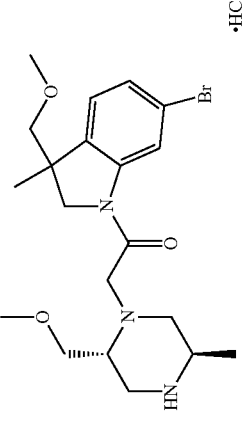 | 1-[6-Bromo-3-(methoxymethyl)-3-methyl-2,3-dihydro-1H-indol-1-yl]-2-[(2R,5R)-2-(methoxymethyl)-5-methylpiperazin-1-yl]ethan-1-one hydrochloride | 8.35 (1H, d), 7.29 (1H, dd), 7.23 (1H, d), 4.57-4.35 (2H, m), 4.35-4.04 (2H, m), 4.04-3.67 (6H, m), 3.67-3.52 (2H, m), 3.46 (2H, s), 1.45 (3H, d), 1.40 (3H, s). | m/z: 440 | 2 |
| 128 | 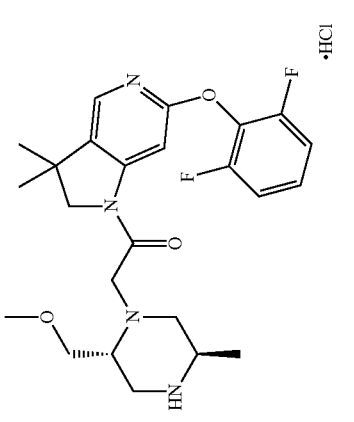 | 1-[6-(2,6-Difluorophenoxy)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one hydrochloride | 8.07 (1H, s), 7.66 (1H, s), 7.45-7.31 (1H, m), 7.26-7.11 (2H, m), 4.41-4.21 (2H, m), 4.07 (2H, s), 4.02-3.80 (1H, m), 3.77-3.35 (7H, m), 1.49 (6H, s), 1.40 (3H, d). | m/z: 461 | 2 |

TABLE 9-continued

| Ex. | Structure | Name | $^1$H NMR Data (Me-d3-OD) | MS Data | Method [a] |
|---|---|---|---|---|---|
| 129 | 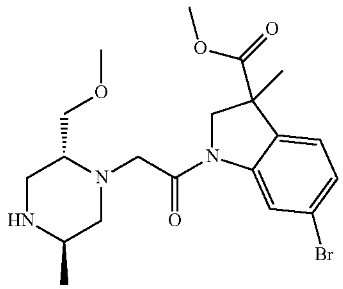 | Methyl 6-bromo-1-{2-[(2R,5R)-2-(methoxymethyl)-5-methylpiperazin-1-yl]acetyl}-3-methyl-2,3-dihydro-1H-indole-3-carboxylate hydrochloride | 8.37 (1H, s), 7.43-7.25 (2H, m), 4.83-4.71 (2H, m), 4.59-4.30 (2H, m), 4.16-3.93 (2H, m), 3.93-3.64 (9H, m), 3.64-3.45 (3H, m), 1.68 (3H, s), 1.49-1.40 (3H, m). | m/z: 454 | 2 |
| 130 | 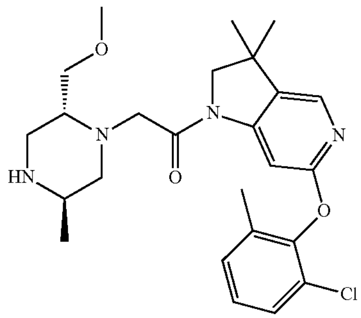 | 1-[6-(2-Chloro-6-methylphenoxy)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one hydrochloride | 8.36 (1H, s), 7.50 (1H, d), 7.46-7.26 (3H, m), 4.21-3.93 (4H, m), 3.71-3.39 (5H, m), 3.30-3.12 (6H, m), 2.30 (3H, s), 1.52 (6H, s), 1.33 (3H, d). | m/z: 473 | 2, purification by prep HPLC, basic method, then salt formation with HCl in EtOAc |
| 131 | 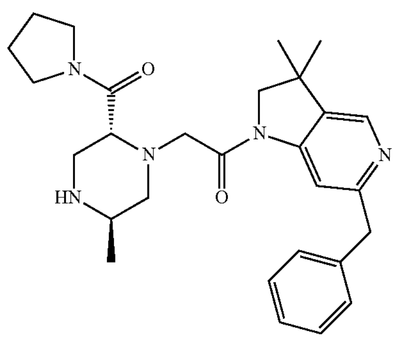 | 1-{6-Benzyl-3,3-dimethyl-1H,2H,3H-pyrrolo[3,2-c]pyridin-1-yl]-2-[(2R,5R)-5-methyl-2-[(pyrrolidin-1-yl)carbonyl]piperazin-1-yl]ethan-1-one dihydrochloride | 8.52 (1H, s), 8.19 (1H, s), 7.40 (2H, m), 7.32 (3H, m), 4.34 (2H, s), 4.21 (2H, m), 4.13 (2H, m), 3.73 (3H, m), 3.58 (1H, m), 3.50 (2H, m), 3.34 (3H, m), 3.22 (1H, m), 3.15 (1H, m), 2.92 (1H, m), 1.93 (2H, m), 1.85 (2H, m), 1.50 (3H, s), 1.48 (3H, s), 1.31 (3H, d) | m/z: 476 | 3, EtOAc used as co-solvent |

TABLE 9-continued

| Ex. | Structure | Name | $^1$H NMR Data (Me-d3-OD) | MS Data | Method $^a$ |
|---|---|---|---|---|---|
| 132 | 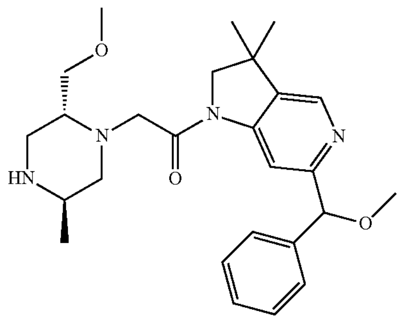 | 1-{6-[(Methoxy(phenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one dihydrochloride | 8.52 (1H, s), 8.23 (1H, s), 7.46 (5H, s), 5.73 (1H, s), 4.16-4.04 (4H, m), 3.58 (3H, s), 3.52-3.47 (4H, m), 3.27-3.19 (6H, m), 1.51 (6H, d), 1.37-1.28 (3H, m). | m/z: 453 | 2 |
| 133 | 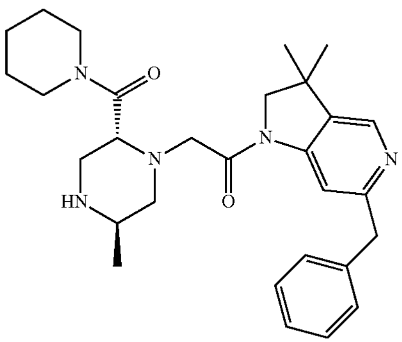 | 1-(6-Benzyl-3,3-dimethyl-1H,2H,3H-pyrrolo[3,2-c]pyridin-1-yl)-2-[(2R,5R)-5-methyl-2-[(piperidin-1-yl)carbonyl]piperazin-1-yl]ethan-1-one dihydrochloride | 8.52 (1H, s), 8.21 (1H, s), 7.41 (3H, m), 7.33 (2H, m), 4.54 (1H, dd), 4.34 (2H, s), 4.13 (1H, d), 4.10 (1H, d), 3.75 (2H, br s), 3.72 (1H, dd), 3.70-3.35 (6H, m), 3.20 (1H, m), 3.03 (1H, t), 1.70-1.53 (6H, m), 1.50 (6H, s), 1.32 (3H, d) | m/z: 490 | 3. EtOAc used as co-solvent |
| 134 | 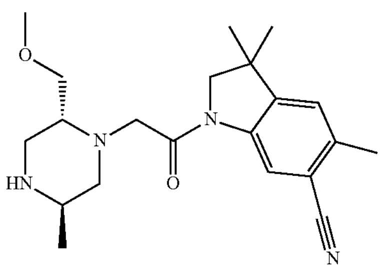 [SMILES: COC[C@H]1CN[C@H](C)CN1CC(=O)N1CC(C)(C)c2cc(C)c(C#N)cc21] | 1-{2-[(2R,5R)-2-(Methoxymethyl)-5-methylpiperazin-1-yl]acetyl}-3,3,5-trimethyl-2,3-dihydro-1H-indole-6-carbonitrile | 8.39-8.32 (1H, m), 7.30 (1H, s), 4.09-4.00 (1H, m), 3.91 (1H, d), 3.80 (1H, d), 3.53-3.45 (1H, m), 3.45-3.36 (2H, m), 3.23 (3H, s), 2.99-2.82 (3H, m), 2.78-2.62 (2H, m), 2.51 (3H, s), 2.33 (1H, t), 1.38 (6H, d), 1.06 (3H, d). | m/z: 371 | 3, no MeOH co-solvent, purification by prep HPLC, basic method |

TABLE 9-continued

| Ex. | Structure | Name | ¹H NMR Data (Me-d3-OD) | MS Data | Method [a] |
|---|---|---|---|---|---|
| 135 | (structure with morpholine carbonyl piperazine linked to 6-chloro-3,3-diethyl-2,3-dihydroindole; ·HCl) | 1-(6-Chloro-3,3-diethyl-2,3-dihydro-1H-indol-1-yl)-2-[(2R,5R)-5-methyl-2-[(morpholin-4-yl)carbonyl]piperazin-1-yl]ethan-1-one hydrochloride | 8.18 (1H, s), 7.22-7.06 (2H, m), 5.13 (1H, d), 4.21-4.01 (2H, m), 4.01-3.87 (2H, m), 3.83-3.61 (10H, m), 3.58-3.42 (3H, m), 1.84-1.53 (4H, m), 1.42 (3H, d), 0.87-0.66 (6H, m). | m/z: 463 | 2 |
| 136 | (structure with methoxymethyl piperazine linked to 3-methyl-3-phenyl-2,3-dihydro-1H-indole-6-carbonitrile) | 1-{2-[(2R,5R)-2-(Methoxymethyl)-5-methylpiperazin-1-yl]acetyl}-3-methyl-3-phenyl-2,3-dihydro-1H-indole-6-carbonitrile | 8.53 (1H, s), 7.52-7.41 (1H, m), 7.41-7.16 (6H, m), 4.74 (0.5H, s), 4.43-4.30 (1H, m), 4.17 (0.5H, d), 3.90-3.71 (1H, m), 3.49-3.38 (1H, m), 3.23-3.03 (4H, m), 2.86 (2H, dd), 2.79-2.49 (3H, m), 2.32 (0.5H, t), 2.21-2.10 (0.5H, m), 1.81 (3H, d), 1.09-0.88 (3H, m). | m/z: 419 | 2, purification by preparative HPLC, basic method |
| 137 | (structure with methoxymethyl piperazine linked to 6-benzyl-3,3-dimethyl-pyrrolo[3,2-b]pyridine; ·HCl) | 1-{6-Benzyl-3,3-dimethyl-1H,2H,3H-pyrrolo[3,2-b]pyridin-1-yl}-2-[(2R,5R)-2-(methoxymethyl)-5-methylpiperazin-1-yl]ethan-1-one hydrochloride | 8.84 (1H, s), 8.37 (1H, s), 7.41-7.23 (5H, m), 4.32 (2H, d), 4.25-4.11 (4H, m), 3.89 (1H, d), 3.79-3.54 (5H, m), 3.47-3.35 (2H, m), 3.31 (3H, s), 1.61 (6H, s), 1.39 (3H, d). | m/z: 423 | 3, no MeOH co-solvent |

TABLE 9-continued

| Ex. | Structure | Name | ¹H NMR Data (Me-d3-OD) | MS Data | Method |
|---|---|---|---|---|---|
| 138 | 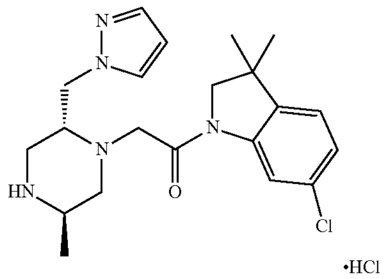 [SMILES: C[C@@H]1CN(CC(=O)N2CC(C)(C)c3ccc(Cl)cc32)[C@@H](Cn2cccn2)CN1 ; Cl] | 1-(6-Chloro-3,3-dimethyl-2,3-dihydro-1H-indol-1-yl)-2-[(2R,5R)-5-methyl-2-(1H-pyrazol-1-ylmethyl)piperazin-1-yl]ethan-1-one hydrochloride | 8.16 (1H, d), 7.84 (1H, d), 7.65 (1H, s), 7.26 (1H, d), 7.19-7.07 (1H, m), 6.40 (1H, s), 4.85-4.66 (3H, m), 4.60 (1H, d), 4.47 (2H, d), 3.94 (2H, s), 3.89-3.71 (2H, m), 3.71-3.47 (2H, m), 1.50-1.29 (9H, m). | m/z: 402 | 4 |
| 139 | 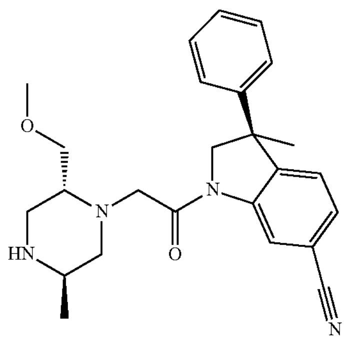 [SMILES: COC[C@H]1CN[C@H](C)CN1CC(=O)N1C[C@@](C)(c2ccccc2)c2ccc(C#N)cc21] | (3S)-1-{2-[(2R,5R)-2-(Methoxymethyl)-5-methylpiperazin-1-yl]acetyl}-3-methyl-3-phenyl-2,3-dihydro-1H-indole-6-carbonitrile | 8.53 (1H, s), 7.44 (1H, dd), 7.39-7.19 (6H, m), 4.45-4.27 (2H, m), 3.76 (1H, d), 3.42 (1H, dd), 3.36 (1H, s), 3.13 (3H, s), 2.98-2.72 (3H, m), 2.72-2.55 (2H, m), 2.32 (1H, t), 1.80 (3H, s), 1.03 (3H, d). | m/z: 419 | Chiral HPLC separation of Example 136[b] |
| 140 | 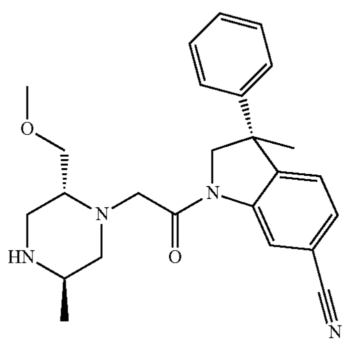 [SMILES: COC[C@H]1CN[C@H](C)CN1CC(=O)N1C[C@](C)(c2ccccc2)c2ccc(C#N)cc21] | (3R)-1-{2-[(2R,5R)-2-(Methoxymethyl)-5-methylpiperazin-1-yl]acetyl}-3-methyl-3-phenyl-2,3-dihydro-1H-indole-6-carbonitrile | 8.52 (1H, s), 7.46 (1H, dd), 7.39-7.11 (6H, m), 4.75 (1H, d), 4.17 (1H, d), 3.84 (1H, d), 3.50-3.36 (2H, m), 3.26-2.99 (4H, m), 2.94-2.79 (1H, m), 2.79-2.41 (4H, m), 2.15 (1H, t), 1.81 (3H, s), 0.97 (3H, d). | m/z: 419 | Chiral HPLC separation of Example 136[b] |

TABLE 9-continued

| Ex. | Structure | Name | $^1$H NMR Data (Me-d3-OD) | MS Data | Method[a] |
|---|---|---|---|---|---|
| 141 | 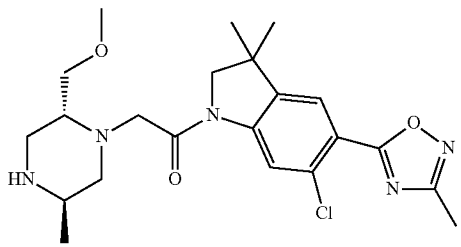 [SMILES: COC[C@H]1CN[C@H](C)CN1CC(=O)N1CC(C)(C)c2cc(-c3nc(C)no3)c(Cl)cc21] | 1-[6-Chloro-3,3-dimethyl-5-(3-methyl-1,2,4-oxadiazol-5-yl)-2,3-dihydro-1H-indol-1-yl]-2-[(2R,5R)-2-(methoxymethyl)-5-methylpiperazin-1-yl]ethan-1-one | 8.39 (1H, s), 7.89 (1H, s), 4.16-4.04 (1H, m), 3.99 (1H, d), 3.82 (1H, d), 3.51 (1H, d), 3.47 (1H, d), 3.39 (1H, s), 3.23 (3H, s), 2.98-2.82 (3H, m), 2.74 (1H, s), 2.70-2.60 (1H, m), 2.47 (3H, s), 2.36 (1H, t), 1.43 (6H, d), 1.07 (3H, d). | m/z: 448 | 2 |
| 142 | 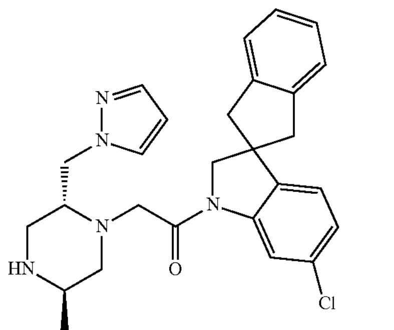 | 1-[6-Chloro-1,1′,2′,3-tetrahydrospiro[indene-2,3′-indole]-1′-yl]-2-[(2R,5R)-5-methyl-2-(1H-pyrazol-1-ylmethyl)piperazin-1-yl]ethan-1-one hydrochloride | 8.21 (1H, s), 7.79 (1H, s), 7.59 (1H, s), 7.35-7.20 (4H, m), 7.17 (1H, d), 7.09 (1H, d), 6.36 (1H, s), 4.76-4.66 (1H, m), 4.66-4.55 (1H, m), 4.38 (1H, d), 4.32-4.19 (2H, m), 4.14 (2H, s), 3.75-3.55 (2H, m), 3.47 (1H, d), 3.26-3.04 (2H, m), 1.38 (3H, d). | m/z: 476 | 4 |
| 143 | 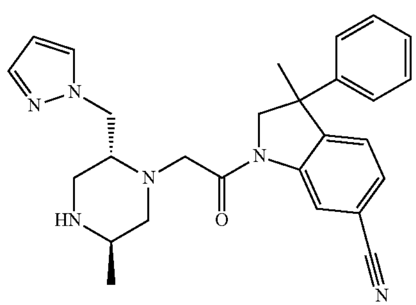 | 3-Methyl-1-{2-[(2R,5R)-5-methyl-2-((1H-pyrazol-1-ylmethyl)piperazin-1-yl]acetyl}-3-phenyl-2,3-dihydro-1H-indole-6-carbonitrile hydrochloride | 8.53 (1H, s), 7.78 (1H, dd), 7.58 (0.5H, d), 7.56-7.43 (1.5H, m), 7.43-7.18 (6H, m), 6.39-6.27 (1H, m), 4.77-4.64 (1H, m), 4.64-4.49 (1H, m), 4.48-4.06 (5H, m), 3.70-3.39 (3H, m), 3.30-3.20 (1H, m), 3.15 (1H, t), 1.83 (3H, d), 1.35 (3H, dd). | m/z: 455 | 2 |

TABLE 9-continued

| Ex. | Structure | Name | ¹H NMR Data (Me-d3-OD) | MS Data | Method a |
|---|---|---|---|---|---|
| 144 | 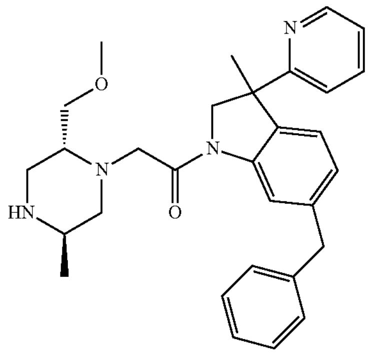 | 1-[6-Benzyl-3-methyl-3-(pyridin-2-yl)-2,3-dihydro-1H-indol-1-yl]-2-[(2R,5R)-2-(methoxymethyl)-5-methylpiperazin-1-yl]ethan-1-one hydrochloride | 8.81 (1H, d), 8.66-8.55 (1H, m), 8.26-8.16 (1H, m), 8.08-7.92 (2H, m), 7.37-7.04 (7H, m), 4.73-4.32 (4H, m), 4.26-4.11 (1H, m), 4.11-4.00 (2H, m), 4.00-3.82 (3H, m), 3.82-3.53 (4H, m), 2.09-1.91 (3H, m), 1.43 (3H, d). | m/z: 485 | 2 |
| 145 | 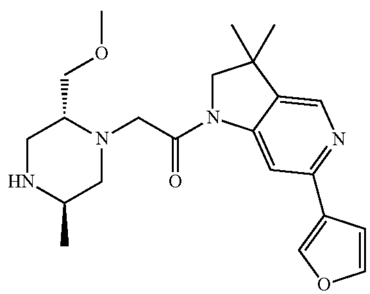 | 1-[6-(Furan-3-yl)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.61 (1H, s), 8.51 (2H, d), 7.86 (1H, t), 7.09 (1H, dd), 4.27-4.07 (5H, m), 3.73-3.39 (7H, m), 2.85 (3H, s), 1.56 (6H, s), 1.38 (3H, d). | m/z: 399 | 2 |
| 146 | 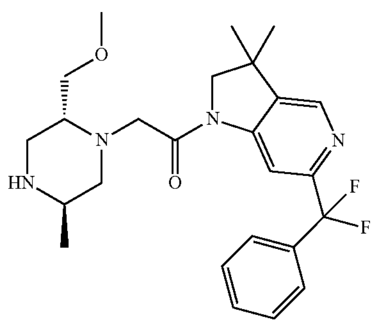 | 1-{6-[Difluoro(phenyl)methyl]-3,3-dimethyl-1H,2H,3H-pyrrolo[3,2-c]pyridin-1-yl}-2-[(2R,5R)-2-(methoxymethyl)-5-methylpiperazin-1-yl]ethan-1-one hydrochloride | 8.65 (1H, s), 8.47 (1H, s), 7.69-7.50 (5H, m), 4.20-4.10 (2H, m), 4.08 (2H, s), 3.66-3.43 (5H, m), 3.29 (4H, s), 3.23 (1H, d), 3.11 (1H, d), 1.53 (6H, s), 1.35 (3H, d). | m/z: 459 | 2 |

TABLE 9-continued

| Ex. | Structure | Name | ¹H NMR Data (Me-d3-OD) | MS Data | Method a |
|---|---|---|---|---|---|
| 147 | 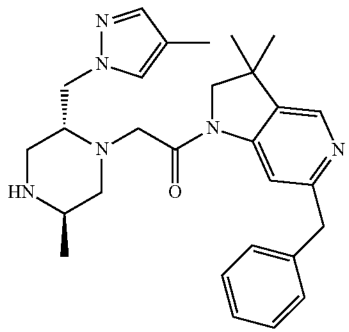 | 1-[6-Benzyl-3,3-dimethyl-1H,2H,3H-pyrrolo[3,2-c]pyridin-1-yl]-2-[(2R,5R)-5-methyl-2-[(4-methyl-1H-pyrazol-1-yl)methyl]piperazin-1-yl]ethan-1-one hydrochloride | 8.55 (1H, s), 8.21 (1H, s), 7.63 (1H, s), 7.45-7.38 (3H, m), 7.38-7.31 (3H, m), 4.56 (1H, dd), 4.48-4.29 (3H, m), 4.29-4.04 (4H, m), 3.98 (1H, s), 3.45 (1H, d), 3.31-3.24 (2H, m), 3.19-3.08 (1H, m), 2.97 (1H, t), 1.98 (3H, s), 1.52 (6H, d), 1.32 (3H, d). | m/z: 473 | 4 |
| 148 | 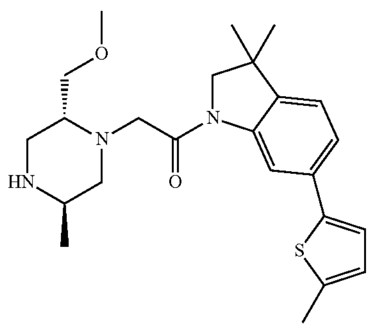 | 1-[3,3-Dimethyl-6-(5-methylthiophen-2-yl)-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.57 (1H, s), 8.45 (1H, s), 7.81 (1H, d), 7.08 (1H, dd), 4.23-4.07 (4H, m), 3.73-3.41 (6H, m), 3.30-3.10 (3H, m), 2.64 (3H, s), 1.55 (6H, s), 1.37 (3H, d). | m/z: 429 | 2 |

TABLE 9-continued

| Ex. | Structure | Name | ¹H NMR Data (Me-d3-OD) | MS Data | Method a |
|---|---|---|---|---|---|
| 149 | 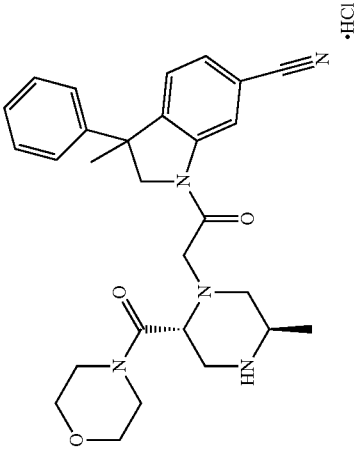 | 3-Methyl-1-{2-[(2R,5R)-5-methyl-2-[(morpholin-4-yl)carbonyl]piperazin-1-yl]acetyl}-3-phenyl-2,3-dihydro-1H-indole-6-carbonitrile hydrochloride | 8.54 (1H, s), 7.57-7.47 (1H, m), 7.38-7.24 (6H, m), 4.99-4.90 (0.5H, m), 4.49 (0.5H, d), 4.36-4.05 (2H, m), 4.05-3.84 (2H, m), 3.84-3.37 (12.5H, m), 3.05 (0.5H, t), 1.89-1.75 (3H, m), 1.37 (3H, dd). | m/z: 488 | 2 |
| 150 | 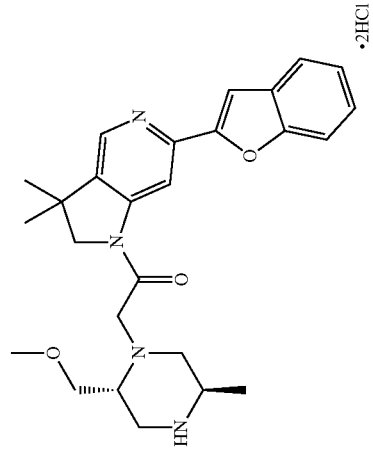 | 1-[6-(1-Benzofuran-2-yl)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.92 (1H, s), 8.58 (1H, s), 7.99 (1H, s), 7.86 (1H, d), 7.74 (1H, d), 7.64-7.54 (1H, m), 7.44 (1H, t), 4.26-4.14 (2H, m), 4.09 (2H, s), 3.84-3.68 (2H, m), 3.62 (3H, s), 3.56-3.39 (3H, m), 2.84 (3H, s), 1.58 (6H, s), 1.37 (3H, d). | m/z: 449 | 2 |

TABLE 9-continued

| Ex. | Structure | Name | ¹H NMR Data (Me-d3-OD) | MS Data | Method ᵃ |
|---|---|---|---|---|---|
| 151 | 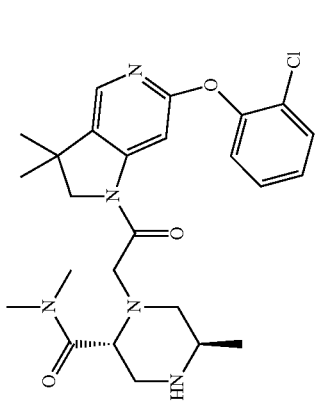 | (2R,5R)-1-{2-[6-(2-Chlorophenoxy)-3,3-dimethyl-1H,2H,3H-pyrrolo[3,2-c]pyridin-1-yl]-2-oxoethyl}-N,N,5-trimethylpiperazine-2-carboxamide dihydrochloride | 8.35 (1H, s), 7.62-7.47 (3H, m), 7.46 (1H, s), 4.53 (1H, dd), 4.14 (1H, d), 3.78 (2H, s), 3.57-3.41 (2H, m), 3.23-3.13 (4H, m), 3.07-2.97 (1H, m), 2.97-2.84 (3H, m), 1.51 (6H, d), 1.33 (3H, d). | m/z: 486 | 2 |
| 152 | 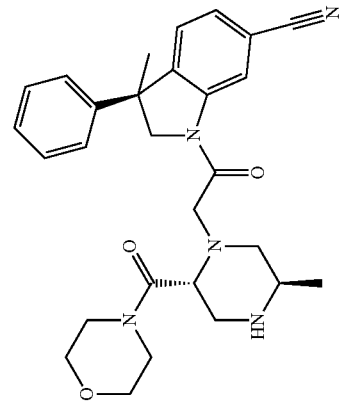 | (3S)-3-Methyl-1-{2-[(2R,5R)-5-methyl-2-[(morpholin-4-yl)carbonyl]piperazin-1-yl]acetyl}-3-phenyl-2,3-dihydro-1H-indole-6-carbonitrile | 8.51 (1H, s), 7.47 (1H, dd), 7.40-7.20 (6H, m), 4.47 (1H, d), 4.35 (1H, d), 3.89 (1H, d), 3.84-3.42 (10H, m), 3.04-2.89 (3H, m), 2.89-2.79 (1H, m), 2.42 (1H, t), 1.80 (3H, s), 1.08 (3H, d). | m/z: 488 | Chiral HPLC separation of Example 149ᶜ |
| 153 | 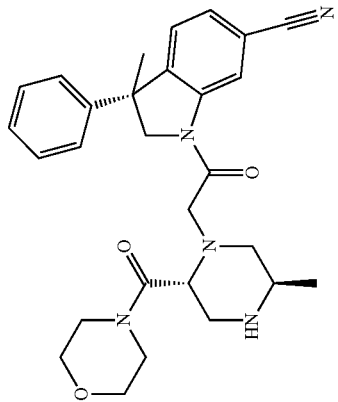 | (3R)-3-Methyl-1-{2-[(2R,5R)-5-methyl-2-[(morpholin-4-yl)carbonyl]piperazin-1-yl]acetyl}-3-phenyl-2,3-dihydro-1H-indole-6-carbonitrile | 8.50 (1H, s), 7.50 (1H, dd), 7.40-7.20 (6H, m), 5.04 (1H, d), 4.14 (1H, d), 3.83-3.51 (10H, m), 3.14 (1H, d), 2.97 (1H, dd), 2.84-2.70 (2H, m), 2.55 (1H, s), 2.21-2.10 (1H, m), 1.88-1.77 (3H, m), 0.96 (3H, d). | m/z: 488 | Chiral HPLC separation of Example 149ᶜ |

TABLE 9-continued

| Ex. | Structure | Name | ¹H NMR Data (Me-d3-OD) | MS Data | Method [a] |
|---|---|---|---|---|---|
| 154 | 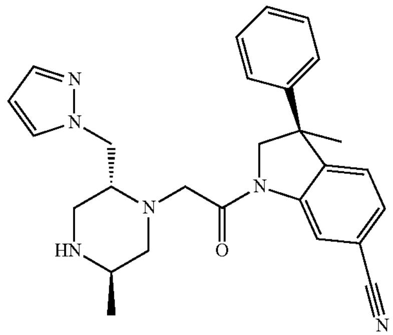 [SMILES: C[C@@H]1CN(CC(=O)N2C[C@@](C)(c3ccccc3)c3ccc(C#N)cc32)[C@@H](Cn2cccn2)CN1] | (3S)-3-Methyl-1-{2-[(2R,5R)-5-methyl-2-(1H-pyrazol-1-ylmethyl)piperazin-1-yl]acetyl}-3-phenyl-2,3-dihydro-1H-indole-6-carbonitrile | 8.52 (1H, s), 7.64 (1H, d), 7.46 (1H, dd), 7.43-7.17 (7H, m), 6.22 (1H, s), 4.45 (1H, dd), 4.32 (1H, d), 4.26 (1H, d), 4.08 (1H, dd), 3.82 (1H, d), 3.41 (1H, d), 3.18-3.07 (1H, m), 2.97-2.83 (2H, m), 2.70 (1H, dd), 2.60 (1H, dd), 2.32 (1H, t), 1.79 (3H, s), 1.04 (3H, d). | m/z: 455 | Chiral HPLC separation of Example 143[c] |
| 155 | 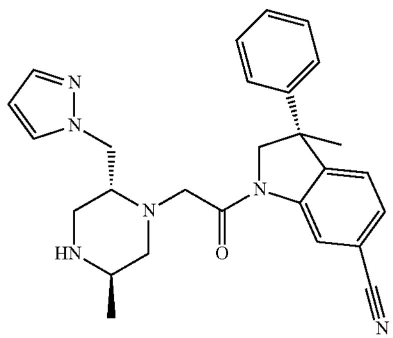 [SMILES: C[C@@H]1CN(CC(=O)N2C[C@](C)(c3ccccc3)c3ccc(C#N)cc32)[C@@H](Cn2cccn2)CN1] | (3R)-3-Methyl-1-{2-[(2R,5R)-5-methyl-2-(1H-pyrazol-1-ylmethyl)piperazin-1-yl]acetyl}-3-phenyl-2,3-dihydro-1H-indole-6-carbonitrile | 8.52 (1H, s), 7.67 (1H, d), 7.53-7.40 (2H, m), 7.39-7.18 (6H, m), 6.26 (1H, t), 4.56 (1H, d), 4.46 (1H, dd), 4.20-4.09 (2H, m), 3.87 (1H, d), 3.24 (1H, s), 3.01-2.91 (1H, m), 2.82-2.65 (2H, m), 2.59 (2H, dd), 2.22-2.11 (1H, m), 1.82 (3H, s), 0.96 (3H, d). | m/z: 455 | Chiral HPLC separation of Example 143[c] |
| 156 | 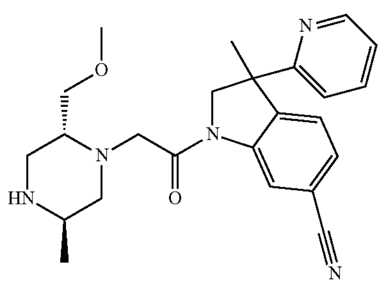 | 1-{2-[(2R,5R)-2-(Methoxymethyl)-5-methyl]piperazin-1-yl]acetyl]-3-methyl-3-(pyridin-2-yl)-2,3-dihydro-1H-indole-6-carbonitrile hydrochloride [mixture of diastereoisomers] | 8.84-8.75 (1H, m), 8.63-8.53 (1H, m), 8.52-8.43 (0.8H, m), 8.06-7.97 (0.8H, m), 7.96-7.87 (1.6H, m), 7.59 (0.8H, d), 7.52 (0.2H, dd), 7.45 (0.8H, d), 7.38 (0.2H, d), 4.64-4.34 (2H, m), 4.20-3.99 (1H, m), 3.99-3.65 (1H, m), 3.47 (4H, s), 1.44 (3H, d). | m/z: 470 | 2 |

TABLE 9-continued

| Ex. | Structure | Name | ¹H NMR Data (Me-d3-OD) | MS Data | Method[a] |
|---|---|---|---|---|---|
| 157 | ·HCl | 1-{6-Benzyl-3,3-dimethyl-1H,2H,3H-pyrrolo[3,2-c]pyridin-1-yl}-2-[(2R,5R)-2-[(4-fluoro-1H-pyrazol-1-yl)methyl]-5-methylpiperazin-1-yl]ethan-1-one hydrochloride | 8.53 (1H, s), 8.19 (1H, s), 7.74 (1H, d), 7.50-7.24 (6H, m), 4.53-4.40 (1H, m), 4.40-4.23 (3H, m), 4.23-3.96 (4H, m), 3.90 (1H, d), 3.43-3.36 (1H, m), 3.30-3.26 (1H, m), 3.22-3.15 (1H, m), 3.15-3.03 (1H, m), 2.96 (1H, t), 1.51 (6H, d), 1.30 (3H, d). | m/z: 477 | 4 |
| 158 | ·2HCl | (2R,5R)-1-(2-{6-[Difluoro(phenyl)methyl]-3,3-dimethyl-1H,2H,3H-pyrrolo[3,2-c]pyridin-1-yl}-2-oxoethyl)-N,N,5-trimethylpiperazine-2-carboxamide dihydrochloride | 8.70 (1H, s), 8.48 (1H, s), 7.70-7.54 (5H, m), 4.62 (1H, dd), 4.21 (1H, d), 4.16 (1H, d), 3.91-3.81 (2H, m), 3.63-3.47 (2H, m), 3.27-3.17 (4H, m), 3.13-2.99 (1H, m), 2.95 (3H, s), 1.53 (6H, d), 1.36 (3H, d). | m/z: 486 | 2 |

TABLE 9-continued

| Ex. | Structure | Name | ¹H NMR Data (Me-d3-OD) | MS Data | Method ᵃ |
|---|---|---|---|---|---|
| 159 | 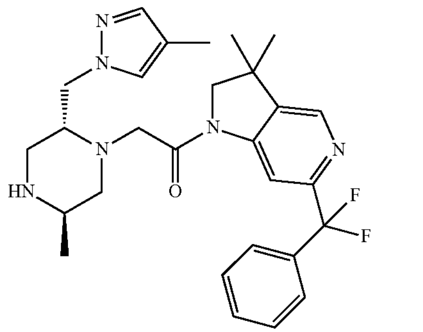 | 1-{6-[Difluoro(phenyl)methyl]-3,3-dimethyl-1H,2H,3H-pyrrolo[3,2-c]pyridin-1-yl}-2-[(2R,5R)-5-methyl-2-[(4-methyl-1H-pyrazol-1-yl)methyl]piperazin-1-yl]ethan-1-one dihydrochloride | 8.71 (1H, s), 8.45 (1H, s), 7.71-7.57 (5H, m), 7.54 (1H, s), 7.29 (1H, s), 4.49 (1H, dd), 4.30 (1H, dd), 4.15-4.10 (2H, m), 3.95-3.85 (1H, m), 3.85-3.66 (3H, m), 3.24-3.03 (3H, m), 2.92 (1H, t), 2.85 (3H, s), 1.54 (6H, d), 1.33-1.29 (3H, m). | m/z: 509 | 2 |
| 160 | 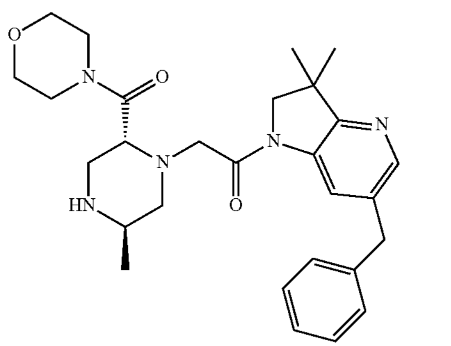 | 1-{6-Benzyl-3,3-dimethyl-1H,2H,3H-pyrrolo[3,2-b]pyridin-1-yl}-2-[(2R,5R)-5-methyl-2-[(morpholin-4-yl)carbonyl]piperazin-1-yl]ethan-1-one dihydrochloride | 1H NMR (Me-d3-OD) 8.84 (1H, s), 8.38 (1H, s), 7.40-7.27 (5H, m), 4.91 (1H, dd), 4.23 (2H, s), 4.20 (1H, d), 4.18 (1H, d), 4.05 (2H, s), 3.80-3.45 (11H, m), 3.39 (1H, m), 3.27 (1H, m), 1.62 (3H, s), 1.61 (3H, s), 1.40 (3H, d) | m/z: 492 | 3, EtOAc used as co-solvent |

TABLE 9-continued

| Ex. | Structure | Name | $^1$H NMR Data (Me-d3-OD) | MS Data | Method [a] |
|---|---|---|---|---|---|
| 161 | 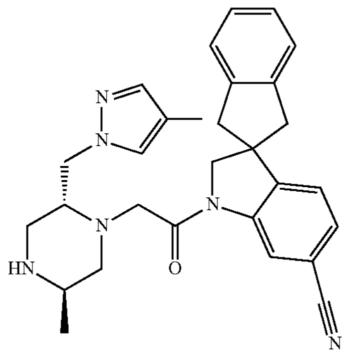 [SMILES: Cc1cnn(C[C@H]2CN[C@H](C)CN2CC(=O)N2CC3(Cc4ccccc4C3)c3ccc(C#N)cc32)c1] | 1'-{2-[(2R,5R)-5-Methyl-2-[(4-methyl-1H-pyrazol-1-yl)methyl]piperazin-1-yl]acetyl}-1,1',2',3-tetrahydrospiro[indene-2,3'-indole]-6'-carbonitrile | 8.45 (1H, s), 7.45-7.35 (2H, m), 7.35-7.09 (6H, m), 4.34 (1H, dd), 4.16 (1H, d), 4.08 (1H, d), 4.01 (1H, dd), 3.78 (1H, d), 3.37 (2H, s), 3.32-3.26 (3H, m), 3.07 (1H, d), 2.98-2.79 (2H, m), 2.72 (1H, dd), 2.58 (1H, t), 2.30 (1H, t), 1.93 (3H, s), 1.04 (3H, d). | m/z: 481 | 2, purification by preparative HPLC, basic method |
| 162 | 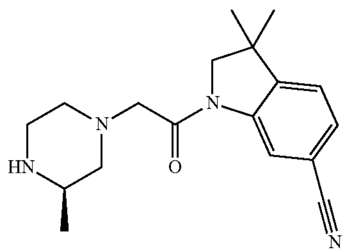 [SMILES: C[C@@H]1CN(CC(=O)N2CC(C)(C)c3ccc(C#N)cc32)CCN1] | 3,3-Dimethyl-1-{2-[(3R)-3-methylpiperazin-1-yl]acetyl}-2,3-dihydro-1H-indole-6-carbonitrile | 8.42 (1H, s), 7.52-7.38 (2H, m), 4.03 (2H, s), 3.37 (2H, s), 3.05-2.76 (5H, m), 2.32-2.18 (1H, m), 1.94 (1H, t), 1.40 (6H, s), 1.09 (3H, d). | m/z: 313 | 3, no MeOH co-solvent, followed by basic work-up and trituration of product with MeOH/Et$_2$O |
| 163 | 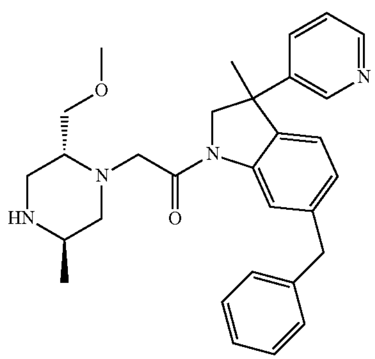 | 1-[6-Benzyl-3-methyl-3-(pyridin-3-yl)-2,3-dihydro-1H-indol-1-yl]-2-[(2R,5R)-2-(methoxymethyl)-5-methylpiperazin-1-yl]ethan-1-one hydrochloride | 8.84-8.73 (2H, m), 8.60 (1H, d), 8.19 (1H, s), 8.09 (1H, dd), 7.34-7.07 (7H, m), 4.54-4.44 (1H, m), 4.44-4.21 (3H, m), 3.99 (3H, m), 3.82-3.58 (5H, m), 3.55-3.38 (3H, m), 2.04-1.87 (3H, m), 1.40 (3H, dd). | m/z: 485 | 2 |

TABLE 9-continued

| Ex. | Structure | Name | ¹H NMR Data (Me-d3-OD) | MS Data | Method [a] |
|---|---|---|---|---|---|
| 164 | 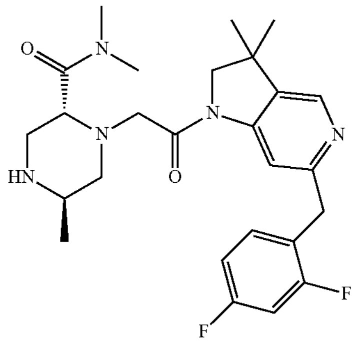 | (2R,5R)-1-(2-{6-[(2,4-Difluorophenyl)methyl]-3,3-dimethyl-1H,2H,3H-pyrrolo[3,2-c]pyridin-1-yl]-2-oxoethyl)-N,N,5-trimethylpiperazine-2-carboxamide dihydrochloride | 8.56 (1H, s), 8.17 (1H, s), 7.54-7.44 (1H, m), 7.14-7.02 (2H, m), 4.57 (1H, dd), 4.38 (2H, s), 3.80 (2H, s), 3.54-3.46 (2H, m), 3.23-3.16 (4H, m), 3.08-2.96 (1H, m), 2.93 (3H, s), 1.50 (6H, d), 1.35 (3H, d). | m/z: 486 | 2 |
| 165 | 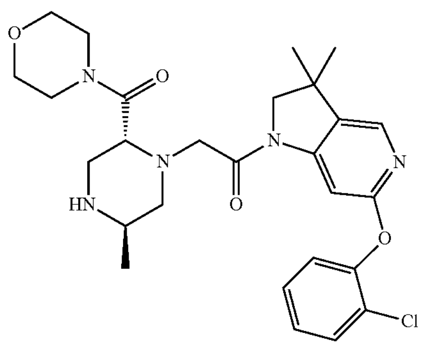 | 1-[6-(2-Chlorophenoxy)-3,3-dimethyl-1H,2H,3H-pyrrolo[3,2-c]pyridin-1-yl]-2-[(2R,5R)-5-methyl-2-[(morpholin-4-yl)carbonyl]piperazin-1-yl]ethan-1-one dihydrochloride | 8.32 (1H, s), 7.75-7.66 (1H, m), 7.61-7.47 (3H, m), 7.45 (1H, s), 4.43 (1H, dd), 4.13 (2H, s), 3.74 (2H, s), 3.70-3.37 (10H, m), 3.26-3.19 (2H, m), 2.95 (1H, dd), 1.50 (6H, d), 1.32 (3H, d). | m/z: 528 | 2 |

TABLE 9-continued

| Ex. | Structure | Name | ¹H NMR Data (Me-d3-OD) | MS Data | Method[a] |
|---|---|---|---|---|---|
| 166 | (structure with •HCl) | 6-[(2,4-Difluorophenyl)methyl]-1-{2-[(2R,5R)-2-(methoxymethyl)-5-methylpiperazin-1-yl]acetyl}-3,3-dimethyl-1H,2H,3H-1,5λ⁵-pyrrolo[3,2-c][1λ⁵]pyridin-5-one hydrochloride | 8.87 (1H, s), 8.12 (1H, s), 7.48 (1H, m), 7.07 (2H, m), 4.46 (2H, s), 4.23 (2H, s), 4.16 (2H, s), 3.76 (1H, m), 3.66-3.42 (6H, m), 3.31 (3H, s), 3.22 (1H, m), 1.52 (6H, s), 1.38 (3H, d) | m/z: 475 | 3, EtOAc as co-solvent |
| 167 | (structure with •HCl) | (2R,5R)-1-(2-{6-[(2,4-Difluorophenyl)methyl]-3,3-dimethyl-5-oxo-1H,2H,3H-1,5λ⁵-pyrrolo[3,2-c][1λ⁵]pyridin-1-yl}-2-oxoethyl)-N,N,5-trimethylpiperazine-2-carboxamide hydrochloride | 8.83 (1H, s), 8.12 (1H, s), 7.48 (1H, m), 7.09 (2H, m), 4.64 (1H, dd), 4.47 (2H, s), 4.17 (1H, d), 4.13 (1H, d), 3.86 (2H, s), 3.54 (2H, m), 3.37 (1H, m), 3.23 (1H, m), 3.20 (3H, s), 3.08 (1H, m), 2.93 (3H, s), 1.52 (3H, s), 1.50 (3H, s), 1.36 (3H, d) | m/z: 502 | 3, EtOAc as co-solvent |
| 168 | (structure with •HCl) | 1-[(3R)-6-Bromo-3-(methoxymethyl)-3-methyl-2,3-dihydro-1H-indol-1-yl]-2-[(2R,5R)-2-(methoxymethyl)-5-methylpiperazin-1-yl]ethan-1-one hydrochloride | 8.35 (1H, d), 7.29 (1H, dd), 7.23 (1H, d), 4.51-4.28 (2H, m), 4.19 (1H, d), 4.11-3.95 (1H, m), 3.92-3.63 (6H, m), 3.60-3.38 (4H, m), 1.55-1.32 (6H, m). | m/z: 440 | Chiral HPLC separation of Example 127[b] |

TABLE 9-continued

| Ex. | Structure | Name | $^1$H NMR Data (Me-d3-OD) | MS Data | Method [a] |
|---|---|---|---|---|---|
| 169 | 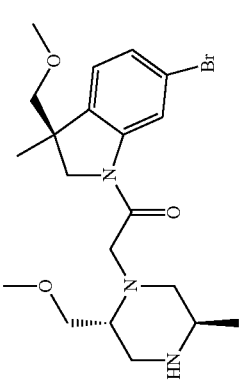 •HCl | 1-[(3S)-6-Bromo-3-(methoxymethyl)-3-methyl-2,3-dihydro-1H-indol-1-yl]-2-[(2R,5R)-2-(methoxymethyl)-5-methylpiperazin-1-yl]ethan-1-one hydrochloride | 8.34 (1H, d), 7.28 (1H, dd), 7.22 (1H, d), 4.38-4.21 (2H, m), 4.17 (1H, d), 3.94 (1H, d), 3.88-3.71 (3H, m), 3.71-3.57 (3H, m), 3.54-3.39 (4H, m), 1.46-1.35 (6H, m). | m/z: 440 | Chiral HPLC separation of Example 127[b] |
| 170 | 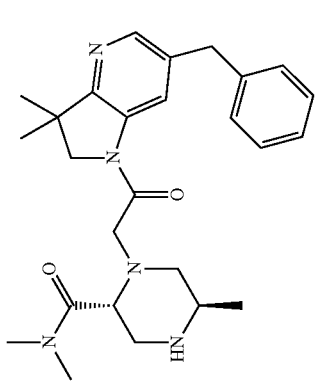 •2HCl | (2R,5R)-1-(2-{6-Benzyl-3,3-dimethyl-1H,2H,3H-pyrrolo[3,2-b]pyridin-1-yl}-2-oxoethyl)-N,N,5-trimethylpiperazine-2-carboxamide dihydrochloride | 8.87 (1H, s), 8.38 (1H, s), 7.40-7.25 (5H, m), 4.90 (1H, dd), 4.23 (2H, s), 4.21 (1H, d), 4.15 (1H, d), 4.03 (2H, m), 3.73-3.58 (3H, m), 3.36-3.27 (2H, m), 3.22 (1H, s), 2.96 (3H, s), 1.62 (3H, s), 1.60 (3H, s), 1.41 (3H, d) | m/z: 450 | 3, EtOAc used as co-solvent |
| 171 | 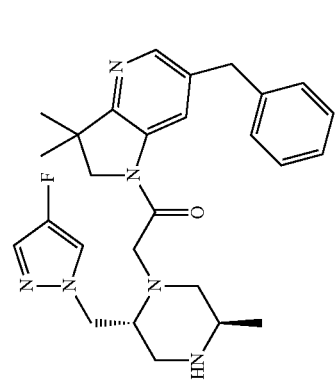 •2HCl | 1-{6-Benzyl-3,3-dimethyl-1H,2H,3H-pyrrolo[3,2-b]pyridin-1-yl}-2-[(2R,5R)-2-[(4-fluoro-1H-pyrazol-1-yl)methyl]-5-methylpiperazin-1-yl]ethan-1-one dihydrochloride | 8.82 (1H, s), 8.33 (1H, s), 7.73 (1H, d), 7.42-7.24 (6H, m), 4.45 (1H, dd), 4.29 (1H, dd), 4.23-3.95 (6H, m), 3.90-3.77 (1H, m), 3.76-3.69 (6H, m), 3.26-3.21 (1H, m), 3.16 (1H, dd), 3.05 (1H, t), 2.94 (1H, m), 1.60 (6H, d), 1.30 (3H, d). | m/z: 477 | 2 |

TABLE 9-continued

| Ex. | Structure | Name | ¹H NMR Data (Me-d3-OD) | MS Data | Method[a] |
|---|---|---|---|---|---|
| 172 | 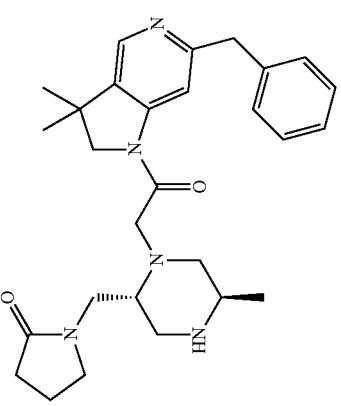 | 1-{[(2R,5R)-1-(2-{6-Benzyl-3,3-dimethyl-1H,2H,3H-pyrrolo[3,2-c]pyridin-1-yl}-2-oxoethyl)-5-methyl]piperazin-2-yl]methyl}pyrrolidin-2-one dihydrochloride | 8.56 (1H, s), 8.21 (1H, s), 7.43-7.32 (5H, m), 4.36 (2H, s), 4.21 (1H, d), 4.15-4.04 (3H, m), 3.77 (2H, m), 3.51 (2H, m), 3.40 (2H, m), 3.29 (2H, m), 3.16 (1H, t), 3.05 (1H, t), 2.31 (1H, m), 2.12 (1H, m), 2.01 (1H, m), 1.84 (1H, m), 1.52 (3H, s), 1.51 (3H, s), 1.32 (3H, d) | m/z: 476 | 3, EtOAc used as co-solvent |
| 173 | 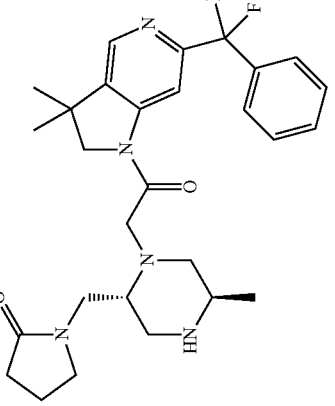 | 1-{[(2R,5R)-1-(2-{6-[Difluoro(phenyl)methyl]-3,3-dimethyl-1H,2H,3H-pyrrolo[3,2-c]pyridin-1-yl}-2-oxoethyl)-5-methyl]piperazin-2-yl]methyl}pyrrolidin-2-one dihydrochloride | 8.72 (1H, s), 8.48 (1H, s), 7.68-7.55 (5H, m), 4.22-4.05 (4H, m), 3.76-3.70 (2H, m), 3.56 (1H, m), 3.47 (2H, m), 3.40 (1H, dm), 3.26 (2H, m), 3.12 (1H, m), 3.04 (1H, m), 2.35 (1H, m), 2.16 (1H, m), 2.03 (1H, m), 1.89 (1H, m), 1.54 (3H, s), 1.53 (3H, s), 1.33 (3H, d) | m/z: 512 | 3, EtOAc used as co-solvent |

TABLE 9-continued

| Ex. | Structure | Name | $^1$H NMR Data (Me-d3-OD) | MS Data | Method [a] |
|---|---|---|---|---|---|
| 174 | (structure) ·HCl | 1-[(3R)-6-Benzyl-3-methyl-3-(3-methyl-1,2-oxazol-5-yl)-2,3-dihydro-1H-indol-1-yl]-2-[(2R,5R)-2-(methoxymethyl)-5-methylpiperazin-1-yl]ethan-1-one hydrochloride | 8.09 (1H, s), 7.32-7.14 (6H, m), 7.07 (1H, d), 6.12 (1H, s), 4.58 (1H, d), 4.29 (1H, d), 4.18-4.04 (2H, m), 4.00 (2H, s), 3.81-3.69 (2H, m), 3.69-3.47 (4H, m), 3.29 (3H, s), 2.25 (3H, s), 1.79 (3H, s), 1.38 (3H, d). | m/z: 489 | 2, then chiral HPLC separation[c] |
| 175 | (structure) ·HCl | 1-[(3S)-6-Benzyl-3-methyl-3-(3-methyl-1,2-oxazol-5-yl)-2,3-dihydro-1H-indol-1-yl]-2-[(2R,5R)-2-(methoxymethyl)-5-methylpiperazin-1-yl]ethan-1-one hydrochloride | 8.09 (1H, s), 7.31-7.15 (6H, m), 7.06 (1H, d), 6.14-6.08 (1H, m), 4.49 (1H, d), 4.18-4.05 (3H, m), 4.05-3.96 (2H, m), 3.72-3.37 (8H, m), 3.26 (3H, s), 2.25 (3H, s), 1.78 (3H, s), 1.36 (3H, d). | m/z: 489 | 2, then chiral HPLC separation[c] |

TABLE 9-continued

| Ex. | Structure | Name | ¹H NMR Data (Me-d3-OD) | MS Data | Method a |
|---|---|---|---|---|---|
| 176 | 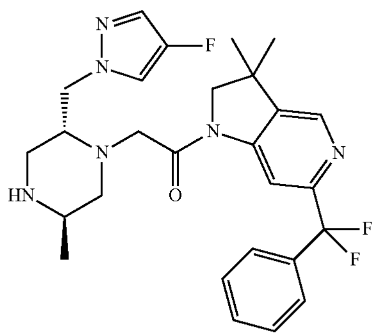 | 1-[6-[Difluoro(phenyl)methyl]-3,3-dimethyl-1H,2H,3H-pyrrolo[3,2-c]pyridin-1-yl]-2-[(2R,5R)-2-[(4-fluoro-1H-pyrazol-1-yl)methyl]-5-methylpiperazin-1-yl]ethan-1-one hydrochloride | 8.72 (1H, s), 8.45 (1H, s), 7.75 (1H, d), 7.71-7.54 (5H, m), 7.32 (1H, d), 4.45 (1H, dd), 4.31 (1H, dd), 4.25-4.09 (3H, m), 4.03 (1H, d), 3.88 (1H, s), 3.31-3.22 (2H, m), 3.21-3.03 (2H, m), 2.93 (1H, t), 1.55 (6H, d), 1.31 (3H, d). | m/z: 513 | 4 |
| 177 | 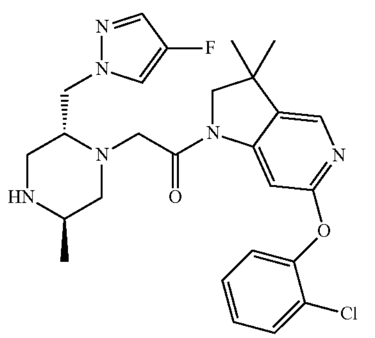 | 1-[6-(2-Chlorophenoxy)-3,3-dimethyl-1H,2H,3H-pyrrolo[3,2-c]pyridin-1-yl]-2-[(2R,5R)-2-[(4-fluoro-1H-pyrazol-1-yl)methyl]-5-methylpiperazin-1-yl]ethan-1-one hydrochloride | 8.37 (1H, s), 7.78-7.67 (2H, m), 7.67-7.50 (3H, m), 7.43 (1H, s), 7.32 (1H, d), 4.39 (1H, dd), 4.26 (1H, dd), 4.21-4.05 (3H, m), 3.97 (1H, d), 3.86-3.73 (1H, m), 3.24 (1H, dd), 3.10 (1H, dd), 3.06-2.96 (1H, m), 2.90 (1H, t), 1.52 (6H, d), 1.27 (3H, d). | m/z: 513 | 4 |

TABLE 9-continued

| Ex. | Structure | Name | ¹H NMR Data (Me-d3-OD) | MS Data | Method a |
|---|---|---|---|---|---|
| 178 | 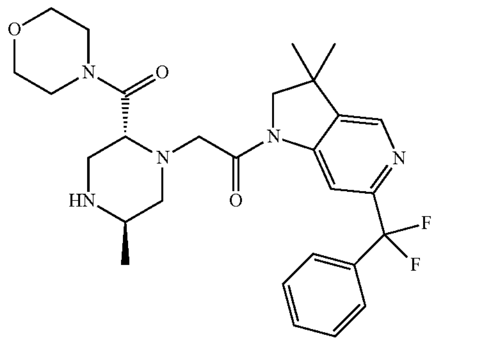 | 1-{6-[Difluoro(phenyl)methyl]-3,3-dimethyl-1H,2H,3H-pyrrolo[3,2-c]pyridin-1-yl}-2-[(2R,5R)-5-methyl-2-[(morpholin-4-yl)carbonyl]piperazin-1-yl]ethan-1-one dihydrochloride | 8.74 (1H, s), 8.48 (1H, s), 7.70-7.54 (5H, m), 4.68 (1H, dd), 4.23-4.19 (2H, m), 3.93 (2H, s), 3.77-3.58 (9H, m), 3.53 (2H, m), 3.42 (1H, dd), 3.12 (1H, m), 1.54 (3H, s), 1.53 (3H, s), 1.36 (3H, d) | m/z: 528 | 3, EtOAc used as co-solvent |
| 179 | 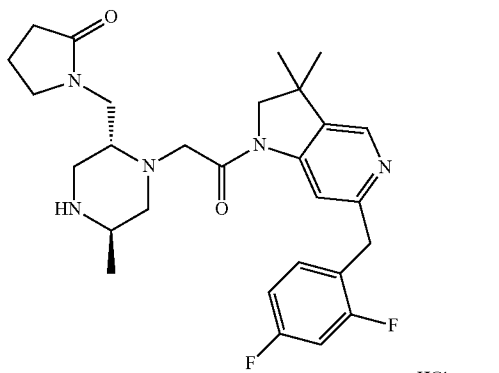 [SMILES: C[C@@H]1CN(CC(=O)N2CC(C)(C)c3cnc(Oc4ccccc4Cl)cc32)[C@@H](CN2CCCC2=O)CN1 ; Cl] | 1-{[(2R,5R)-1-(2-{6-[(2,4-Difluorophenyl)methyl]-3,3-dimethyl-1H,2H,3H-pyrrolo[3,2-c]pyridin-1-yl}-2-oxoethyl)-5-methylpiperazin-2-yl]methyl}pyrrolidin-2-one hydrochloride | 8.61-8.55 (1H, m), 8.15 (1H, s), 7.54-7.45 (1H, m), 7.14-7.02 (2H, m), 4.39 (2H, s), 4.21-4.02 (4H, m), 3.80-3.63 (2H, m), 3.58-3.49 (1H, m), 3.48-3.39 (2H, m), 3.22 (2H, d), 3.14-3.05 (1H, m), 3.04-2.94 (1H, m), 2.39-2.27 (1H, m), 2.17-2.06 (1H, m), 2.06-1.96 (1H, m), 1.89-1.79 (1H, m), 1.52 (6H, d), 1.31 (3H, d). | m/z: 512 | 4 |

TABLE 9-continued

| Ex. | Structure | Name | ¹H NMR Data (Me-d3-OD) | MS Data | Method a |
|---|---|---|---|---|---|
| 180 | 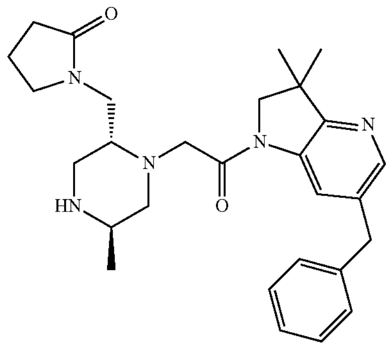 | 1-{[(2R,5R)-1-(2-{6-Benzyl-3,3-dimethyl-1H,2H,3H-pyrrolo[3,2-b]pyridin-1-yl}-2-oxoethyl)-5-methyl]piperazin-2-yl]methyl}pyrrolidin-2-one dihydrochloride | 8.86-8.76 (1H, m), 8.41-8.33 (1H, m), 7.39-7.26 (5H, m), 4.21 (2H, s), 4.19-4.08 (4H, m), 3.89-3.69 (2H, m), 3.61-3.39 (5H, m), 3.23-3.06 (2H, m), 2.44-2.25 (1H, m), 2.19-2.06 (1H, m), 1.96-1.80 (1H, m), 1.60 (6H, d), 1.34 (3H, d). | m/z: 476 | 2 |
| 181 | 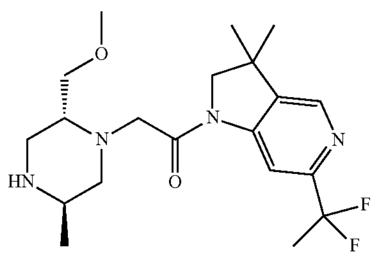 | 1-[6-(1,1-Difluoroethyl)-3,3-dimethyl-1H,2H,3H-pyrrolo[3,2-c]pyridin-1-yl]-2-[(2R,5R)-2-(methoxymethyl)-5-methylpiperazin-1-yl]ethan-1-one dihydrochloride | 8.73 (1H, s), 8.58 (1H, s), 4.39-4.26 (2H, m), 4.26-4.12 (2H, m), 3.89-3.47 (7H, m), 2.14 (3H, t), 1.56 (6H, s), 1.40 (3H, d). | m/z: 397 | 2 |
| 182 | 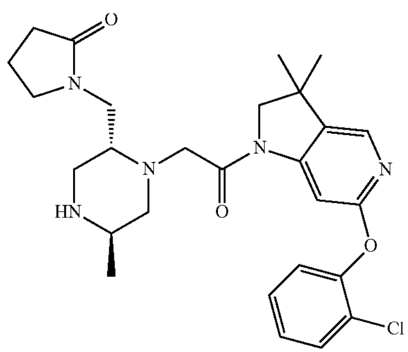 | 1-{[(2R,5R)-1-{2-[6-(2-Chlorophenoxy)-3,3-dimethyl-1H,2H,3H-pyrrolo[3,2-c]pyridin-1-yl]-2-oxoethyl}-5-methylpiperazin-2-yl]methyl}pyrrolidin-2-one hydrochloride | 8.33 (1H, d), 7.70 (1H, d), 7.53 (3H, m), 7.46 (1H, s), 4.05 (3H, d), 3.95-3.85 (1H, m), 3.74-3.65 (1H, m), 3.61-3.53 (1H, m), 3.49-3.39 (3H, m), 3.21 (1H, s), 3.14-3.04 (1H, m), 3.00-2.87 (2H, m), 2.37-2.29 (1H, m), 2.12-1.98 (3H, m), 1.92-1.82 (1H, m), 1.51 (6H, d), 1.28 (3H, d). | m/z: 512 | 4 |

TABLE 9-continued

| Ex. | Name | 1H NMR Data (Me-d3-OD) | MS Data | Method a |
|---|---|---|---|---|
| 183 | 1-{3-Chloro-7,7-dimethyl-5H,6H,7H-pyrrolo[3,2-c]pyridazin-5-yl}-2-[(2R,5R)-2-(methoxymethyl)-5-methylpiperazin-1-yl]ethan-1-one hydrochloride | 8.02 (1H, s), 4.10-4.02 (2H, m), 3.97-3.90 (2H, m), 3.58-3.55 (2H, m), 3.54-3.47 (2H, m), 3.44-3.39 (2H, m), 3.24-3.17 (2H, m), 3.17-3.10 (2H, m), 3.10-3.01 (1H, m), 1.52 (6H, d), 1.33 (3H, d). | m/z: 386 | 2 |
| 184 | 1-{[(2R,5R)-1-{2-[6-(1,1-Difluoroethyl)-3,3-dimethyl-1H,2H,3H-pyrrolo[3,2-c]pyridin-1-yl]-2-oxoethyl}-5-methylpiperazin-2-yl]methyl}pyrrolidin-2-one dihydrochloride | 8.69 (1H, s), 8.55 (1H, s), 4.21-4.11 (3H, m), 3.82-3.67 (2H, m), 3.67-3.56 (2H, m), 3.56-3.40 (3H, m), 3.19-3.06 (1H, m), 3.06-2.94 (1H, m), 2.43-2.30 (1H, m), 2.28-2.19 (1H, m), 2.19-2.04 (4H, m), 2.00-1.90 (1H, m), 1.55 (6H, s), 1.34 (3H, d). | m/z: 450 | 2 |
| 185 | 1-{[(2R,5R)-1-(2-{6-[(2,4-Difluorophenyl)methyl]-3,3-dimethyl-1H,2H,3H-pyrrolo[3,2-c]pyridin-1-yl}-2-oxoethyl)-5-methylpiperazin-2-yl]methyl}-1,2-dihydropyrimidin-2-one dihydrochloride | 9.07 (1H, br d), 8.85 (1H, br d), 8.57 (1H, s), 8.18 (1H, s), 7.51 (1H, m), 7.06 (2H, m), 6.98 (1H, br t), 4.65 (1H, dd), 4.38 (2H, s), 4.34 (1H, m), 4.22 (2H, m), 4.17 (1H, d), 4.04 (1H, d), 3.73 (2H, m), 3.52 (2H, m), 3.23 (1H, dd), 3.13 (1H, dd), 2.93 (1H, dd), 1.53 (6H, s), 1.33 (3H, d). | m/z: 523 | 3, EtOAc used as co-solvent |

TABLE 9-continued

| Ex. | Structure | Name | ¹H NMR Data (Me-d3-OD) | MS Data | Method[a] |
|---|---|---|---|---|---|
| 186 | a HCl salt | 1-[6-(1,1-Difluoropropyl)-3,3-dimethyl-1H,2H,3H-pyrrolo[3,2-b]pyridin-1-yl]-2-[(2R,5R)-5-methyl-2-{[(3R)-3-methylmorpholin-4-yl]methyl}piperazin-1-yl]ethan-1-one, a hydrochloride salt | 1H NMR (400 MHz, Me-d3-OD): 8.67 (1H, s), 8.47 (1H, s), 4.32-3.89 (9H, m), 3.81 (2H, s), 3.52 (5H, d), 3.11 (1H, d), 2.36-2.21 (2H, m), 2.20-2.04 (1H, m), 1.82 (1H, s), 1.56-1.50 (6H, m), 1.49-1.38 (3H, m), 1.14-0.97 (6H, m). | m/z: 480 | 4, Ethyl acetate/4M HCl dioxane |
| 187 | •2HCl | 1-{[(2R,5R)-1-(2-{6-Benzoyl-3,3-dimethyl-1H,2H,3H-pyrrolo[3,2-b]pyridin-1-yl}-2-oxoethyl)-5-methylpiperazin-2-yl]methyl}pyrrolidin-2-one dihydrochloride | 8.88 (1H, s), 8.63 (1H, s), 7.86 (2H, d), 7.73 (1H, t), 7.60 (2H, t), 4.39 (2H, s), 4.29-3.97 (4H, m), 3.85 (2H, dd), 3.77-3.46 (6H, m), 2.45-2.19 (2H, m), 1.57 (6H, d), 1.39 (3H, d). | m/z: 490 | 2 |

TABLE 9-continued

| Ex. | Structure | Name | 1H NMR Data (Me-d3-OD) | MS Data | Method a |
|---|---|---|---|---|---|
| 188 | 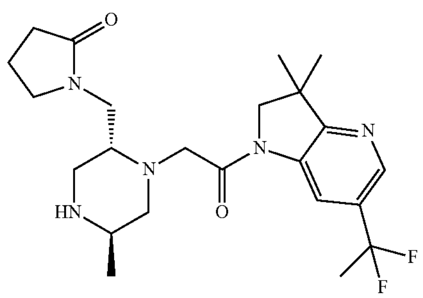 | 1-{[(2R,5R)-1-{2-[6-(1,1-Difluoroethyl)-3,3-dimethyl-1H,2H,3H-pyrrolo[3,2-b]pyridin-1-yl]-2-oxoethyl}-5-methylpiperazin-2-yl]methyl}pyrrolidin-2-one dihydrochloride | 8.71 (1H, s), 8.49 (1H, s), 4.36-4.15 (2H, m), 4.14-4.02 (2H, m), 4.01-3.77 (2H, m), 3.67-3.58 (2H, m), 3.56-3.39 (4H, m), 3.21-3.12 (1H, m), 2.44-2.30 (1H, m), 2.28-2.15 (1H, m), 2.10-1.91 (6H, m), 1.52 (6H, d), 1.37 (3H, d). | m/z: 450 | 2 |
| 189 | 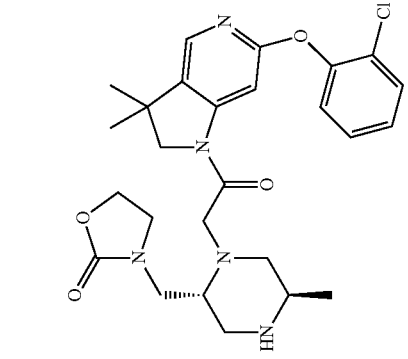 | 3-{[(2R,5R)-1-{2-[6-(2-Chlorophenoxy)-3,3-dimethyl-1H,2H,3H-pyrrolo[3,2-c]pyridin-1-yl]-2-oxoethyl}-5-methylpiperazin-2-yl]methyl}-1,3-oxazolidin-2-one hydrochloride | 8.40 (1H, s), 7.76-7.67 (1H, m), 7.62-7.49 (3H, m), 7.46 (1H, s), 4.41-4.29 (1H, m), 4.23-3.97 (5H, m), 3.72-3.53 (4H, m), 3.53-3.36 (3H, m), 3.25-3.17 (1H, m), 3.16-2.97 (2H, m), 1.52 (6H, s), 1.30 (3H, d). | m/z: 514 | 2, purification by HPLC, basic method, then HCl salt formation with HCl-EtOAc |

TABLE 9-continued

| Ex. | Structure | Name | $^1$H NMR Data (Me-d3-OD) | MS Data | Method[a] |
|---|---|---|---|---|---|
| 190 | 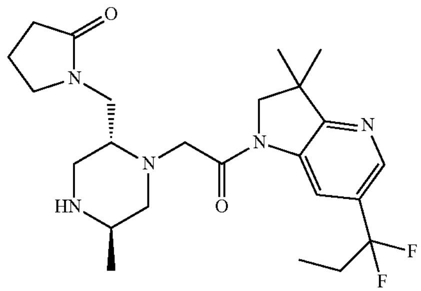 | 1-{[(2R,5R)-1-{2-[6-(1,1-Difluoropropyl)-1H,2H,3H-pyrrolo[3,2-b]pyridin-1-yl]-2-oxoethyl}-5-methylpiperazin-2-yl]methyl}pyrrolidin-2-one hydrochloride | 8.70 (1H, d), 8.47 (1H, s), 4.33 (1H, d), 4.27 (1H, d), 4.16-4.04 (2H, m), 4.04-3.92 (1H, m), 3.84 (1H, dd), 3.66-3.60 (2H, m), 3.60-3.37 (5H, m), 3.24-3.16 (1H, m), 2.44-2.16 (4H, m), 2.16-2.05 (1H, m), 2.00-1.91 (1H, m), 1.54 (6H, d), 1.38 (3H, d), 1.05 (3H, t). | m/z: 464 | 2 |
| 191 | 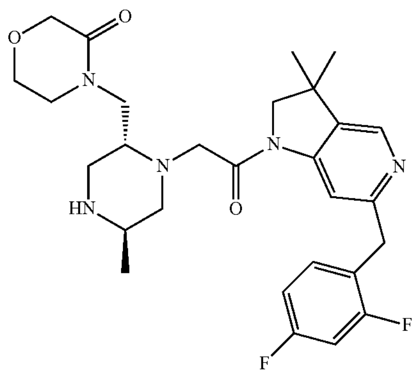 | 4-{[(2R,5R)-1-(2-{6-[(2,4-Difluorophenyl)methyl]-3,3-dimethyl-1H,2H,3H-pyrrolo[3,2-c]pyridin-1-yl}-2-oxoethyl)-5-methylpiperazin-2-yl]methyl}morpholin-3-one hydrochloride | 8.62 (1H, d), 8.15 (1H, d), 7.57-7.44 (1H, m), 7.15-7.01 (2H, m), 4.53-4.29 (3H, m), 4.29-3.80 (9H, m), 3.80-3.40 (7H, m), 3.16-2.97 (1H, m), 1.62-1.46 (6H, m), 1.44-1.32 (3H, m). | m/z: 528 | 2 |

TABLE 9-continued

| Ex. | Structure | Name | ¹H NMR Data (Me-d3-OD) | MS Data | Method[a] |
|---|---|---|---|---|---|
| 192 | (structure with HCl) | 1-{[(2R,5R)-1-(2-{6-[(2,4-Difluorophenyl)methyl]-3,3-dimethyl-1H,2H,3H-pyrrolo[3,2-c]pyridin-1-yl]-2-oxoethyl})-5-methylpiperazin-2-yl]methyl}piperidin-2-one hydrochloride | 8.64 (1H, d), 8.22-8.11 (1H, m), 7.57-7.44 (1H, m), 7.15-7.00 (2H, m), 4.71-4.53 (1H, m), 4.40 (2H, d), 4.29-4.05 (4H, m), 3.94-3.61 (4H, m), 3.61-3.41 (4H, m), 3.24-3.06 (1H, m), 2.49-2.16 (2H, m), 1.94-1.75 (4H, m), 1.62-1.49 (6H, m), 1.45-1.31 (3H, m). | m/z: 526 | 2 |
| 193 | (structure with 2HCl) | 1-{[(2R,5R)-1-(2-{6-[(2,4-Difluorophenyl)methyl]-3,3-dimethyl-1H,2H,3H-pyrrolo[3,2-c]pyridin-1-yl]-2-oxoethyl})-5-methylpiperazin-2-yl]methyl}-1,2-dihydropyridin-2-one dihydrochloride | 8.58 (1H, s), 8.07 (1H, s), 7.69 (1H, m), 7.52 (1H, m), 7.42 (1H, m), 7.10 (2H, m), 6.49 (1H, m), 6.36 (1H, m), 4.52 (1H, dd), 4.39 (2H, m), 4.16 (2H, s), 4.14 (1H, d), 4.10 (1H, d), 3.97 (1H, dd), 3.82 (1H, br m), 3.44 (1H, br m), 3.38 (1H, m), 3.22 (1H, m), 3.07 (2H, m), 1.53 (3H, s), 1.49 (3H, s), 1.31 (3H, s) | m/z: 522 | 3, EtOAc used as co-solvent |

TABLE 9-continued

| Ex. | Structure | Name | ¹H NMR Data (Me-d3-OD) | MS Data | Method ᵃ |
|---|---|---|---|---|---|
| 194 | 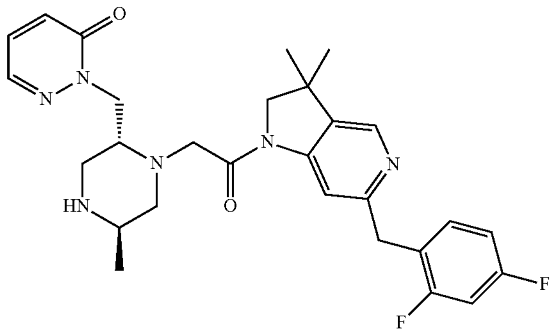 | 2-{[(2R,5R)-1-(2-{6-[(2,4-Difluorophenyl)methyl]-3,3-dimethyl-1H,2H,3H-pyrrolo[3,2-c]pyridin-1-yl}-2-oxoethyl)-5-methylpiperazin-2-yl]methyl}-2,3-dihydropyridazin-3-one dihydrochloride | 8.60 (1H, s), 8.03 (1H, s), 7.87 (1H, dd), 7.49 (1H, m), 7.31 (1H, dd), 7.11 (2H, m), 6.90 (1H, dd), 4.51 (1H, dd), 4.38 (2H, m), 4.22 (1H, m), 4.15-4.04 (3H, m), 3.81 (1H, m), 3.72 (1H, m), 3.50 (1H, m), 3.39 (1H, m), 3.18 (1H, dd), 3.12 (1H, t), 3.02 (1H, t), 1.52 (3H, s), 1.50 (3H, s), 1.30 (3H, d) | m/z: 523 | 3, EtOAc used as co-solvent |
| 195 | 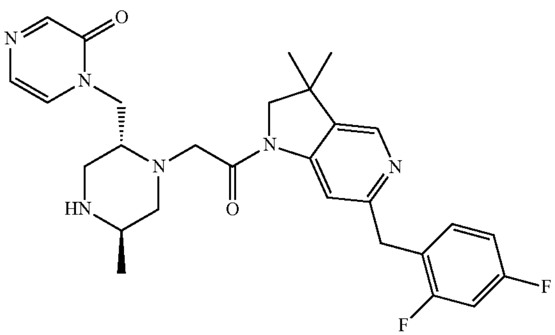 | 1-{[(2R,5R)-1-(2-{6-[(2,4-Difluorophenyl)methyl]-3,3-dimethyl-1H,2H,3H-pyrrolo[3,2-c]pyridin-1-yl}-2-oxoethyl)-5-methylpiperazin-2-yl]methyl}-1,2-dihydropyrazin-2-one dihydrochloride | 8.60 (1H, s), 8.07 (1H, s), 7.97 (1H, s), 7.61 (1H, d), 7.50 (1H, m), 7.35 (1H, d), 7.09 (2H, m), 4.42 (1H, dd), 4.38 (2H, m), 4.22 (1H, m), 4.14 (3H, m), 3.75 (3H, m), 3.43 (1H, m), 3.19 (1H, m), 3.02 (2H, m), 1.54 (3H, s), 1.50 (3H, s), 1.31 (3H, s) | m/z: 523 | 3, EtOAc used as co-solvent |

TABLE 9-continued

| Ex. | Structure | Name | ¹H NMR Data (Me-d3-OD) | MS Data | Method [a] |
|---|---|---|---|---|---|
| 196 | 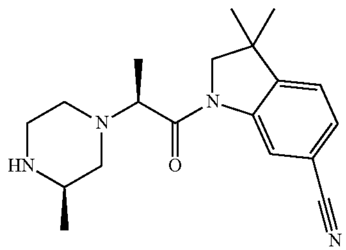 | 3,3-Dimethyl-1-[(2S)-2-[(3R)-3-methylpiperazin-1-yl]propanoyl]-2,3-dihydro-1H-indole-6-carbonitrile hydrochloride | 8.48 (1H, s), 7.58-7.45 (2H, m), 4.45-4.35 (1H, m), 4.25 (1H, d), 3.99 (1H, d), 3.62 (5H, d), 3.03 (1H, t), 1.62-1.55 (3H, m), 1.46-1.41 (9H, m). | m/z: 327 | 3, no MeOH co-solvent |
| 197 | 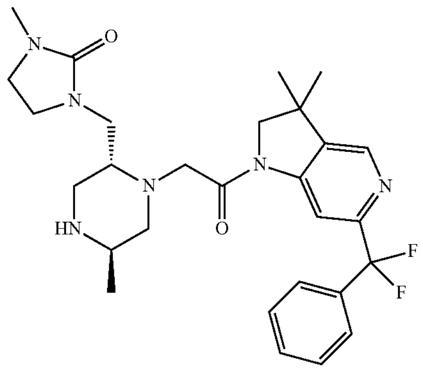 | 1-{[(2R,5R)-1-(2-{6-[Difluoro(phenyl)methyl]-3,3-dimethyl-1H,2H,3H-pyrrolo[3,2-c]pyridin-1-yl}-2-oxoethyl)-5-methylpiperazin-2-yl]methyl}-3-methylimidazolidin-2-one hydrochloride | 8.79 (1H, s), 8.47 (1H, s), 7.72-7.53 (5H, m), 4.53 (2H, s), 4.24 (1H, d), 4.17 (1H, d), 3.95 (1H, m), 3.85-3.38 (9H, m), 3.30-3.11 (2H, m), 2.64 (3H, s), 1.56 (6H, d), 1.40 (3H, d). | m/z: 527 | 2 |
| 198 | 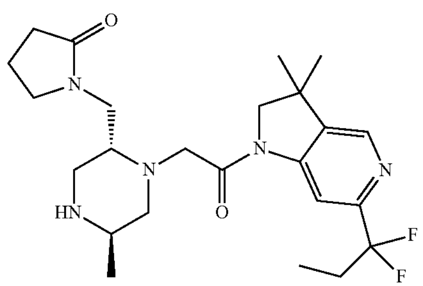 [SMILES: CCC(F)(F)c1cc2c(cn1)C(C)(C)CN2C(=O)CN1C[C@@H](C)NC[C@@H]1CN1CCCC1=O] | 1-{[(2R,5R)-1-{2-[6-(1,1-Difluoropropyl)-3,3-dimethyl-1H,2H,3H-pyrrolo[3,2-c]pyridin-1-yl]-2-oxoethyl}-5-methylpiperazin-2-yl]methyl}pyrrolidin-2-one | 8.40 (1H, s), 8.30 (1H, s), 4.00 (1H, d), 3.94 (1H, d), 3.81 (1H, d), 3.76-3.58 (3H, m), 3.42 (1H, q), 3.21 (1H, m), 3.07 (1H, dd), 2.98-2.81 (3H, m), 2.57 (2H, q), 2.42-2.19 (3H, m), 2.19-2.05 (1H, m), 2.05-1.93 (1H, m), 1.93-1.79 (1H, m), 1.46 (6H, d), 1.07 (3H, d), 0.97 (3H, t). | m/z: 464 | 4, then purification by preparative HPLC, basic method |

TABLE 9-continued

| Ex. | Name | ¹H NMR Data (Me-d3-OD) | MS Data | Method[a] |
|---|---|---|---|---|
| 199 | 1-{[(2R,5R)-1-(2-{6-[(2,4-Difluorophenyl)methyl]-3,3-dimethyl-1H,2H,3H-pyrrolo[3,2-b]pyridin-1-yl}-2-oxoethyl)-5-methylpiperazin-2-yl]methyl}pyrrolidin-2-one dihydrochloride | 8.80 (1H, s), 8.39 (1H, s), 7.52-7.40 (1H, m), 7.09-6.96 (2H, m), 4.23 (2H, s), 4.19-4.08 (4H, m), 3.88-3.71 (2H, m), 3.65-3.52 (2H, m), 3.50-3.42 (2H, m), 3.21 (1H, d), 3.17-3.07 (1H, m), 2.40-2.26 (1H, m), 2.22-2.10 (1H, m), 1.95-1.83 (1H, m), 1.65-1.57 (6H, m), 1.35 (3H, d). | m/z: 512 | 2 |
| 200 | 3-{[(2R,5R)-1-(2-{6-[(2,4-Difluorophenyl)methyl]-3,3-dimethyl-1H,2H,3H-pyrrolo[3,2-b]pyridin-1-yl}-2-oxoethyl)-5-methylpiperazin-2-yl]methyl}-1,3-oxazolidin-2-one dihydrochloride | 8.82 (1H, s), 8.37 (1H, s), 7.47 (1H, m), 7.02 (2H, m), 4.39 (1H, m), 4.31 (1H, m), 4.22 (2H, d), 4.19-4.03 (4H, m), 3.78-3.69 (3H, m), 3.61 (1H, m), 3.51-3.43 (2H, m), 3.32 (1H, m), 3.21 (2H, m), 3.09 (1H, t), 1.60 (6H, s), 1.34 (3H, d) | m/z: 514 | 3, EtOAc used as co-solvent |

TABLE 9-continued

| Ex. | Structure | Name | ¹H NMR Data (Me-d3-OD) | MS Data | Method $^a$ |
|---|---|---|---|---|---|
| 201 | 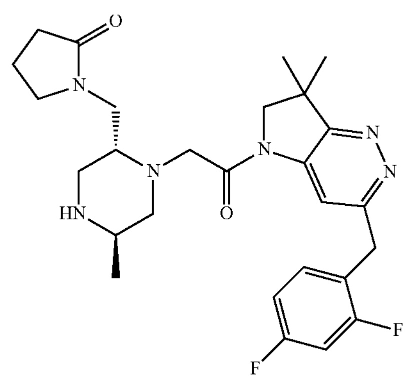 | 1-{[(2R,5R)-1-(2-{3-[(2,4-Difluorophenyl)methyl]-7,7-dimethyl-5H,6H,7H-pyrrolo[3,2-c]pyridazin-5-yl}-2-oxoethyl)-5-methylpiperazin-2-yl]methyl}pyrrolidin-2-one hydrochloride | 8.16 (1H, d), 7.63-7.50 (1H, m), 7.18-7.01 (2H, m), 4.49 (2H, s), 4.35-4.13 (4H, m), 3.80-3.64 (3H, m), 3.60-3.47 (3H, m), 3.29-3.20 (2H, m), 3.09-2.99 (1H, m), 2.48-2.25 (2H, m), 2.25-2.14 (1H, m), 2.13-1.94 (2H, m), 1.68-1.51 (6H, m), 1.32 (3H, d). | m/z: 513 | 2 |
| 202 | 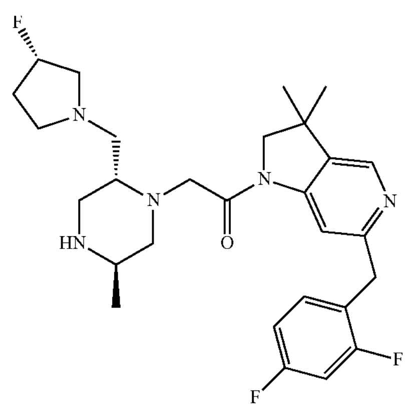 | 1-{6-[(2,4-Difluorophenyl)methyl]-3,3-dimethyl-1H,2H,3H-pyrrolo[3,2-c]pyridin-1-yl}-2-{[(2R,5R)-2-{[(3S)-3-fluoropyrrolidin-1-yl]methyl}-5-methylpiperazin-1-yl]ethan-1-one dihydrochloride | 8.64-8.54 (1H, m), 8.17 (1H, s), 7.57-7.44 (1H, m), 7.14-7.01 (2H, m), 5.51 (1H, d), 4.45-4.34 (2H, m), 4.34-4.20 (2H, m), 4.20-4.11 (1H, m), 4.11-4.00 (2H, m), 4.00-3.67 (4H, m), 3.67-3.52 (2H, m), 3.46 (2H, d), 3.30-3.23 (2H, m), 3.16-3.01 (1H, m), 2.47 (2H, bs), 1.54 (6H, d), 1.34 (3H, d). | m/z: 516 | 2 |

TABLE 9-continued

| Ex. | Structure | Name | ¹H NMR Data (Me-d3-OD) | MS Data | Method ᵃ |
|---|---|---|---|---|---|
| 203 | 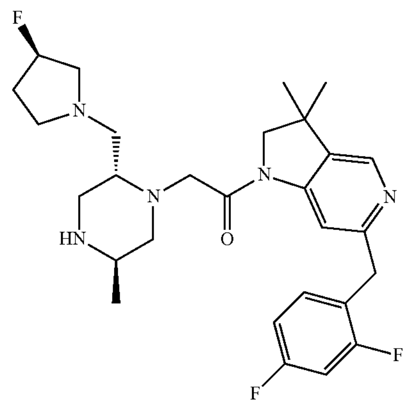 | 1-{6-[(2,4-Difluorophenyl)methyl]-3,3-dimethyl-1H,2H,3H-pyrrolo[3,2-c]pyridin-1-yl}-2-[(2R,5R)-2-{[(3R)-3-fluoropyrrolidin-1-yl]methyl}-5-methylpiperazin-1-yl]ethan-1-one dihydrochloride | 8.63-8.54 (1H, m), 8.16 (1H, s), 7.57-7.44 (1H, m), 7.15-6.98 (2H, m), 5.50 (1H, d), 4.39 (2H, s), 4.34-4.21 (2H, m), 4.14-4.03 (2H, m), 3.94-3.67 (3H, m), 3.67-3.55 (2H, m), 3.51-3.38 (3H, m), 3.31-3.25 (2H, m), 3.10 (1H, dd), 2.49 (2H, s), 1.54 (6H, d), 1.34 (3H, d). | m/z: 516 | 2 |
| 204 | 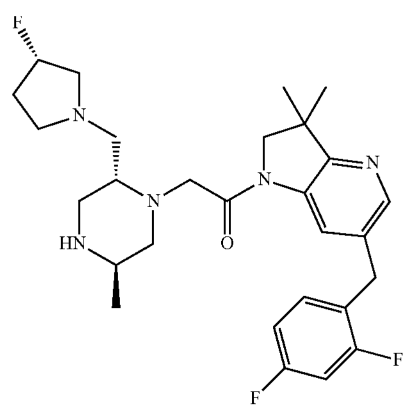 | 1-{6-[(2,4-Difluorophenyl)methyl]-3,3-dimethyl-1H,2H,3H-pyrrolo[3,2-b]pyridin-1-yl}-2-[(2R,5R)-2-{[(3S)-3-fluoropyrrolidin-1-yl]methyl}-5-methylpiperazin-1-yl]ethan-1-one dihydrochloride | 8.81 (1H, s), 8.40 (1H, s), 7.52-7.40 (1H, m), 7.09-6.96 (2H, m), 5.53 (1H, d), 4.26 (4H, m), 4.14-3.94 (3H, m), 3.93-3.67 (4H, m), 3.59 (2H, d), 3.43 (2H, d), 3.28 (2H, d), 3.18-3.03 (1H, m), 2.71-2.32 (2H, m), 1.68-1.57 (6H, m), 1.34 (3H, d). | m/z: 516 | 2 |

TABLE 9-continued

| Ex. | Structure | Name | ¹H NMR Data (Me-d3-OD) | MS Data | Method ᵃ |
|---|---|---|---|---|---|
| 205 | 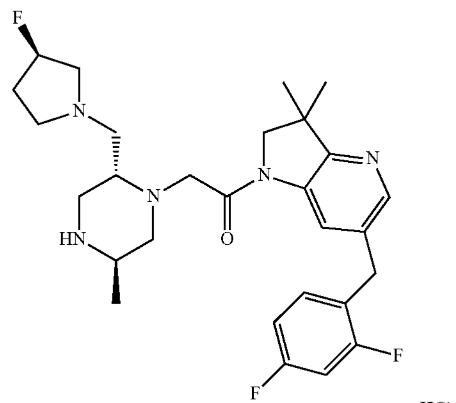 | 1-{6-[(2,4-Difluorophenyl)methyl]-3,3-dimethyl-1H,2H,3H-pyrrolo[3,2-b]pyridin-1-yl}-2-[(2R,5R)-2-[[(3R)-3-fluoropyrrolidin-1-yl]methyl]-5-methylpiperazin-1-yl]ethan-1-one hydrochloride | 8.82 (1H, s), 8.42 (1H, s), 7.52-7.41 (1H, m), 7.08-6.95 (2H, m), 5.63-5.43 (1H, m), 4.26 (4H, d), 4.10-3.88 (3H, m), 3.88-3.69 (3H, m), 3.66-3.54 (2H, m), 3.40 (2H, d), 3.18-3.05 (1H, m), 2.51 (2H, s), 1.62 (6H, d), 1.34 (3H, d). | m/z: 516 | 3, EtOAc used as co-solvent |
| 206 | 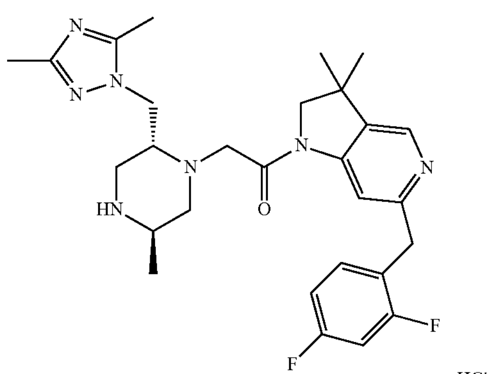 | 1-{6-[(2,4-Difluorophenyl)methyl]-3,3-dimethyl-1H,2H,3H-pyrrolo[3,2-c]pyridin-1-yl}-2-[(2R,5R)-2-[[dimethyl-1H-1,2,4-triazol-1-yl]methyl]-5-methylpiperazin-1-yl]ethan-1-one hydrochloride | 8.61-8.52 (1H, m), 8.18 (1H, s), 7.56-7.43 (1H, m), 7.14-6.99 (2H, m), 4.78 (1H, d), 4.47 (1H, dd), 4.42-4.35 (2H, m), 4.19 (2H, s), 4.09 (2H, s), 4.06-3.93 (1H, m), 3.43 (2H, d), 3.18 (1H, d), 3.11-2.94 (2H, m), 2.80-2.70 (3H, m), 2.46 (3H, s), 1.57-1.49 (6H, m), 1.32 (3H, d). | m/z: 524 | 2 |

TABLE 9-continued

| Ex. | Structure | Name | $^1$H NMR Data (Me-d3-OD) | MS Data | Method [a] |
|---|---|---|---|---|---|
| 207 | 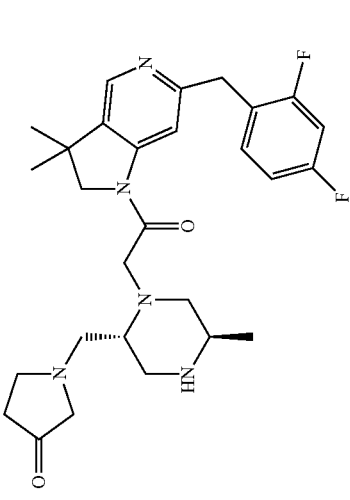 | 1-[[(2R,5R)-1-(2-{6-[(2,4-Difluorophenyl)methyl]-3,3-dimethyl-1H,2H,3H-pyrrolo[3,2-c]pyridin-1-yl]-2-oxoethyl)-5-methylpiperazin-2-yl]methyl}pyrrolidin-3-one dihydrochloride | 8.64-8.53 (1H, m), 8.26-8.13 (1H, m), 7.56-7.44 (1H, m), 7.14-7.01 (2H, m), 4.39 (2H, s), 4.31-4.19 (2H, m), 4.19-3.91 (3H, m), 3.67 (6H, d), 3.12-3.00 (1H, m), 2.96-2.67 (1H, m), 2.57-2.15 (1H, m), 1.61-1.47 (6H, m), 1.39-1.27 (3H, m). | m/z: 512 | 2 |
| 208 | 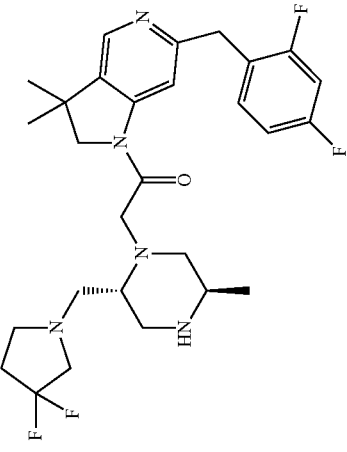 | 1-{6-[(2,4-Difluorophenyl)methyl]-3,3-dimethyl-1H,2H,3H-pyrrolo[3,2-c]pyridin-1-yl}-2-[(2R,5R)-2-[(3,3-difluoropyrrolidin-1-yl)methyl]-5-methylpiperazin-1-yl]ethan-1-one dihydrochloride | 8.59 (1H, s), 8.17 (1H, s), 7.57-7.45 (1H, m), 7.13-7.00 (2H, m), 4.40 (2H, s), 4.32-4.18 (2H, m), 4.12 (2H, s), 4.08-3.91 (2H, m), 3.91-3.71 (4H, m), 3.70-3.54 (1H, m), 3.54-3.40 (2H, m), 3.12 (1H, dd), 2.79-2.61 (2H, m), 1.62-1.49 (6H, m), 1.35 (3H, d). | m/z: 534 | 2 |

TABLE 9-continued

| Ex. | Structure | Name | $^1$H NMR Data (Me-d3-OD) | MS Data | Method [a] |
|---|---|---|---|---|---|
| 209 | (structure) •2HCl | 3-{[(2R,5R)-1-(2-{6-[(2,4-Difluorophenyl)methyl]-3,3-dimethyl-1H,2H,3H-pyrrolo[3,2-c]pyridin-1-yl]-2-oxoethyl)-5-methylpiperazin-2-yl]methyl}-1,3-oxazolidin-2-one dihydrochloride | 8.58 (1H, s), 8.19 (1H, s), 7.50 (1H, m), 7.09 (2H, m), 4.40 (2H, s), 4.32 (1H, m), 4.17 (1H, d), 4.08 (1H, d), 4.04 (1H, m), 3.98 (1H, t), 3.72-3.64 (3H, m), 3.62 (1H, m), 3.50-3.36 (3H, m), 3.32 (1H, m), 3.18 (2H, m), 3.00 (1H, m), 1.51 (6H, s), 1.32 (3H, d) | m/z: 514 | 3, EtOAc used as co-solvent |
| 210 | (structure) •HCl | 1-{[(2R,5R)-1-(2-{6-[Difluoro(phenyl)methyl]-3,3-dimethyl-1H,2H,3H-pyrrolo[3,2-b]pyridin-1-yl]-2-oxoethyl)-5-methylpiperazin-2-yl]methyl}pyrrolidin-2-one hydrochloride | 8.69 (1H, s), 8.55 (1H, s), 7.64-7.47 (5H, m), 4.26-4.09 (3H, m), 3.93-3.84 (2H, m), 3.78-3.67 (2H, m), 3.59-3.43 (5H, m), 3.24-3.14 (1H, m), 2.47-2.38 (1H, m), 2.38-2.32 (1H, m), 2.27-2.16 (1H, m), 2.14-1.96 (2H, m), 1.56 (6H, d), 1.43 (3H, d). | m/z: 512 | 2 |

TABLE 9-continued

| Ex. | Structure | Name | $^1$H NMR Data (Me-d3-OD) | MS Data | Method [a] |
|---|---|---|---|---|---|
| 211 | 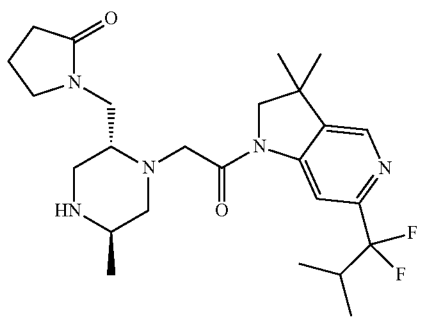 | 1-{[(2R,5R)-1-{2-[6-(1,1-Difluoro-2-methylpropyl)-3,3-dimethyl-1H,2H,3H-pyrrolo[3,2-c]pyridin-1-yl]-2-oxoethyl}-5-methylpiperazin-2-yl]methyl}pyrrolidin-2-one hydrochloride | 8.75 (1H, s), 8.53 (1H, s), 4.49-4.28 (2H, m), 4.28-4.11 (2H, m), 3.95 (1H, s), 3.89-3.77 (1H, m), 3.77-3.60 (2H, m), 3.60-3.40 (4H, m), 3.26-3.18 (1H, m), 2.70-2.49 (1H, m), 2.49-2.35 (1H, m), 2.35-2.18 (1H, m), 2.18-1.92 (2H, m), 1.58 (6H, s), 1.39 (3H, d), 1.15-1.07 (6H, m). | m/z: 478 | 4 |
| 212 | 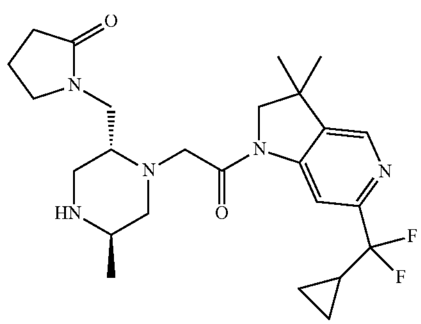 | 1-{[(2R,5R)-1-{2-[6-(Cyclopropyldifluoromethyl)-3,3-dimethyl-1H,2H,3H-pyrrolo[3,2-c]pyridin-1-yl]-2-oxoethyl}-5-methylpiperazin-2-yl]methyl}pyrrolidin-2-one hydrochloride | 8.78-8.69 (1H, m), 8.63 (1H, s), 4.34-4.08 (4H, m), 3.85-3.75 (2H, m), 3.65-3.42 (5H, m), 3.23-3.05 (2H, m), 2.44-2.34 (1H, m), 2.32-2.18 (1H, m), 2.12-1.94 (2H, m), 1.88-1.71 (1H, m), 1.66-1.51 (6H, m), 1.42-1.27 (4H, m), 0.97-0.87 (4H, m). | m/z: 476 | 4 |

TABLE 9-continued

| Ex. | Structure | Name | ¹H NMR Data (Me-d3-OD) | MS Data | Method[a] |
|---|---|---|---|---|---|
| 213 | (structure) ·2HCl | 1-{6-[Difluoro(phenyl)methyl]-3,3-dimethyl-1H,2H,3H-pyrrolo[3,2-c]pyridin-1-yl}-2-[(2R,5R)-2-{[(3R)-3-fluoropyrrolidin-1-yl]methyl}-5-methylpiperazin-1-yl]ethan-1-one dihydrochloride | 8.73 (1H, s), 8.48 (1H, s), 7.70-7.55 (5H, m), 5.52 (1H, dm), 4.30 (2H, m), 4.07 (2H, m), 3.81 (2H, m), 3.58 (2H, m), 3.43 (3H, m), 3.28 (2H, m), 3.12 (2H, m), 2.67 (1H, br m), 2.46 (2H, br m), 1.56 (3H, s), 1.53 (3H, s), 1.34 (3H, s) | m/z: 516 | 3, EtOAc used as co-solvent |
| 214 | (structure) ·HCl | 1-[6-(1,1-Difluoropropyl)-3,3-dimethyl-1H,2H,3H-pyrrolo[3,2-c]pyridin-1-yl]-2-[(2R,5R)-2-{[(3R)-3-fluoropyrrolidin-1-yl]methyl}-5-methylpiperazin-1-yl]ethan-1-one hydrochloride | 8.73 (1H, s), 8.63-8.50 (1H, m), 5.52 (1H, d), 4.34 (2H, s), 4.26-3.35 (11H, m), 3.25-3.06 (1H, m), 2.79-2.26 (4H, m), 1.58 (6H, d), 1.36 (3H, d), 1.18-1.05 (3H, m). | m/z: 468 | 4 |

TABLE 9-continued

| Ex. | Structure | Name | ¹H NMR Data (Me-d3-OD) | MS Data | Method a |
|---|---|---|---|---|---|
| 215 | 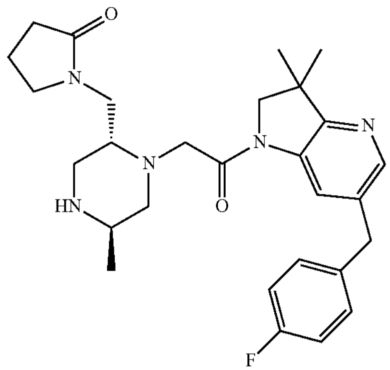 | 1-{[(2R,5R)-1-(2-{6-[(4-Fluorophenyl)methyl]-3,3-dimethyl-1H,2H,3H-pyrrolo[3,2-b]pyridin-1-yl]-2-oxoethyl)-5-methylpiperazin-2-yl]methyl}pyrrolidin-2-one dihydrochloride | 8.78 (1H, s), 8.37 (1H, s), 7.34 (2H, dd), 7.10 (2H, t), 4.21 (2H, s), 4.18-4.05 (4H, m), 3.84-3.70 (2H, m), 3.69-3.60 (1H, m), 3.60-3.49 (2H, m), 3.49-3.39 (2H, m), 3.22-3.03 (2H, m), 2.38-2.26 (1H, m), 2.20-2.08 (1H, m), 1.93-1.81 (1H, m), 1.60 (6H, d), 1.34 (3H, d). | m/z: 494 | 2 |
| 216 | 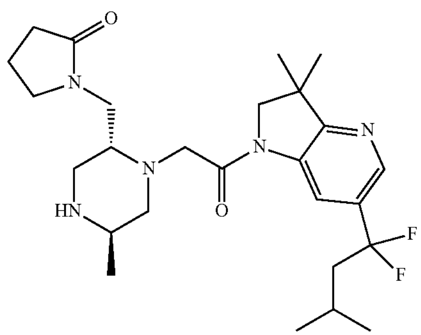 | 1-{[(2R,5R)-1-{2-[6-(1,1-Difluoro-3-methylbutyl)-3,3-dimethyl-1H,2H,3H-pyrrolo[3,2-b]pyridin-1-yl]-2-oxoethyl}-5-methylpiperazin-2-yl]methyl}pyrrolidin-2-one dihydrochloride | 8.66 (1H, s), 8.44 (1H, s), 4.34-4.13 (3H, m), 4.12-4.01 (2H, m), 3.95 (1H, d), 3.89-3.76 (1H, m), 3.67-3.57 (2H, m), 3.54-3.38 (4H, m), 2.43-2.30 (1H, m), 2.25-2.18 (1H, m), 2.17-2.02 (3H, m), 1.91-1.79 (1H, m), 1.52 (6H, d), 1.40-1.34 (5H, m), 1.01 (6H, d). | m/z: 492 | 2 |

TABLE 9-continued

| Ex. | Structure | Name | $^1$H NMR Data (Me-d3-OD) | MS Data | Method [a] |
|---|---|---|---|---|---|
| 217 | (structure) ·HCl | 1-{[(2R,5R)-1-{2-[6-(1,1-Difluorobutyl)-3,3-dimethyl-1H,2H,3H-pyrrolo[3,2-b]pyridin-1-yl]-2-oxoethyl}-5-methylpiperazin-2-yl]methyl}pyrrolidin-2-one hydrochloride | 8.72 (1H, s), 8.48 (1H, s), 4.36 (2H, d), 4.08 (3H, m), 3.84 (1H, dd), 3.73-3.38 (7H, m), 2.44-2.30 (1H, m), 2.30-2.15 (3H, m), 2.15-1.96 (2H, m), 1.60-1.43 (9H, m), 1.39 (3H, d), 1.00 (3H, t). | m/z: 478 | 4, heated at 50° C. |
| 218 | (structure) ·2HCl | 1-{[(2R,5R)-1-(2-{6-[Difluoro(phenyl)methyl]-3,3-dimethyl-1H,2H,3H-pyrrolo[3,2-c]pyridin-1-yl}-2-oxoethyl)-5-methylpiperazin-2-yl]methyl}pyrrolidine-2,5-dione dihydrochloride | 8.76-8.67 (1H, m), 8.46 (1H, s), 7.72-7.54 (5H, m), 4.34-4.14 (3H, m), 4.02 (1H, d), 3.83-3.69 (2H, m), 3.64-3.38 (3H, m), 3.04 (1H, t), 2.95-2.80 (1H, m), 2.73-2.63 (4H, m), 1.64-1.52 (6H, m), 1.30 (3H, d). | m/z: 526 | 2 |

TABLE 9-continued

| Ex. | Structure | Name | ¹H NMR Data (Me-d3-OD) | MS Data | Method [a] |
|---|---|---|---|---|---|
| 219 | 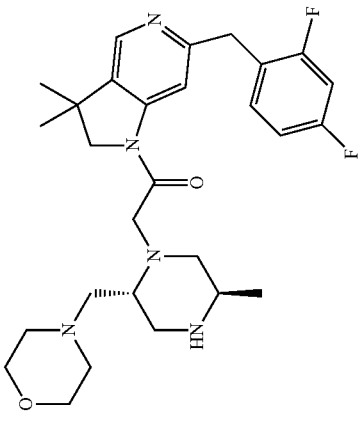 | 1-{6-[(2,4-Difluorophenyl)methyl]-3,3-dimethyl-1H,2H,3H-pyrrolo[3,2-c]pyridin-1-yl}-2-[(2R,5R)-5-methyl-2-(morpholin-4-ylmethyl)piperazin-1-yl]ethan-1-one dihydrochloride | 8.61 (1H, s), 8.14 (1H, s), 7.60-7.46 (1H, m), 7.16-7.01 (2H, m), 4.41 (2H, s), 4.26 (2H, s), 4.13 (2H, s), 3.94 (5H, m), 3.78-3.44 (6H, m), 3.29-3.16 (2H, m), 3.07 (1H, dd), 1.54 (6H, d), 1.37 (3H, d). | m/z: 514 | 2 |
| 220 | 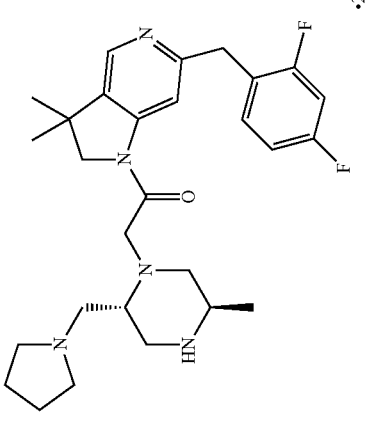 | 1-{6-[(2,4-Difluorophenyl)methyl]-3,3-dimethyl-1H,2H,3H-pyrrolo[3,2-c]pyridin-1-yl}-2-[(2R,5R)-5-methyl-2-(pyrrolidin-1-ylmethyl)piperazin-1-yl]ethan-1-one dihydrochloride | 8.58 (1H, s), 8.16 (1H, s), 7.57-7.46 (1H, m), 7.14-7.01 (2H, m), 4.40 (2H, s), 4.34-4.19 (2H, m), 4.06 (3H, m), 3.76 (5H, m), 3.63-3.44 (3H, m), 3.12-2.99 (1H, m), 2.28-1.94 (5H, m), 1.54 (6H, d), 1.37-1.31 (3H, m). | m/z: 498 | 2 |

TABLE 9-continued

| Ex. | Name | ¹H NMR Data (Me-d3-OD) | MS Data | Method a |
|---|---|---|---|---|
| 221 | 1-{6-[Difluoro(phenyl)methyl]-3,3-dimethyl-1H,2H,3H-pyrrolo[3,2-b]pyridin-1-yl}-2-{(2R,5R)-2-{[(3R)-3-fluoropyrrolidin-1-yl]methyl}-5-methylpiperazin-1-yl]ethan-1-one dihydrochloride | 8.55 (1H, s), 8.46 (1H, s), 7.60-7.46 (5H, m), 5.52 (1H, d), 4.20-4.09 (2H, m), 3.98 (2H, d), 3.87-3.73 (2H, m), 3.69-3.52 (3H, m), 3.17-3.06 (1H, m), 2.79-2.26 (2H, m), 1.50 (6H, d), 1.35 (3H, d). | m/z: 516 | 2 |
| 222 | 1-[6-(1,1-Difluoroethyl)-3,3-dimethyl-1H,2H,3H-pyrrolo[3,2-b]pyridin-1-yl]-2-{(2R,5R)-5-methyl-2-{[1H,2H,3H-pyrrolo[2,3-b]pyridin-1-yl]methyl}piperazin-1-yl}ethan-1-one dihydrochloride | 8.86 (1H, s), 8.53 (1H, s), 7.69 (1H, d), 7.57 (1H, d), 6.78 (1H, t), 4.69 (1H, d), 4.34 (1H, dd), 4.29-3.93 (8H, m), 3.54 (1H, s), 3.23-3.12 (1H, m), 3.11-2.98 (1H, m), 2.06 (3H, t), 1.59 (6H, d), 1.36 (3H, d). | m/z: 485 | 2 |

TABLE 9-continued

| Ex. | Structure | Name | ¹H NMR Data (Me-d3-OD) | MS Data | MS Method [a] |
|---|---|---|---|---|---|
| 223 | (structure) ·HCl | 1-{6-(1,1-Difluorobutyl)-3,3-dimethyl-1H,2H,3H-pyrrolo[3,2-b]pyridin-1-yl]-2-[(2R,5R)-2-{[(3R)-3-fluoropyrrolidin-1-yl]methyl}-5-methylpiperazin-1-yl]ethan-1-one hydrochloride | 8.96 (1H, s), 8.58 (1H, s), 5.52 (1H, d), 4.34 (2H, s), 4.17-4.05 (2H, m), 3.97 (2H, s), 3.90-3.73 (3H, m), 3.73-3.57 (3H, m), 3.56-3.43 (3H, m), 3.43-3.37 (2H, m), 3.24-3.12 (1H, m), 2.57-2.36 (1H, m), 2.36-2.12 (2H, m), 1.66 (6H, d), 1.61-1.50 (2H, m), 1.37 (3H, d), 1.02 (3H, t). | m/z: 482 | 3, no MeOH co-solvent |
| 224 | (structure) ·2HCl | 1-{6-[Difluoro(phenyl)methyl]-3,3-dimethyl-1H,2H,3H-pyrrolo[3,2-c]pyridin-1-yl}-2-[(2R,5R)-5-methyl-2-(morpholin-4-ylmethyl)piperazin-1-yl]ethan-1-one dihydrochloride | 8.77 (1H, s), 8.43 (1H, s), 7.74-7.54 (5H, m), 4.32 (2H, s), 4.00 (8H, d), 3.78-3.65 (2H, m), 3.60 (2H, s), 3.55-3.45 (2H, m), 3.06 (1H, dd), 1.58 (6H, d), 1.37 (3H, d). | m/z: 514 | 2 |

TABLE 9-continued

| Ex. | Structure | Name | ¹H NMR Data (Me-d3-OD) | MS Data | Method ᵃ |
|---|---|---|---|---|---|
| 225 | •HCl | 1-{[(2R,5R)-1-{2-[6-(1,1-Difluoro-3-methylbutyl)-3,3-dimethyl-1H,2H,3H-pyrrolo[3,2-c]pyridin-1-yl]-2-oxoethyl}-5-methylpiperazin-2-yl]methyl}pyrrolidin-2-one hydrochloride | 8.75-8.66 (1H, m), 8.54 (1H, s), 4.23-4.04 (4H, m), 3.86-3.70 (2H, m), 3.64-3.57 (1H, m), 3.53-3.44 (2H, m), 3.41 (1H, dd), 3.28-3.23 (1H, m), 3.17-3.08 (1H, m), 3.08-2.97 (1H, m), 2.46-2.16 (4H, m), 2.12-1.90 (3H, m), 1.55 (6H, s), 1.34 (3H, d), 1.05 (6H, d). | m/z: 492 | 3, EtOAc used as co-solvent |
| 226 | •2HCl | 1-{[(2R,5R)-1-{2-[6-(Cyclobutyldifluoromethyl)-3,3-dimethyl-1H,2H,3H-pyrrolo[3,2-b]pyridin-1-yl]-2-oxoethyl}-5-methylpiperazin-2-yl]methyl}pyrrolidin-2-one dihydrochloride | 8.67 (1H, s), 8.42 (1H, s), 4.42-4.20 (2H, m), 4.17-3.96 (3H, m), 3.93-3.76 (1H, m), 3.71-3.39 (7H, m), 2.47-2.32 (1H, m), 2.30-2.17 (3H, m), 2.16-1.81 (7H, m), 1.53 (6H, d), 1.39 (3H, d). | m/z: 490 | 2 |
| 227 | •HCl | 1-{[(2R,5R)-1-{2-[6-(1,1-Difluorobutyl)-3,3-dimethyl-1H,2H,3H-pyrrolo[3,2-c]pyridin-1-yl]-2-oxoethyl}-5-methylpiperazin-2-yl]methyl}pyrrolidin-2-one hydrochloride | 8.75-8.68 (1H, m), 8.53 (1H, s), 4.26-4.00 (4H, m), 3.83-3.66 (3H, m), 3.66-3.54 (1H, m), 3.54-3.36 (3H, m), 3.29-3.18 (2H, m), 3.18-2.94 (2H, m), 2.44-2.14 (4H, m), 2.14-2.00 (1H, m), 2.00-1.88 (1H, m), 1.62-1.50 (7H, m), 1.33 (3H, d), 1.09-0.89 (3H, m). | m/z: 478 | 3, EtOAc used as co-solvent |

TABLE 9-continued

| Ex. | Structure | Name | $^1$H NMR Data (Me-d3-OD) | MS Data | Method$^a$ |
|---|---|---|---|---|---|
| 228 | 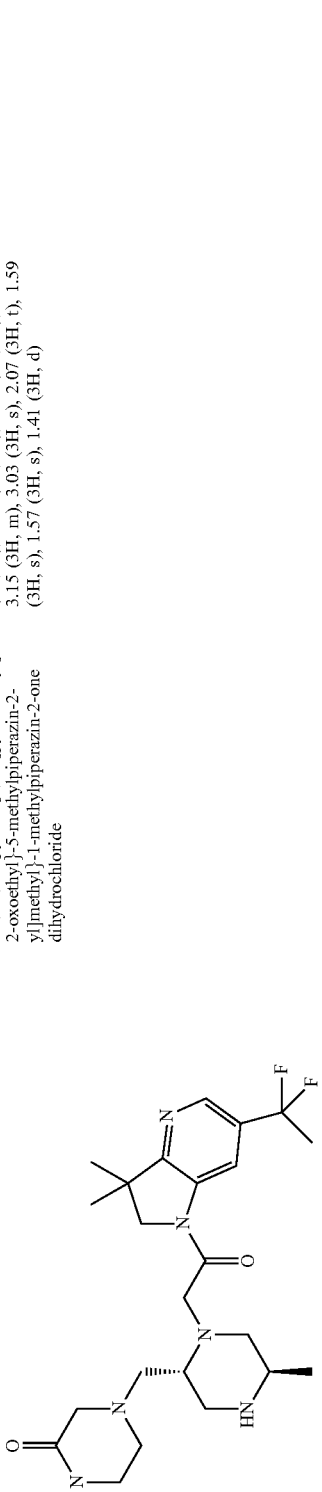 | 4-{[(2R,5R)-1-{2-[6-(1,1-Difluoroethyl)-3,3-dimethyl-1H,2H,3H-pyrrolo[3,2-b]pyridin-1-yl]-2-oxoethyl}-5-methylpiperazin-2-yl]methyl}-1-methylpiperazin-2-one dihydrochloride | 8.82 (1H, s), 8.56 (1H, s), 4.23 (2H, s), 4.18 (2H, s), 4.05 (1H, d), 3.98 (2H, m), 3.80-3.60 (6H, m), 3.56 (1H, dd), 3.46 (1H, dd), 3.38-3.15 (3H, m), 3.03 (3H, s), 2.07 (3H, t), 1.59 (3H, s), 1.57 (3H, s), 1.41 (3H, d) | m/z: 479 | 3, EtOAc used as co-solvent |
| 229 | 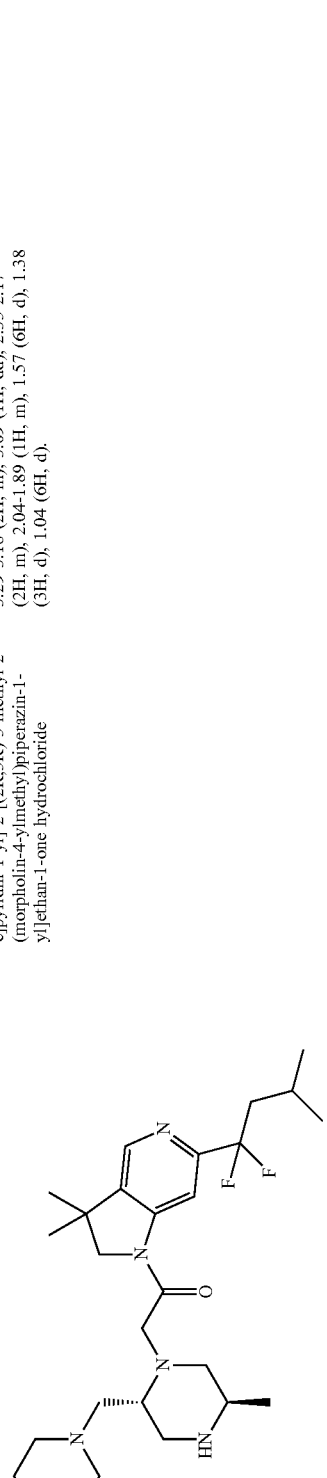 | 1-[6-(1,1-Difluoro-3-methylbutyl)-3,3-dimethyl-1H,2H,3H-pyrrolo[3,2-c]pyridin-1-yl]-2-[(2R,5R)-5-methyl-2-(morpholin-4-ylmethyl)piperazin-1-yl]ethan-1-one hydrochloride | 8.67 (1H, s), 8.51 (1H, s), 4.28 (2H, s), 4.21-3.83 (8H, m), 3.83-3.44 (6H, m), 3.38 (1H, d), 3.29-3.18 (2H, m), 3.09 (1H, dd), 2.35-2.17 (2H, m), 2.04-1.89 (1H, m), 1.57 (6H, d), 1.38 (3H, d), 1.04 (6H, d). | m/z: 494 | 3, EtOAc used as co-solvent |

TABLE 9-continued

| Ex. | Structure | Name | ¹H NMR Data (Me-d3-OD) | MS Data | Method[a] |
|---|---|---|---|---|---|
| 230 | 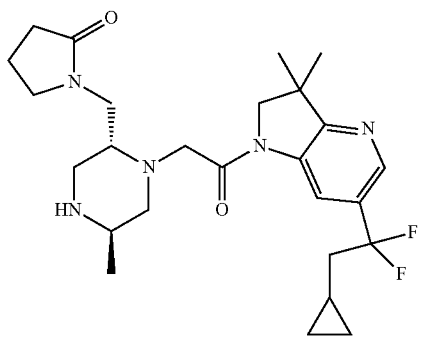 | 1-{[(2R,5R)-1-{2-[6-(2-Cyclopropyl-1,1-difluoroethyl)-3,3-dimethyl-1H,2H,3H-pyrrolo[3,2-b]pyridin-1-yl]-2-oxoethyl}-5-methylpiperazin-2-yl]methyl}pyrrolidin-2-one formate | 8.52 (1H, d), 8.44 (1H, s), 8.33 (1H, s), 4.05-3.89 (3H, m), 3.87-3.57 (4H, m), 3.23-3.05 (3H, m), 3.01-2.79 (1H, m), 2.42-2.25 (1H, m), 2.21-1.94 (4H, m), 1.92-1.75 (1H, m), 1.44 (6H, d), 1.31 (3H, d), 0.81-0.63 (1H, m), 0.53-0.41 (2H, m), 0.17-0.02 (2H, m). | m/z: 490 | 2 |
| 231 | 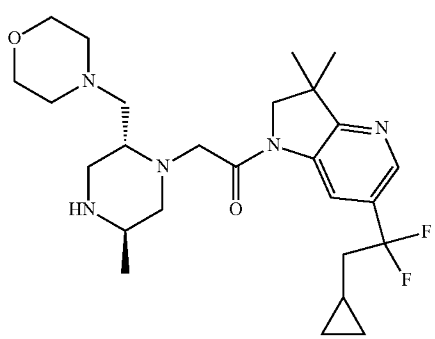 | 1-[6-(2-Cyclopropyl-1,1-difluoroethyl)-3,3-dimethyl-1H,2H,3H-pyrrolo[3,2-b]pyridin-1-yl]-2-[(2R,5R)-5-methyl-2-(morpholin-4-ylmethyl)piperazin-1-yl]ethan-1-one dihydrochloride | 8.75 (1H, d), 8.50 (1H, s), 4.28-4.20 (2H, m), 4.15-4.00 (6H, m), 3.90 (1H, t), 3.69 (1H, s), 3.66-3.53 (3H, m), 3.16-3.07 (1H, m), 2.27-2.11 (2H, m), 1.56 (6H, d), 1.38 (3H, d), 0.95-0.83 (1H, m), 0.83-0.71 (1H, m), 0.56-0.44 (2H, m), 0.19-0.08 (2H, m). | m/z: 492 | 3, EtOAc used as co-solvent |

TABLE 9-continued

| Ex. | Structure | Name | $^1$H NMR Data (Me-d3-OD) | MS Data | Method [a] |
|---|---|---|---|---|---|
| 232 | 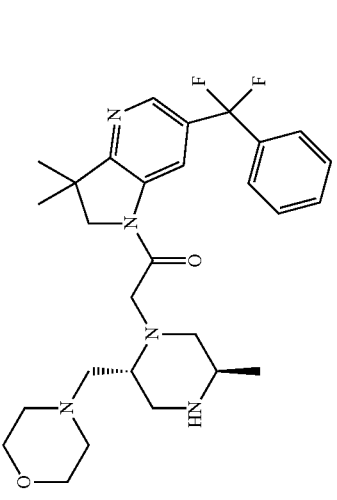 •2HCl | 1-[6-[Difluoro(phenyl)methyl]-3,3-dimethyl-1H,2H,3H-pyrrolo[3,2-b]pyridin-1-yl]-2-[(2R,5R)-5-methyl-2-(morpholin-4-ylmethyl)piperazin-1-yl]ethan-1-one dihydrochloride | 8.50 (1H, s), 8.42 (1H, d), 7.62-7.48 (5H, m), 4.20-3.73 (10H, m), 3.73-3.45 (4H, m), 3.07 (1H, dd), 1.51-1.46 (6H, m), 1.37 (3H, d). | m/z: 514 | 3, EtOAc used as co-solvent |
| 233 | 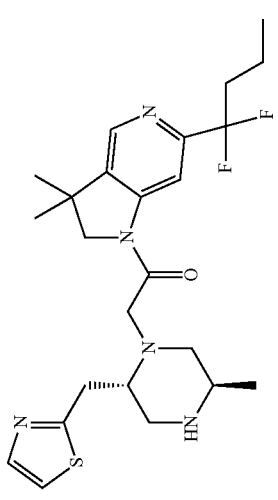 •HCl | 1-[6-(1,1-Difluorobutyl)-3,3-dimethyl-1H,2H,3H-pyrrolo[3,2-b]pyridin-1-yl]-2-[(2S,5R)-5-methyl-2-(1,3-thiazol-2-ylmethyl)piperazin-1-yl]ethan-1-one hydrochloride | 8.69 (1H, s), 8.53 (1H, s), 7.86 (1H, d), 7.70 (1H, d), 4.23-4.15 (2H, m), 4.14 (2H, s), 4.04-3.94 (1H, m), 3.63 (1H, dd), 3.59-3.37 (4H, m), 3.20-3.13 (1H, m), 3.13-3.01 (1H, m), 2.41-2.25 (2H, m), 1.61-1.53 (8H, m), 1.34 (3H, d), 1.04 (3H, t). | m/z: 478 | 3, EtOAc used as co-solvent |

TABLE 9-continued

| Ex. | Structure | Name | ¹H NMR Data (Me-d3-OD) | MS Data | Method a |
|---|---|---|---|---|---|
| 234 | 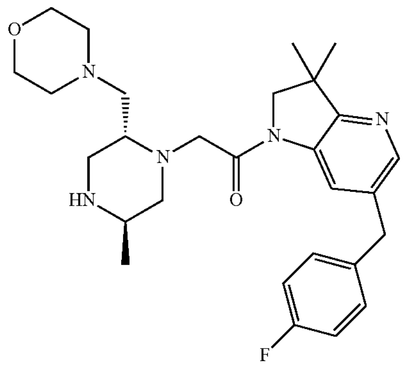 | 1-{6-[(4-Fluorophenyl)methyl]-3,3-dimethyl-1H,2H,3H-pyrrolo[3,2-b]pyridin-1-yl}-2-[(2R,5R)-5-methyl-2-(morpholin-4-ylmethyl)piperazin-1-yl]ethan-1-one dihydrochloride | 8.75 (1H, s), 8.39 (1H, s), 7.35 (2H, dd), 7.11 (2H, t), 4.38-4.15 (4H, m), 4.15-3.81 (7H, m), 3.81-3.66 (1H, m), 3.66-3.37 (5H, m), 3.29-3.18 (2H, m), 3.18-2.99 (1H, m), 1.63 (6H, d), 1.37 (3H, d). | m/z: 496 | 3, EtOAc used as co-solvent |
| 235 | 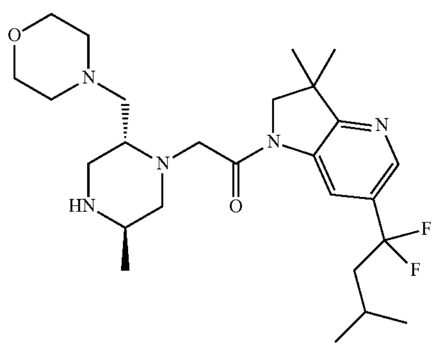 [SMILES: CC(C)CC(F)(F)c1cnc2c(c1)N(C(=O)CN1C[C@@H](C)NC[C@@H]1CN1CCOCC1)CC2(C)C] | 1-[6-(1,1-Difluoro-3-methylbutyl)-3,3-dimethyl-1H,2H,3H-pyrrolo[3,2-b]pyridin-1-yl]-2-[(2R,5R)-5-methyl-2-(morpholin-4-ylmethyl)piperazin-1-yl]ethan-1-one | 8.50 (1H, s), 8.30 (1H, s), 4.10-3.95 (2H, m), 3.95-3.68 (2H, m), 3.48 (4H, m), 3.18-2.99 (1H, m), 2.98-2.76 (3H, m), 2.67-2.58 (2H, m), 2.57-2.48 (3H, m), 2.35-2.26 (2H, m), 2.16-2.06 (3H, m), 1.90-1.71 (1H, m), 1.45 (6H, d), 1.08 (3H, d), 0.98 (6H, d). | m/z: 494 | 3, no MeOH co-solvent, purified by preparative HPLC, basic method |

TABLE 9-continued

| Ex. | Structure | Name | ¹H NMR Data (Me-d3-OD) | MS Data | Method[a] |
|---|---|---|---|---|---|
| 236 | 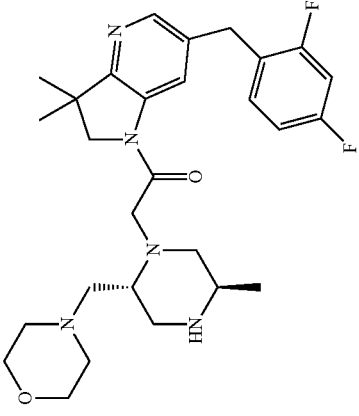 •2HCl | 1-{6-[(2,4-Difluorophenyl)methyl]-3,3-dimethyl-1H,2H,3H-pyrrolo[3,2-b]pyridin-1-yl}-2-[(2R,5R)-5-methyl-2-(morpholin-4-ylmethyl)piperazin-1-yl]ethan-1-one dihydrochloride | 8.82 (1H, s), 8.45 (1H, s), 7.57-7.43 (1H, m), 7.11-6.94 (2H, m), 4.46-4.21 (4H, m), 4.21-3.82 (7H, m), 3.82-3.57 (4H, m), 3.49-3.35 (4H, m), 3.13 (1H, dd), 1.75-1.53 (6H, m), 1.39 (3H, d). | m/z: 514 | 3, EtOAc used as co-solvent |
| 237 | 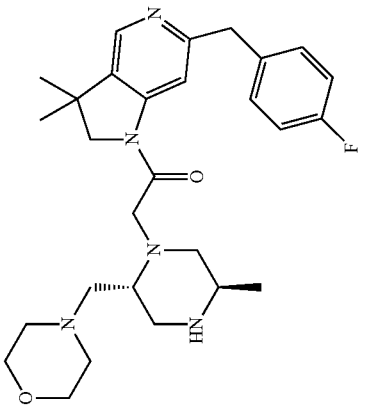 •HCl | 1-{6-[(4-Fluorophenyl)methyl]-3,3-dimethyl-1H,2H,3H-pyrrolo[3,2-c]pyridin-1-yl}-2-[(2R,5R)-5-methyl-2-(morpholin-4-ylmethyl)piperazin-1-yl]ethan-1-one hydrochloride | 8.59 (1H, s), 8.13 (1H, s), 7.39 (2H, dd), 7.23-7.11 (2H, m), 4.38 (2H, s), 4.25 (2H, s), 4.22-3.78 (8H, m), 3.71-3.44 (5H, m), 3.31-3.20 (4H, m), 3.08-2.97 (1H, m), 1.54 (6H, d), 1.37 (3H, d). | m/z: 496 | 3, EtOAc used as co-solvent |

TABLE 9-continued

| Ex. | Structure | Name | ¹H NMR Data (Me-d3-OD) | MS Data | Method |
|---|---|---|---|---|---|
| 238 | 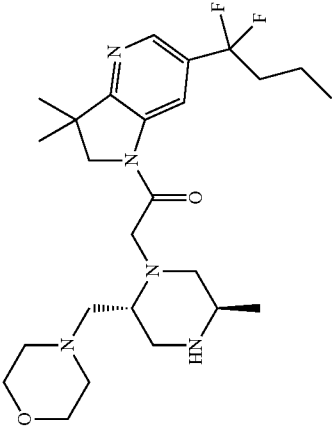 | 1-[6-(1,1-Difluorobutyl)-3,3-dimethyl-1H,2H,3H-pyrrolo[3,2-b]pyridin-1-yl]-2-[(2R,5R)-5-methyl-2-(morpholin-4-ylmethyl)piperazin-1-yl]ethan-1-one hydrochloride | 8.67 (1H, d), 8.46 (1H, s), 4.29-4.18 (2H, m), 4.07 (7H, m), 3.96-3.82 (2H, m), 3.68-3.41 (6H, m), 3.20-3.04 (2H, m), 2.31-2.14 (2H, m), 1.56-1.49 (8H, m), 1.38 (3H, d), 1.00 (3H, t). | m/z: 480 | 3, no MeOH co-solvent, purification by prep. HPLC, then HCl salt formation with HCl-dioxane in EtOAc |
| 239 | 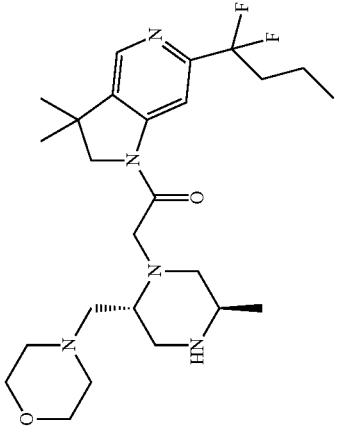 | 1-[6-(1,1-Difluorobutyl)-3,3-dimethyl-1H,2H,3H-pyrrolo[3,2-c]pyridin-1-yl]-2-[(2R,5R)-5-methyl-2-(morpholin-4-ylmethyl)piperazin-1-yl]ethan-1-one hydrochloride | 8.65 (1H, s), 8.47 (1H, s), 4.24 (2H, s), 4.18-3.83 (7H, m), 3.70-3.46 (5H, m), 3.15-3.02 (1H, m), 2.40-2.23 (2H, m), 1.61-1.44 (8H, m), 1.38 (3H, d), 1.02 (3H, t). | m/z: 480 | 3, EtOAc used as co-solvent |

TABLE 9-continued

| Ex. | Structure | Name | ¹H NMR Data (Me-d3-OD) | MS Data | Method [a] |
|---|---|---|---|---|---|
| 240 | 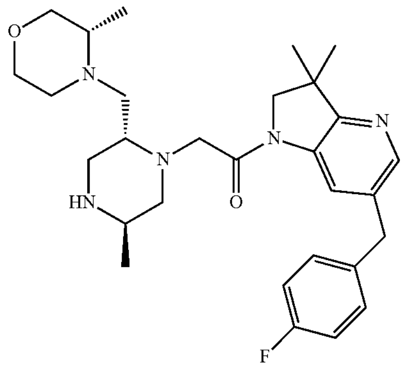 | 1-{6-[(4-Fluorophenyl)methyl]-3,3-dimethyl-1H,2H,3H-pyrrolo[3,2-b]pyridin-1-yl}-2-[(2R,5R)-5-methyl-2-{[(3S)-3-methylmorpholin-4-yl]methyl}piperazin-1-yl]ethan-1-one dihydrochloride | 8.71 (1H, s), 8.42 (1H, s), 7.35 (2H, dd), 7.12 (2H, t), 4.30-3.97 (8H, m), 3.79 (2H, s), 3.60 (4H, s), 3.48-3.37 (3H, m), 3.22-2.92 (2H, m), 1.62 (6H, s), 1.50-1.35 (6H, m). | m/z: 510 | 3, EtOAc used as co-solvent |
| 241 | 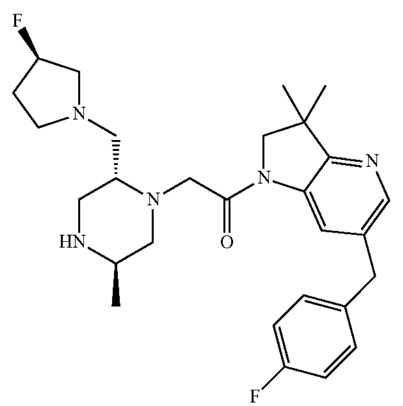 | 1-{6-[(4-Fluorophenyl)methyl]-3,3-dimethyl-1H,2H,3H-pyrrolo[3,2-b]pyridin-1-yl}-2-[(2R,5R)-2-{[(3R)-3-fluoropyrrolidin-1-yl]methyl}-5-methylpiperazin-1-yl]ethan-1-one dihydrochloride | 8.79 (1H, s), 8.39 (1H, s), 7.34 (2H, dd), 7.10 (2H, t), 5.52 (1H, d), 4.28 (2H, s), 4.20 (2H, s), 4.03 (2H, d), 3.98-3.69 (4H, m), 3.58 (2H, d), 3.11 (1H, t), 2.80-2.32 (2H, m), 2.03 (1H, s), 1.62 (6H, d), 1.34 (3H, d). | m/z: 498 | 3, EtOAc used as co-solvent |

TABLE 9-continued

| Ex. | Structure | Name | $^{1}$H NMR Data (Me-d3-OD) | MS Data | Method [a] |
|---|---|---|---|---|---|
| 242 | (structure) ·HCl | 1-{[(2R,5R)-1-(2-{6-[(2-Fluorophenyl)methyl]-3,3-dimethyl-1H,2H,3H-pyrrolo[3,2-c]pyridin-1-yl]-2-oxoethyl)-5-methylpiperazin-2-yl]methyl}pyrrolidin-2-one hydrochloride | 8.58 (1H, s), 8.19 (1H, s), 7.50-7.37 (2H, m), 7.31-7.22 (1H, m), 7.19 (1H, t), 4.40 (2H, s), 4.15-4.05 (3H, m), 3.78 (2H, dd), 3.60-3.49 (2H, m), 3.49-3.38 (2H, m), 3.27 (2H, d), 3.17 (1H, t), 3.13-3.01 (1H, m), 2.40-2.25 (1H, m), 2.18-2.05 (1H, m), 2.03-1.94 (1H, m), 1.94-1.79 (1H, m), 1.52 (6H, d), 1.33 (3H, d). | m/z: 494 | 3, EtOAc used as co-solvent |
| 243 | (structure) ·2HCl | 2-[(2R,5S)-2-{[(2R,6S)-2,6-Dimethylmorpholin-4-yl]methyl}-5-methylpiperazin-1-yl]-1-{6-[(4-fluorophenyl)methyl]-3,3-dimethyl-1H,2H,3H-pyrrolo[3,2-b]pyridin-1-yl}ethan-1-one dihydrochloride | 8.68 (1H, s), 8.40 (1H, s), 7.34 (2H, dd), 7.17-7.06 (2H, m), 4.24 (4H, d), 4.07-3.82 (5H, m), 3.70-3.38 (6H, m), 3.08 (1H, dd), 2.88-2.72 (2H, m), 1.61 (6H, d), 1.37 (3H, d), 1.31 (3H, d), 1.23 (3H, d). | m/z: 524 | 3, EtOAc used as co-solvent |

TABLE 9-continued

| Ex. | Structure | Name | $^1$H NMR Data (Me-d3-OD) | MS Data | Method [a] |
|---|---|---|---|---|---|
| 244 | 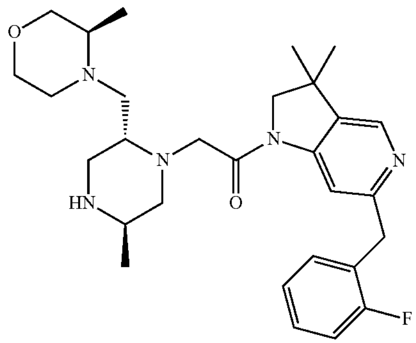 | 1-{6-[(2-Fluorophenyl)methyl]-3,3-dimethyl-1H,2H,3H-pyrrolo[3,2-c]pyridin-1-yl}-2-[(2R,5R)-5-methyl-2-{[(3R)-3-methylmorpholin-4-yl]methyl}piperazin-1-yl]ethan-1-one hydrochloride | 8.68-8.60 (1H, m), 8.13 (1H, s), 7.55-7.47 (1H, m), 7.47-7.39 (1H, m), 7.34-7.25 (1H, m), 7.22 (1H, t), 4.48-4.35 (2H, m), 4.29-3.99 (7H, m), 3.86-3.40 (8H, m), 3.30-3.14 (3H, m), 3.08-2.94 (1H, m), 1.54 (6H, s), 1.52-1.33 (6H, m). | m/z: 510 | 3, EtOAc used as co-solvent |
| 245 | 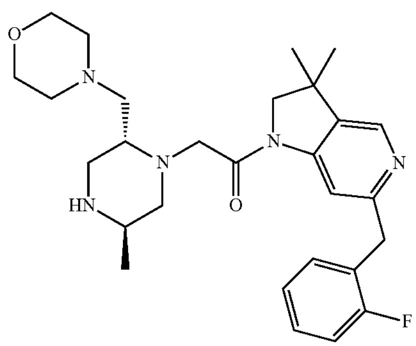 | 1-{6-[(2-Fluorophenyl)methyl]-3,3-dimethyl-1H,2H,3H-pyrrolo[3,2-c]pyridin-1-yl}-2-[(2R,5R)-5-methyl-2-(morpholin-4-ylmethyl)piperazin-1-yl]ethan-1-one hydrochloride | 8.61 (1H, s), 8.16 (1H, s), 7.53-7.39 (2H, m), 7.33-7.25 (1H, m), 7.21 (1H, t), 4.42 (2H, s), 4.25 (2H, s), 4.11-3.41 (13H, m), 3.27-2.99 (3H, m), 1.54 (6H, d), 1.37 (3H, d). | m/z: 496 | 3, EtOAc used as co-solvent |

TABLE 9-continued

| Ex. | Structure | Name | ¹H NMR Data (Me-d3-OD) | MS Data | Method [a] |
|---|---|---|---|---|---|
| 246 | 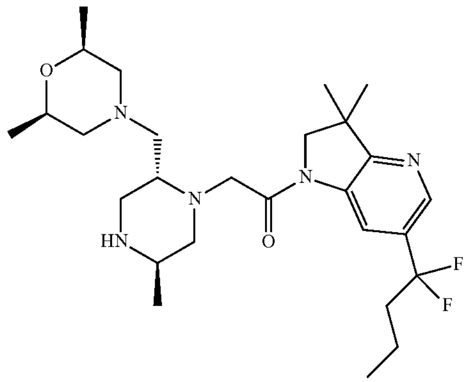 | 1-[6-(1,1-Difluorobutyl)-3,3-dimethyl-1H,2H,3H-pyrrolo[3,2-b]pyridin-1-yl]-2-{(2R,5R)-2-{[(2R,6S)-2,6-dimethylmorpholin-4-yl]methyl}-5-methylpiperazin-1-yl]ethan-1-one dihydrochloride | 8.62 (1H, d), 8.46 (1H, s), 4.27-4.17 (2H, m), 4.15-4.05 (4H, m), 3.91 (1H, d), 3.75 (1H, d), 3.67-3.37 (5H, m), 3.14 (1H, dd), 2.95-2.74 (2H, m), 2.31-2.13 (2H, m), 1.56-1.48 (8H, m), 1.39 (3H, d), 1.33 (3H, d), 1.27 (3H, d), 1.00 (3H, t). | m/z: 508 | 3, EtOAc used as co-solvent |
| 247 | 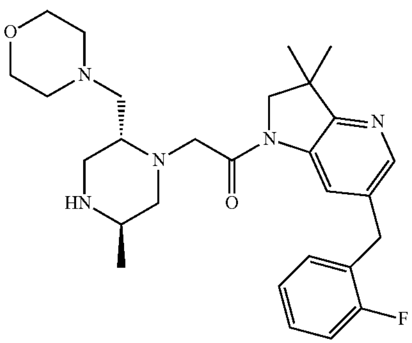 | 1-{6-[(2-Fluorophenyl)methyl]-3,3-dimethyl-1H,2H,3H-pyrrolo[3,2-b]pyridin-1-yl}-2-[(2R,5R)-5-methyl-2-(morpholin-4-ylmethyl)piperazin-1-yl]ethan-1-one dihydrochloride | 8.68 (1H, s), 8.41 (1H, s), 7.46-7.32 (2H, m), 7.27-7.10 (2H, m), 4.30-3.74 (13H, m), 3.63-3.49 (3H, m), 3.07 (1H, dd), 1.58 (6H, s), 1.37 (3H, d). | m/z: 496 | 3, EtOAc used as co-solvent |

TABLE 9-continued

| Ex. | Structure | Name | ¹H NMR Data (Me-d3-OD) | MS Data | Method a |
|---|---|---|---|---|---|
| 248 | 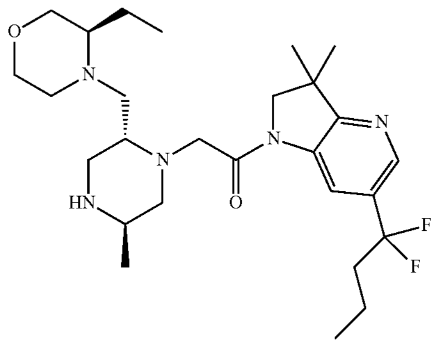 | 1-[6-(1,1-Difluorobutyl)-3,3-dimethyl-1H,2H,3H-pyrrolo[3,2-b]pyridin-1-yl]-2-[(2R,5R)-2-{[(3R)-3-ethylmorpholin-4-yl]methyl}-5-methylpiperazin-1-yl]ethan-1-one dihydrochloride | 8.60 (1H, s), 8.44 (1H, s), 4.31-3.90 (9H, m), 3.79 (2H, d), 3.66-3.59 (1H, m), 3.14-3.03 (1H, m), 2.30-1.72 (4H, m), 1.57-1.20 (13H, m), 1.13-0.96 (6H, m). | m/z: 508 | 3, EtOAc used as co-solvent |
| 249 | 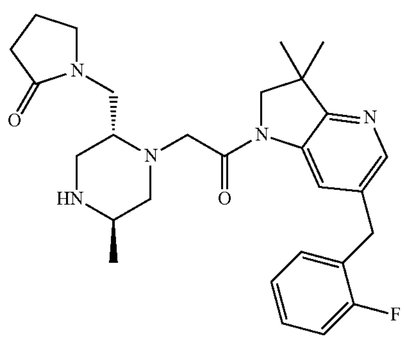 | 1-{[(2R,5R)-1-(2-{6-[(2-Fluorophenyl)methyl]-3,3-dimethyl-1H,2H,3H-pyrrolo[3,2-b]pyridin-1-yl}-2-oxoethyl)-5-methylpiperazin-2-yl]methyl}pyrrolidin-2-one hydrochloride | 8.85 (1H, s), 8.43 (1H, s), 7.43 (1H, t), 7.40-7.30 (1H, m), 7.26-7.18 (1H, m), 7.14 (1H, t), 4.40-4.29 (2H, m), 4.26 (2H, s), 4.23-4.06 (2H, m), 4.01-3.88 (1H, m), 3.82 (1H, dd), 3.67 (1H, d), 3.63-3.38 (5H, m), 3.28-3.12 (2H, m), 2.40-2.25 (1H, m), 2.22-2.10 (1H, m), 2.09-1.98 (1H, m), 1.98-1.85 (1H, m), 1.61 (6H, d), 1.37 (3H, d). | m/z: 494 | 3, EtOAc used as co-solvent |

TABLE 9-continued

| Ex. | Structure | Name | ¹H NMR Data (Me-d3-OD) | MS Data | Method [a] |
|---|---|---|---|---|---|
| 250 | 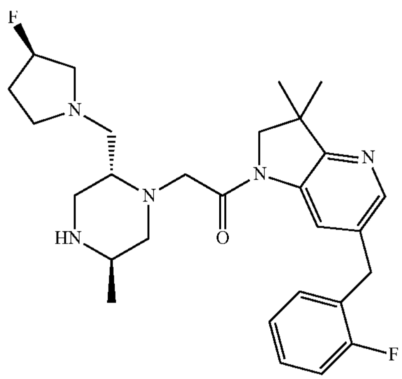 | 1-{6-[(2-Fluorophenyl)methyl]-3,3-dimethyl-1H,2H,3H-pyrrolo[3,2-b]pyridin-1-yl}-2-[(2R,5R)-2-{[(3R)-3-fluoropyrrolidin-1-yl]methyl}-5-methylpiperazin-1-yl]ethan-1-one dihydrochloride | 8.85 (1H, s), 8.43 (1H, s), 7.48-7.30 (2H, m), 7.26-7.09 (2H, m), 5.52 (1H, d), 4.26 (4H, d), 4.11-3.95 (3H, m), 3.87-3.69 (3H, m), 3.62-3.54 (1H, m), 3.17-3.04 (1H, m), 2.72-2.37 (2H, m), 1.62 (6H, d), 1.34 (3H, d). | m/z: 498 | 3, EtOAc used as co-solvent |
| 251 | 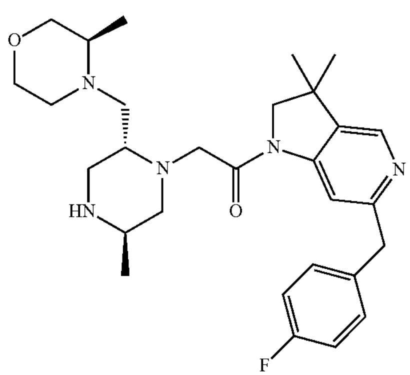 | 1-{6-[(4-Fluorophenyl)methyl]-3,3-dimethyl-1H,2H,3H-pyrrolo[3,2-c]pyridin-1-yl}-2-[(2R,5R)-5-methyl-2-{[(3R)-3-methylmorpholin-4-yl]methyl}piperazin-1-yl]ethan-1-one dihydrochloride | 8.63 (1H, s), 8.15-8.04 (1H, m), 7.47-7.34 (2H, m), 7.18 (2H, t), 4.44-4.34 (2H, m), 4.34-3.94 (7H, m), 3.85-3.45 (9H, m), 3.20 (2H, t), 3.12-2.93 (1H, m), 1.55 (6H, s), 1.48-1.32 (6H, m). | m/z: 510 | 3, EtOAc used as co-solvent |

TABLE 9-continued

| Ex. | Structure | Name | $^1$H NMR Data (Me-d3-OD) | MS Data | Method [a] |
|---|---|---|---|---|---|
| 252 | 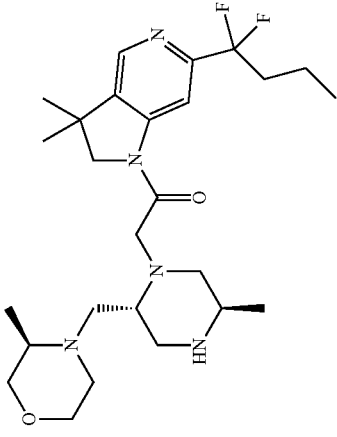 | 1-[6-(1,1-Difluorobutyl)-3,3-dimethyl-1H,2H,3H-pyrrolo[3,2-c]pyridin-1-yl]-2-[(2R,5R)-5-methyl-2-{[(3R)-3-methylmorpholin-4-yl]methyl}piperazin-1-yl]ethan-1-one dihydrochloride | 8.72-8.66 (1H, m), 8.49 (1H, s), 4.34-3.96 (8H, m), 3.96-3.37 (9H, m), 3.13-2.94 (1H, m), 2.40-2.25 (2H, m), 1.62-1.29 (15H, m), 1.02 (3H, t). | m/z: 494 | 3, EtOAc used as co-solvent |
| 253 | 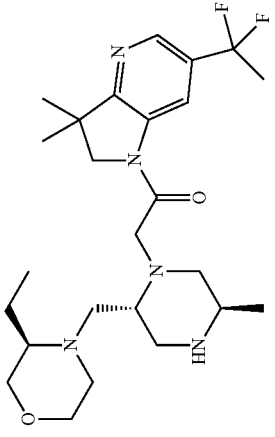 | 1-[6-(1,1-Difluoroethyl)-3,3-dimethyl-1H,2H,3H-pyrrolo[3,2-b]pyridin-1-yl]-2-[(2R,5R)-3-ethylmorpholin-4-yl]methyl}-5-methylpiperazin-1-yl]ethan-1-one dihydrochloride | 8.68 (1H, s), 8.50 (1H, s), 4.28-3.95 (8H, m), 3.80 (2H, s), 3.68 (3H, m), 3.62 (2H, s), 3.16-3.02 (1H, m), 2.28-1.65 (6H, m), 1.56-1.31 (10H, m), 1.20-0.97 (3H, m). | m/z: 480 | 3, EtOAc used as co-solvent |

TABLE 9-continued

| Ex. | Structure | Name | $^1$H NMR Data (Me-d3-OD) | MS Data | Method[a] |
|---|---|---|---|---|---|
| 254 | 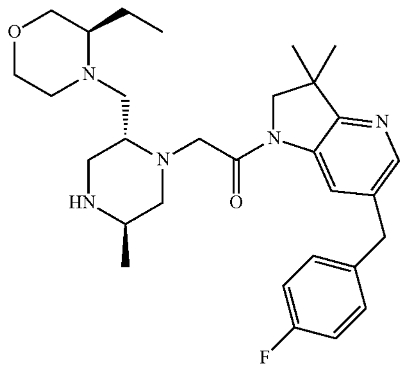 | 2-[(2R,5R)-2-[[(3R)-3-Ethylmorpholin-4-yl]methyl]-5-methylpiperazin-1-yl]-1-[6-[(4-fluorophenyl)methyl]-3,3-dimethyl-1H,2H,3H-pyrrolo[3,2-b]pyridin-1-yl]ethan-1-one dihydrochloride | 8.68 (1H, d), 8.46 (1H, s), 7.42-7.31 (2H, m), 7.19-7.07 (2H, m), 4.32-3.96 (10H, m), 3.77 (3H, s), 3.64-3.55 (2H, m), 1.98 (2H, d), 1.61 (6H, s), 1.53-1.31 (4H, m), 1.23-0.85 (4H, m). | m/z: 524 | 3, EtOAc used as co-solvent |
| 255 | 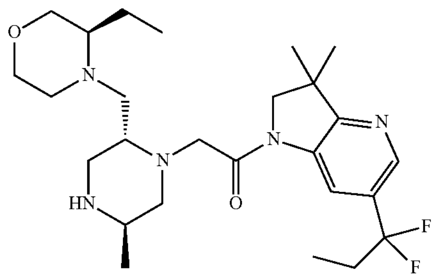 | 1-[6-(1,1-Difluoropropyl)-3,3-dimethyl-1H,2H,3H-pyrrolo[3,2-b]pyridin-1-yl]-2-[(2R,5R)-2-[[(3R)-3-ethylmorpholin-4-yl]methyl]-5-methylpiperazin-1-yl]ethan-1-one dihydrochloride | 8.67 (1H, s), 8.47 (1H, s), 4.32-3.89 (9H, m), 3.81 (2H, s), 3.52 (5H, d), 3.11 (1H, d), 2.36-2.21 (2H, m), 2.20-2.04 (1H, m), 1.82 (1H, s), 1.56-1.50 (6H, m), 1.49-1.38 (3H, m), 1.14-0.97 (6H, m). | m/z: 494 | 3, EtOAc used as co-solvent |
| 256 | 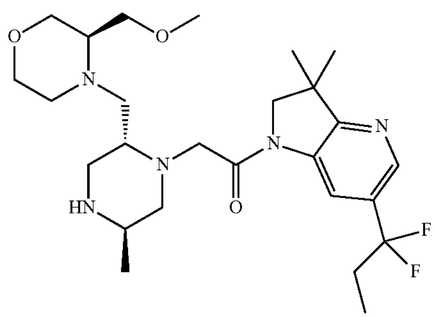 | 1-[6-(1,1-Difluoropropyl)-3,3-dimethyl-1H,2H,3H-pyrrolo[3,2-b]pyridin-1-yl]-2-[(2R,5R)-2-[[(3R)-3-(methoxymethyl)morpholin-4-yl]methyl]-5-methylpiperazin-1-yl]ethan-1-one dihydrochloride | 8.62 (1H, s), 8.44 (1H, s), 4.23-3.93 (10H, m), 3.83 (2H, d), 3.76-3.54 (3H, m), 3.46 (2H, d), 3.06 (1H, dd), 2.35-2.19 (2H, m), 1.51 (6H, d), 1.45 (3H, d), 1.04 (3H, t). | m/z: 510 | 3, EtOAc used as co-solvent |

Example 257: 1-(6-Benzyl-3,3-dimethyl-2,3-dihydro-pyrrolo[2,3-b]pyridin-1-yl)-2-((2R,5R)-2-methoxymethyl-5-methyl-piperazin-1-yl)-ethanone hydrochloride

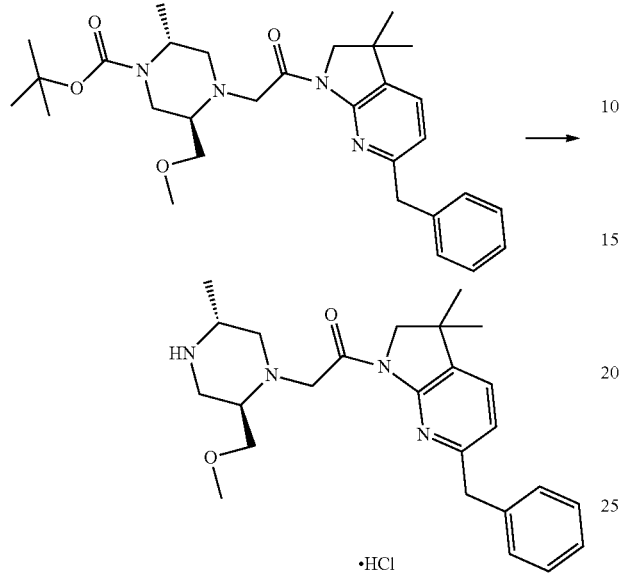

(2R,5R)-4-[2-(6-Benzyl-3,3-dimethyl-2,3-dihydro-pyrrolo[2,3-b]pyridin-1-yl)-2-oxo-ethyl]-5-methoxymethyl-2-methyl-piperazine-1-carboxylic acid tert-butyl ester (200 mg, 0.38 mmol) was dissolved in DCM (10 mL) and placed under a nitrogen atmosphere. TFA (2 mL) was added to the reaction which was stirred at room temperature for 40 minutes. The reaction was concentrated in vacuo. The residue was partitioned between DCM (100 mL) and aqueous sodium hydrogen carbonate (100 mL). The layers were separated and the aqueous layer was extracted with DCM (2×100 mL). The organic extracts were dried over magnesium sulfate, filtered and concentrated. Chromatography: (silica; 30 g packed in DCM and eluted with 5% MeOH in DCM-5-10% MeOH:DCM:0.5% NH₄OH). gave product. This material was dissolved in EtOAc and the solution treated with 2M HCl in Et₂O and concentrated in vacuo giving a white solid which was dried in an oven at 40° C. overnight giving the title compound (132 mg). ¹H NMR (Me-d3-OD): 7.60 (1H, s), 7.33 (4H, s), 7.24 (1H, s), 7.03 (1H, s), 4.76 (1H, d), 4.67-4.54 (1H, m), 4.10 (2H, d), 3.84 (3H, s), 3.53 (6H, s), 3.26 (1H, d), 3.20 (3H, s), 1.38 (9H, s). MS: [M+H]⁺=423.

Example 258: 1-[3,3-Dimethyl-6-(1H-tetrazol-5-yl)-2,3-dihydro-indol-1-yl]-2-((2R,5R)-2-methoxymethyl-5-methyl-piperazin-1-yl)-ethanone hydrochloride

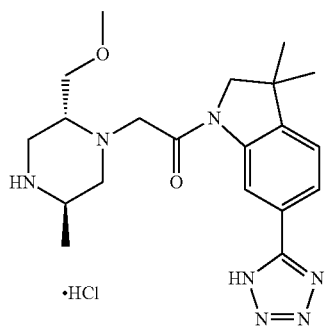 [SMILES: COC[C@H]1CN[C@H](C)CN1CC(=O)N1CC(C)(C)c2ccc(-c3nnn[nH]3)cc21 ; Cl]

A stirred solution of 1-{2-[(2R,5R)-2-(methoxymethyl)-5-methylpiperazin-1-yl]acetyl}-3,3-dimethyl-2,3-dihydro-1H-indole-6-carbonitrile hydrochloride (25 mg, 0.06 mmol) in DMF (1 mL) was treated with sodium azide (9.0 mg, 0.13 mmol) and ammonium chloride (4.0 mg, 0.06 mmol), and heated under reflux under nitrogen. After 16 h the mixture was filtered and concentrated in vacuo. The residue was purified by preparative HPLC, basic method then treated with a saturated solution of HCl in EtOAc followed by concentration to dryness in vacuo to give the title compound (1.2 mg, 4%). ¹H NMR (Me-d3-OD): 8.86-8.78 (1H, m), 7.77 (1H, d), 7.33 (1H, d), 3.95 (1H, d), 3.88 (1H, d), 3.78 (1H, d), 3.68 (1H, d), 3.62-3.46 (2H, m), 3.39-3.33 (3H, m), 3.33 (3H, s), 3.13 (1H, d), 3.07-2.91 (2H, m), 1.49-1.35 (6H, s), 1.29 (3H, d). MS: [M+H]⁺=400.

Example 259: 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride

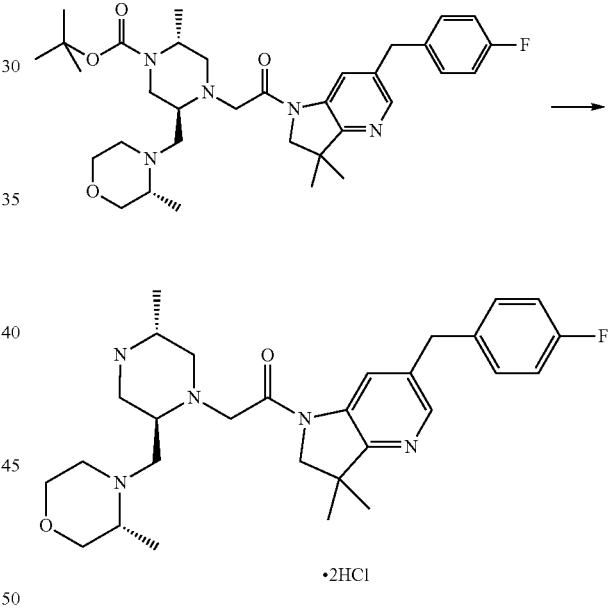

(2R,5S)-4-{2-[6-(4-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (1.9 g, 3.29 mmol) was dissolved in EtOAc (48 mL) and 4 M HCl in dioxane (82 mL) and stirred at room temperature for 18 h. The solvent was removed in vacuo and resulting solid triturated with diethyl ether and dried in a vacuum oven at 40° C., to give the title compound (1.36 g). ¹H NMR (DMSO-d6): 11.71-10.46 (1H, m), 10.14 (1H, s), 9.52 (1H, s), 8.31 (1H, s), 8.25 (1H, s), 7.32 (2H, dd), 7.15 (2H, t), 4.12-4.01 (4H, m), 4.01-3.56 (7H, m), 3.45 (4H, s), 3.22 (2H, d), 3.17 (2H, s), 3.09 (1H, d), 2.89 (1H, d), 1.41 (6H, s), 1.24 (6H, m). MS: [M+H]⁺=510.

Example 260: 1-[6-(1,1-Difluoro-butyl)-3,3-dimethyl-2,3-dihydro-pyrrolo[3,2-b]pyridin-1-yl]-2-[(2R,5R)-5-methyl-2-((R)-3-methyl-morpholin-4-yl methyl)-piperazin-1-yl]-ethanone dihydrochloride

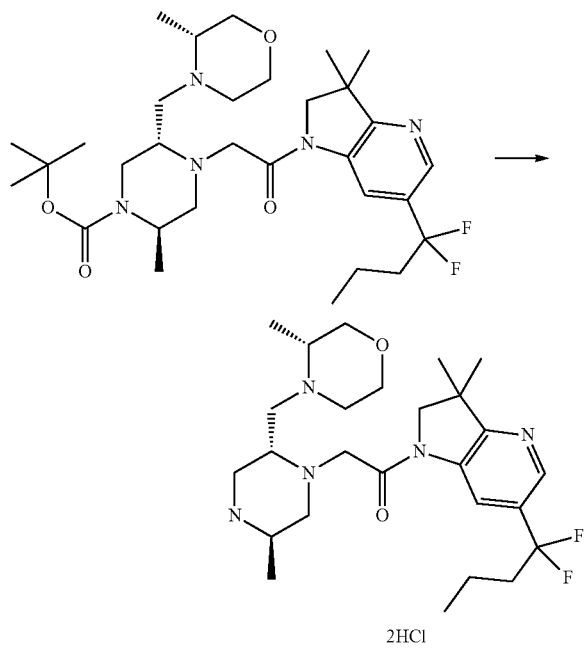

4N HCl in dioxane (35 mL) was added to a solution of (2R,5S)-4-{2-[6-(1,1-difluoro-butyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (2.1 g) in EtOAc (10 mL). The resulting suspension was stirred for 1 h at room temperature. The solvent was then removed in vacuo. The solid was triturated in Et$_2$O, collected by filtration, washed with Et$_2$O and dried in vacuo to give the title compound (1.7 g) as a yellow solid. $^1$H NMR (Me-d3-OD): 8.77 (1H, s), 8.52 (1H, s), 4.36-3.91 (9H, m), 3.91-3.41 (8H, m), 3.18-2.99 (1H, m), 2.34-2.15 (2H, m), 1.67-1.36 (15H, m), 1.00 (3H, t). MS: [M+H]$^+$=494.

Example 261: 1-[6-(2-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-yl methyl)-piperazin-1-yl]-ethanone dihydrochloride

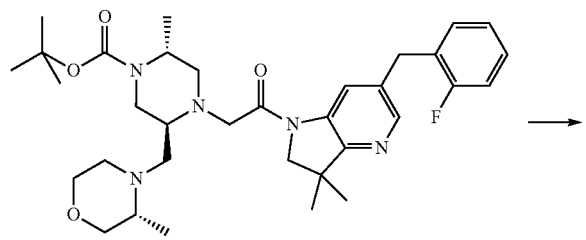

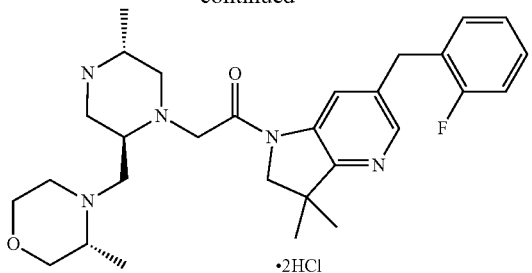

(2R,5S)-4-{2-[6-(2-Fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (1.43 g, 2.35 mmol) was dissolved in EtOAc (34 mL) and 4 M HCl in dioxane (59 mL) and stirred at room temperature for 18 h. The solvent was removed in vacuo, then residue was re-dissolved in methanol and concentrated. The crude product was purified by recrystallisation (isopropanol/diethyl ether) to give the title compound (0.90 g). $^1$H NMR (DMSO-d6): 10.64-10.27 (1H, m), 9.97-9.64 (1H, m), 9.43-9.02 (1H, m), 8.23 (1H, s), 8.08 (1H, s), 7.43-7.35 (1H, m), 7.35-7.26 (1H, m), 7.22-7.13 (2H, m), 4.07-3.84 (8H, m), 3.69-3.30 (6H, m), 3.26-2.95 (4H, m), 2.91-2.82 (1H, m), 1.32 (6H, d), 1.28-1.13 (6H, m). MS: [M+H]$^+$=510.

Example 262: 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-yl methyl)-piperazin-1-yl]-ethanone 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone dihydrochloride (1.8 g) was dissolved in water (50 mL) and the resulting solution extracted with ethyl acetate (50 mL). The aqueous phase was basified (pH 8) with saturated aqueous NaHCO$_3$ then was extracted with DCM (5×50 mL). The combined DCM extracts were dried (Na$_2$SO$_4$) and evaporated in vacuo to give the title compound (1.72 g) as a foam. $^1$H NMR (Me-d3-OD): 8.24 (1H, s), 8.07 (1H, d), 7.24 (2H, dd), 7.03 (2H, t), 4.19-4.06 (1H, m), 3.99 (3H, d), 3.90 (1H, d), 3.71 (1H, d), 3.65-3.48 (2H, m), 3.19-2.70 (8H, m), 2.60-2.40 (2H, m), 2.26 (1H, s), 2.09-1.93 (1H, m), 1.87 (1H, d), 1.41 (6H, d), 1.04 (3H, d), 0.97 (3H, d).

Example 262a: 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-yl methyl)-piperazin-1-yl]-ethanone To a vigorously stirred solution of (2R,5S)-4-{2-[6-(4-fluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (11.3 g, 18.5 mmol) in ethyl acetate (100 mL) at 20° C. was added a solution of HCl in dioxan (100 mL) and stirring was continued for 18 h. The resulting fine yellow precipitate was collected by filtration and dried in vacuo. This material was suspended in water (200 mL) and extracted with EtOAc (200 mL). The organic phase was washed with 0.1 M aqueous HCl (50 mL) and the combined aqueous extracts were cooled in an ice bath and basified by the dropwise addition of 5 M aqueous NaOH. Resulting mixture was extracted with DCM (4×60 mL) and the combined extracts were dried (Na$_2$SO$_4$) and evaporated in vacuo to give the title compound (8.29 g) as a colourless foam. $^1$H NMR and MS data were consistent with those obtained above for Example 262. IR $v_{C=O}$ 1685 cm$^{-1}$.

Example 263: 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone hydrochloride 1-[6-(4-Fluoro-benzyl)-3,3-dimethyl-2,3-dihydro-pyrrolo[3,2-b]pyridin-1-yl]-2-[(2R,5R)-5-methyl-2-((R)-3-methyl-morpholin-4-ylmethyl)-piperazin-1-yl]-ethanone (1.72 g) was dissolved in EtOAc (40 mL) then treated dropwise with a mixture of 4 M HCl in dioxane and EtOAc (40 mL) while stirring at ambient temperature. The resulting clear solution was allowed to stand for 64 h then was evaporated in vacuo to give a foam which was dissolved in isopropanol then re-evaporated. The resulting residue was triturated with ether to afford the title compound (1.43 g) as a white powder. $^1$H NMR (Me-d3-OD): 8.19 (1H, s), 8.13 (1H, s), 7.31-7.19 (2H, m), 7.04 (2H, t), 4.16-3.79 (7H, m), 3.79-3.42 (4H, m), 3.02 (5H, m), 2.61-1.92 (2H, m), 1.42 (6H, d), 1.32 (3H, s), 1.17 (3H, d), 1.16-0.77 (3H, m).

Example 264: 1-[6-(2,4-Difluoro-benzyl)-3,3-dimethyl-2,3-dihydro-pyrrolo[3,2-b]pyridin-1-yl]-2-[(2R,5R)-5-methyl-2-((R)-3-methyl-morpholin-4-yl methyl)-piperazin-1-yl]-ethanone, dihydrochloride

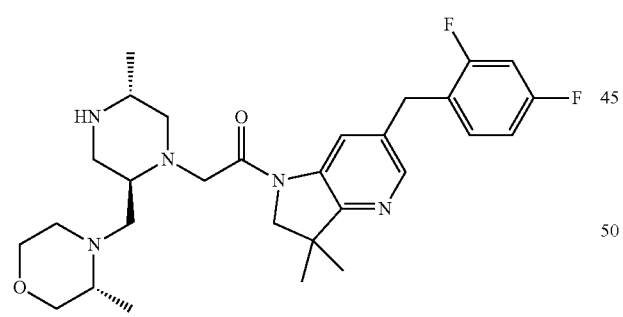

A mixture of (2R,5S)-4-{2-[6-(2,4-difluoro-benzyl)-3,3-dimethyl-2,3-dihydro-pyrrolo[3,2-b]pyridin-1-yl]-2-oxo-ethyl}-2-methyl-5-((R)-3-methyl-morpholin-4-ylmethyl)-piperazine-1-carboxylic acid tert-butyl ester (0.103 g), ethyl acetate (10 mL) and 4 M HCl in dioxan (10 mL) was stirred at 20° C. for 18 h and the resulting solid collected by filtration to give the title compound (0.075 g). $^1$H NMR (Me-d3-OD): 8.76 (1H, s), 8.48 (1H, s), 7.56-7.44 (1H, m), 7.11-6.98 (2H, m), 4.27 (5H, d), 4.16-3.96 (5H, m), 3.82 (3H, s), 3.66-3.41 (5H, m), 3.18 (4H, d), 1.62 (6H, s), 1.41 (6H, br m). MS: [M+H]$^+$=528.

Example 265: 1-[6-(4-Fluoro-benzyl)-3,3-dimethyl-2,3-dihydro-pyrrolo[3,2-b]pyridin-1-yl]-2-((R)-3-methyl-piperazin-1-yl)-ethanone

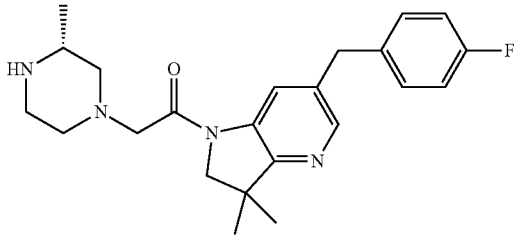 [SMILES: C[C@@H]1CN(CC(=O)N2CC(C)(C)c3ncc(Cc4ccc(F)cc4)cc32)CCN1]

Prepared from (R)-4-{2-[6-(4-Fluoro-benzyl)-3,3-dimethyl-2,3-dihydro-pyrrolo[3,2-b]pyridin-1-yl]-2-oxo-ethyl}-2-methyl-piperazine-1-carboxylic acid tert-butyl ester in an analogous manner to Example 264. $^1$H NMR (Me-d3-OD): 8.75 (1H, s), 8.37 (1H, s), 7.33 (2H, dd), 7.09 (2H, t), 4.41 (2H, s), 4.19 (2H, s), 4.16 (2H, s), 3.87-3.68 (4H, m), 3.61-3.41 (2H, m), 3.27 (1H, t), 1.59 (6H, s), 1.44 (3H, d). MS: [M+H]$^+$=397.

Example 266: 3,3-Dimethyl-1-[(2S)-2-[(3R)-3-methylpiperazin-1-yl]butanoyl]-2,3-dihydro-1H-indole-6-carbonitrile, hydrochloride salt

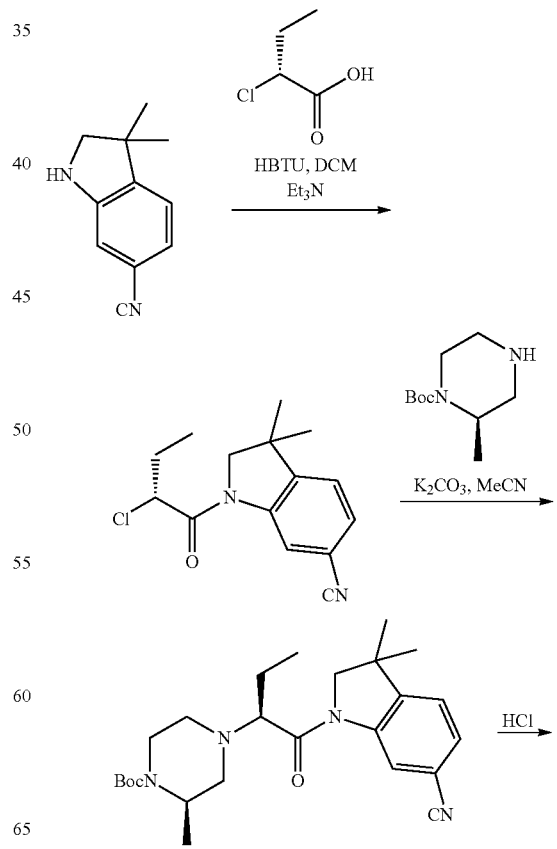

-continued

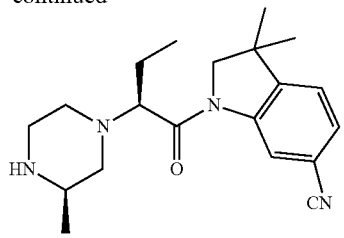

To a stirred solution of (R)-2-chloro-1-butyric acid (0.47 mL, 4.60 mmol) in DCM was added HBTU (2.18 g, 5.75 mmol). After stirring for 30 min, triethylamine (0.96 mL, 6.9 mmol) and 3,3-dimethyl-2,3-dihydro-1H-indole-6-carbonitrile (0.80 g, 4.6 mmol) were added, the resulting mixture was stirred overnight. A drop of DMF was added and the reaction was stirred overnight. The reaction mixture was then diluted with ethyl acetate and washed with water. The organics were separated, dried with sodium sulfate and concentrated. The residue was purified by flash column chromatography on silica gel eluting with 20% ethyl acetate in heptane to give (R)-1-(2-chlorobutanoyl)-3,3-dimethylindoline-6-carbonitrile containing un-reacted 3,3-dimethyl-2,3-dihydro-1H-indole-6-carbonitrile. The mixture was taken up in DCM and washed with 2M HCl solution. The organics were dried with sodium sulfate and concentrated, to give (R)-1-(2-chlorobutanoyl)-3,3-dimethylindoline-6-carbonitrile (0.38 g). $^1$H NMR (400 MHz, CDCl$_3$) 8.53 (s, 1H), 7.38 (d, 1H), 7.25 (d, 1H), 4.22-4.29 (m, 1H), 4.15 (d, 1H), 3.87 (d, 1H), 2.19-2.04 (m, 2H), 1.39 (s, 6H), 1.09 (t, 3H).

To a suspension of (R)-1-(2-chlorobutanoyl)-3,3-dimethylindoline-6-carbonitrile (0.1 g, 0.36 mmol), (R)-2-methylpiperazine-1-carboxylic acid tert-butyl ester (0.072 g, 0.36 mmol) in acetonitrile (2.5 mL) was added potassium carbonate (0.049 g, 0.36 mmol) and the reaction heated to 50° C. for 48 h followed by 80° C. for 24 h and 60° C. for 36 h. The reaction mixture was then diluted with ethyl acetate and washed with water. The organics were separated, dried with sodium sulfate and concentrated. The residue was purified by flash column chromatography on silica gel; eluting with 20-30% ethyl acetate in heptane to give (R)-4-[(S)-1-(6-cyano-3,3-dimethyl-2,3-dihydro-indole-1-carbonyl)-propyl]-2-methyl-piperazine-1-carboxylic acid tert-butyl ester (0.023 g). MS: [M+H]$^+$=441.

4M HCl in dioxane (1 mL) was added to (R)-1-(2-chlorobutanoyl)-3,3-dimethylindoline-6-carbonitrile (22 mg, 0.049 mmol) and the resulting mixture stirred at RT for 2 h. The reaction mixture was concentrated and the resulting solids were triturated with diethyl ether to give 3,3-dimethyl-1-((S)-2-((R)-3-methylpiperazin-1-yl)butanoyl)indoline-6-carbonitrile hydrochloride (3.9 mg). MS: [M+H]$^+$=341. The supernatant was also concentrated to give a second batch of 3,3-dimethyl-1-((S)-2-((R)-3-methylpiperazin-1-yl)butanoyl)indoline-6-carbonitrile hydrochloride (11.3 mg, combined purity ~70%). MS: [M+H]$^+$=341.

Biological Assays
Expression and Purification of XIAP, cIAP-1 and cIAP-2 BIR3 Domains The recombinant BIR3 domain of human XIAP (residues 252-350) fused to a His-tag, human cIAP-1 (residues 267-363) fused to a GST-tag and human cIAP-2 (residues 244-337) fused to a His-tag were overexpressed from *Escherichia coli* cells grown in TB medium. Protein was isolated from lysates using Ni-NTA affinity chromatography (XIAP/cIAP-2) or glutathione sepharase 4B affinity chromatography (cIAP-1). Affinity tags for XIAP and cIAP-1 were cleaved with thrombin in 25 mM HEPES pH 7.5, 100 mM NaCl, 50 μM Zn(OAc)$_2$ and 1 mM Ca(OAc)$_2$ followed by purification of BIR3 domains by size-exclusion chromatography. The His-tag was uncleaved for cIAP-2 and the protein was not concentrated above 3 mg/ml due to aggregation induced covalent self-oligomerization issues. The purified protein was stored in 25 mM Tris pH 7.5, 100 mM NaCl at −80° C.

XIAP, cIAP-1 and cIAP-2 In Vitro Competitive Displacement Binding Assays

Modified SMAC peptides and compounds were tested for their ability to displace the fluorescent tracer from either XIAP, cIAP-1 or cIAP-2. BIR3 domains of cIAP-1, cIAP-2 and XIAP were incubated with test compounds or SMAC based peptides and their respective peptide probes (Peptide Protein Research) in assay buffer (50 mM Hepes pH 7.5, 0.025% Tween-20, 0.01% BSA, and 1 mM DTT). Positive controls consisted of BIR3 proteins and tracer (no inhibition) and negative controls contained tracer only (100% inhibition). The samples were incubated at room temperature for 1 hr (XIAP and cIAP-2) or 3 hrs (cIAP-1) prior to being read in the BMG Pherastar in Fluorescence Polarization mode (FP 485 nm, 520 nm, 520 nm). IC$_{50}$ values were determined from dose-response plots using nonlinear least-squares analysis.

Final Conditions for XIAP, cIAP-1 and cIAP-2 Assays

| Protein | Protein Conc | Peptide Probe | Peptide Conc |
|---|---|---|---|
| XIAP | 20 nM | AbuRPFK(5&6FAM)-amide | 5 nM |
| cIAP-1 | 4 nM | AbuRPFK(5&6FAM)-amide | 2 nM |
| cIAP-1 | 12 nM | AVPIK(5&6FAM)-amide | 2 nM |
| cIAP-2 | 20 nM | AVPWK(5&6FAM)-amide | 2 nM |

The compounds of Examples 1-24, 26-43 and 85 were tested in the cIAP1 assay using Peptide Probe AVPIK (5&6FAM)-amide (Probe A). The remaining compounds were tested in the cIAP1 assay using Peptide Probe AbuRPFK(5&6FAM)-amide probe (Probe B). The compound of Example 25 was tested in the cIAP1 assay using Peptide Probe AVPIK(5&6FAM)-amide (Probe A) and Peptide Probe AbuRPFK(5&6FAM)-amide probe (Probe B). The compounds of Examples 12, 15, 20, 24, 29, 33, 35, 38, 40-49, 51-65, 67-72, 74-80, 83-84, 86-87, 89-100, 102-103, 106-110 and 114-130, 132, 134-146, 148-156, 161-163, 165, 168-170, 174-175, 177, 181, 183-184, 186-190, 198, 211-212, 214, 220, 222, 226, 228, 231, 235, 253, 255-257 and 265 have IC$_{50}$ values of less than 10 μM or provide at least 50% inhibition of the activity at a concentration of 10 μM in the assay whereas the compounds of Examples 35, 40, 42-45, 47-48, 56, 58-60, 62-64, 67, 70-72, 74-80, 83, 86-87, 89-100, 102-103, 106-110 and 114-130, 132, 134-146, 148-155, 161, 163, 165, 168-170, 174-175, 177, 181, 183-184, 186-190, 198, 211-212, 214, 220, 222, 226, 228, 231, 235, 253 and 255-256 have IC$_{50}$ values of less than 1 μM or provide at least 50% inhibition of the activity at a concentration of 1 μM. Preferred compounds of the invention have IC$_{50}$ values of less than 0.1 μM against XIAP and/or cIAP1 and or cIAP2. Data for the compounds of the invention in the above assays are provided in Table 10.

Anti-Proliferative Activity

Inhibition of cell growth is measured using the Alamar Blue assay (Nociari, M. M, Shalev, A., Benias, P., Russo, C. *Journal of Immunological Methods* 1998, 213, 157-167). The method is based on the ability of viable cells to reduce resazurin to its fluorescent product resorufin. For each proliferation assay cells are plated onto 96 well plates and allowed to recover for 16 hours prior to the addition of inhibitor compounds (in 0.1% DMSO v/v) for a further 72 hours. At the end of the incubation period 10% (v/v) Alamar Blue is added and incubated for a further 6 hours prior to determination of fluorescent product at 535 nM ex/590 nM em.

The anti-proliferative activities of compounds of the invention can be determined by measuring the ability of the compounds to inhibit growth in 3 cancer cell lines:

EVSA-T (human breast carcinoma) DSMZ cat. no. ACC 433

MDA-MB-231 (human breast carcinoma) ECACC cat. no. 92020424

HCT116 (human colon carcinoma) ECACC cat. no. 91091005 (insensitive cell line used as a control for non-specific cytoxicity)

Many compounds of the invention were found to have $EC_{50}$ values of less than 1 μM in EVSA-T cell line assays (and less than 10 μM against the MDA-MB-231 cell line) and preferred compounds have $EC_{50}$ values of less than 0.1 μM in EVSA-T cell assays (and less than 1 μM against the MDA-MB-231 cell line) and $EC_{50}$>10 μM against HCT116 cells.

In an assay using the cell line EVSA-T, Examples 29, 41-45, 47-48, 56, 58-60, 62-64, 67-68, 70-71, 74-80, 82-83, 86-94, 96-97, 99-101, 104-106, 108-112, 118-122, 126, 128, 130, 131-133, 135-137, 140-141, 143-153, 157-161, 163-167, 170-180, 182, 184-186, 188-195, 197-256 and 259-264 have an $EC_{50}$ of less than 10 μM. In an assay using the cell line MDA-MB-231, Examples 47-48, 58, 60, 63-64, 67, 75-80, 82-83, 86-91, 93-94, 96-97, 99-101, 104-106, 110-112, 119, 121-122, 128, 130, 131-133, 137, 144, 146-148, 150-151, 157-160, 163-167, 170-180, 182, 184-186, 188-195, 197-221, 223-256 and 259-264 have an $EC_{50}$ of less than 10 μM. Data for the compounds of the invention in the above assays are provided in Table 10.

TABLE 10

| Ex. | IC50 or PI Xiap (μM) | IC50 or PI cIAP1 (μM) | EVSA-T prolif (μM) |
|---|---|---|---|
| 1 | 8.8 | 40 | |
| 2 | 41 | 79 | |
| 3 | 79 | 48%@99 | |
| 4 | 13 | 29 | |
| 5 | 49%@160 | 78 | |
| 6 | 51 | 95 | |
| 7 | 43%@1600 | −30%@5000 | |
| 8 | 59%@160 | 46%@160 | |
| 9 | 130 | 170 | |
| 10 | 51 | 51%@160 | |
| 11 | 59%@100 | 46%@100 | |
| 12 | 2.4 | 1.5 | |
| 13 | 59 | 63 | |
| 14 | 53%@99 | 46%@160 | |
| 15 | 19 | 6.8 | |
| 16 | 42%@77 | 56%@250 | |
| 17 | 110 | 44%@160 | |
| 18 | 47%@49 | 43%@49 | |
| 19 | 150 | 17 | |
| 20 | 5.5 | 3.7 | |
| 21 | 45%@160 | 27 | |
| 22 | 5.9 | 36 | |
| 23 | 18 | 11 | |
| 24 | 7.4 | 2 | |
| 25 | 1.6 | 60 (A); 61 (B) | |
| 26 | 2.4 | 27 | |
| 27 | 2.5 | 59 | |
| 28 | 17 | 42 | |
| 29 | 0.91 | 1.4 | 4.6 |
| 30 | 4.1 | 60%@99 | |
| 31 | 51%@49 | 62%@49 | |
| 32 | 2.6 | 57 | |
| 33 | 1.2 | 3.8 | |
| 34 | 9.8 | 20 | |
| 35 | 1.1 | 0.96 | 28% at 10 |
| 36 | 240 | 56%@500 | |
| 37 | 1.8 | 23 | |
| 38 | 5.5 | 2.1 | |
| 39 | 55%@3 | 46%@1 | −15% at |
| 40 | 0.96 | 0.82 | 45% at 10 |
| 41 | 0.47 | 1.3 | 5.7 |
| 42 | 0.77 | 0.067 | 2.6 |
| 43 | 0.64 | 0.45 | 2.4 |
| 44 | 1.5 | 0.65 | 6.6 |
| 45 | 1.1 | 0.58 | 5.2 |
| 46 | 9 | 4.8 | |
| 47 | 0.27 | 0.39 | 1.8 |
| 48 | 0.097 | 0.064 | 0.25 |
| 49 | 0.64 | 4.1 | 2% at 10 |
| 50 | 14 | 15 | |
| 51 | 1.1 | 3.2 | |
| 52 | 0.95 | 2.5 | |
| 53 | 9.7 | 9.8 | |
| 54 | 1.8 | 2.1 | |
| 55 | 12 | 8.2 | |
| 56 | 0.11 | 0.13 | 2.3 |
| 57 | 0.81 | 2 | |
| 58 | 0.076 | 0.045 | 0.17 |
| 59 | 0.31 | 0.5 | 9.7 |
| 60 | 0.084 | 0.067 | 0.69 |
| 61 | 0.22 | 1.6 | −0% at 10 |
| 62 | 0.64 | 0.32 | 3.8 |
| 63 | 0.16 | 0.01 | 0.1 |
| 64 | 0.27 | 0.14 | 1 |
| 65 | 6 | 1.3 | |
| 66 | 44%@10 | 53%@3 | |
| 67 | 0.31 | 0.017 | 0.35 |
| 68 | 0.23 | 1.2 | 6.4 |
| 69 | 0.28 | 1.4 | 54% at 10 |
| 70 | 0.38 | 0.82 | 7.9 |
| 71 | 0.49 | 0.54 | 7.7 |
| 72 | 2.2 | 0.31 | |
| 73 | 46%@3 | 60%@1 | |
| 74 | 0.39 | 0.099 | 0.56 |
| 75 | 0.24 | 0.016 | 0.5 |
| 76 | 0.064 | 0.016 | 0.78 |
| 77 | 0.17 | 0.009 | 0.16 |
| 78 | 0.53 | 0.035 | 1.9 |
| 79 | 1 | 0.025 | 0.49 |
| 80 | 1.5 | 0.033 | 0.78 |
| 81 | 51%@300 | 36%@100 | |
| 82 | 0.22 | 86%@0.01 | 0.034 |
| 83 | 0.35 | 0.11 | 2 |
| 84 | 8.8 | 1.3 | |
| 85 | 52%@500 | 45%@250 | |
| 86 | 0.29 | 0.012 | 0.31 |
| 87 | 0.24 | 0.024 | 0.51 |
| 88 | 0.17 | 84%@0.01 | 0.04 |
| 89 | 0.29 | 0.016 | 0.99 |
| 90 | 0.27 | 0.079 | 0.33 |
| 91 | 0.29 | 0.019 | 0.2 |
| 92 | 1.2 | 0.27 | 4.8 |
| 93 | 0.49 | 0.059 | 1 |
| 94 | 0.22 | 0.014 | 0.33 |
| 95 | 3.1 | 0.68 | |
| 96 | 0.34 | 0.077 | 3 |
| 97 | 0.34 | 0.017 | 0.32 |
| 98 | 0.86 | 0.023 | |
| 99 | 0.11 | 0.012 | 0.18 |
| 100 | 0.12 | 0.014 | 0.45 |
| 101 | 0.072 | 62%@0.01 | 0.14 |
| 102 | 3.2 | 0.65 | |
| 103 | 0.42 | 0.87 | 12% at 10 |
| 104 | 0.085 | 71%@0.01 | 0.49 |
| 105 | 0.19 | 74%@0.01 | 0.055 |

TABLE 10-continued

| Ex. | IC50 or PI Xiap (μM) | IC50 or PI cIAP1 (μM) | EVSA-T prolif (μM) |
|---|---|---|---|
| 106 | 0.11 | 0.023 | 0.44 |
| 107 | 1.4 | 0.55 | |
| 108 | 0.27 | 0.28 | |
| 109 | 0.063 | 0.15 | 4.8 |
| 110 | 0.075 | 0.035 | 0.6 |
| 111 | 0.074 | 63%@0.01 | 0.071 |
| 112 | 0.067 | 69%@0.01 | 0.095 |
| 113 | — | 6%@100 | |
| 114 | 10 | 1.5 | |
| 115 | 5.3 | 0.67 | |
| 116 | 27 | 1.9 | |
| 117 | 0.79 | 0.71 | |
| 118 | 0.71 | 0.24 | 3.4 |
| 119 | 0.52 | 0.096 | 0.87 |
| 120 | 0.26 | 0.17 | 6.8 |
| 121 | 0.19 | 0.021 | 0.38 |
| 122 | 0.22 | 0.029 | 0.29 |
| 123 | 1.3 | 0.52 | |
| 124 | 4 | 0.55 | |
| 125 | 29 | 0.73 | |
| 126 | 0.38 | 0.086 | 1.8 |
| 127 | 1.2 | 0.35 | |
| 128 | 0.38 | 0.12 | 1.1 |
| 129 | 1.3 | 0.48 | |
| 130 | 0.2 | 0.044 | 0.23 |
| 131 | 0.13 | 63%@0.01 | 0.088 |
| 132 | 0.12 | 0.045 | 0.66 |
| 133 | 0.091 | 71%@0.01 | 0.11 |
| 134 | 0.78 | 0.59 | |
| 135 | 0.4 | 0.079 | 1.6 |
| 136 | 0.11 | 0.19 | 2.8 |
| 137 | 0.22 | 0.014 | 0.47 |
| 138 | 0.64 | 0.33 | |
| 139 | 0.23 | 0.19 | |
| 140 | 0.094 | 0.22 | 8.6 |
| 141 | 0.82 | 0.28 | 9 |
| 142 | 0.22 | 0.15 | 20% at 1 |
| 143 | 0.1 | 0.2 | 8.8 |
| 144 | 0.24 | 0.012 | 0.73 |
| 145 | 1 | 0.18 | 9.8 |
| 146 | 0.075 | 0.017 | 0.64 |
| 147 | 49%@0.04 | 80%@0.01 | 0.11 |
| 148 | 0.36 | 0.045 | 2 |
| 149 | 0.055 | 0.13 | 9.2 |
| 150 | 0.27 | 0.014 | 0.73 |
| 151 | 48%@0.04 | 0.019 | 0.59 |
| 152 | 0.065 | 0.11 | 3.7 |
| 153 | 54%@0.04 | 0.16 | 4 |
| 154 | 0.13 | 0.17 | |
| 155 | 0.072 | 0.26 | |
| 156 | 1.5 | 1.3 | |
| 157 | 0.065 | 78%@0.012 | 0.095 |
| 158 | 0.049 | 51%@0.01 | 0.3 |
| 159 | 56%@0.04 | 72%@0.012 | 0.12 |
| 160 | 0.15 | 61%@0.01 | 0.27 |
| 161 | 0.06 | 0.11 | 1.7 |
| 162 | 5.5 | 7.9 | |
| 163 | 0.16 | 0.013 | 0.45 |
| 164 | 0.12 | 86%@0.012 | 0.045 |
| 165 | 65%@0.04 | 0.014 | 0.65 |
| 166 | 0.15 | 76%@0.012 | 0.13 |
| 167 | 0.1 | 84%@0.012 | 0.26 |
| 168 | 4 | 0.89 | |
| 169 | 0.92 | 0.32 | |
| 170 | 0.18 | 0.011 | 0.26 |
| 171 | 0.11 | 64%@0.012 | 0.12 |
| 172 | 58%@0.04 | 78%@0.012 | 0.056 |
| 173 | 73%@0.04 | 80%@0.012 | 0.036 |
| 174 | 0.76 | 0.19 | 2.5 |
| 175 | 0.11 | 0.011 | 0.2 |
| 176 | 52%@0.04 | 70%@0.012 | 0.026 |
| 177 | 0.049 | 0.018 | 0.27 |
| 178 | 50%@0.04 | 60%@0.012 | 0.067 |
| 179 | 56%@0.04 | 97%@0.012 | 0.0044 |
| 180 | 0.044 | 82%@0.012 | 0.026 |
| 181 | 0.33 | 0.25 | |
| 182 | 73%@0.04 | 62%@0.012 | 0.067 |
| 183 | 1.7 | 0.63 | |
| 184 | 0.05 | 0.031 | 0.65 |
| 185 | 0.077 | 94%@0.012 | 0.01 |
| 186 | 59%@0.04 | 0.011 | 0.025 |
| 187 | 0.11 | 0.032 | |
| 188 | 0.057 | 0.04 | 0.63 |
| 189 | 70%@0.04 | 0.014 | 0.19 |
| 190 | 0.046 | 0.029 | 0.4 |
| 191 | 0.047 | 94%@0.012 | 0.017 |
| 192 | 0.058 | 95%@0.012 | 0.0088 |
| 193 | 44%@0.04 | 98%@0.012 | 0.016 |
| 194 | 0.055 | 99%@0.012 | 0.0098 |
| 195 | 0.067 | 96%@0.012 | 0.036 |
| 196 | 5.6 | 31 | |
| 197 | 68%@0.04 | 76%@0.012 | 0.049 |
| 198 | 69%@0.04 | 0.023 | 0.88 |
| 199 | 0.063 | 97%@0.012 | 0.0056 |
| 200 | 0.074 | 96%@0.012 | 0.0088 |
| 201 | 0.081 | 88%@0.012 | 0.0052 |
| 202 | 0.077 | 88%@0.012 | 0.0021 |
| 203 | 0.073 | 97%@0.012 | 0.0032 |
| 204 | 0.11 | 91%@0.012 | 0.021 |
| 205 | 0.1 | 97%@0.012 | 0.019 |
| 206 | 0.079 | 97%@0.012 | 0.0017 |
| 207 | 0.057 | 98%@0.012 | 0.004 |
| 208 | 0.064 | 99%@0.012 | 0.004 |
| 209 | 0.047 | 90%@0.012 | 0.019 |
| 210 | 61%@0.04 | 80%@0.012 | 0.054 |
| 211 | 0.046 | 0.022 | 0.63 |
| 212 | 0.045 | 0.014 | 0.27 |
| 213 | 61%@0.04 | 82%@0.012 | 0.006 |
| 214 | 0.082 | 0.024 | 0.19 |
| 215 | 42%@0.04 | 98%@0.012 | 0.006 |
| 216 | 0.044 | 68%@0.012 | 0.051 |
| 217 | 58%@0.04 | 66%@0.012 | 0.05 |
| 218 | 0.061 | 78%@0.012 | 0.065 |
| 219 | 0.053 | 93%@0.012 | 0.005 |
| 220 | 0.45 | 0.014 | 0.049 |
| 221 | 0.073 | 78%@0.012 | 0.054 |
| 222 | 0.22 | 0.14 | 9.6 |
| 223 | 0.12 | 62%@0.012 | 0.081 |
| 224 | 77%@0.04 | 83%@0.012 | 0.019 |
| 225 | 62%@0.04 | 72%@0.012 | 0.048 |
| 226 | 0.046 | 0.021 | 0.4 |
| 227 | 60%@0.04 | 78%@0.012 | 0.027 |
| 228 | 0.099 | 0.024 | 0.68 |
| 229 | 53%@0.04 | 73%@0.012 | 0.038 |
| 230 | 53%@0.04 | 60%@0.012 | 0.11 |
| 231 | 0.065 | 0.0095 | 0.067 |
| 232 | 48%@0.04 | 77%@0.012 | 0.036 |
| 233 | 0.076 | 62%@0.012 | 0.091 |
| 234 | 0.074 | 95%@0.012 | 0.0096 |
| 235 | 0.21 | 0.021 | 0.031 |
| 236 | 0.058 | 96%@0.012 | 0.0078 |
| 237 | 0.055 | 97%@0.012 | 0.0046 |
| 238 | 0.051 | 69%@0.012 | 0.068 |
| 239 | 52%@0.04 | 72%@0.012 | 0.032 |
| 240 | 0.088 | 96%@0.012 | 0.0057 |
| 241 | 0.093 | 98%@0.012 | 0.0072 |
| 242 | 65%@0.04 | 92%@0.012 | 0.013 |
| 243 | 0.047 | 100%@0.012 | 0.025 |
| 244 | 67%@0.04 | 98%@0.012 | 0.0022 |
| 245 | 0.047 | 86%@0.012 | 0.0042 |
| 246 | 0.043 | 76%@0.012 | 0.031 |
| 247 | 0.066 | 80%@0.012 | 0.033 |
| 248 | 69%@0.04 | 91%@0.012 | 0.01 |
| 249 | 56%@0.04 | 90%@0.012 | 0.01 |
| 250 | 0.091 | 89%@0.012 | 0.016 |
| 251 | 68%@0.04 | 99%@0.012 | 0.00065 |
| 252 | 72%@0.04 | 91%@0.012 | 0.004 |
| 253 | 0.05 | 0.017 | 0.051 |
| 254 | 51%@0.04 | 98%@0.012 | 0.0019 |
| 255 | 49%@0.04 | 0.014 | 0.032 |
| 256 | 0.053 | 0.024 | 0.078 |
| 257 | 7.2 | 0.68 | |
| 258 | 58%@10 | 37%@30 | |
| 259\|262\|263 | 63%@0.04 | 96%@0.012 | 0.00091 |

TABLE 10-continued

| Ex. | IC50 or PI Xiap (μM) | IC50 or PI cIAP1 (μM) | EVSA-T prolif (μM) |
|---|---|---|---|
| 260 | 73%@0.04 | 90%@0.012 | 0.0044 |
| 261 | 55%@0.04 | 96%@0.012 | 0.0021 |
| 264 | 68%@0.04 | 98%@0.012 | 0.001 |
| 265 | 1.5 | 0.041 | |
| 266 | −6%@150 | 24%@50 | −20%@10 |

Where more than one data point has been obtained, the table above shows an average (e.g. geometric mean) of these data points (to 2 significant figures).

The invention claimed is:
1. A pharmaceutical composition comprising a compound of formula (I):

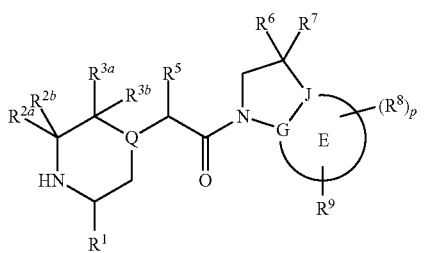

or a tautomeric or stereochemically isomeric form, N-oxide, pharmaceutically acceptable salt or solvate thereof; wherein Ring E represents phenyl, pyrimidinyl, pyridazinyl, pyridyl, or pyridinonyl;
G and J are independently selected from C and N;
Q is $CR^4$ or N;
$R^1$ is selected from $C_{1-4}$ alkyl, $C_{2-4}$ alkenyl and —$(CH_2)_s$—$C_{3-8}$ cycloalkyl, wherein said $C_{1-4}$ alkyl, $C_{2-4}$ alkenyl, and $C_{3-8}$ cycloalkyl may be optionally substituted by one or more $R^a$ groups;
$R^a$ is selected from halogen, —OH and —O—$C_{1-6}$ alkyl;
$R^{2a}$ and $R^{2b}$ are independently selected from hydrogen, $C_{1-6}$ alkyl, $C_{2-6}$ alkenyl, $C_{2-6}$ alkynyl, —C(=O)NH$_{(2-q)}$($C_{1-6}$ alkyl)$_q$, —$(CH_2)_s$-(3-12 membered heterocyclyl), and —$(CH_2)_s$—$C_{3-12}$ carbocyclyl, or $R^{2a}$ and $R^{2b}$ groups, together with the carbon atom to which they are attached, can join to form a 3-10 membered saturated carbocyclyl or heterocyclyl group, wherein said $C_{1-6}$ alkyl, $C_{2-6}$ alkenyl, $C_{2-6}$ alkynyl, heterocyclyl and carbocyclyl groups may be optionally substituted by one or more $R^b$ groups;
$R^{3a}$ and $R^{3b}$ are independently selected from hydrogen, $C_{1-6}$ alkyl, $C_{2-6}$ alkenyl, $C_{2-6}$ alkynyl, —C(=O)NH$_{(2-q)}$($C_{1-6}$ alkyl)$_q$, —$(CH_2)_s$-(3-12 membered heterocyclyl), —$(CH_2)_s$—$C_{3-12}$ carbocyclyl, —C(=O)-(3-12 membered heterocyclyl), and —C(=O)—$C_{3-12}$ carbocyclyl, or $R^{3a}$ and $R^{3b}$ groups, together with the carbon atom to which they are attached, can join to form a 3-10 membered saturated carbocyclyl or heterocyclyl group, wherein said $C_{1-6}$ alkyl, $C_{2-6}$alkenyl, $C_{2-6}$alkynyl, heterocyclyl and carbocyclyl groups may be optionally substituted by one or more $R^b$ groups;
$R^4$ is selected from hydrogen, $C_{1-6}$ alkyl, $C_{2-6}$ alkenyl, $C_{2-6}$ alkynyl, —C(=O)NH$_{(2-q)}$($C_{1-6}$ alkyl)$_q$, —$(CH_2)_s$-(3-12 membered heterocyclyl), —$(CH_2)_s$—$C_{3-12}$ carbocyclyl, —C(=O)-(3-12 membered heterocyclyl), and —C(=O)—$C_{3-12}$ carbocyclyl, wherein said $C_{1-6}$ alkyl, $C_{2-6}$ alkenyl, $C_{2-6}$ alkynyl, heterocyclyl and carbocyclyl groups may be optionally substituted by one or more $R^b$ groups;
$R^5$ is selected from hydrogen, $C_{1-6}$ alkyl, $C_{2-6}$ alkenyl, $C_{2-6}$ alkynyl, —$(CH_2)_s$—$C_{3-8}$ cycloalkyl and —$(CH_2)_s$—$C_{3-8}$ cycloalkenyl, wherein said $C_{1-6}$ alkyl, $C_{2-6}$ alkenyl, $C_{2-6}$ alkynyl, $C_{3-8}$ cycloalkyl and $C_{3-8}$ cycloalkenyl may be optionally substituted by one or more $R^a$ groups;
$R^6$ and $R^7$ are independently selected from hydrogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CR^xR^y)_s$—O—$R^z$, —O—$(CR^xR^y)_n$—$OR^z$, —$(CH_2)_s$—CN, —$S(O)_q$—$R^x$, —C(=O)$R^x$, —C(=S)$R^x$, —C(=N)$R^x$, —$(CR^xR^y)_s$—C(=O)$OR^z$, —$(CR^xR^y)_s$—O—C(=O)—$R^z$, —$(CR^xR^y)_s$—C(=O)NR$^xR^y$, —$(CH_2)_s$—NR$^x$C(=O)$R^y$, —$(CH_2)_s$—OC(=O)NR$^xR^y$, —$(CH_2)_s$—NR$^x$C(=O)$OR^y$, —$(CH_2)_s$—NR$^xR^y$, —NR$^x$—$(CH_2)_s$—$R^z$, —$(CR^xR^y)_s$—C(=S)NR$^z$, —$(CR^xR^y)_s$—C(=N)NR$^z$, —$(CH_2)_s$—O—C(=O)—$C_{1-4}$alkyl-NR$^xR^y$, —$(CH_2)_s$—NR$^x$—$(CH_2)_n$—O—C(=O)—$R^z$, —$(CH_2)_s$—NR$^x$—$(CH_2)_s$—$SO_2$—$R^y$, —$(CH_2)_s$—NH—$SO_2$—NR$^xR^y$ and —$(CH_2)_s$—$SO_2$NR$^xR^y$ groups, or $R^6$ and $R^7$ groups, together with the carbon atom to which they are attached, can join to form a 3-10 membered fully or partially saturated carbocyclyl or heterocyclyl group, which may be optionally fused to a 5-6 membered aromatic carbocyclyl or heterocyclyl ring,
wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more $R^b$ groups;
$R^8$ and $R^9$ are independently selected from hydrogen, halogen, $C_{1-8}$ alkyl, $C_{2-8}$ alkenyl, $C_{2-8}$ alkynyl, —Y—$C_{3-12}$ carbocyclyl, —Z-(3-12 membered heterocyclyl), —$(CR^xR^y)_s$—O—$R^z$, —O—$(CR^xR^y)_n$—$OR^z$, =O, =S, nitro, $Si(R^x)_4$, —$(CH_2)_s$—CN, —$S(O)_q$—$(CR^xR^y)_s$—$R^z$, —C(=O)$R^x$, —C(=S)$R^x$, —C(=N)$R^x$, —$(CR^xR^y)_s$—C(=O)$OR^z$, —$(CR^xR^y)_s$—O—C(=O)—$R^z$, —$(CR^xR^y)_s$—C(=O)NR$^xR^y$, —$(CH_2)_s$—NR$^x$C(=O)$R^y$, —$(CH_2)_s$—OC(=O)NR$^xR^y$, —$(CH_2)_s$—NR$^x$C(=O)$OR^y$, —$(CH_2)_s$—NR$^xR^y$, —NR$^x$—$(CH_2)_s$—$R^z$, —$(CR^xR^y)_s$—C(=S)NR$^z$, —$(CR^xR^y)_s$—C(=N)NR$^x$, —S(O)(=NR$^x$)$R^y$, —$(CH_2)_s$—O—C(=O)—$C_{1-4}$alkyl-NR$^xR^y$, —$(CH_2)_s$—NR$^x$—$(CH_2)_n$—O—C(=O)—$R^z$, —$(CH_2)_s$—NR$^x$—$(CH_2)_s$—$SO_2$—$R^y$, —$(CH_2)_s$—NH—$SO_2$—NR$^xR^y$, —$(CH_2)_s$—$SO_2$NR$^xR^y$ groups and —P(=O)($R^x$)$_2$, wherein said $C_{1-8}$ alkyl, $C_{2-8}$ alkenyl and $C_{2-8}$ alkynyl groups may be optionally substituted by one or more $R^b$ groups and wherein said carbocyclyl and heterocyclyl groups may be optionally substituted by one or more $R^b$ groups;
$R^b$ is independently selected from halogen, $C_{1-6}$ alkyl, $C_{2-6}$ alkenyl, $C_{2-6}$ alkynyl, —$(CH_2)_s$—$C_{3-8}$ cycloalkyl, —$(CH_2)_s$—$C_{3-8}$ cycloalkenyl, —$(CH_2)_s$-phenyl, —$(CH_2)_s$-(4-7 membered saturated heterocyclyl), —$(CR^xR^y)_s$—O—$R^z$, —O—$(CR^xR^y)_n$—$OR^z$, halo$C_{1-6}$ alkyl, halo$C_{1-6}$ alkoxy, $C_{1-6}$ alkanol, =O, =S, nitro, $Si(R^x)_4$, —$(CH_2)_s$—CN, —$S(O)_q$—$R^x$, —C(=O)$R^x$, —$(CR^xR^y)_s$—C(=O)$OR^z$, —$(CR^xR^y)_s$—O—C(=O)—$R^z$, —$(CR^xR^y)_s$—C(=O)NR$^xR^y$, —$(CH_2)_s$—NR$^x$C(=O)$R^y$, —$(CH_2)_s$—OC(=O)NR$^xR^y$, —(CH$_2$)$_s$—NR$^x$C(=O)OR$^y$   —(CH$_2$)$_s$—NR$^x$R$^y$, —NR$^x$—(CH$_2$)$_s$—R$^z$,   —(CH$_2$)$_s$—O—C(=O)—C$_{1-4}$alkyl-NR$^x$R$^y$, —(CH$_2$)$_s$—NR$^x$—(CH$_2$)$_n$—O—C(=O)—R$^z$,   —(CH$_2$)$_s$—NR$^x$—(CH$_2$)$_s$—SO$_2$—R$^y$, —(CH$_2$)$_s$—NH—SO$_2$—NR$^x$R$^y$,   —(CH$_2$)$_s$—SO$_2$NR$^x$R$^y$ groups and —P(=O)(R$^x$)$_2$, wherein said C$_{1-6}$ alkyl, C$_{2-6}$ alkenyl, C$_{2-6}$ alkynyl, C$_{3-8}$ cycloalkyl, C$_{3-8}$ cycloalkenyl and heterocyclyl groups may be optionally substituted by one or more R$^x$ groups;

R$^x$, R$^y$ and R$^z$ independently represent halogen, hydrogen, C$_{1-6}$ alkyl, C$_{2-6}$ alkenyl, C$_{2-6}$ alkynyl, —(CH$_2$)$_s$—C$_{3-8}$ cycloalkyl, —(CH$_2$)$_s$—C$_{3-8}$ cycloalkenyl, —(CH$_2$)$_s$-phenyl, —(CH$_2$)$_s$-(4-7 membered saturated heterocyclyl), C$_{1-6}$ alkanol optionally substituted with one or more halo, —C(=O)OC$_{1-6}$ alkyl, hydroxy, C$_{1-6}$ alkoxy, haloC$_{1-6}$ alkyl, —(CH$_2$)$_n$—O—C$_{1-6}$ alkyl, —C(=O)—(CH$_2$)$_n$—C$_{1-6}$ alkoxy, —(CH$_2$)$_s$—CN, C$_{1-6}$ alkyl-N(H)$_{2-q}$(C$_{1-6}$alkyl)$_q$,   —N(H)$_{2-q}$(C$_{1-6}$alkyl)$_q$, —C(=O)—N(H)$_{2-q}$(C$_{1-6}$alkyl)$_q$,   —(CH$_2$)$_s$—NH—SO$_2$—N(H)$_{2-q}$ (C$_{1-6}$alkyl)$_q$, —(CH$_2$)$_s$—N(C$_{1-4}$alkyl)-SO$_2$—N(H)$_{2-q}$(C$_{1-6}$alkyl)$_q$ or   —(CH$_2$)$_s$—O—C(=O)—C$_{1-4}$alkyl-N(H)$_{2-q}$(C$_{1-6}$ alkyl)$_q$, and when attached to nitrogen, carbon, silicon or phosphorus atom R$^x$ and R$^y$ may join to form a 3-7 membered ring optionally containing one or two additional heteroatoms selected from O, N, S and oxidised forms of N or S;

Y and Z are independently selected from a bond, —(CR$^x$R$^y$)$_m$—, —C(=CR$^x$)—, —C(=O)—, —NR$^x$, —C(=O)NR$^x$—, —NR$^x$C(=O)—, —(CR$^x$R$^y$)$_q$—O—, —O—(CR$^x$R$^y$)$_q$—, —S(O)$_2$—NH, NH—S(O)$_2$— and —S(O)$_q$—;

s independently represents an integer from 0-4;
n independently represents an integer from 1-4;
p independently represents an integer from 0-4;
q represents an integer from 0-2; and
m represents an integer from 1-2.

2. A pharmaceutical composition as defined in claim 1, wherein Q represents N.

3. A pharmaceutical composition as defined in claim 1, wherein ring E represents pyridyl, pyridazinyl or phenyl.

4. A pharmaceutical composition as defined in claim 1, wherein R$^1$ represents methyl.

5. A pharmaceutical composition as defined in claim 1, wherein R$^{2a}$ and R$^{2b}$ are hydrogen.

6. A pharmaceutical composition as defined in claim 1, wherein:
(i) R$^{3a}$ and R$^{3b}$ are independently selected from hydrogen, C$_{1-6}$ alkyl, —C(=O)NH$_{(2-q)}$(C$_{1-6}$ alkyl)$_q$, —(CH$_2$)$_s$-(3-12 membered heterocyclyl), —(CH$_2$)$_s$—C$_{3-12}$ carbocyclyl, —C(=O)-(3-12 membered heterocyclyl), and —C(=O)—C$_{3-12}$ carbocyclyl wherein said C$_{1-6}$ alkyl, heterocyclyl and carbocyclyl groups may be optionally substituted by one or more R$^b$ groups; or
(ii) one of R$^{3a}$ and R$^{3b}$ represents hydrogen and the other represents:
C$_{1-6}$ alkyl, optionally substituted by halogen, —(CR$^x$R$^y$)$_s$—O—R$^z$; —(CH$_2$)$_s$—NR$^x$C(=O)R$^y$);
—C(=O)NH$_{(2-q)}$(C$_{1-6}$ alkyl)$_q$;
—(CH$_2$)$_s$-(3-6 membered heterocyclyl); or
—C(=O)-(3-6 membered heterocyclyl)
wherein said heterocyclyl groups may be optionally substituted by one or more R$^b$ groups; or
(iii) R$^{3b}$ is hydrogen, and R$^{3a}$ is —CH$_2$-(6 membered saturated heterocyclyl), wherein said heterocyclyl group may be optionally substituted by one or more R$^b$ groups; or (iv) R$^{3b}$ is hydrogen, and R$^{3a}$ is —CH$_2$-(4-morpholinyl) optionally substituted by one or more R$^b$ groups.

7. A pharmaceutical composition as defined in claim 1, wherein R$^5$ represents hydrogen.

8. A pharmaceutical composition as defined in claim 1, wherein;
(i) R$^6$ and R$^7$ are independently selected from hydrogen, C$_{1-6}$ alkyl, —Y—C$_{3-6}$ carbocyclyl; —Z-(3-12 membered heterocyclyl); —(CR$^x$R$^y$)$_s$—C(=O)OR$^z$; and (CR$^x$R$^y$)$_s$—O—R$^z$; or
(ii) R$^6$ and R$^7$ are both methyl; or
(iii) R$^6$ and R$^7$ groups, together with the carbon atom to which they are attached, join to form a 3-6 membered fully saturated carbocyclyl or heterocyclyl group, and which may be optionally fused to a 5-6 membered aromatic carbocyclyl or heterocyclyl ring, wherein said carbocyclyl and heterocyclyl groups may be optionally substituted by 1, 2 or 3 R$^b$ groups.

9. A pharmaceutical composition as defined in claim 1, wherein p is 0, or p is 1 and R$^8$ is selected from halogen, =O, C$_{1-6}$ alkyl and —(CR$^x$R$^y$)$_s$—O—R$^z$.

10. A pharmaceutical composition as defined in claim 1, wherein:
(i) R$^9$ is selected from halogen, —(CH$_2$)$_s$—CN, C$_{1-8}$ alkyl, —Y—C$_{3-12}$ carbocyclyl, —Z-(3-12 membered heterocyclyl),   —S(O)$_q$—(CR$^x$R$^y$)$_s$—R$^z$ and —(CH$_2$)$_s$—SO$_2$NR$^x$R$^y$, wherein said carbocyclyl groups or heterocyclyl groups may be optionally substituted by one or more R$^b$ groups; or
(ii) R$^9$ is selected from chlorine, fluorine, bromine, —CN, methyl, ethyl, propyl, isobutyl, butyl, —(CH$_2$)$_2$—CH(CH$_3$)$_2$), —CH$_2$-phenyl, —CF$_2$-phenyl, —CH(CH$_3$)-phenyl, —CH(OCH$_3$)-phenyl, —C(=CH$_2$)-phenyl, —O-phenyl, —SO$_2$-phenyl, —C(=O)-phenyl, —CF$_2$-cyclopropyl, —CF$_2$-cyclobutyl, —CF$_2$—CH$_2$-cyclobutyl, -cyclopentyl, -cyclopentenyl, —CH$_2$-cyclohexyl, cyclohexyl, cyclohexenyl, -pyrazolyl, -furanyl, -thienyl, -oxadiazolyl, -tetrazolyl, -benzofuranyl, —CH$_2$-pyrrolidinyl, —SO$_2$CH$_3$, —SO$_2$—CH$_2$CH(CH$_3$)$_2$, —SO$_2$—CH$_2$-phenyl, and —SO$_2$N(CH$_3$)$_2$, wherein said phenyl, pyrazolyl, furanyl, thienyl, oxadiazolyl, tetrazolyl, benzofuranyl or pyrrolidinyl groups may be optionally substituted by one or more R$^b$ groups; or
(iii) R$^9$ is selected from —(CR$^x$R$^y$)$_{1-2}$-cyclopropyl, —(CR$^x$R$^y$)-cyclobutyl, —(CR$^x$R$^y$)-phenyl, ethyl, propyl or butyl each of which may be optionally substituted by one or more halogen atoms and wherein R$^x$ and R$^y$ are independently selected from hydrogen and fluorine; or
(iv) R$^9$ is —CH$_2$-(4-fluorophenyl).

11. A pharmaceutical composition as defined in claim 1, wherein the compound is a compound of formula (Ic):

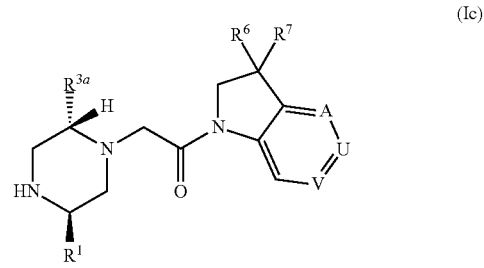

(Ic)

or a tautomeric or stereochemically isomeric form, N-oxide, pharmaceutically acceptable salt or solvate thereof, wherein A is selected from CR⁸ and N;
U is selected from CR⁸ and N; and
V is selected from CR⁹ and N;
provided that no more than two of A, U, and V are nitrogen.

12. A pharmaceutical composition as defined in claim 1, wherein the compound is a compound of formula (Ii)ᵃ or (Ii)ᵇ:

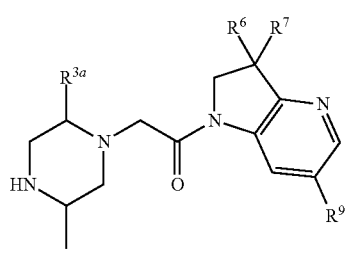

(Ii)ᵃ

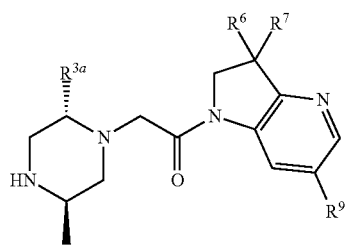

(Ii)ᵇ or a tautomeric or stereochemically isomeric form, N-oxide, pharmaceutically acceptable salt or solvate thereof.

13. A pharmaceutical composition as defined in claim 1, wherein the compound is a compound of formula (Ik)ᵃ or (Ik)ᵇ:

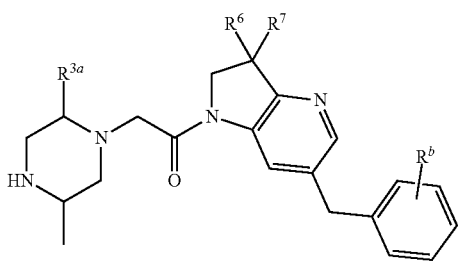

(Ik)ᵃ

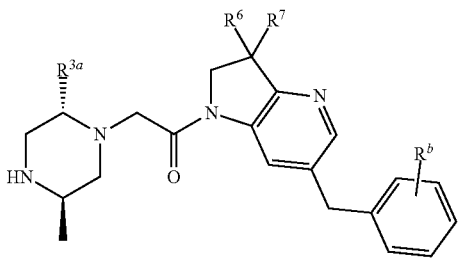

(Ik)ᵇ or a tautomeric or stereochemically isomeric form, N-oxide, pharmaceutically acceptable salt or solvate thereof.

14. A pharmaceutical composition as defined in claim 1, wherein the compound is a compound of formula (Im) or (In):

(Im)

(In)

or a tautomeric or stereochemically isomeric form, N-oxide, pharmaceutically acceptable salt or solvate thereof.

15. A pharmaceutical composition as defined in claim 1, wherein the compound is the free base of a compound selected from Examples 1 to 266 or a tautomeric or stereochemically isomeric form, N-oxide, pharmaceutically acceptable salt or the solvate thereof.

16. A pharmaceutical composition as defined in claim 1, or a tautomeric or stereochemically isomeric form, N-oxide, pharmaceutically acceptable salt or solvate thereof, in combination with one or more therapeutic agents.

* * * * *

UNITED STATES PATENT AND TRADEMARK OFFICE
CERTIFICATE OF CORRECTION

| | |
|---|---|
| PATENT NO. | : 9,676,768 B2 |
| APPLICATION NO. | : 14/663534 |
| DATED | : June 13, 2017 |
| INVENTOR(S) | : Woolford et al. |

Page 1 of 1

It is certified that error appears in the above-identified patent and that said Letters Patent is hereby corrected as shown below:

In the Claims

Column 445, Line 17: Claim 1, delete "$(CH_2)_n$-$C_{1-6}$ alkoxy, -$(CH_2)_s$-CN," and insert -- $(CH_2)_n$-$C_{1-6}$ alkoxy, -C(=O)-$C_{1-6}$alkyl, -$(CH_2)_s$-CN, --

Signed and Sealed this
Twenty-second Day of August, 2017

Joseph Matal
*Performing the Functions and Duties of the*
*Under Secretary of Commerce for Intellectual Property and*
*Director of the United States Patent and Trademark Office*